United States Patent
Lee et al.

(10) Patent No.: US 12,404,278 B2
(45) Date of Patent: Sep. 2, 2025

(54) HETEROCYCLIC COMPOUND AND ORGANIC LIGHT-EMITTING DEVICE COMPRISING SAME

(71) Applicant: LT MATERIALS CO., LTD., Yongin-si (KR)

(72) Inventors: Yun-Ji Lee, Yongin-si (KR); Min-Ji Park, Yongin-si (KR); Won-Jang Jeong, Yongin-si (KR); Dong-Jun Kim, Yongin-si (KR)

(73) Assignee: LT MATERIALS CO., LTD., Yongin (KR)

( * ) Notice: Subject to any disclaimer, the term of this patent is extended or adjusted under 35 U.S.C. 154(b) by 910 days.

(21) Appl. No.: 17/608,297

(22) PCT Filed: Sep. 25, 2020

(86) PCT No.: PCT/KR2020/013036
§ 371 (c)(1),
(2) Date: Nov. 2, 2021

(87) PCT Pub. No.: WO2021/066397
PCT Pub. Date: Apr. 8, 2021

(65) Prior Publication Data
US 2022/0281884 A1     Sep. 8, 2022

(30) Foreign Application Priority Data
Oct. 2, 2019     (KR) .................. 10-2019-0122320

(51) Int. Cl.
*C07D 491/048*     (2006.01)
*C07D 495/04*     (2006.01)
(Continued)

(52) U.S. Cl.
CPC ....... *C07D 491/048* (2013.01); *C07D 495/04* (2013.01); *C07D 519/00* (2013.01);
(Continued)

(58) Field of Classification Search
CPC .............. C07D 491/048; C07D 495/04; C07D 519/00; H01L 51/0067; H01L 51/0072;
(Continued)

(56) References Cited

U.S. PATENT DOCUMENTS

2013/0292653 A1     11/2013     Park et al.
2016/0141515 A1     5/2016      Hayama et al.
(Continued)

FOREIGN PATENT DOCUMENTS

KR     10-2013-0127567 A     11/2013
KR     10-2016-0002408 A     1/2016
(Continued)

OTHER PUBLICATIONS

Zhang et al., Photoredox-Catalyzed Tandem Insertion/Cyclization Reactions of Difluoromethyl and 1,1-difluoroalkyl Radicals with Biphenyl Isocyanides, Organic Letter, 2015 vol. 17, pp. 4401-4403. (Year: 2015).*

(Continued)

*Primary Examiner* — Vu A Nguyen
(74) *Attorney, Agent, or Firm* — Birch, Stewart, Kolasch & Birch, LLP

(57) ABSTRACT

The present specification relates to a heterocyclic compound represented by Chemical Formula 1, and an organic light emitting device including the same.

14 Claims, 2 Drawing Sheets

(51) Int. Cl.
| | |
|---|---|
| *C07D 519/00* | (2006.01) |
| *C07F 9/53* | (2006.01) |
| *H10K 50/11* | (2023.01) |
| *H10K 50/13* | (2023.01) |
| *H10K 50/16* | (2023.01) |
| *H10K 85/60* | (2023.01) |
| *H10K 101/10* | (2023.01) |
| *H10K 101/30* | (2023.01) |
| *H10K 101/40* | (2023.01) |

(52) U.S. Cl.
CPC ......... *C07F 9/5333* (2013.01); *H10K 85/622* (2023.02); *H10K 85/624* (2023.02); *H10K 85/626* (2023.02); *H10K 85/654* (2023.02); *H10K 85/6572* (2023.02); *H10K 85/6574* (2023.02); *H10K 85/6576* (2023.02); *H10K 50/11* (2023.02); *H10K 50/13* (2023.02); *H10K 50/16* (2023.02); *H10K 2101/10* (2023.02); *H10K 2101/30* (2023.02); *H10K 2101/40* (2023.02)

(58) Field of Classification Search
CPC ............ H01L 51/0073; H01L 51/0074; H01L 51/0056; H01L 51/0058; H01L 51/0054; C07F 9/5333
See application file for complete search history.

(56) References Cited

U.S. PATENT DOCUMENTS

| | | |
|---|---|---|
| 2017/0133601 A1 | 5/2017 | Sim et al. |
| 2017/0133602 A1 | 5/2017 | Lee et al. |
| 2019/0103560 A1* | 4/2019 | Jung .................. H05B 33/14 |
| 2020/0308150 A1 | 10/2020 | Lee et al. |

FOREIGN PATENT DOCUMENTS

| | | |
|---|---|---|
| KR | 10-2016-0046703 A | 4/2016 |
| KR | 10-2018-0076358 A | 7/2018 |
| KR | 10-2019-0037925 A | 4/2019 |
| WO | WO 2014/199637 A1 | 12/2014 |

OTHER PUBLICATIONS

International Search Report for PCT/KR2020/013036 mailed on Jan. 21, 2021.

Zhang et al., "Photoredox-Catalyzed Tandem Insertion/Cyclization Reactions of Difluoromethyl and 1,1-Difluoroalkyl Radicals with Biphenyl Isocyanides", Organic Letters, 2015, vol. 17, pp. 4401-4403.

* cited by examiner

[FIG. 1]
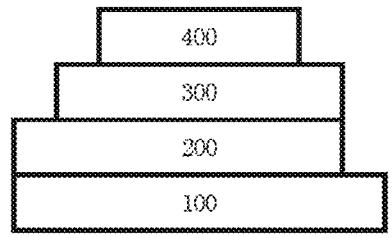
[FIG. 2]
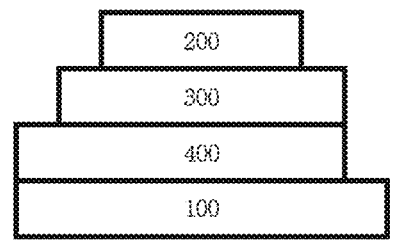
[FIG. 3]
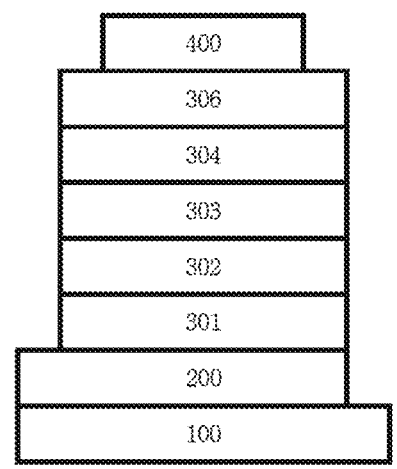

[FIG. 4]
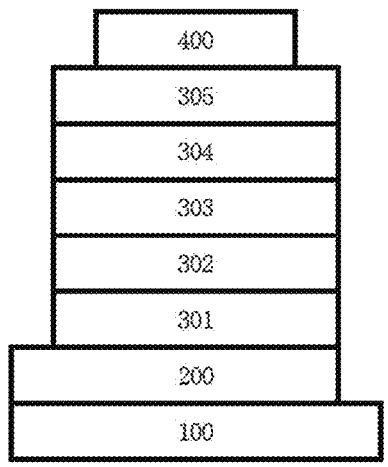
[FIG. 5]
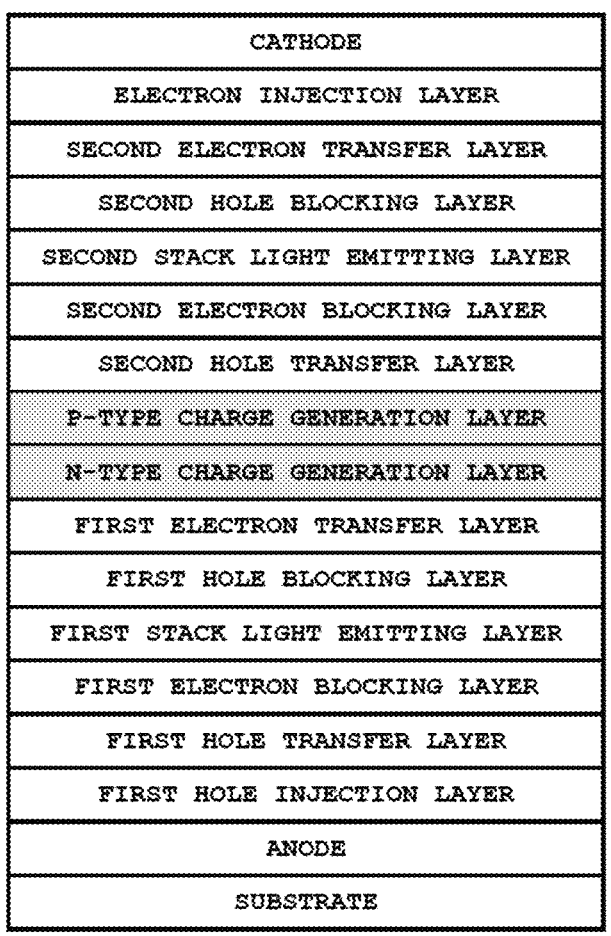

HETEROCYCLIC COMPOUND AND ORGANIC LIGHT-EMITTING DEVICE COMPRISING SAME

TECHNICAL FIELD

The present specification relates to a heterocyclic compound, and an organic light emitting device including the same.

This application claims priority to and the benefits of Korean Patent Application No. 10-2019-0122320, filed with the Korean Intellectual Property Office on Oct. 2, 2019, the entire contents of which are incorporated herein by reference.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

DISCLOSURE

Technical Problem

The present specification is directed to providing a heterocyclic compound, and an organic light emitting device including the same.

Technical Solution

One embodiment of the present specification provides a heterocyclic compound represented by the following Chemical Formula 1.

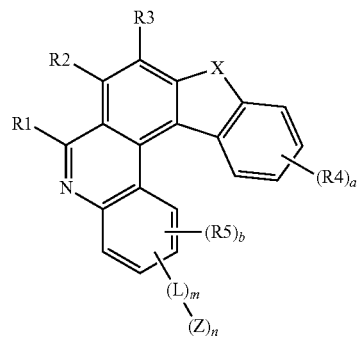

[Chemical Formula 1]

In Chemical Formula 1,
X is O or S,
L is a direct bond; a substituted or unsubstituted C6 to C60 arylene group; or a substituted or unsubstituted C2 to C60 heteroarylene group,
Z and R1 are each independently a substituted or unsubstituted C1 to C60 alkyl group; a substituted or unsubstituted C2 to C60 alkenyl group; a substituted or unsubstituted C2 to C60 alkynyl group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; a substituted or unsubstituted C1 to C20 alkylamine group; a substituted or unsubstituted C6 to C60 arylamine group; a substituted or unsubstituted C2 to C60 heteroarylamine group; or a substituted or unsubstituted phosphine oxide group,
R2 to R5 are each independently hydrogen; deuterium; a halogen group; a cyano group; a substituted or unsubstituted C1 to C60 alkyl group; a substituted or unsubstituted C3 to C60 cycloalkyl group; a substituted or unsubstituted C6 to C60 aryl group; or a substituted or unsubstituted C2 to C60 heteroaryl group,
a is an integer of 1 to 4,
b is an integer of 1 to 3,
m and n are each an integer of 1 to 5, and
when a, b, m and n are each 2 or greater, substituents in the parentheses are the same as or different from each other.

Another embodiment of the present application provides an organic light emitting device including a first electrode; a second electrode provided opposite to the first electrode; and an organic material layer provided between the first electrode and the second electrode, wherein the organic material layer includes the heterocyclic compound represented by Chemical Formula 1.

Another embodiment of the present application provides an organic light emitting device including a first electrode; a first stack provided on the first electrode and including a first light emitting layer; a charge generation layer provided on the first stack; a second stack provided on the charge generation layer and including a second light emitting layer; and a second electrode provided on the second stack, wherein the charge generation layer includes the heterocyclic compound represented by Chemical Formula 1.

Advantageous Effects

A compound described in the present specification can be used as a material of an organic material layer of an organic light emitting device. In the organic light emitting device, the compound is capable of performing a role of a hole injection material, a hole transfer material, a light emitting material, an electron transfer material, an electron injection material or the like. Particularly, the compound can be used as an electron transfer layer material or a charge generation layer material of an organic light emitting device.

Particularly, Chemical Formula 1 has a structure in which dibenzofuran or dibenzothiophene is fused to quinoline, and by having a substituent in the benzine ring of the quinoline, efficiency is improved by properly controlling HOMO and LUMO distributions and thereby allowing charges to migrate smoothly.

Specifically, when using the compound represented by Chemical Formula 1 in an organic material layer, a driving voltage of the device can be lowered, light efficiency can be enhanced, and lifetime properties of the device can be enhanced.

DESCRIPTION OF DRAWINGS

FIG. 1 to FIG. 5 are diagrams each illustrating a lamination structure of an organic light emitting device according to one embodiment of the present specification.
100: Substrate
200: Anode
300: Organic Material Layer
301: Hole Injection Layer
302: Hole Transfer Layer
303: Light Emitting Layer
304: Electron Transfer Layer
305: Electron Injection Layer
306: Charge Generation Layer
400: Cathode

MODE FOR DISCLOSURE

Hereinafter, the present specification will be described in more detail.

In the present specification, a certain part "including" certain constituents means capable of further including other constituents, and does not exclude other constituents unless particularly stated on the contrary.

The term "substitution" means a hydrogen atom bonding to a carbon atom of a compound being changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, "substituted or unsubstituted" means being substituted with one or more substituents selected from the group consisting of a C1 to C60 linear or branched alkyl group; a C2 to C60 linear or branched alkenyl group; a C2 to C60 linear or branched alkynyl group; a C3 to C60 monocyclic or polycyclic cycloalkyl group; a C2 to C60 monocyclic or polycyclic heterocycloalkyl group; a C6 to C60 monocyclic or polycyclic aryl group; a C2 to C60 monocyclic or polycyclic heteroaryl group; a silyl group; a phosphine oxide group; and an amine group, or being unsubstituted, or being substituted with a substituent linking two or more substituents selected from among the substituents illustrated above, or being unsubstituted.

In the present specification, a "case of a substituent being not indicated in a chemical formula or compound structure" means that a hydrogen atom bonds to a carbon atom. However, since deuterium ($^2H$) is an isotope of hydrogen, some hydrogen atoms may be deuterium.

In one embodiment of the present application, a "case of a substituent being not indicated in a chemical formula or compound structure" may mean that positions that may come as a substituent may all be hydrogen or deuterium. In other words, since deuterium is an isotope of hydrogen, some hydrogen atoms may be deuterium that is an isotope, and herein, a content of the deuterium may be from 0% to 100%.

In one embodiment of the present application, in a "case of a substituent being not indicated in a chemical formula or compound structure", hydrogen and deuterium may be mixed in compounds when deuterium is not explicitly excluded such as a deuterium content being 0%, a hydrogen content being 100% or substituents being all hydrogen.

In one embodiment of the present application, deuterium is one of isotopes of hydrogen, is an element having deuteron formed with one proton and one neutron as a nucleus, and may be expressed as hydrogen-2, and the elemental symbol may also be written as D or $^2H$.

In one embodiment of the present application, an isotope means an atom with the same atomic number (Z) but with a different mass number (A), and may also be interpreted as an element with the same number of protons but with a different number of neutrons.

In one embodiment of the present application, a meaning of a content T % of a specific substituent may be defined as T2/T1×100=T % when the total number of substituents that a basic compound may have is defined as T1, and the number of specific substituents among these is defined as T2.

In other words, in one example, having a deuterium content of 20% in a phenyl group represented by

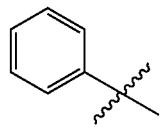 [SMILES: *c1ccccc1]

means that the total number of substituents that the phenyl group may have is 5 (T1 in the formula), and the number of deuterium among these is 1 (T2 in the formula). In other words, having a deuterium content of 20% in a phenyl group may be represented by the following structural formulae.

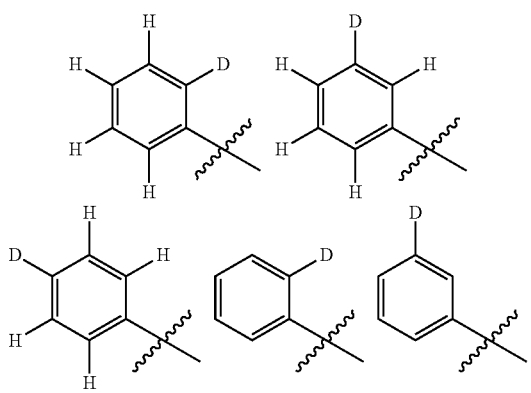

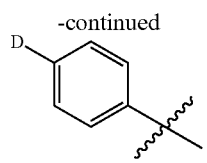

In addition, in one embodiment of the present application, "a phenyl group having a deuterium content of 0%" may mean a phenyl group that does not include a deuterium atom, that is, a phenyl group that has 5 hydrogen atoms.

In the present specification, the halogen may be fluorine, chlorine, bromine or iodine.

In the present specification, the alkyl group includes linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may include a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethylbutyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 4-methylhexyl group, a 5-methylhexyl group and the like, but are not limited thereto.

In the present specification, the alkenyl group includes linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may include a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group includes linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is preferably from 1 to 20. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the cycloalkyl group includes monocyclic or polycyclic having 3 to 60 carbon atoms, and may be further substituted with other substituents. Herein, the polycyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may include a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group includes O, S, Se, N or Si as a heteroatom, includes monocyclic or polycyclic having 2 to 60 carbon atoms, and may be further substituted with other substituents. Herein, the polycyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group includes monocyclic or polycyclic having 6 to 60 carbon atoms, and may be further substituted with other substituents. Herein, the polycyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group includes a spiro group. The number of carbon atoms of the aryl group may be from 6 to 60, specifically from 6 to 40 and more specifically from 6 to 25. Specific examples of the aryl group may include a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the fluorenyl group may be substituted, and adjacent substituents may bond to each other to form a ring.

When the fluorenyl group is substituted,

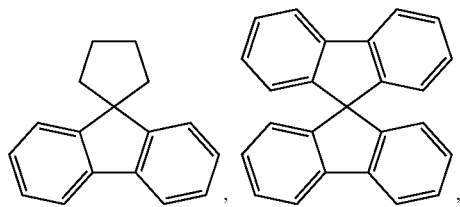

,

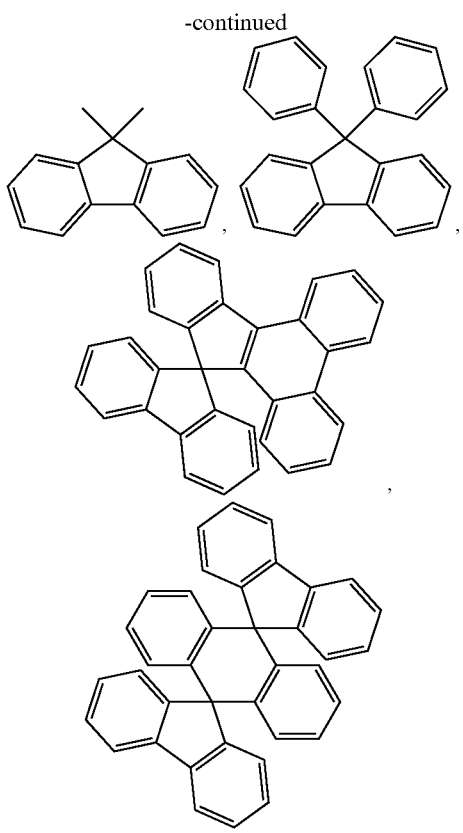

and the like may be included, however, the structure is not limited thereto.

In the present specification, the heteroaryl group includes S, O, Se, N or Si as a heteroatom, includes monocyclic or polycyclic having 2 to 60 carbon atoms, and may be further substituted with other substituents. Herein, the polycyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may include a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydro-dibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl group, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the silyl group is a substituent including Si, having the Si atom directly linked as a radical, and is represented by —Si(R101) (R102) (R103). R101 to R103 are the same as or different from each other, and may be each independently a substituent formed with at least one of hydrogen; deuterium; a halogen group; an alkyl group; an alkenyl group; an alkoxy group; a cycloalkyl group; a heterocycloalkyl group; an aryl group; and a heteroaryl group. Specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the phosphine oxide group is represented by —P(=O) (R104) (R105), and R104 and R105 are the same as or different from each other and may be each independently a substituent formed with at least one of hydrogen; deuterium; a halogen group; an alkyl group; an alkenyl group; an alkoxy group; a cycloalkyl group; a heterocycloalkyl group; an aryl group; and a heteroaryl group. The phosphine oxide group may specifically be substituted with an aryl group, and as the aryl group, the examples described above may be applied. Examples of the phosphine oxide group may include a diphenylphosphine oxide group, a dinaphthylphosphine oxide group and the like, but are not limited thereto.

In the present specification, the amine group is represented by —N(R106) (R107), and R106 and R107 are the same as or different from each other and may be each independently a substituent formed with at least one of hydrogen; deuterium; a halogen group; an alkyl group; an alkenyl group; an alkoxy group; a cycloalkyl group; a heterocycloalkyl group; an aryl group; and a heteroaryl group. The amine group may be selected from the group consisting of —NH$_2$; a monoalkylamine group; a monoarylamine group; a monoheteroarylamine group; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may include a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, descriptions on the aryl group provided above may be applied to the arylene group except that the arylene group is not a monovalent group.

In the present specification, descriptions on the heteroaryl group provided above may be applied to the heteroarylene group except that the heteroarylene group is not a monovalent group.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

As the aliphatic or aromatic hydrocarbon ring or heteroring that the adjacent groups may form, the structures illustrated as the cycloalkyl group, the heterocycloalkyl group, the aryl group and the heteroaryl group described above may be applied except for those that are not a monovalent group.

One embodiment of the present specification provides a heterocyclic compound represented by Chemical Formula 1.

Particularly, Chemical Formula 1 has a structure in which dibenzofuran or dibenzothiophene is fused to quinoline, and by having a substituent in the benzine ring of the quinoline, HOMO and LUMO tend to have a decreased overlap, and light emission efficiency is improved. In addition, through properly controlling an energy level, a migration barrier of charges is lowered, which improves device efficiency. In addition, by attaching a substituent having HT properties, particularly an aryl group, to R1 of the ring including N of the quinoline, the shape of the molecule may be improved, and thermal stability of the molecule may increase therethrough.

In one embodiment of the present specification, X is O or S.

In one embodiment of the present specification, X is O.

In another embodiment, X is S.

In one embodiment of the present specification, L is a direct bond; a substituted or unsubstituted C6 to C60 arylene group; or a substituted or unsubstituted C2 to C60 heteroarylene group.

In one embodiment of the present specification, L is a direct bond; a substituted or unsubstituted C6 to C30 arylene group; or a substituted or unsubstituted C2 to C30 heteroarylene group.

In one embodiment of the present specification, L is a direct bond; or a substituted or unsubstituted C6 to C30 arylene group.

In one embodiment of the present specification, L is a direct bond; a substituted or unsubstituted phenylene group; a substituted or unsubstituted biphenylene group; a substituted or unsubstituted terphenylene group; a substituted or unsubstituted naphthylene group; a substituted or unsubstituted anthracenylene group; a substituted or unsubstituted triphenylenylene group; or a substituted or unsubstituted phenanthrenylene group.

In one embodiment of the present specification, L is a direct bond; a phenylene group; a biphenylene group; a terphenylene group; a naphthylene group; an anthracenylene group; a triphenylenylene group; or a phenanthrenylene group.

In one embodiment of the present specification, L is a direct bond; or a phenylene group.

In one embodiment of the present specification, Z is a substituted or unsubstituted C1 to C60 alkyl group; a substituted or unsubstituted C2 to C60 alkenyl group; a substituted or unsubstituted C2 to C60 alkynyl group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; a substituted or unsubstituted C1 to C20 alkylamine group; a substituted or unsubstituted C6 to C60 arylamine group; a substituted or unsubstituted C2 to C60 heteroarylamine group; or a substituted or unsubstituted phosphine oxide group.

In one embodiment of the present specification, Z is a substituted or unsubstituted C1 to C30 alkyl group; a substituted or unsubstituted C2 to C30 alkenyl group; a substituted or unsubstituted C2 to C30 alkynyl group; a substituted or unsubstituted C3 to C30 cycloalkyl group; a substituted or unsubstituted C2 to C30 heterocycloalkyl group; a substituted or unsubstituted C6 to C30 aryl group; a substituted or unsubstituted C2 to C30 heteroaryl group; a substituted or unsubstituted C1 to C10 alkylamine group; a substituted or unsubstituted C6 to C30 arylamine group; a substituted or unsubstituted C2 to C30 heteroarylamine group; or a substituted or unsubstituted phosphine oxide group.

In one embodiment of the present specification, Z is a substituted or unsubstituted C6 to C30 aryl group; a substituted or unsubstituted C2 to C30 heteroaryl group; or a substituted or unsubstituted phosphine oxide group.

In one embodiment of the present specification, Z is a substituted or unsubstituted phenyl group; a biphenyl group; a terphenyl group; a naphthyl group; a triphenylenyl group; a phenanthrenyl group; an anthracenyl group; a dimethylfluorenyl group; a diphenylfluorenyl group; a spirobifluorenyl group; an isoquinolinyl group; a quinazolinyl group; a phenoxazinyl group; a phenothiazinyl group; an indolocarbazole group; a benzonaphthothiophene group; a substituted or unsubstituted pyrazole group; a substituted or unsubstituted pyridine group; a substituted or unsubstituted pyrimidine group; a substituted or unsubstituted triazine group; a substituted or unsubstituted carbazole group; a substituted or unsubstituted phenanthrolinyl group; a substituted or unsubstituted dibenzofuran group; a substituted or unsubstituted dibenzothiophene group; a substituted or unsubstituted dihydroacridine group; or a substituted or unsubstituted phosphine oxide group.

In one embodiment of the present specification, Z is a phenyl group unsubstituted or substituted with a cyano group, a phenyl group or a carbazole group; a biphenyl group; a terphenyl group; a naphthyl group; a triphenylenyl group; a phenanthrenyl group; an anthracenyl group; a dimethylfluorenyl group; a diphenylfluorenyl group; a spirobifluorenyl group; an isoquinolinyl group; a quinazolinyl group; a phenoxazinyl group; a phenothiazinyl group; an indolocarbazole group; a benzonaphthothiophene group; a pyrazole group unsubstituted or substituted with a phenyl group; a pyridine group unsubstituted or substituted with a phenyl group or a pyridine group; a pyrimidine group unsubstituted or substituted with a phenyl group or a biphenyl group; a triazine group unsubstituted or substituted with one or more substituents selected from the group consisting of a phenyl group unsubstituted or substituted with a naphthyl group or a cyano group, a biphenyl group, a naphthyl group, a dimethylfluorenyl group, a dibenzofuran group, a dibenzothiophene group and a carbazole group unsubstituted or substituted with a phenyl group; a carbazole group unsubstituted or substituted with a phenyl group; a phenanthrolinyl group unsubstituted or substituted with a phenyl group; a dibenzofuran group unsubstituted or substituted with a phenyl group or a naphthyl group; a dibenzothiophene group unsubstituted or substituted with a phenyl group or a naphthyl group; a dihydroacridine group unsubstituted or substituted with a methyl group or a phenyl group; or a phosphine oxide group unsubstituted or substituted with a phenyl group.

In one embodiment of the present specification, R1 is a substituted or unsubstituted C1 to C60 alkyl group; a substituted or unsubstituted C2 to C60 alkenyl group; a substituted or unsubstituted C2 to C60 alkynyl group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; a substituted or unsubstituted C1 to C20 alkylamine group; a substituted or unsubstituted C6 to C60 arylamine group; a substituted or unsubstituted C2 to C60 heteroarylamine group; or a substituted or unsubstituted phosphine oxide group.

In one embodiment of the present specification, R1 is a substituted or unsubstituted C1 to C60 alkyl group; a substituted or unsubstituted C3 to C60 cycloalkyl group; a substituted or unsubstituted C2 to C60 heterocycloalkyl group; a substituted or unsubstituted C6 to C60 aryl group; or a substituted or unsubstituted C2 to C60 heteroaryl group.

In one embodiment of the present specification, R1 is a C6 to C60 substituted or unsubstituted aryl group; or a C2 to C60 substituted or unsubstituted heteroaryl group.

In one embodiment of the present specification, R1 is a C6 to C30 substituted or unsubstituted aryl group; or a C2 to C30 substituted or unsubstituted heteroaryl group.

In one embodiment of the present specification, R1 is a C6 to C30 substituted or unsubstituted aryl group.

In one embodiment of the present specification, R1 is a substituted or unsubstituted phenyl group; a substituted or unsubstituted naphthyl group; a substituted or unsubstituted anthracenyl group; a substituted or unsubstituted phenanthrenyl group; a substituted or unsubstituted pyrenyl group; or a substituted or unsubstituted perylene group.

In one embodiment of the present specification, R1 is a phenyl group unsubstituted or substituted with a naphthyl group; a naphthyl group; an anthracenyl group; a phenanthrenyl group; a pyrenyl group; or a perylene group.

In one embodiment of the present specification, R2 to R5 are each independently hydrogen; deuterium; a halogen group; a cyano group; a substituted or unsubstituted C1 to C60 alkyl group; a substituted or unsubstituted C3 to C60 cycloalkyl group; a substituted or unsubstituted C6 to C60 aryl group; or a substituted or unsubstituted C2 to C60 heteroaryl group.

In one embodiment of the present specification, R2 to R5 are each independently hydrogen; deuterium; a substituted or unsubstituted C1 to C60 alkyl group; a substituted or unsubstituted C6 to C60 aryl group; or a substituted or unsubstituted C2 to C60 heteroaryl group.

In one embodiment of the present specification, R2 to R5 are each independently hydrogen; or deuterium.

In one embodiment of the present specification, R2 to R5 are hydrogen.

In one embodiment of the present specification, m may be 1 or 2.

In one embodiment of the present specification, n may be an integer of 1 to 3.

In the heterocyclic compound provided in one embodiment of the present specification, Chemical Formula 1 is represented by the following Chemical Formula 2 or 3.

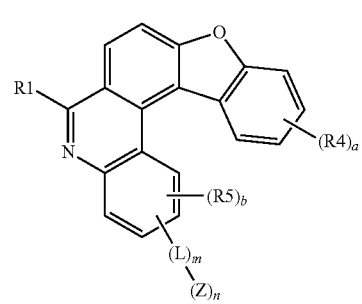

[Chemical Formula 2]

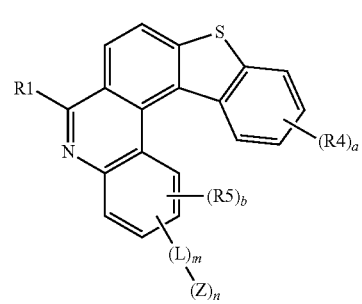

[Chemical Formula 3]

In Chemical Formulae 2 and 3,

L, Z, R1, R4, R5, a, b, m and n have the same definitions as in Chemical Formula 1.

In the heterocyclic compound provided in one embodiment of the present specification, Chemical Formula 1 is represented by any one of the following Chemical Formulae 4 to 6.

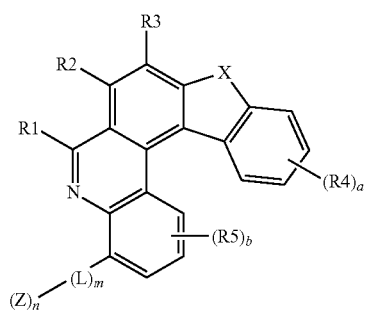

[Chemical Formula 4]

[Chemical Formula 5]
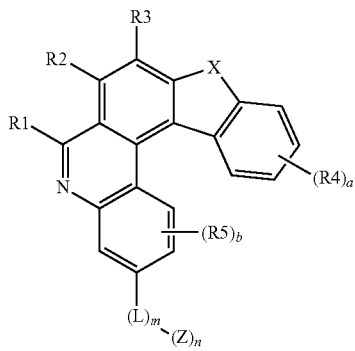
[Chemical Formula 6]
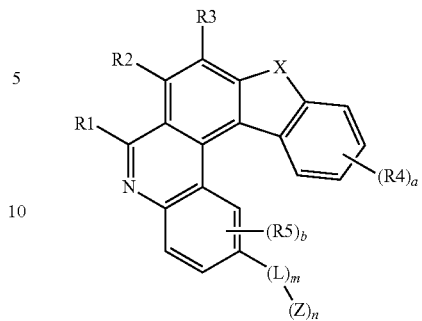
In Chemical Formulae 4 to 6,
X, L, Z, R1 to R5, a, b, m and n have the same definitions as in Chemical Formula 1.
In one embodiment of the present specification, Chemical Formula 1 may be represented by any one of the following compounds, but is not limited thereto.
1
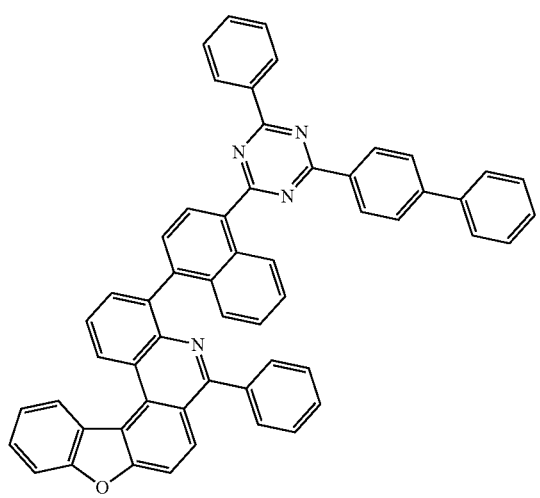
2
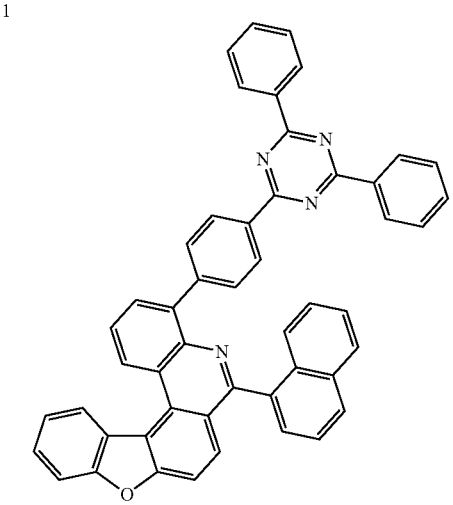
3
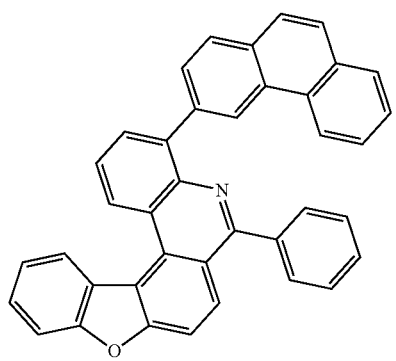
4
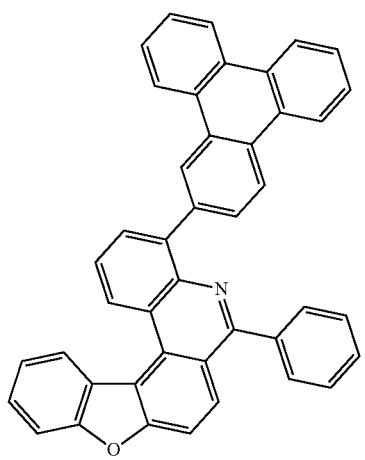 [SMILES: c1ccc(-c2nc3c(-c4ccc5c6ccccc6c6ccccc6c5c4)cccc3c3c2ccc2oc4ccccc4c23)cc1]

-continued
| 5 | 6 |
|---|---|
| 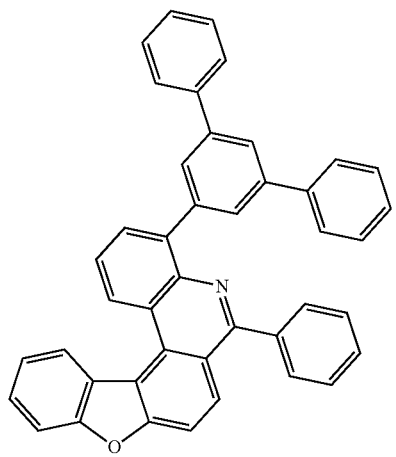 | 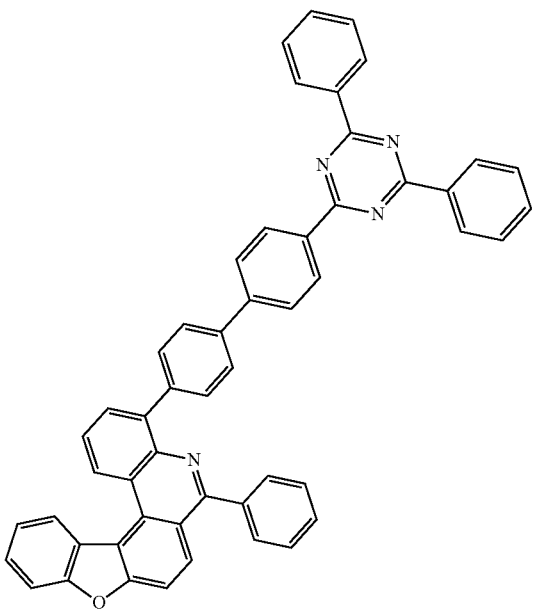 |
| 7 | 8 |
| 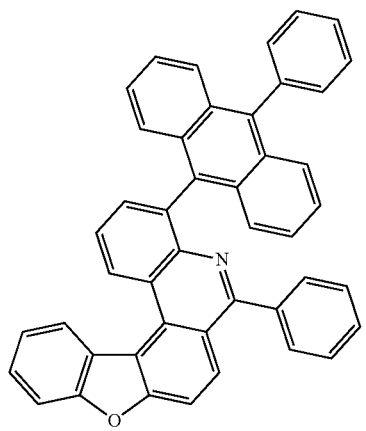 | 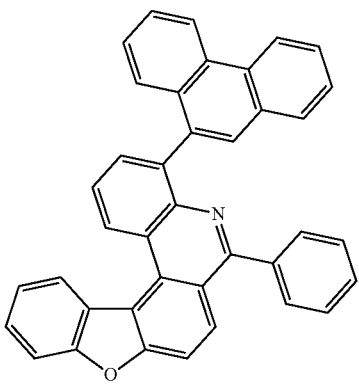 |
| 9 | 10 |
| 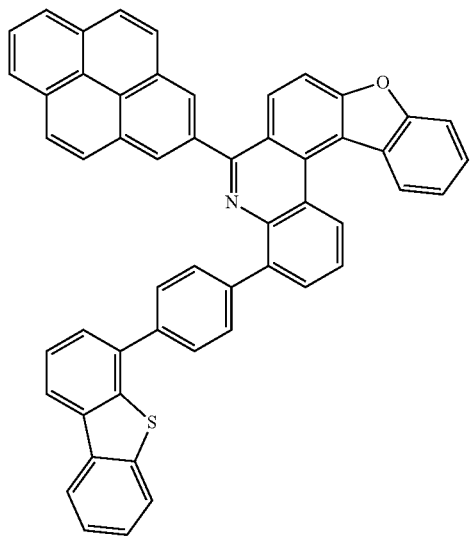 | 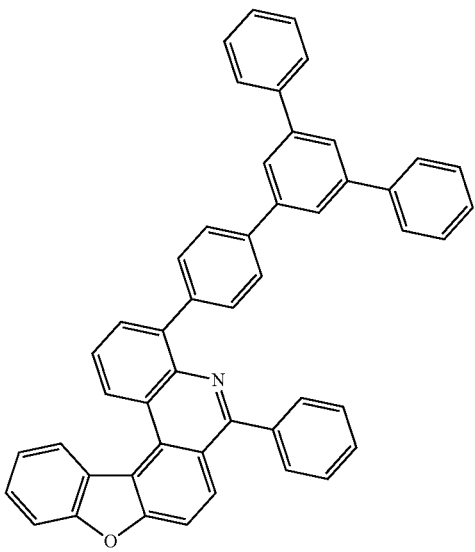 |

-continued
11
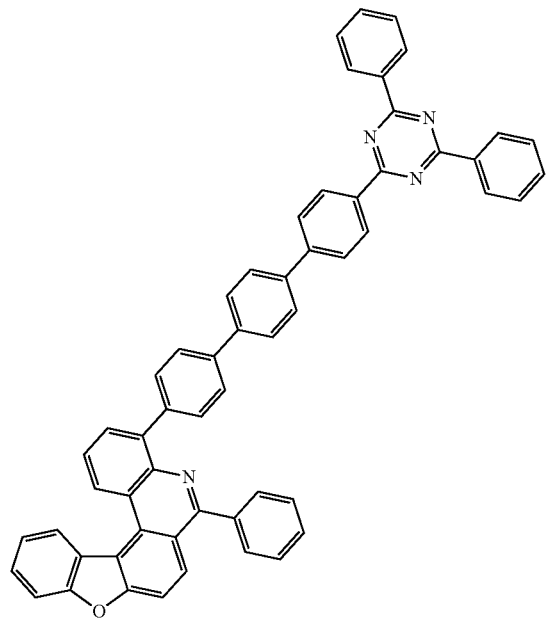
12
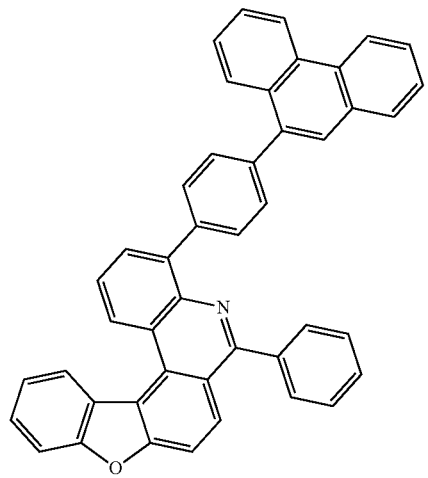
13
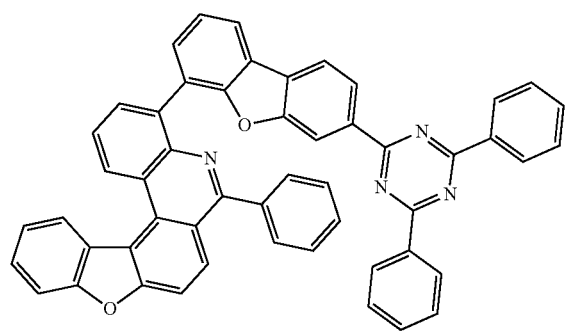
14
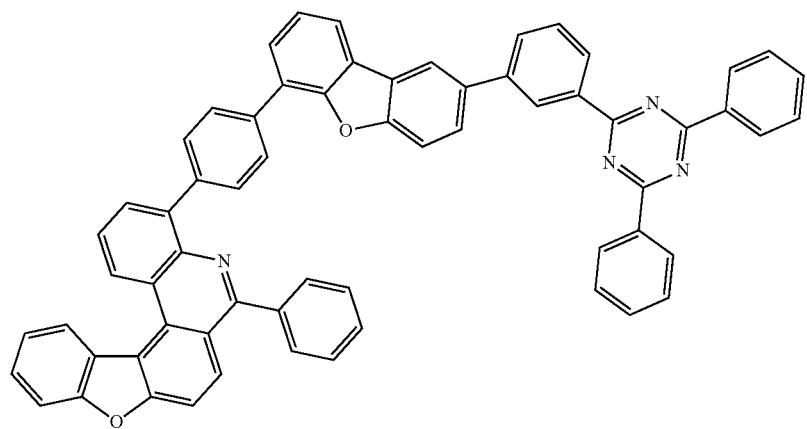

-continued
15
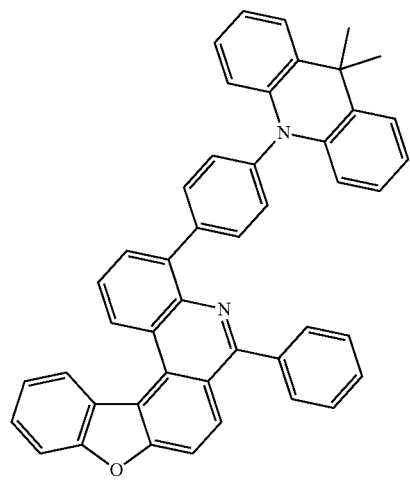
16
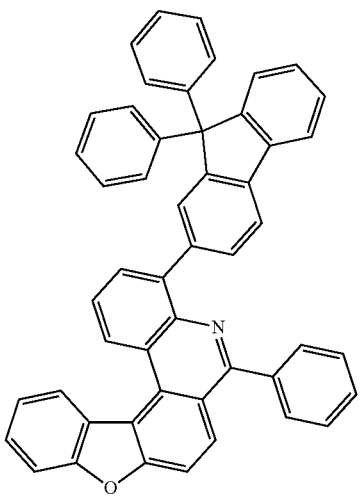
17
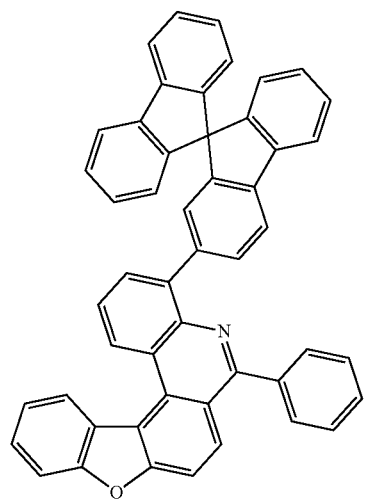
18
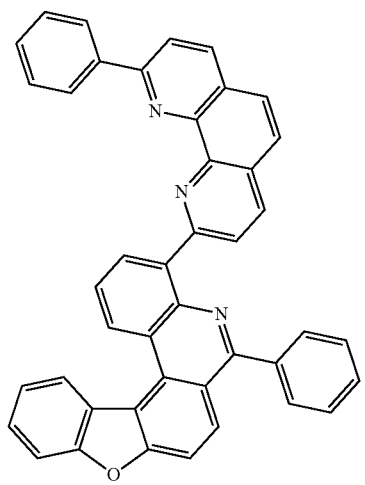
19
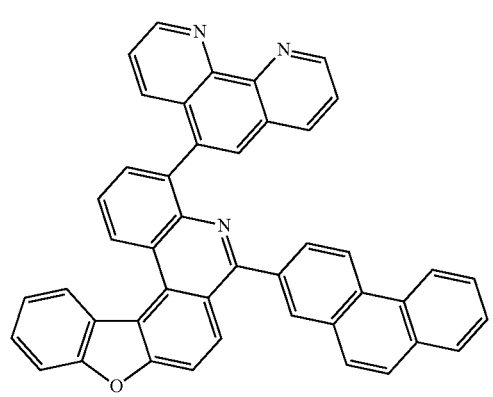
20
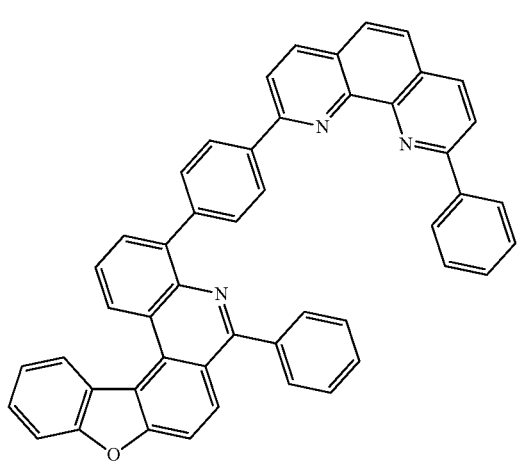

-continued
21
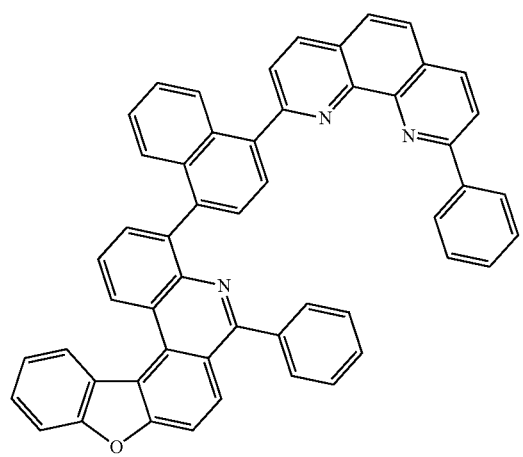
22
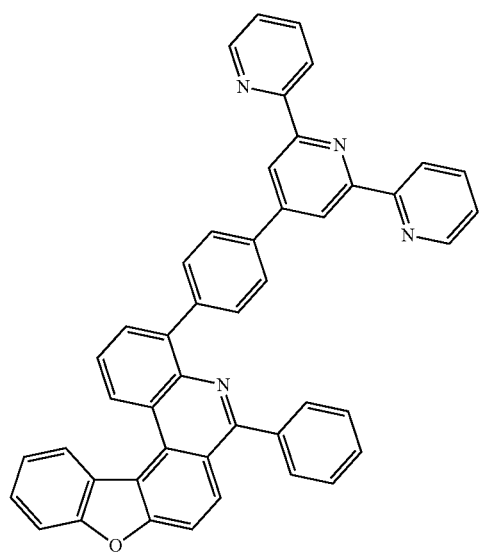
23
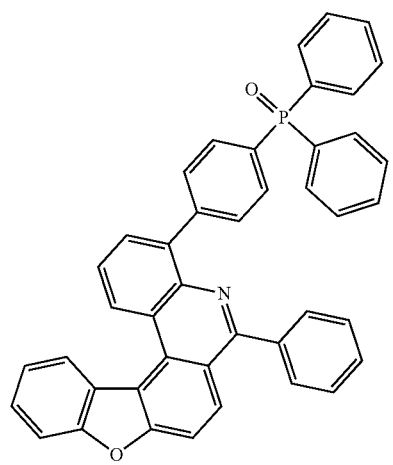
24
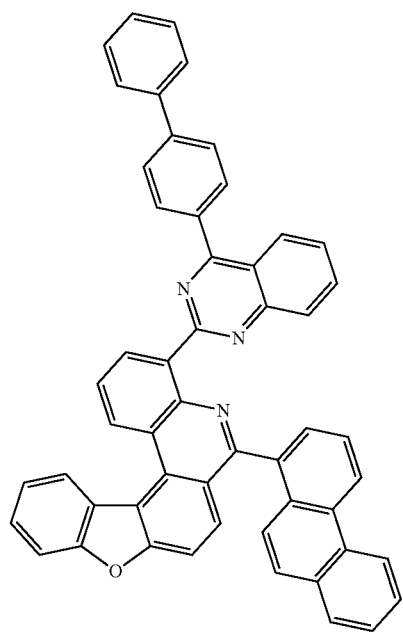

25
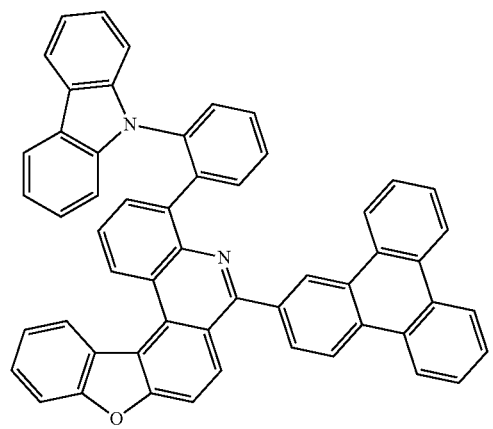
26
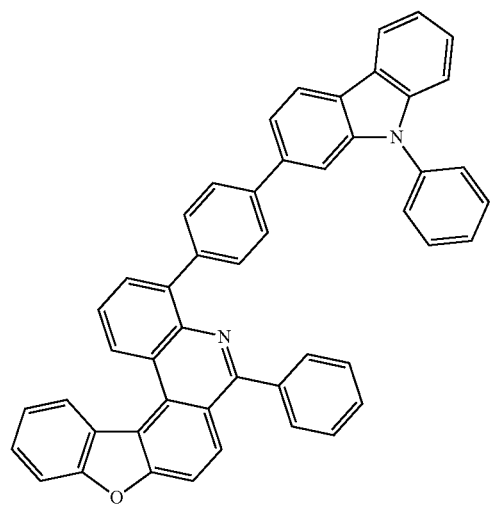
27
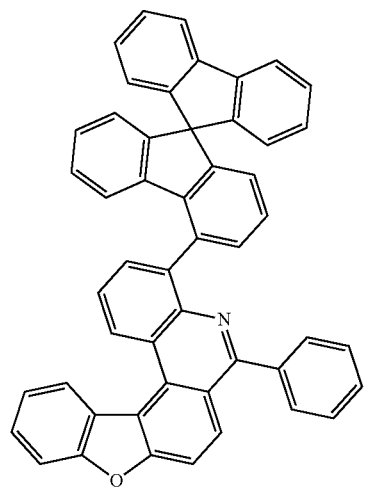
28
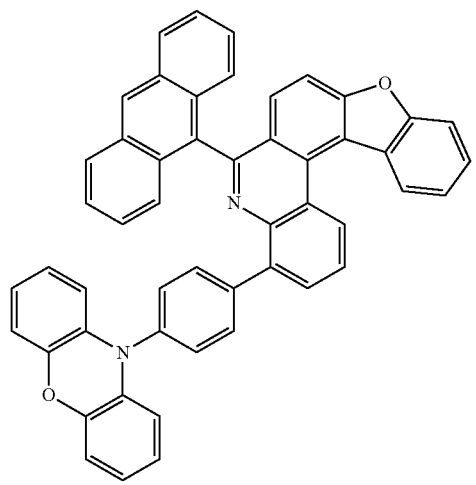
29
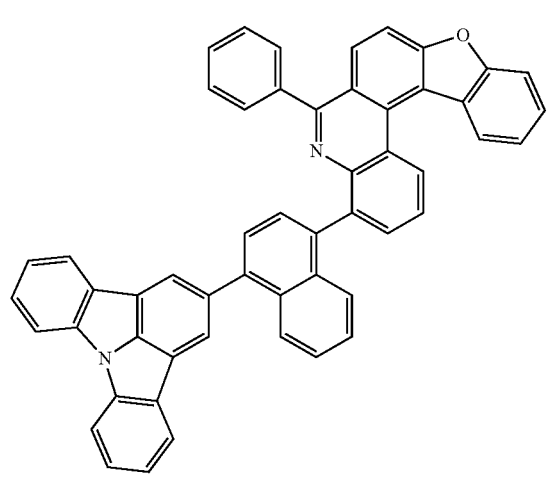
30
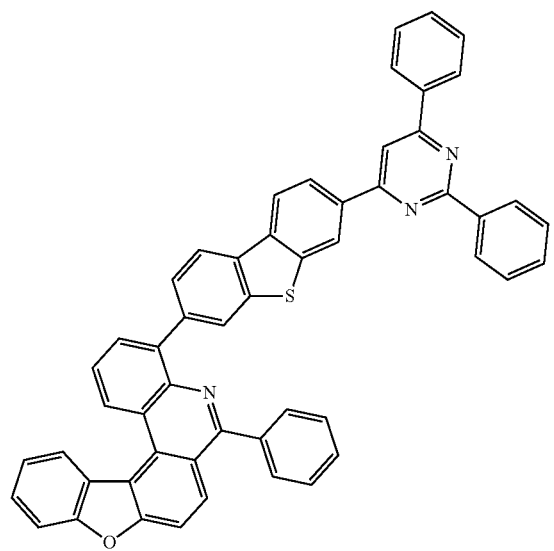

-continued
31 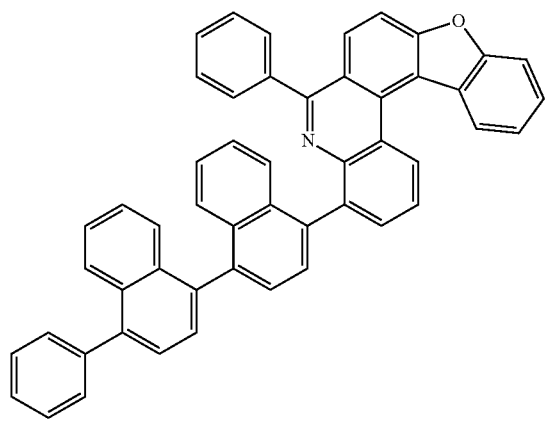
32 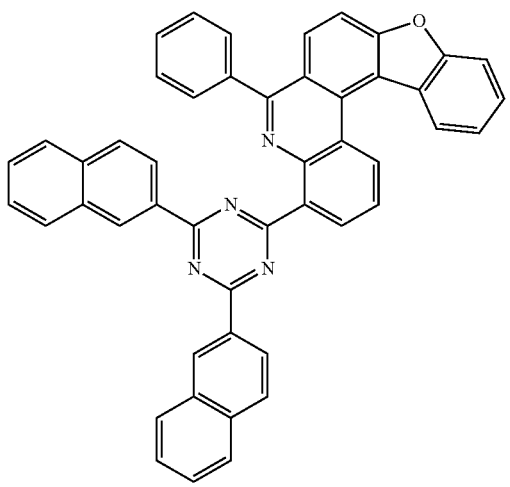
33 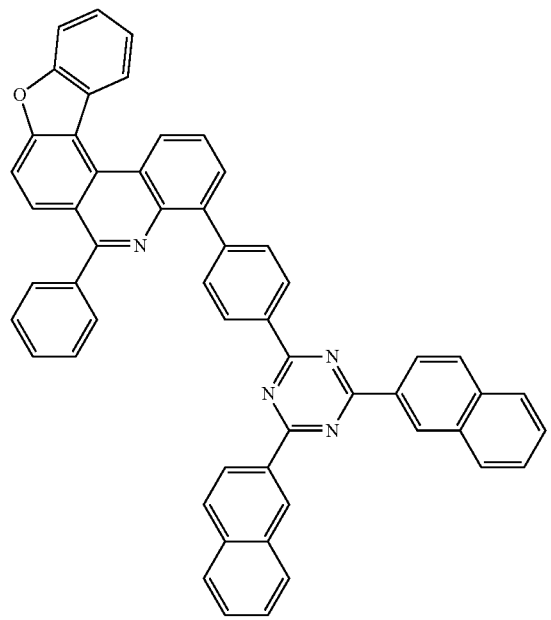
34 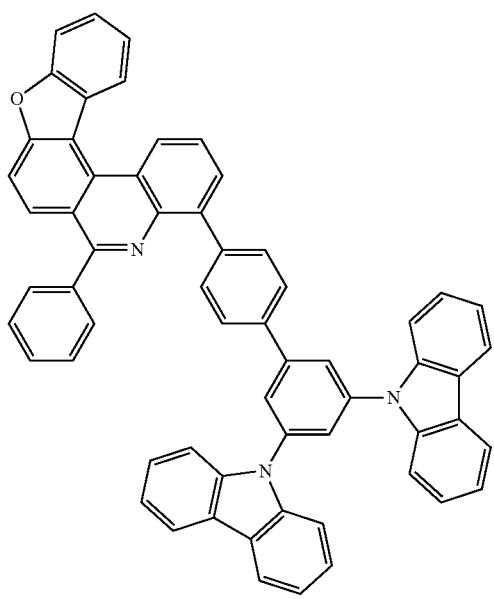
35 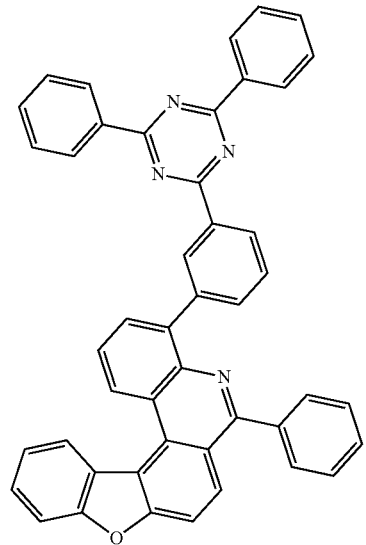
36 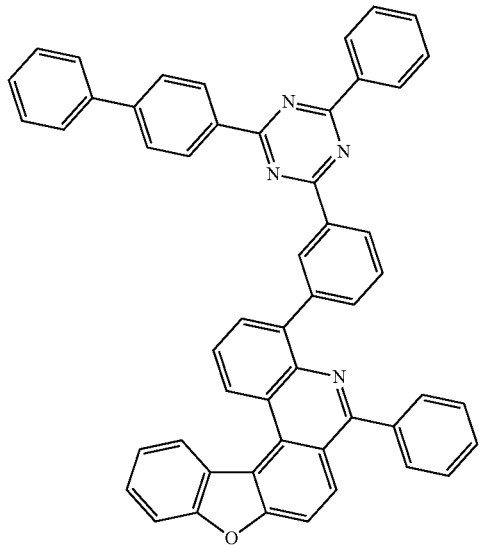

37
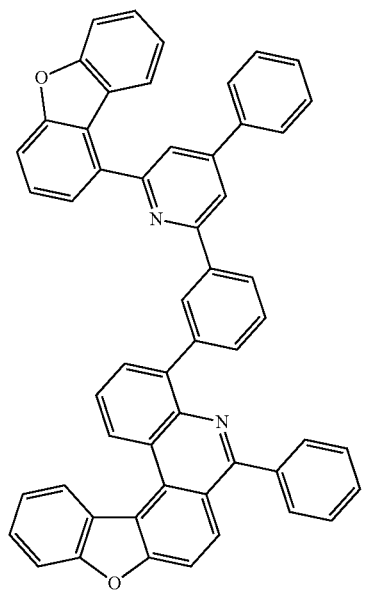
38
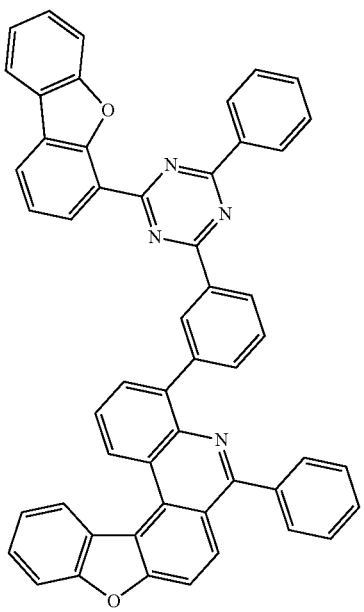
39
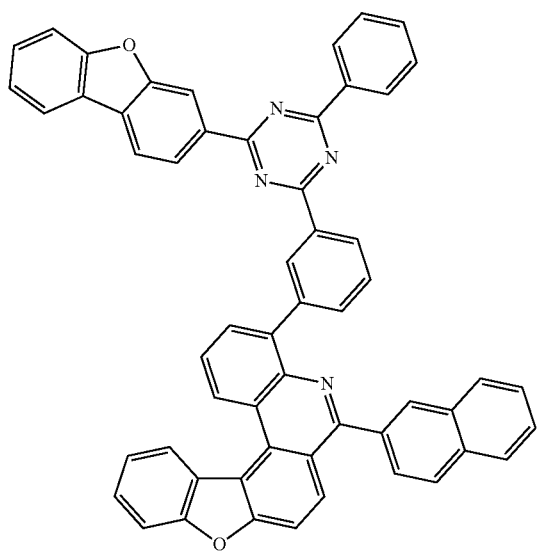
40
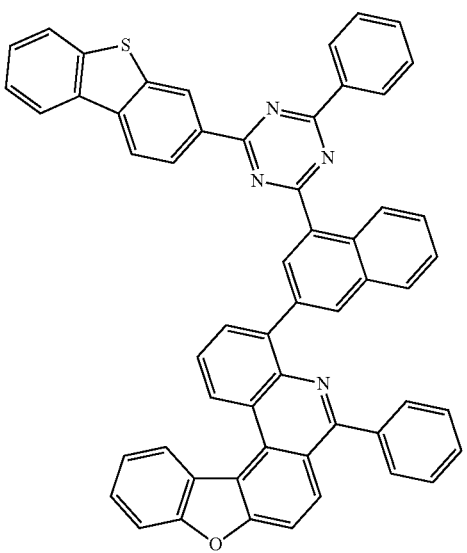

41
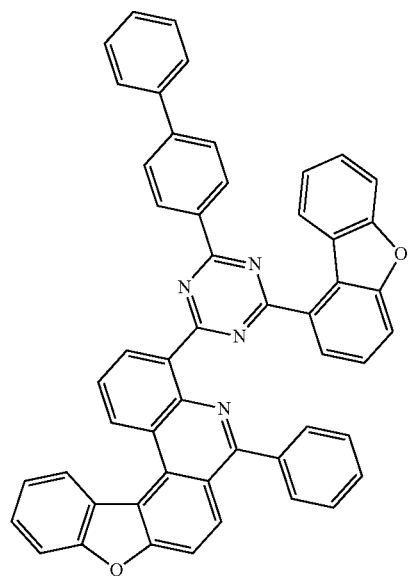
42
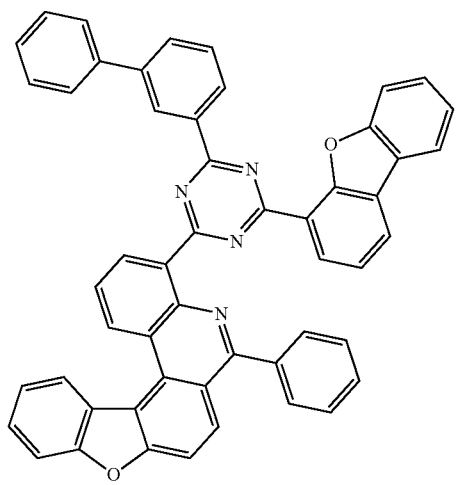
43
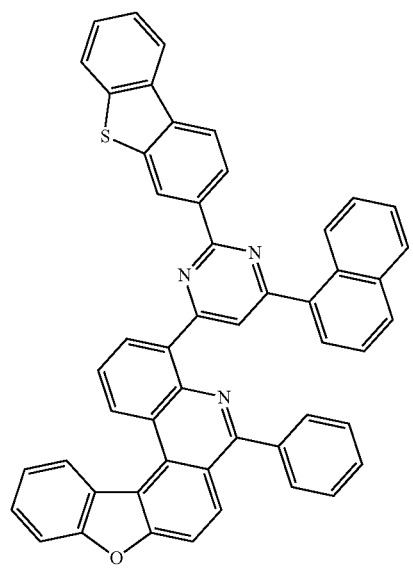
44
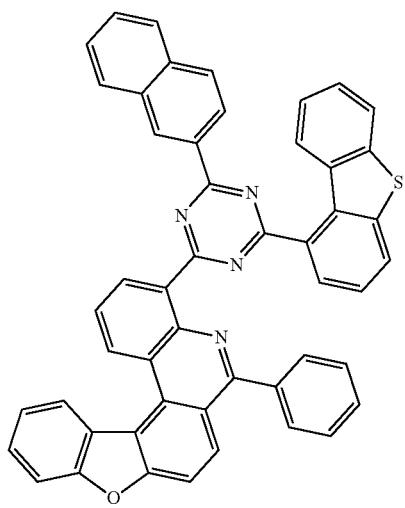

-continued
45
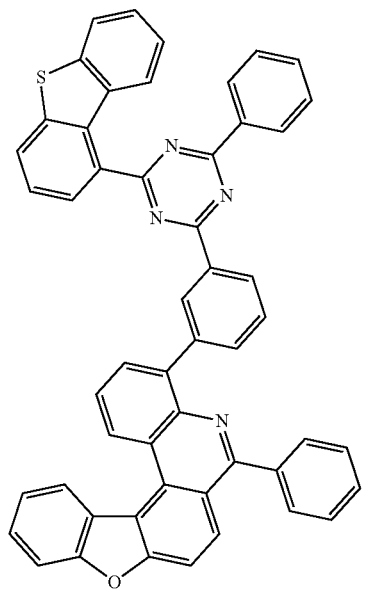
46
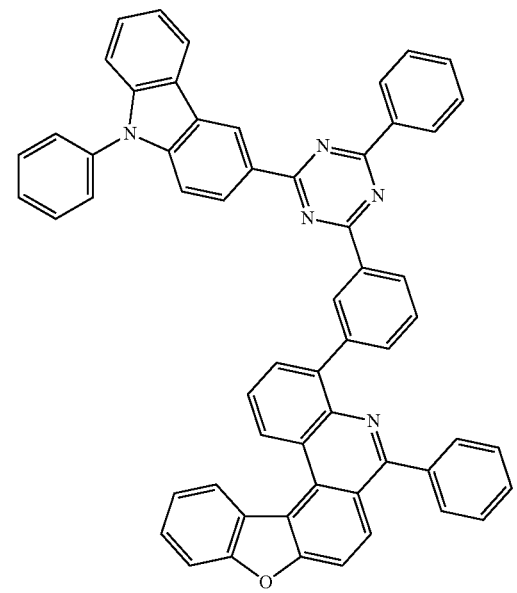
47
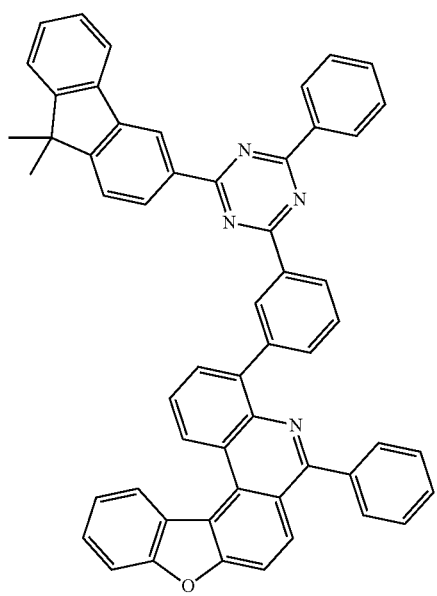
48
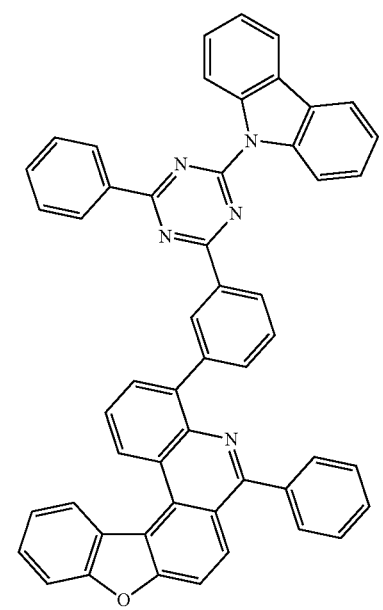
49
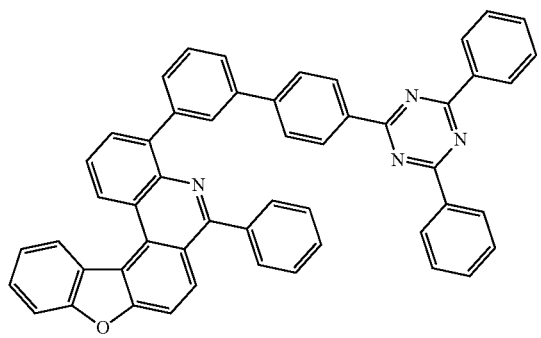
50
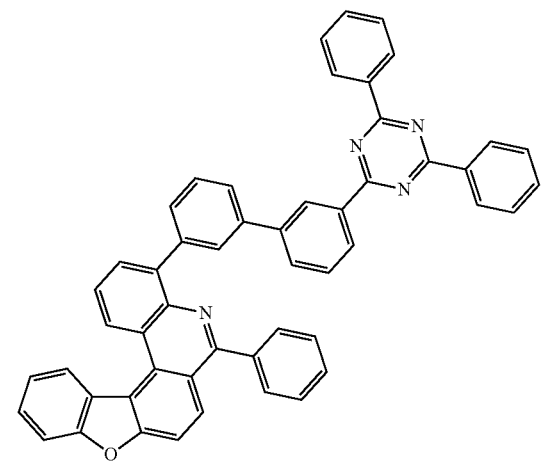

-continued
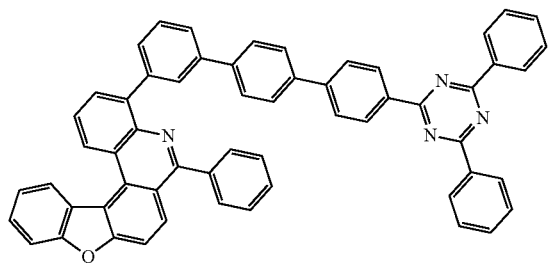
51
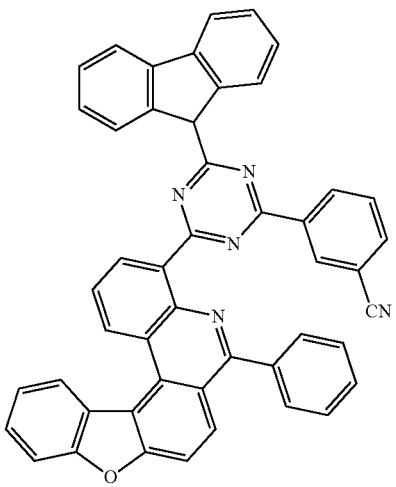
52
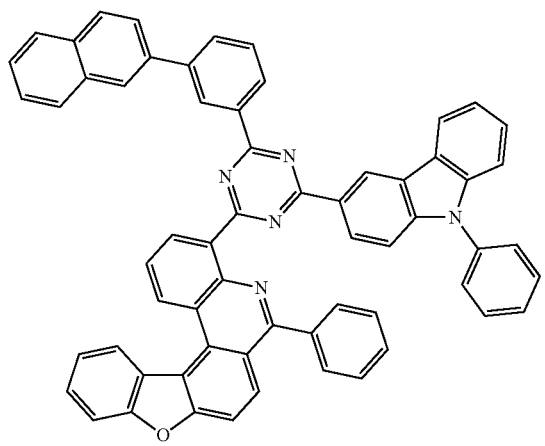
53
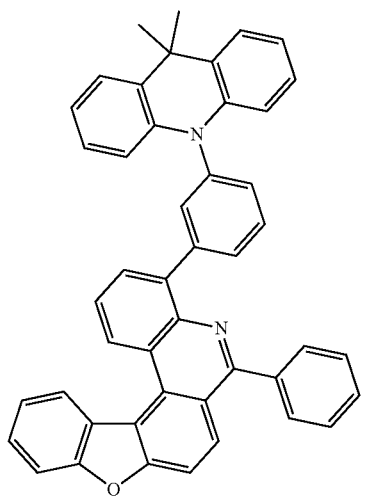
54
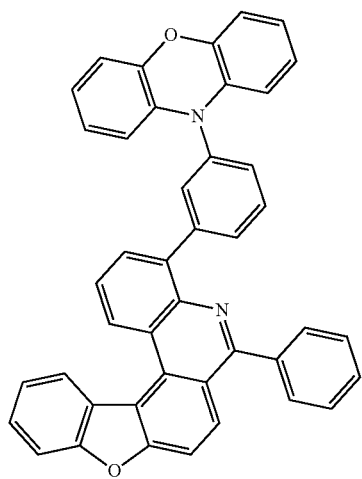
55
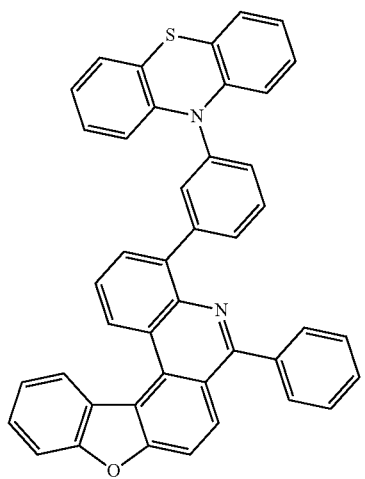
56

-continued
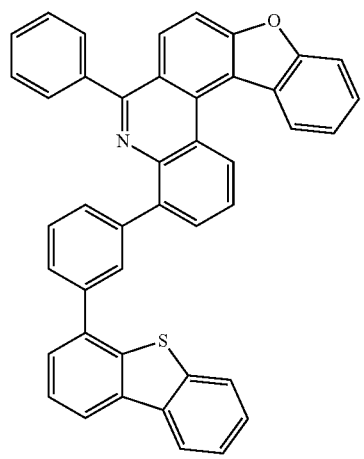
57
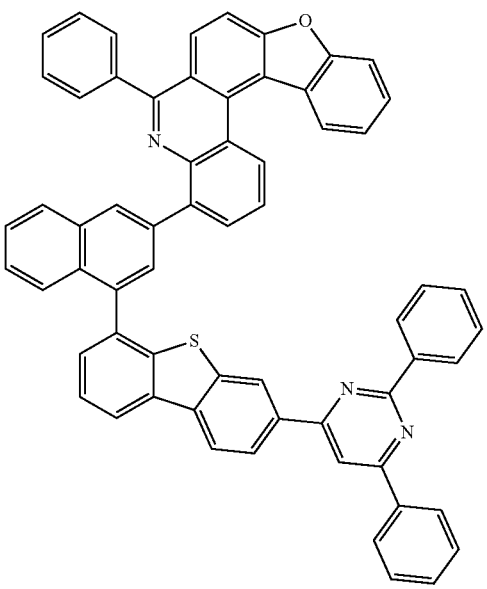
58
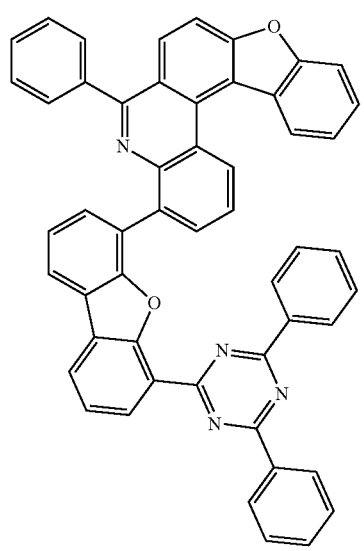
59
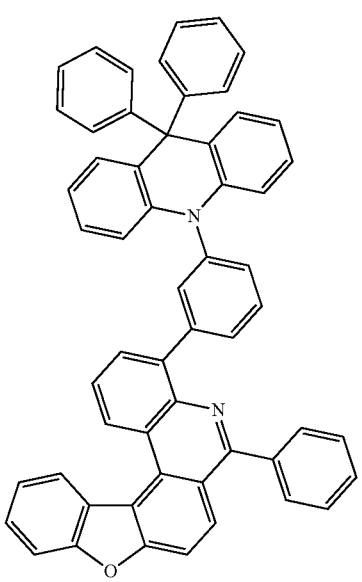
60
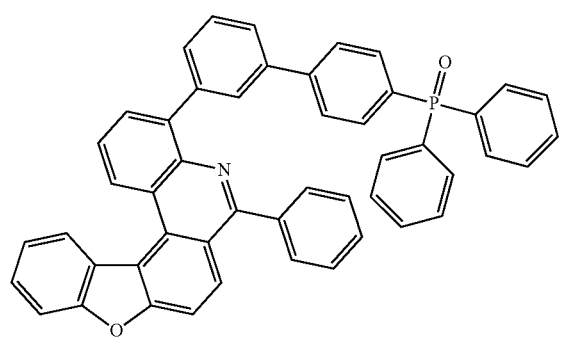
61
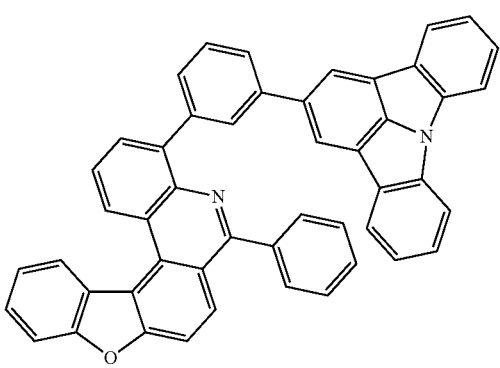
62

-continued
63
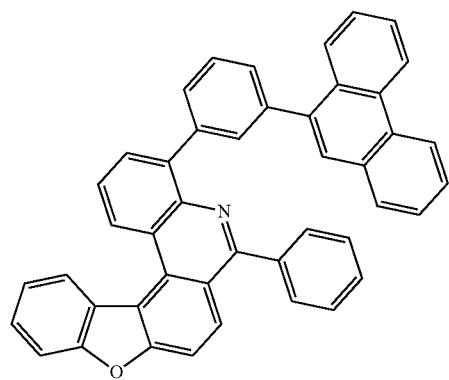
64
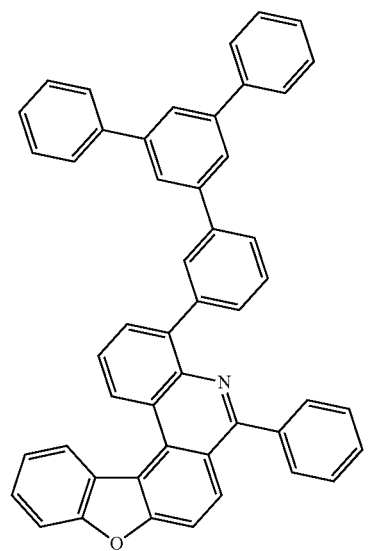
65
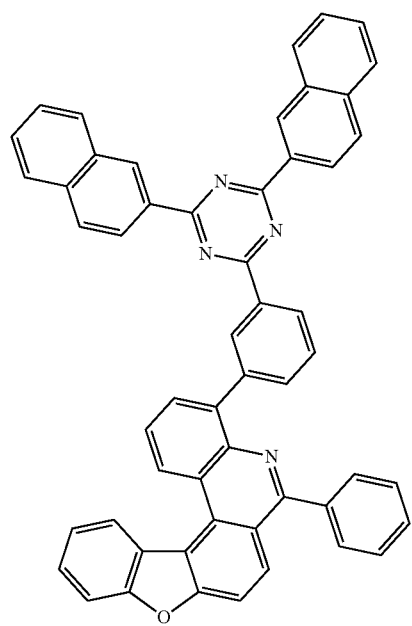
66
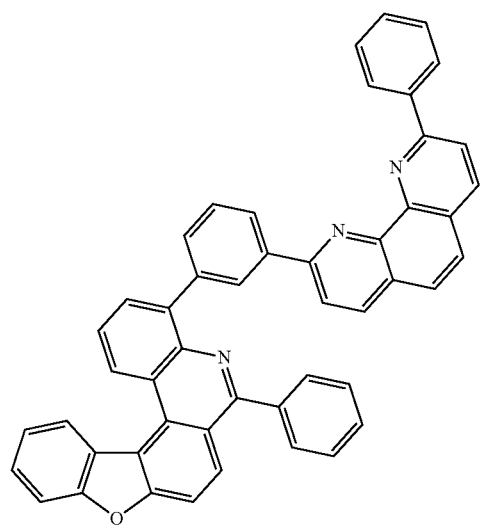

-continued
67
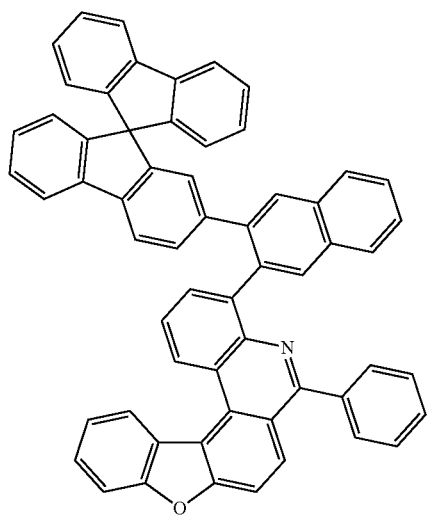
68
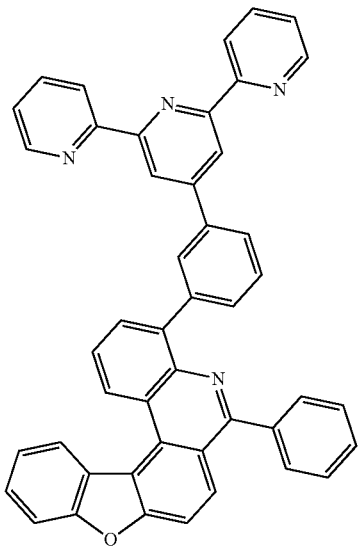
69
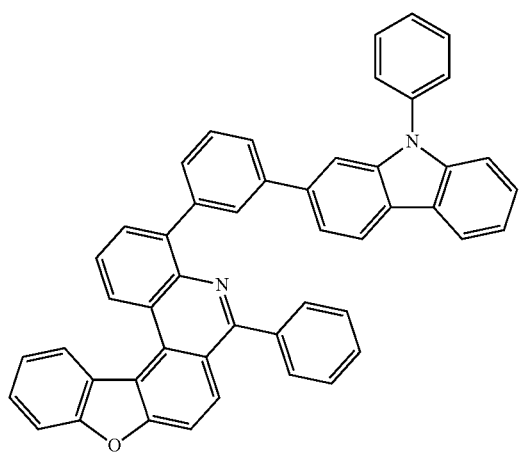
70
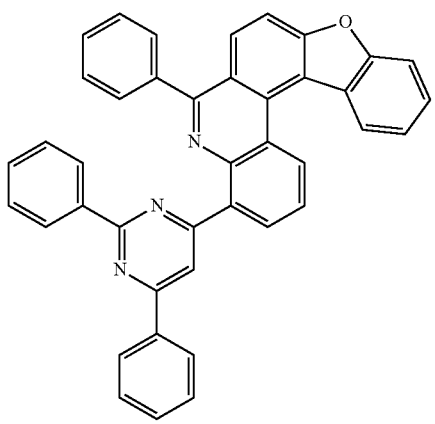
71
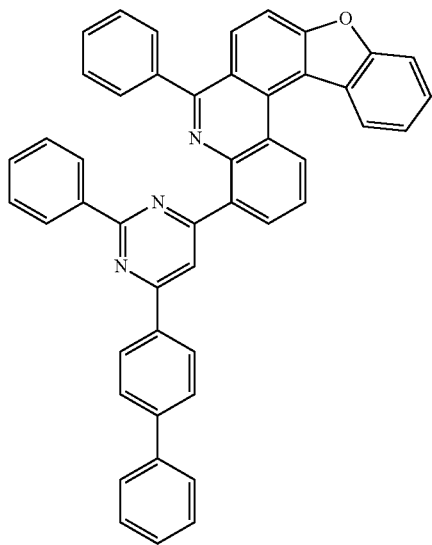
72
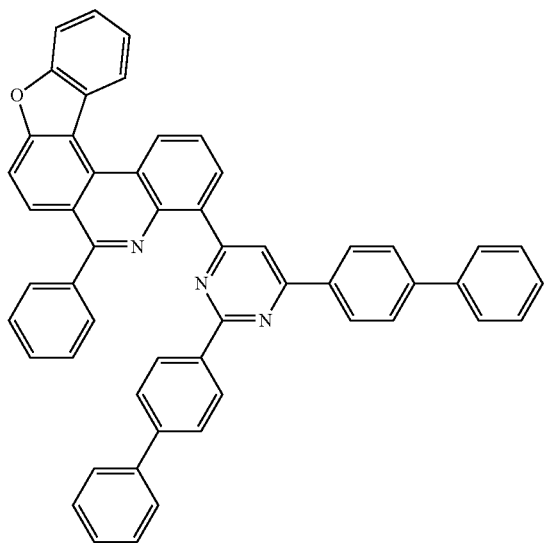

-continued
73
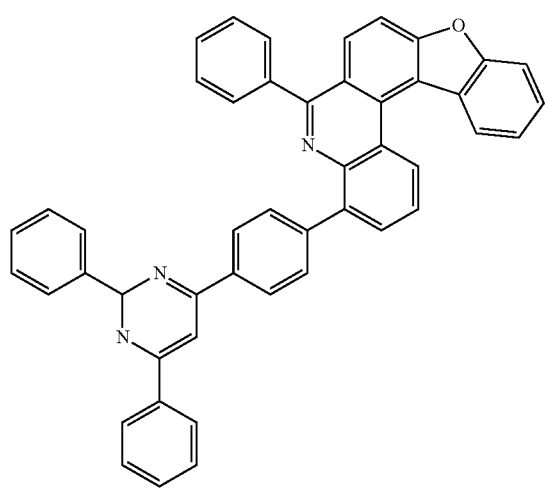
74
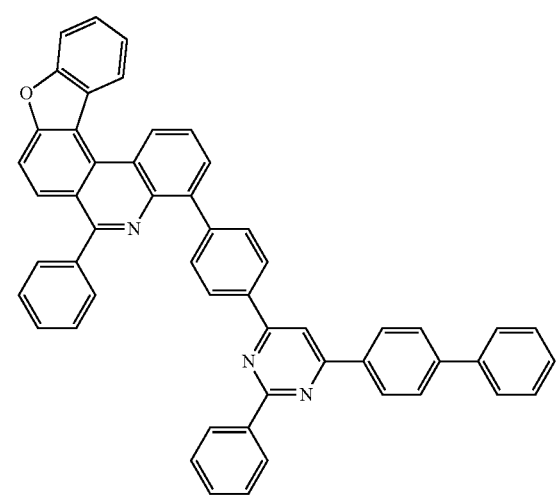
75
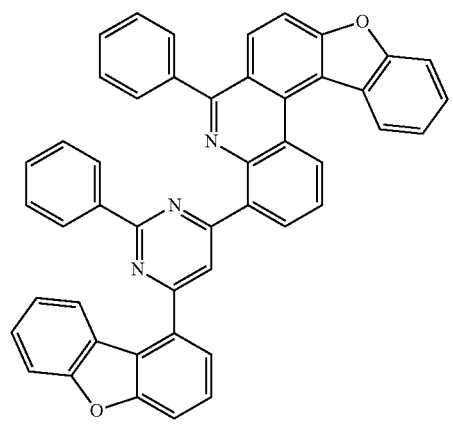
76
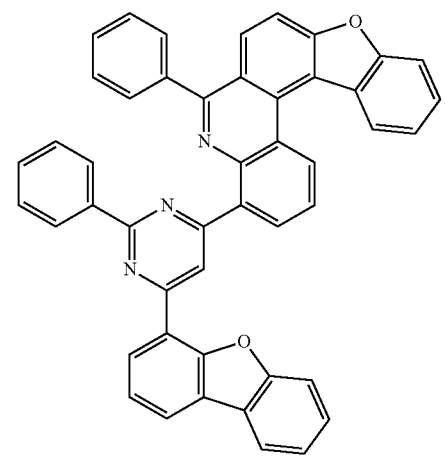
77
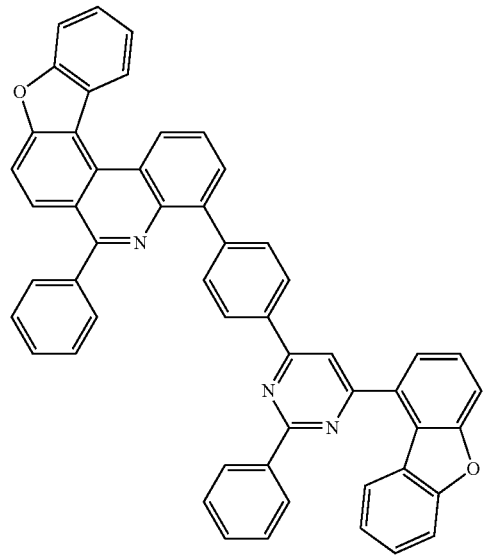
78
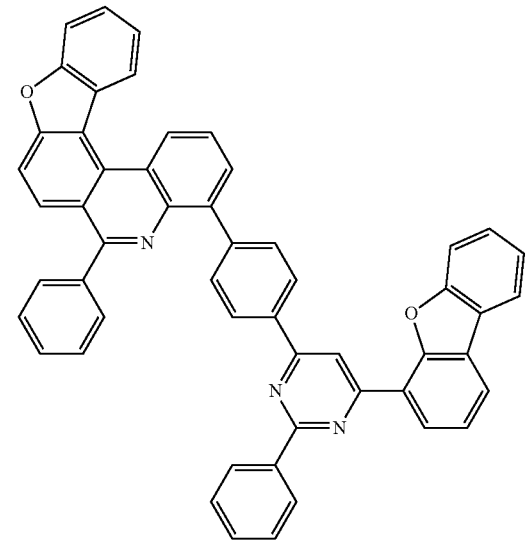

-continued
79
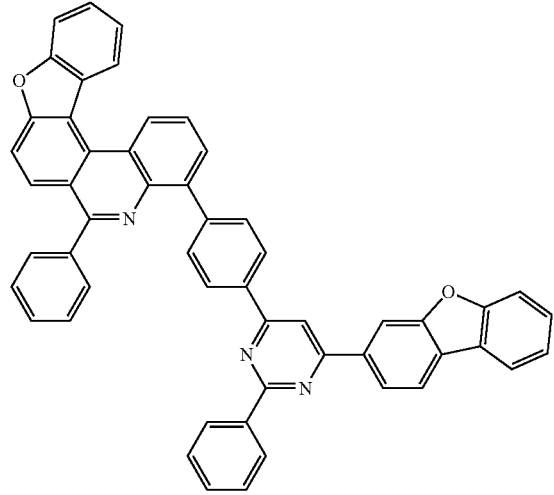
80
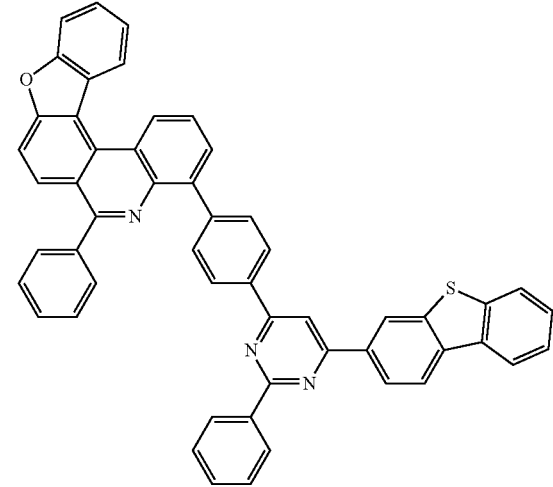
81
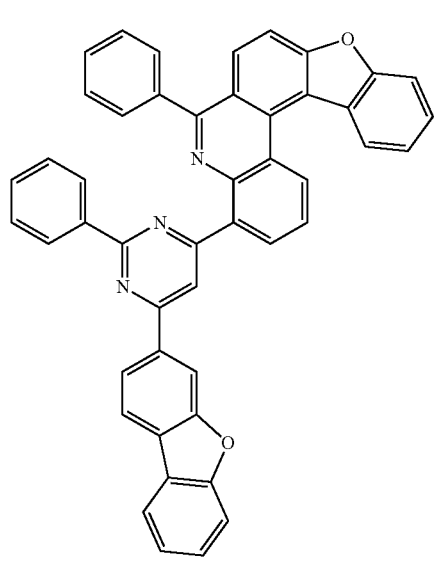
82
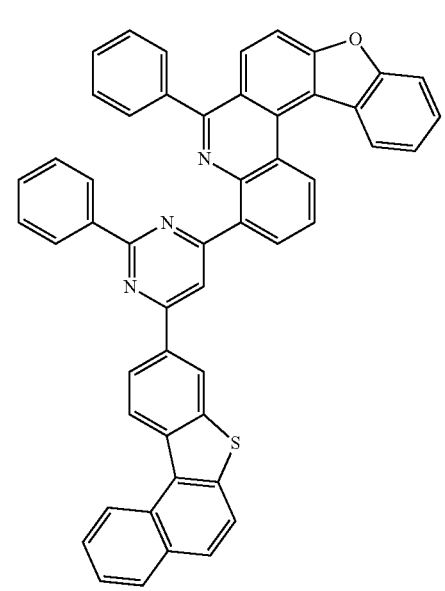
83
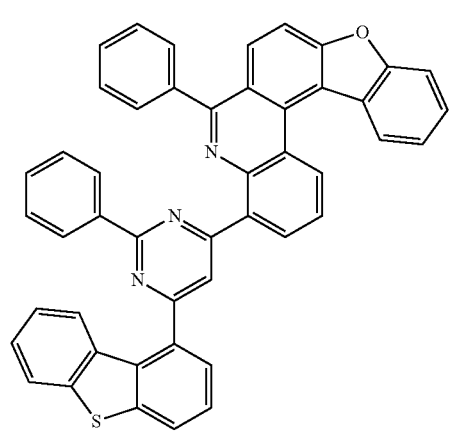
84
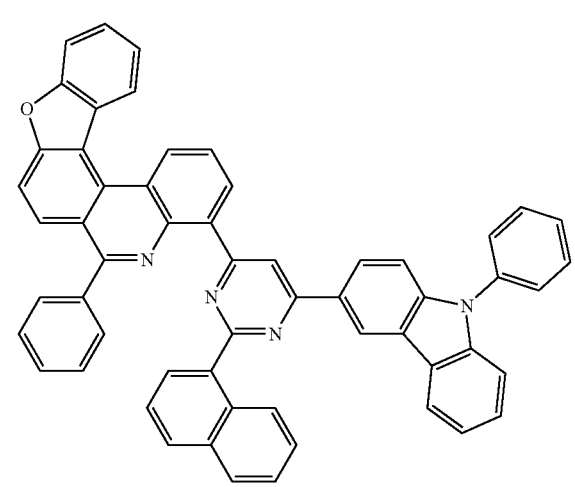

-continued
85
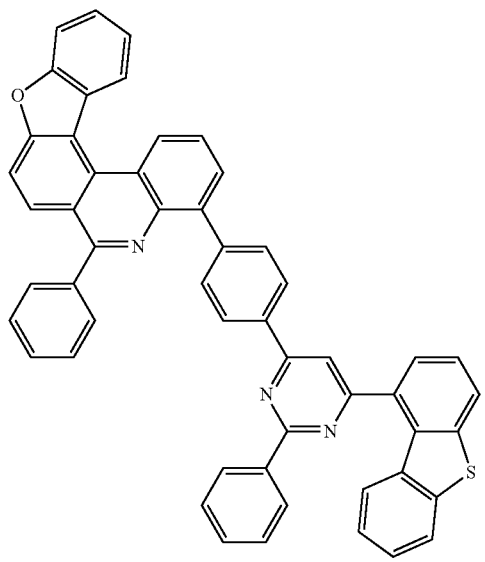
86
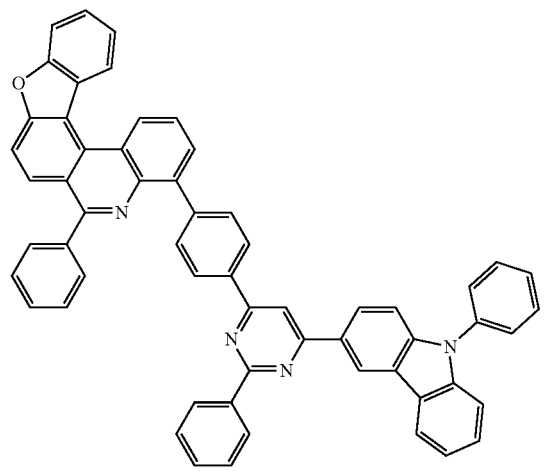
87
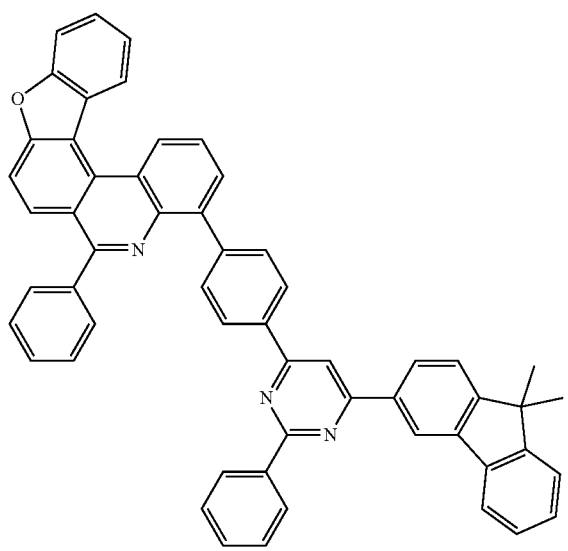
88
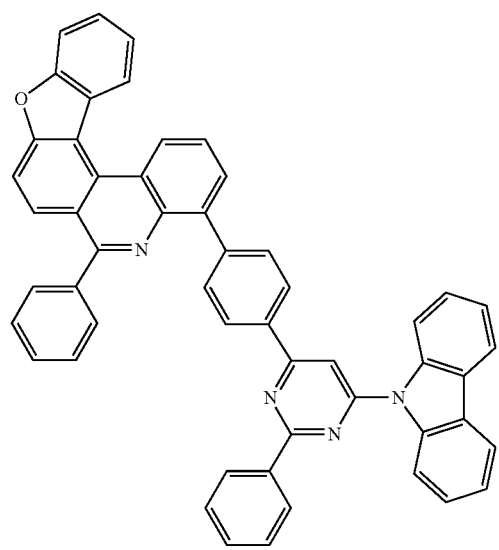
89
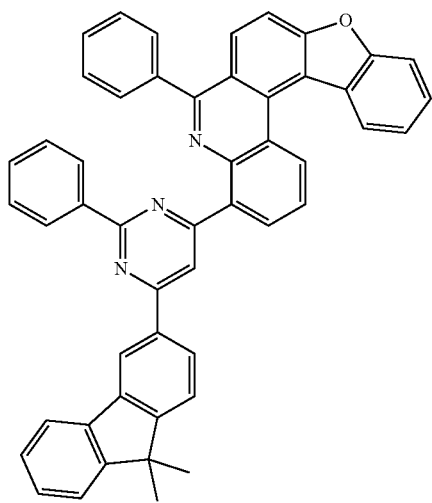
90
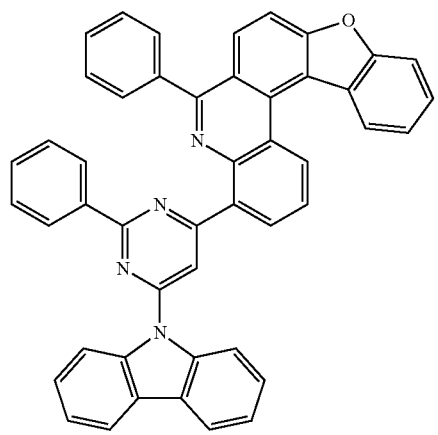

-continued
91
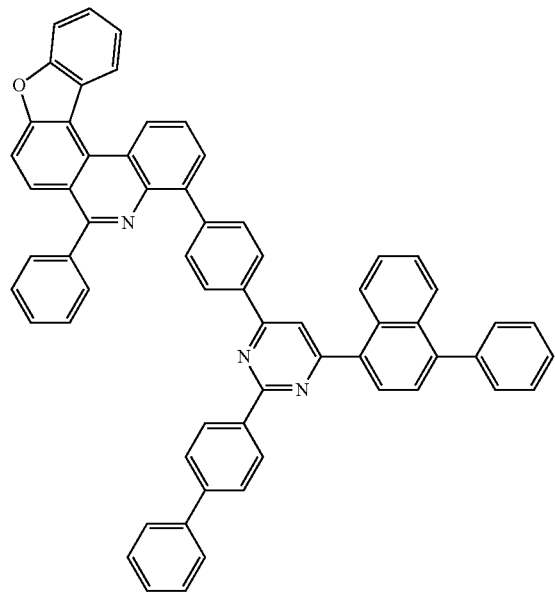
92
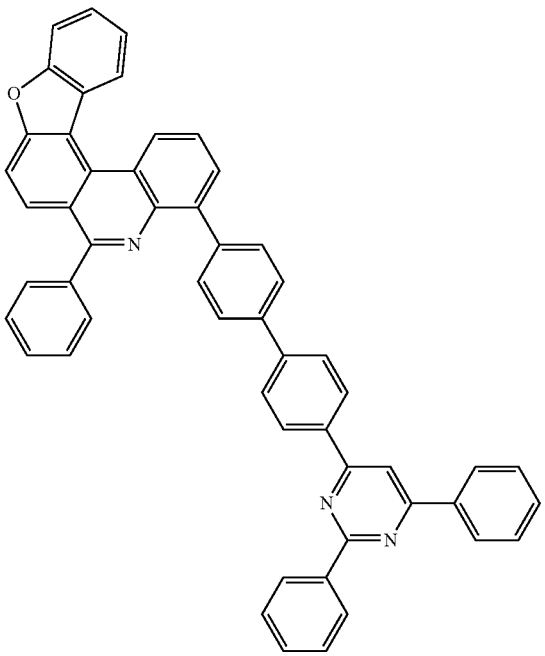
93
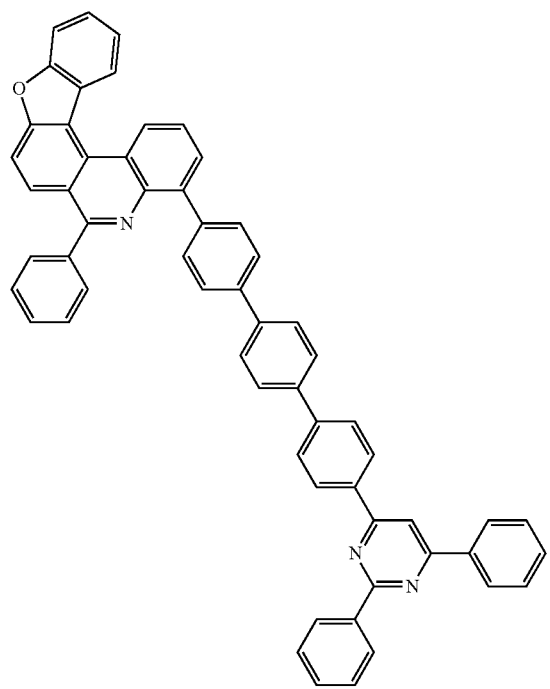
94
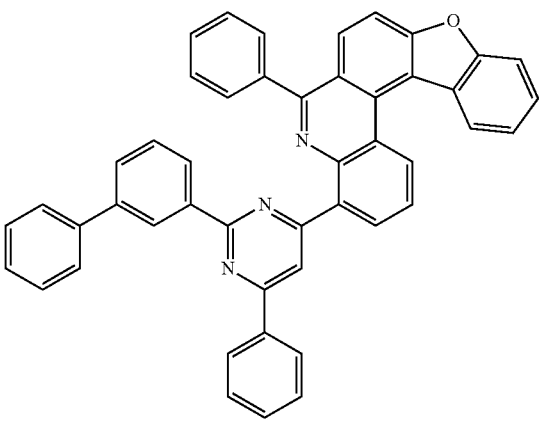

-continued
95
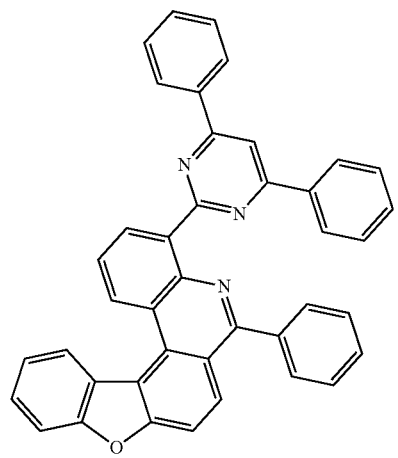
96
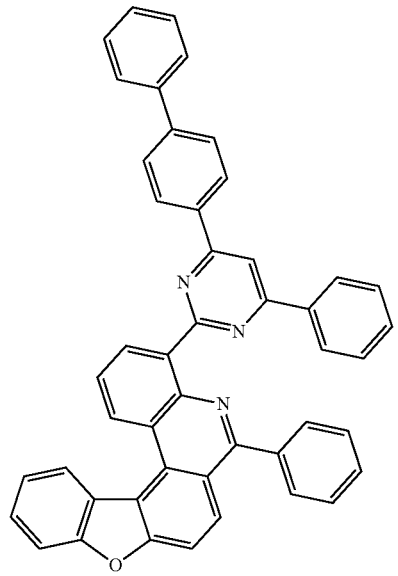
97
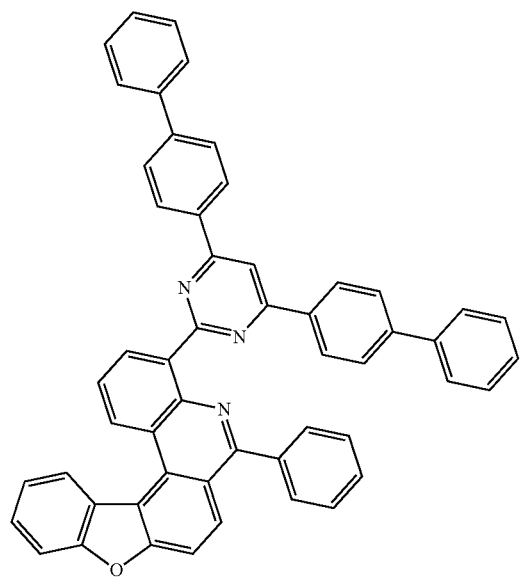
98
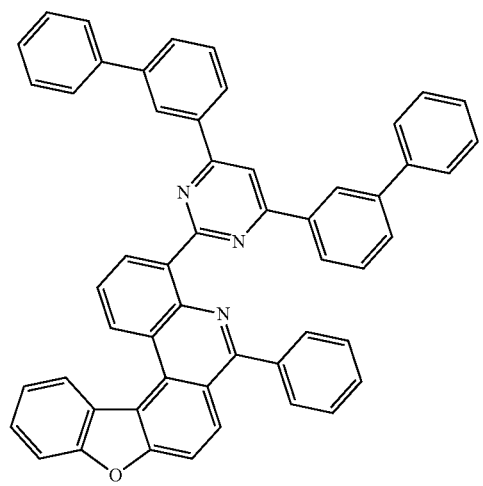

-continued
99
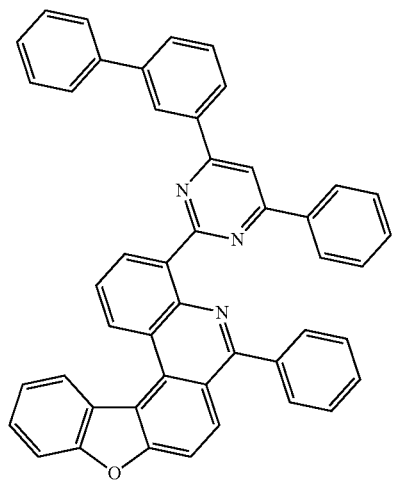
100
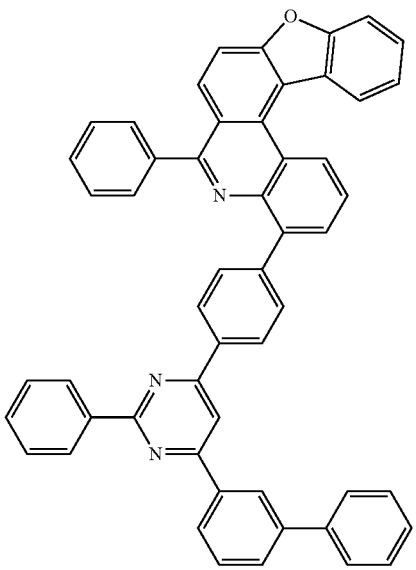
101
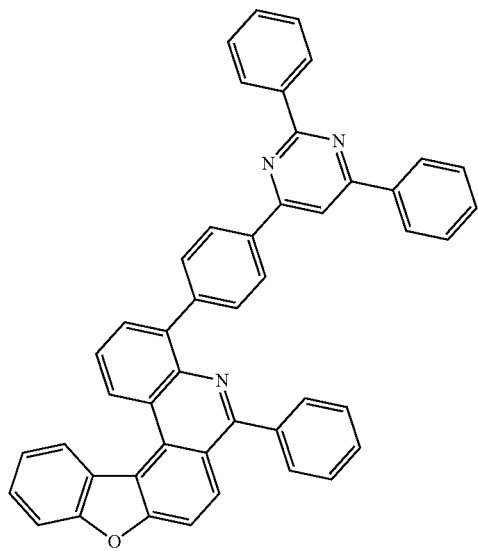
102
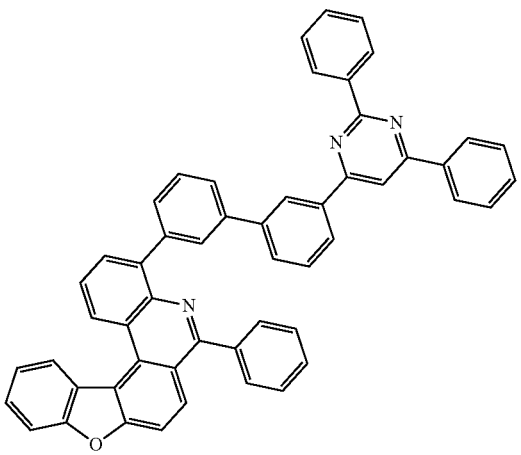

-continued
103
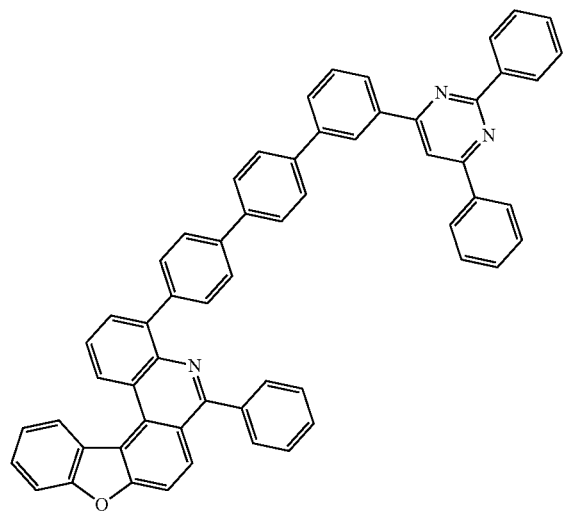
104
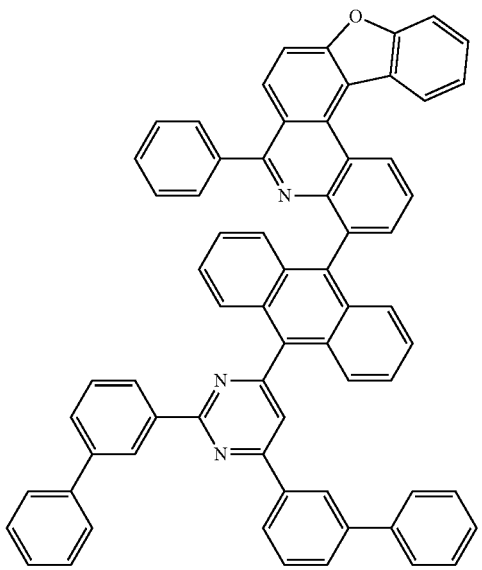
105
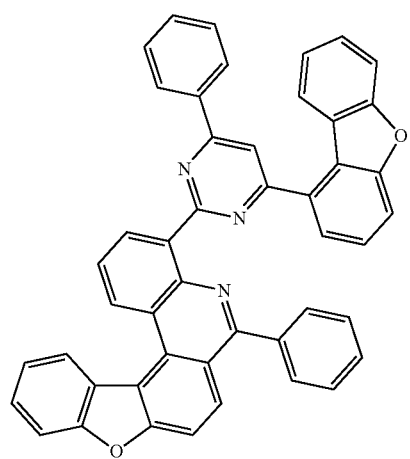
106
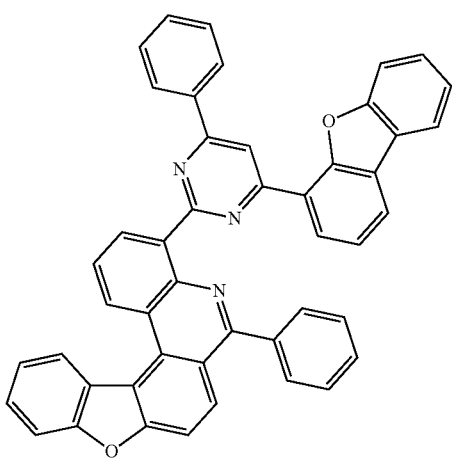

107
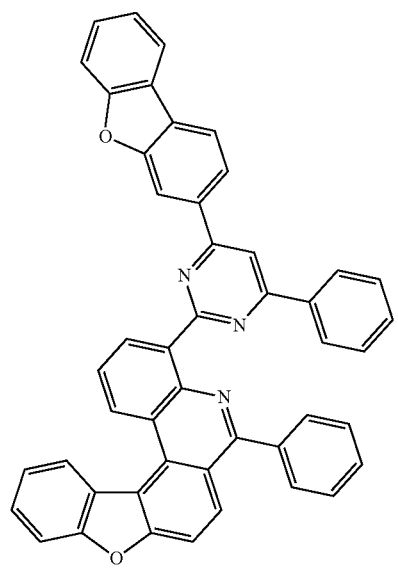
108
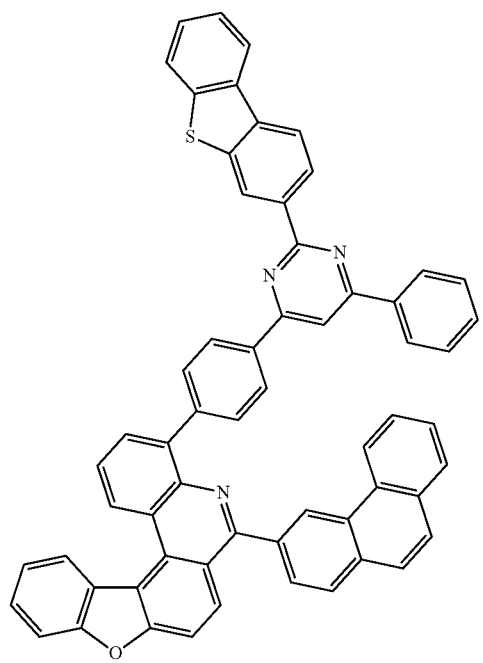
109
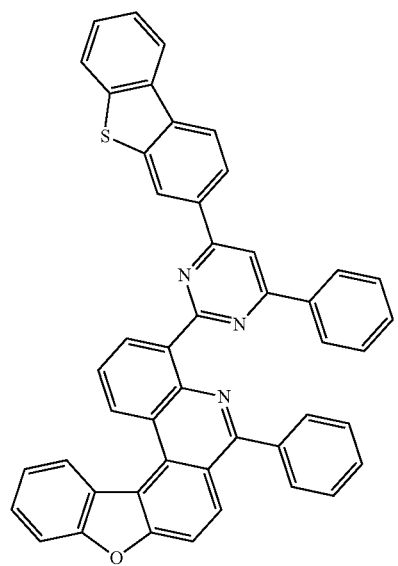
110
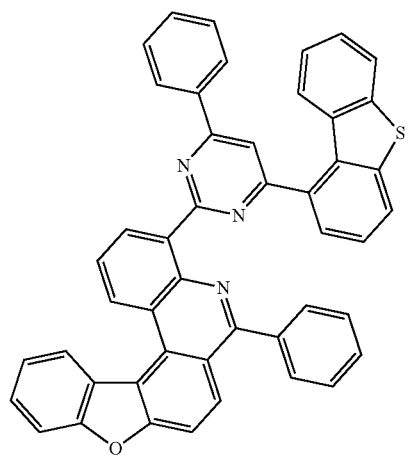

-continued
111
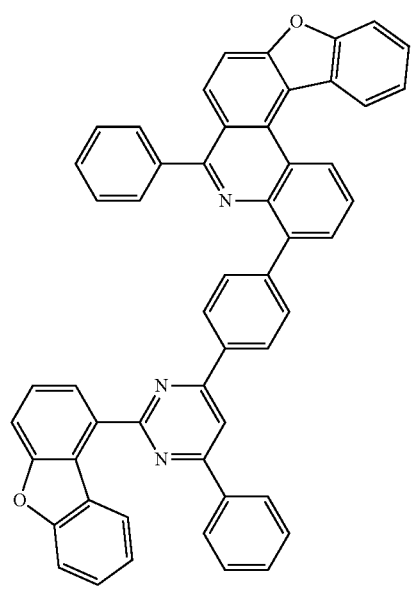
112
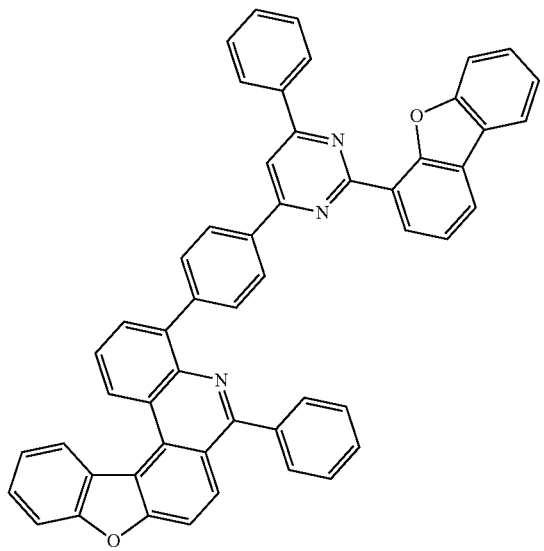
113
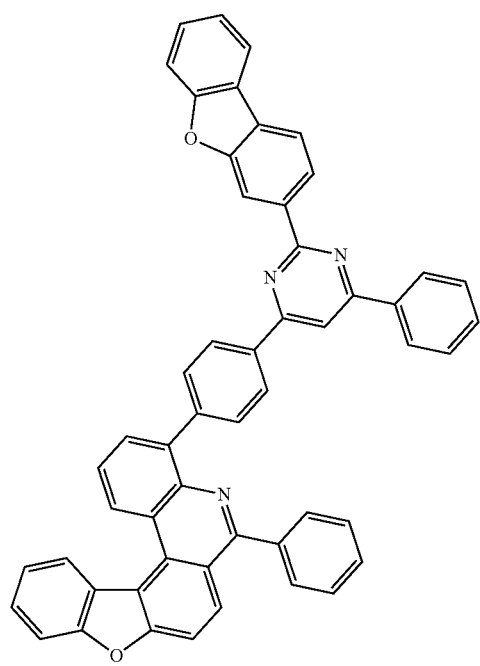
114
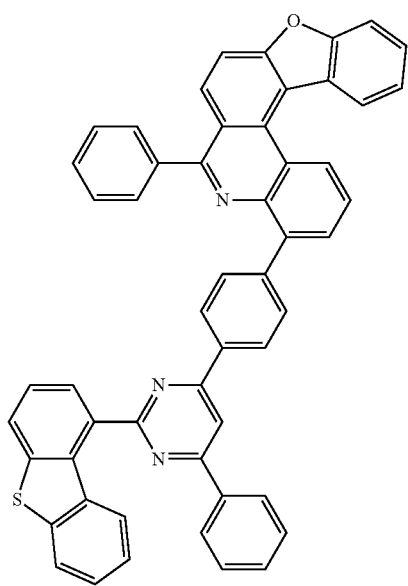

-continued
115 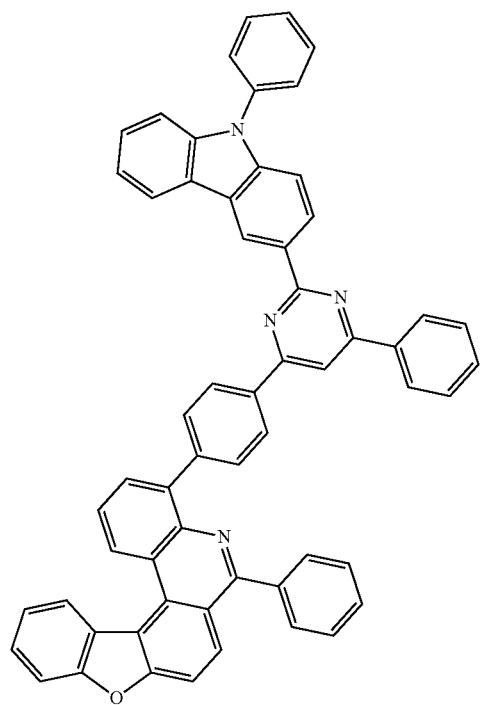
116 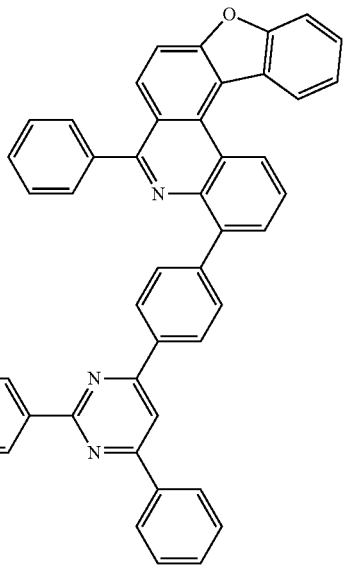
117 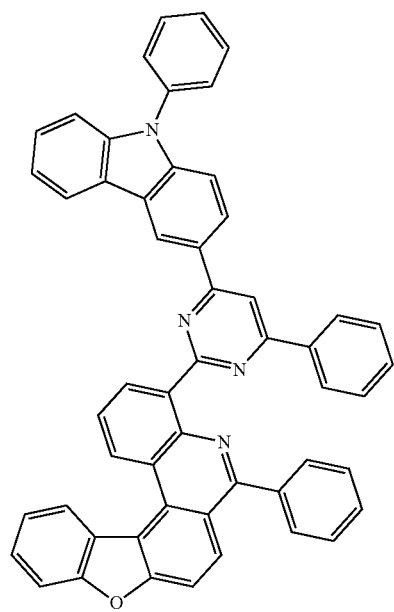
118 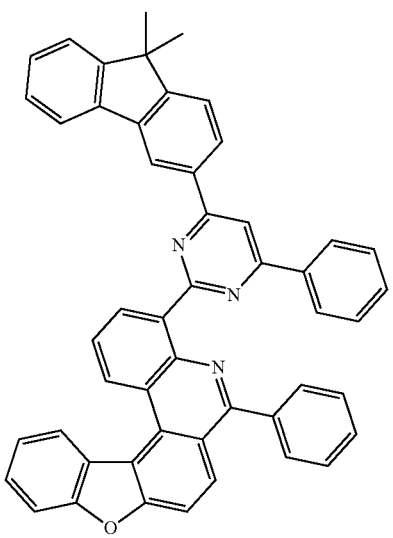

-continued
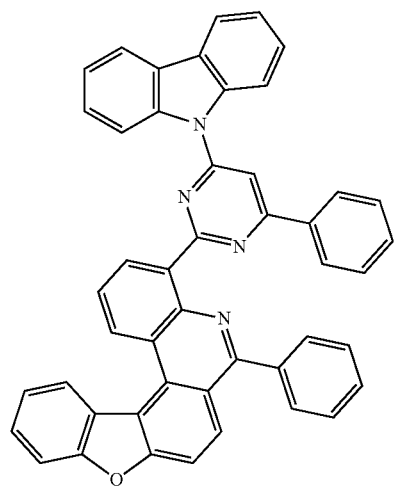
119
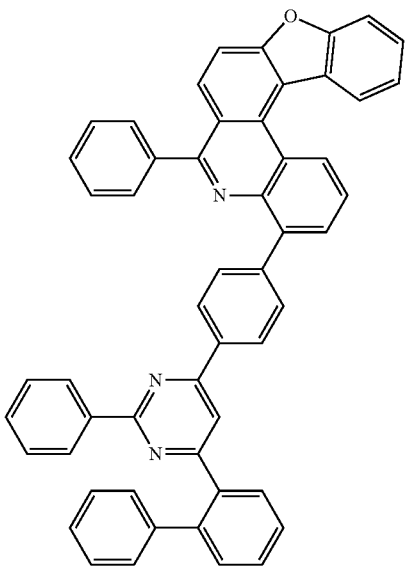
120
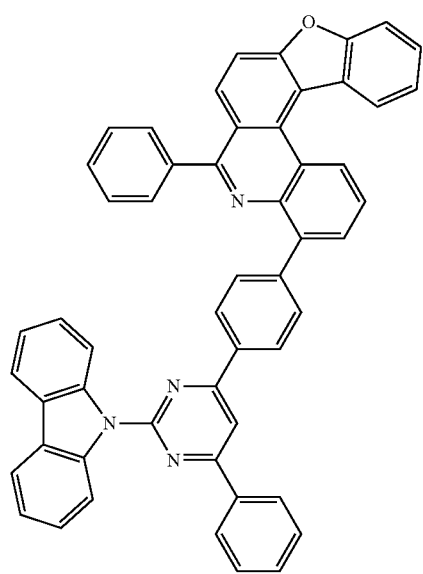
121
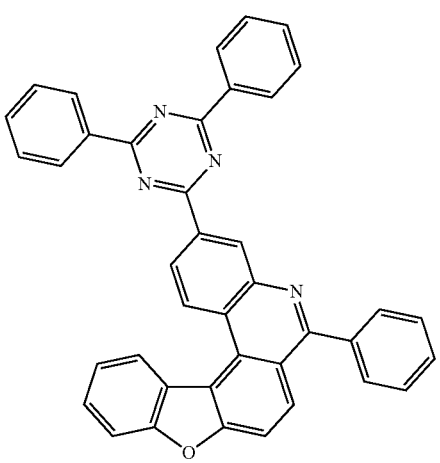
122

123
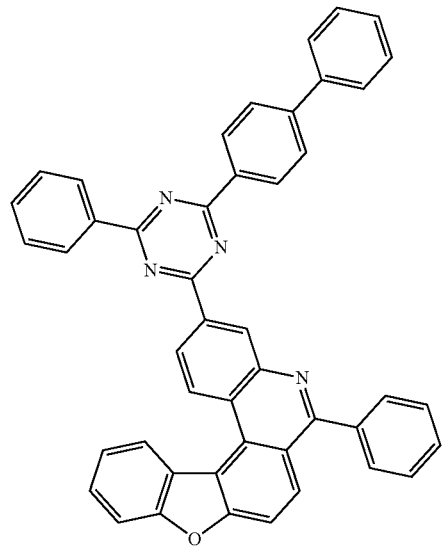
124
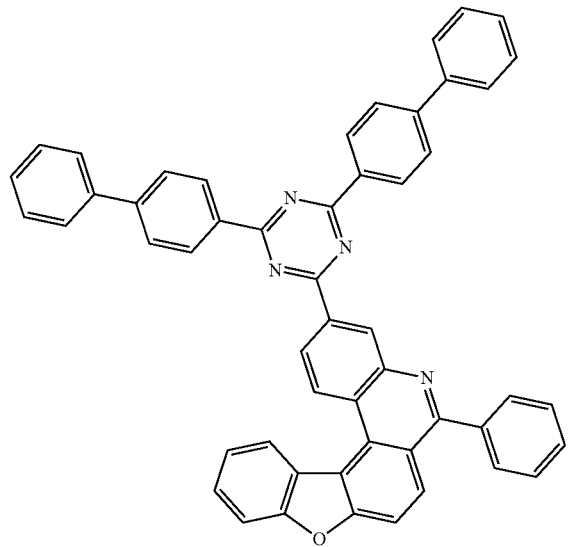
125
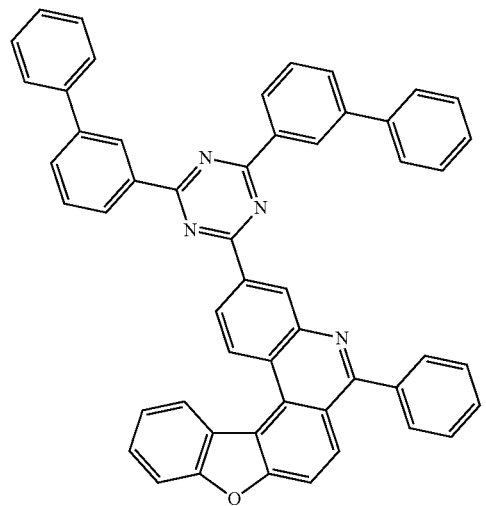
126
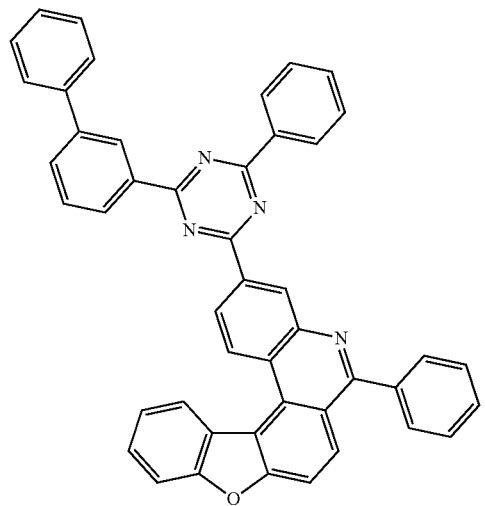

-continued
127
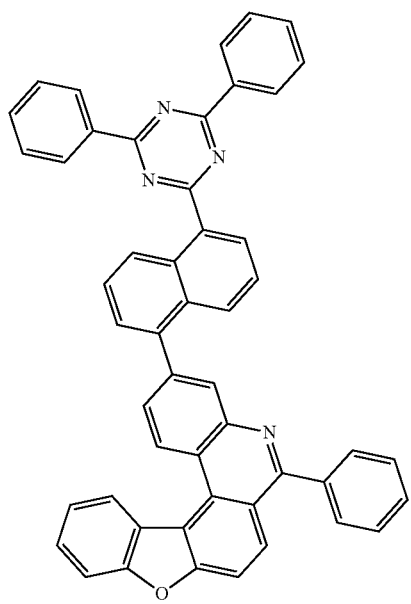
128
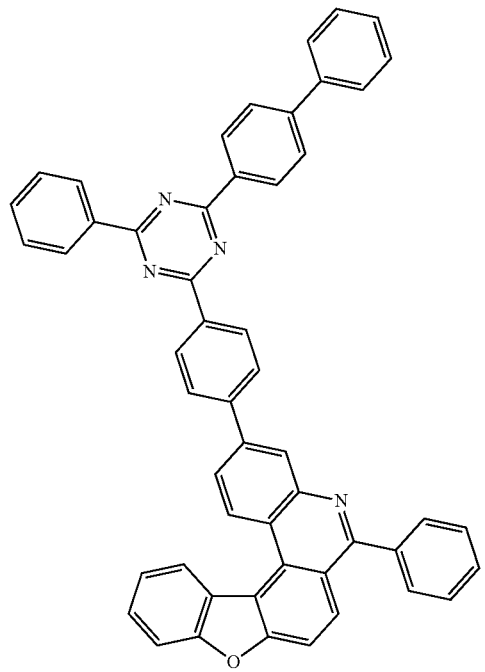
129
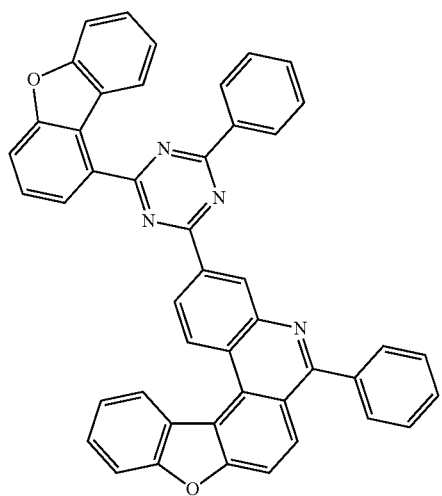
130
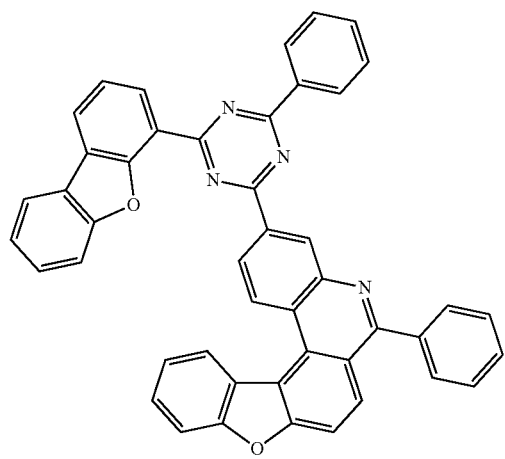

-continued
131
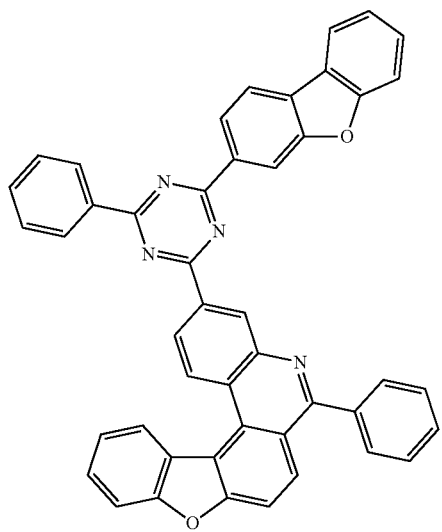
132
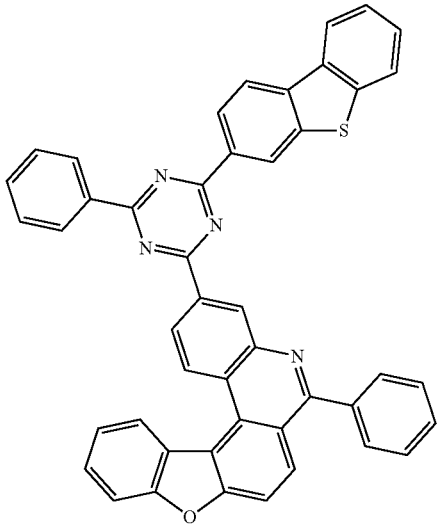
133
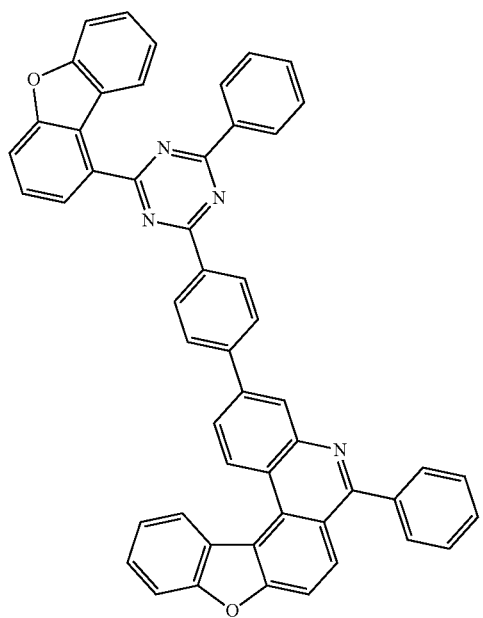
134
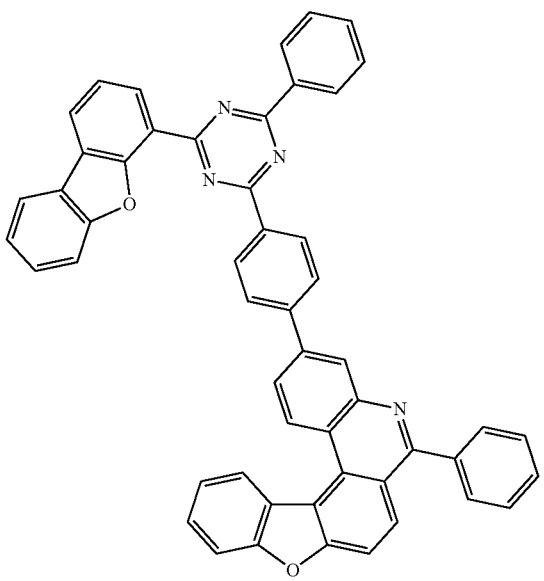

-continued
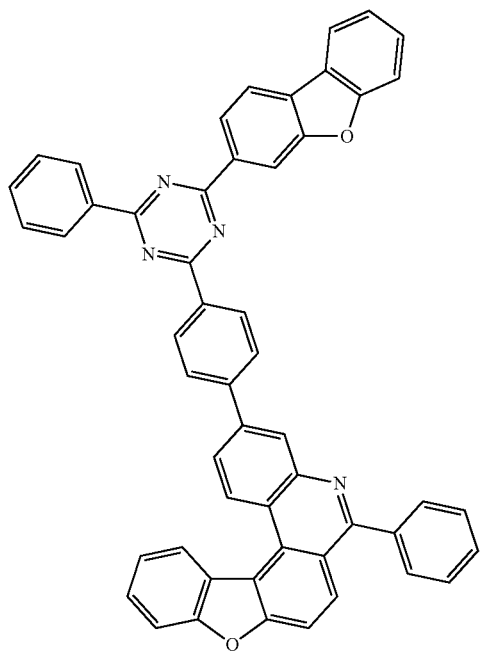
135
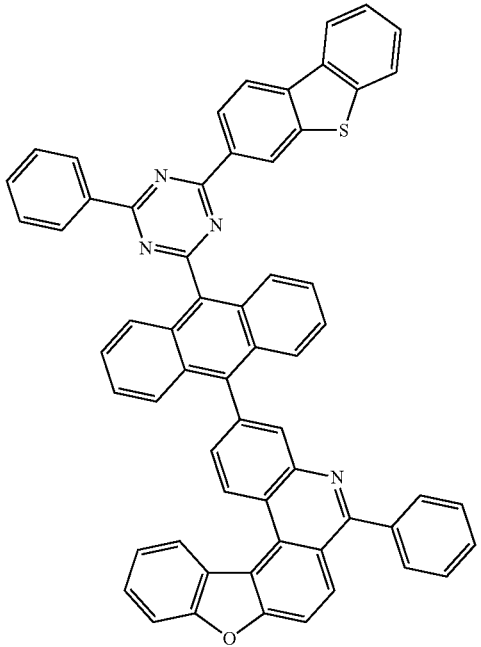
136
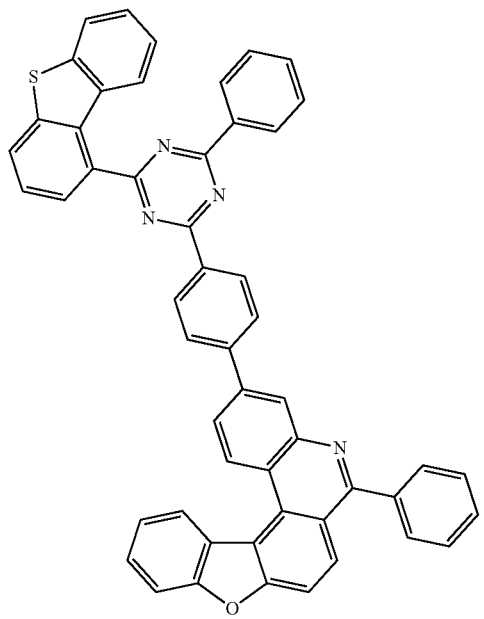
137
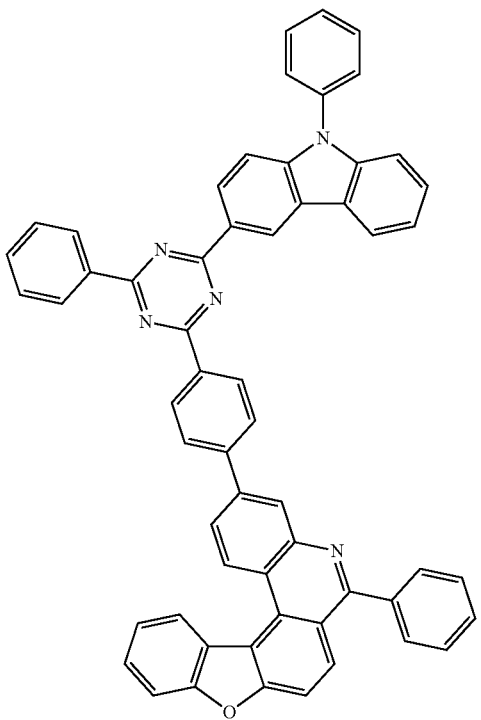
138

-continued
139
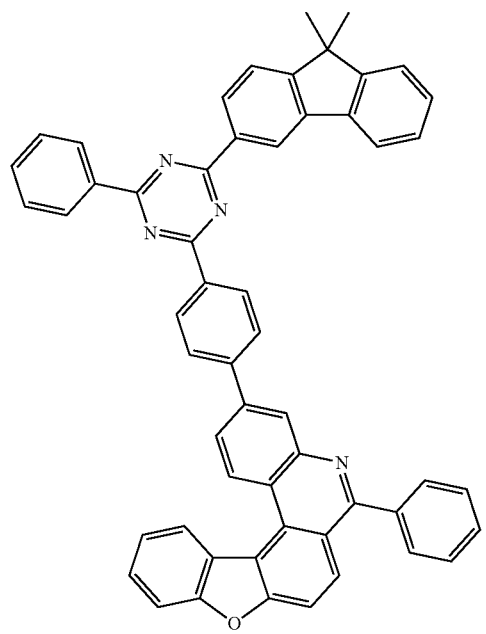
140
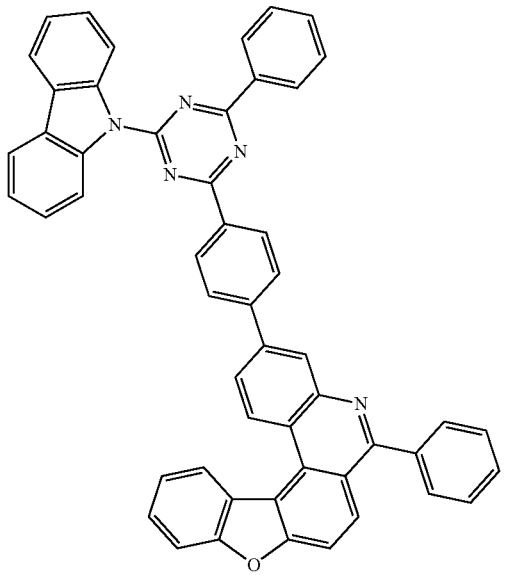
141
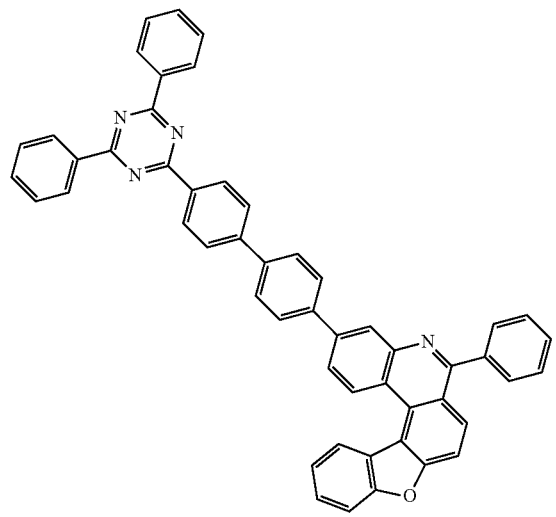
142
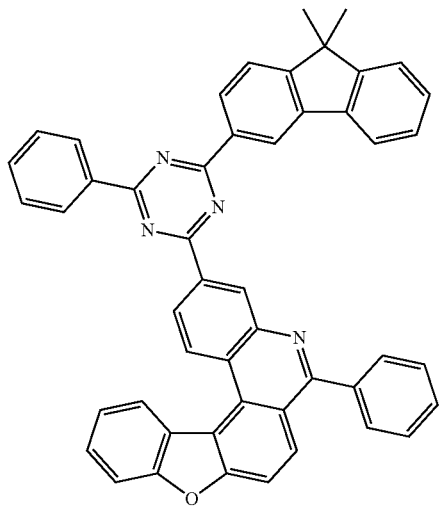
143
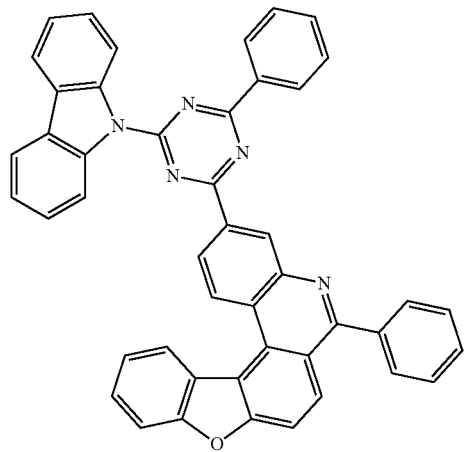

144
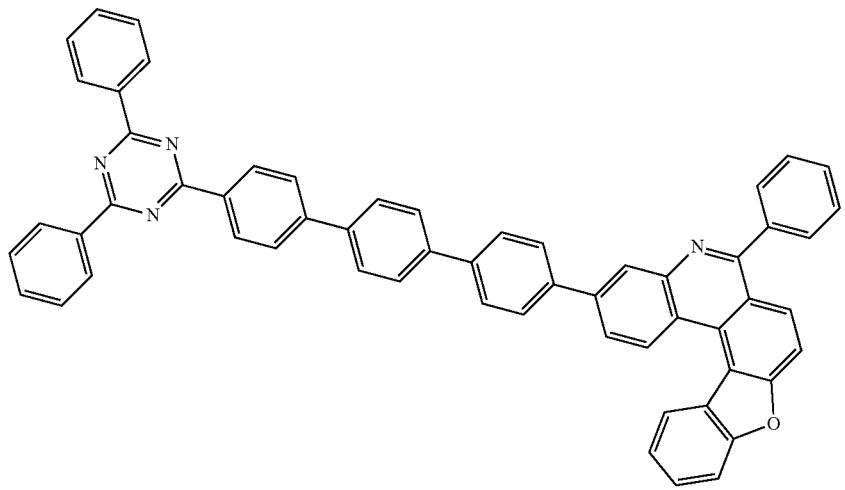
145
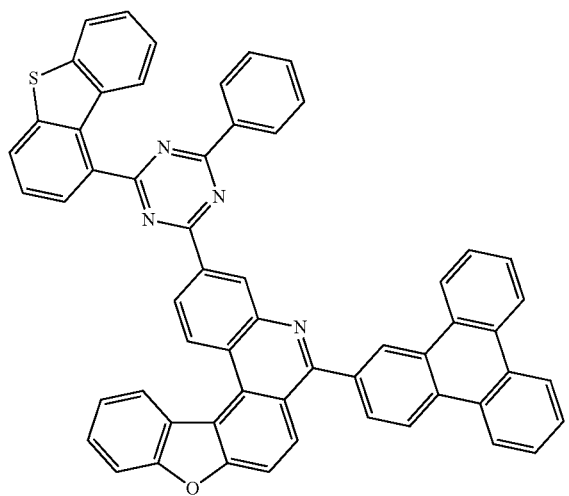
146
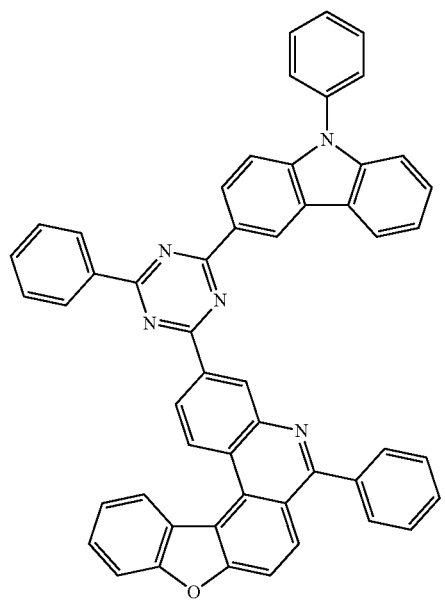
147
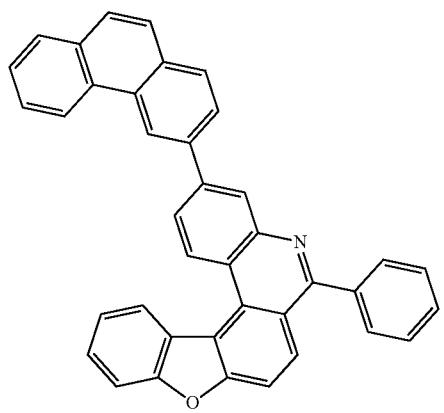
148
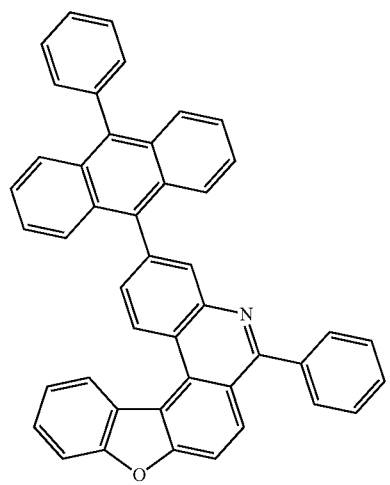

-continued
149
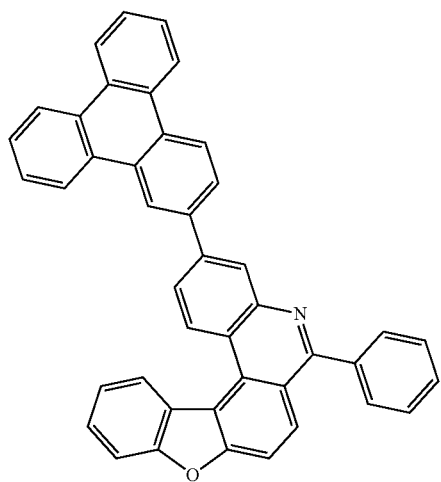
150
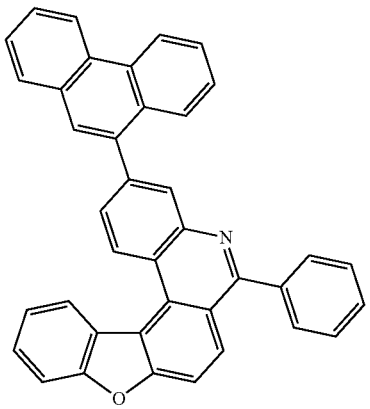
151
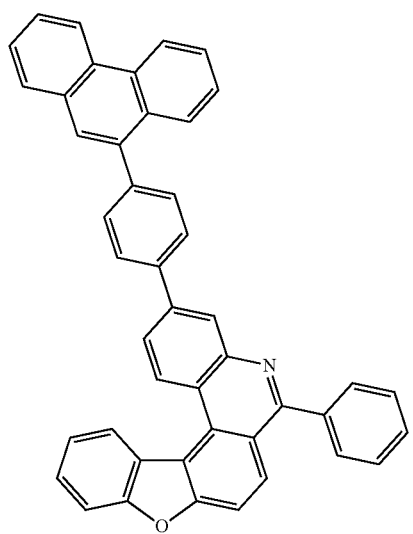
152
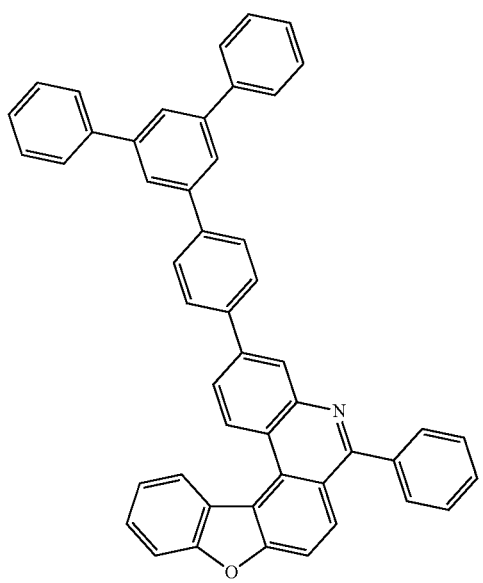
153
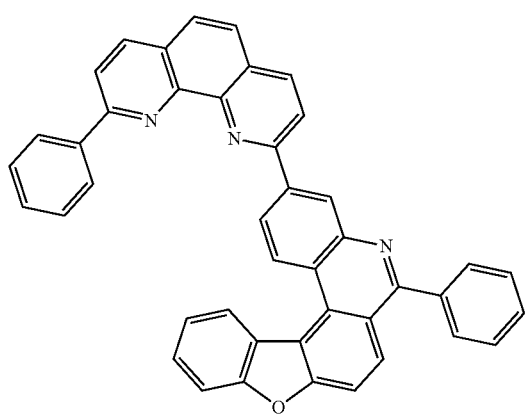
154
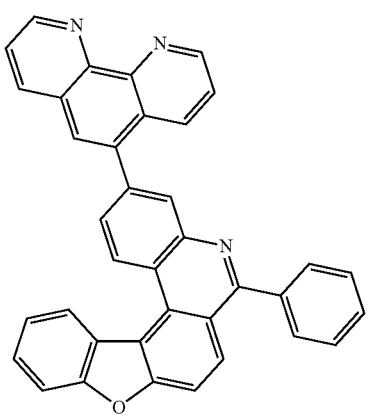

-continued
155
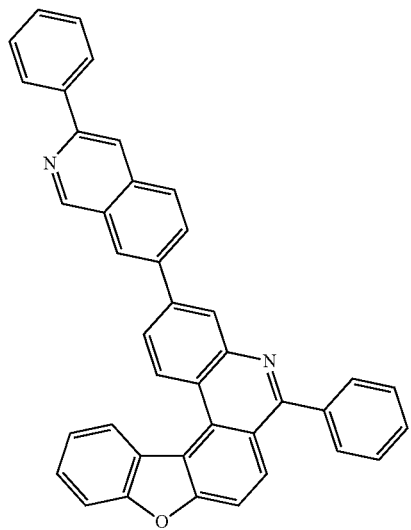
156
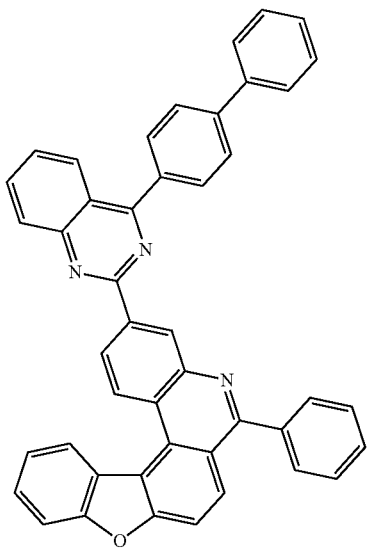
157
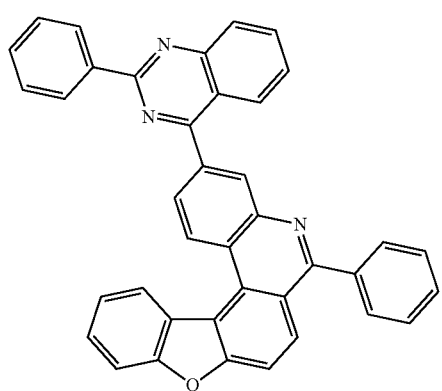
158
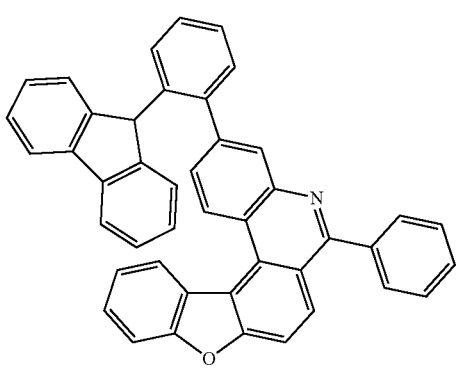
159
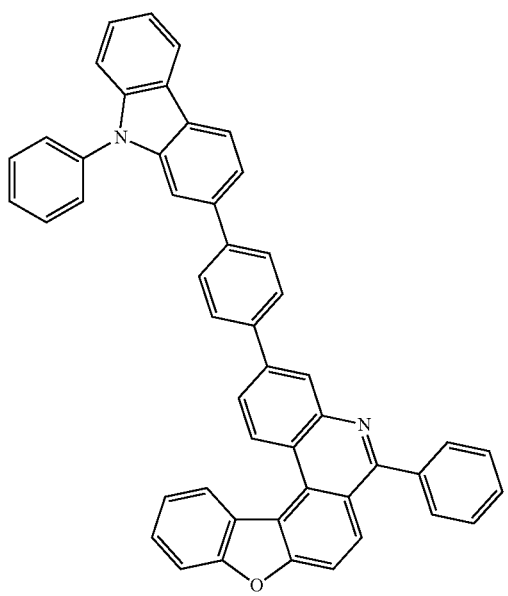
160
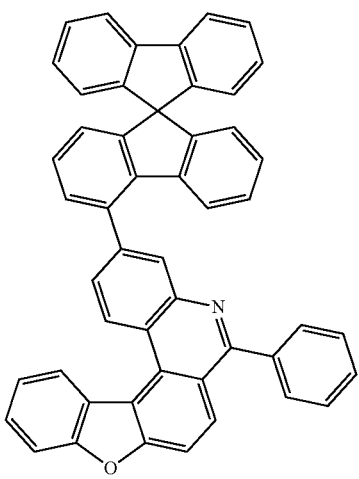

161
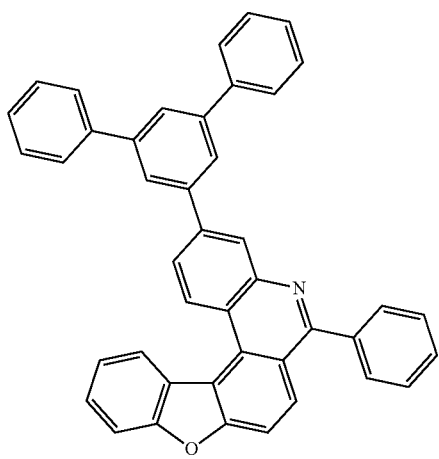
162
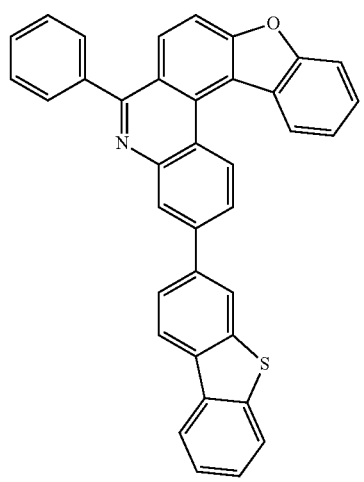
163
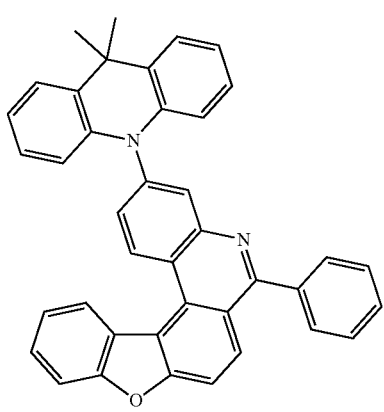
164
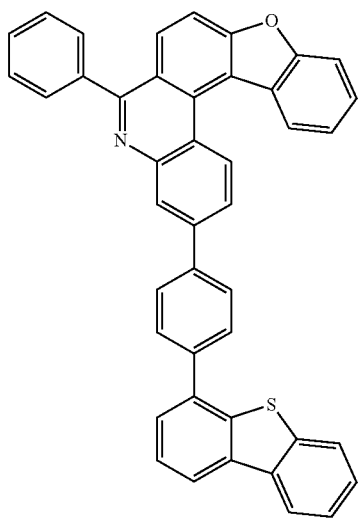
165
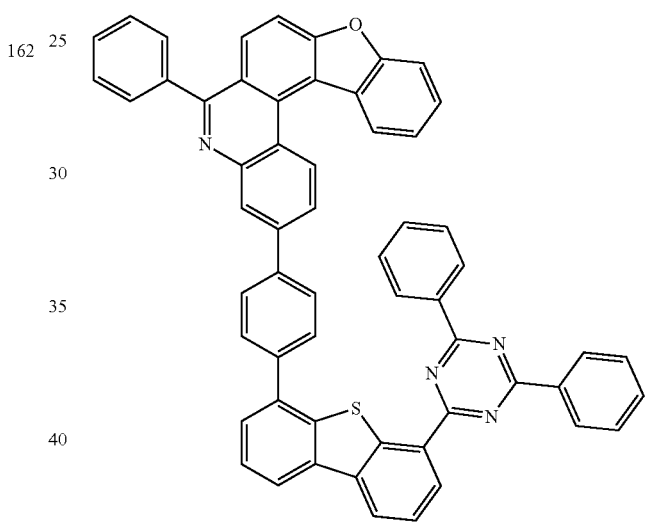
166
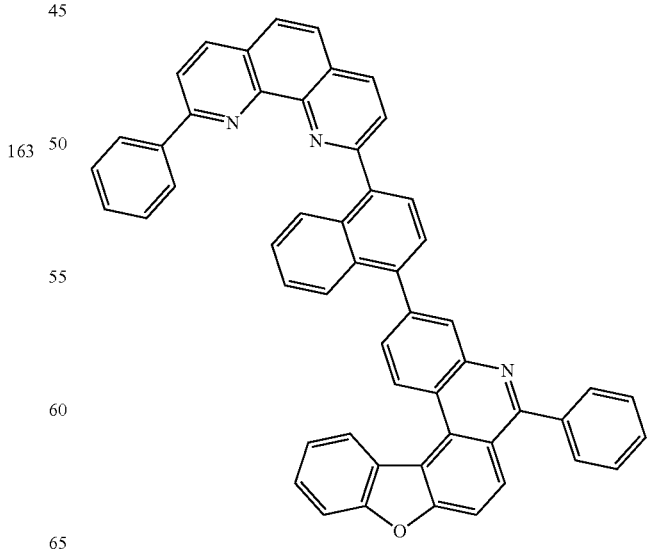

167
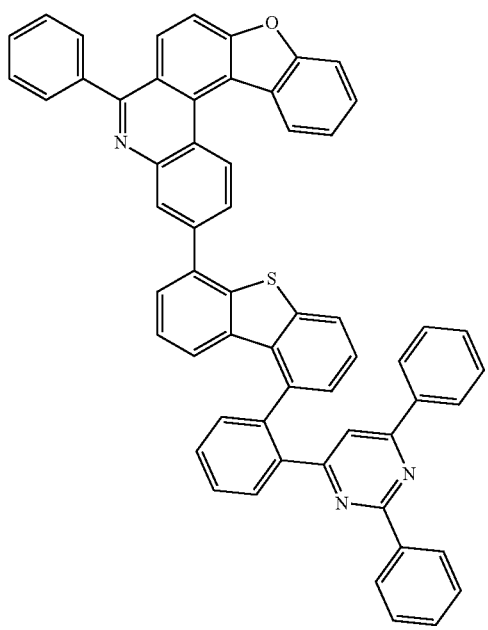
168
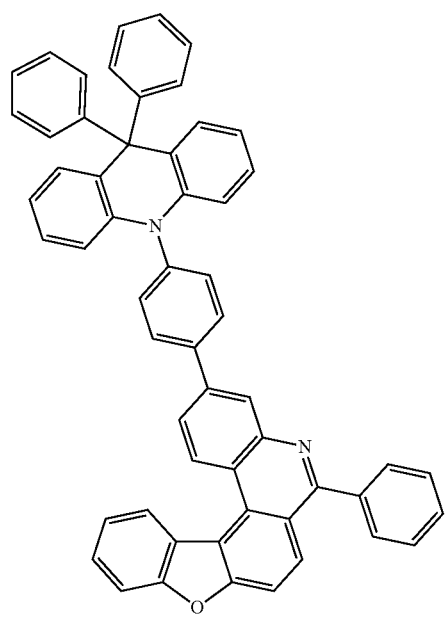
169
170
171
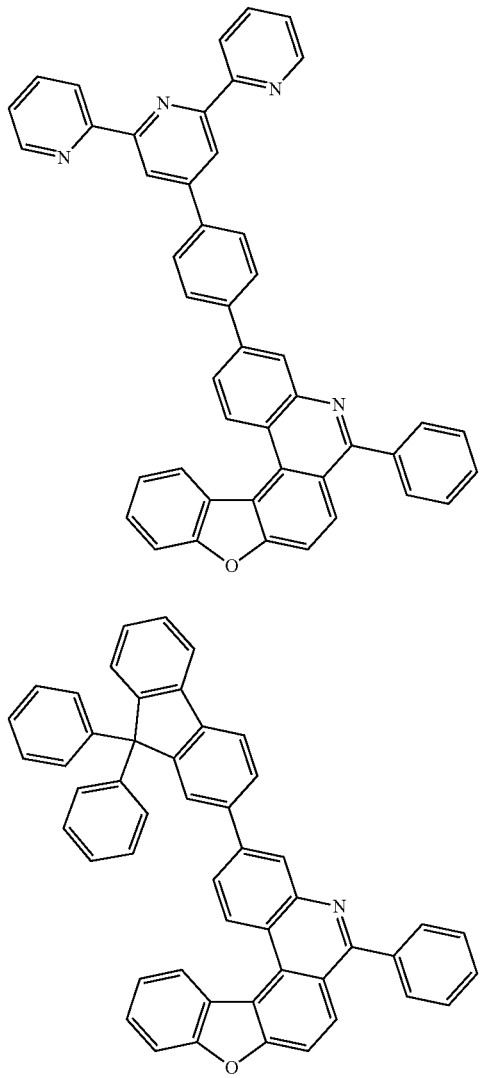

172
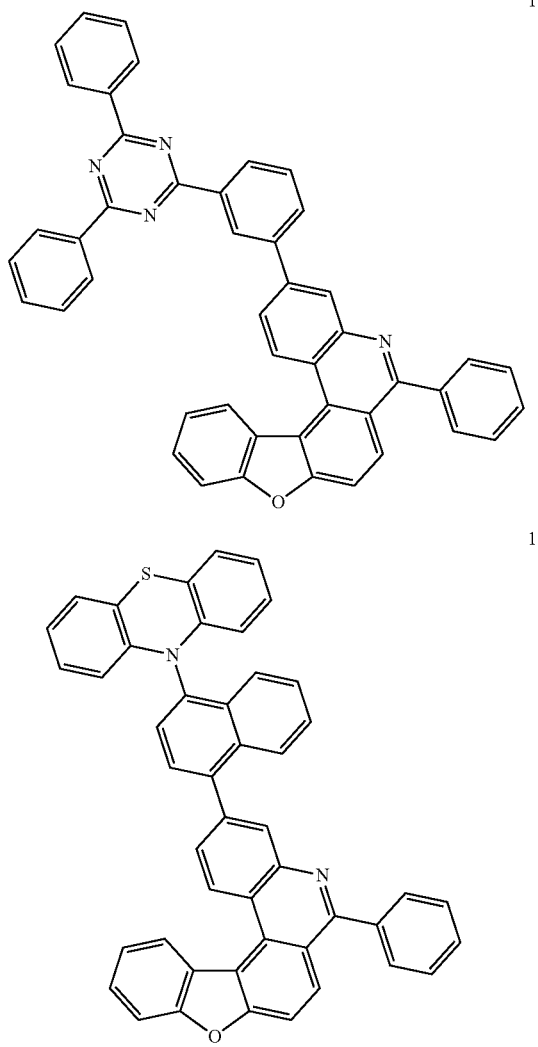
173
175
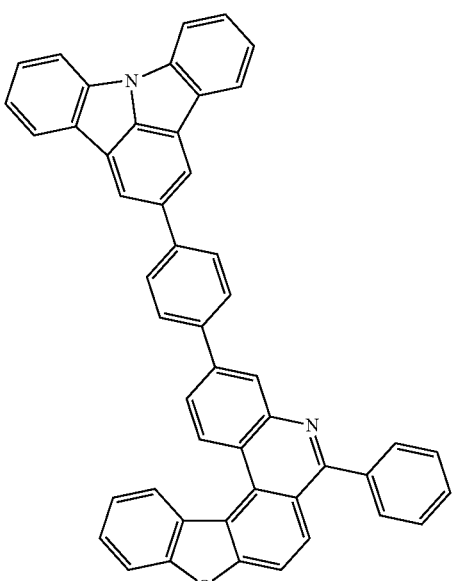
174
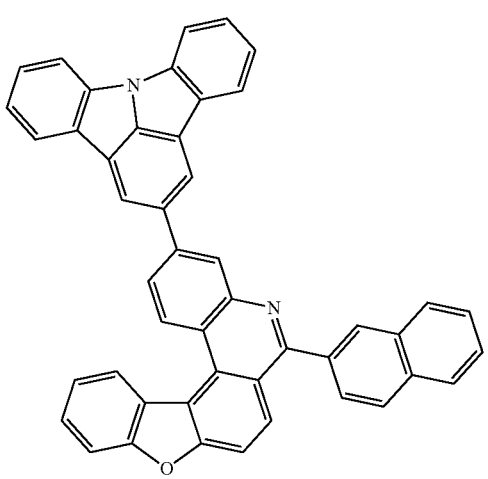
176
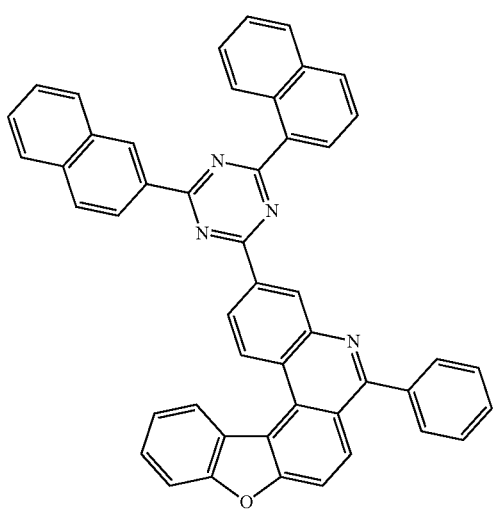

177
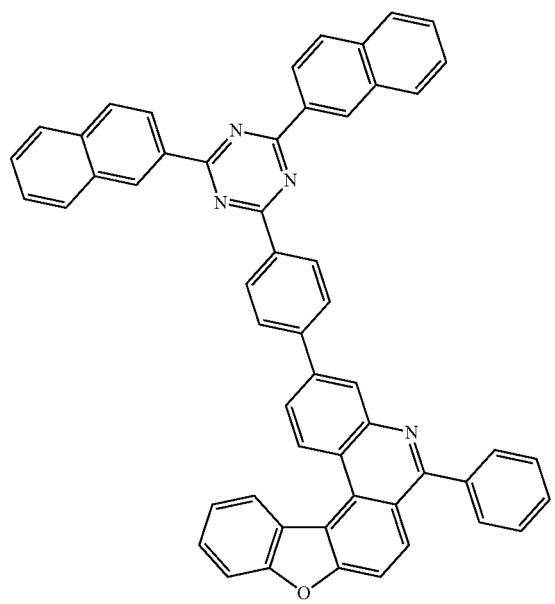
179
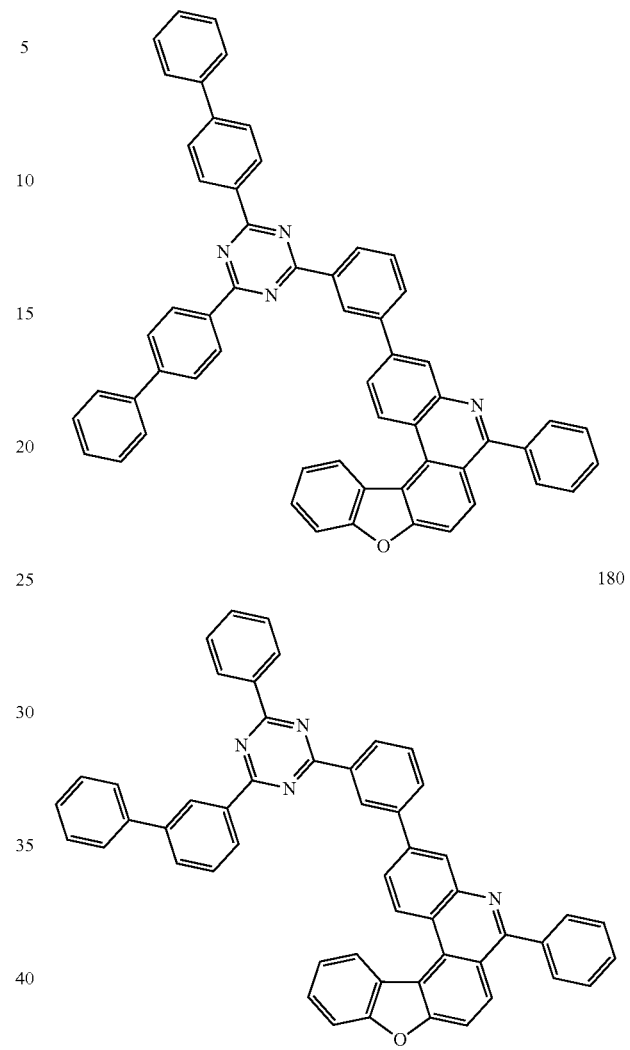
178
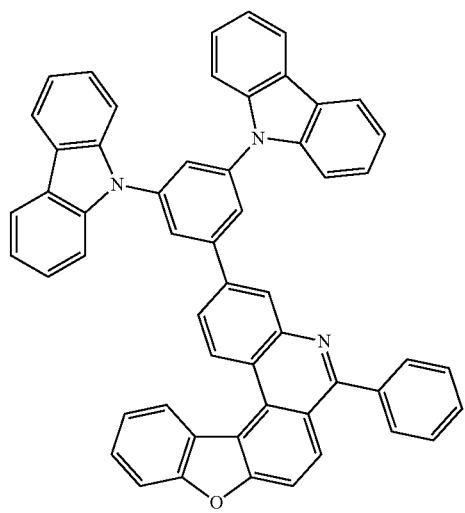
181
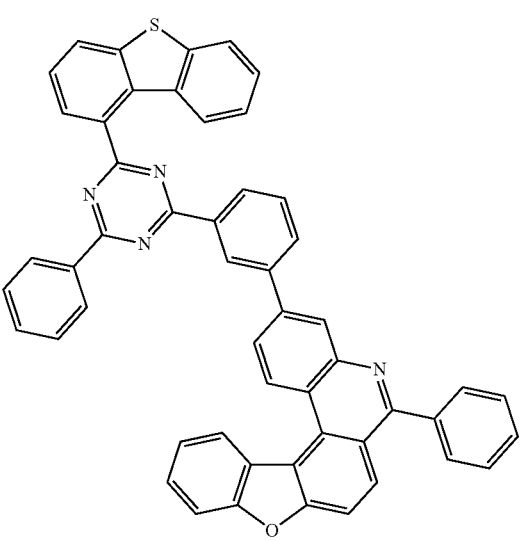

-continued
182
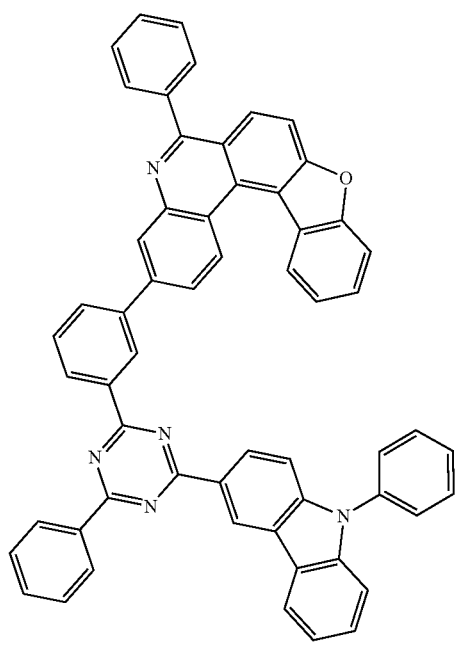
183
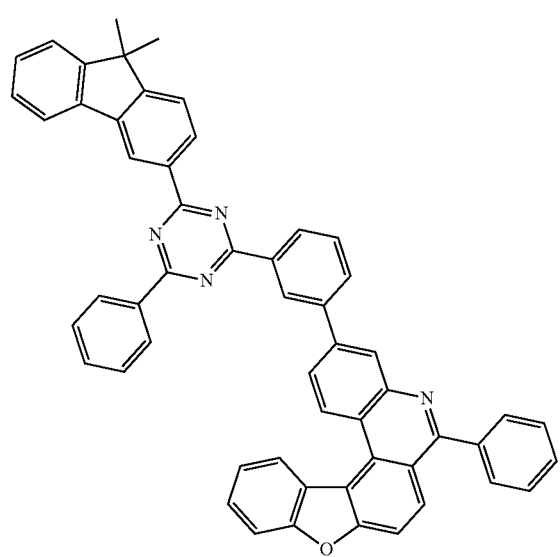
-continued
184
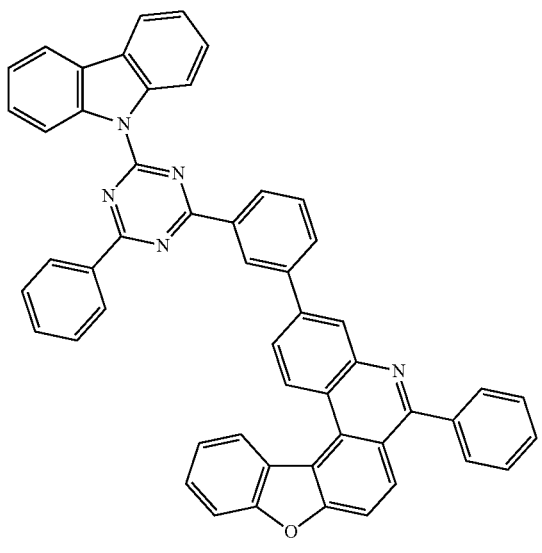
185
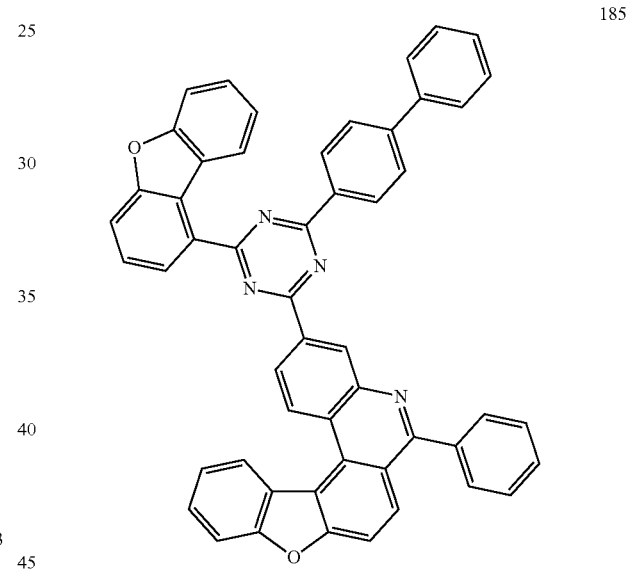
186
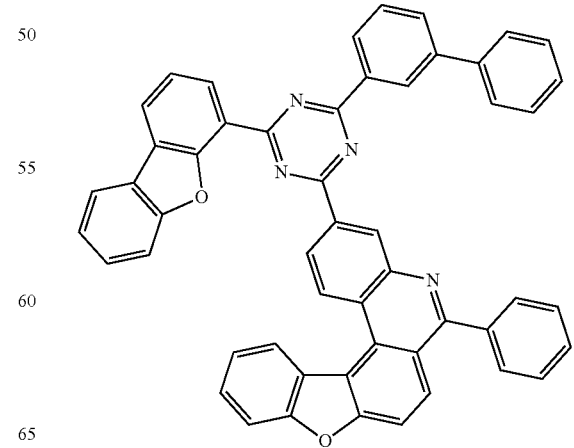

187
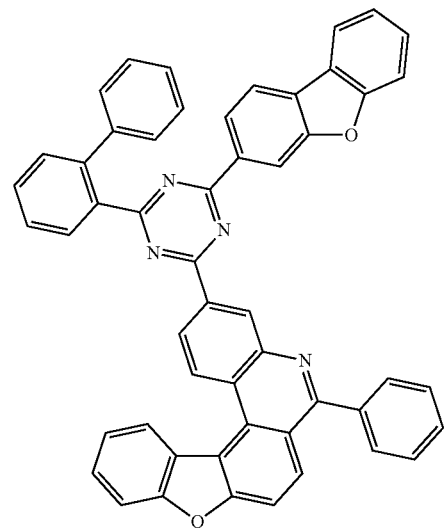
188
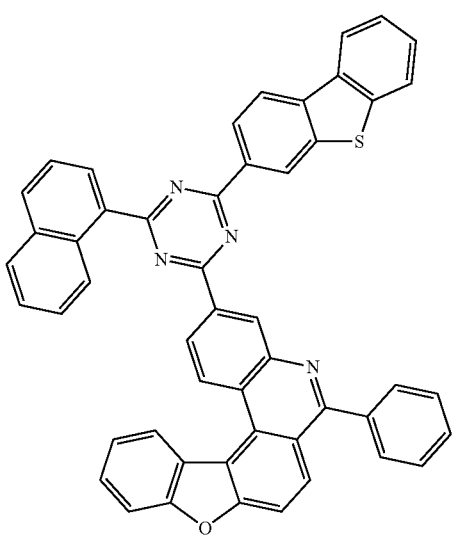
189
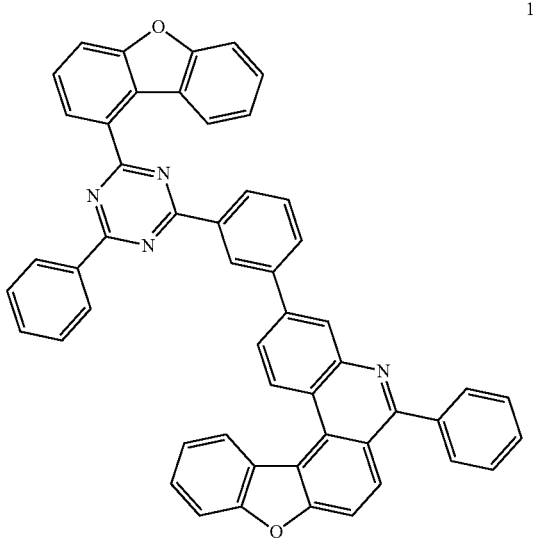
190
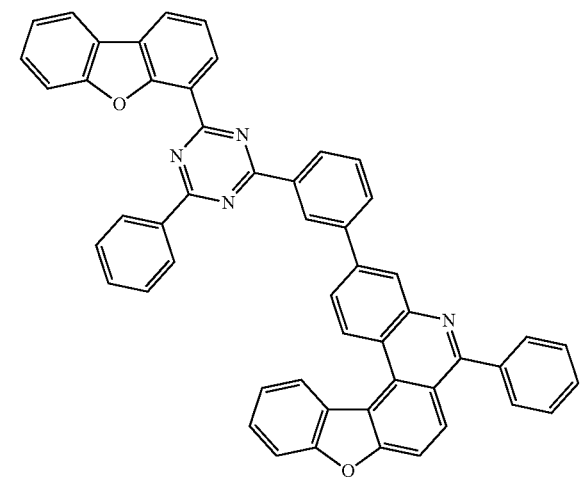
191
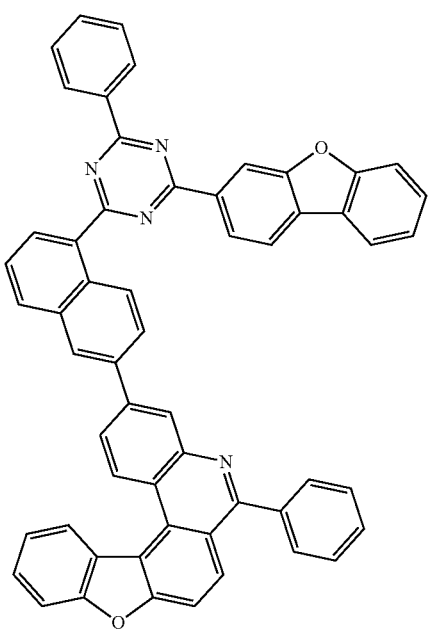

-continued
192
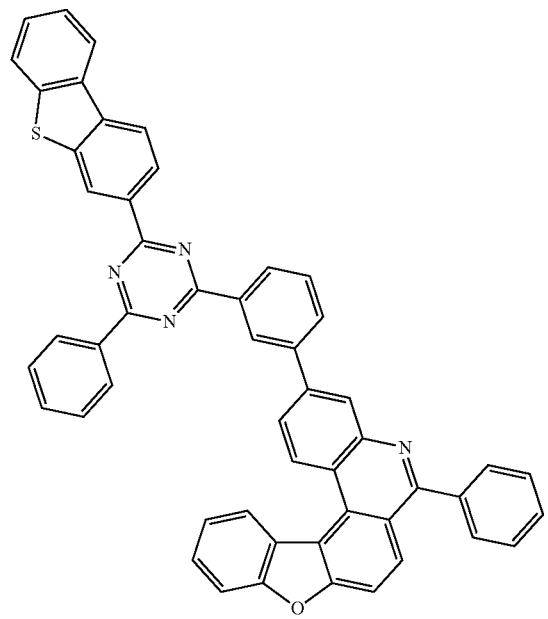
193
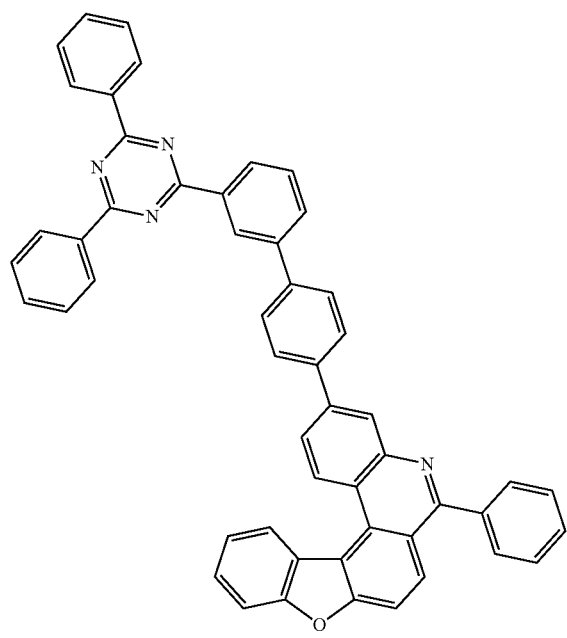
-continued
194
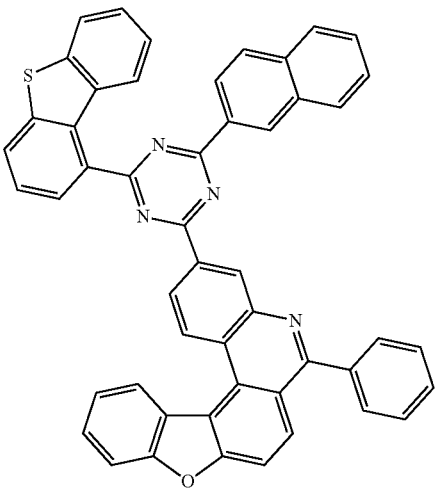
195
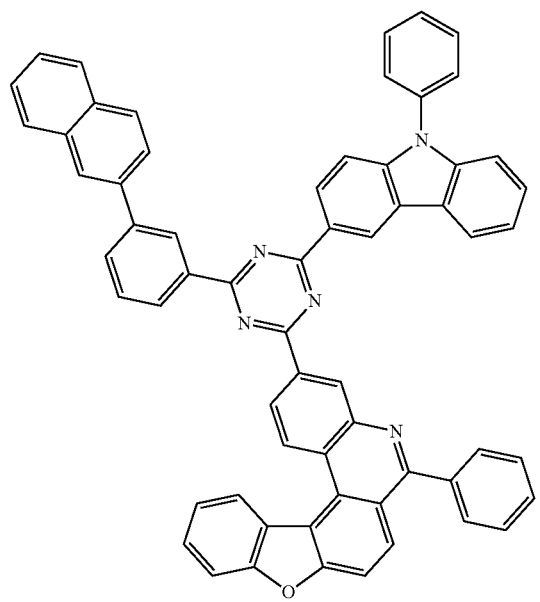
196
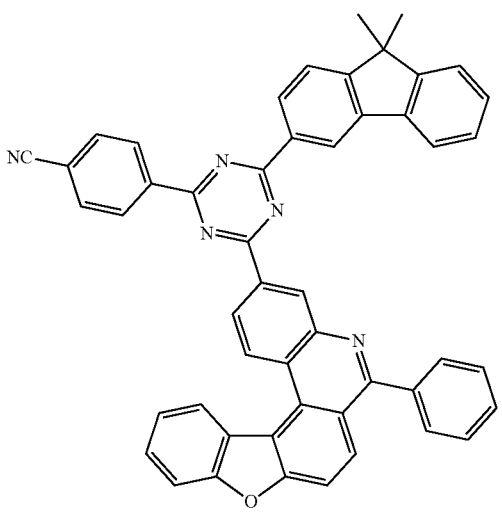

197
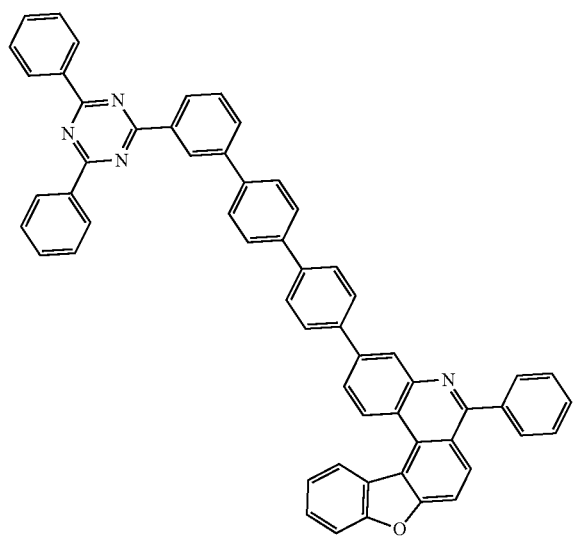
198
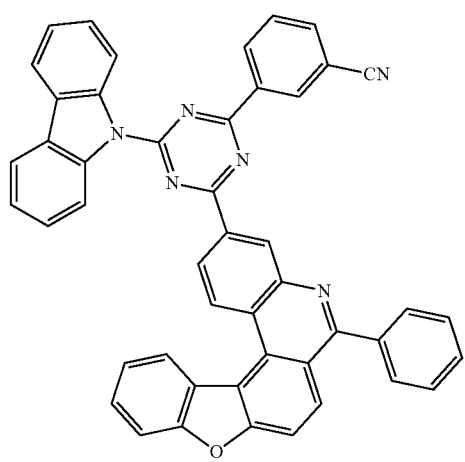
199
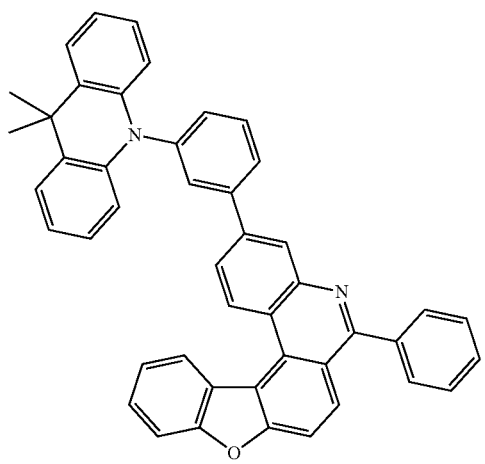
200
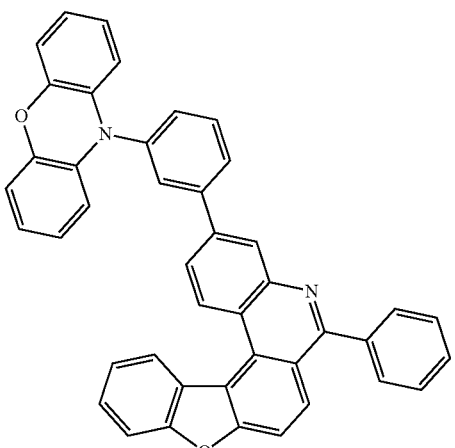
201
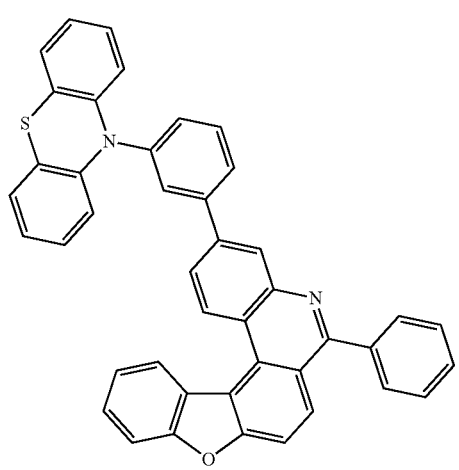
202
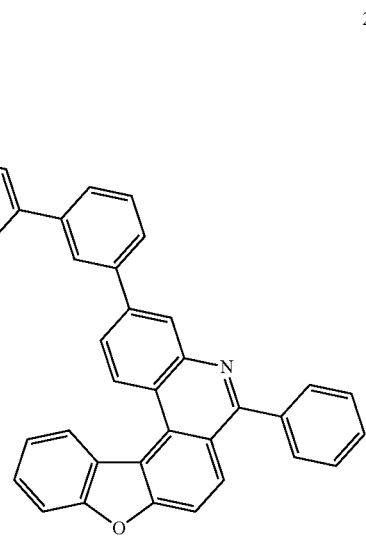

203
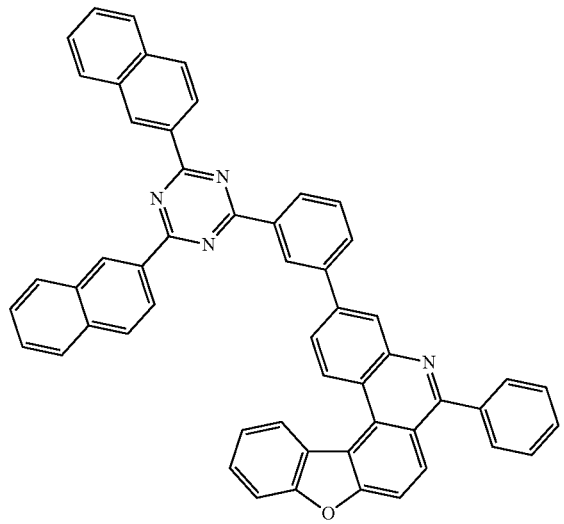
204
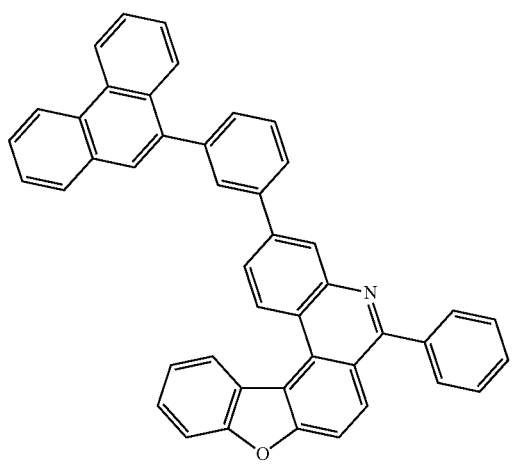
205
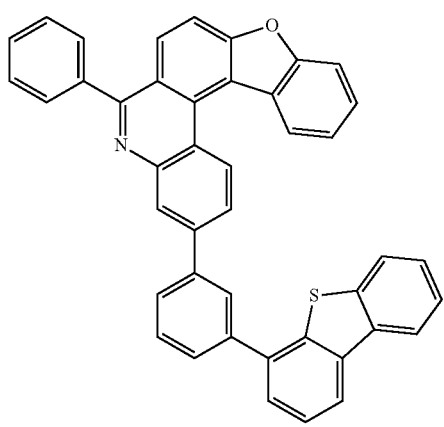
206
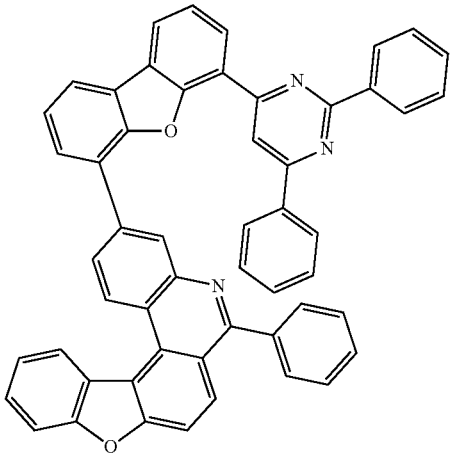
207
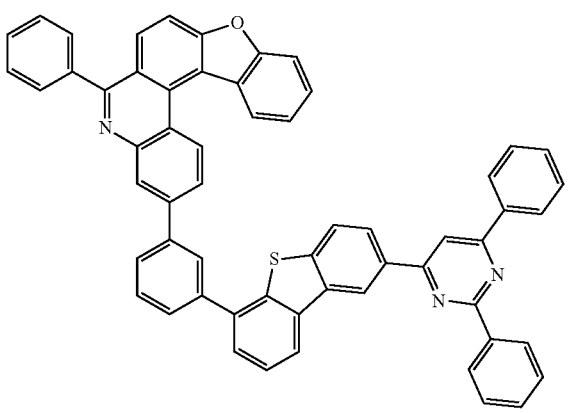
208
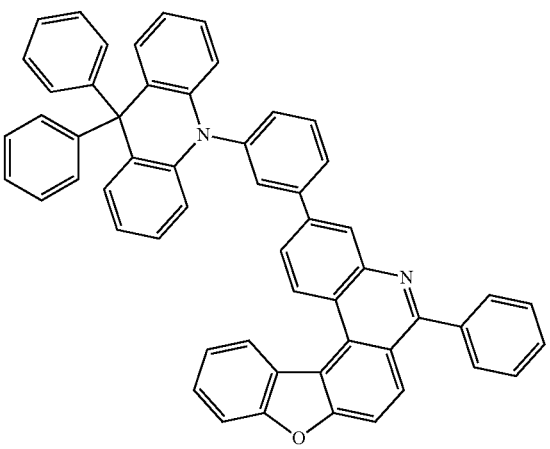

97
-continued
209
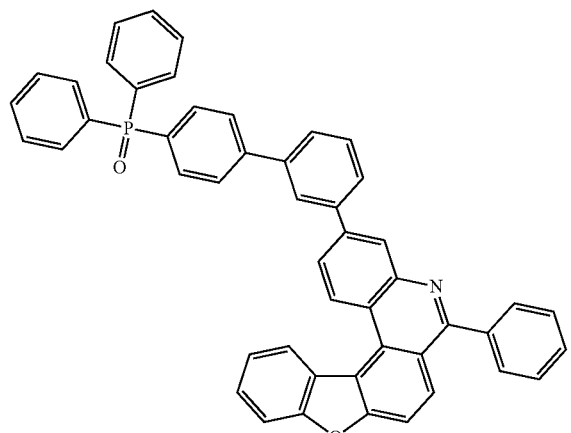
210
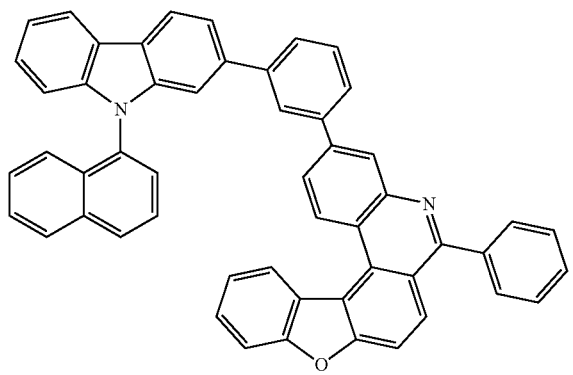
211
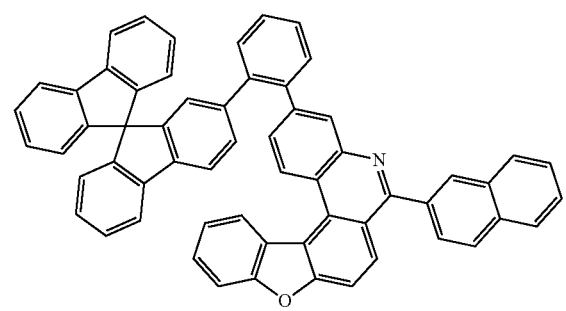
98
-continued
212
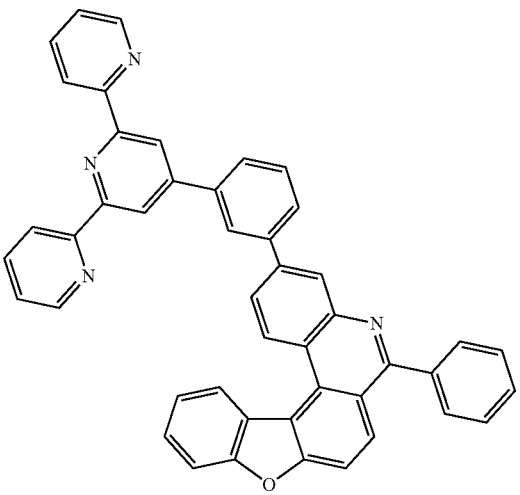
213
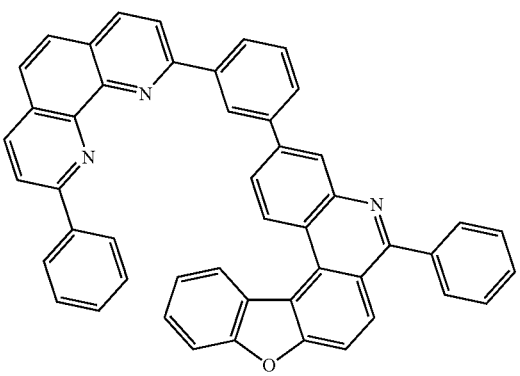
214
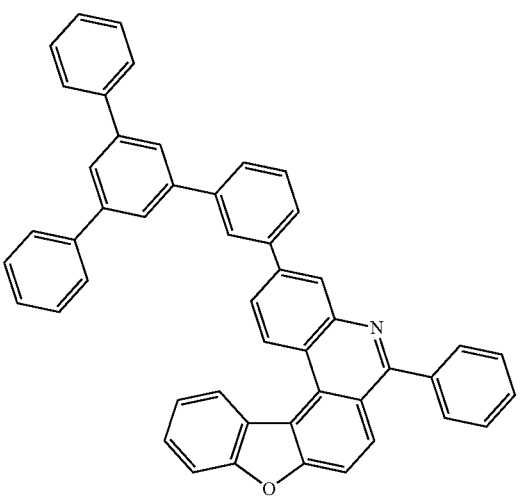

215
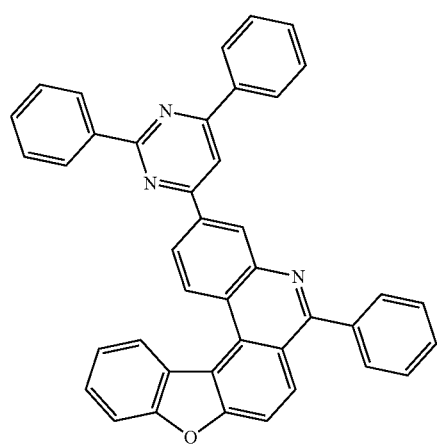
216
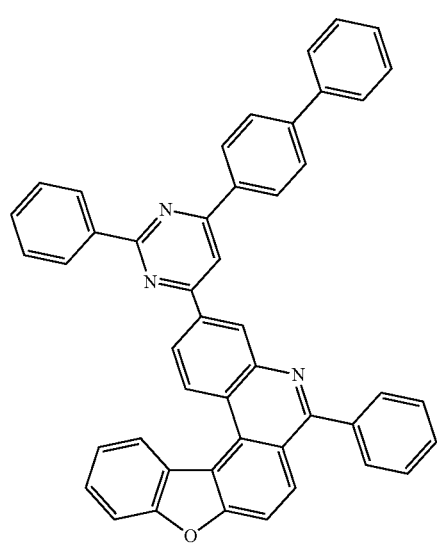
217
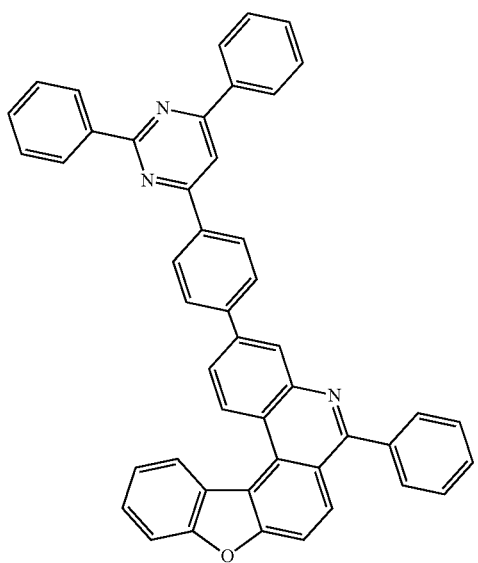
218
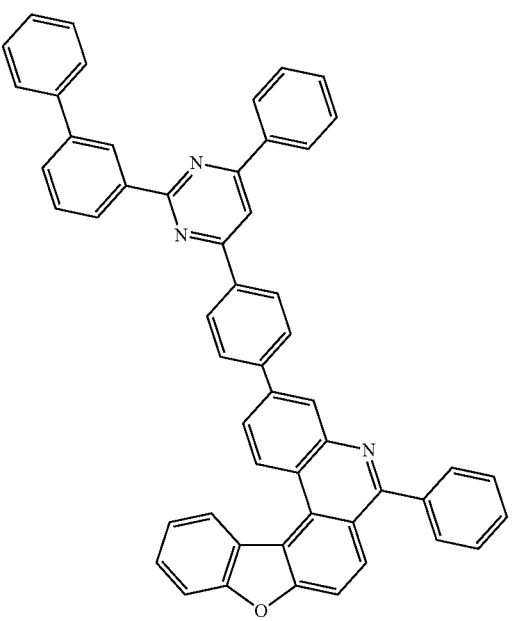
219
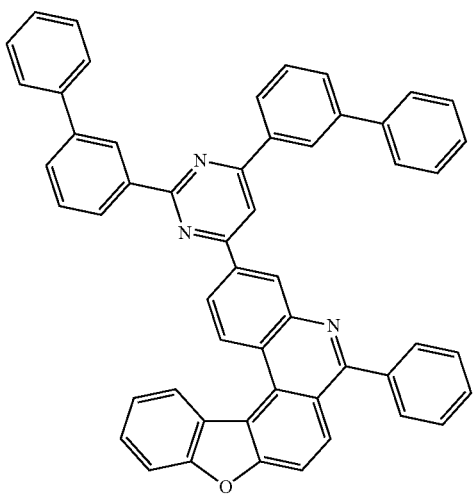

220
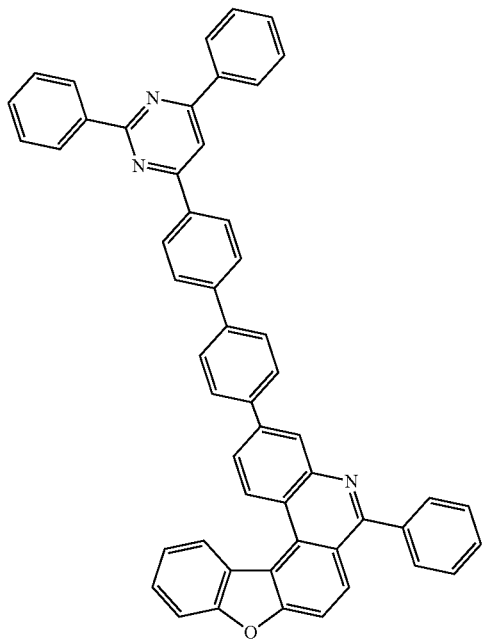
221
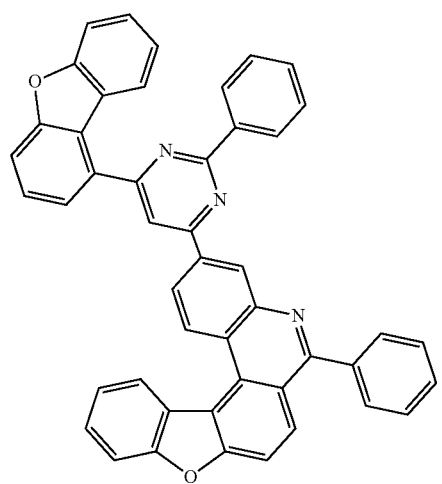
222
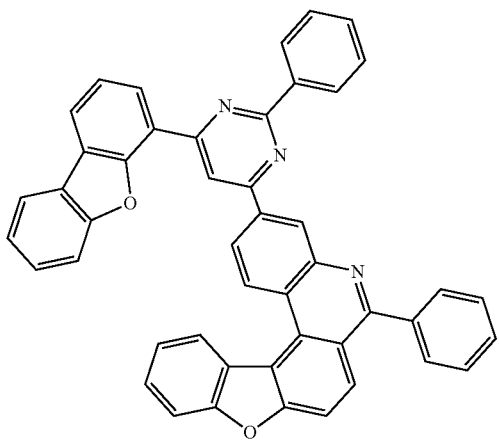
223
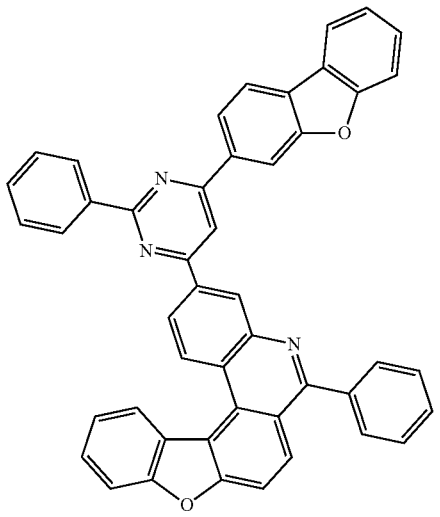
224
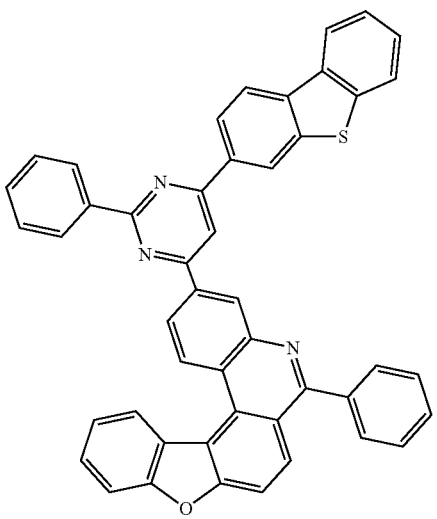
225
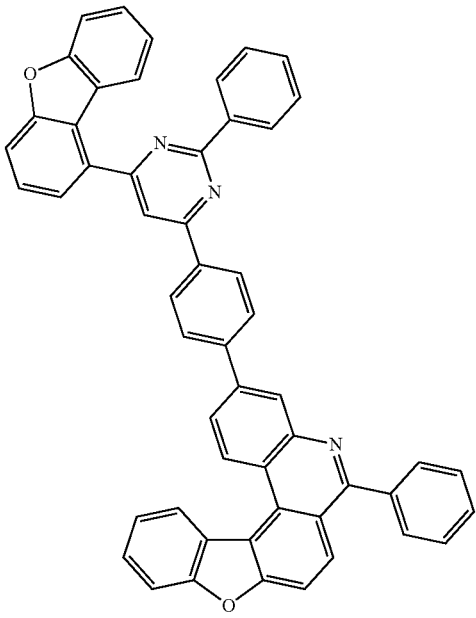

226
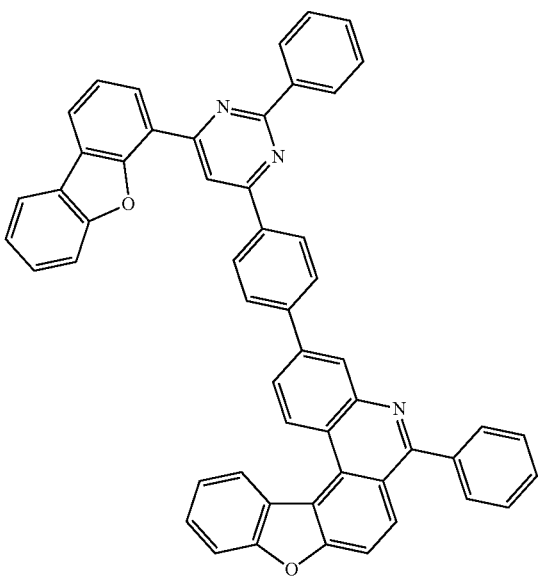
227
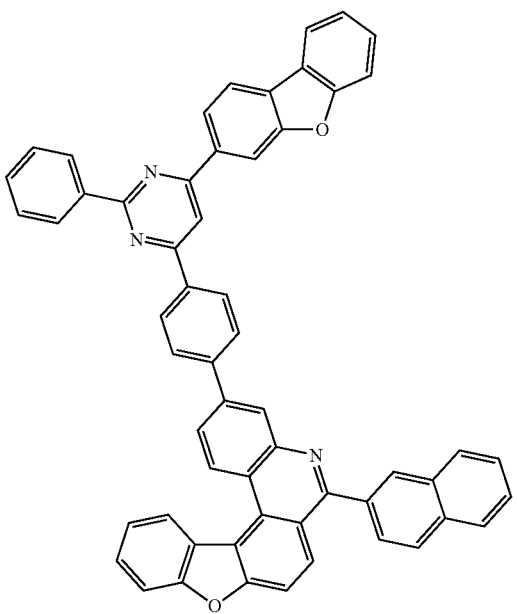
228
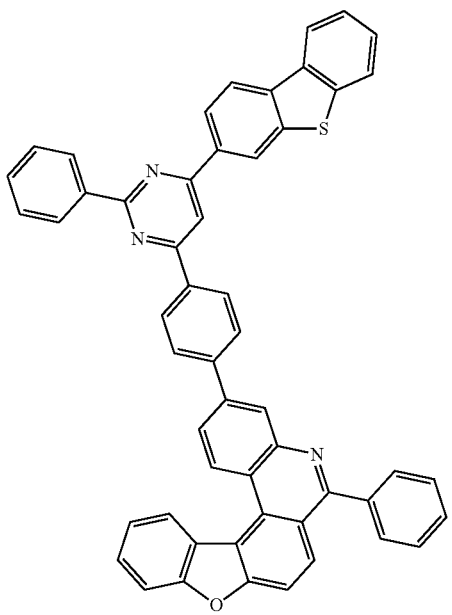
229
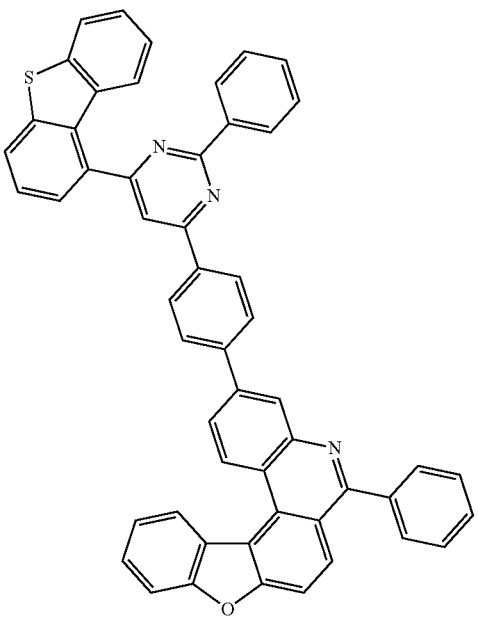

230
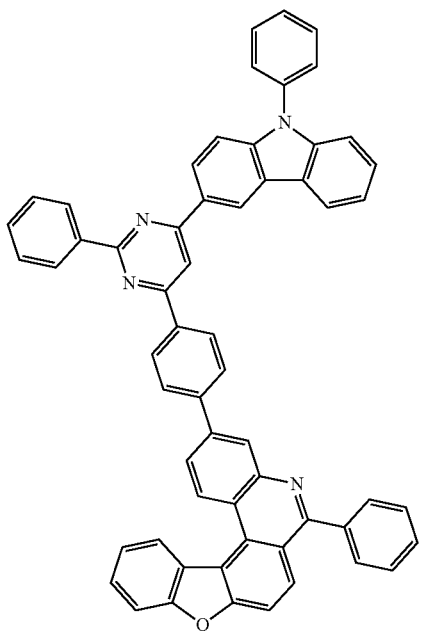
231
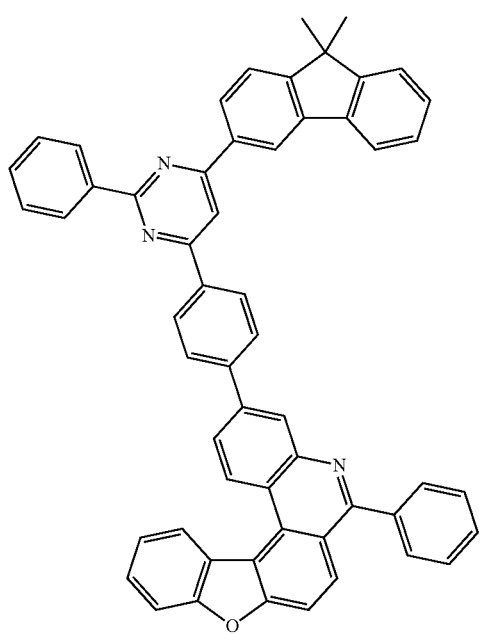
232
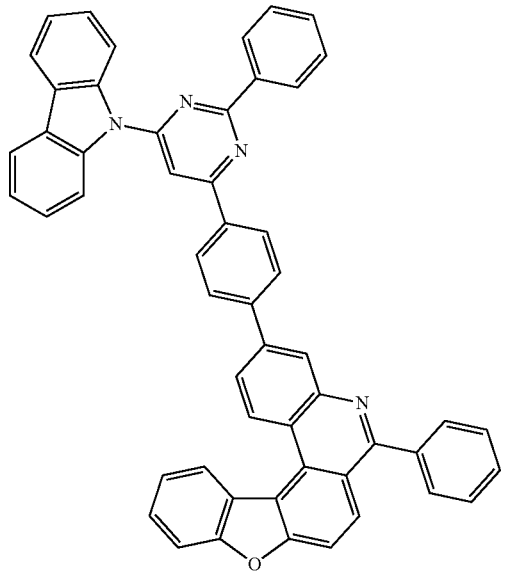
233
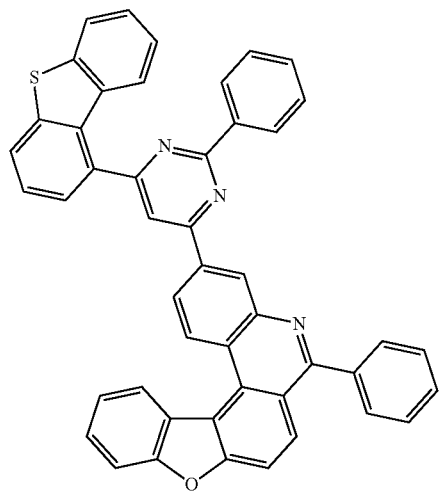
234
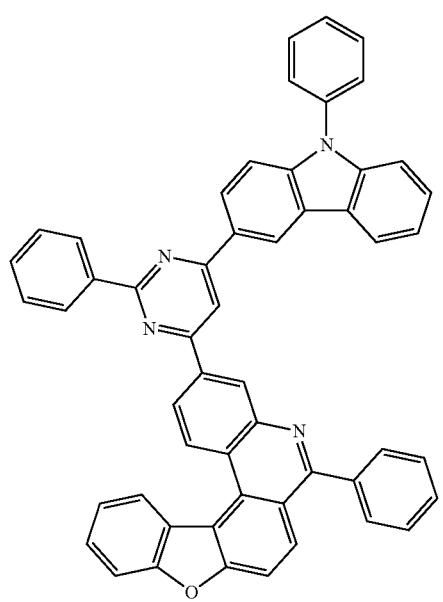

235
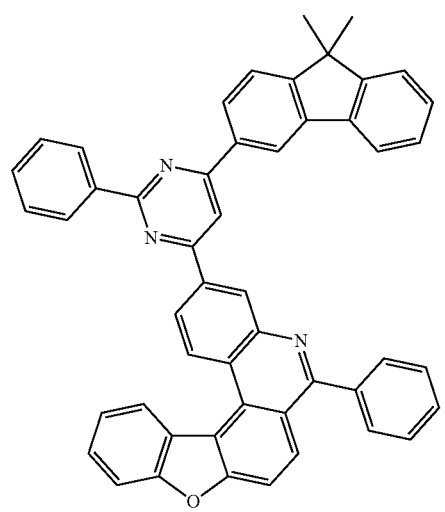
236
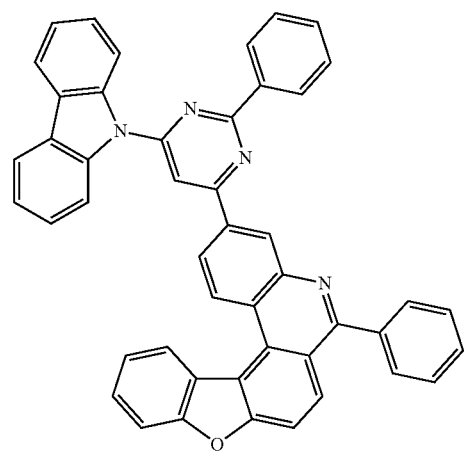
237
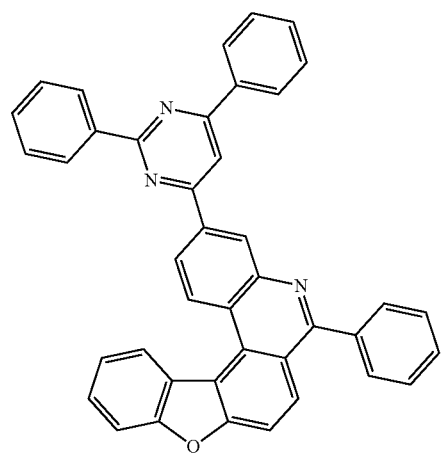
238
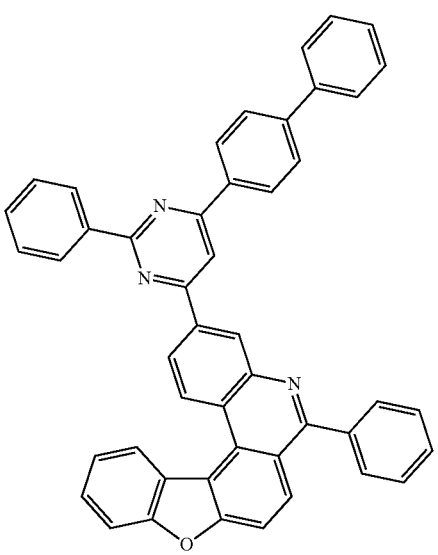
239
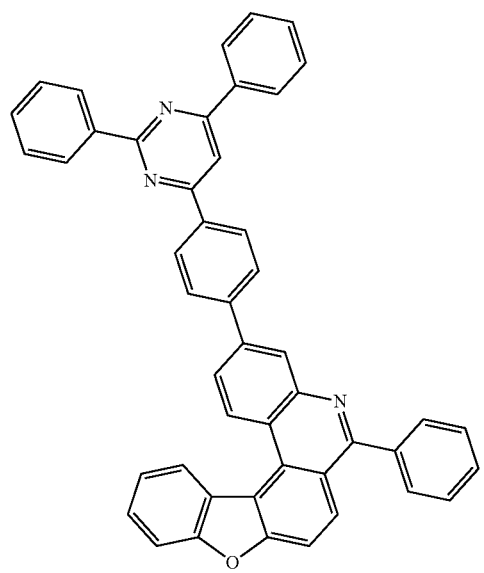

240
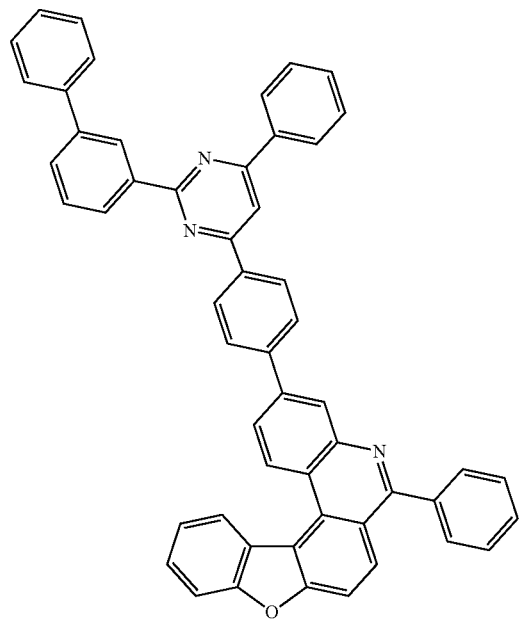
241
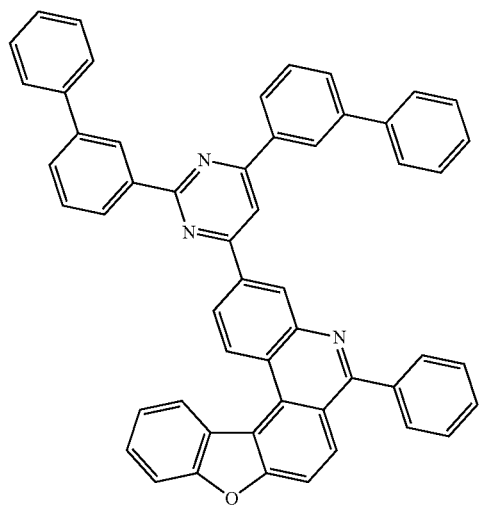
242
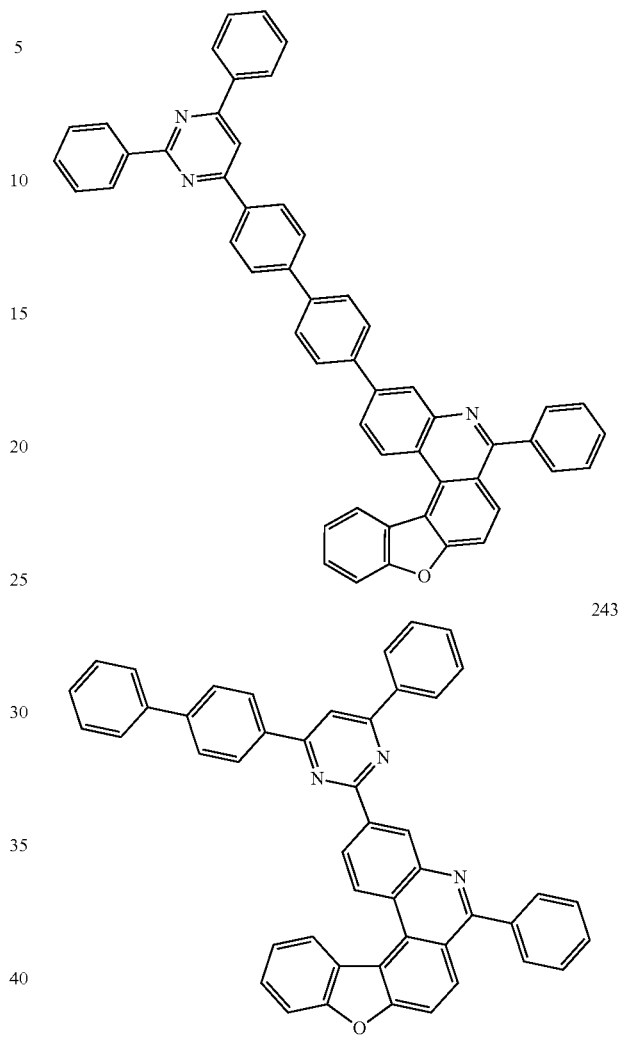
243
244
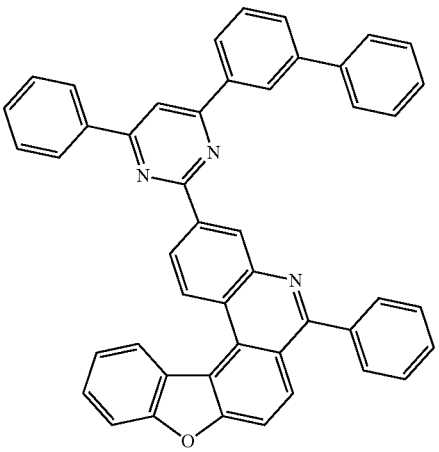

245
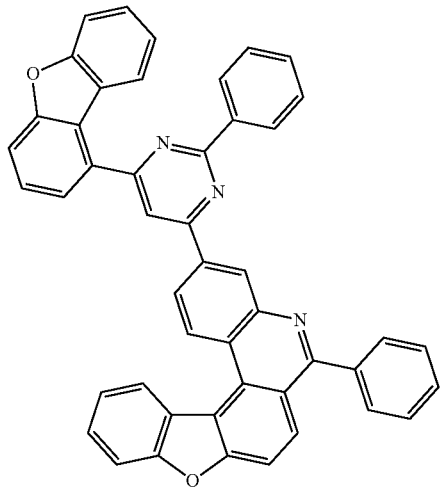
246
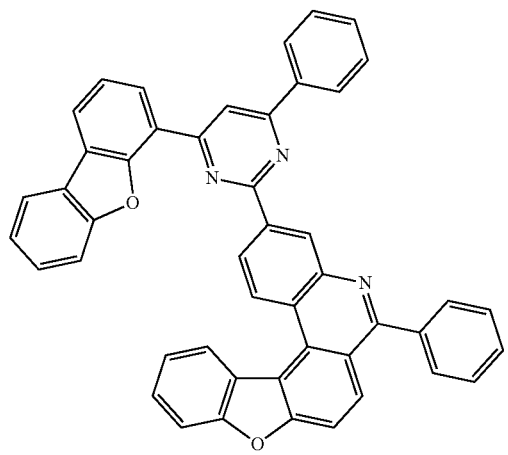
247
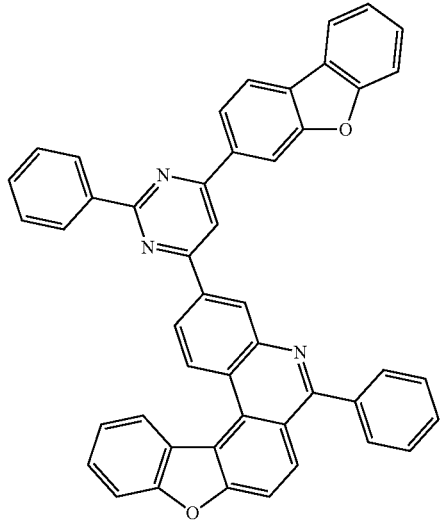
248
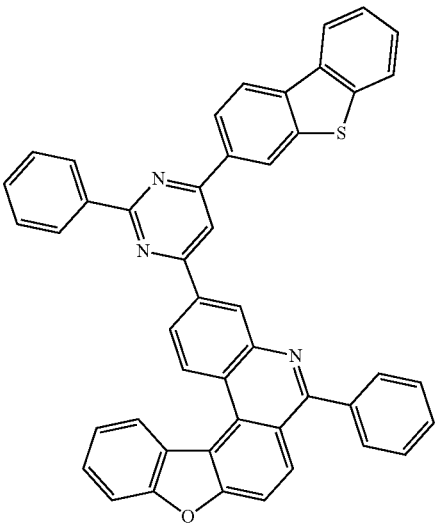
249
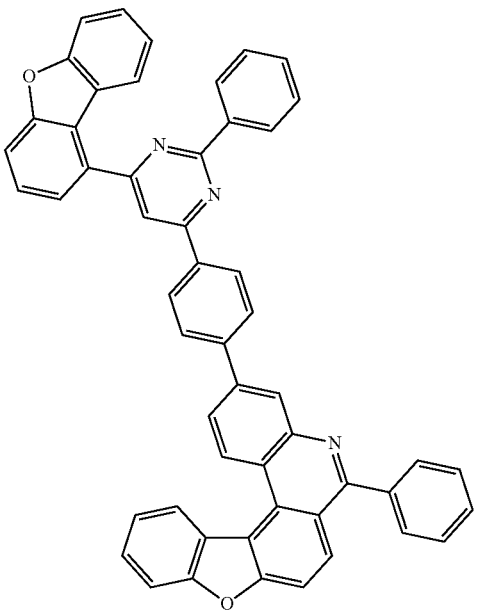

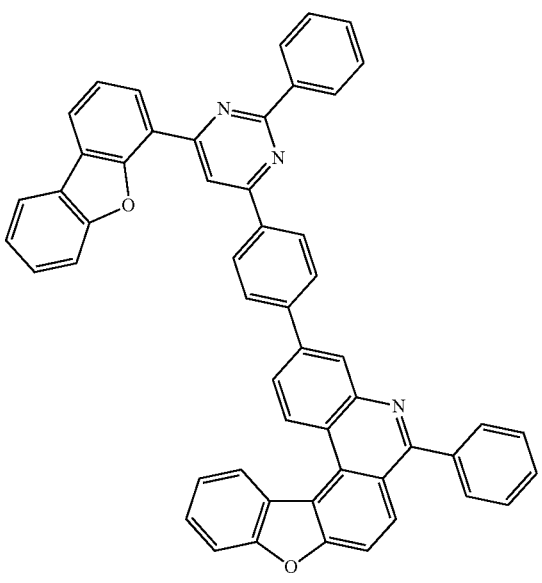
250
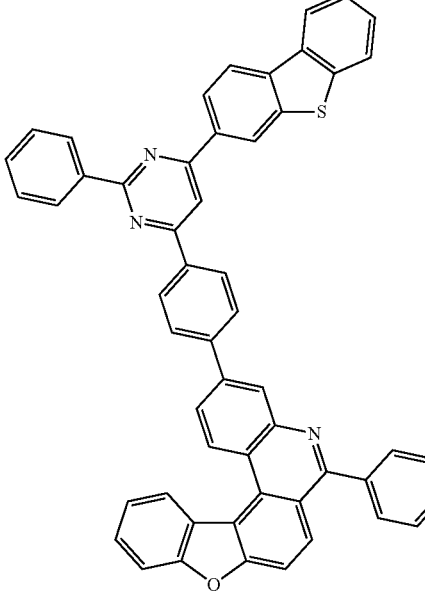
252
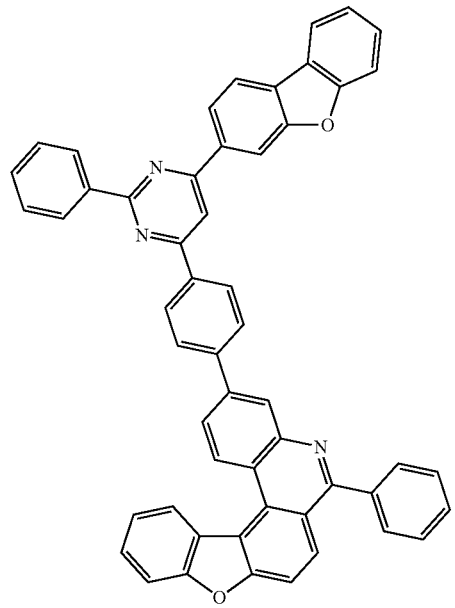
251
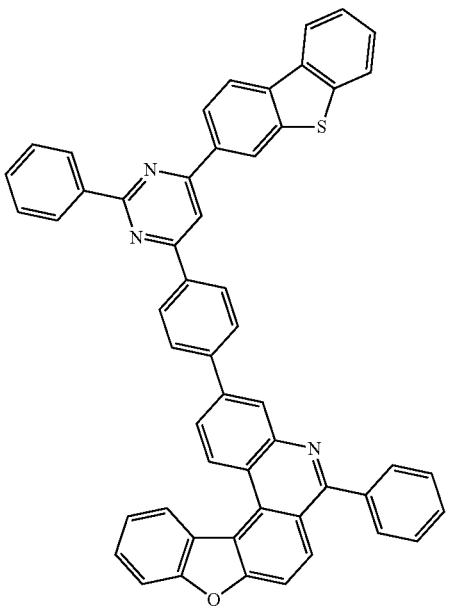
253

115
-continued
254
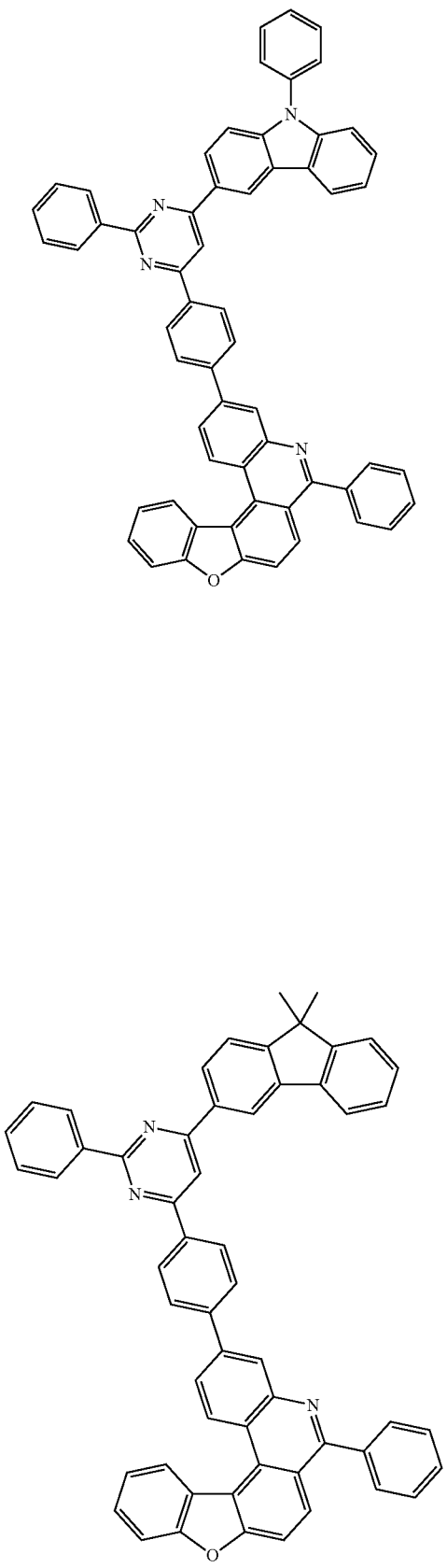
255
116
-continued
256
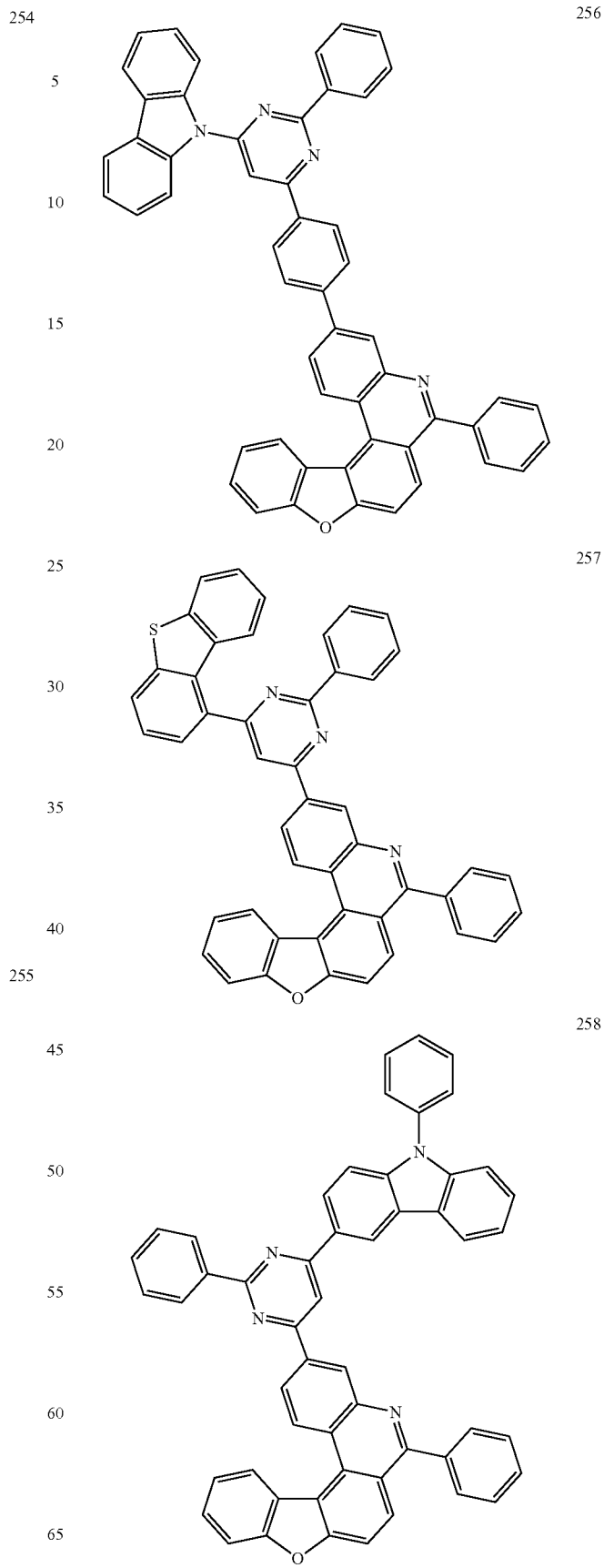
257
258

259
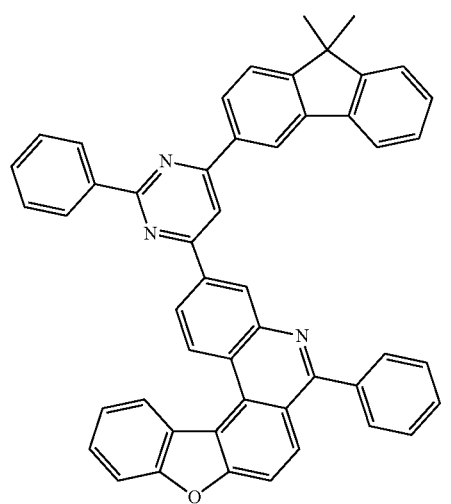
260
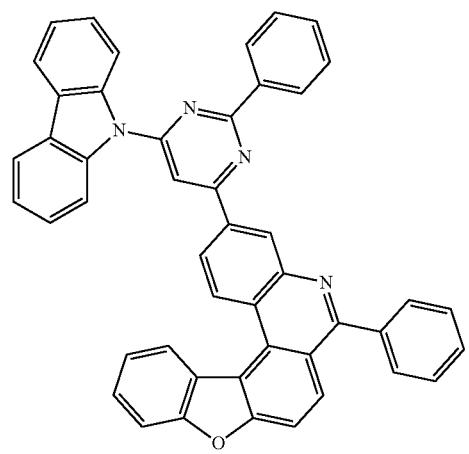
261
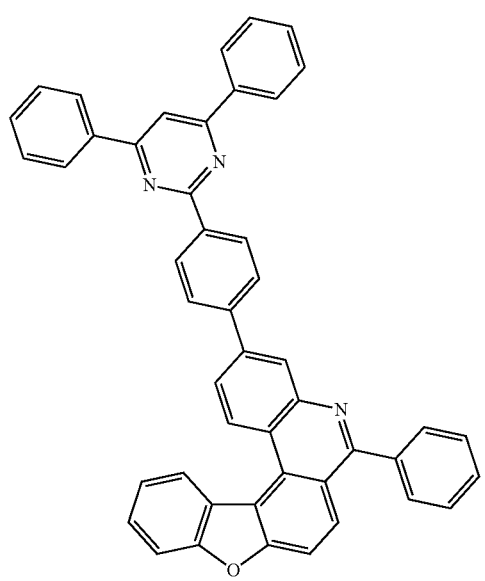
262
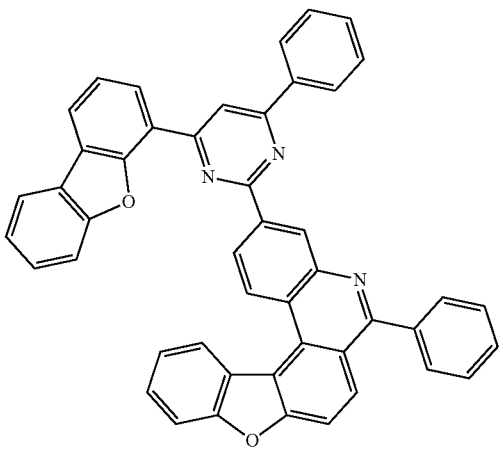
263
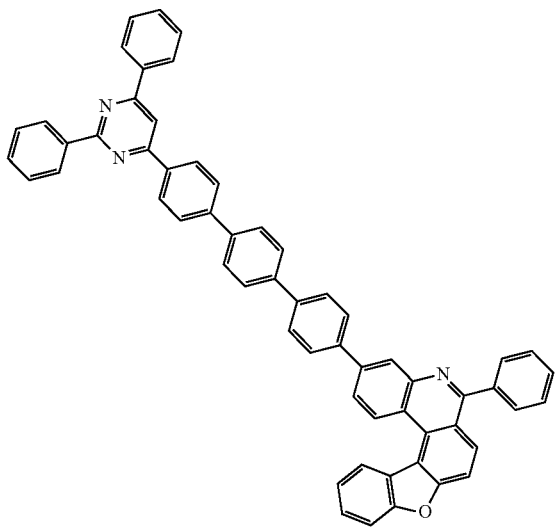
264

265
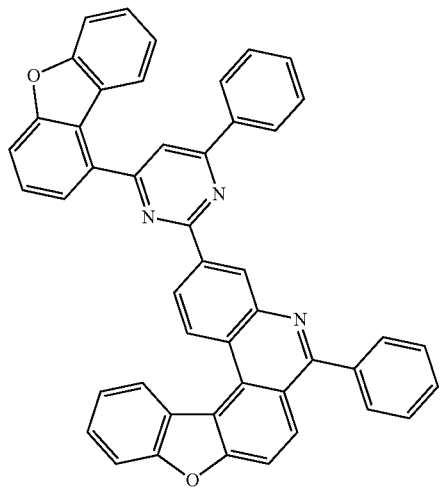
266
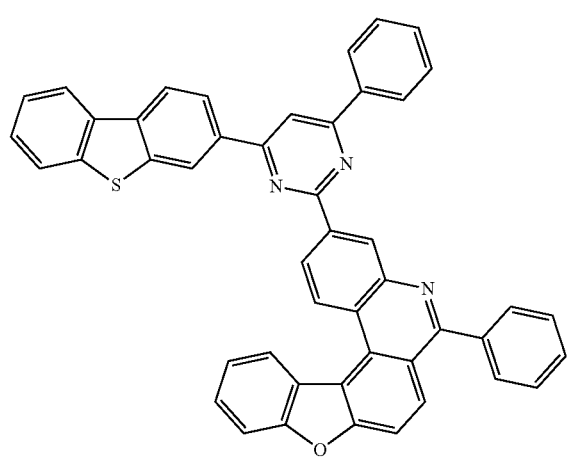
267
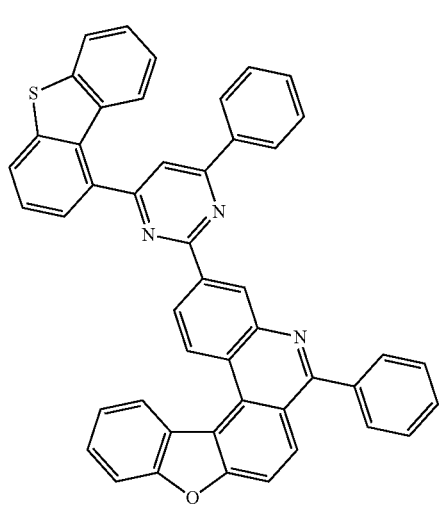
268
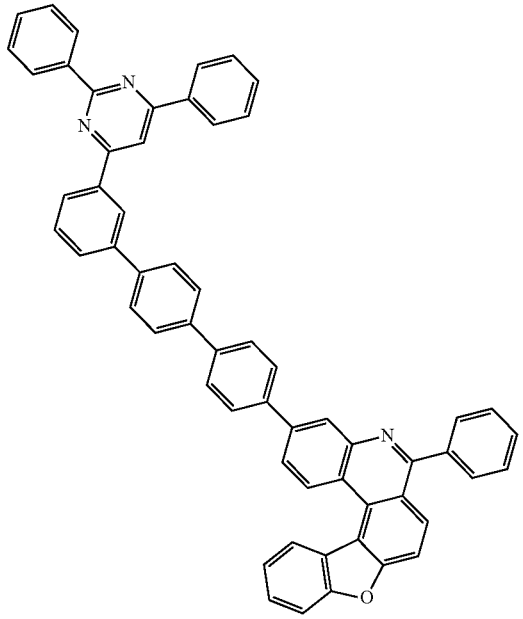
269
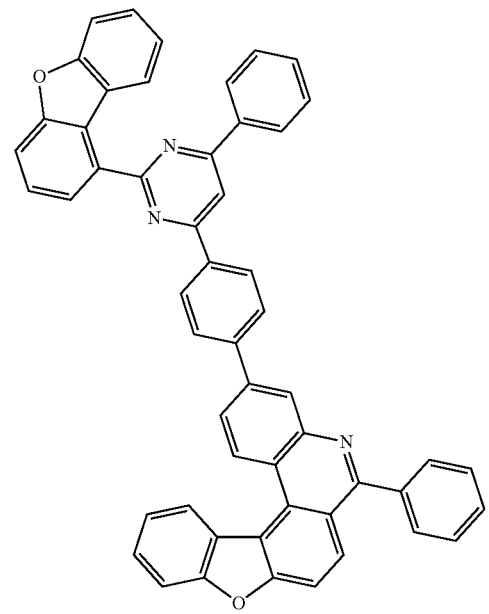

121
-continued
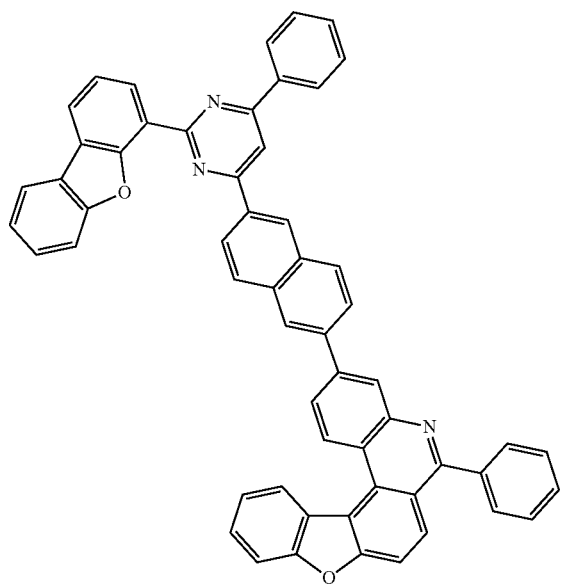
270
122
-continued
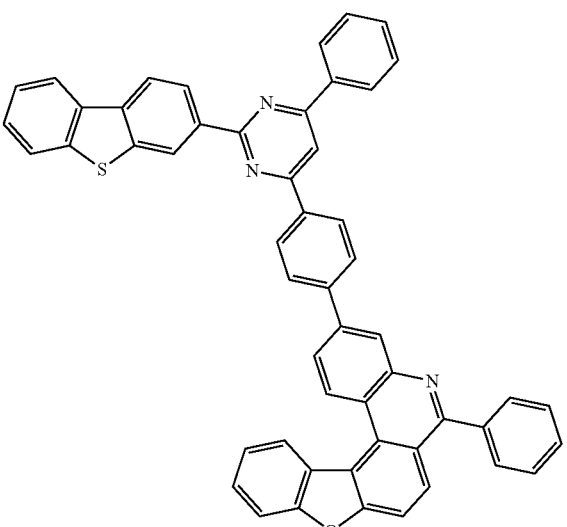
272
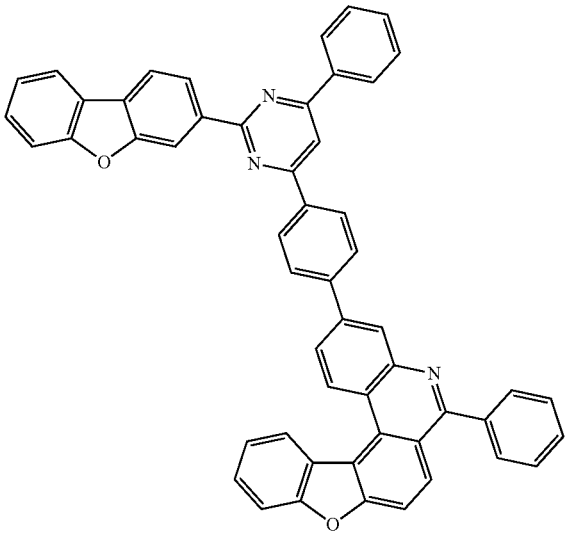
271
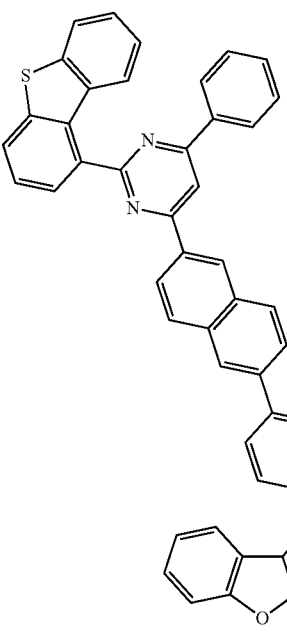
273

274
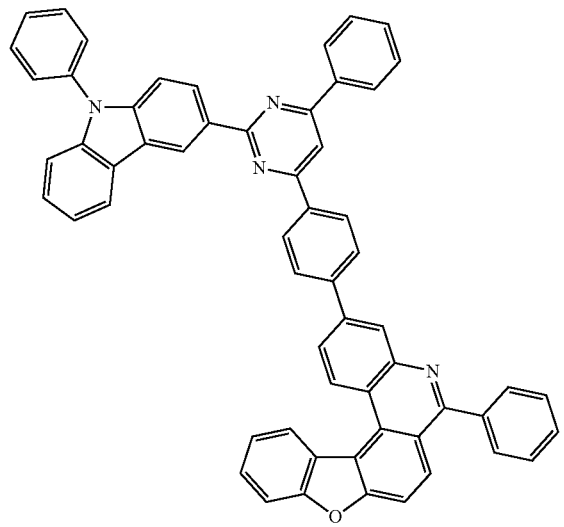
275
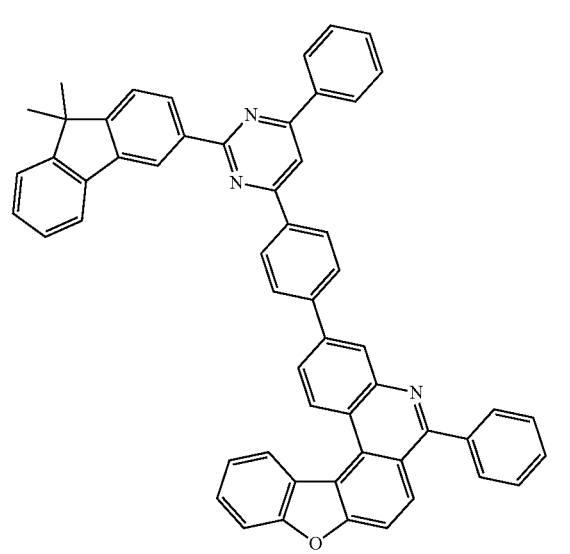
276
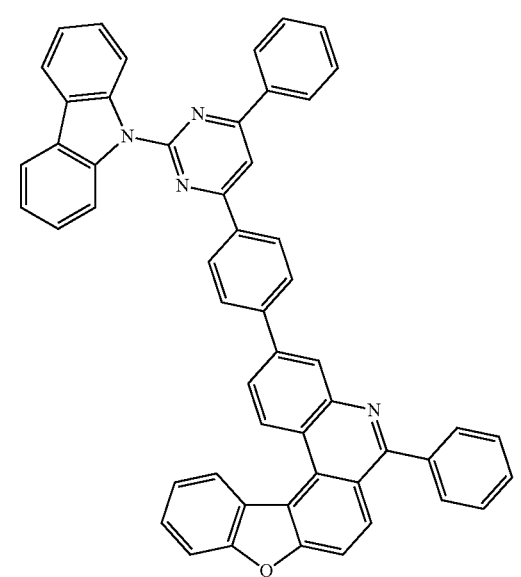
277
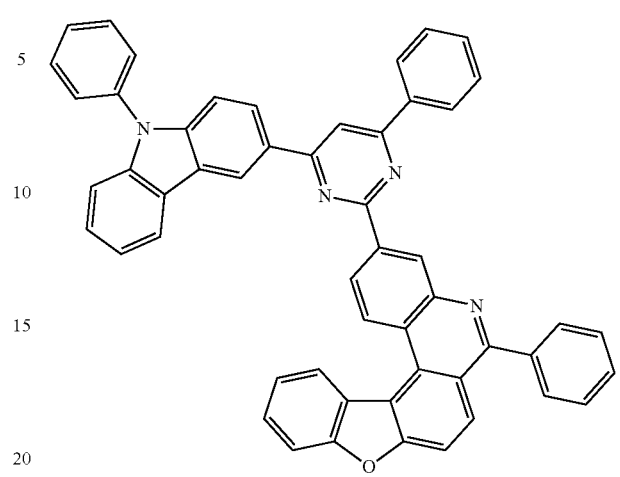
278
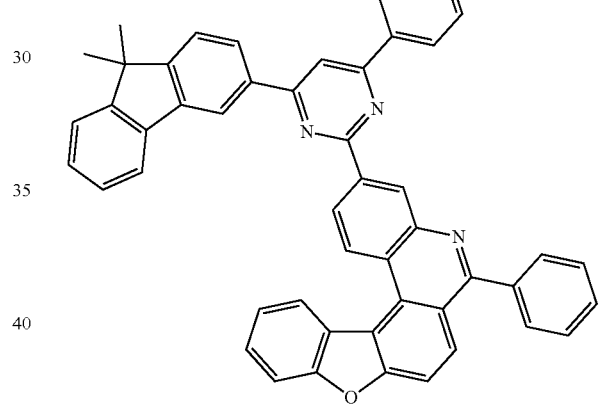
279
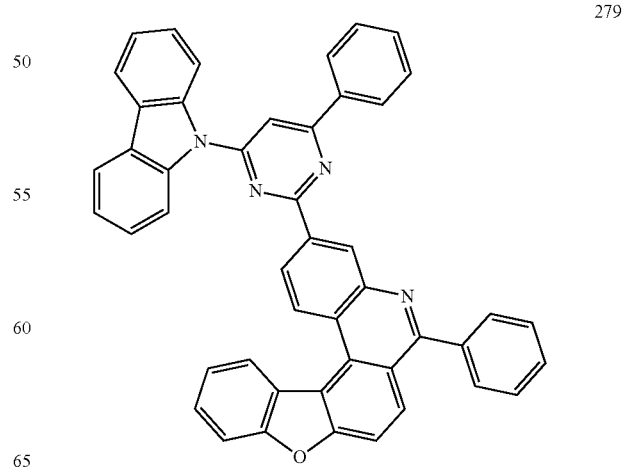

280
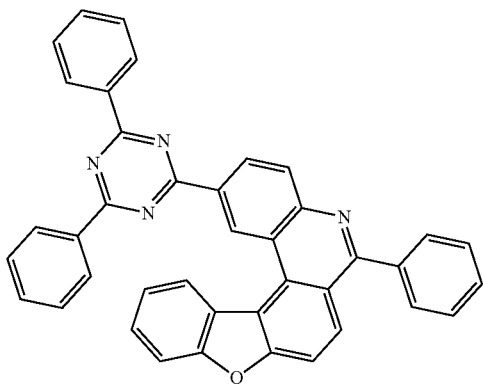
281
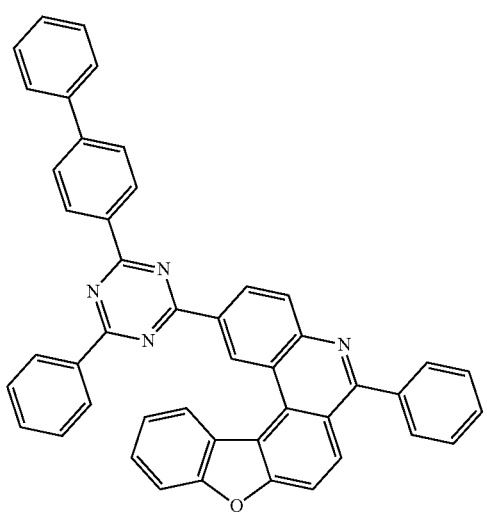
282
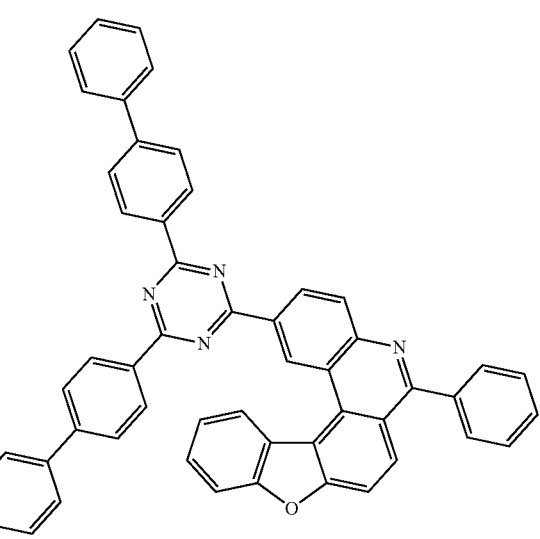
283
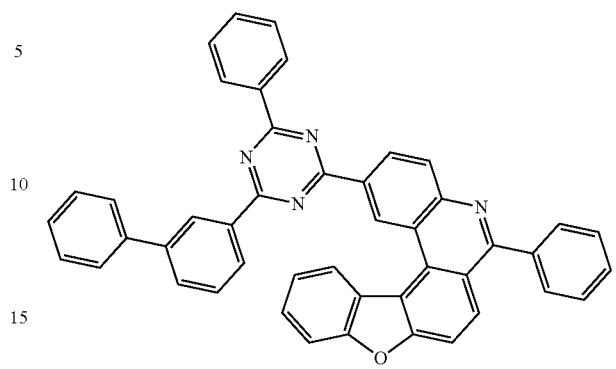
284
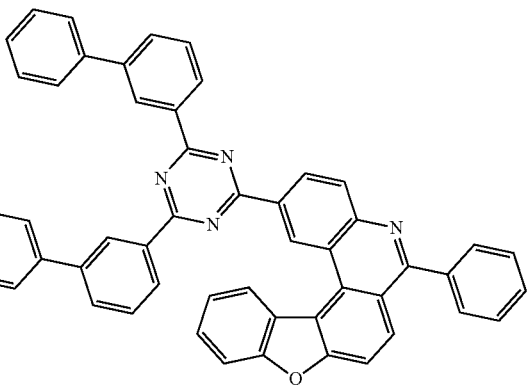
285
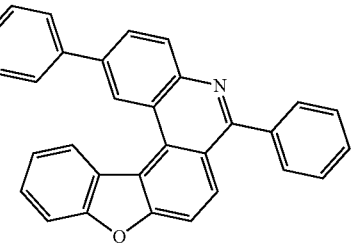

286
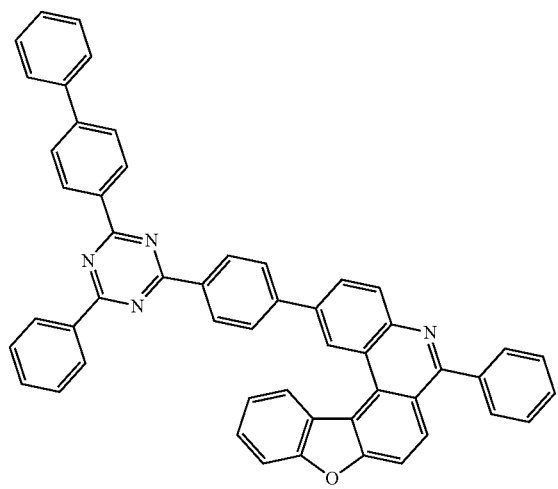
287
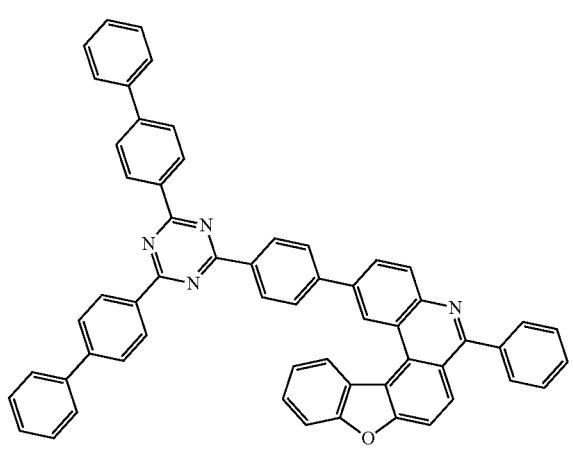
288
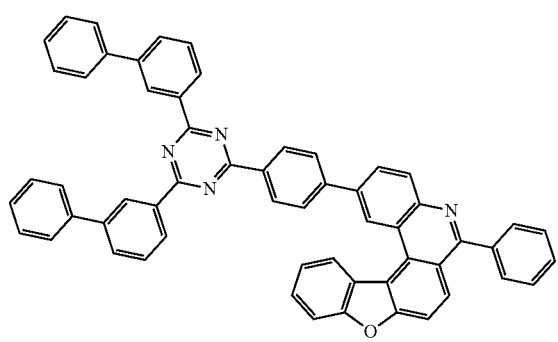
289
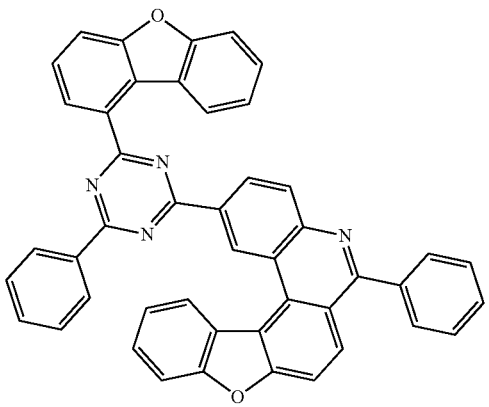
290
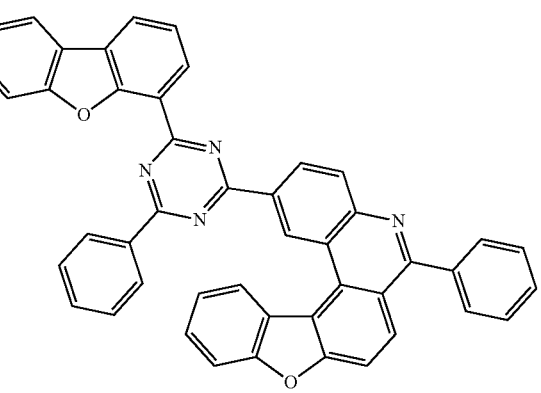
291
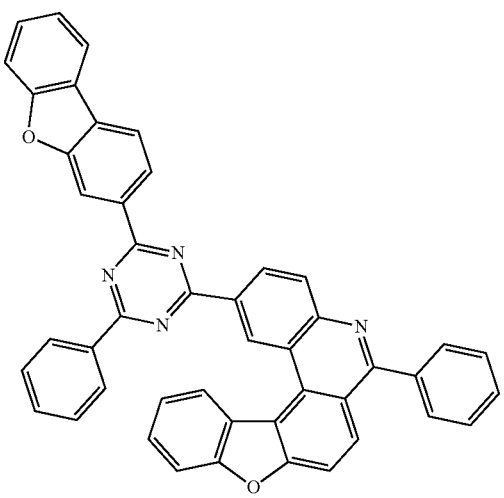

292
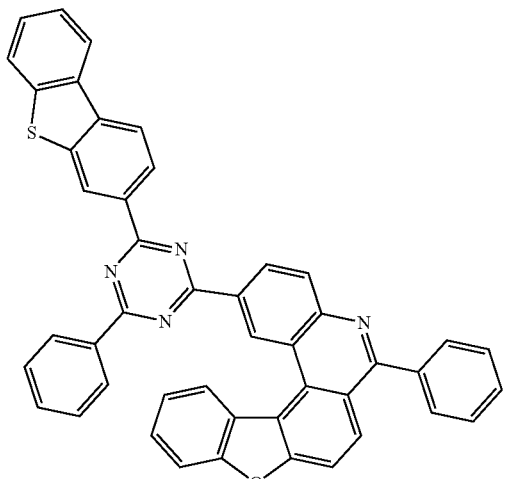
293
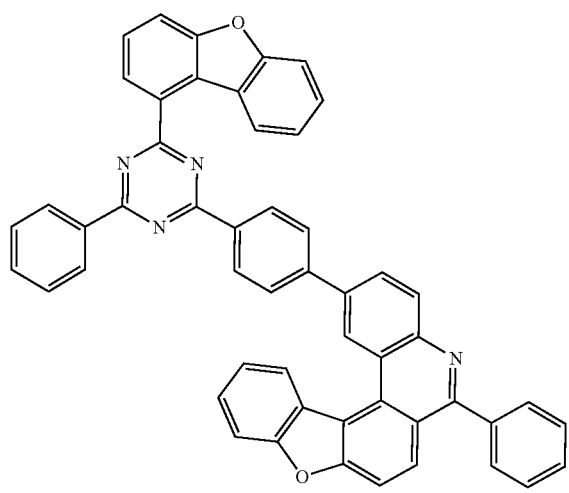
294
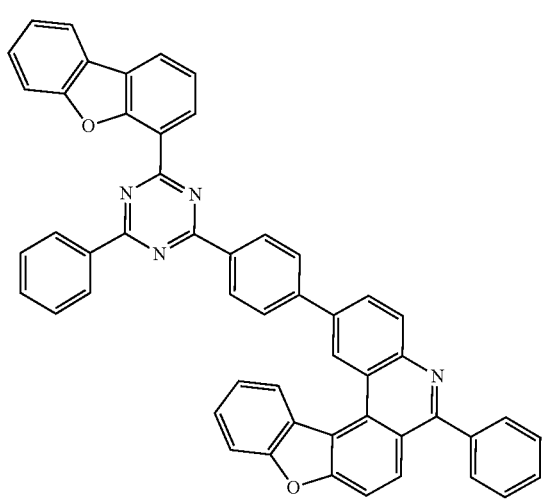
295
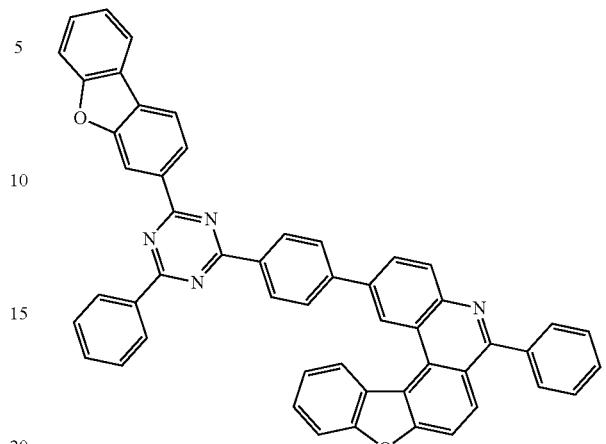
296
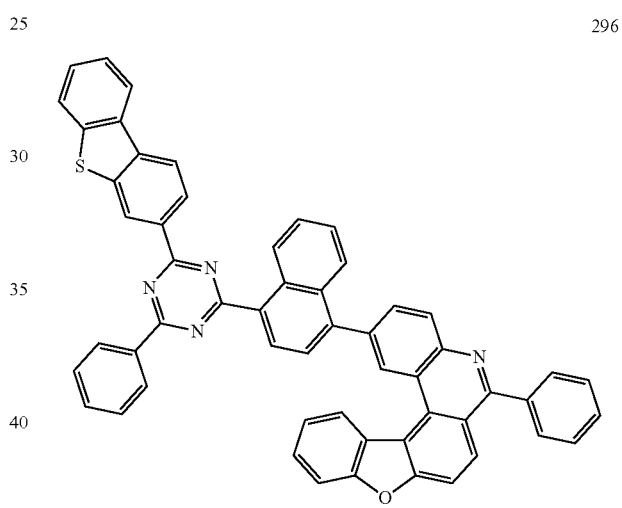
297
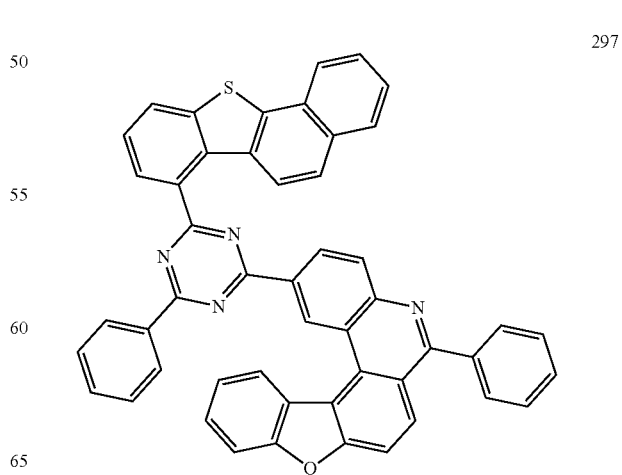

298
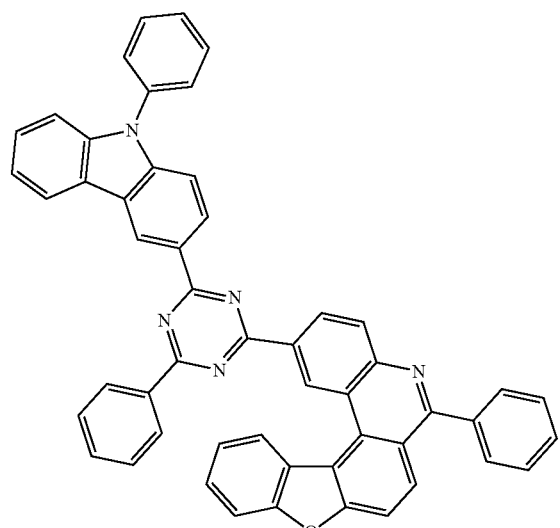
299
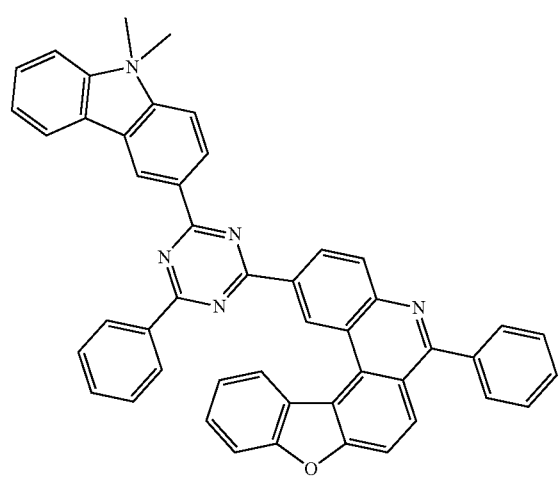
300
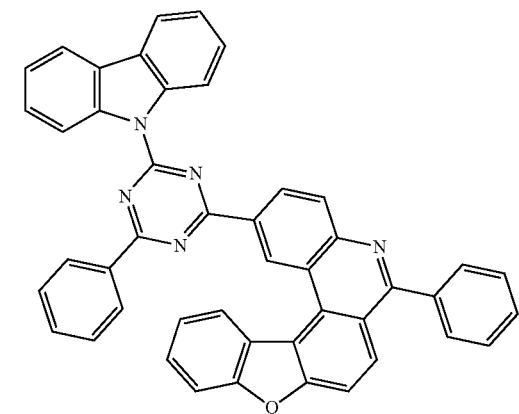
301
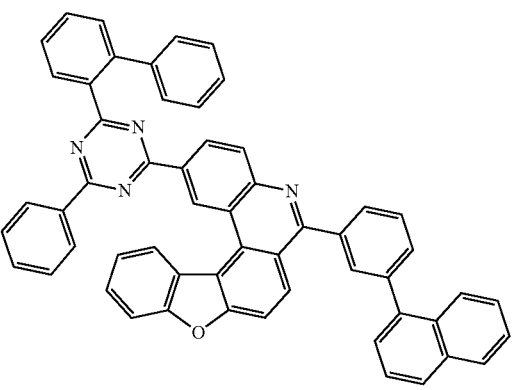
302
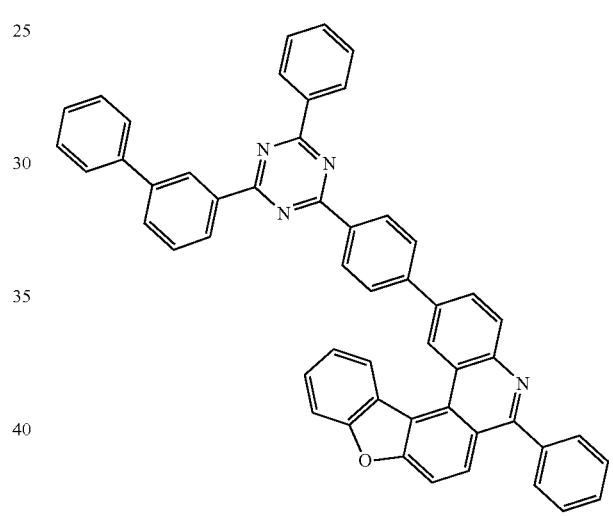
303
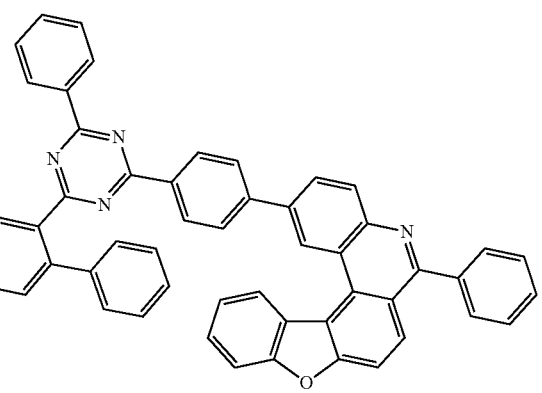

304
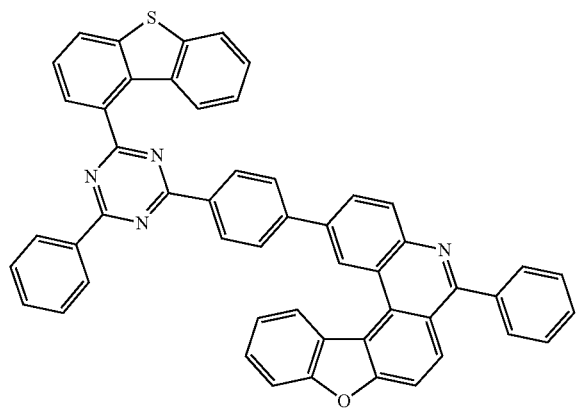
305
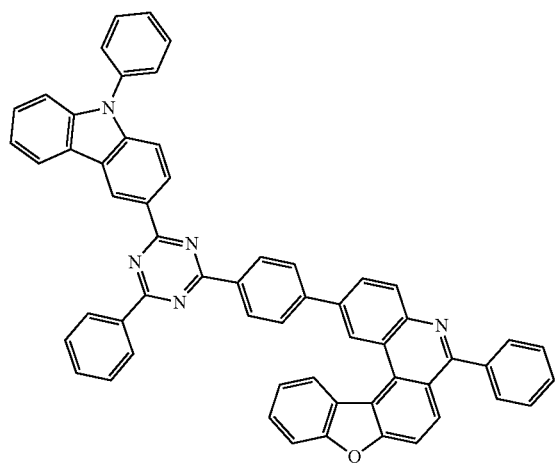
306
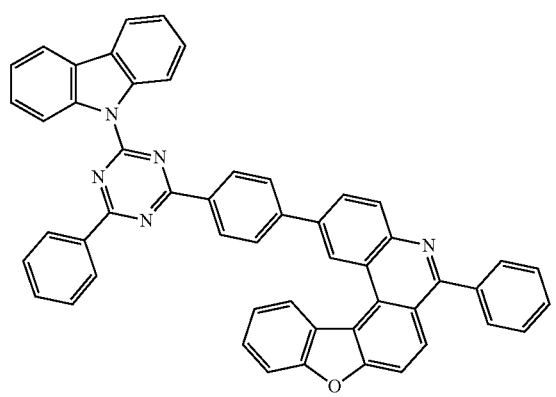
307
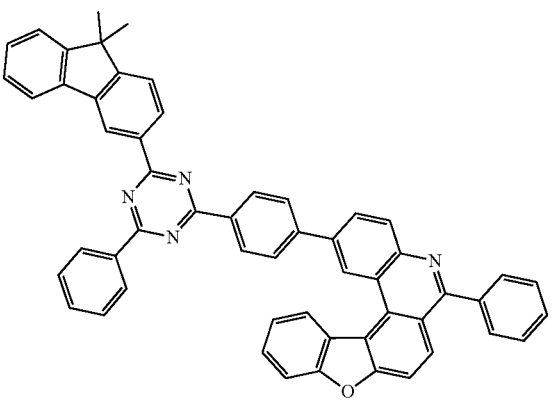
308
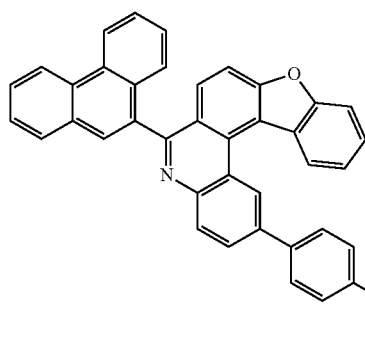
309
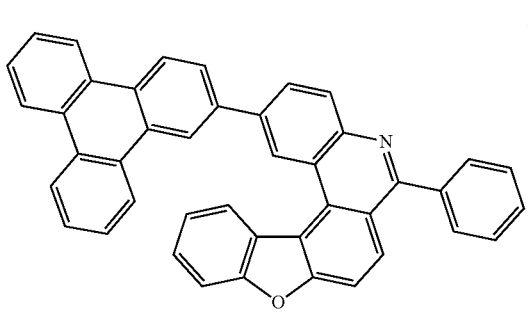
310
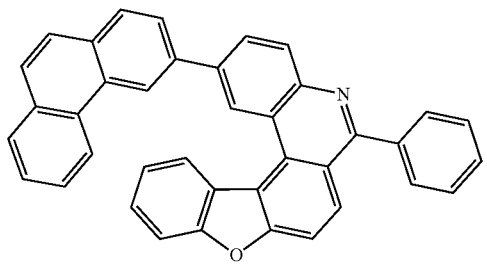

311
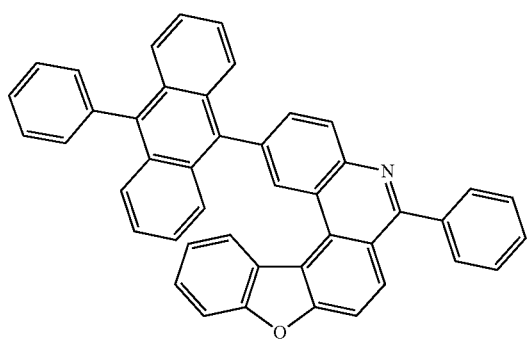
312
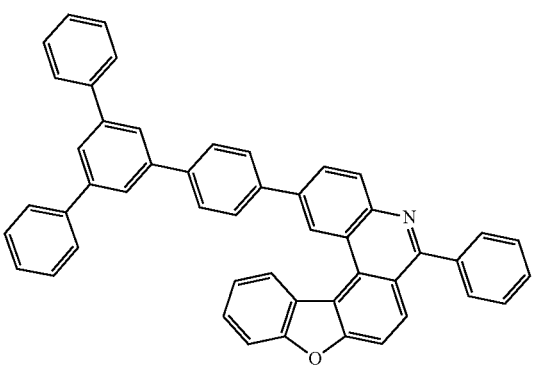
313
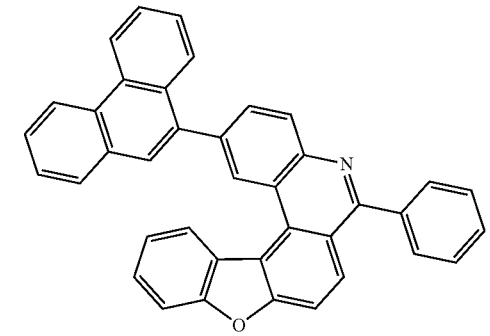
314
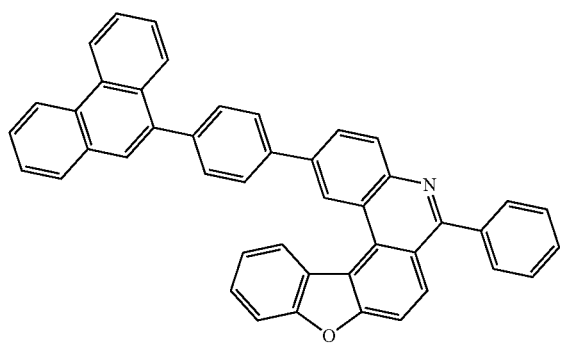
315
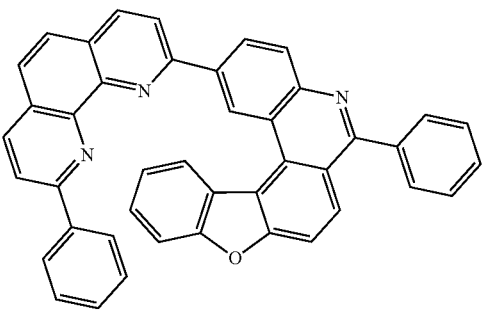
316
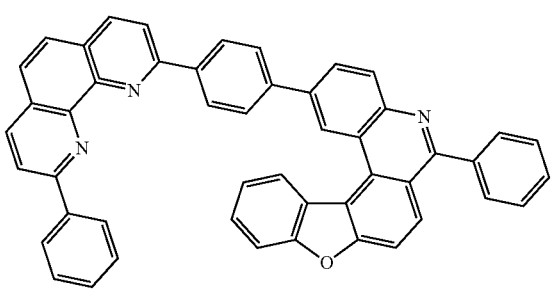
317
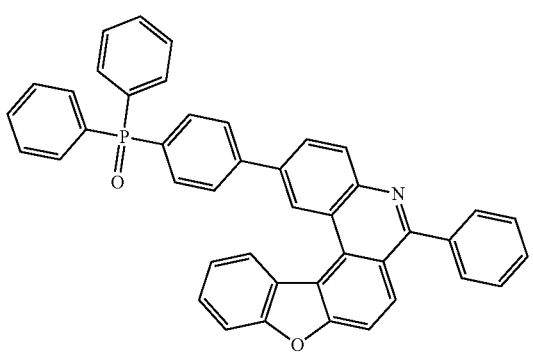
318
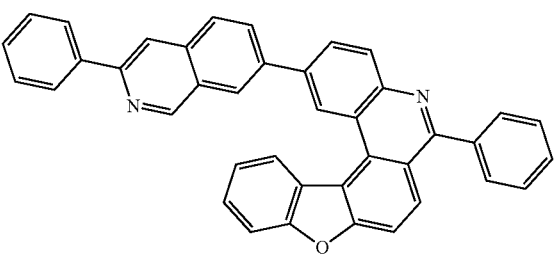

319
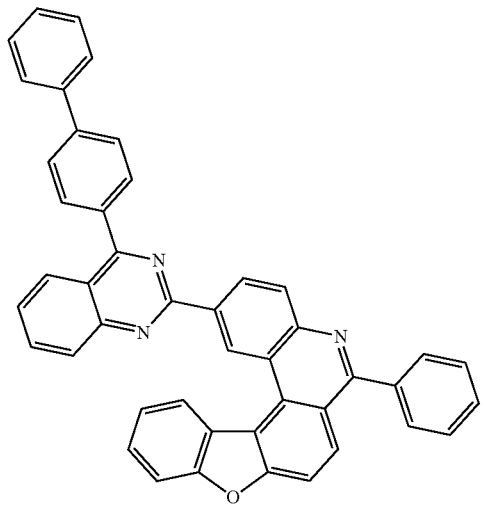
320
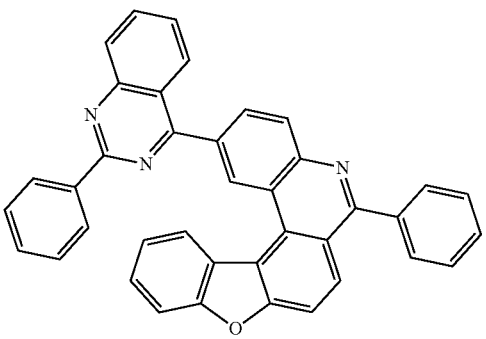
321
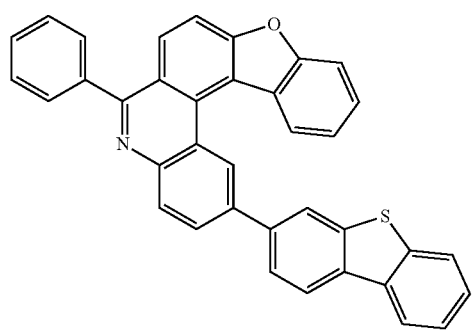
322
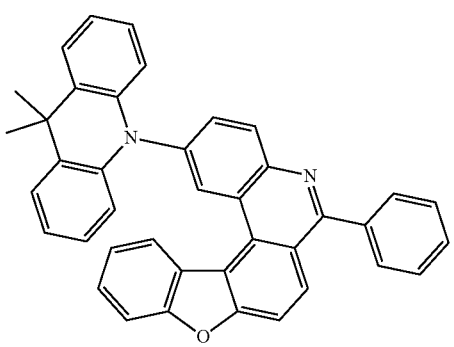
323
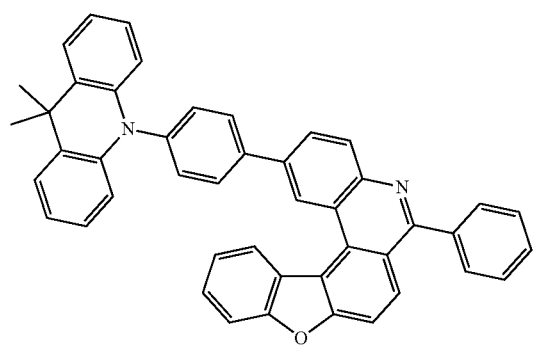
324
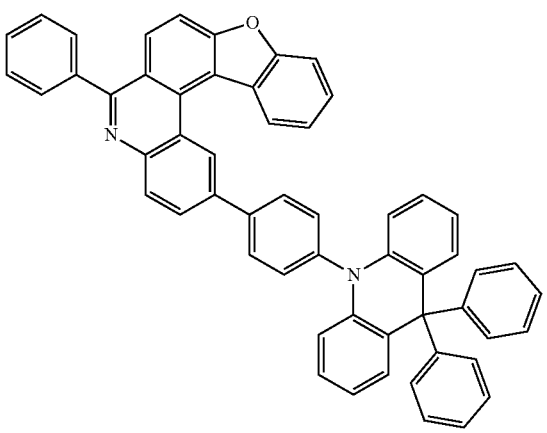

-continued
325
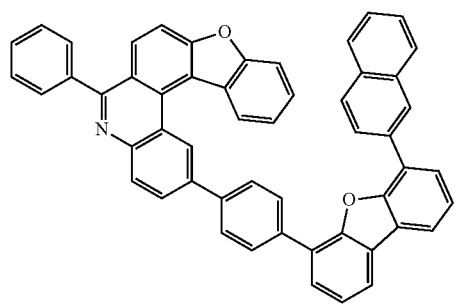
326
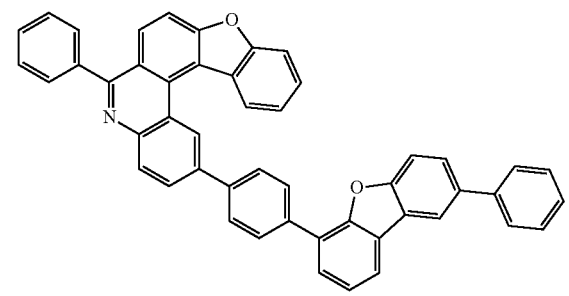
327
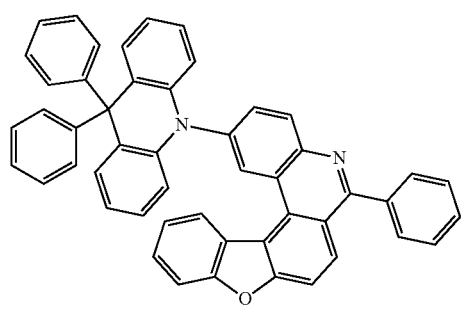
328
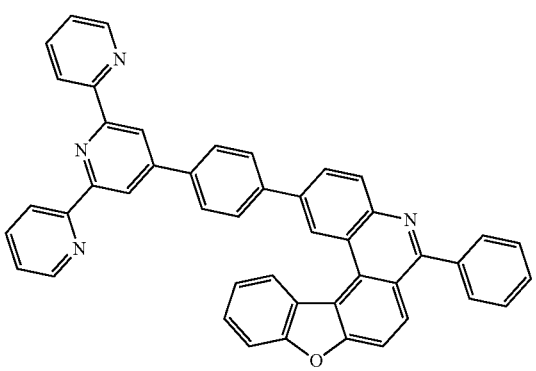
329
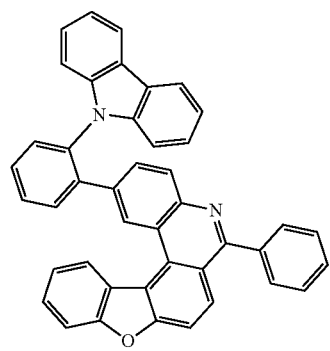
330
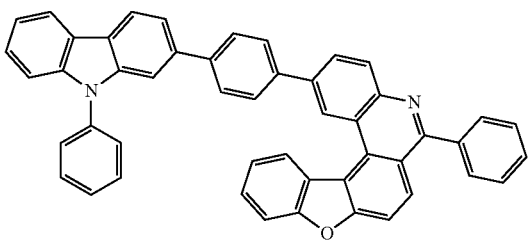
331
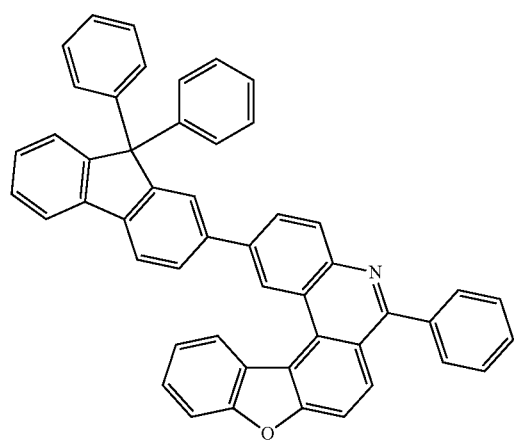
332
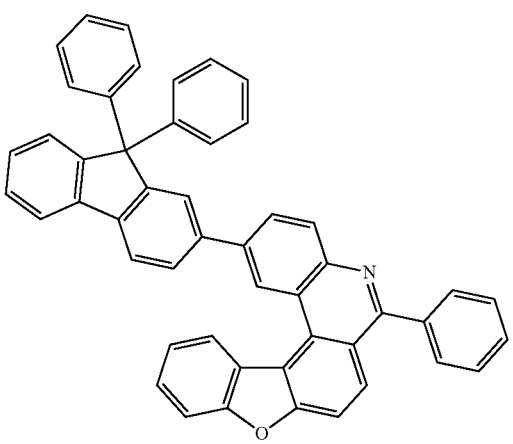

-continued
333
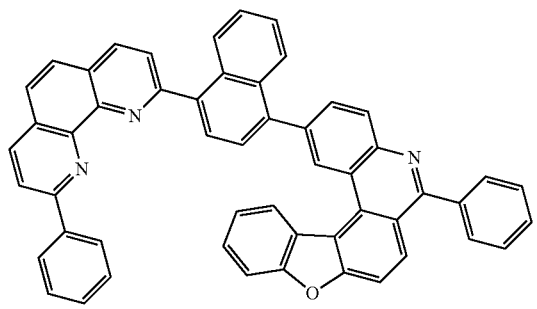
334
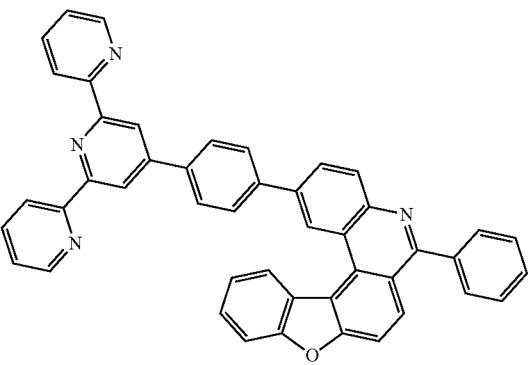
335
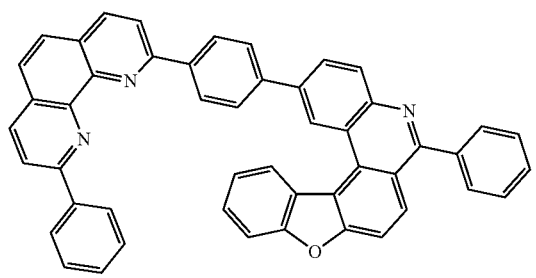
336
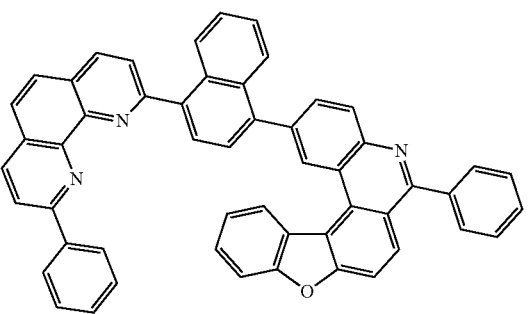
337
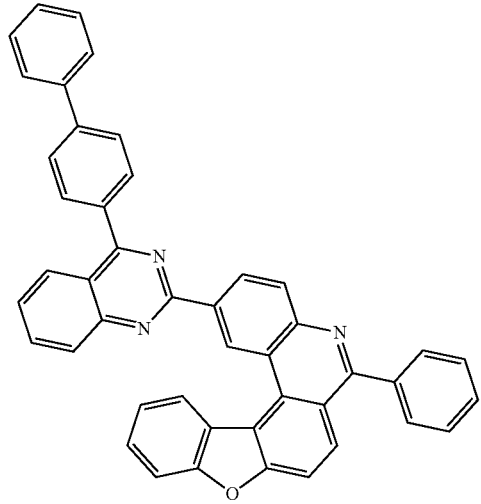
338
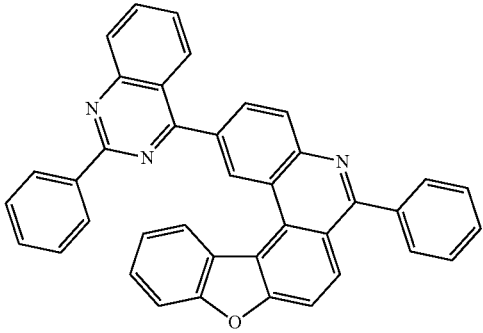
339
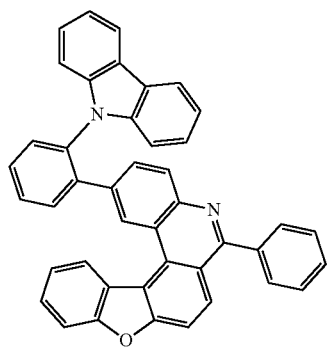
340
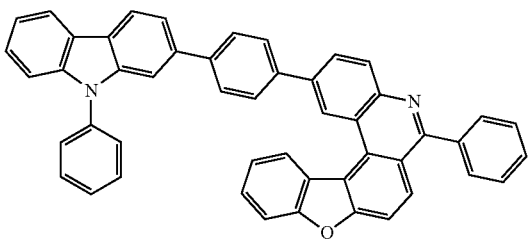

-continued
341
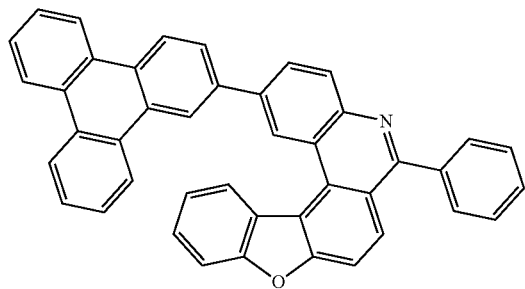
342
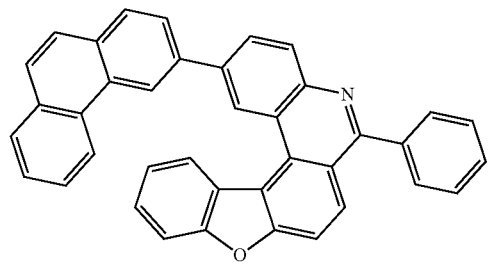
343
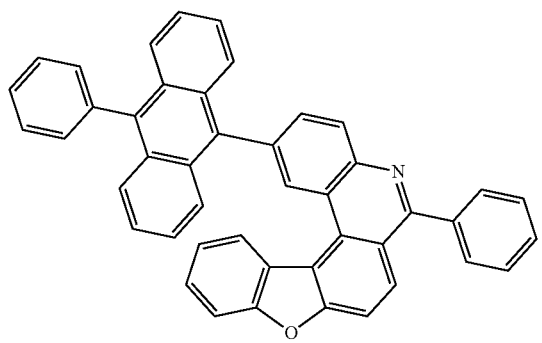
344
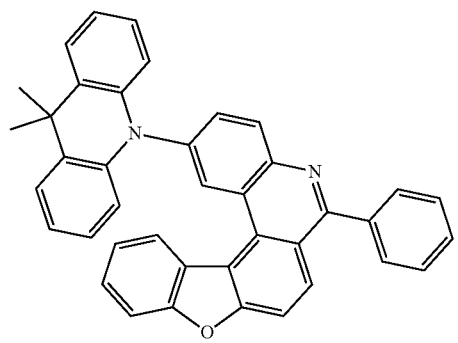
345
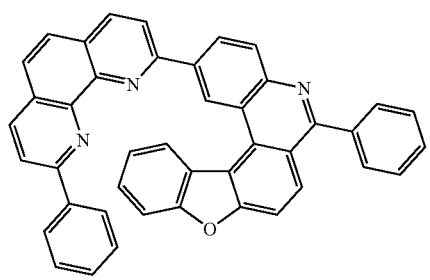
346
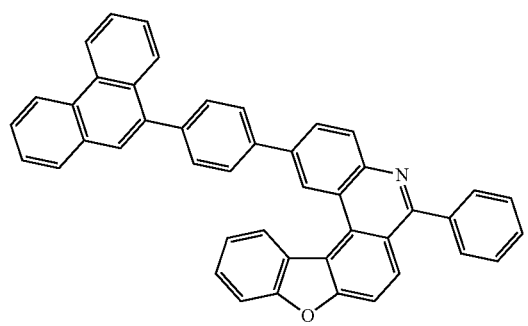
347
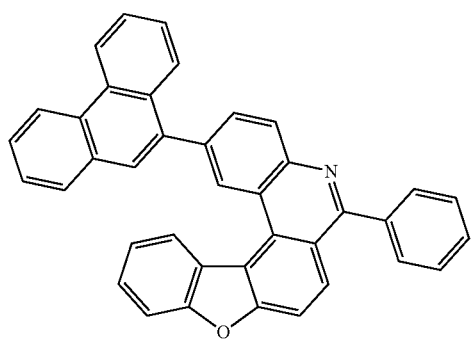
348
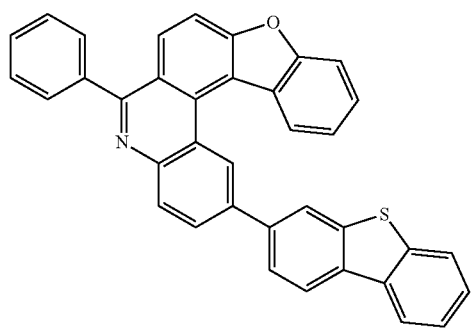
349
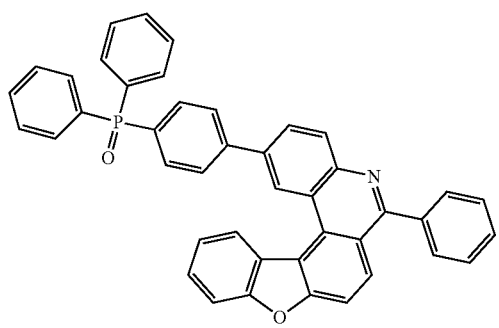
350
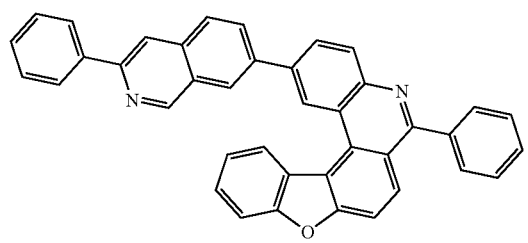

-continued
351
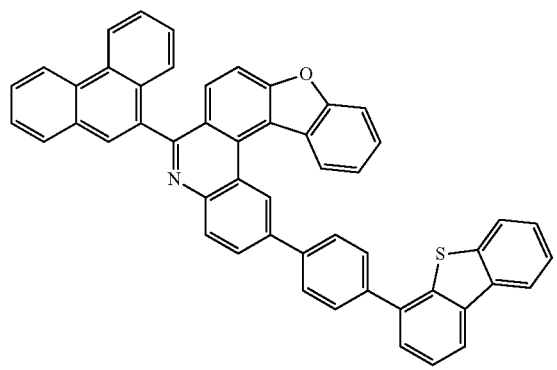
352
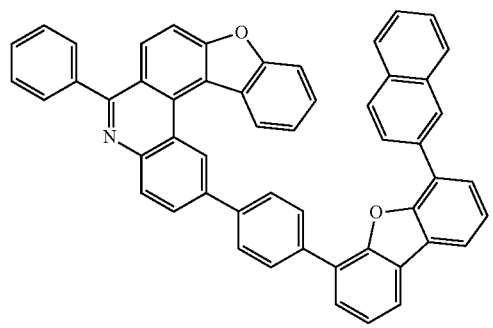
353
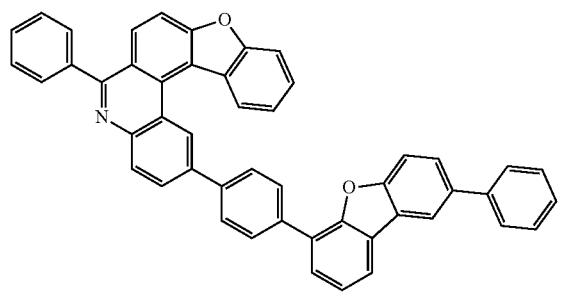
354
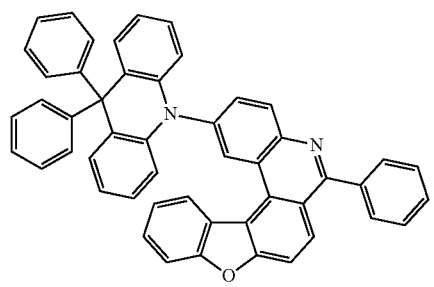
355
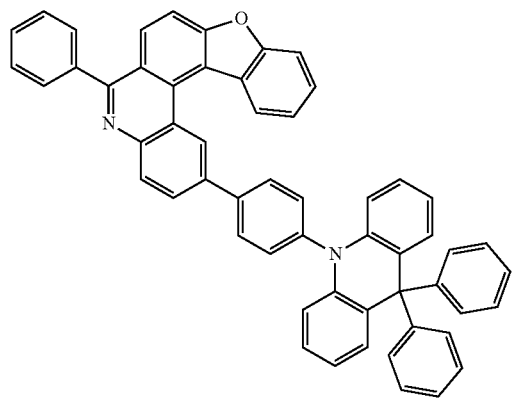
356
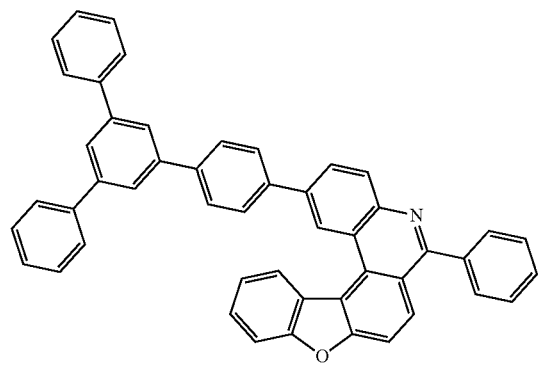

357
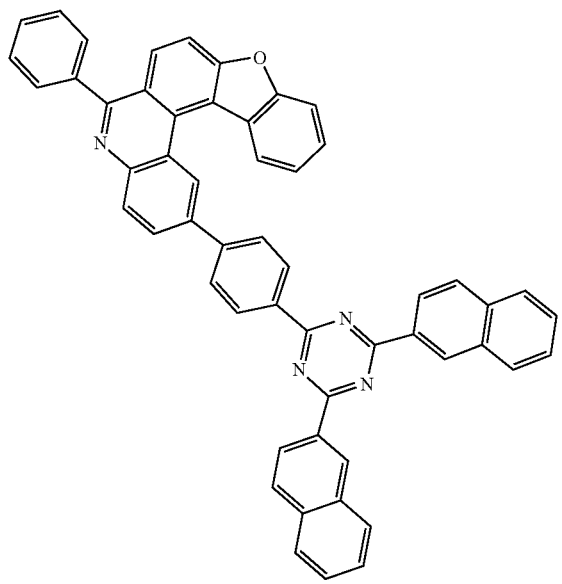
358
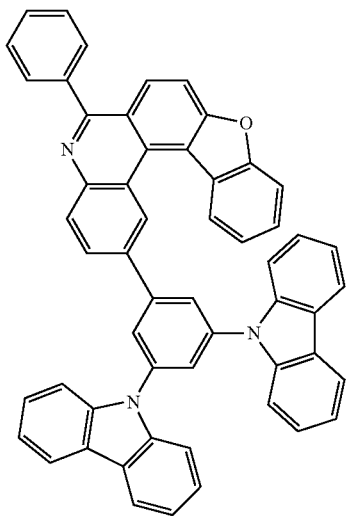
359
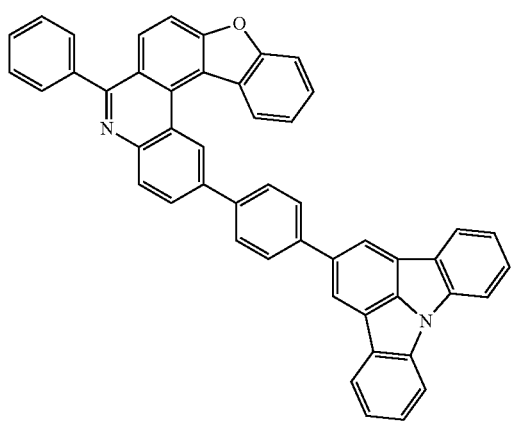
360
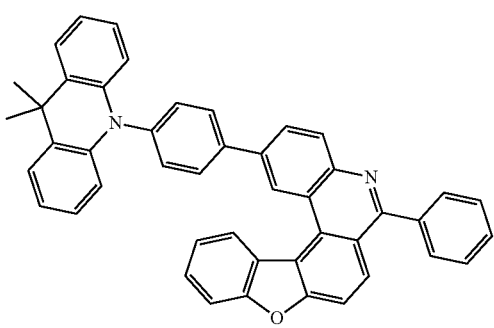
361
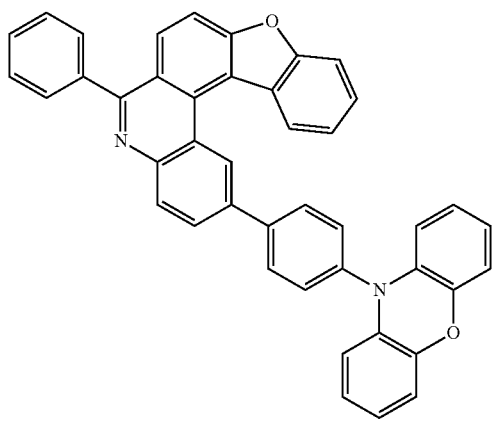
362
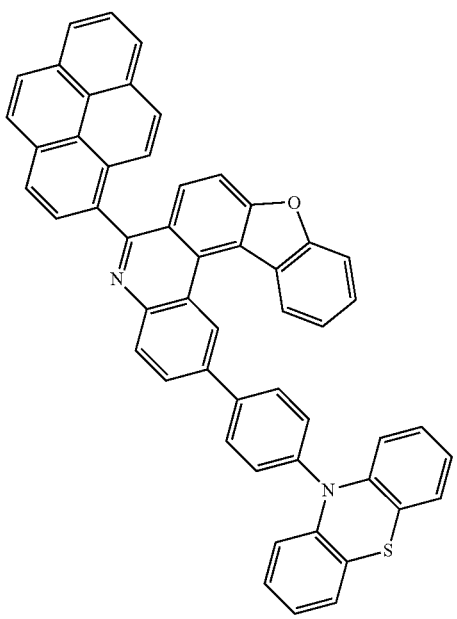

-continued
363
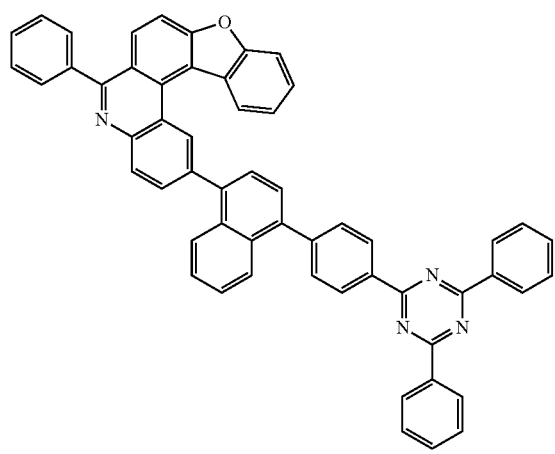
364
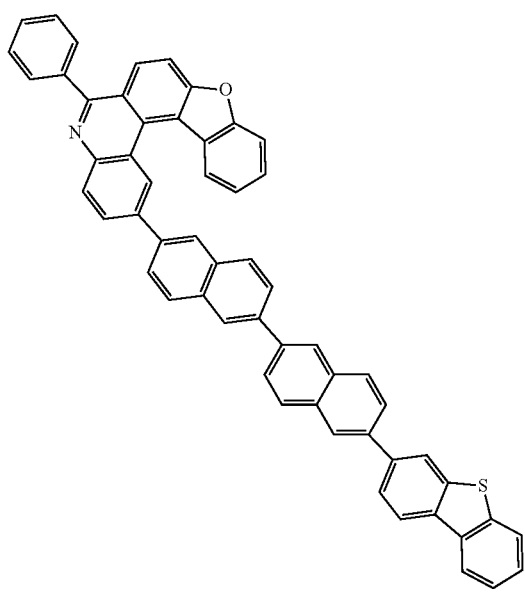
365
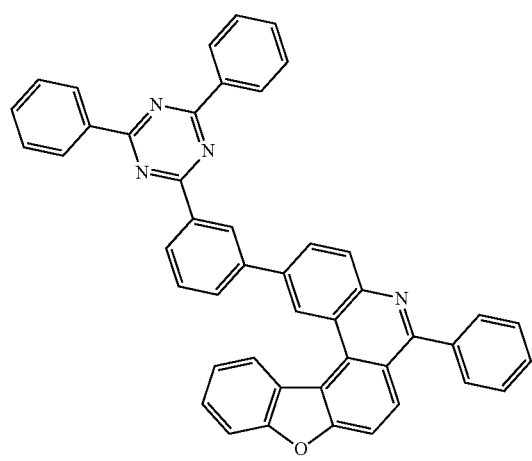
366
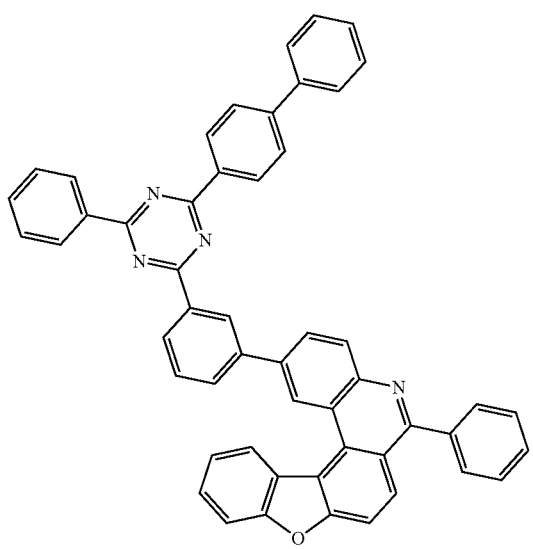
367
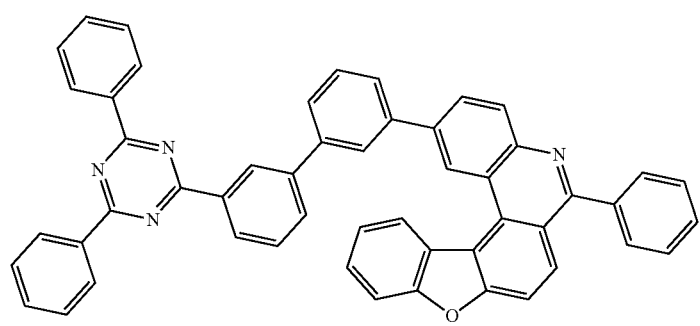

368
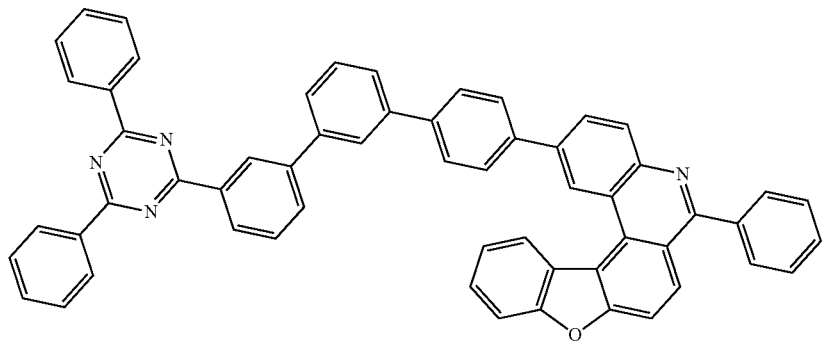
369
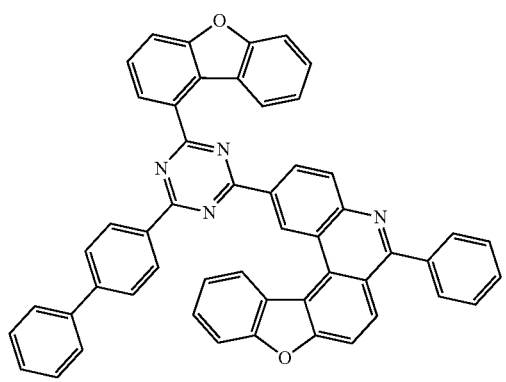
370
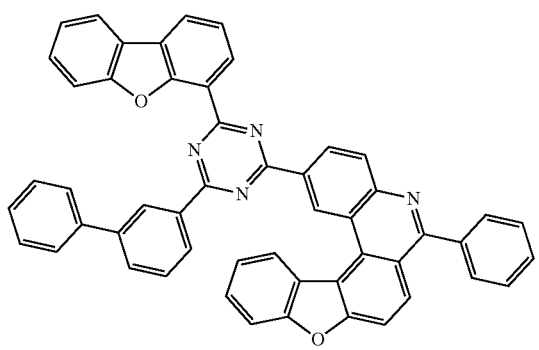
371
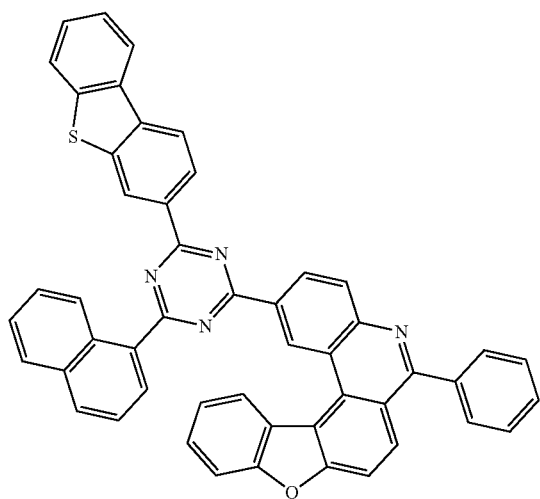
372
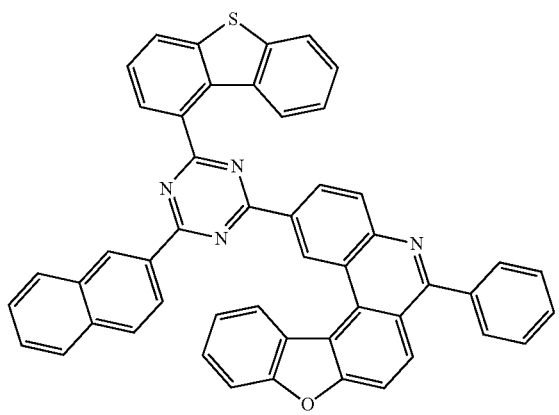

-continued
373
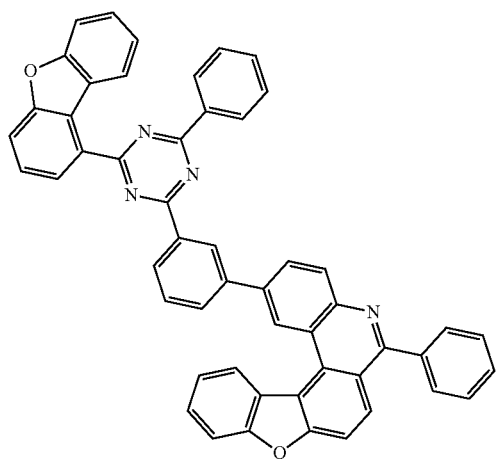
374
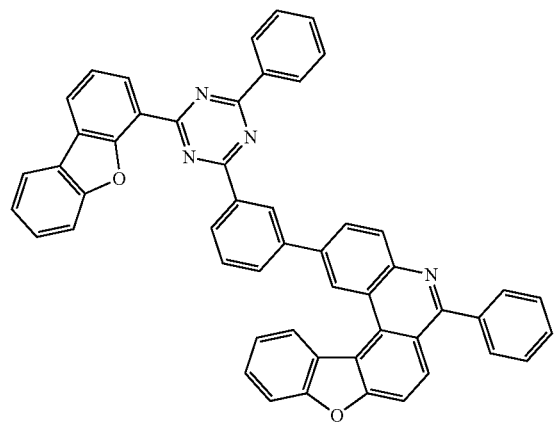
375
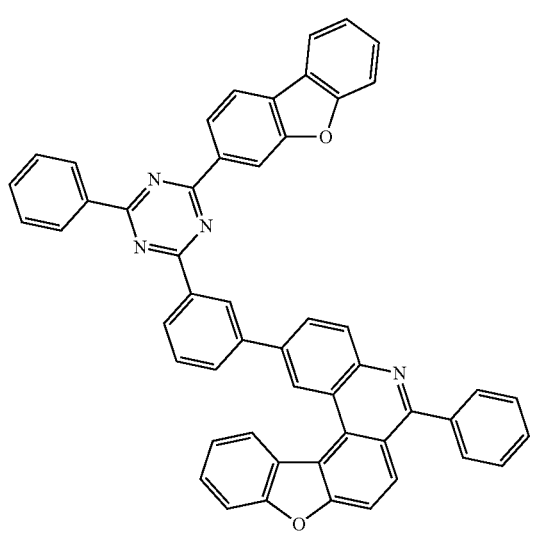
376
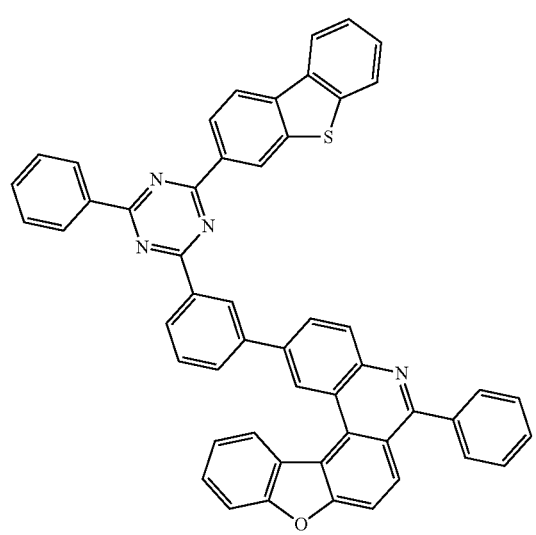
377
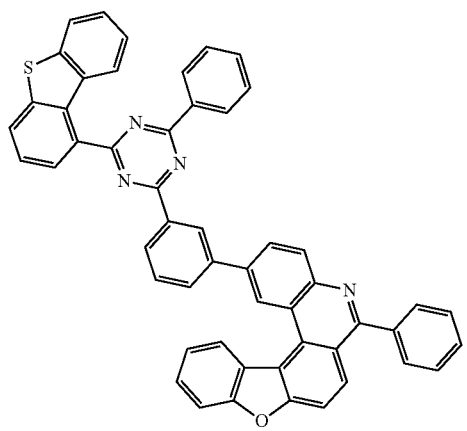
378
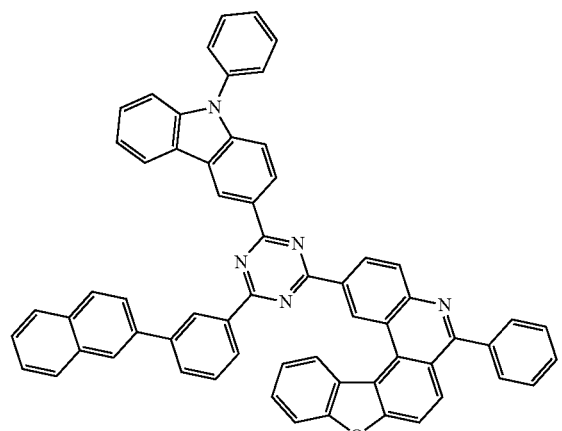

-continued
379
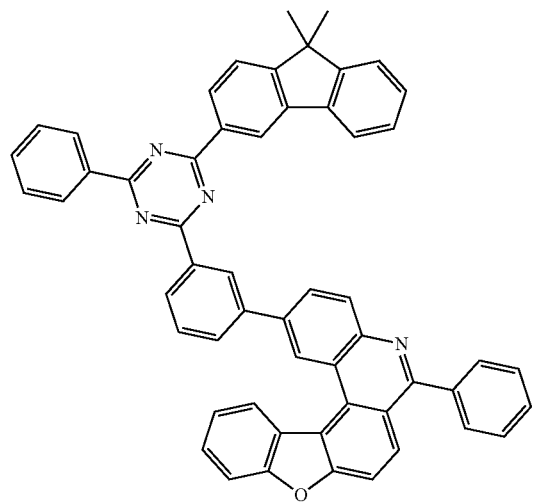
380
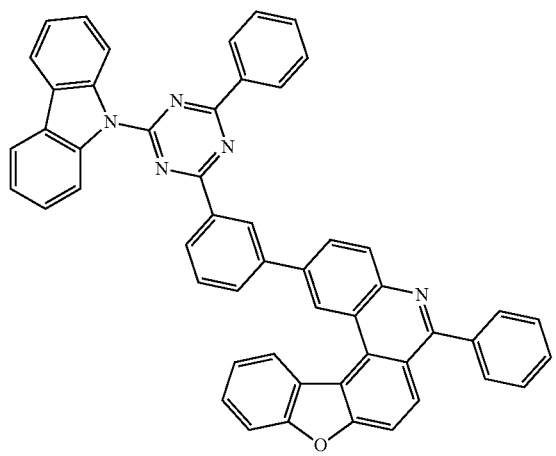
381
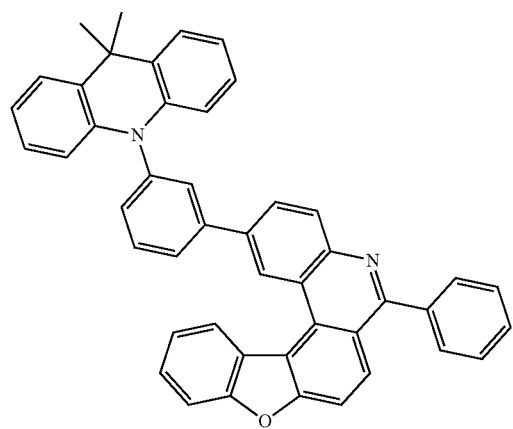
382
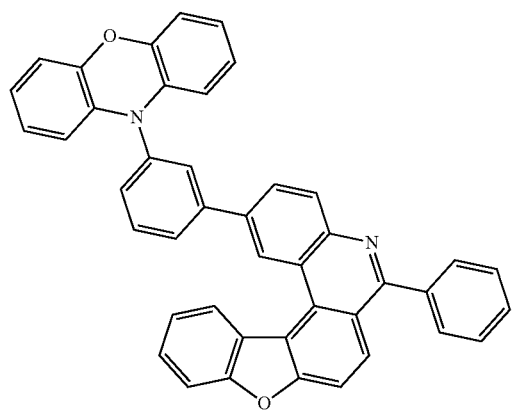
383
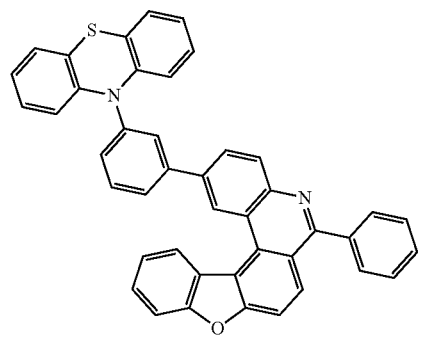
384
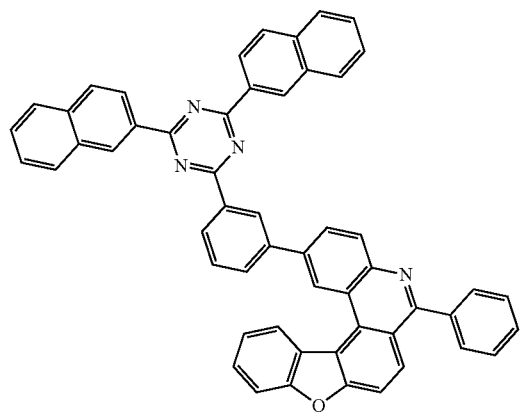

-continued
385
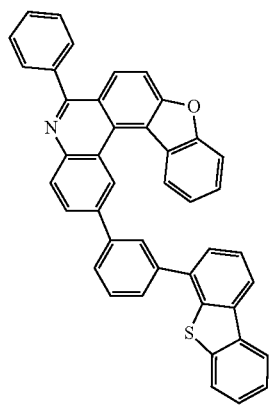
386
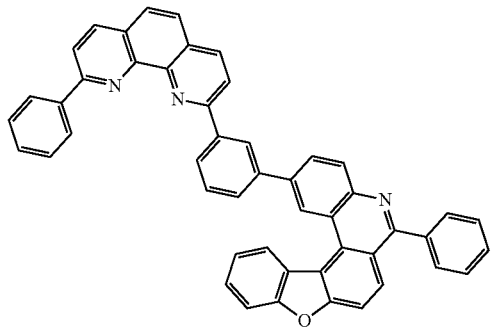
387
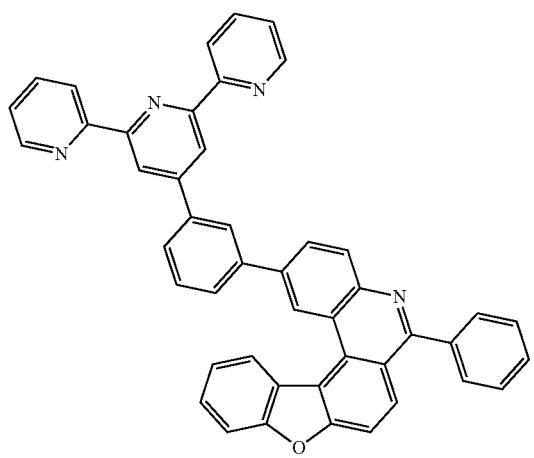
388
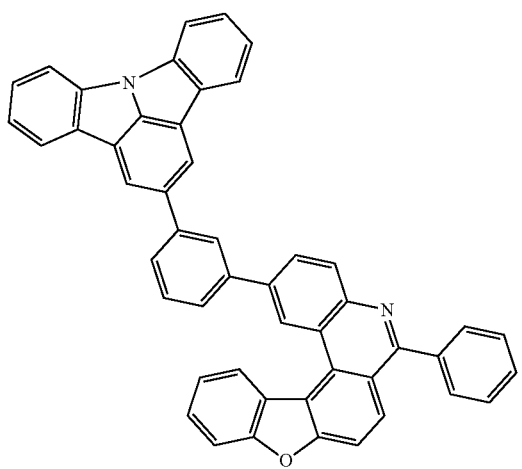
389
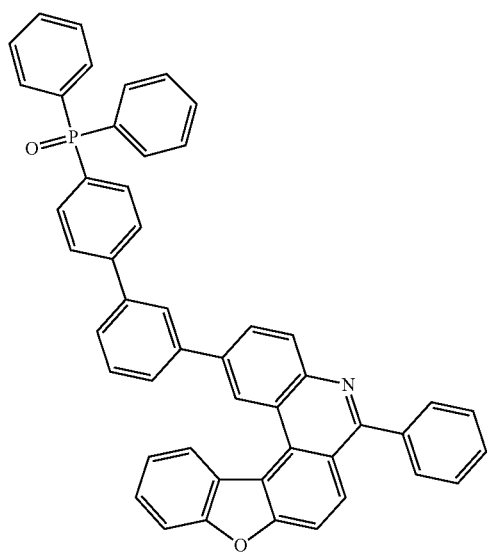
390
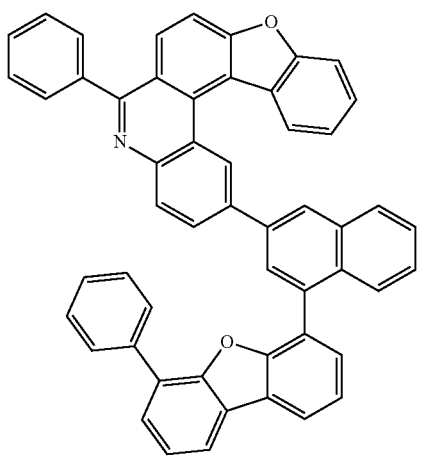

-continued
391
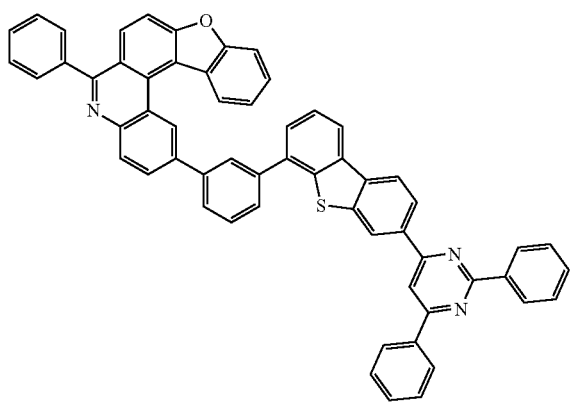
392
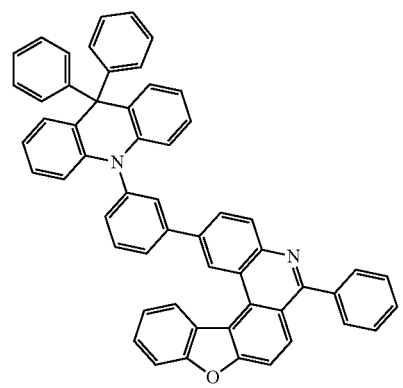
393
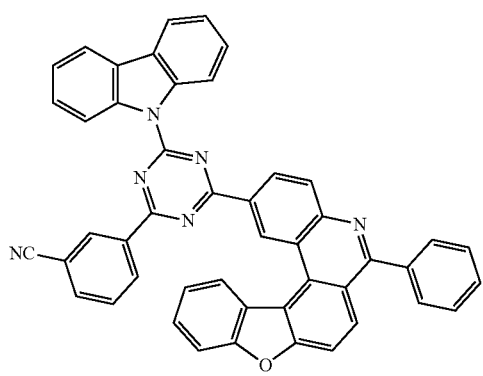
394
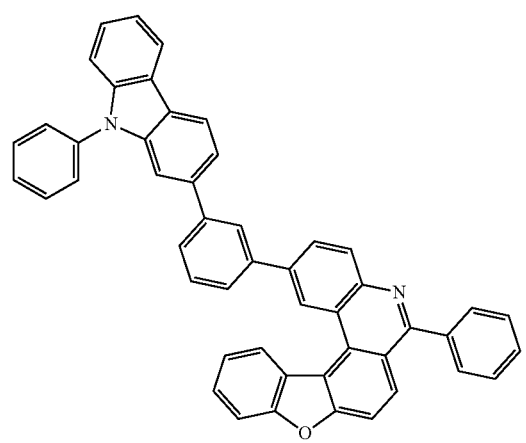
395
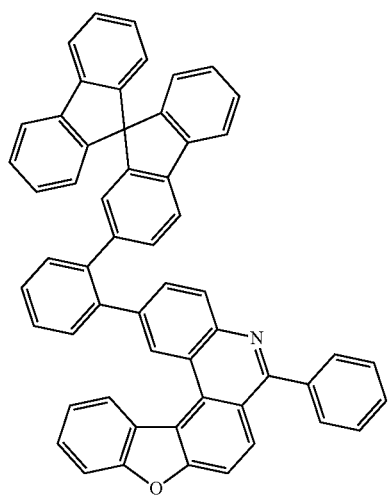
396
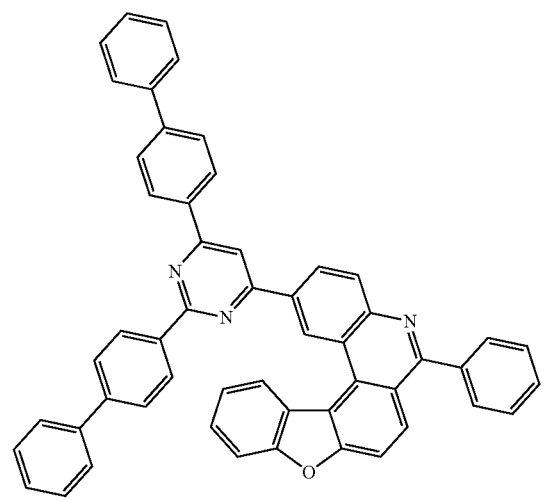

-continued
397
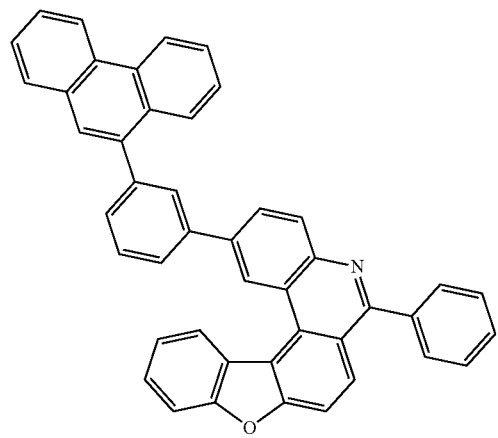
398
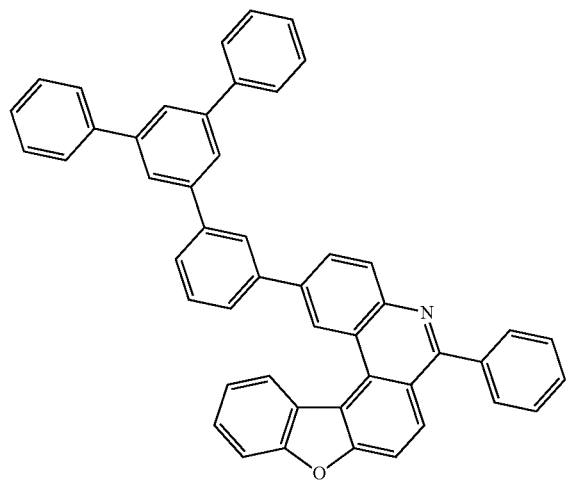
399
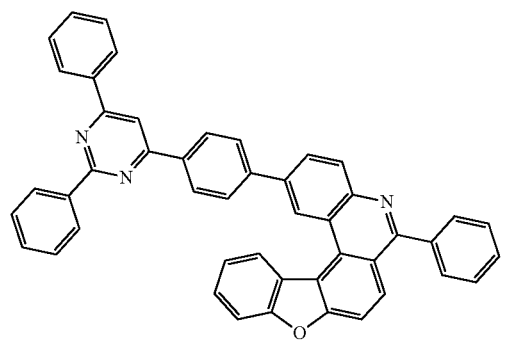
400
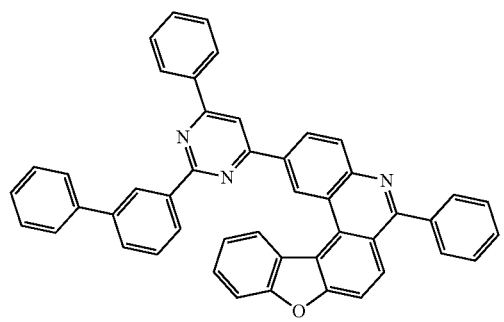
401
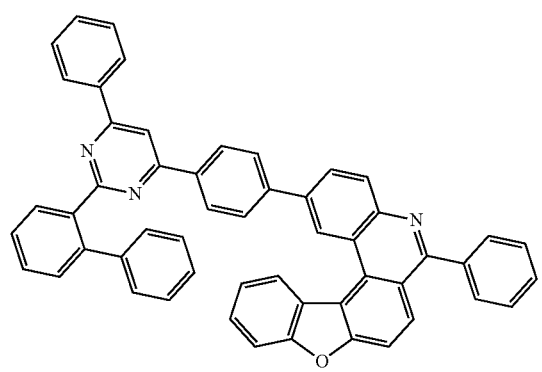
402
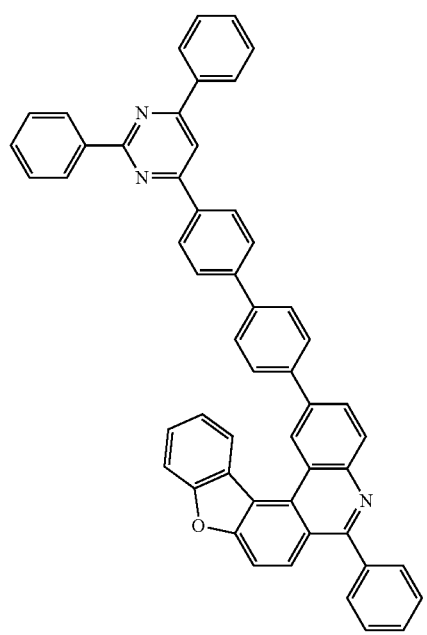

-continued
403
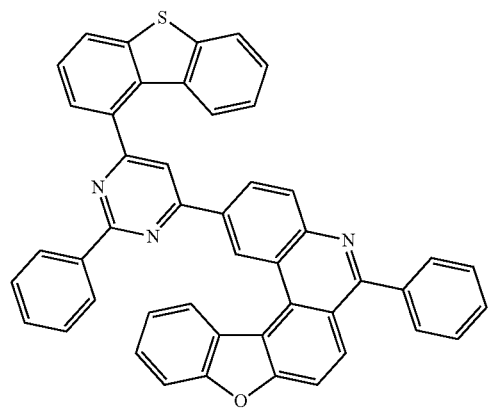
404
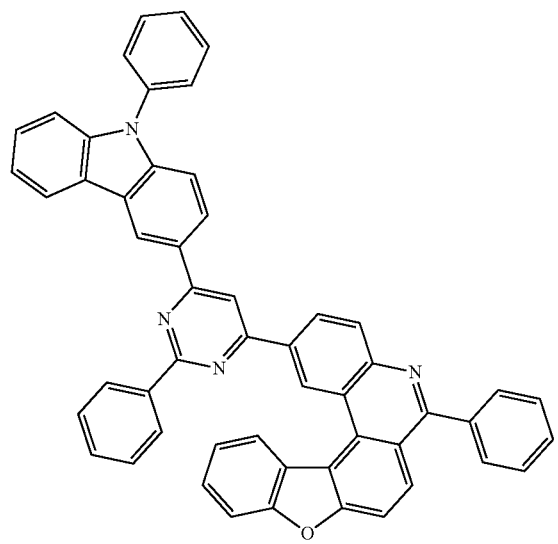
405
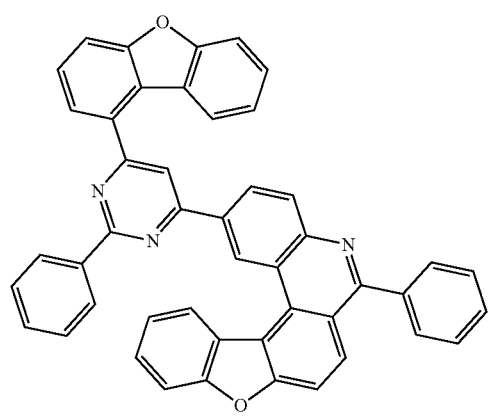
406
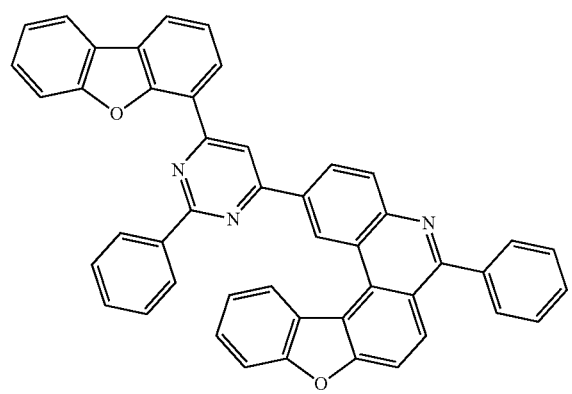
407
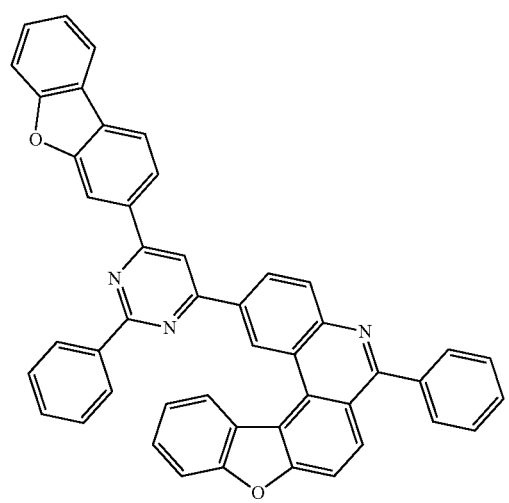
408
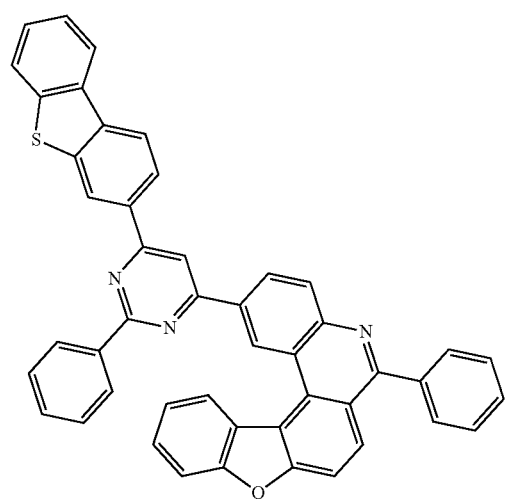

-continued
409
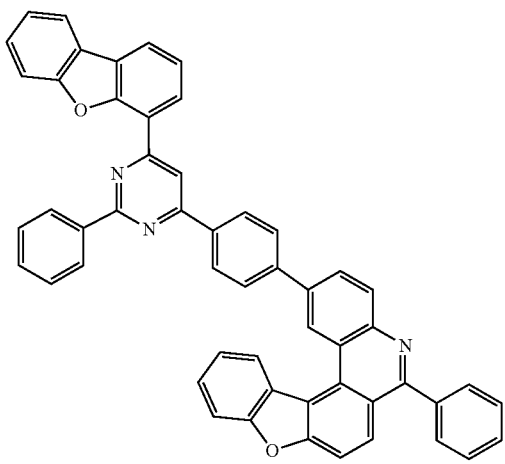
410
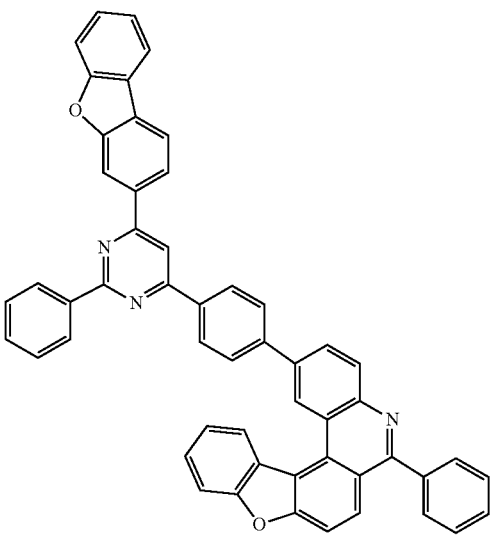
411
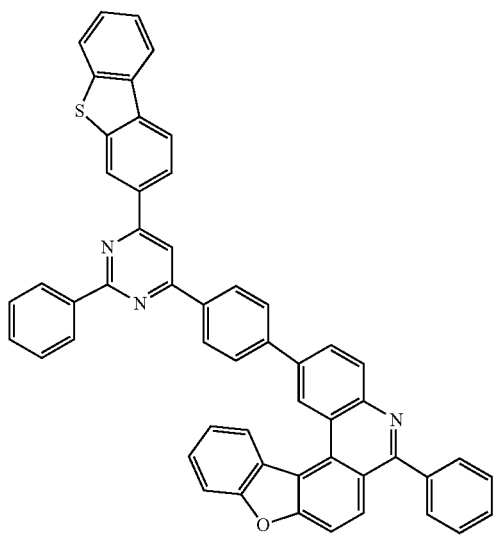
412
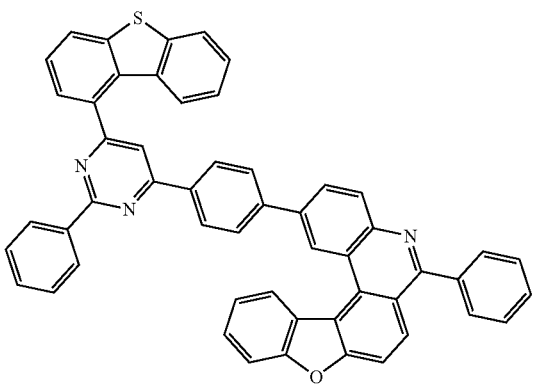
413
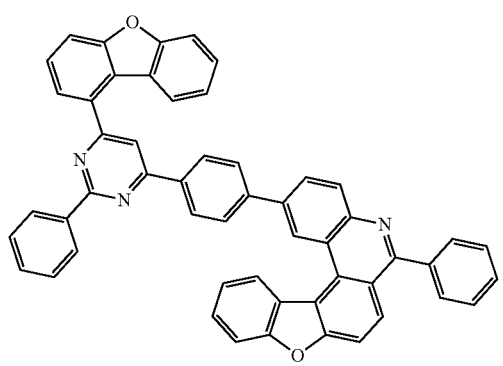
414
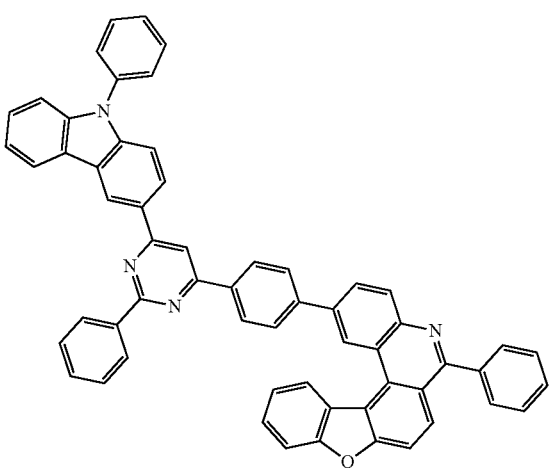

-continued
415
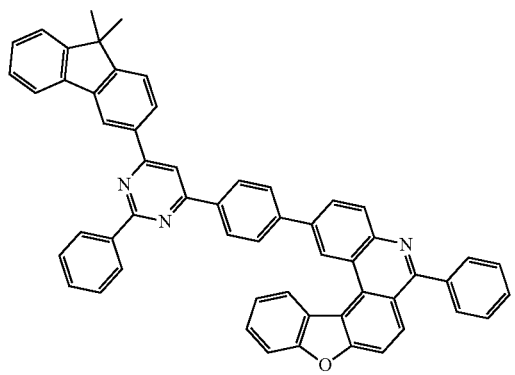
416
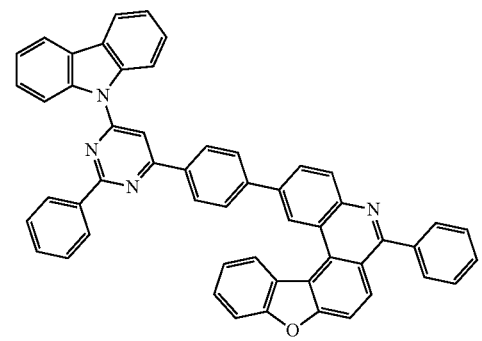
417
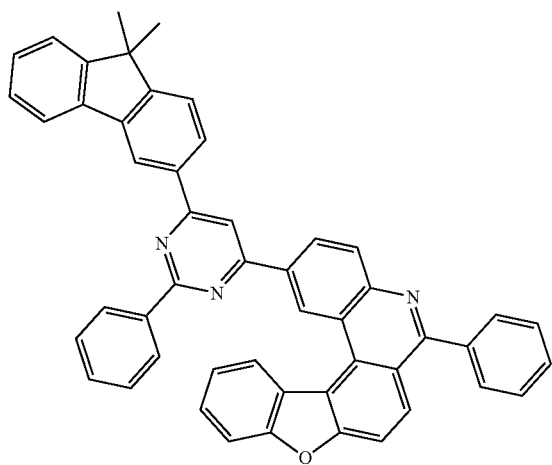
418
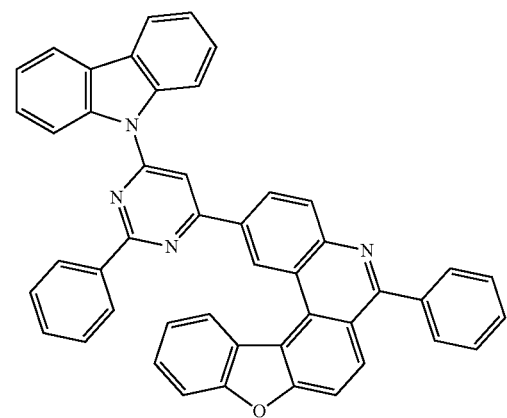
419
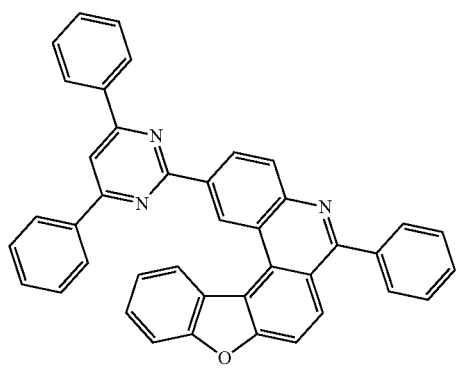
420
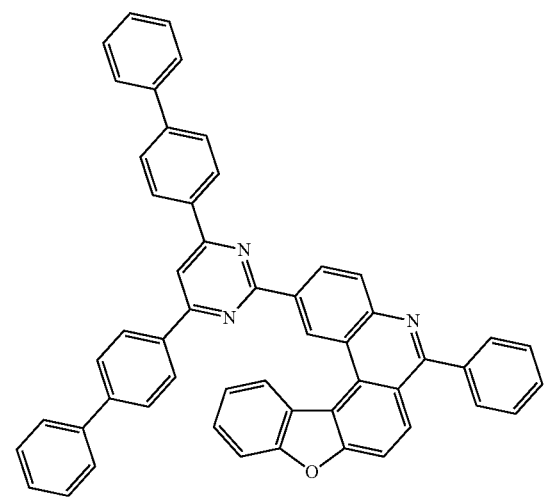

-continued
421
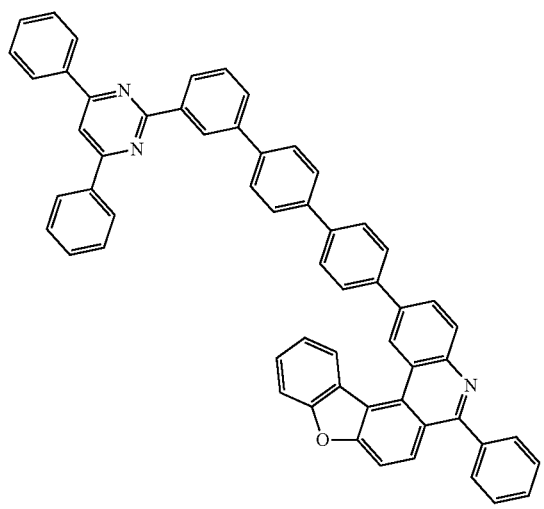
422
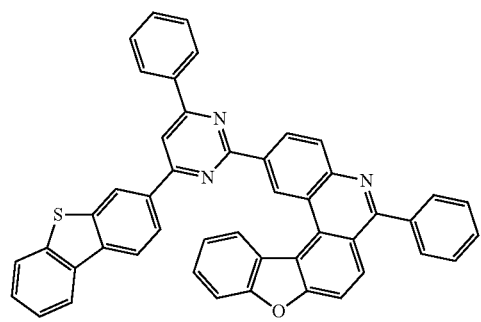
423
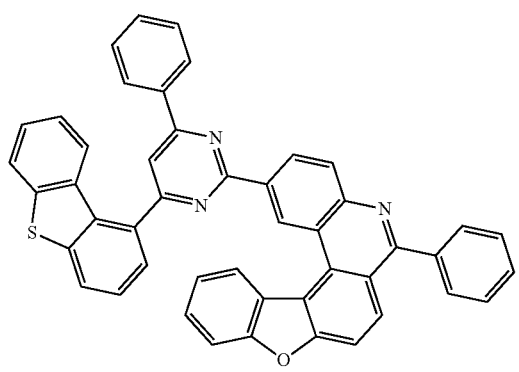
424
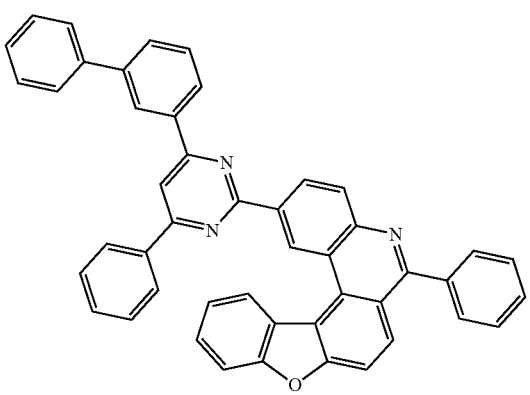
425
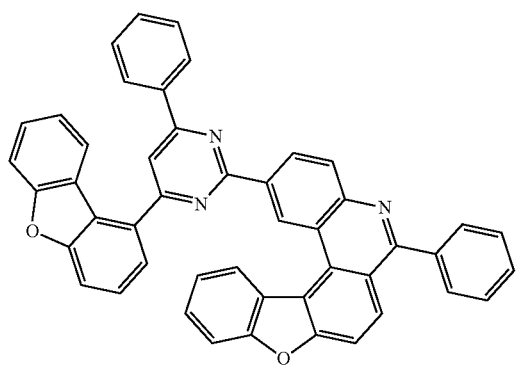
426
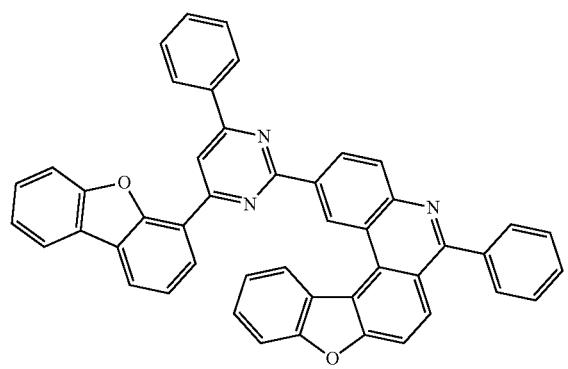

-continued
427
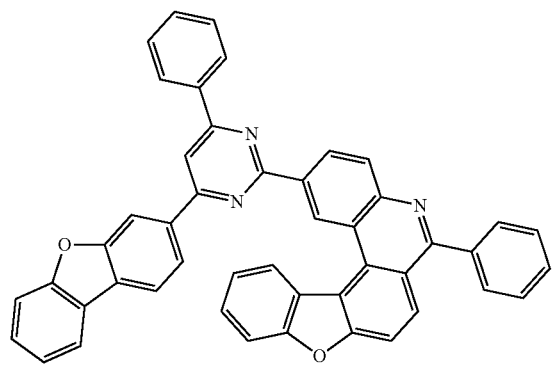
428
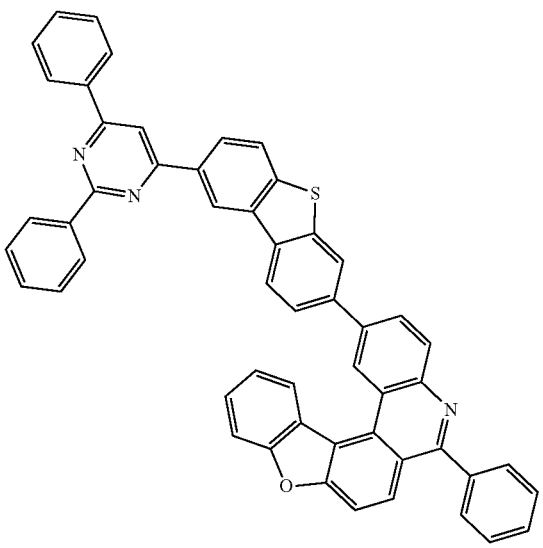
429
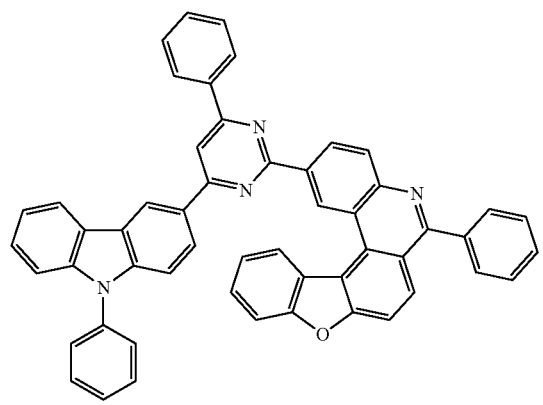
430
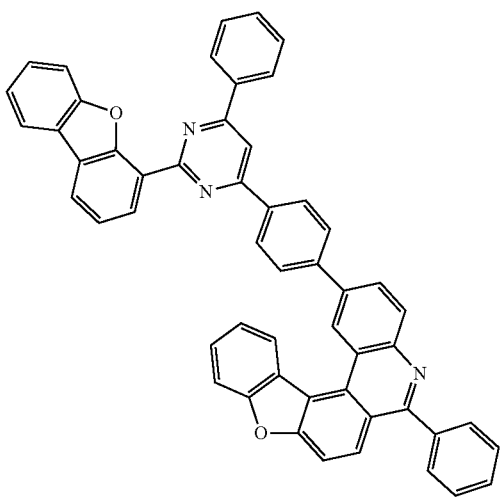
431
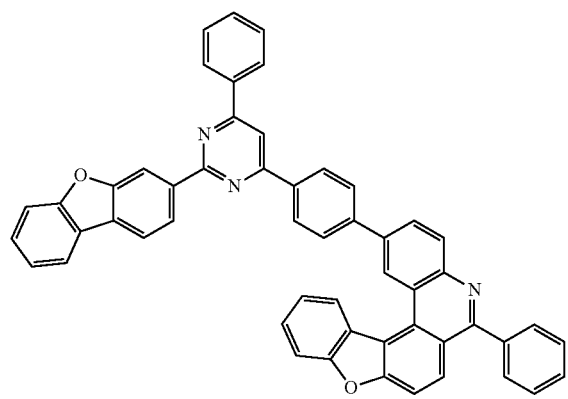
432
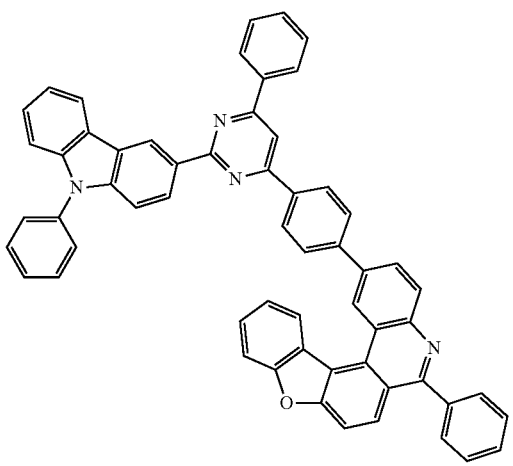

-continued
433
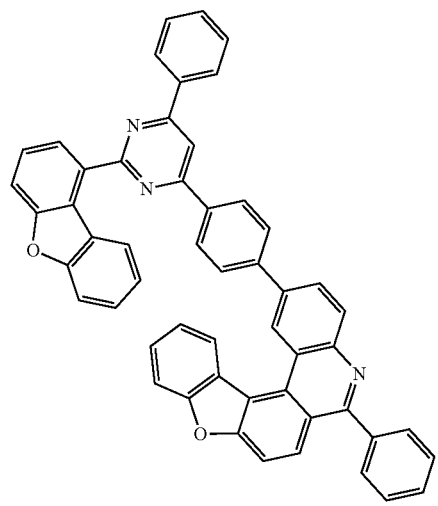
434
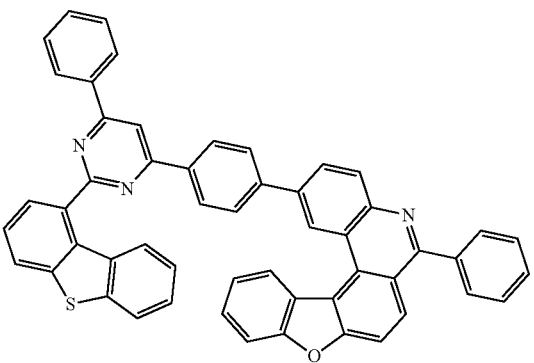
435
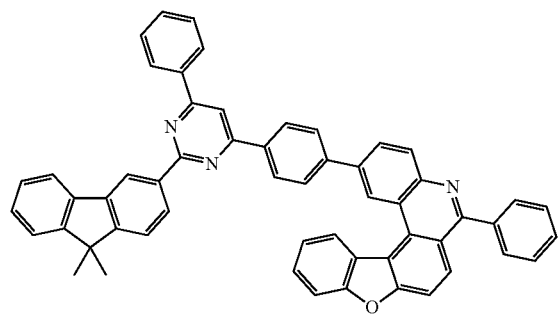
436
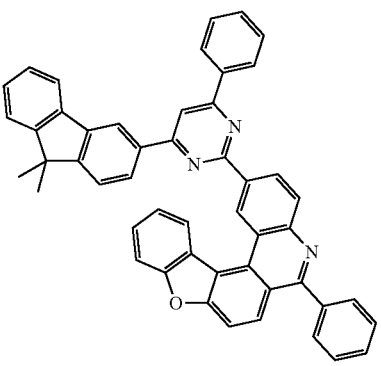
437
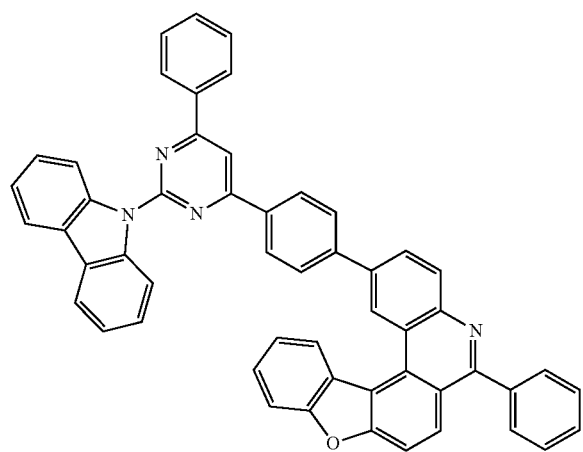
438
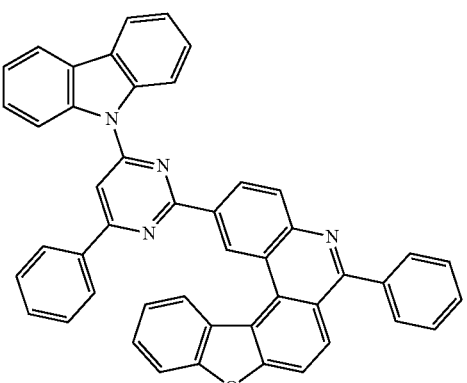

-continued
439
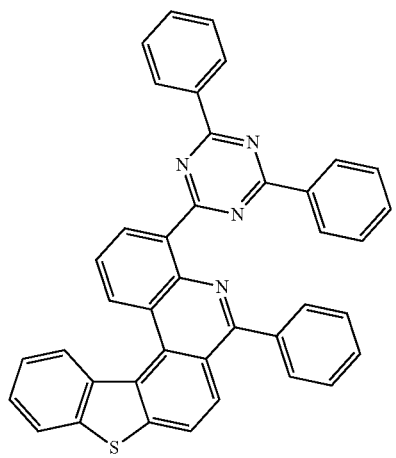
440
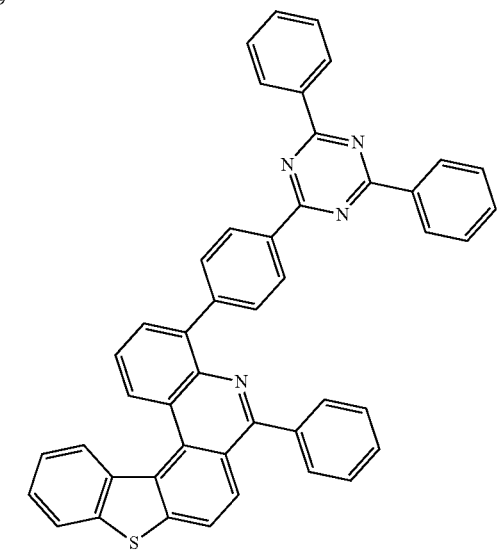
441
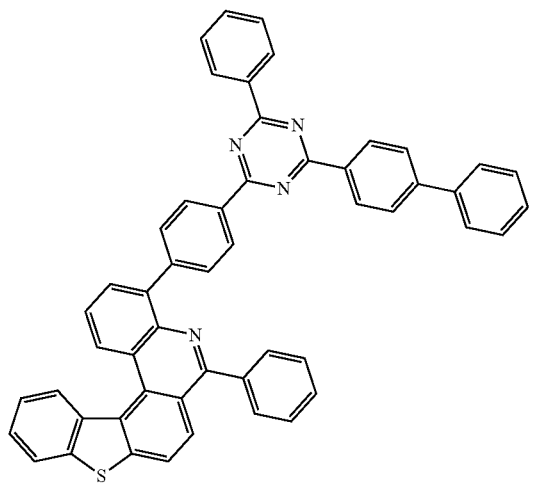
442
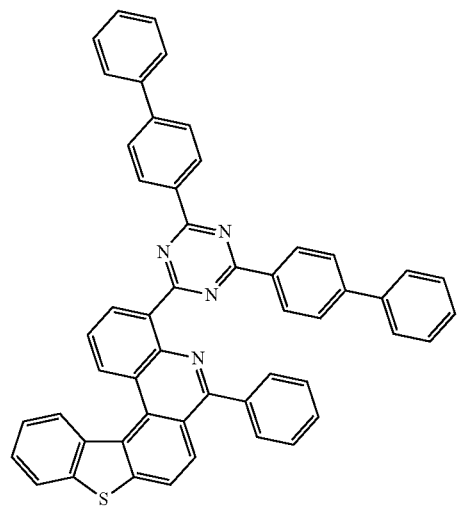
443
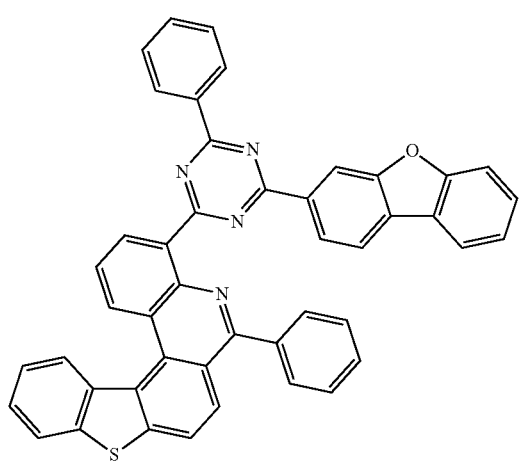
444
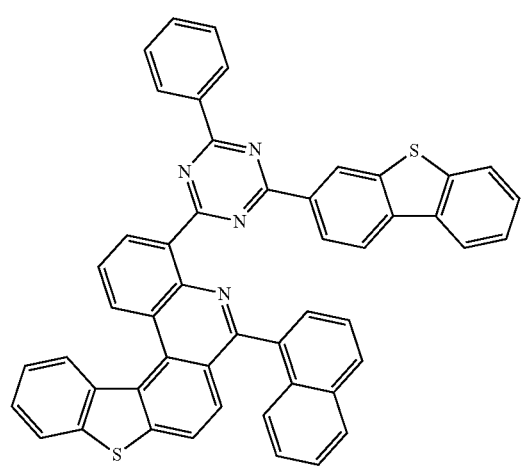

-continued
445
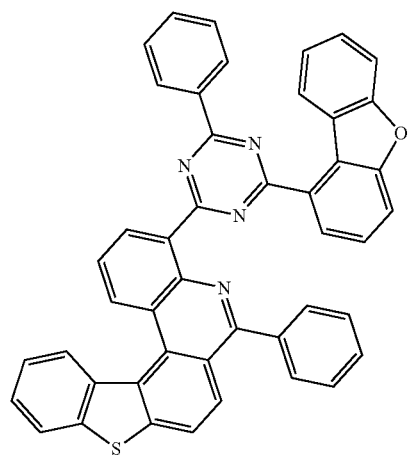
446
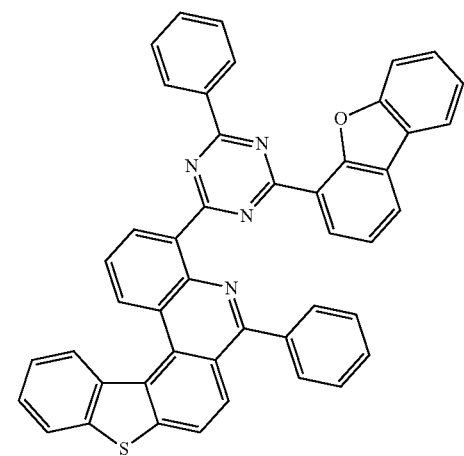
447
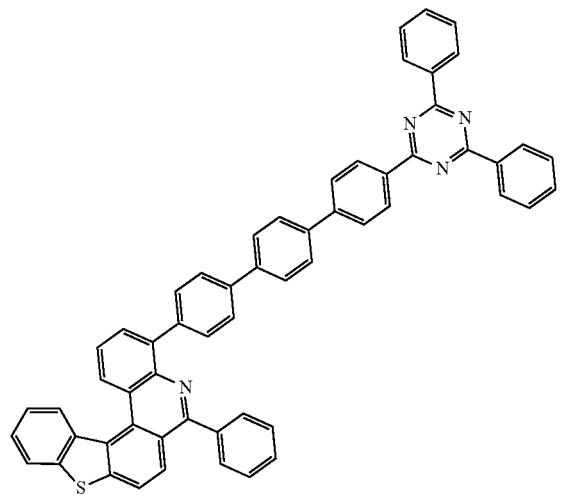
448
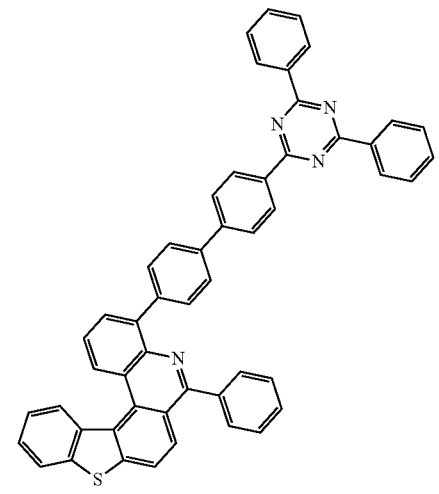
449
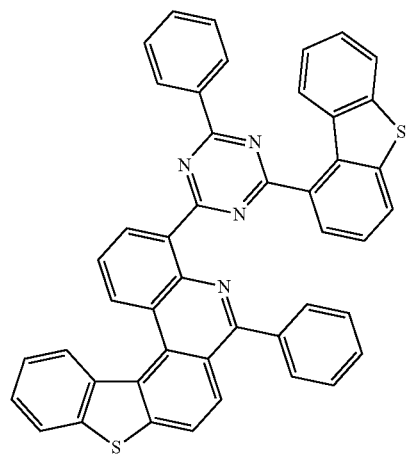
450
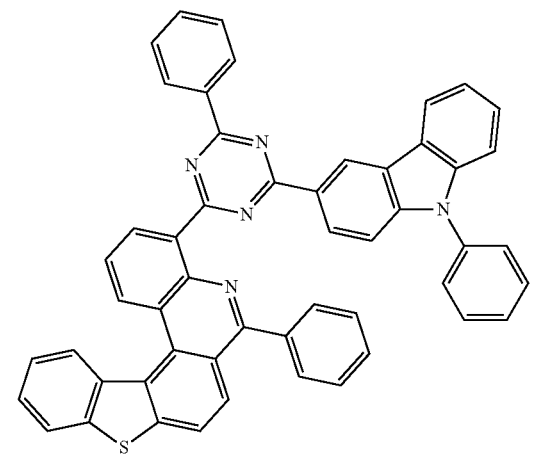

-continued
451
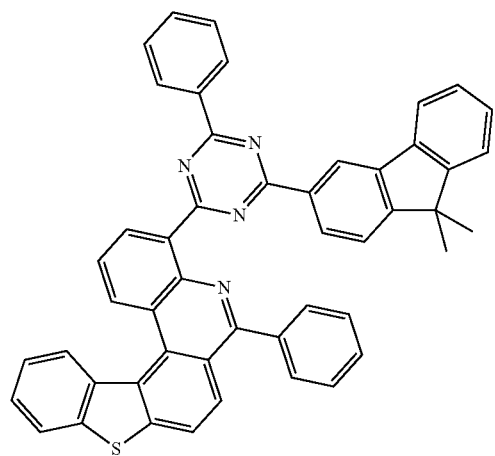
452
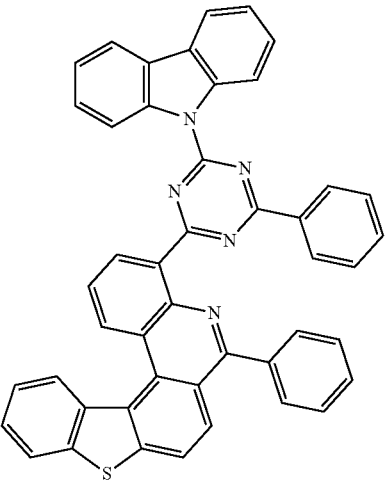
453
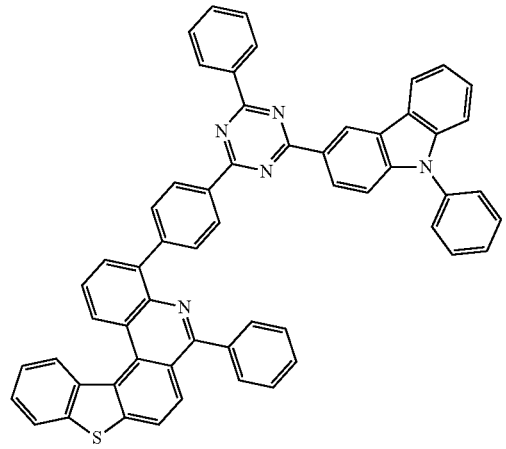
454
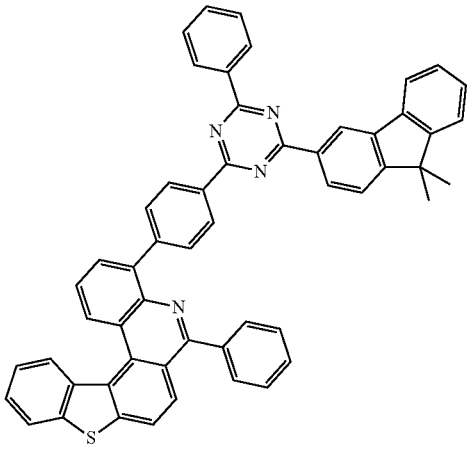
455
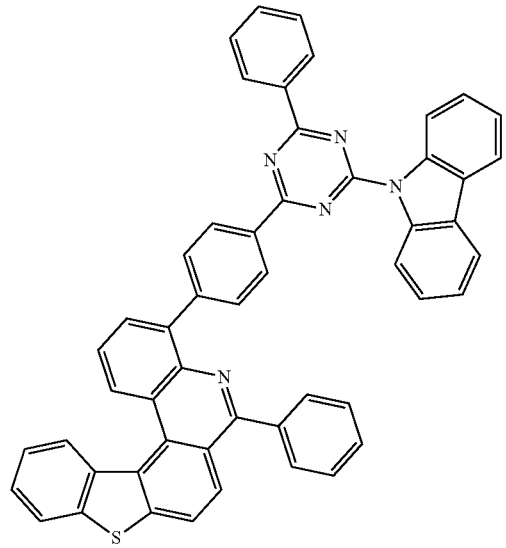
456
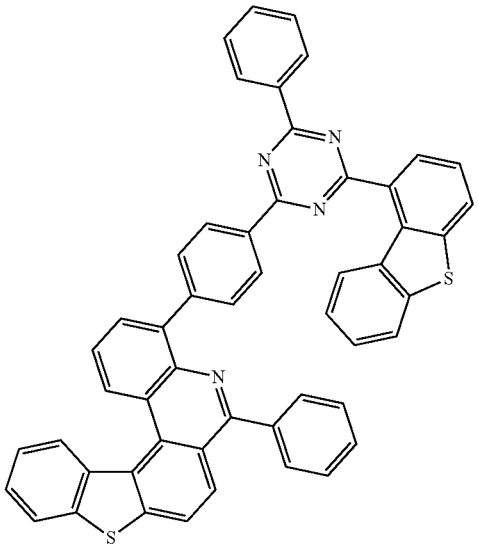

-continued
457
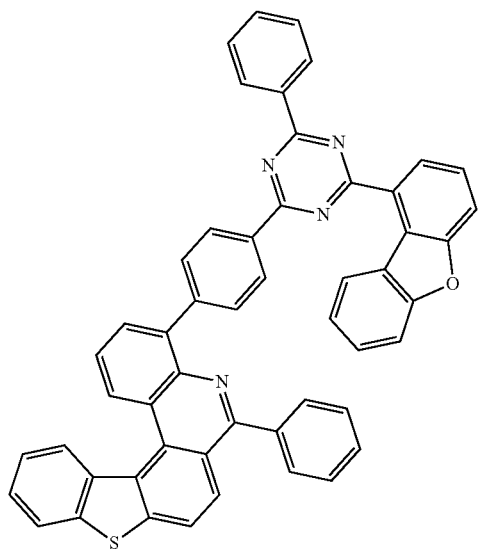
458
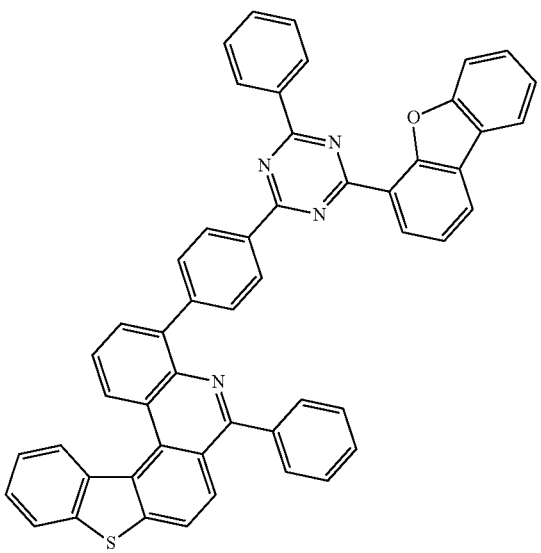
459
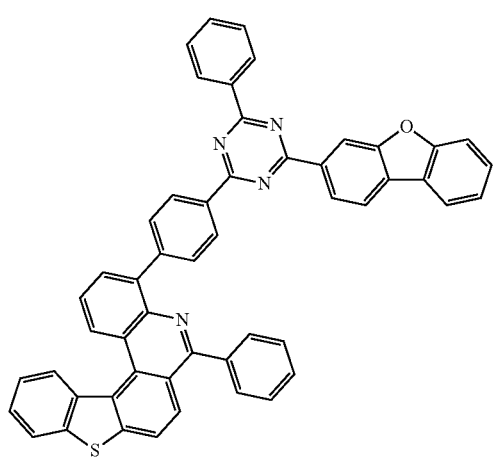
460
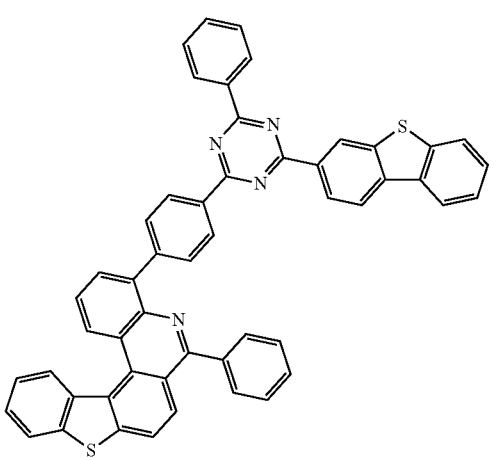
461
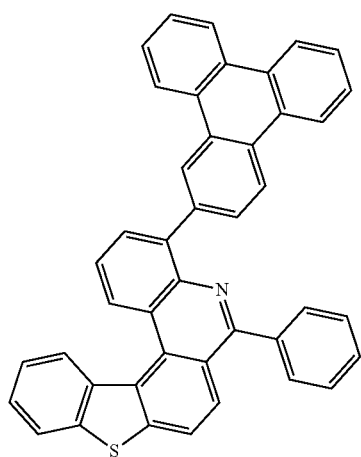
462
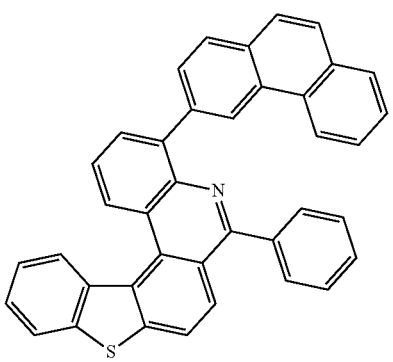

-continued
463 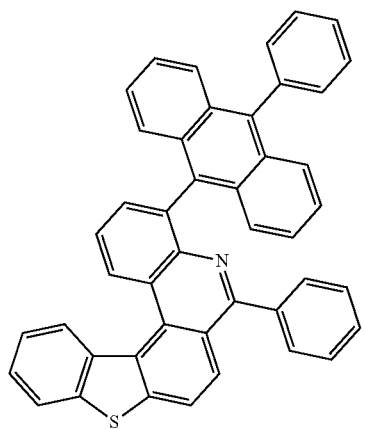
464 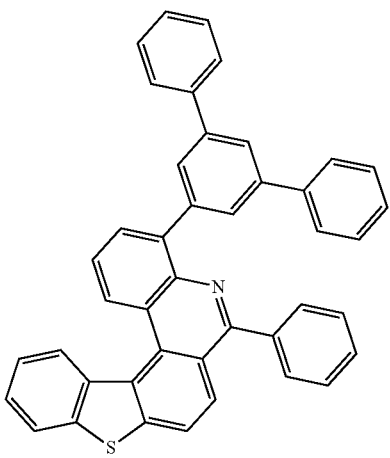
465 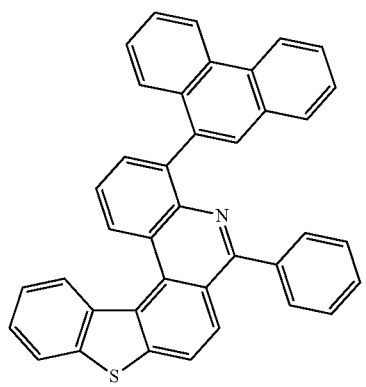
466 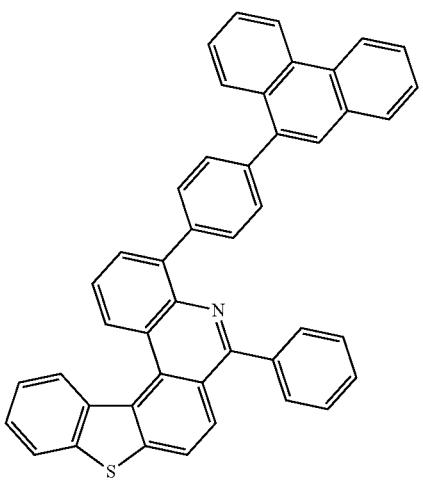
467 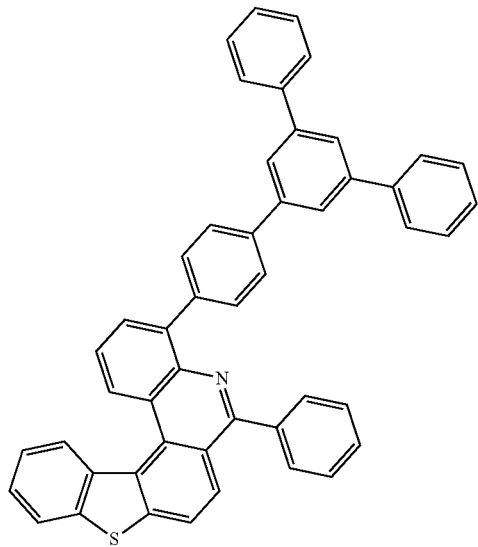
468 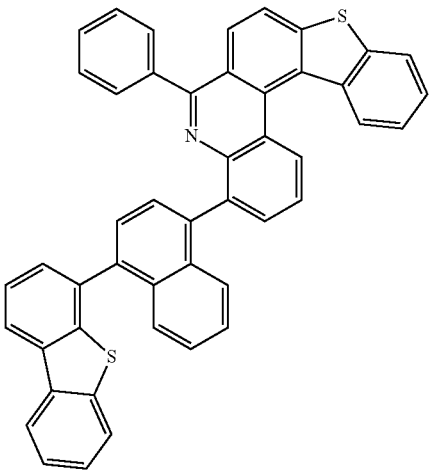

-continued
469
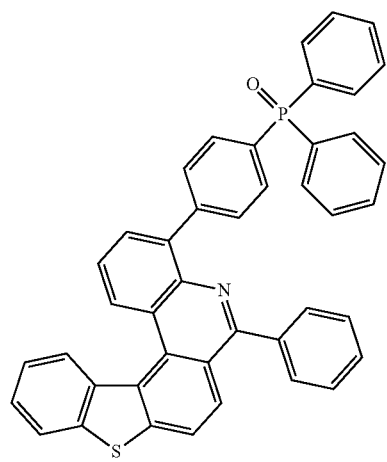
470
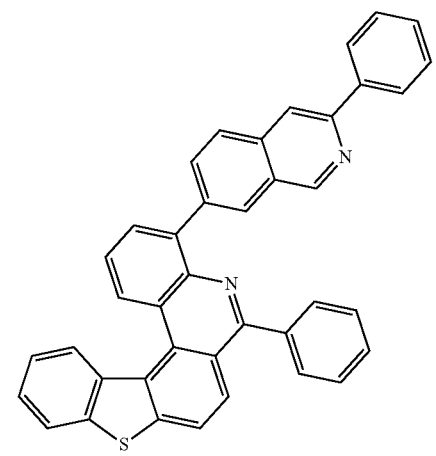
471
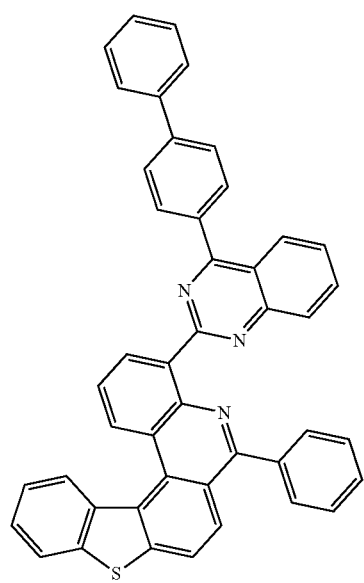
472
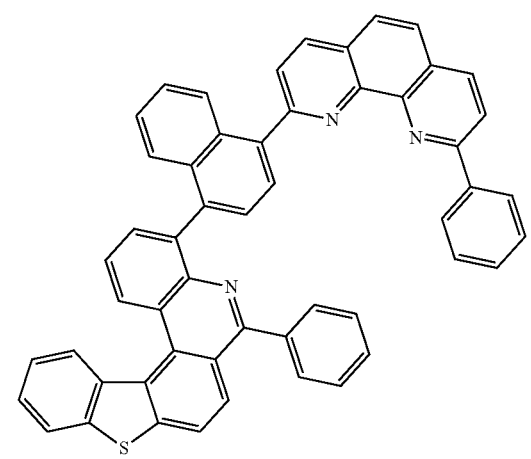
473
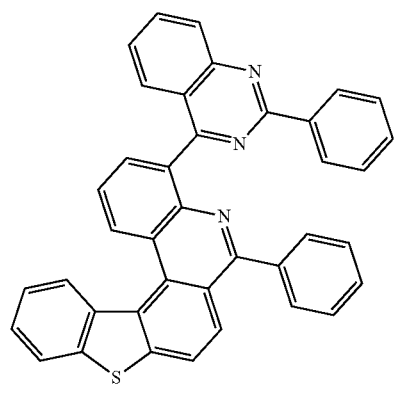
474
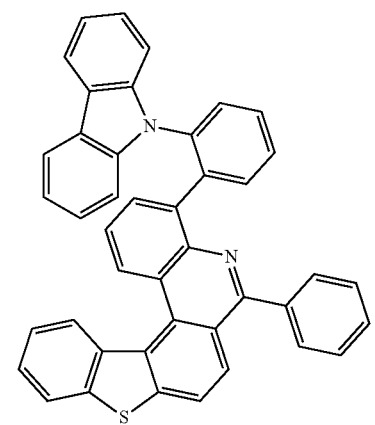

-continued
475
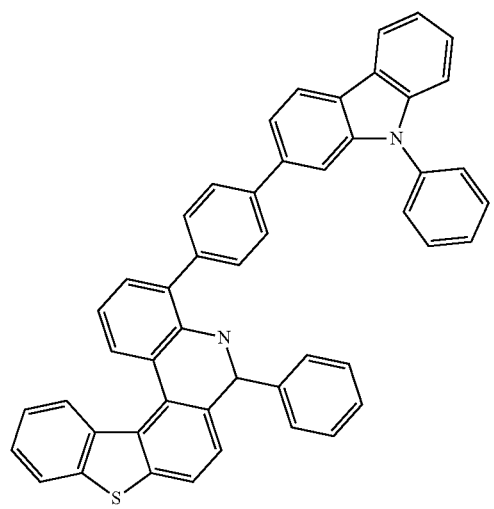
476
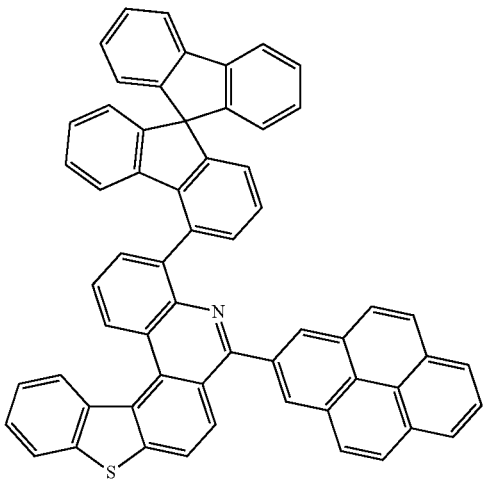
477
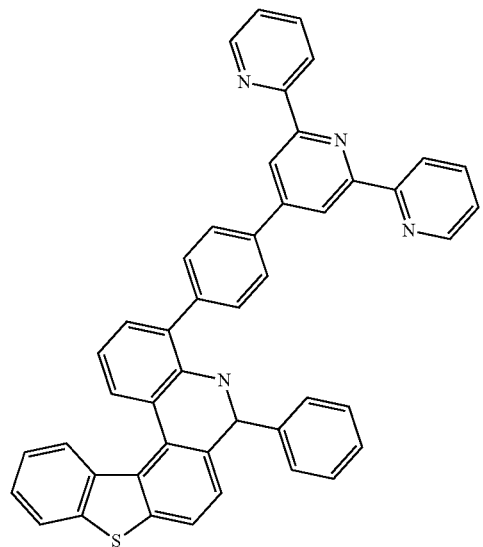
478
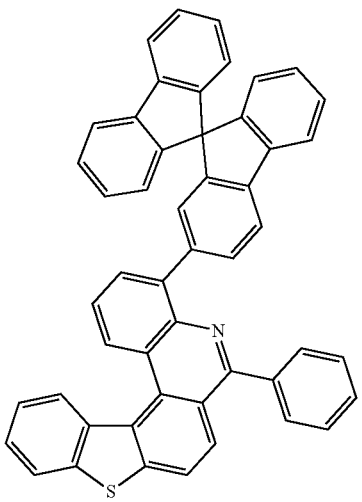
479
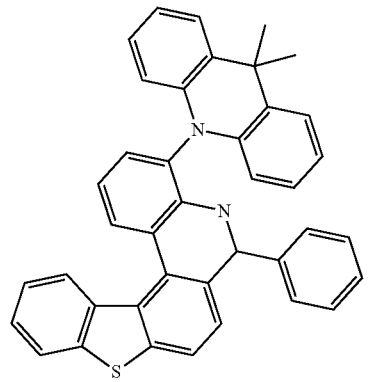
480
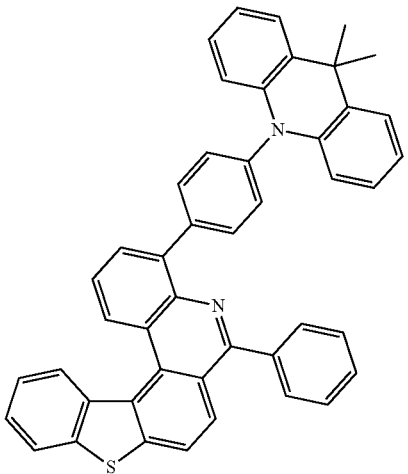

189          190
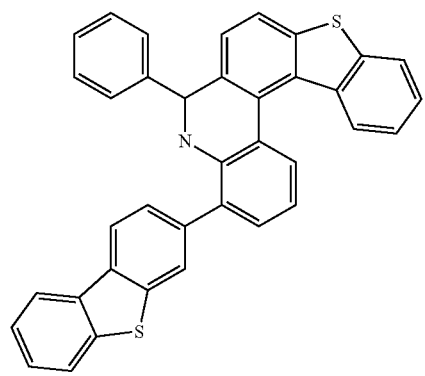
481
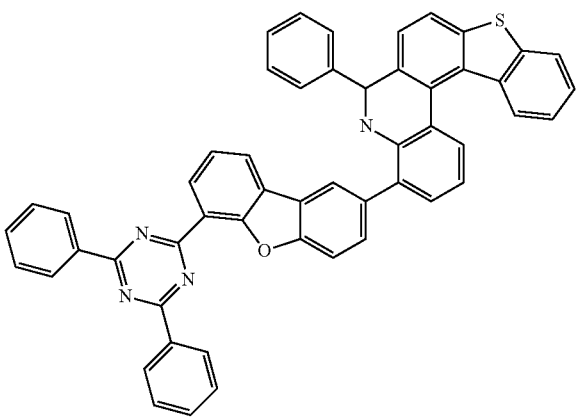
482
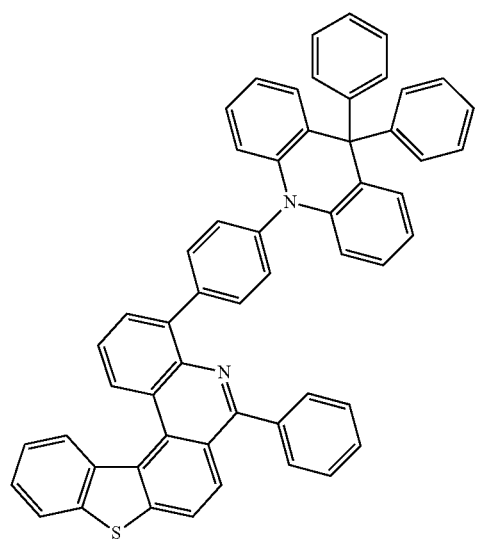
483
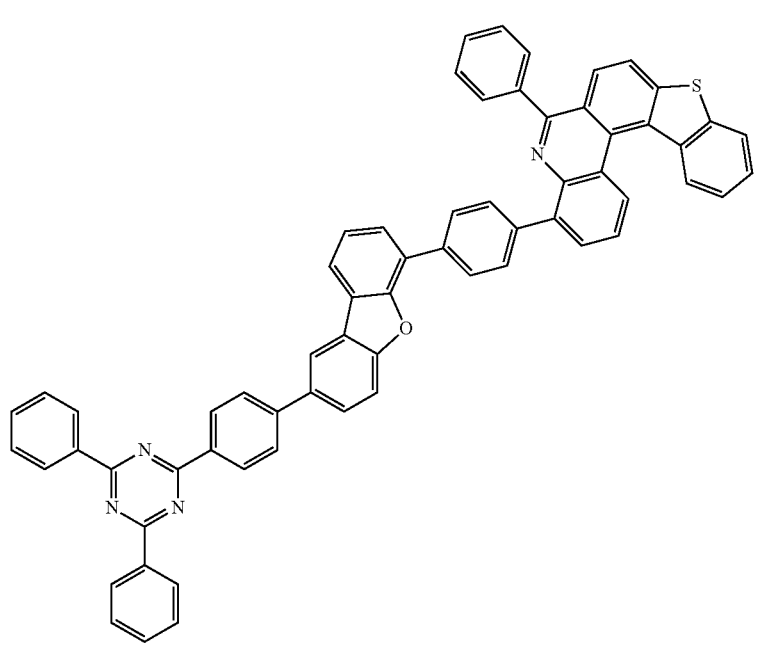
484

-continued
485
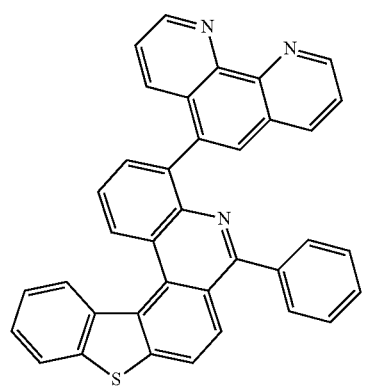
486
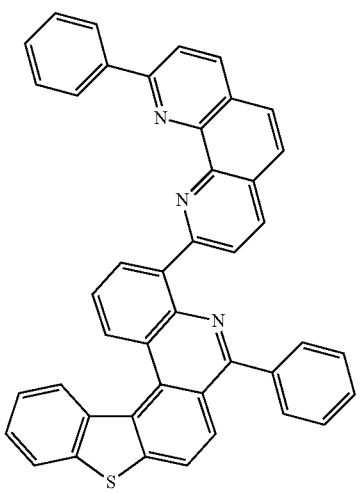
487
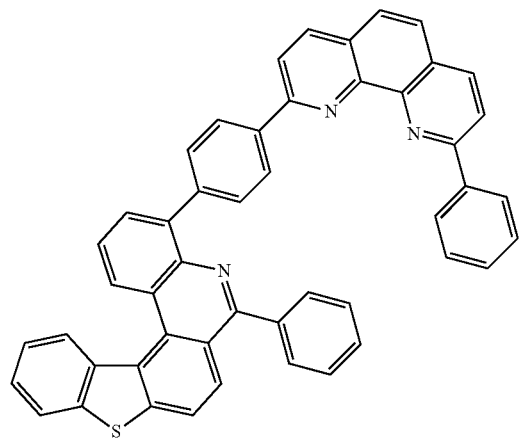
488
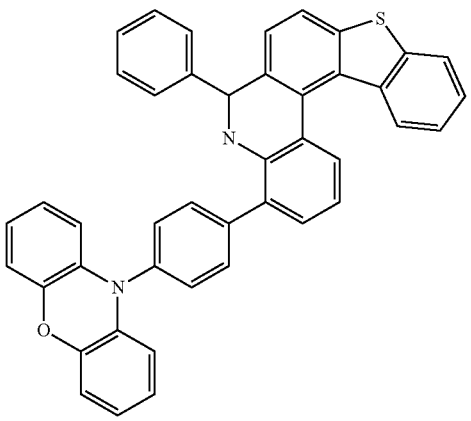
489
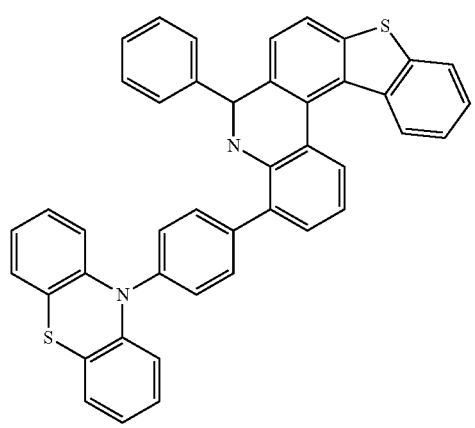
490
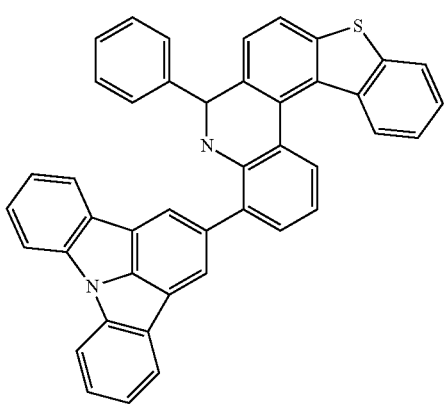

-continued
| 491 | 492 |
|---|---|
| 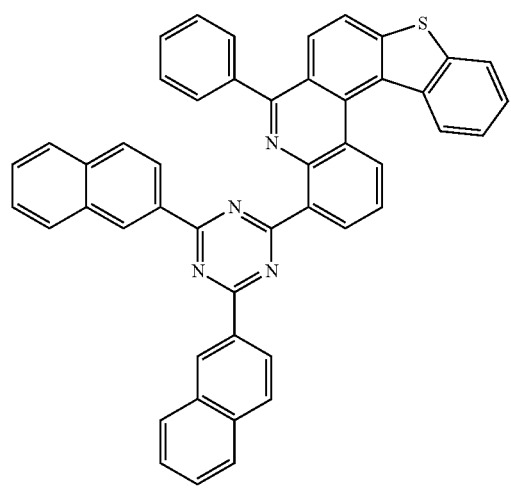 | 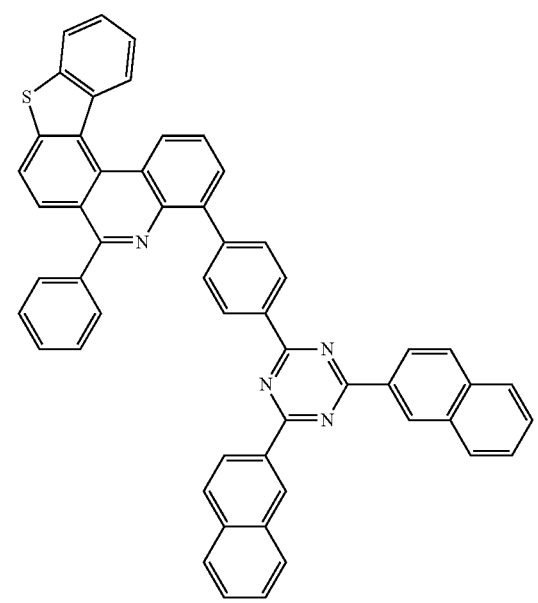 |
| 493 | 494 |
| 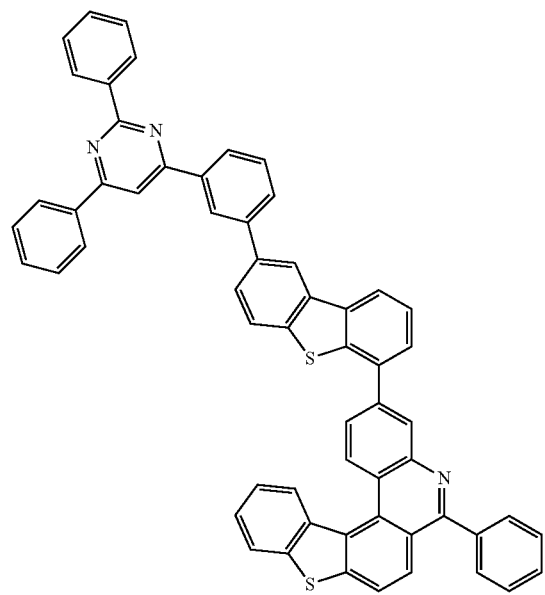 | 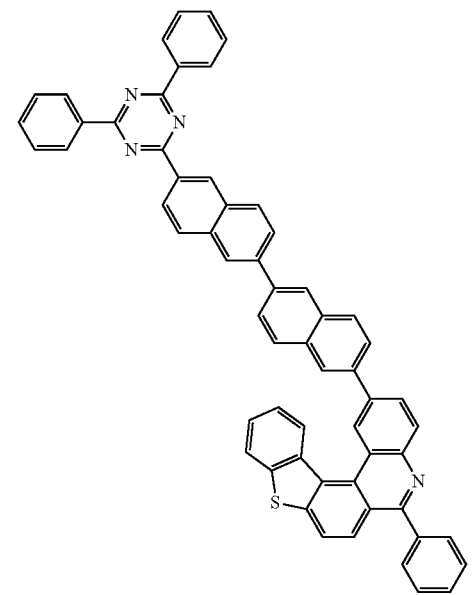 |

-continued
495
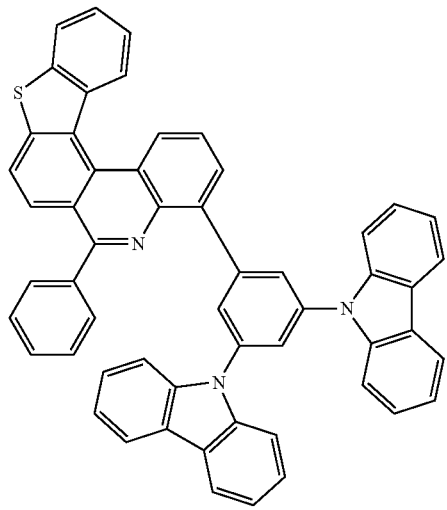
496
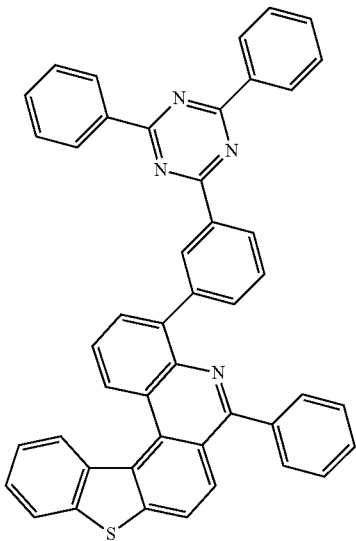
497
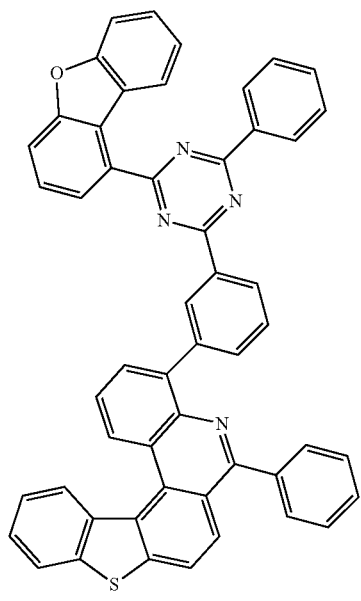
498
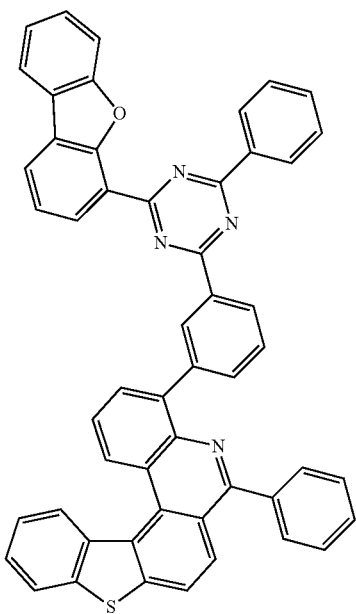

-continued
499
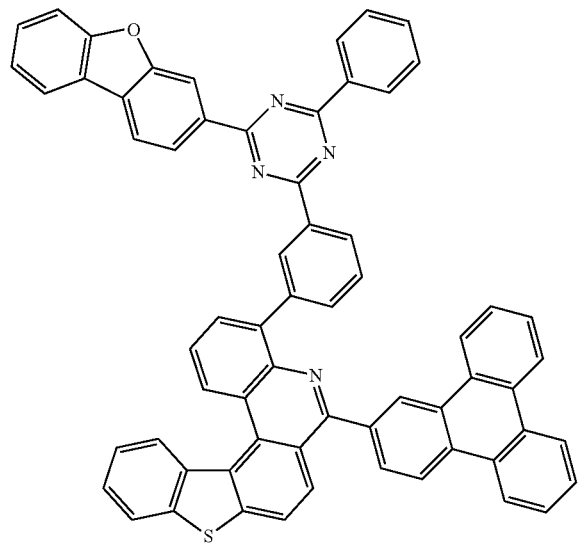
500
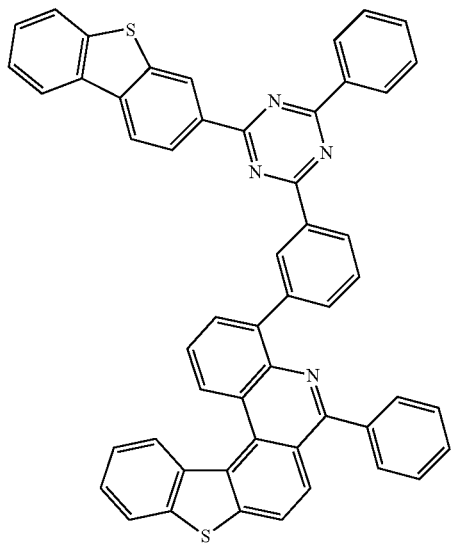
501
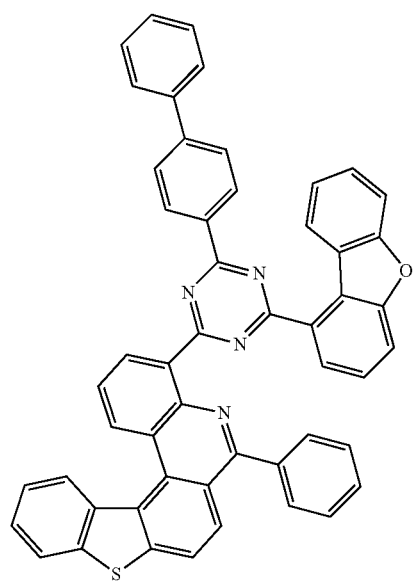
502
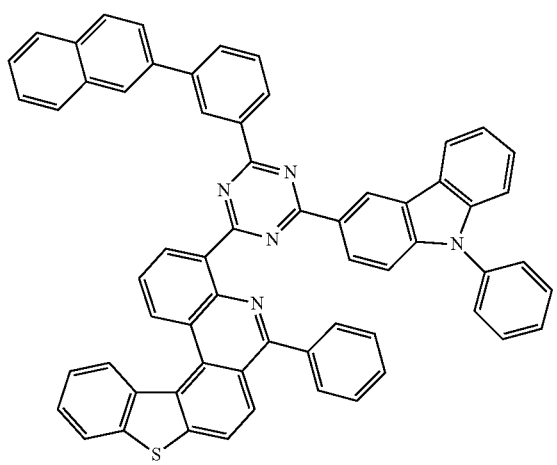
503
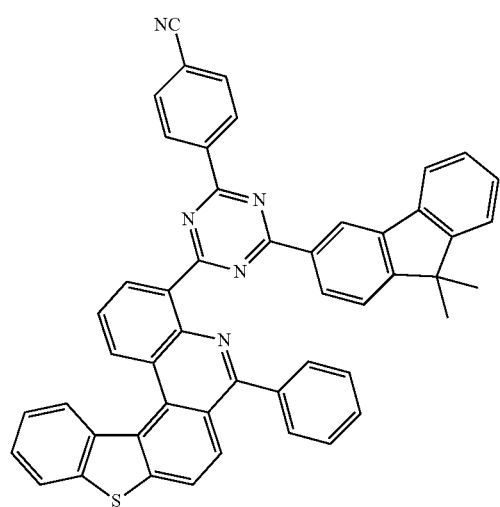
504
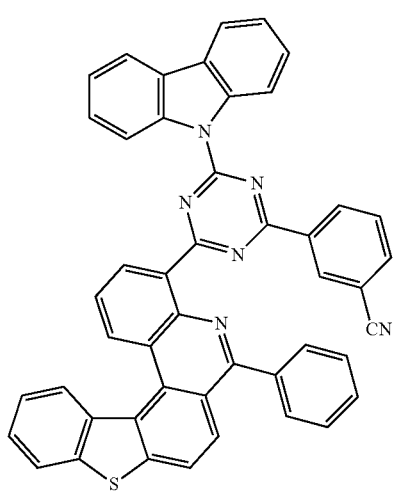

-continued
505 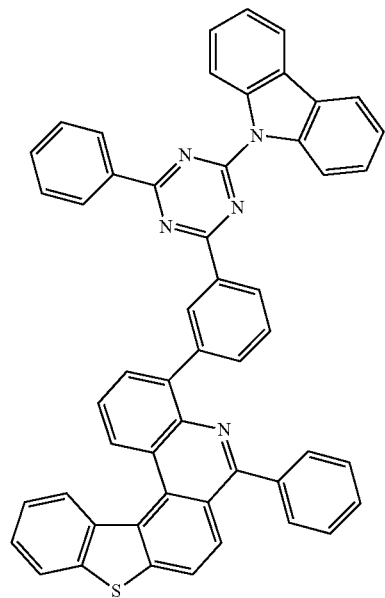
506 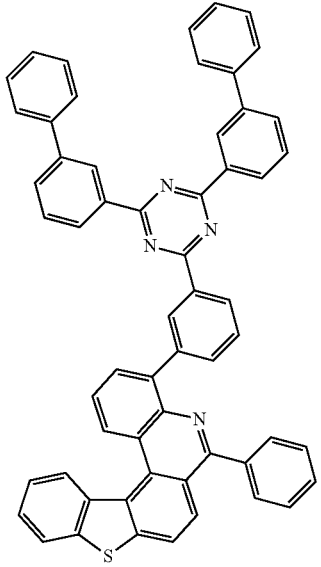
507 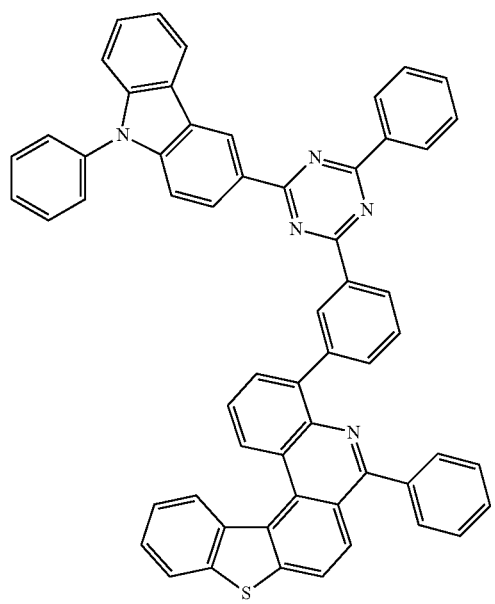
508 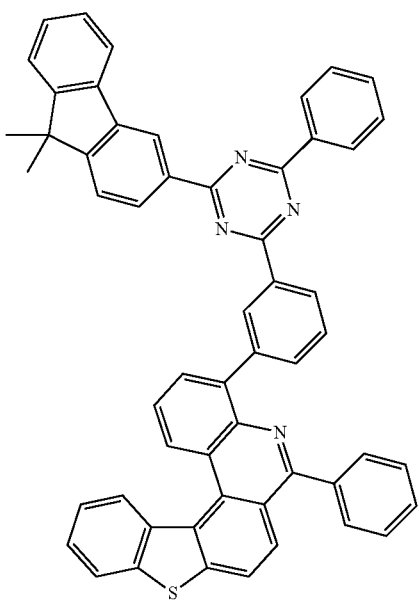

-continued
201
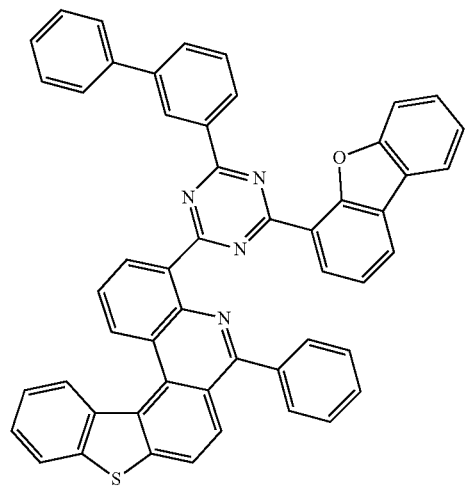
509
202
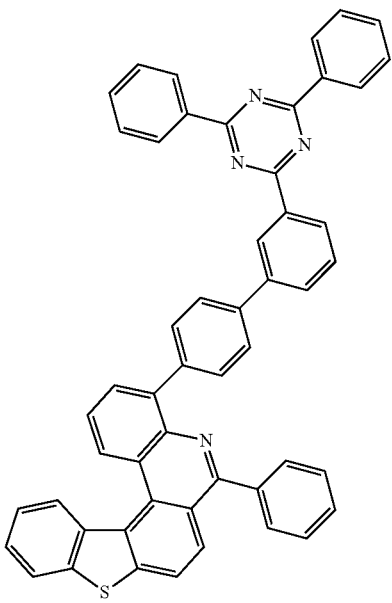
510
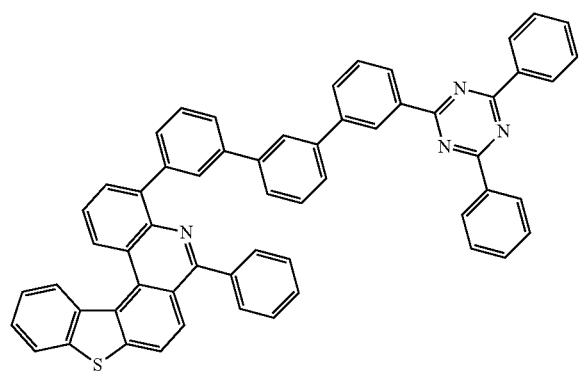
511
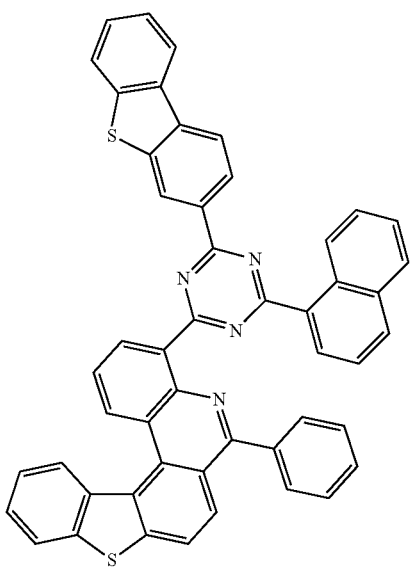
512

-continued
513
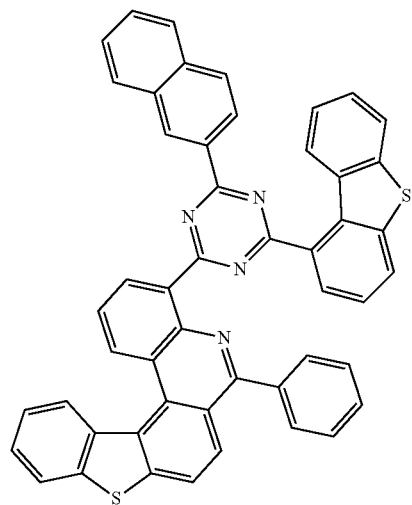
514
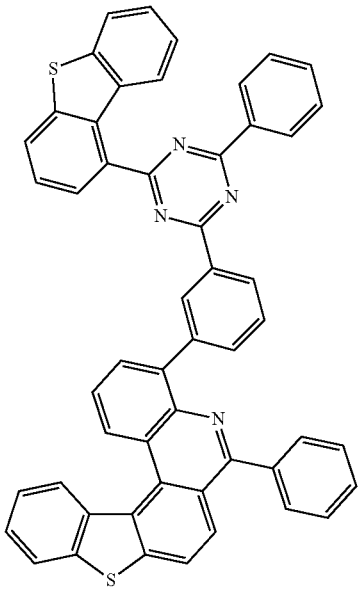
515
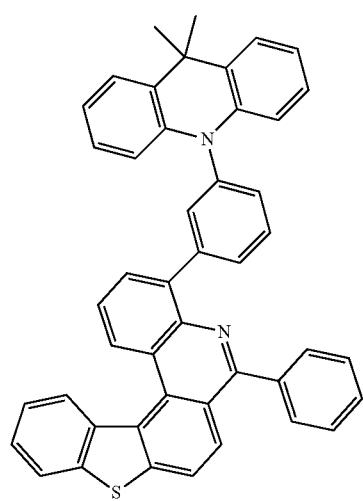
516
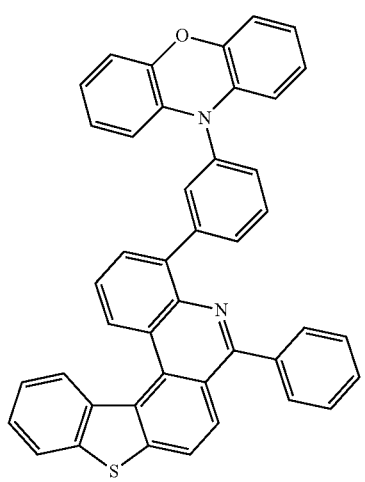
517
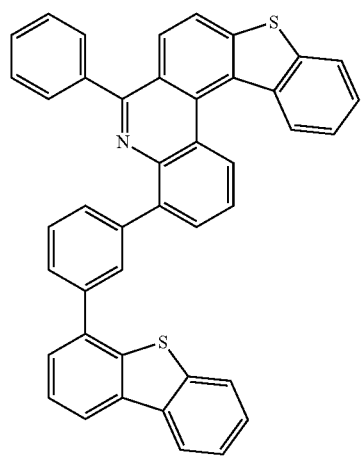
518
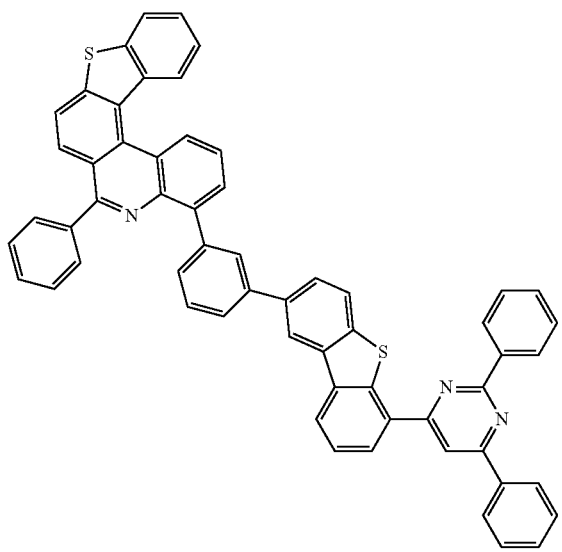

-continued
519
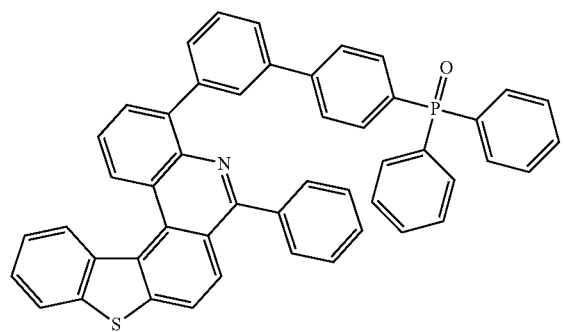
520
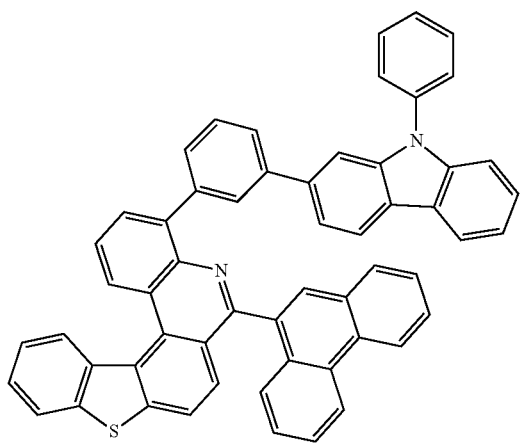
521
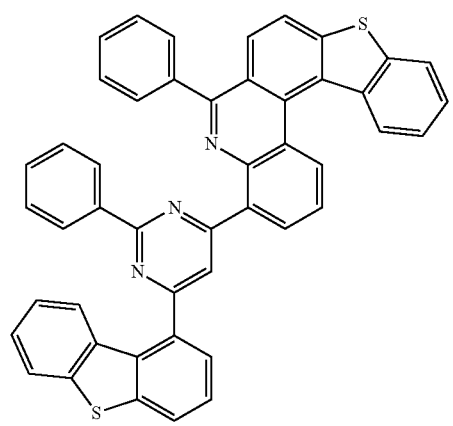
522
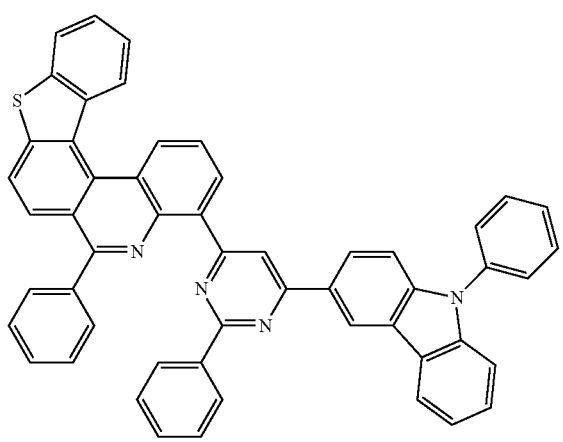
523
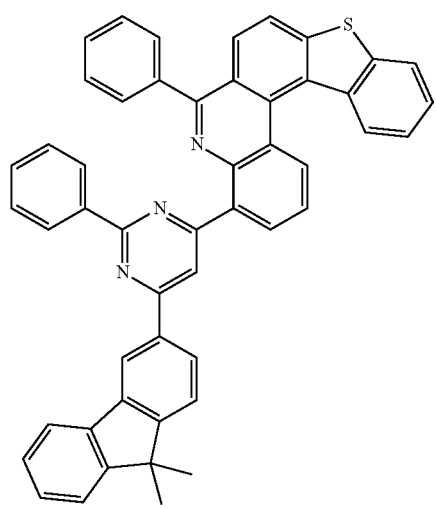
524
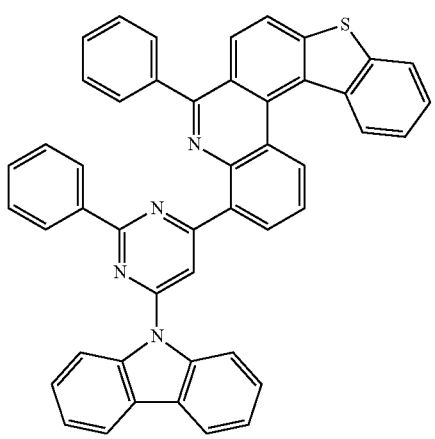

525
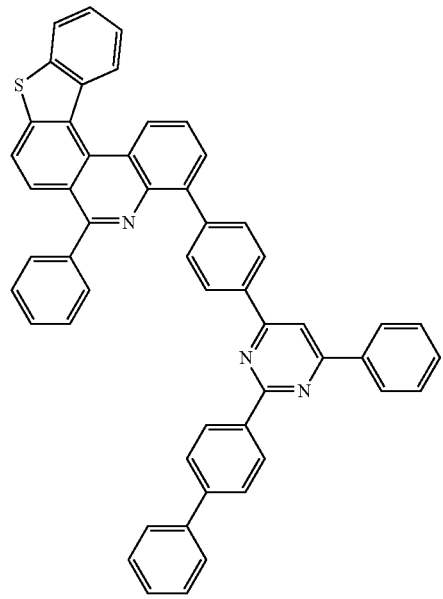
526
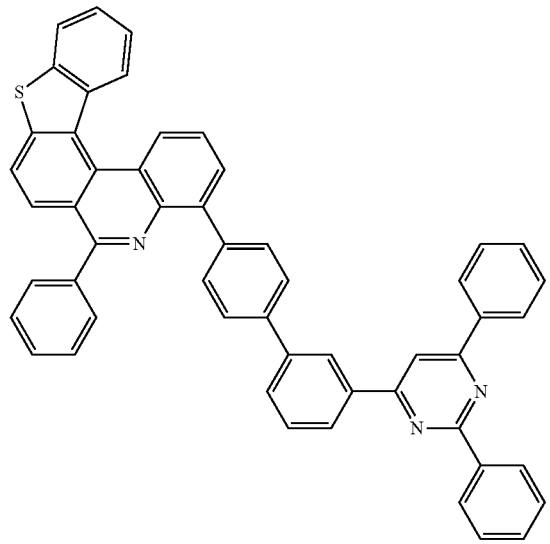
527
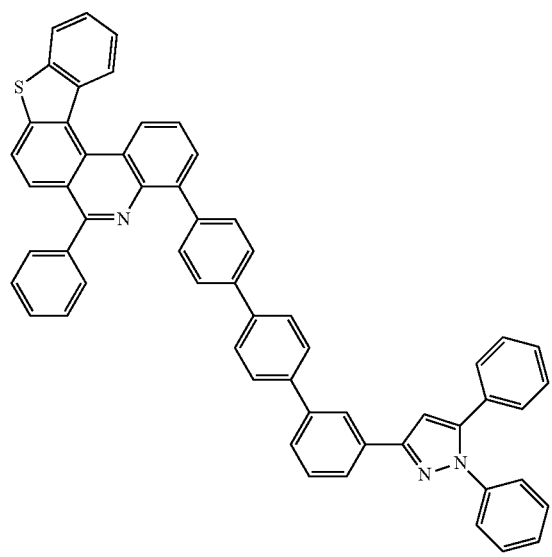
528
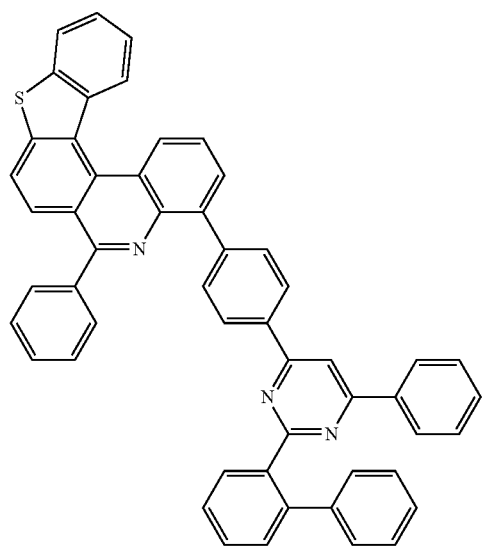

529
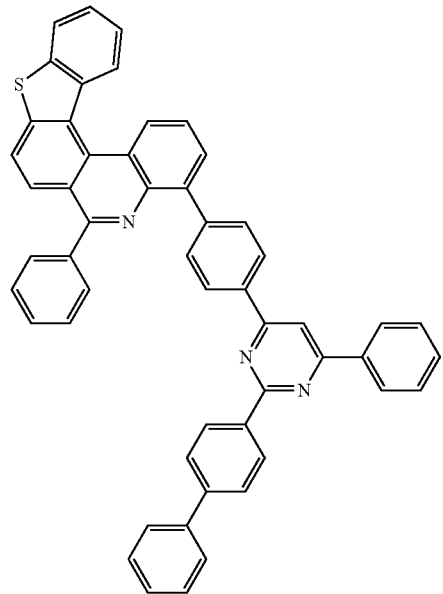
530
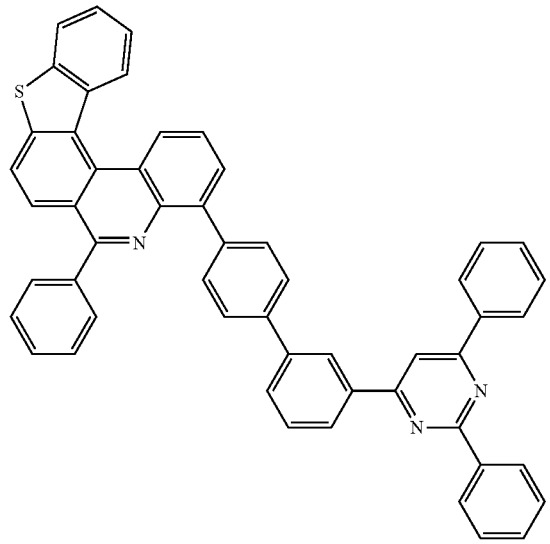
531
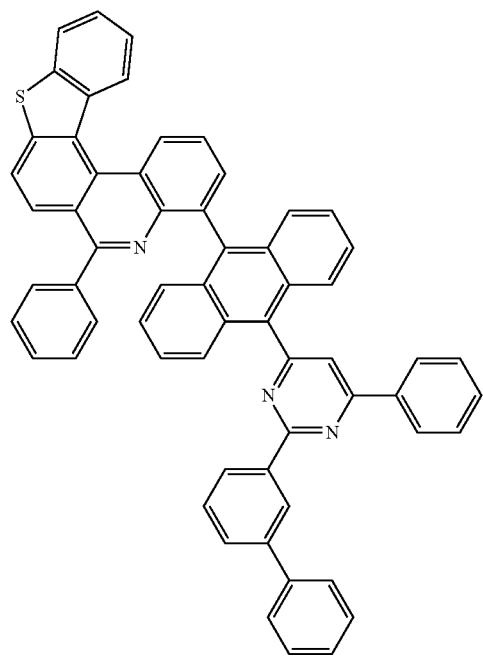
532
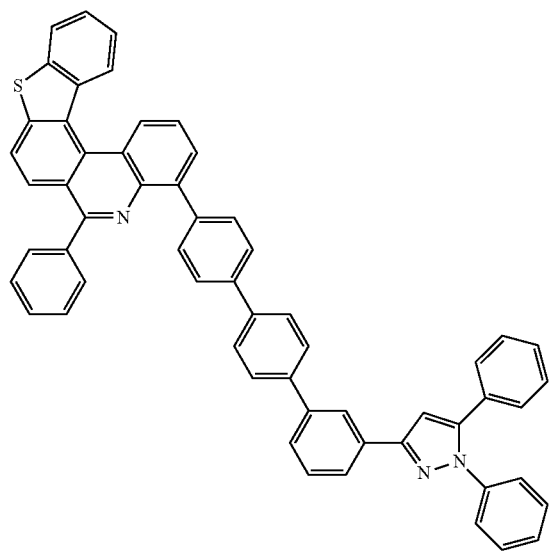

533
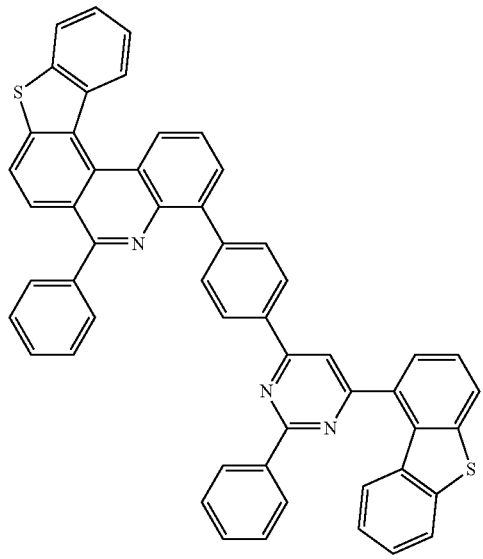
534
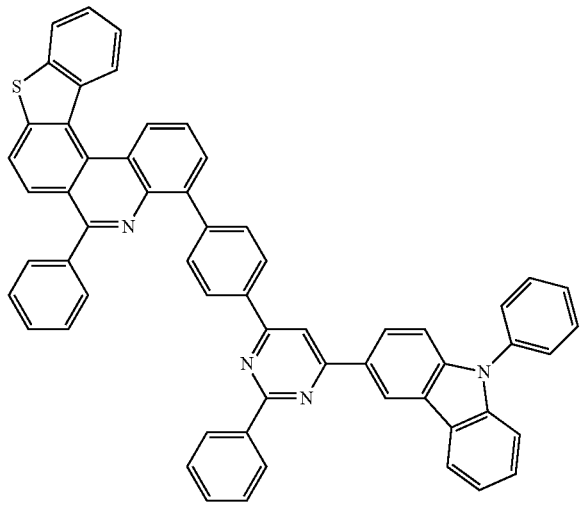
535
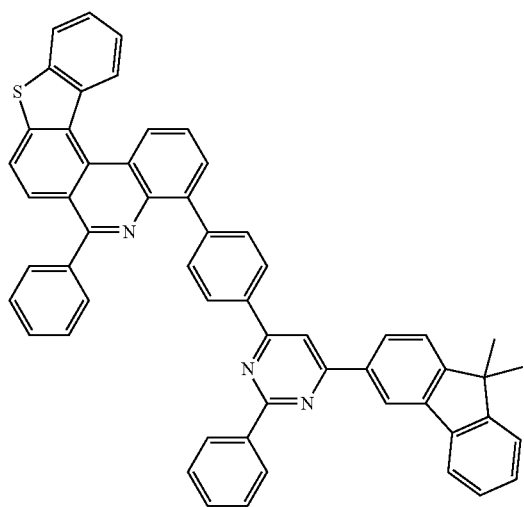
536
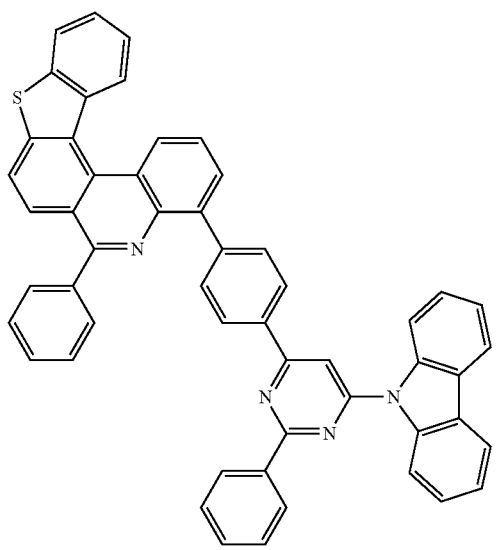
537
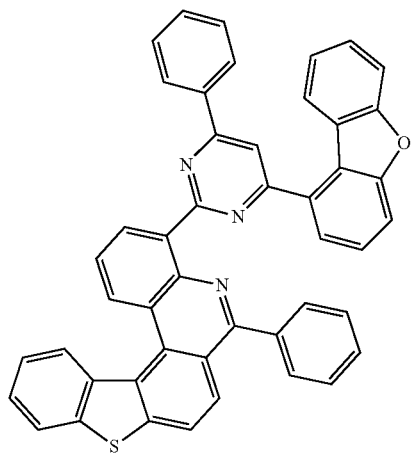
538
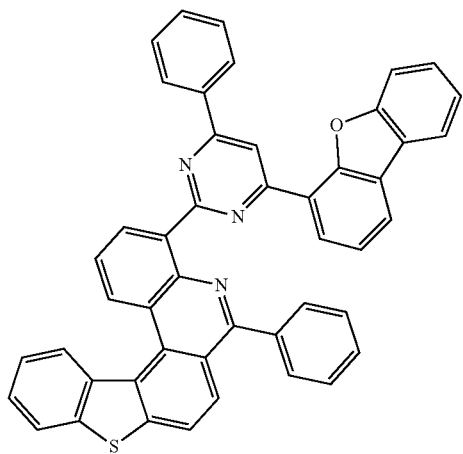

213 | 214
539 | 540
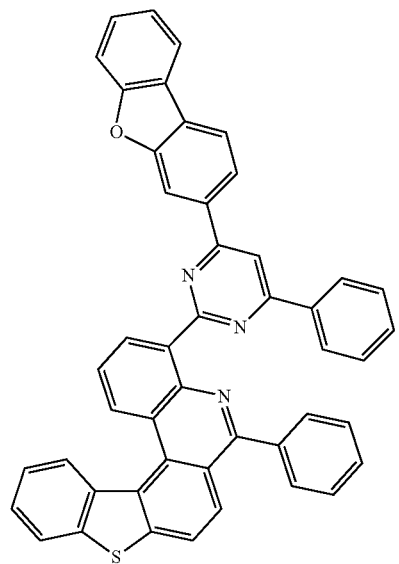
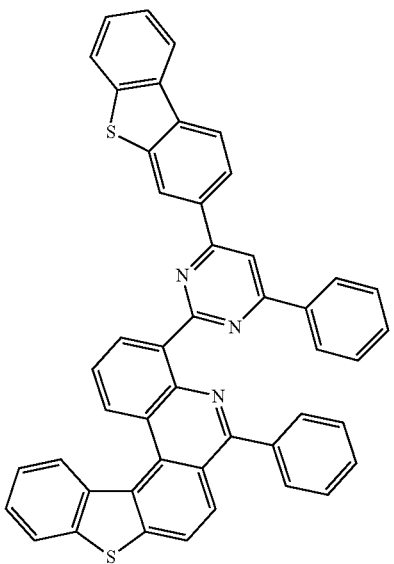
541 | 542
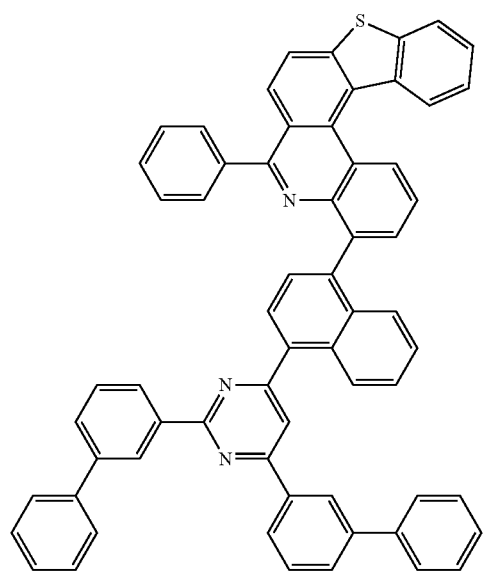
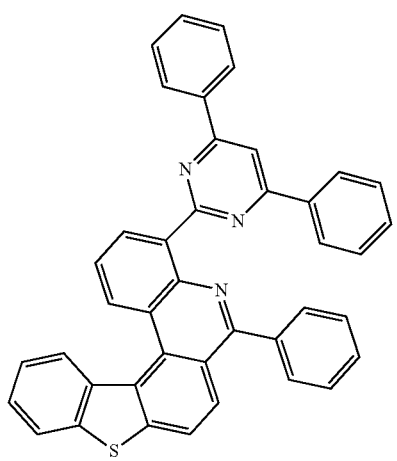

-continued
543
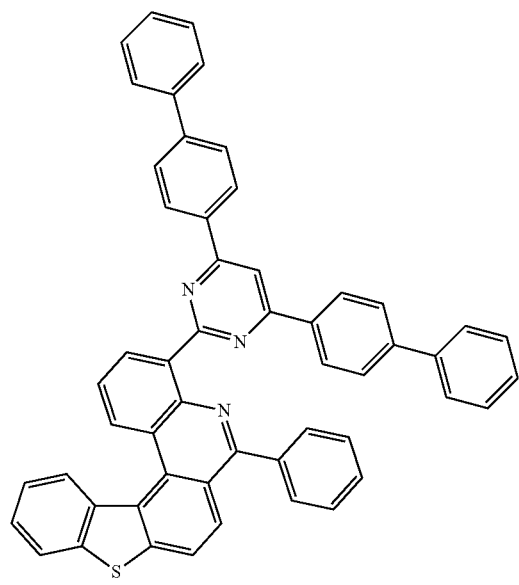
544
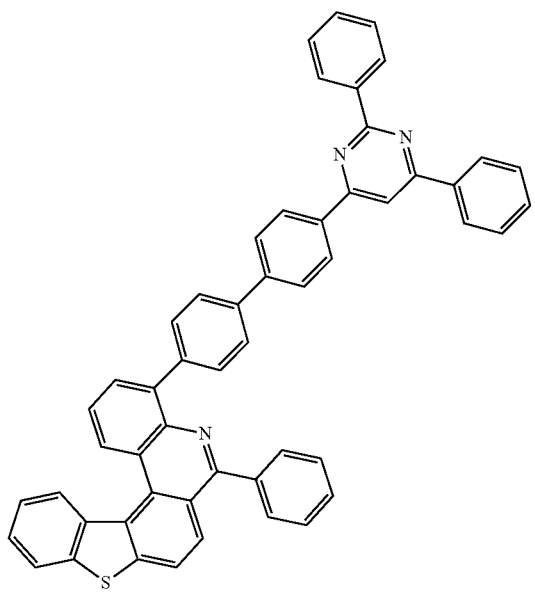
545
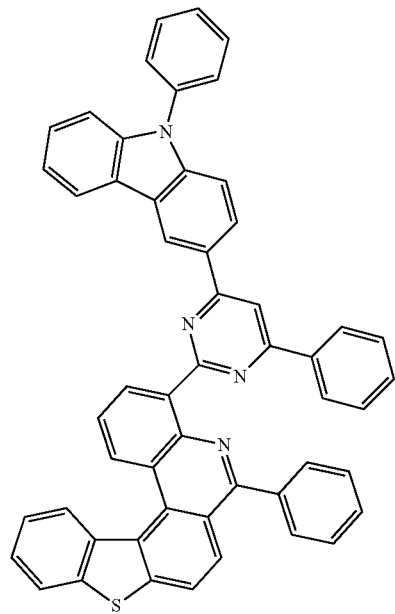
546
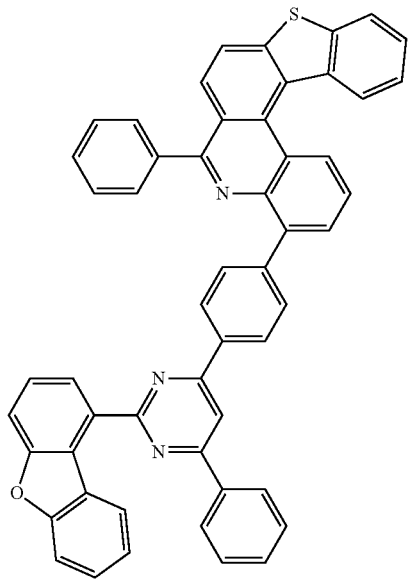

547
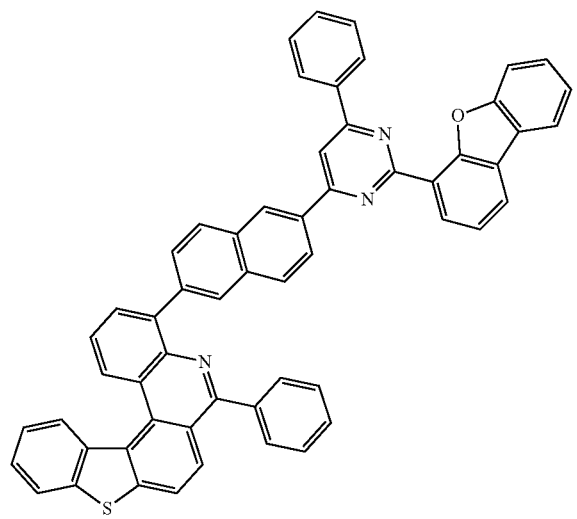
548
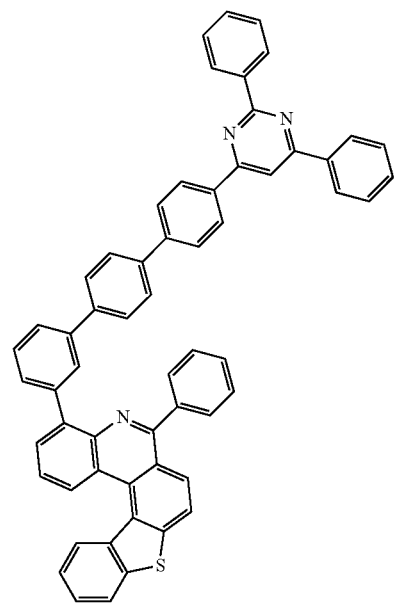
549
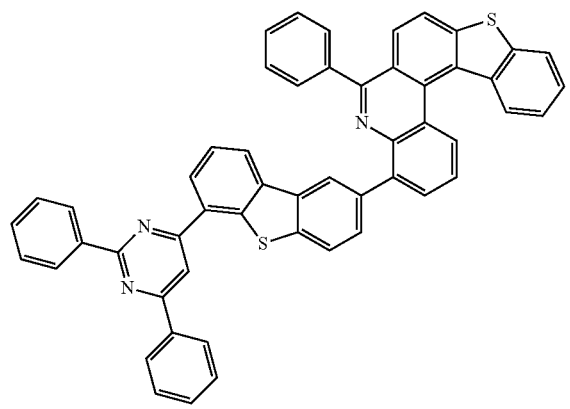
550
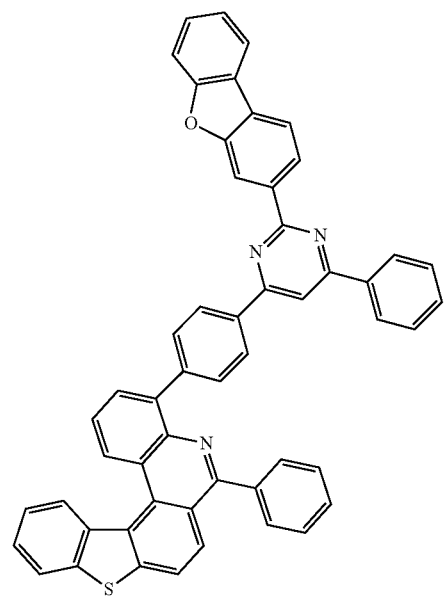

-continued
551
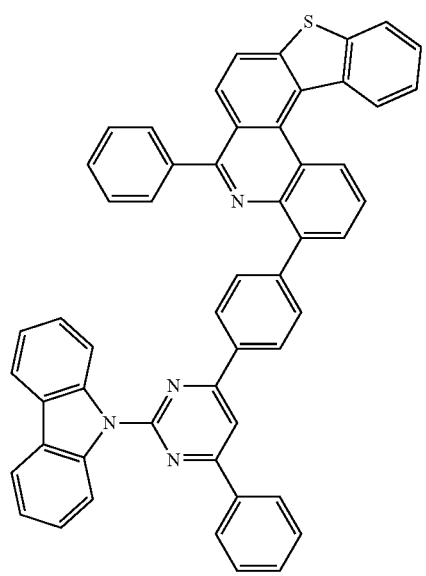
552
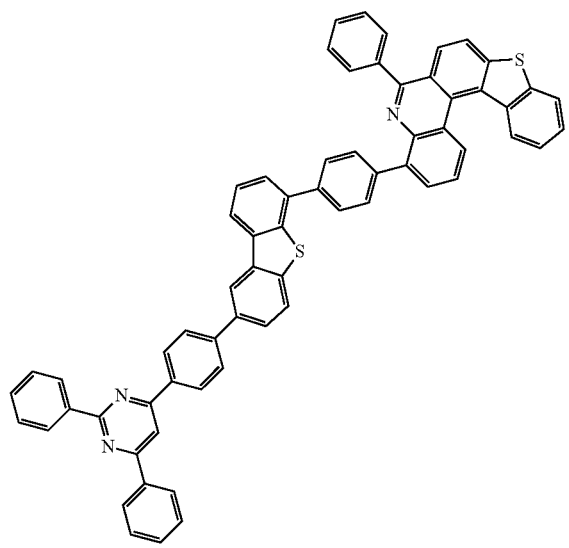
553
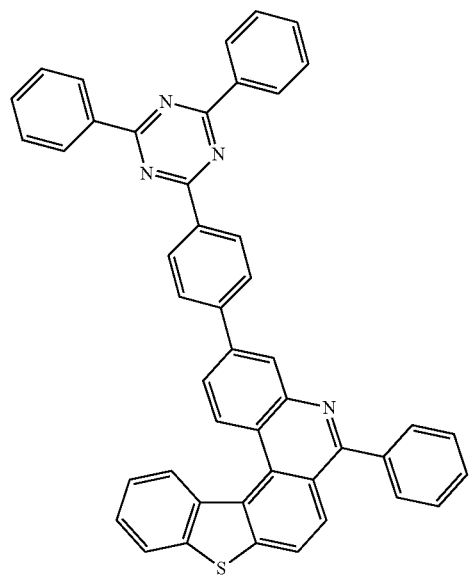
554
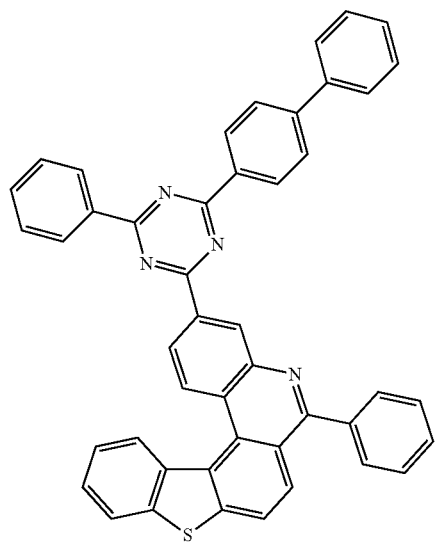

-continued
555
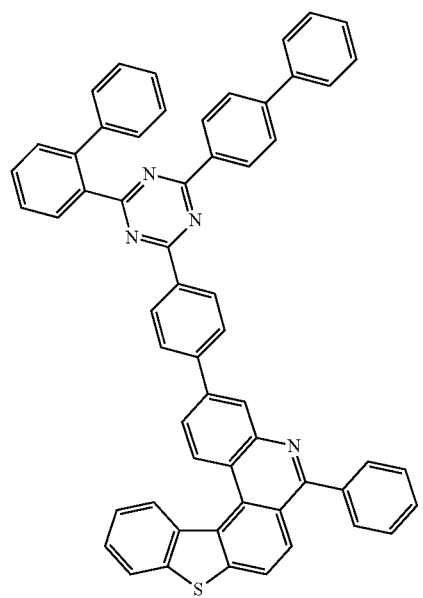
556
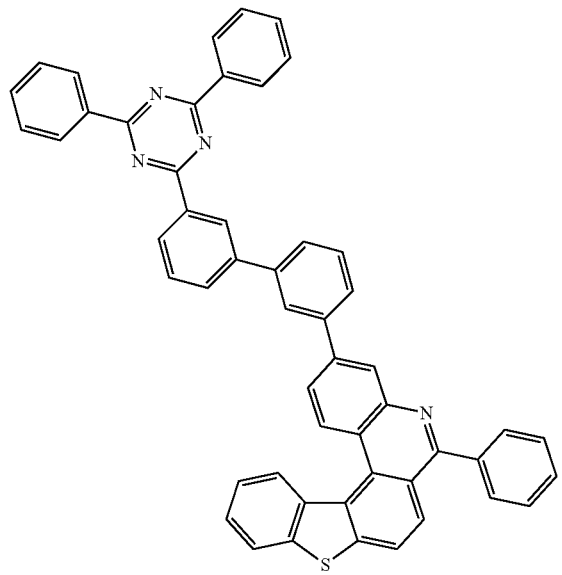
557
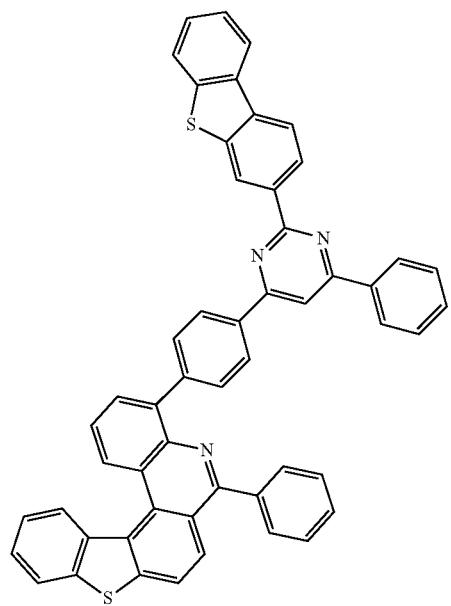
558
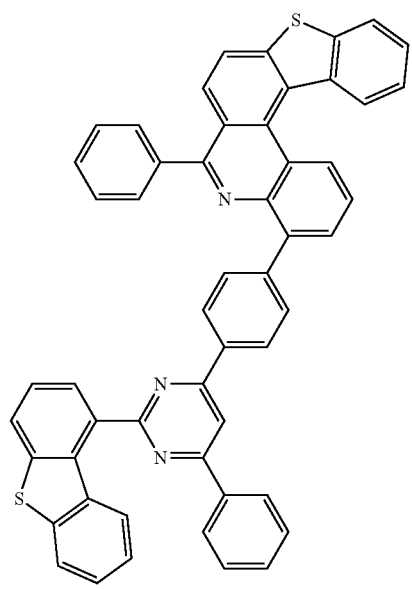

-continued
559
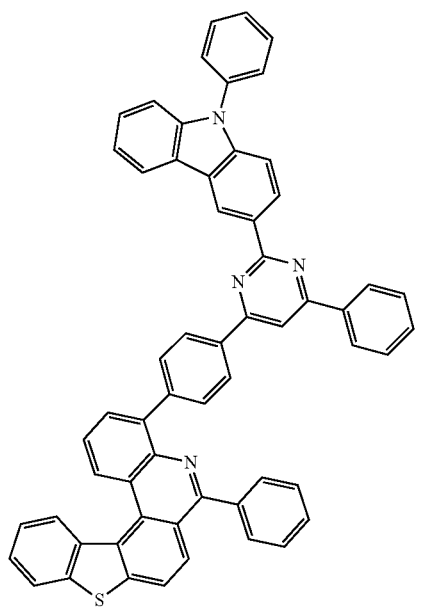
560
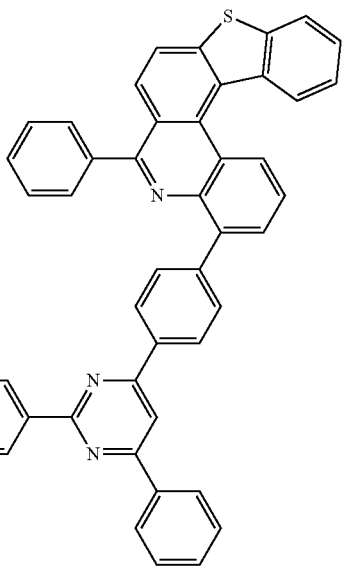
561
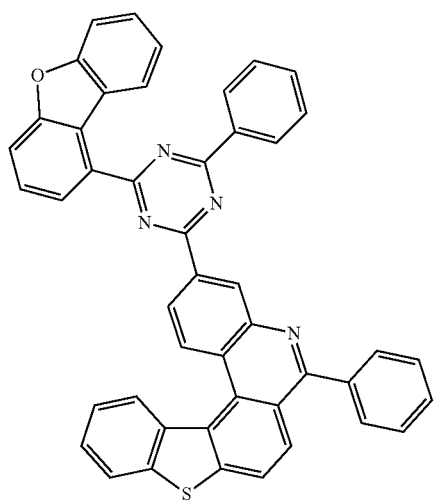
562
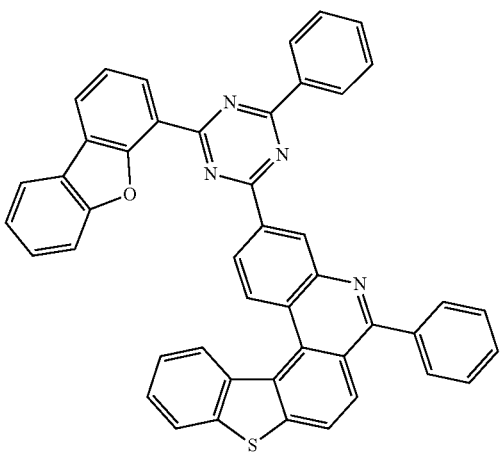
563
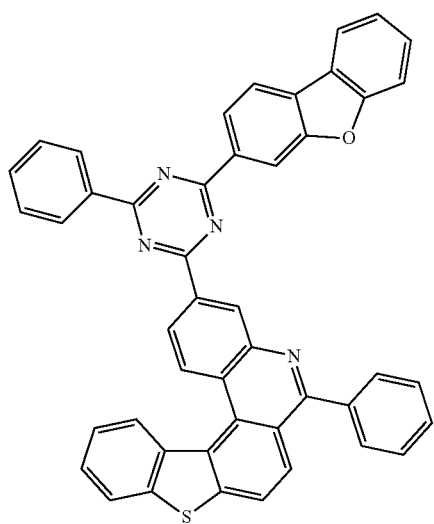
564
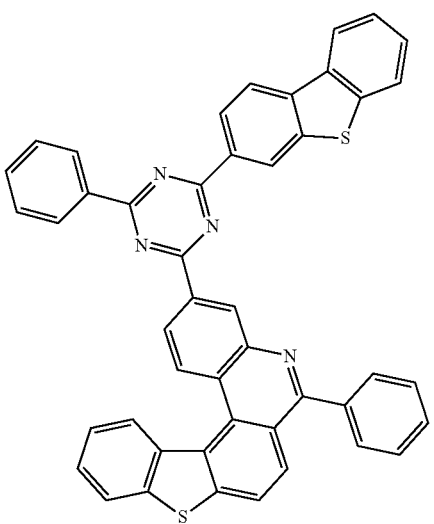

-continued
565
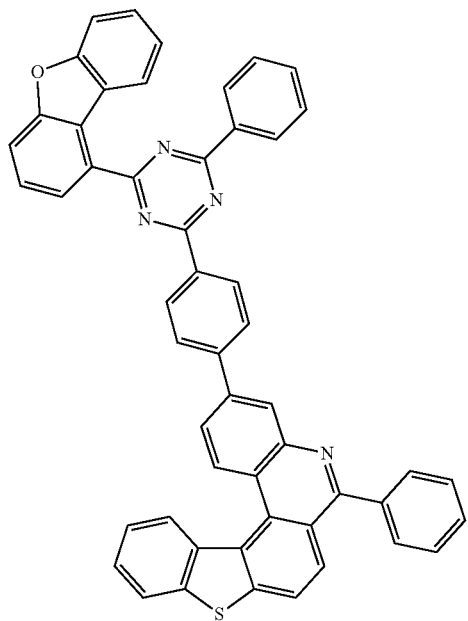
566
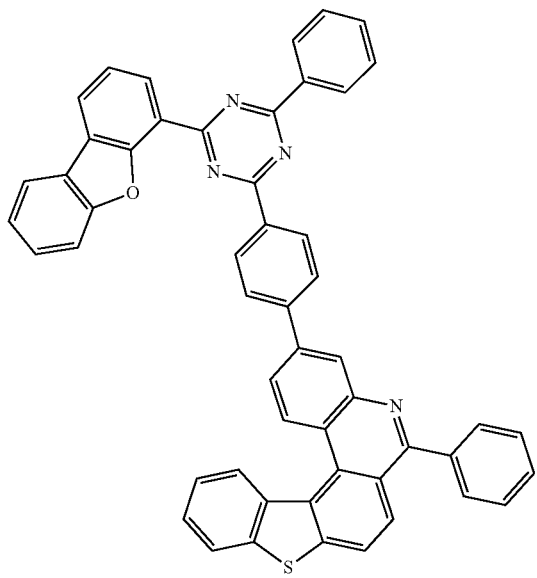
567
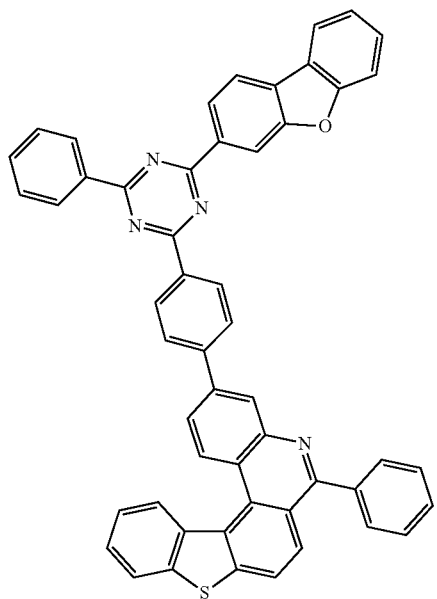
568
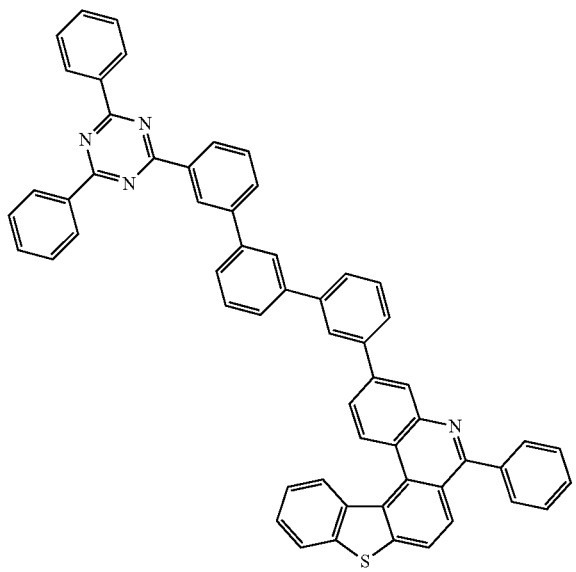

-continued
569
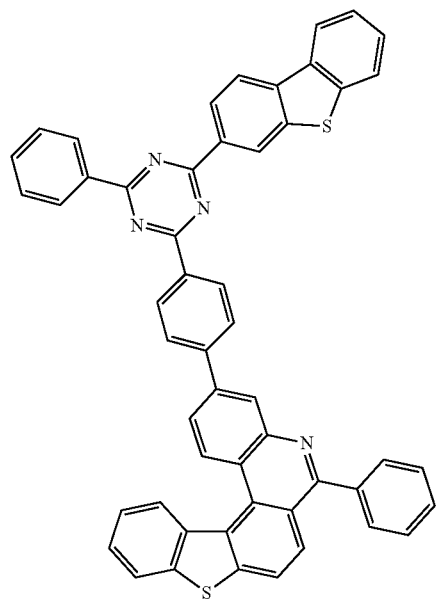
570
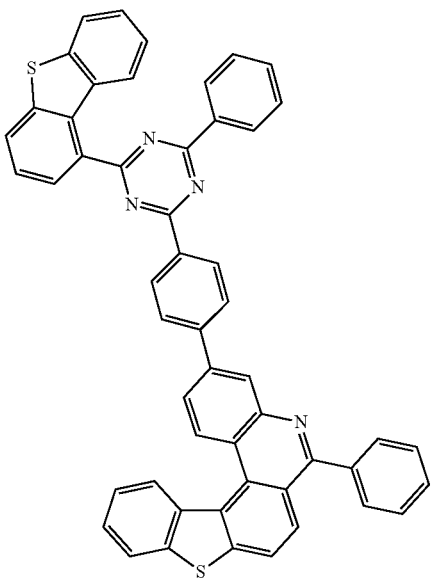
571
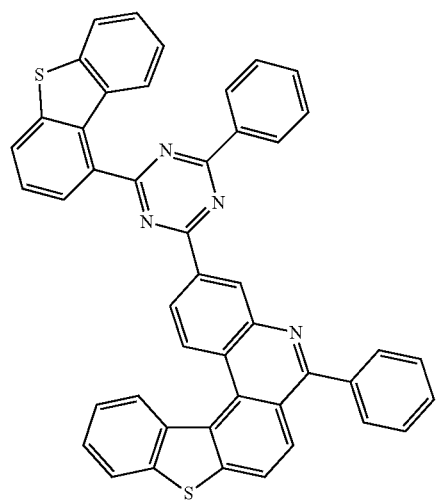
572
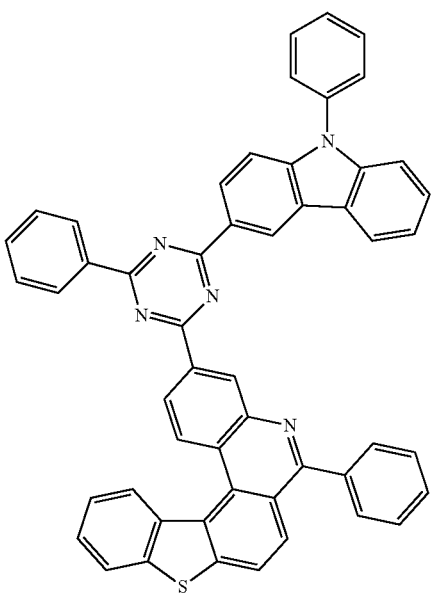

-continued
573 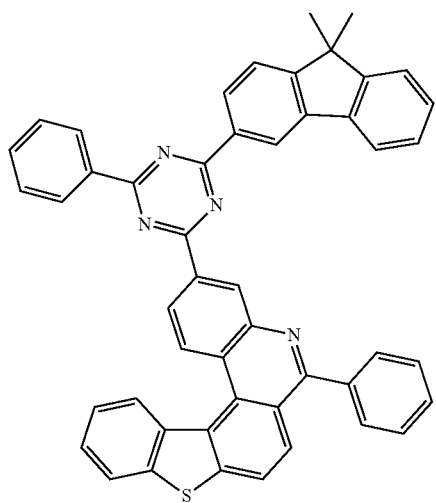
574 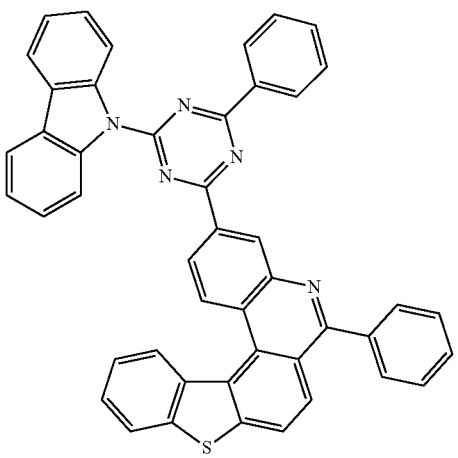
575 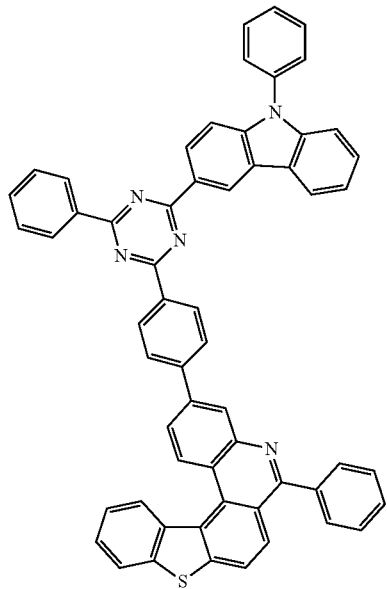
576 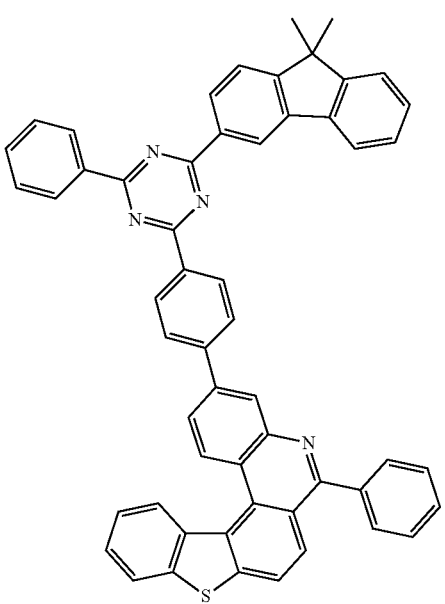

-continued
577
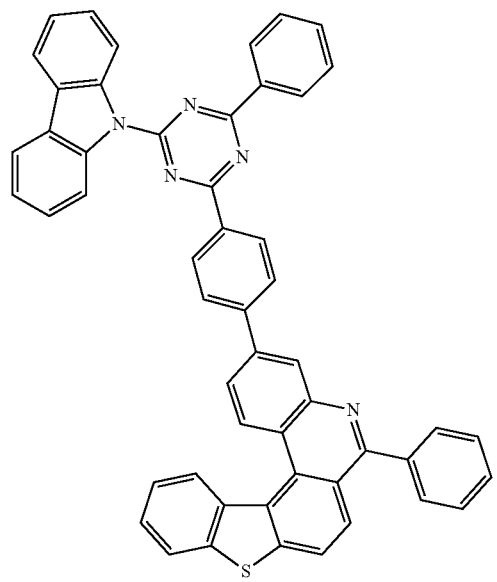
578
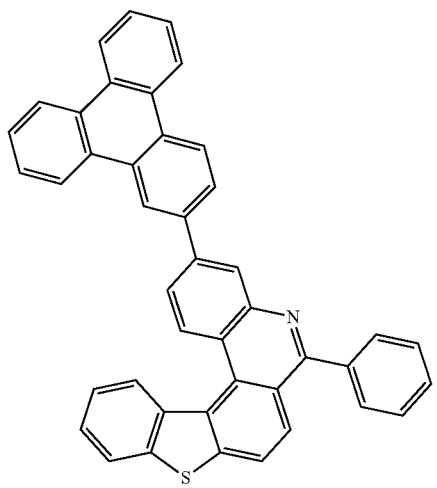
579
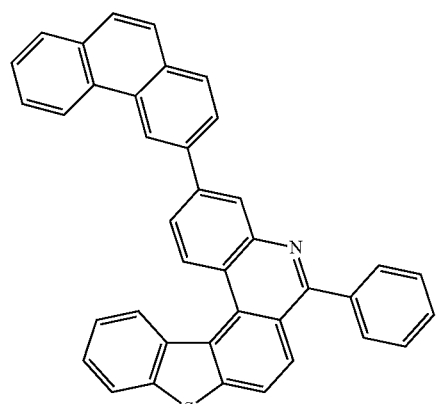
580
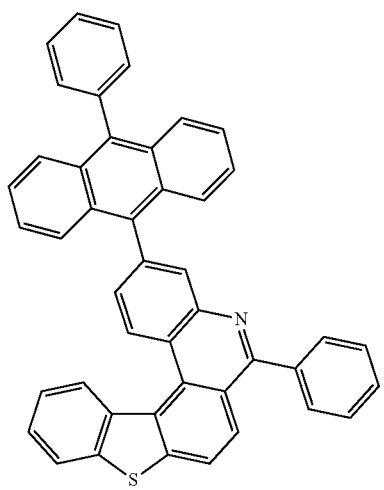
581
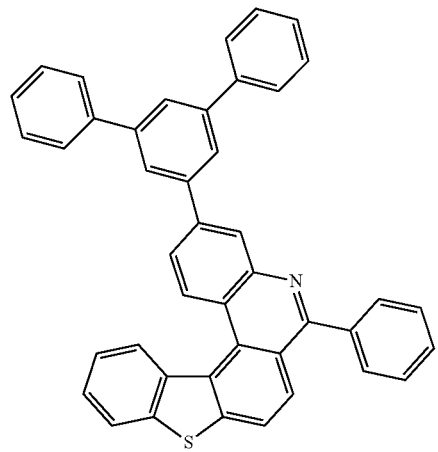
582
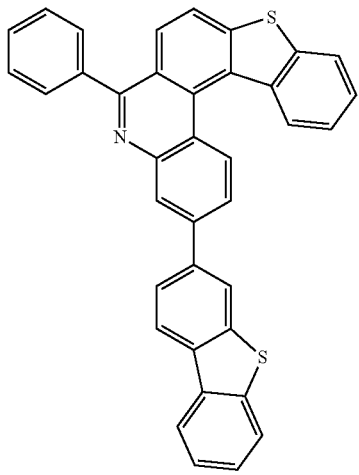

-continued
583
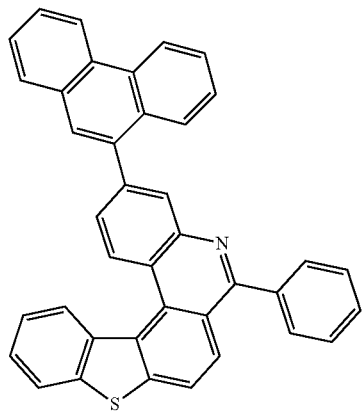
584
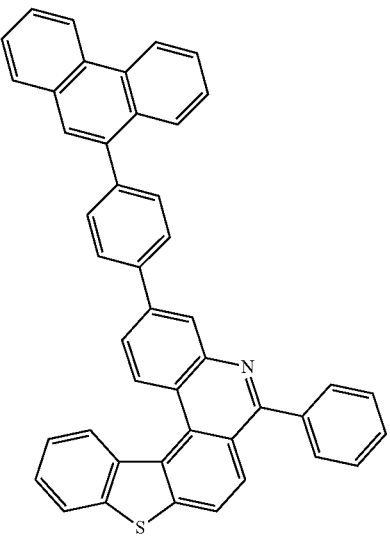
585
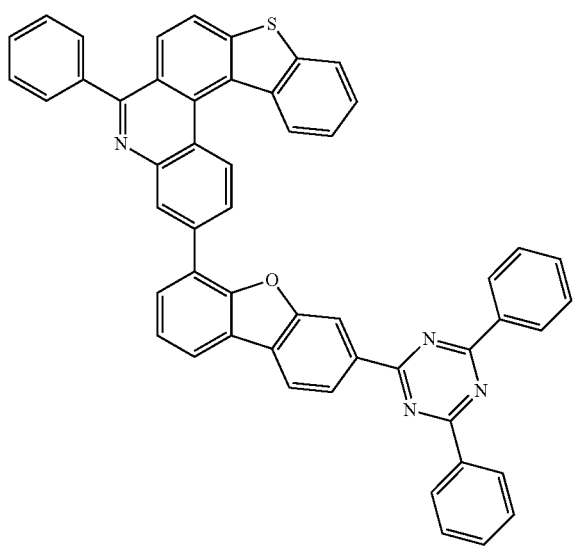
586
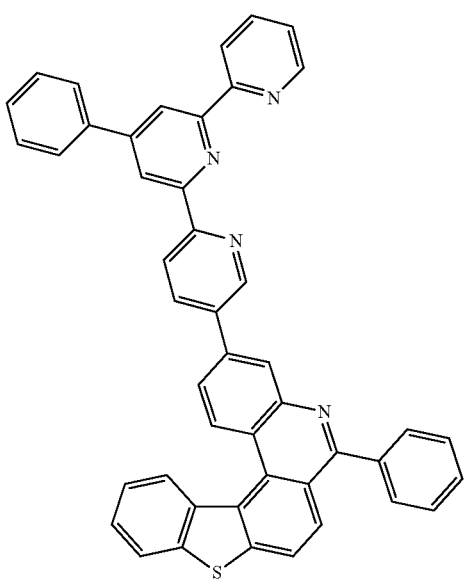
587
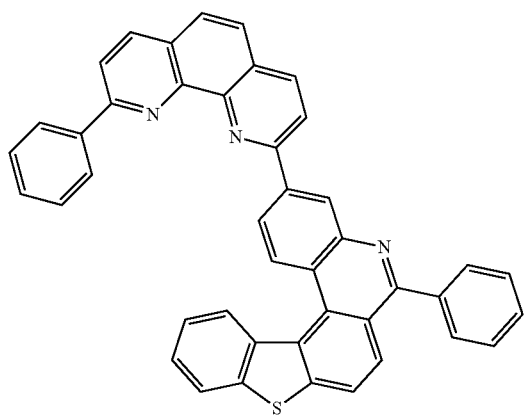
588
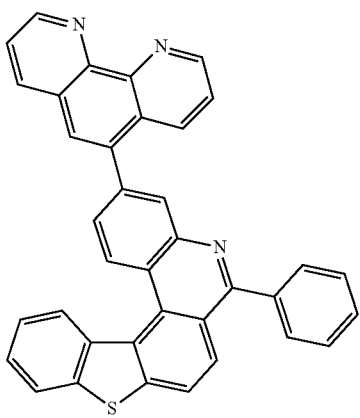

589
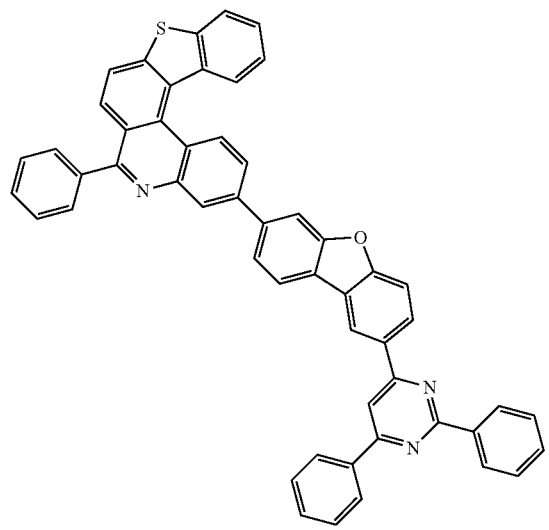
590
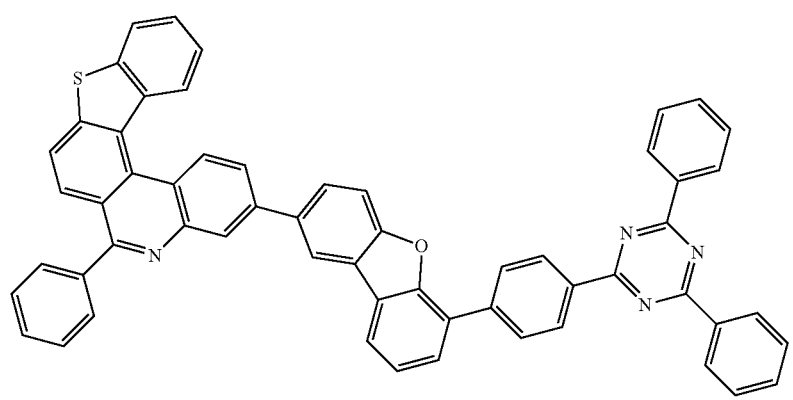
591
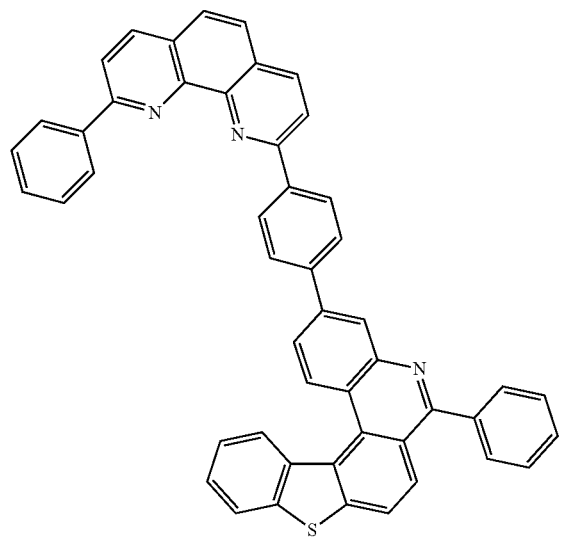
592
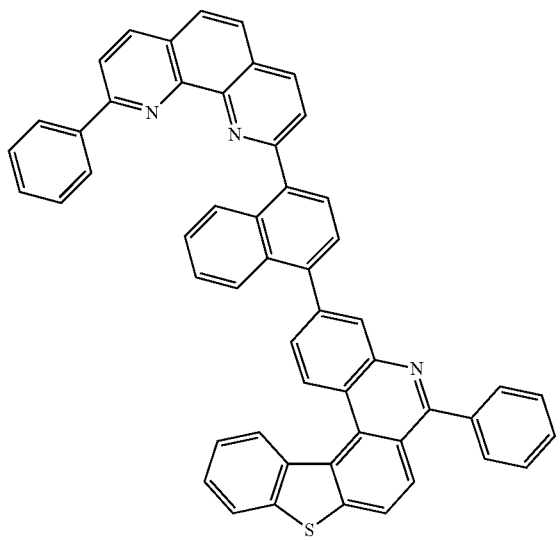

-continued
593
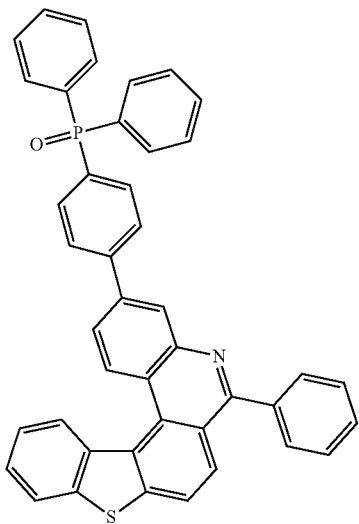
594
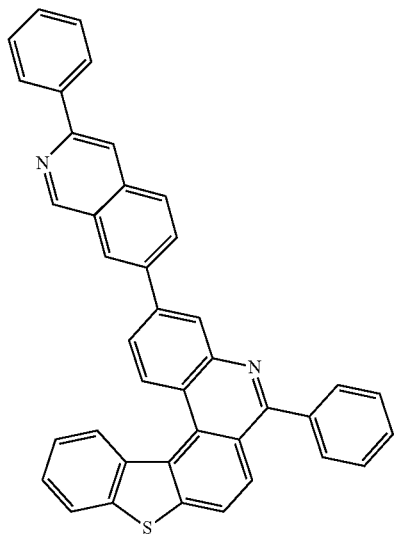
595
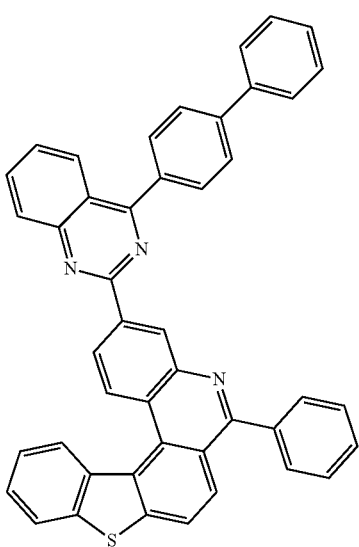
596
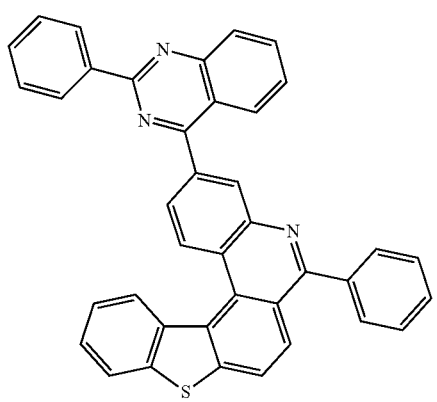
597
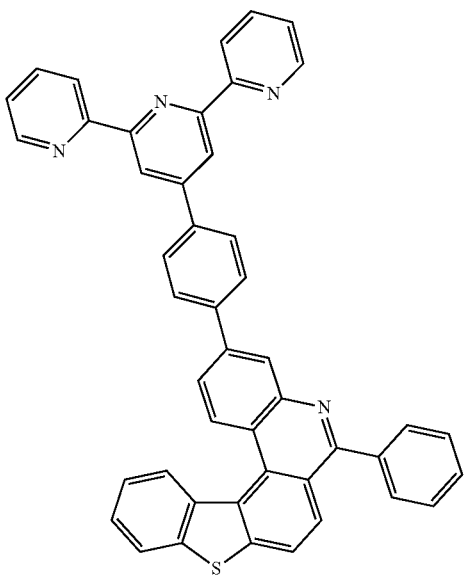
598
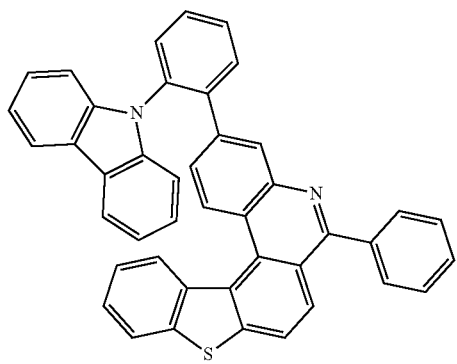

-continued
599
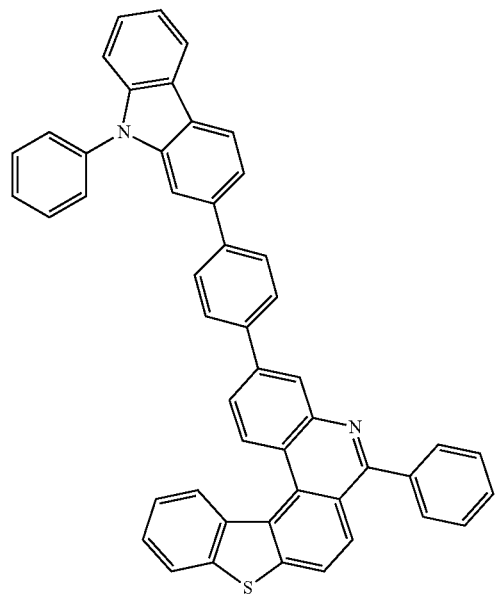
600
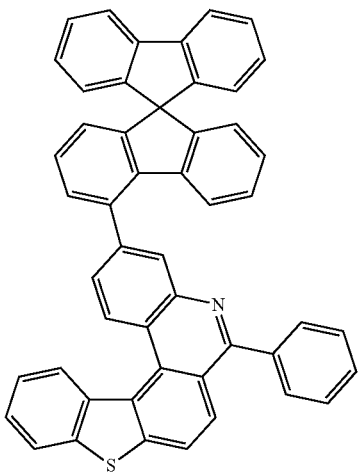
601
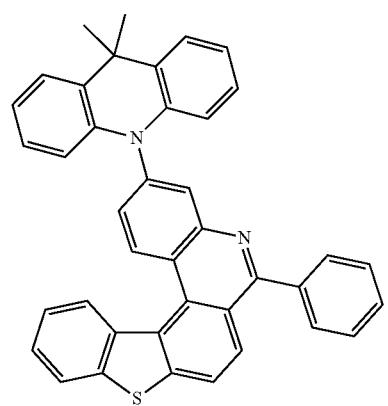
602
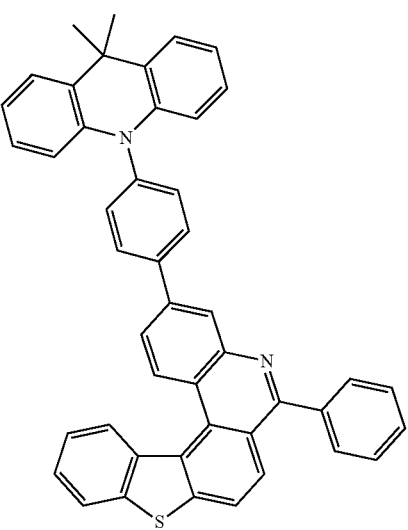

-continued
603
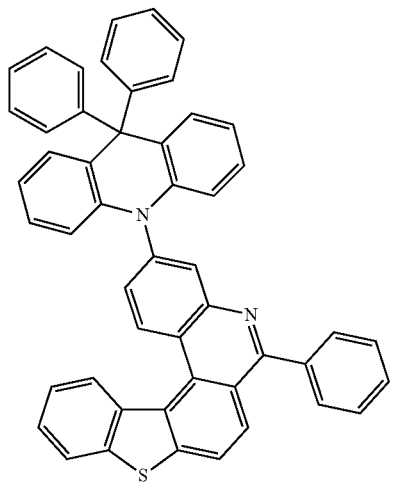
604
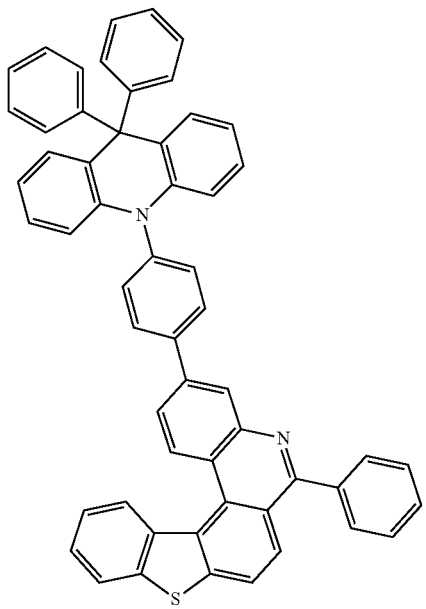
605
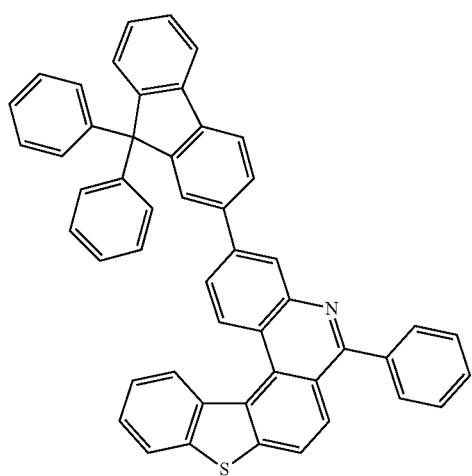
606
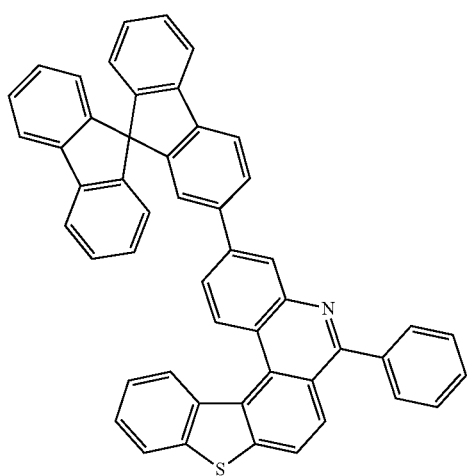
607
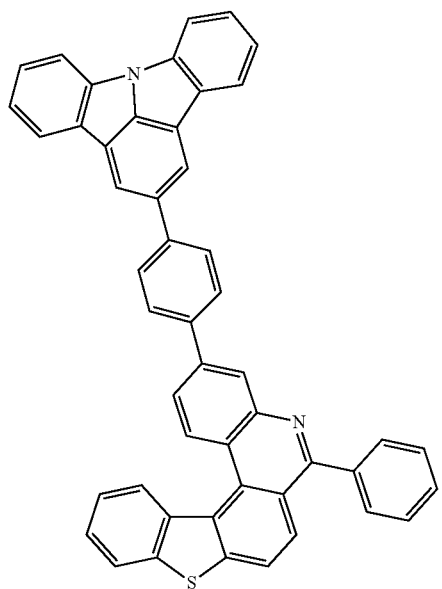
608
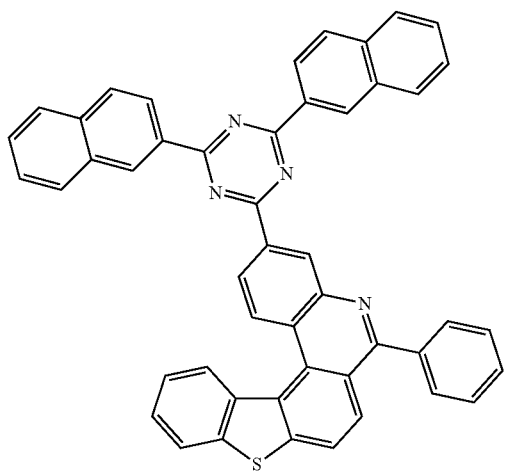

-continued
609
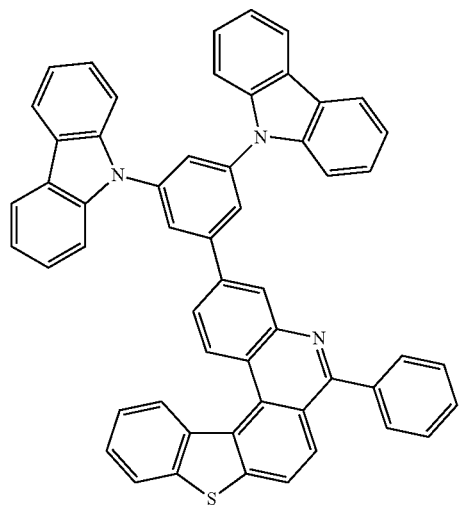
610
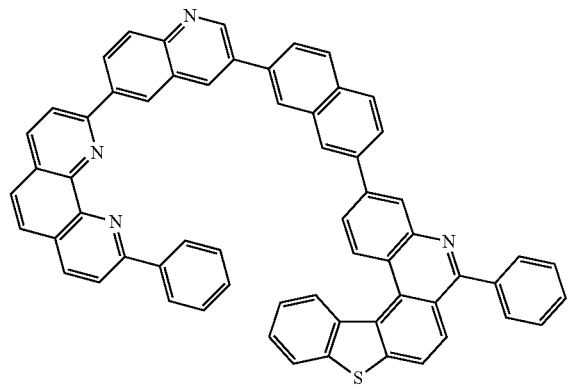
611
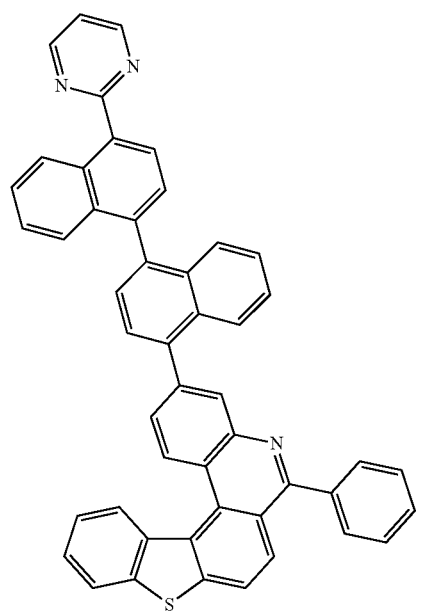
612
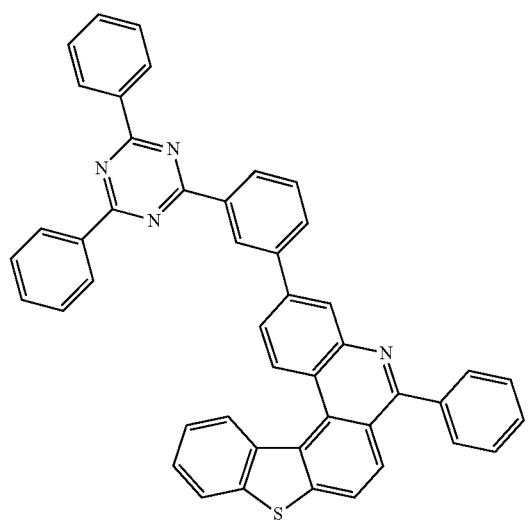

-continued
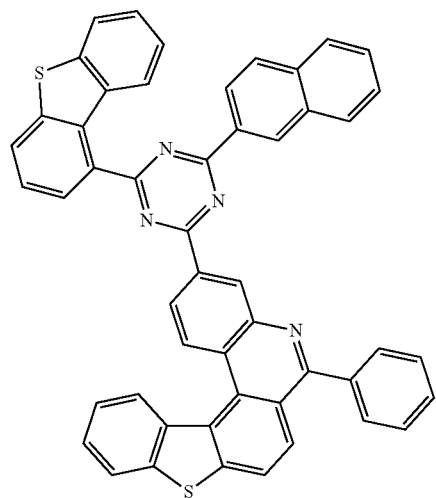
613
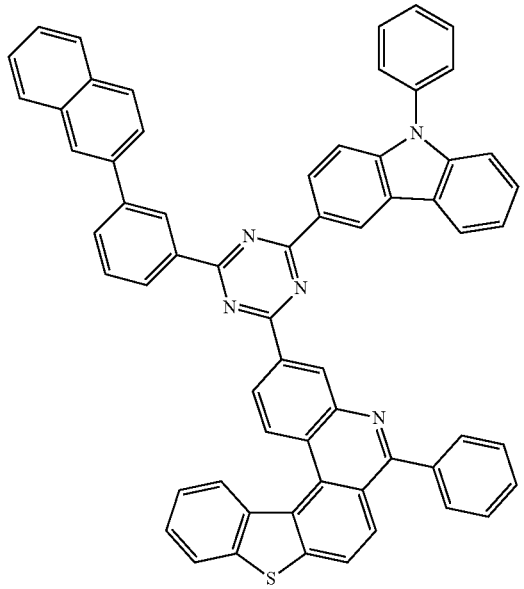
614
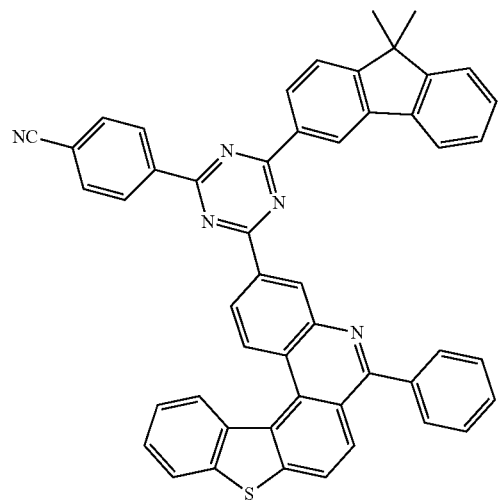
615
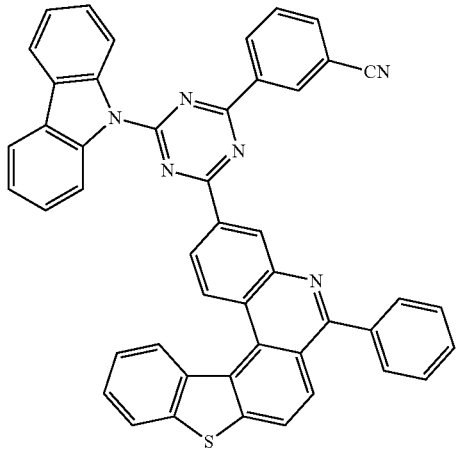
616

-continued
617
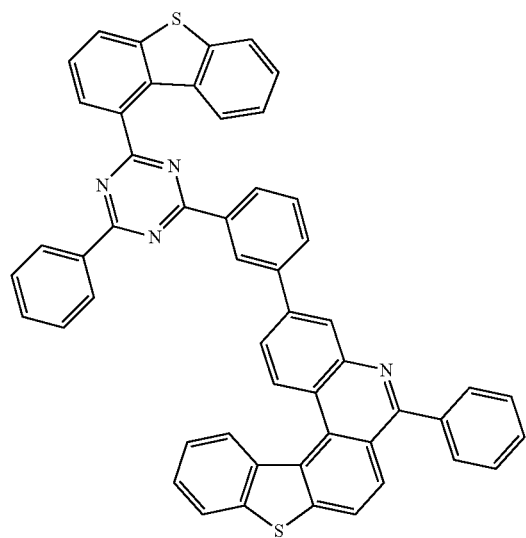
618
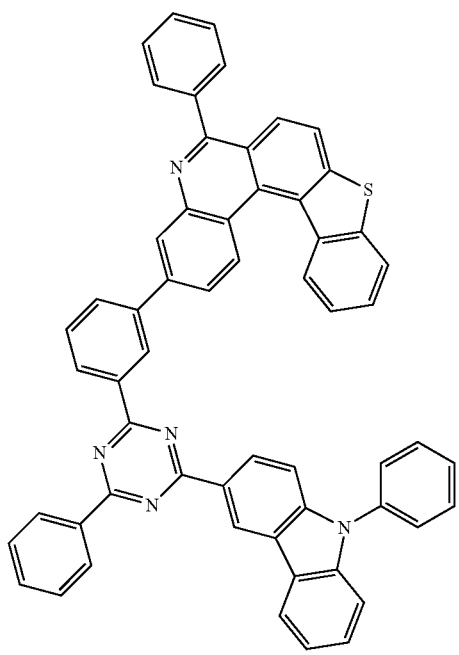
619
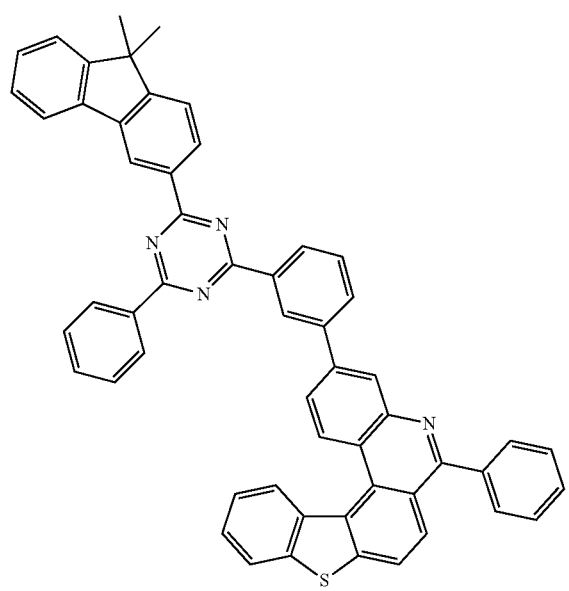
620
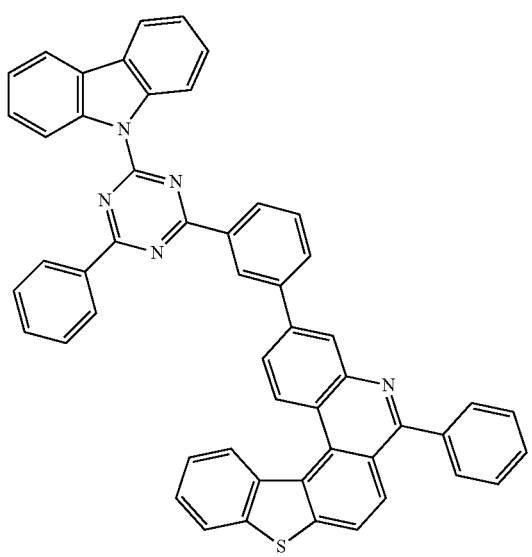

-continued
621
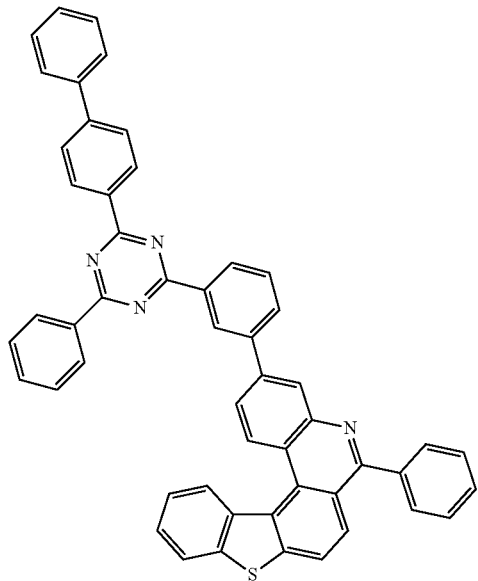
622
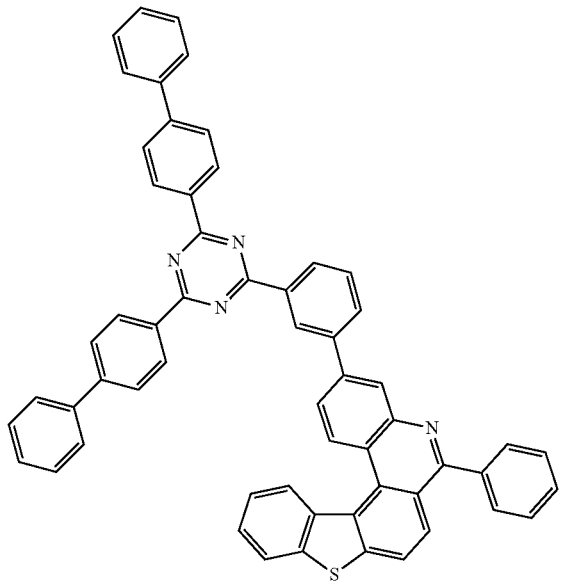
623
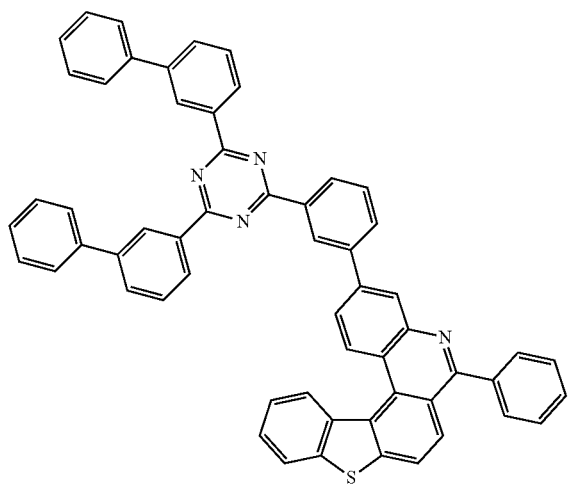
624
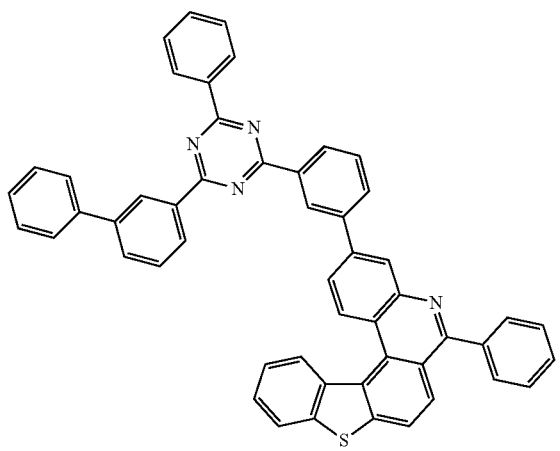
625
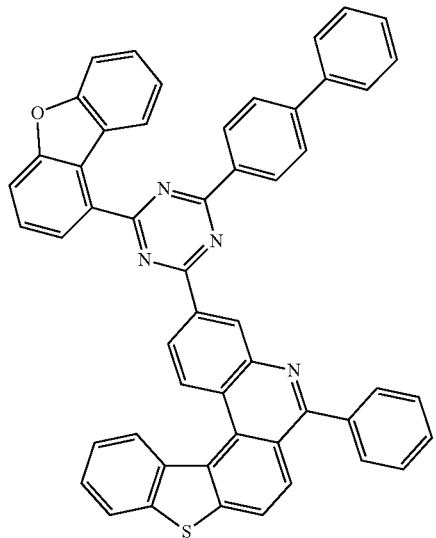
626
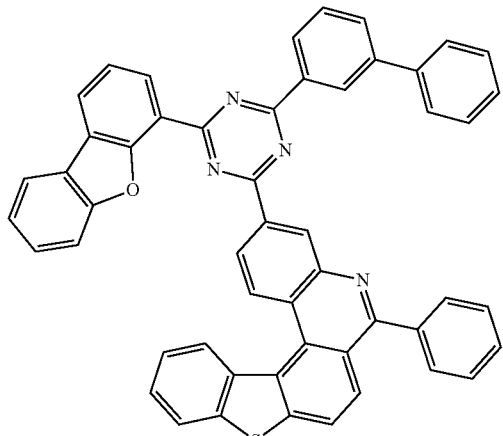

-continued
627
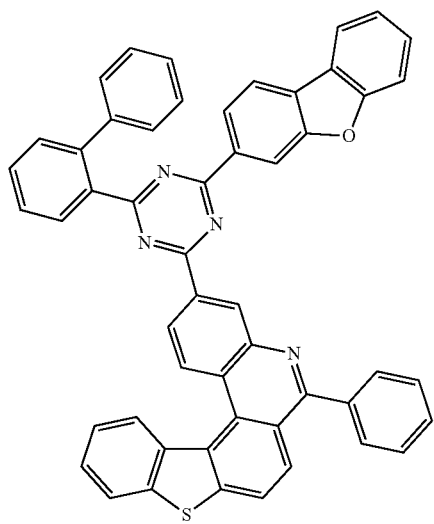
628
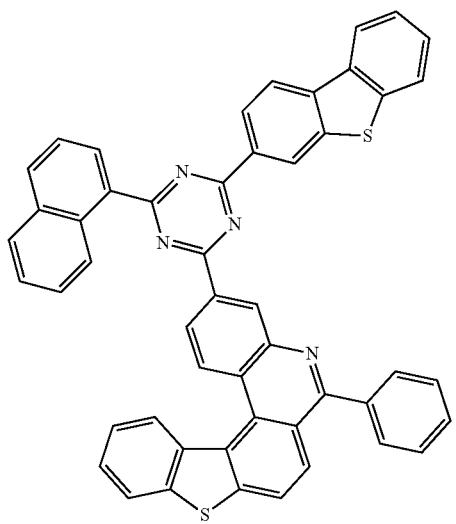
629
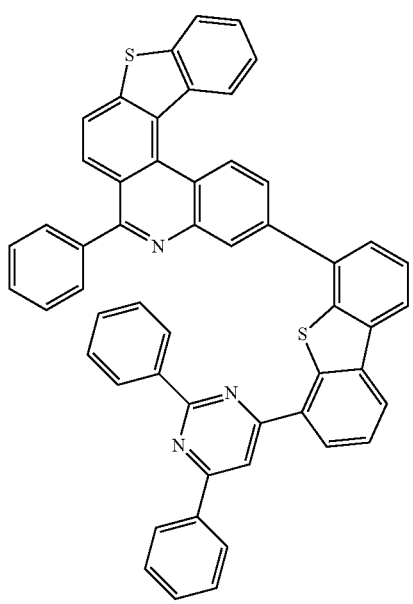
630
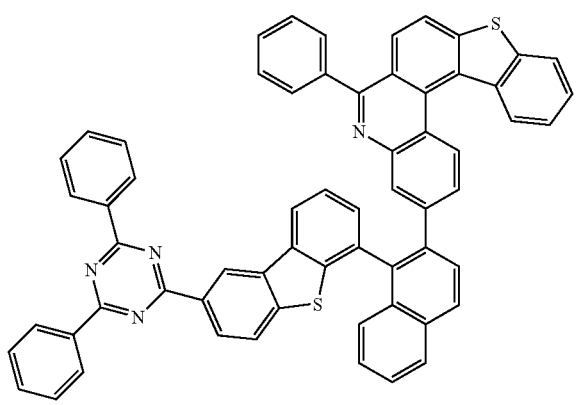
631
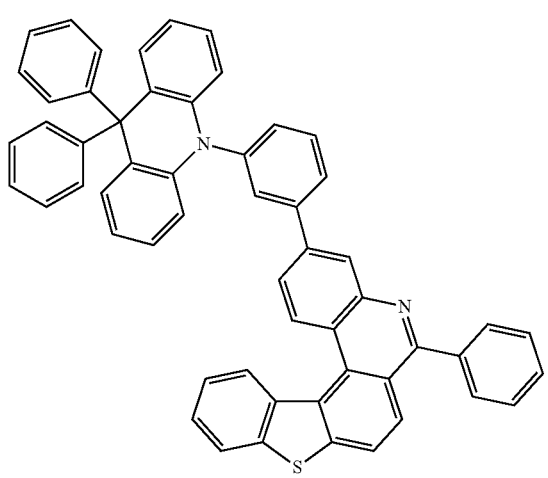
632
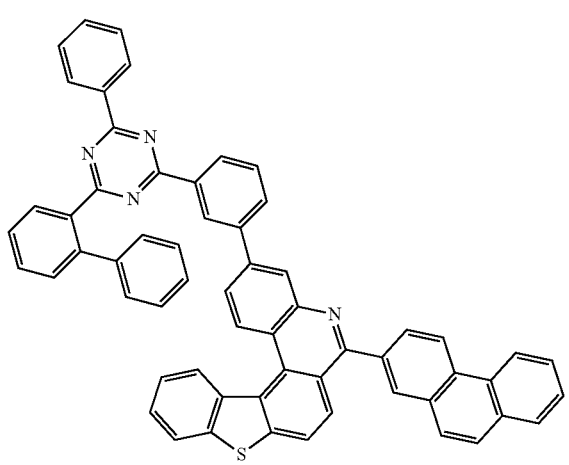

633
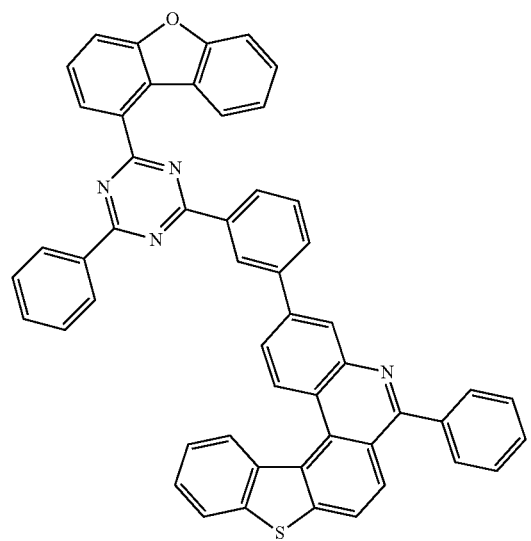
634
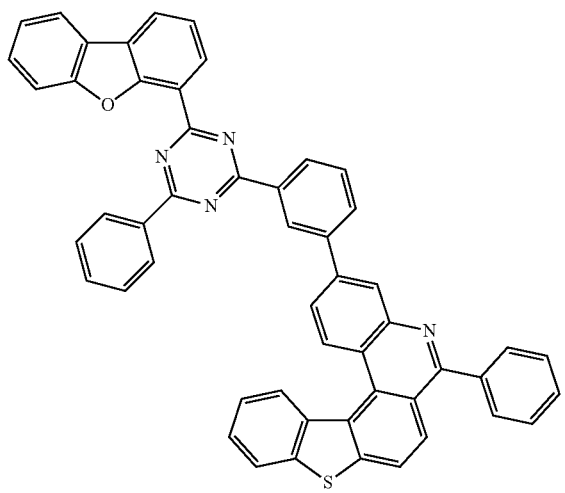
635
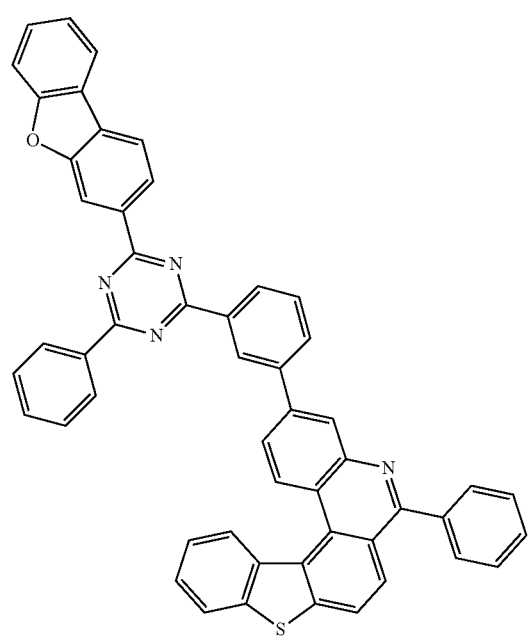
636
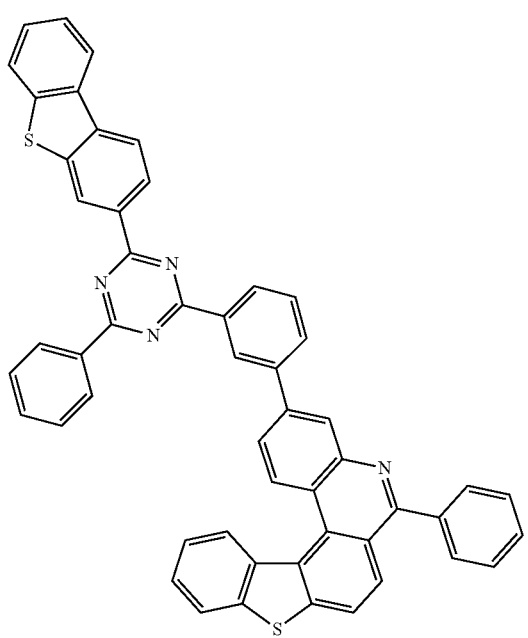

-continued
637
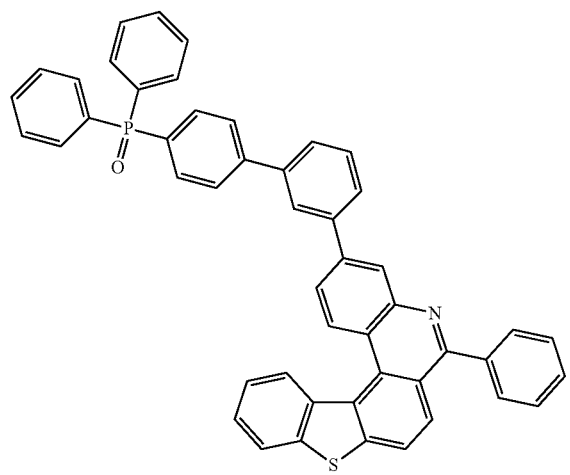
638
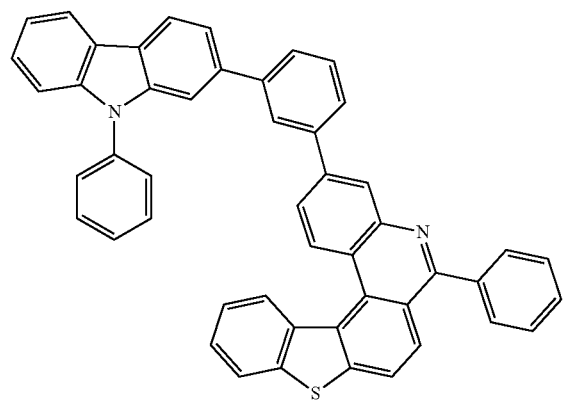
639
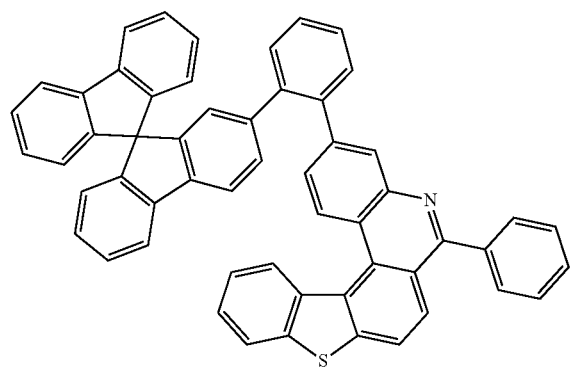
640
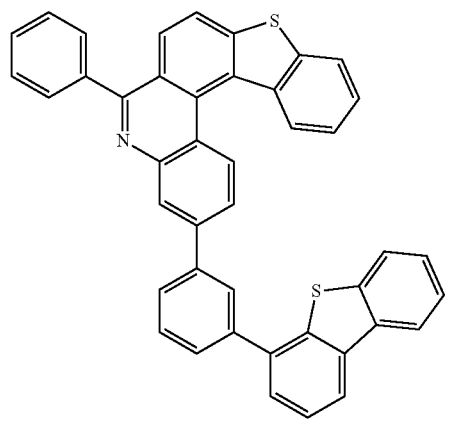
641
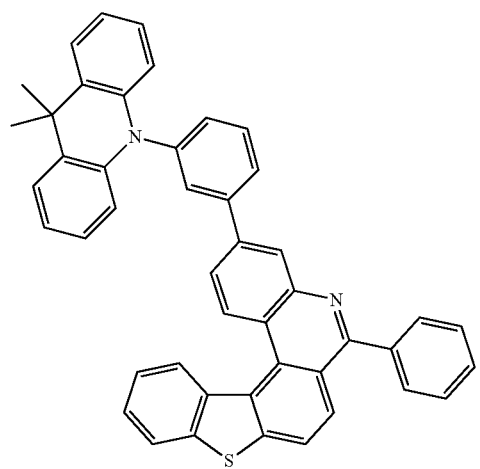
642
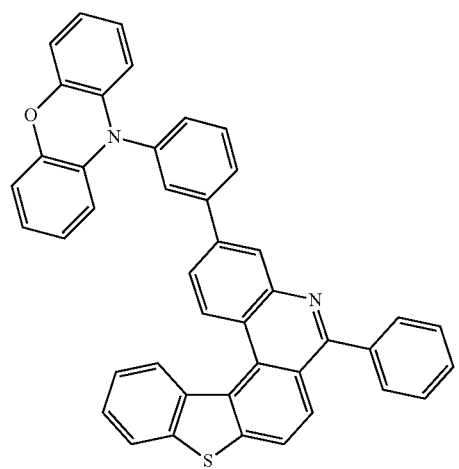

-continued
643
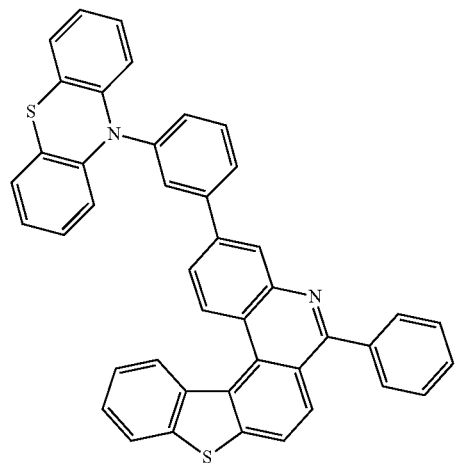
644
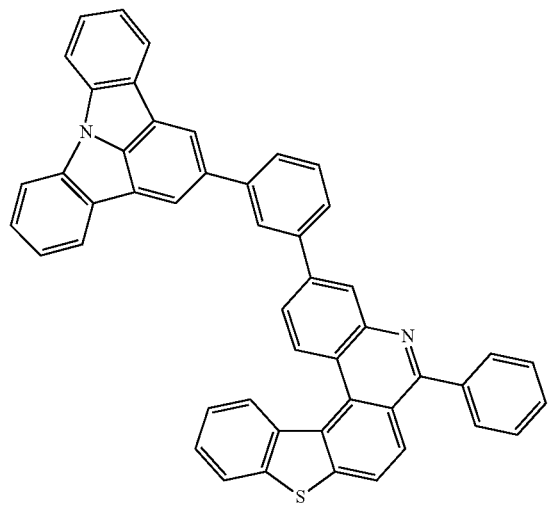
645
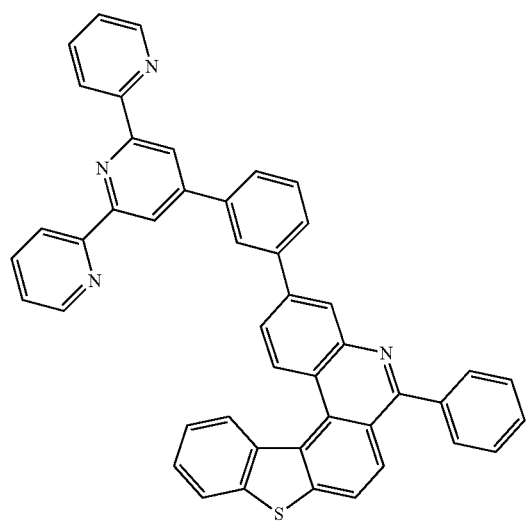
646
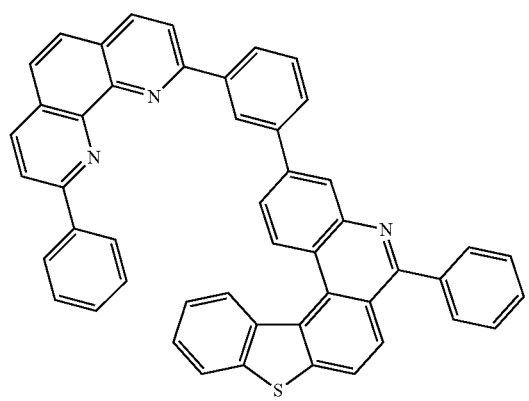
647
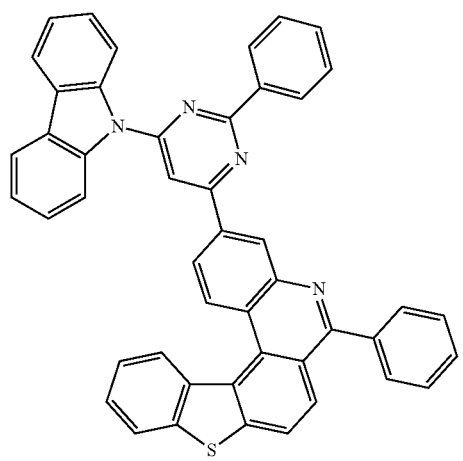
648
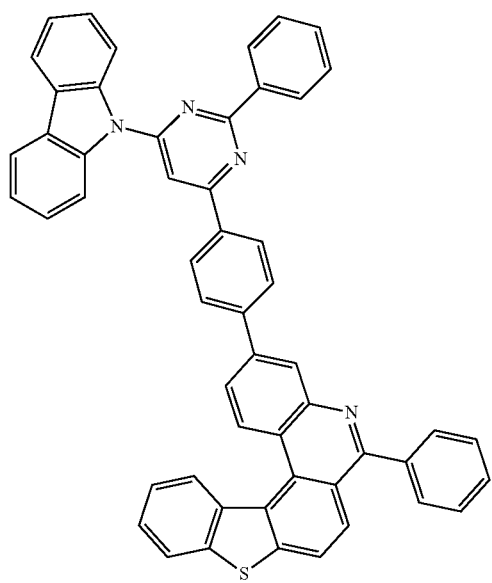

-continued
649
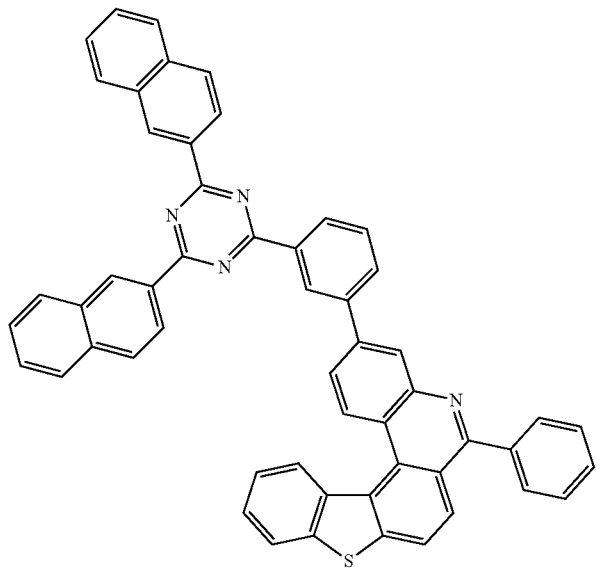
650
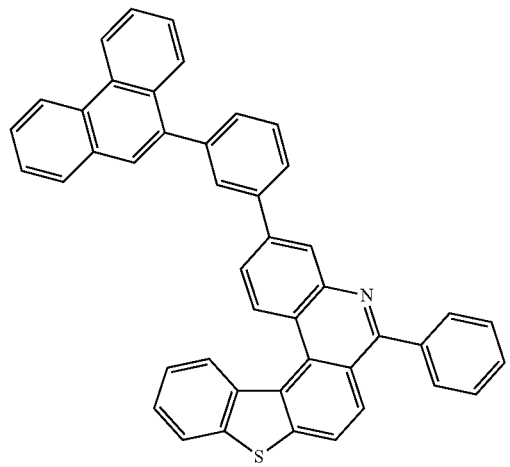
651
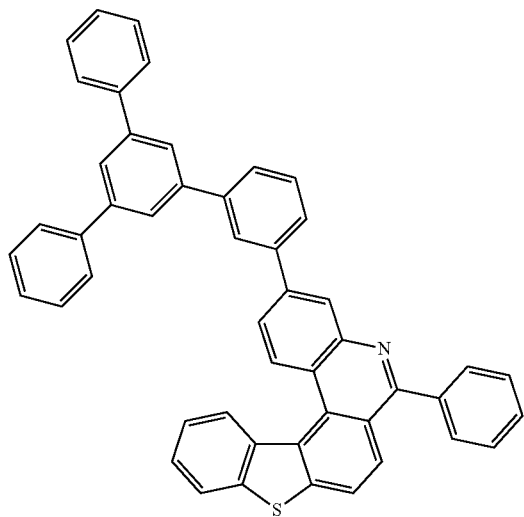
652
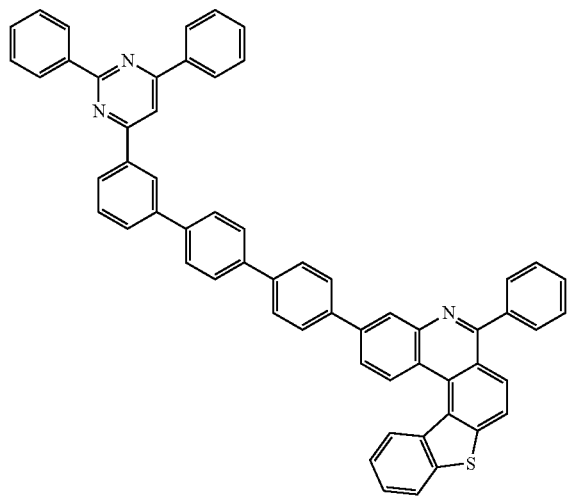
653
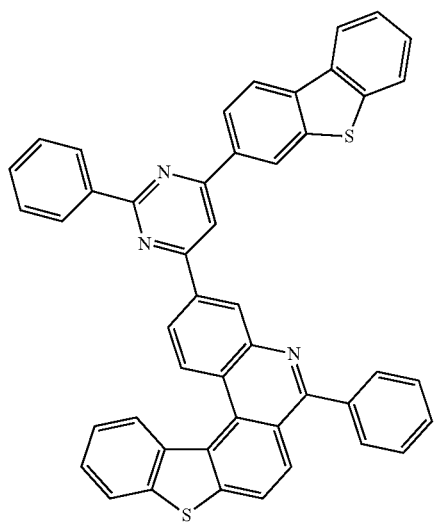
654
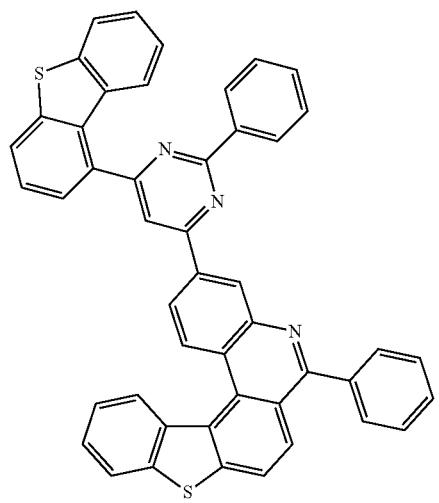

-continued
655 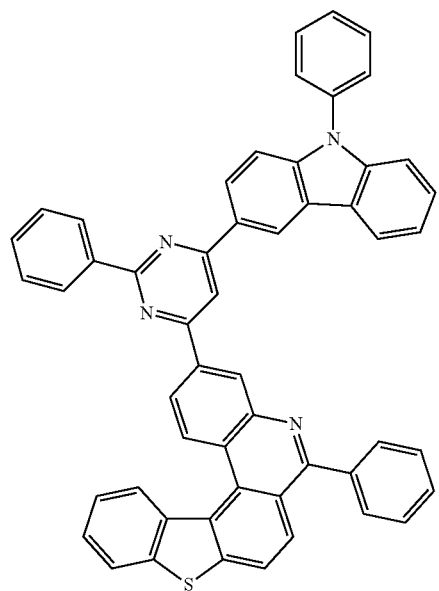
656 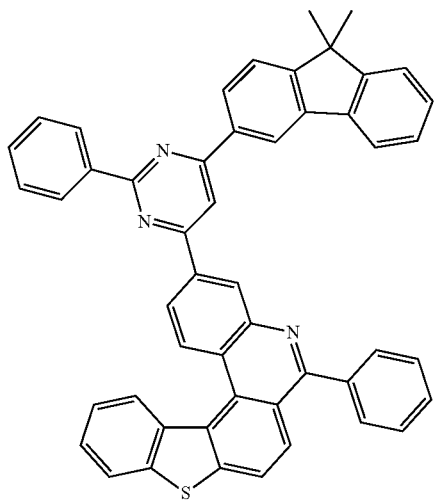
657 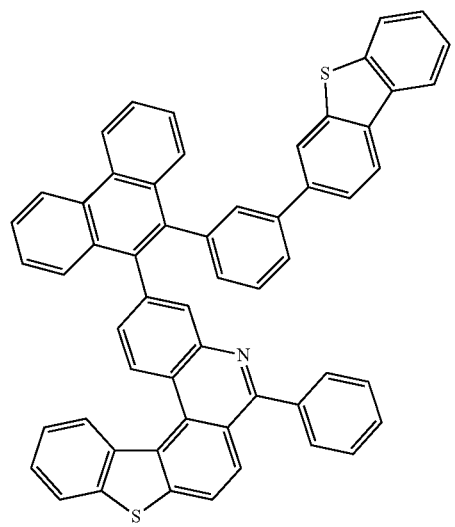
658

659 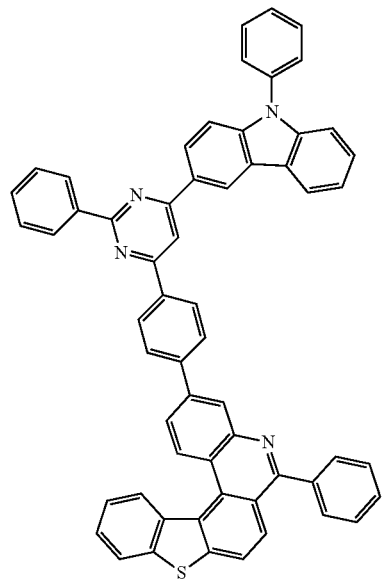
660 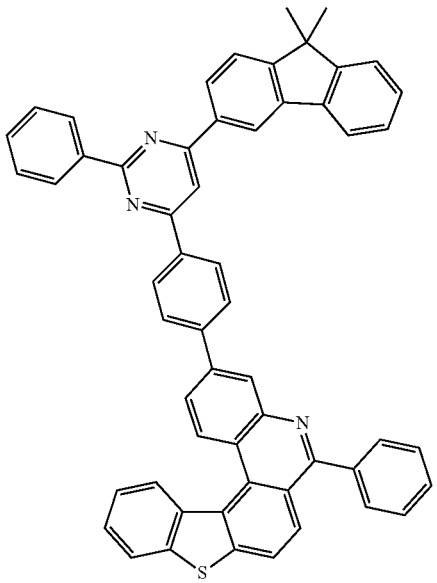
661 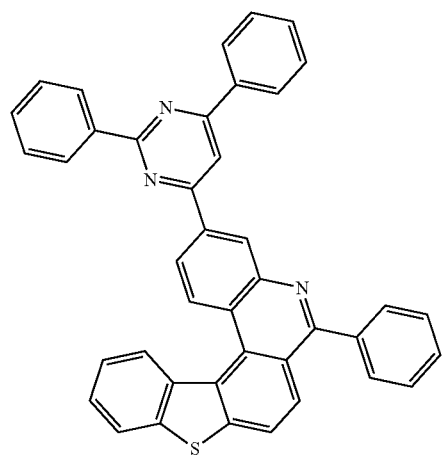
662 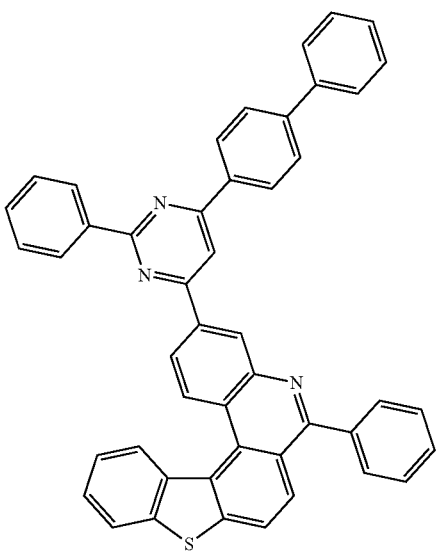

663
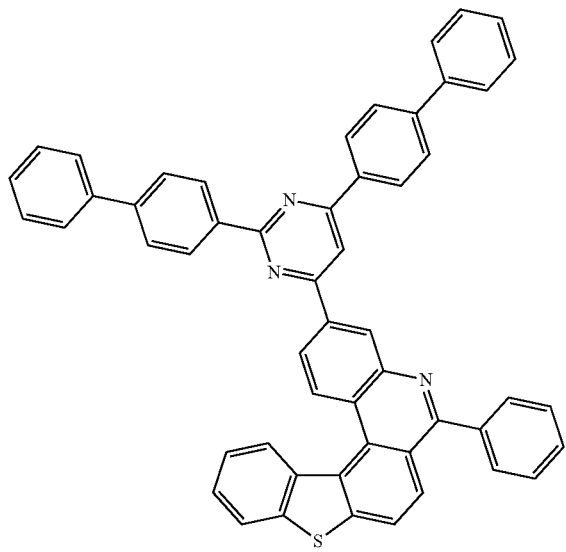
664
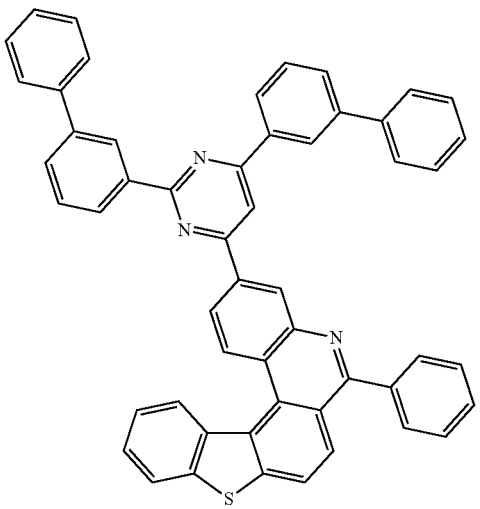
665
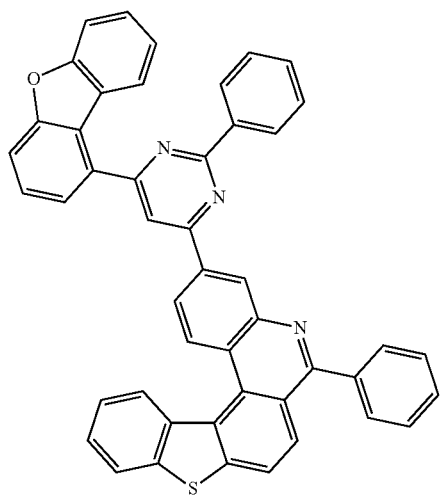
666
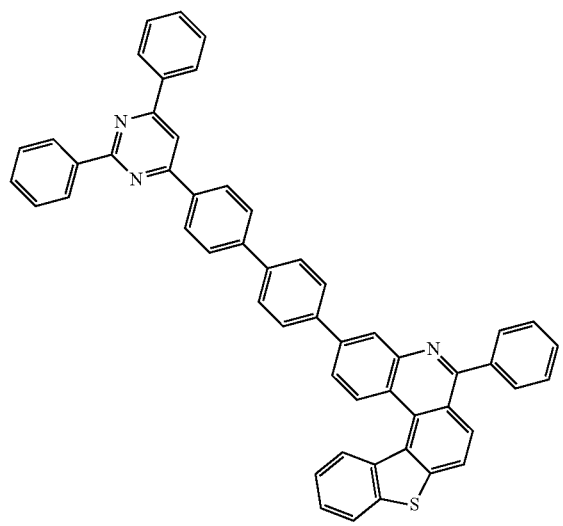
667
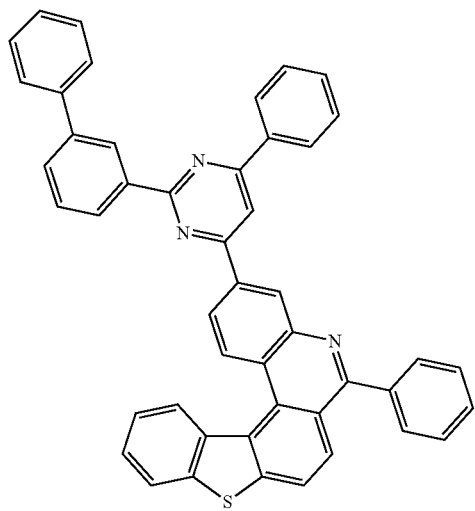
668
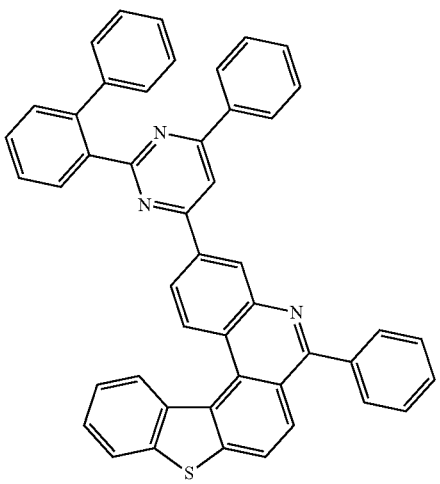

669
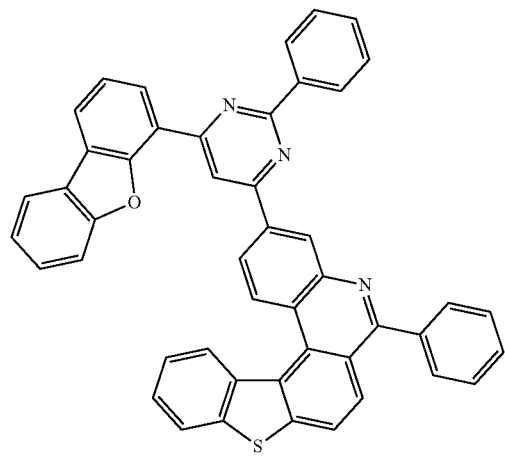
670
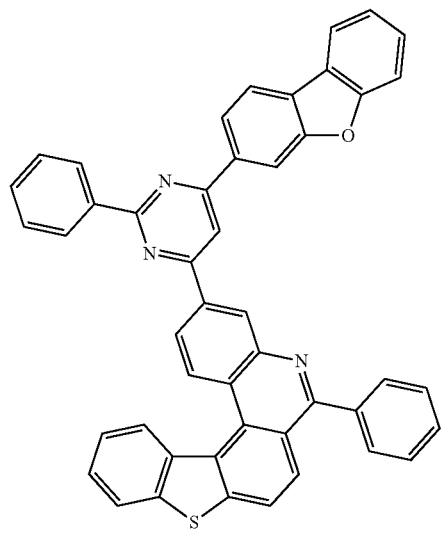
671
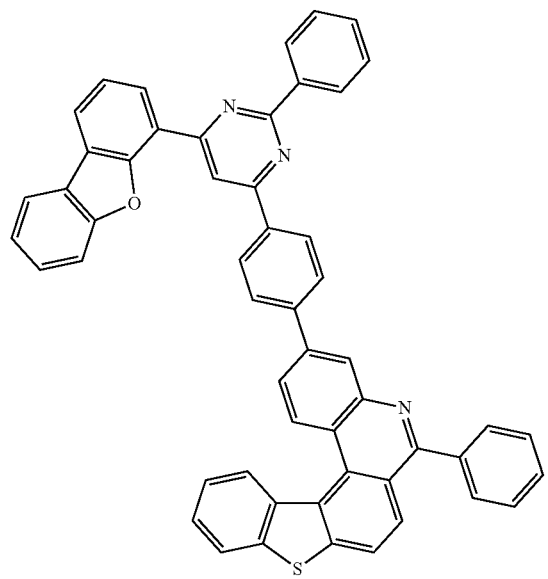
672
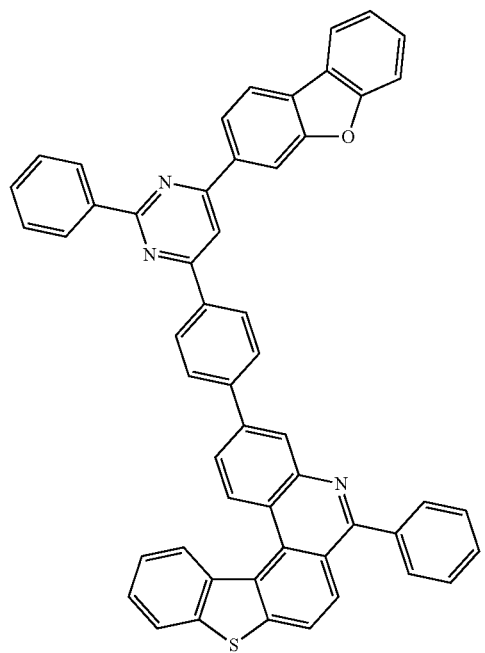

-continued
673
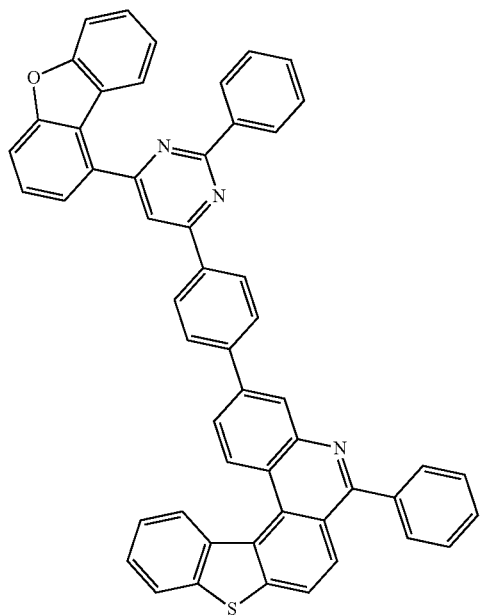
674
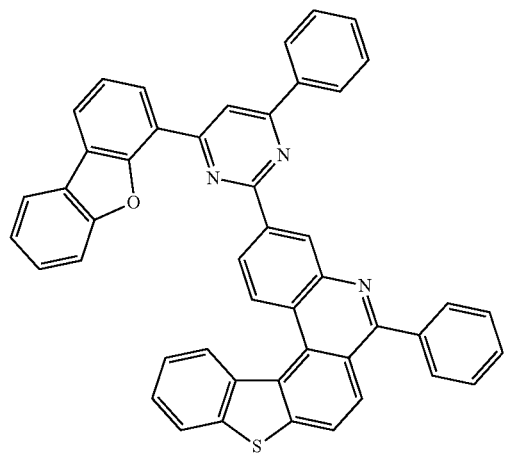
675
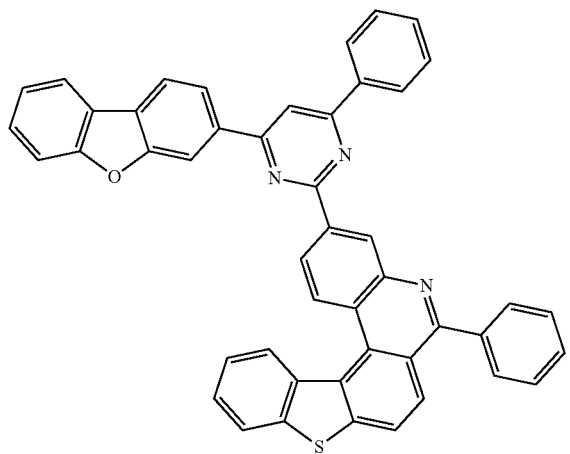
676
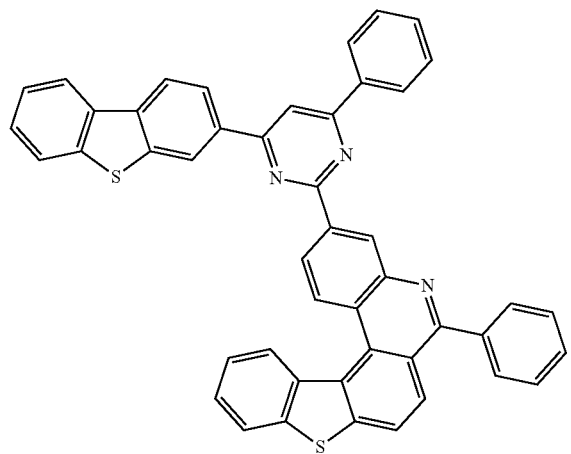
677
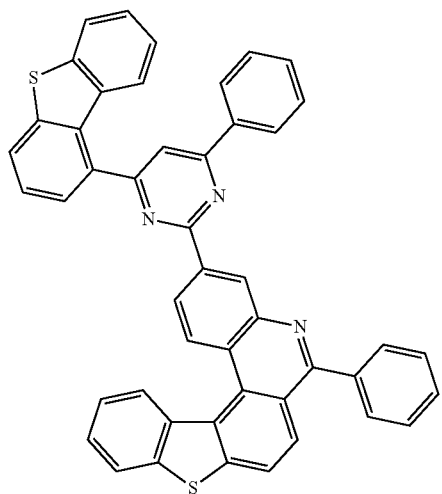
678
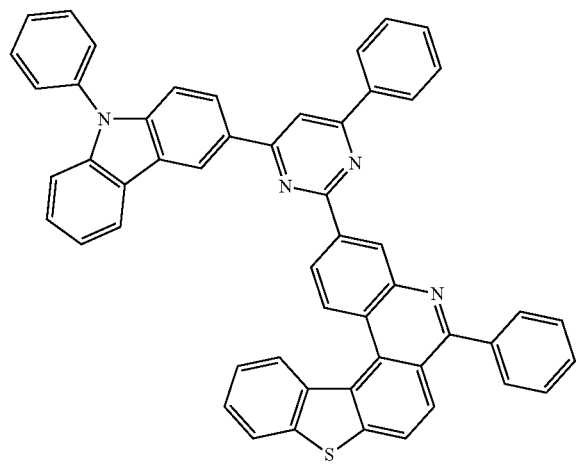

-continued
679
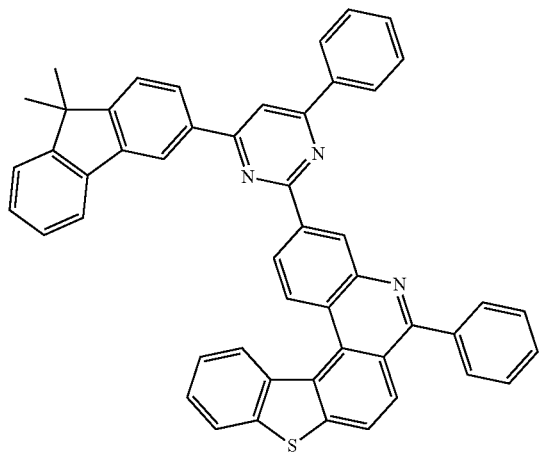
680
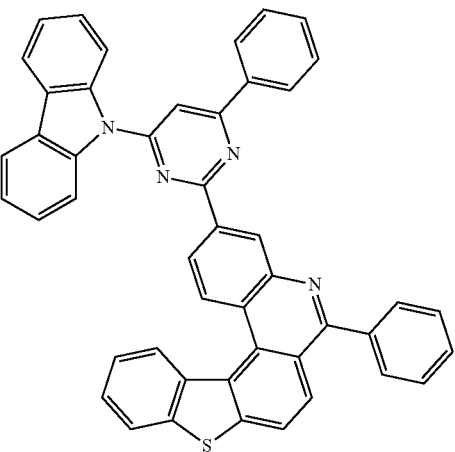
681
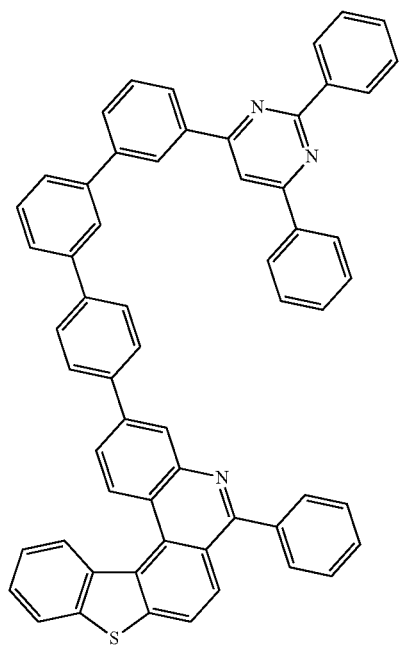
682
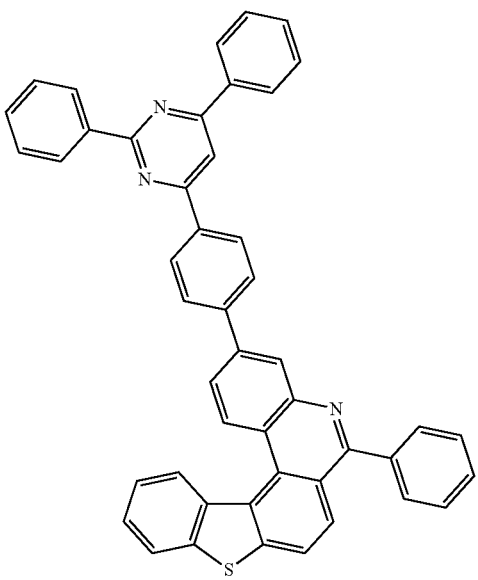
683
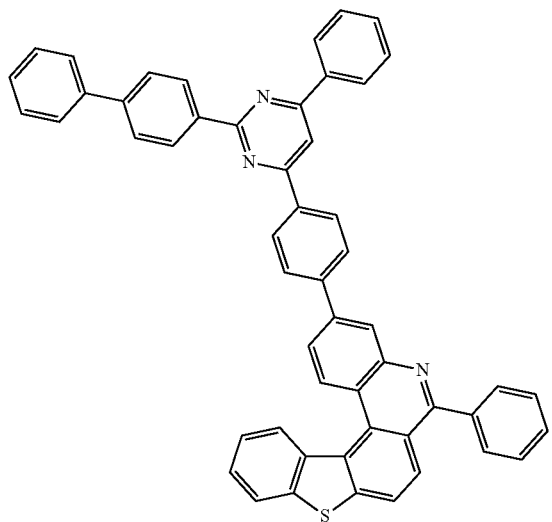
684
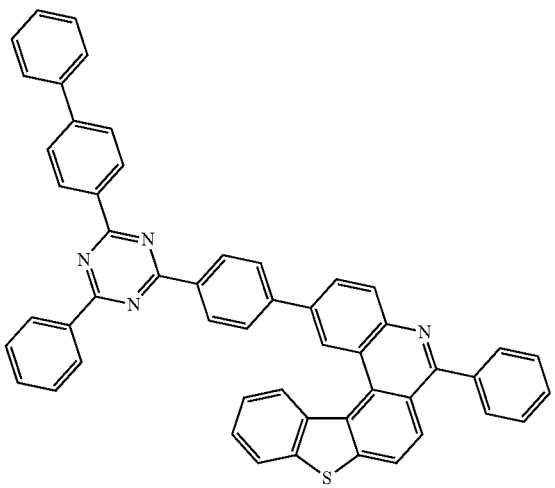

-continued
685
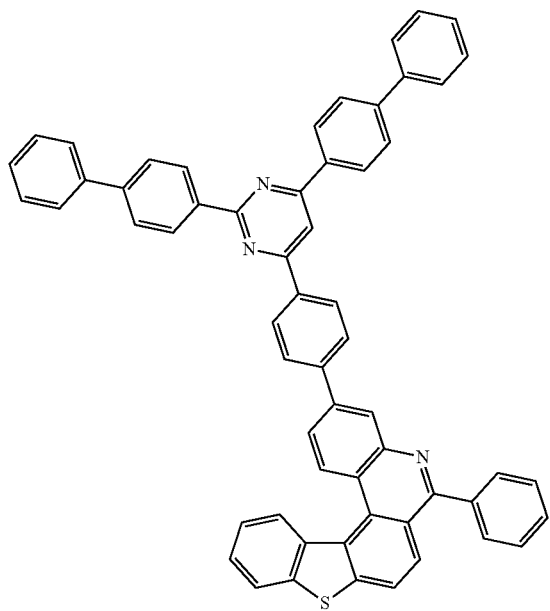
686
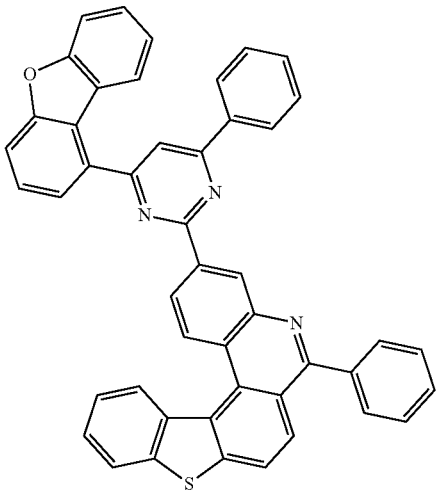
687
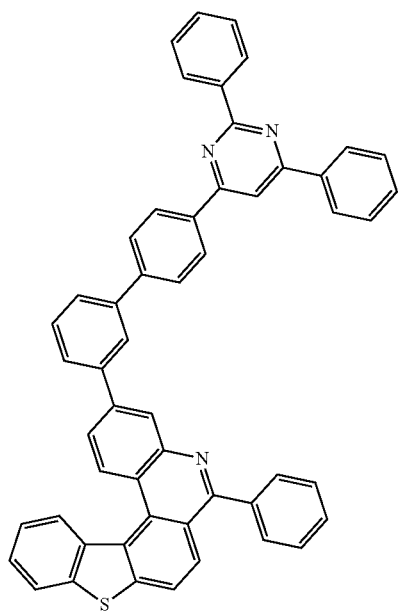
688
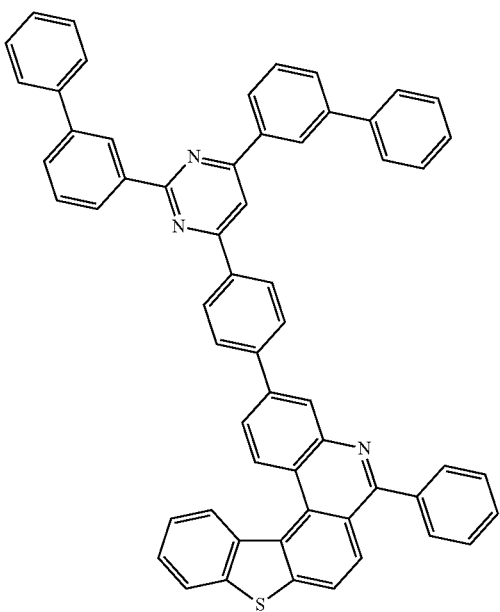

-continued
275
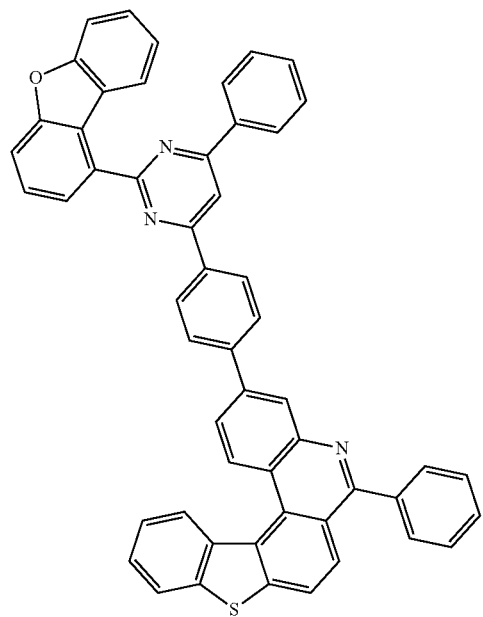
689
276
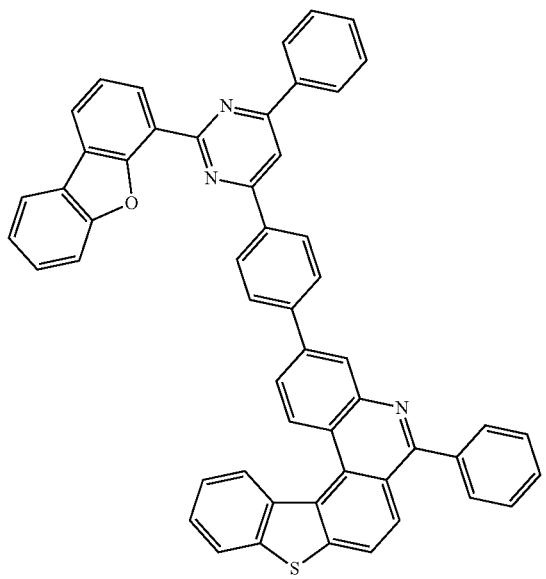
690
691
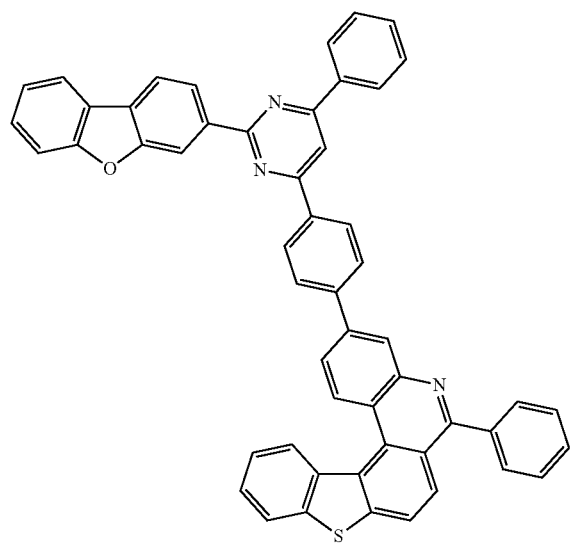
692

277
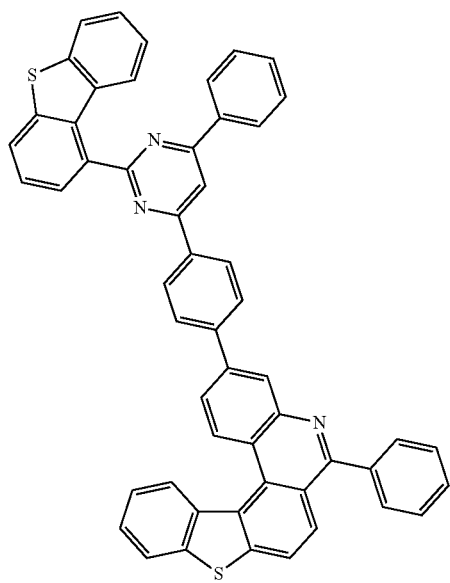
693
278
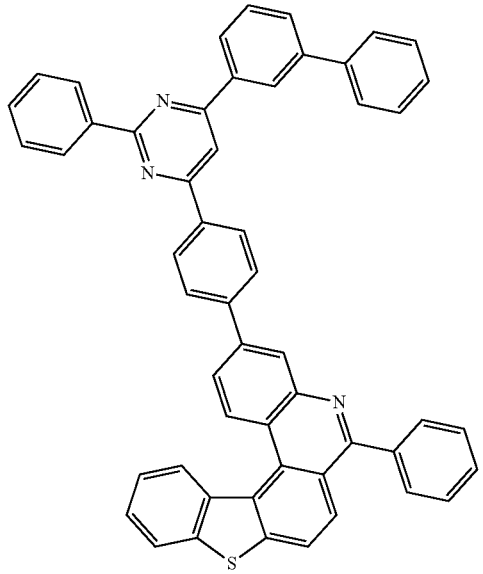
694
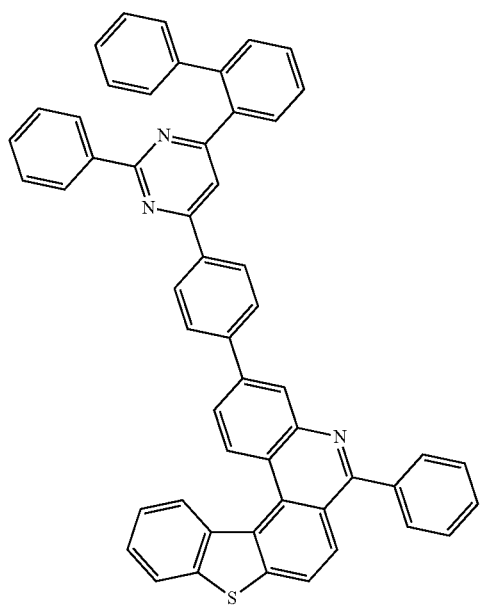
695
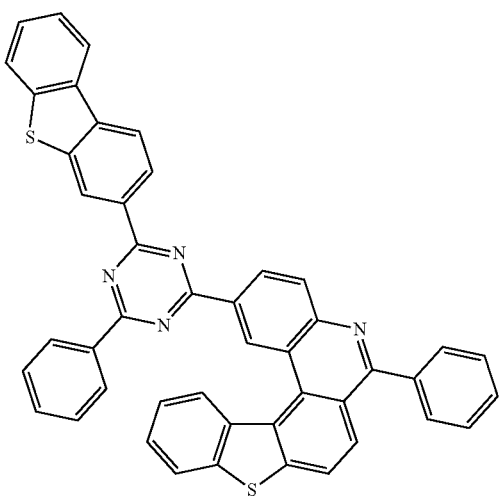
696

-continued
697
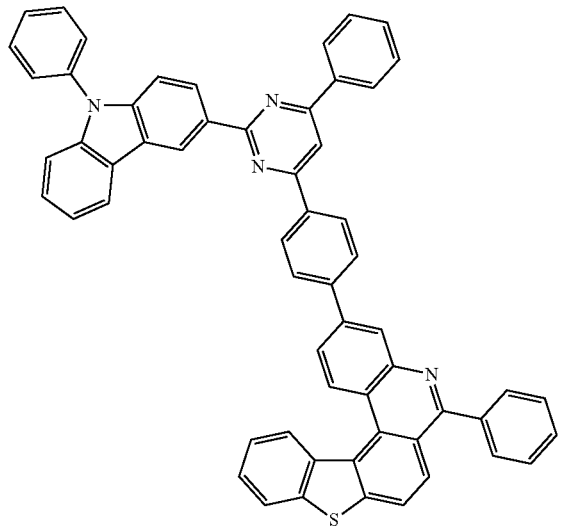
698
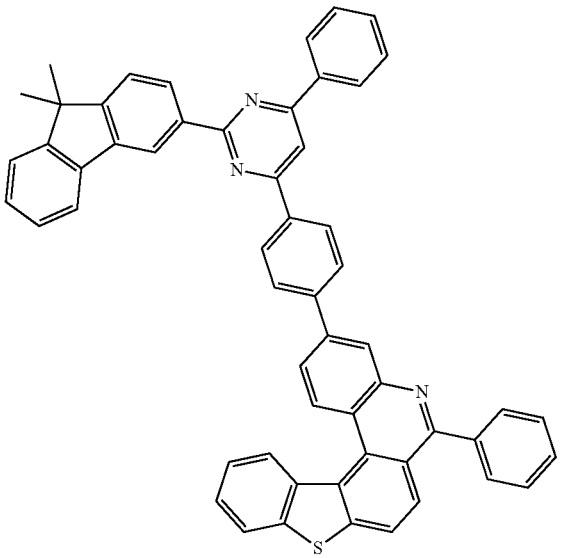
699
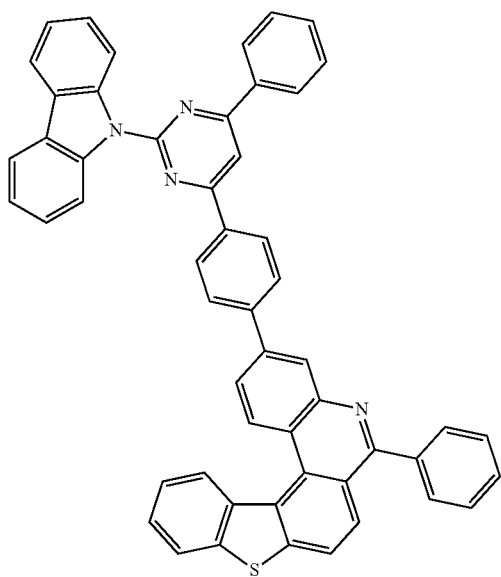
700
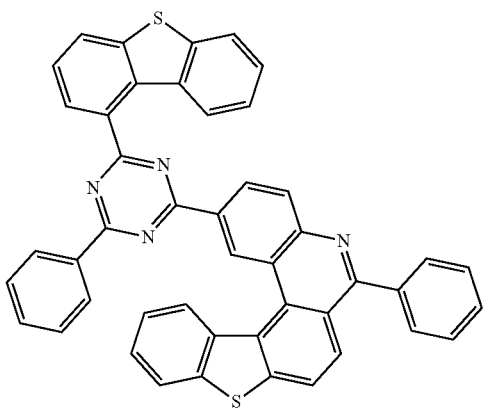
701
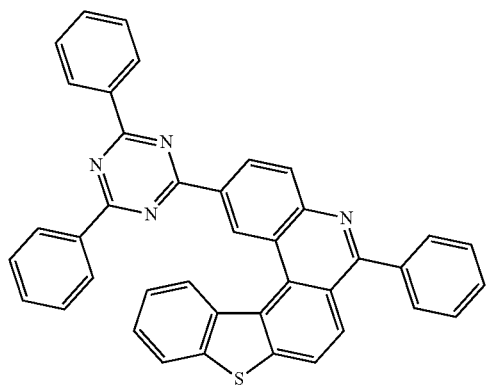
702
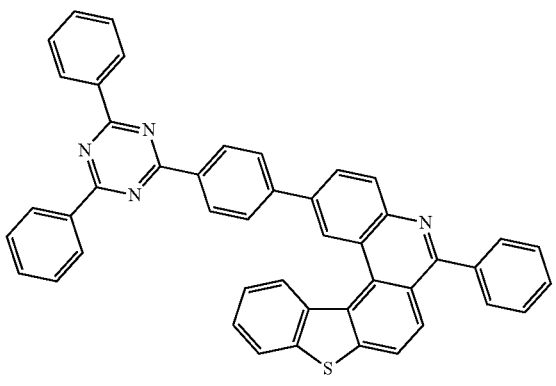

-continued
703
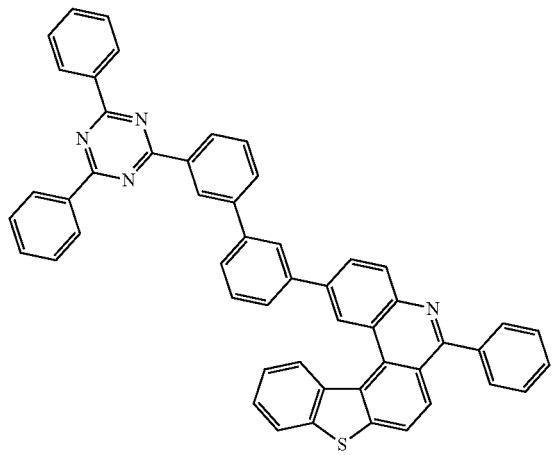
704
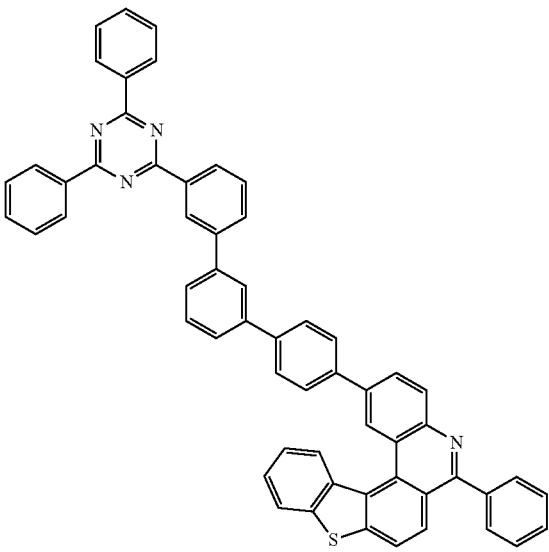
705
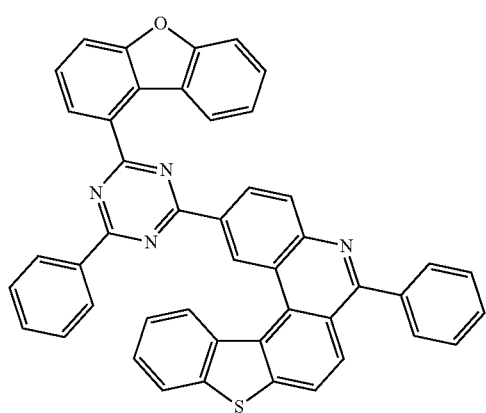
706
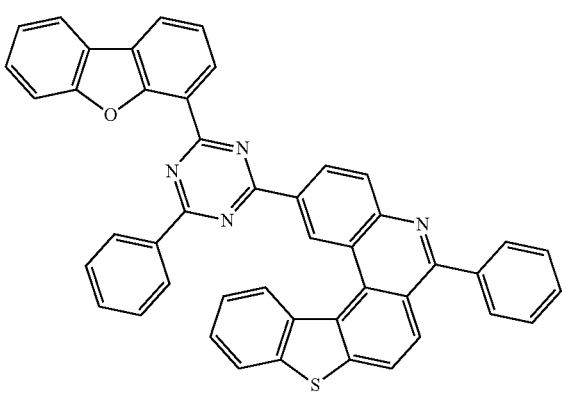
707
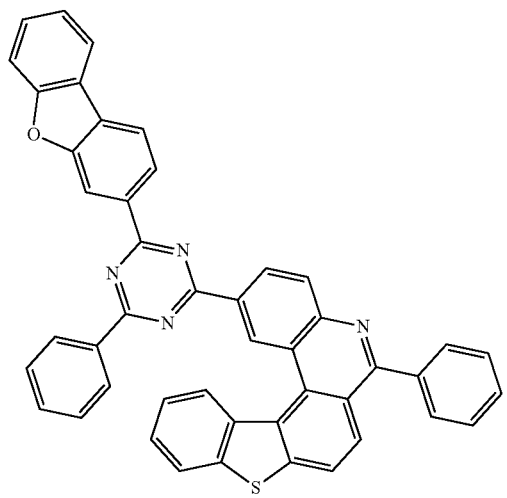
708
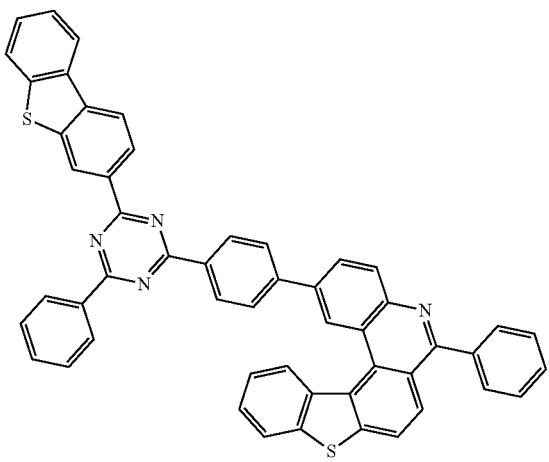

-continued
709
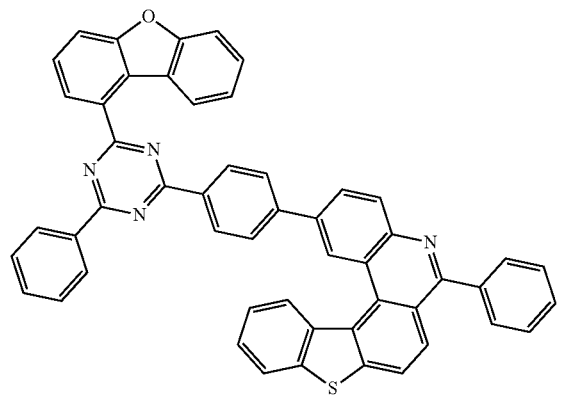
710
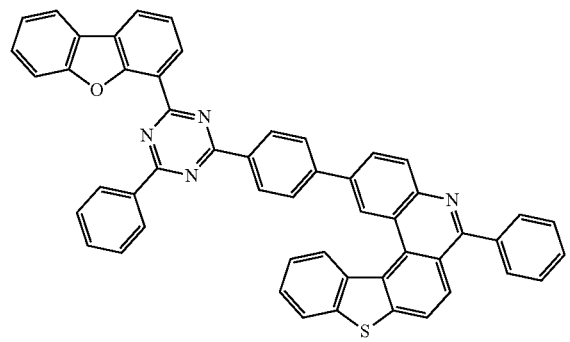
711
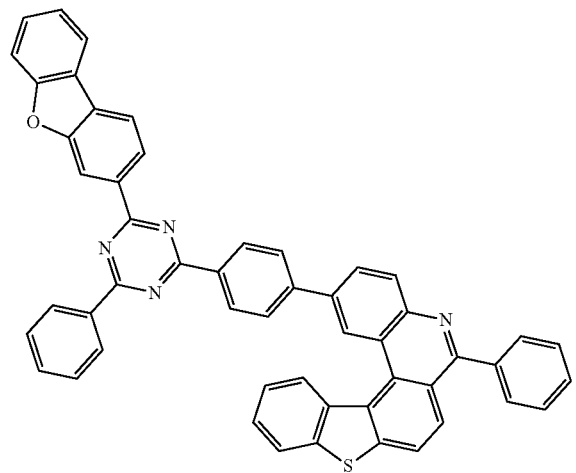
712
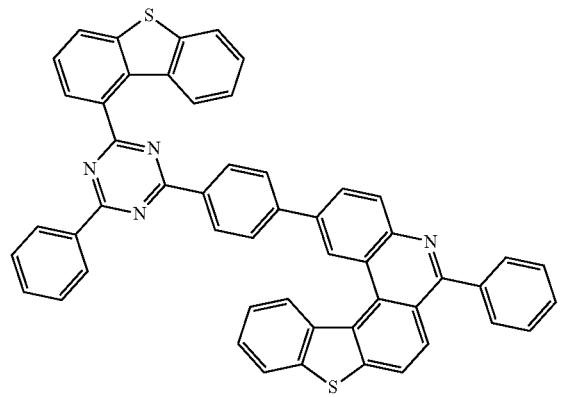
713
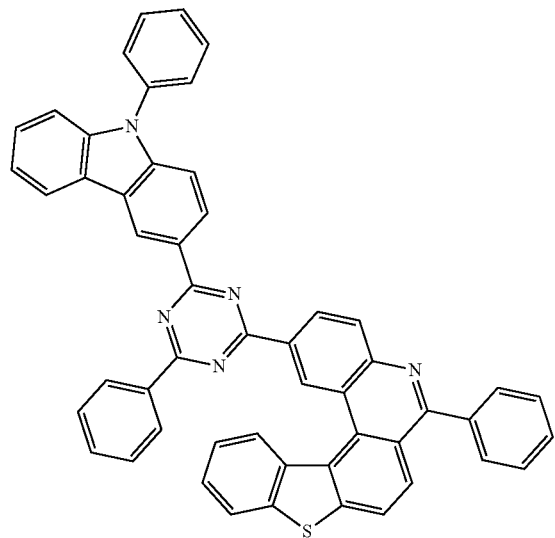
714
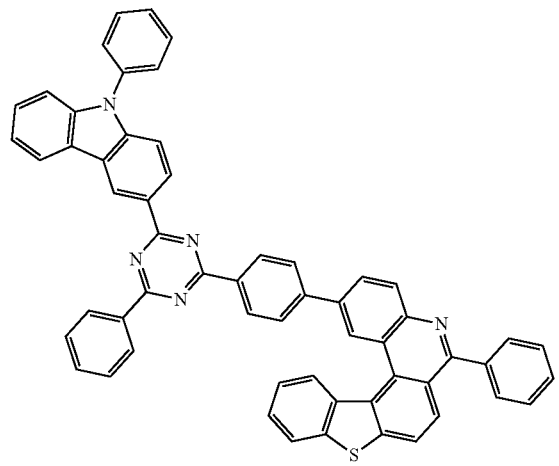

-continued
715
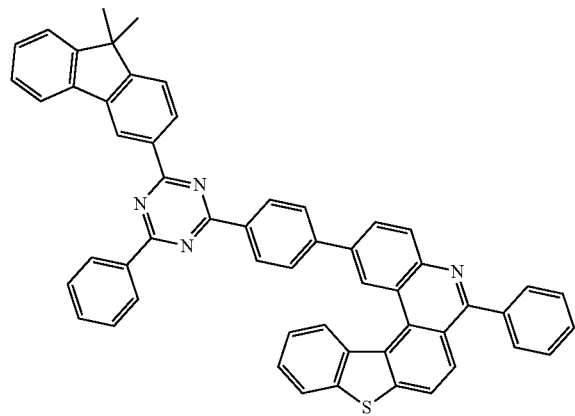
716
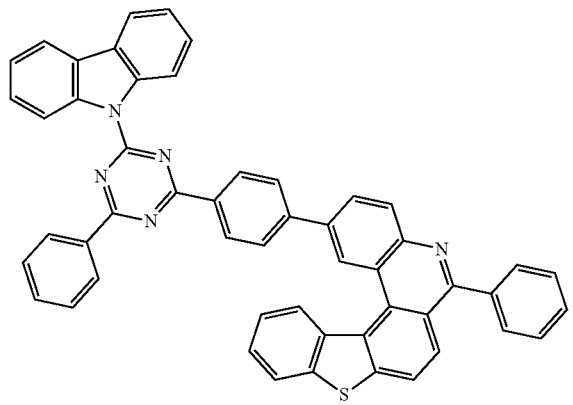
717
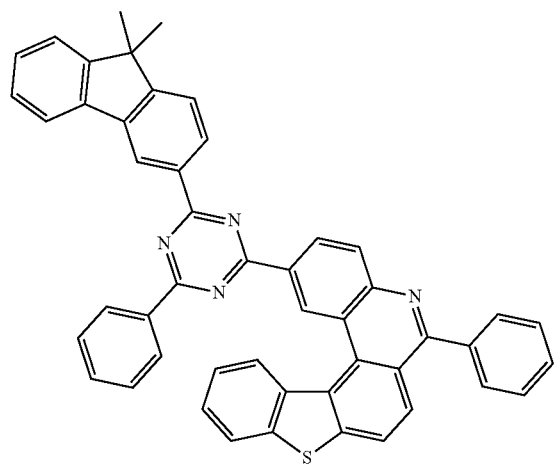
718
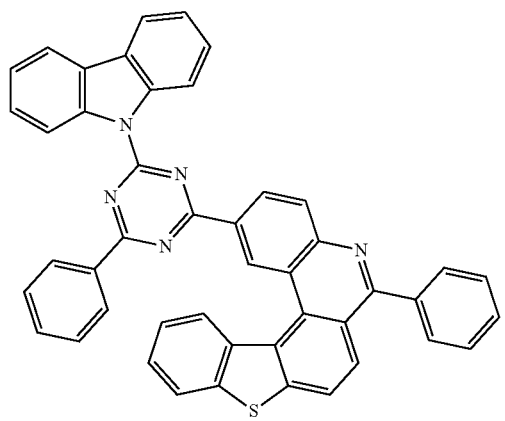
719
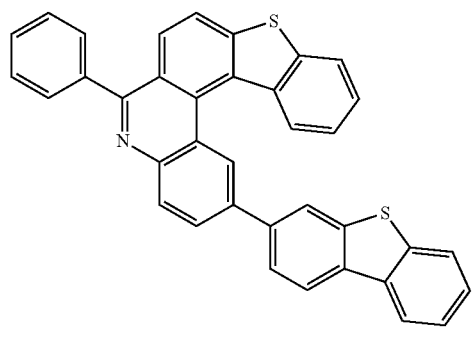
720
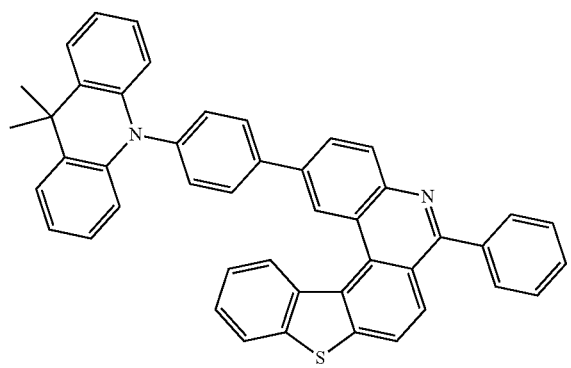

-continued
721
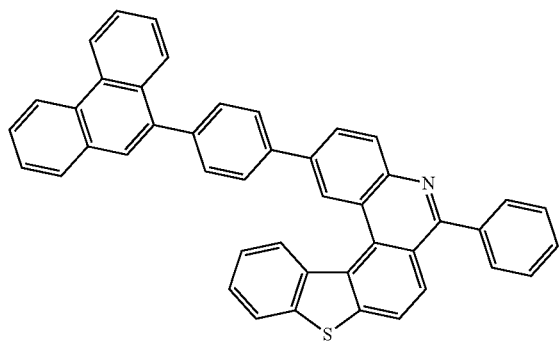
722
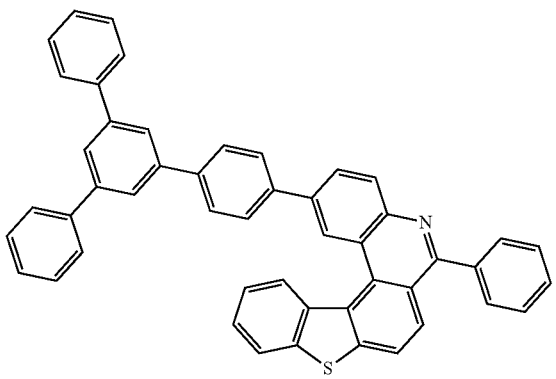
723
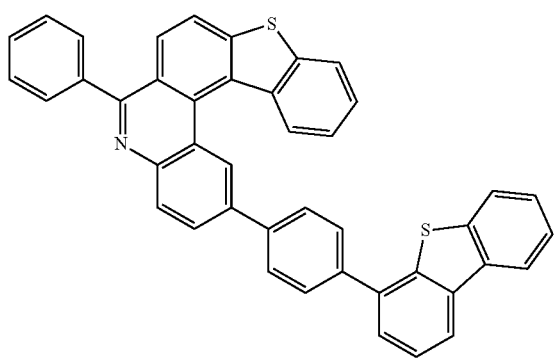
724
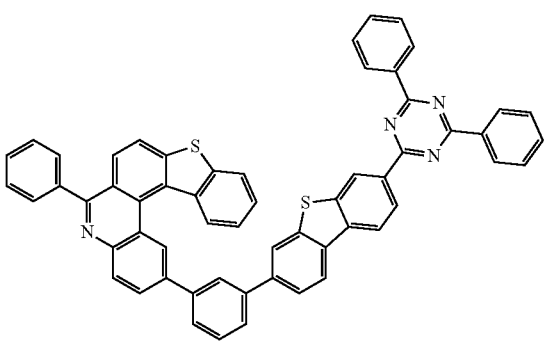
725
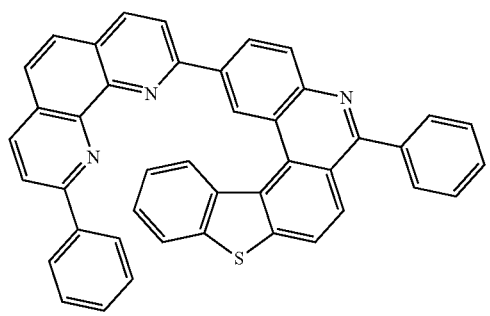
726
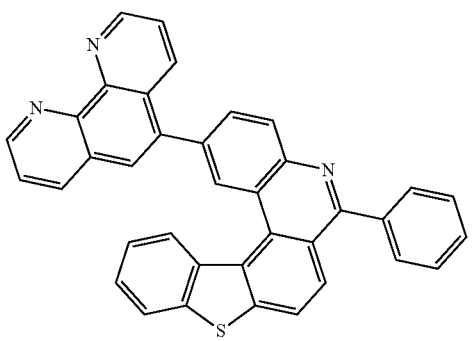
727
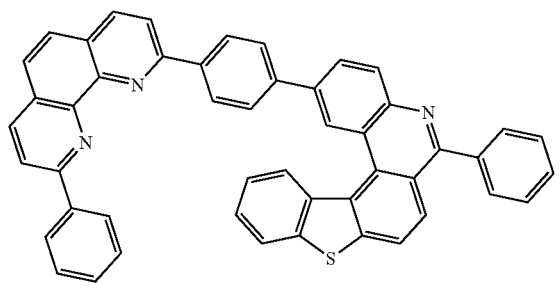
728
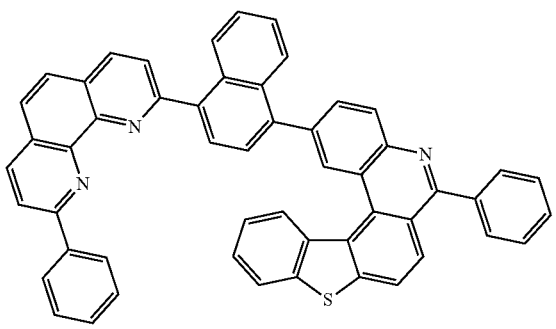

-continued
729
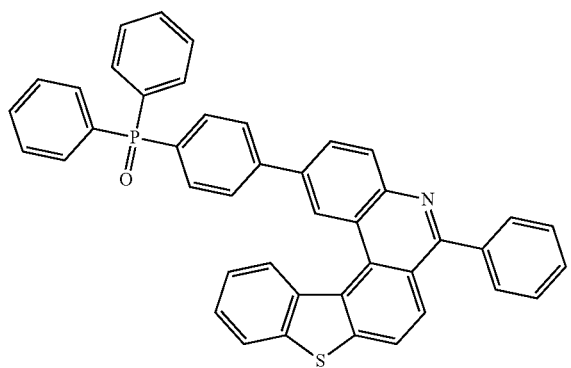
730
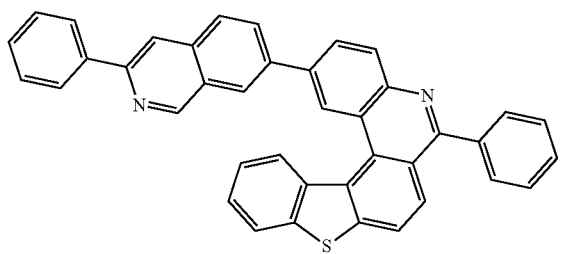
731
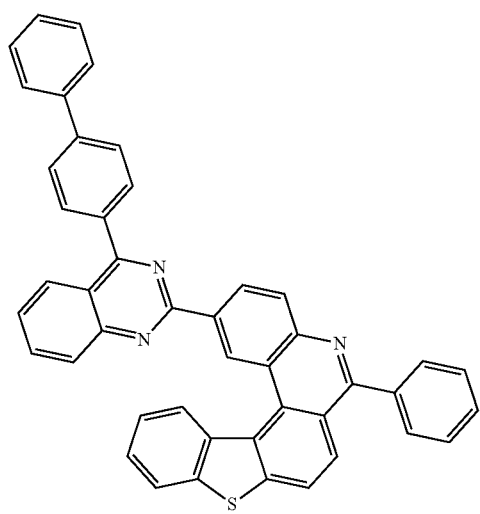
732
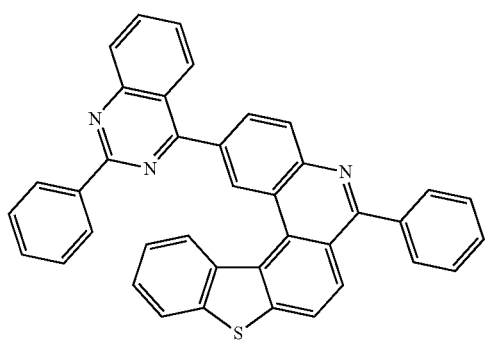
733
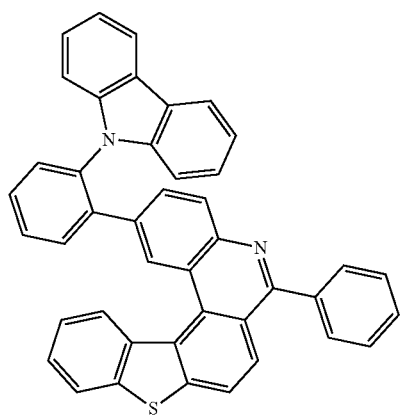
734
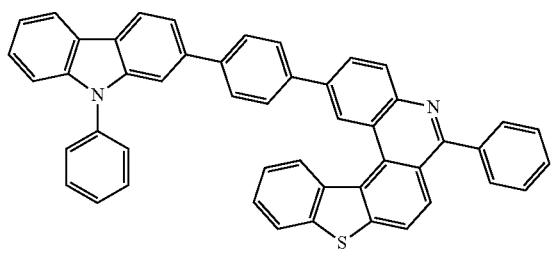

-continued
735
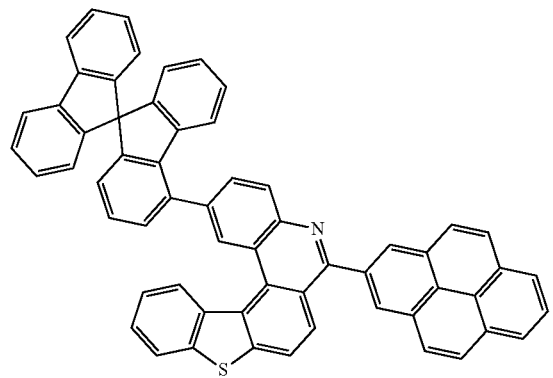
736
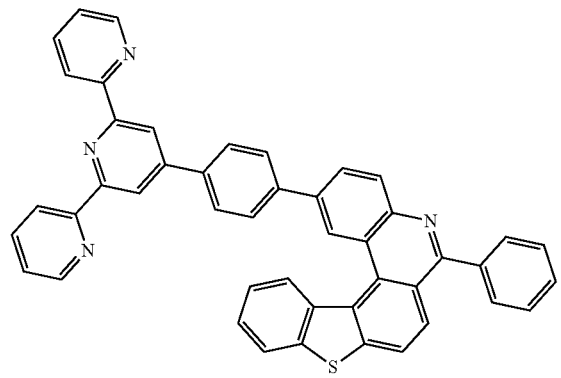
737
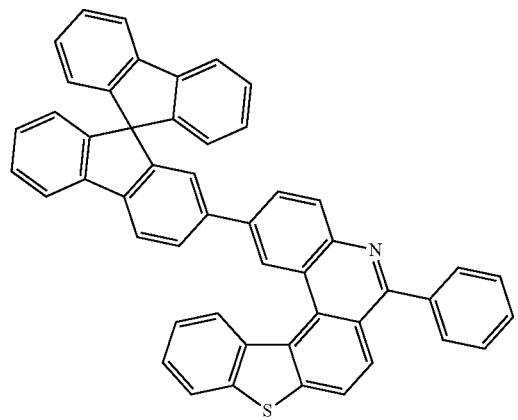
738
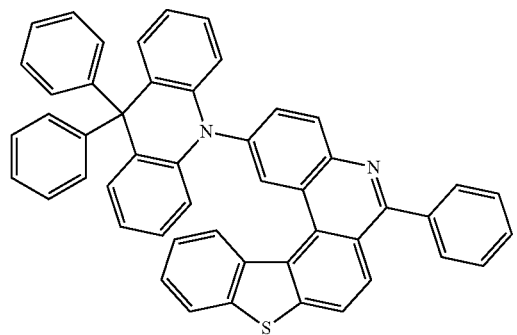
739
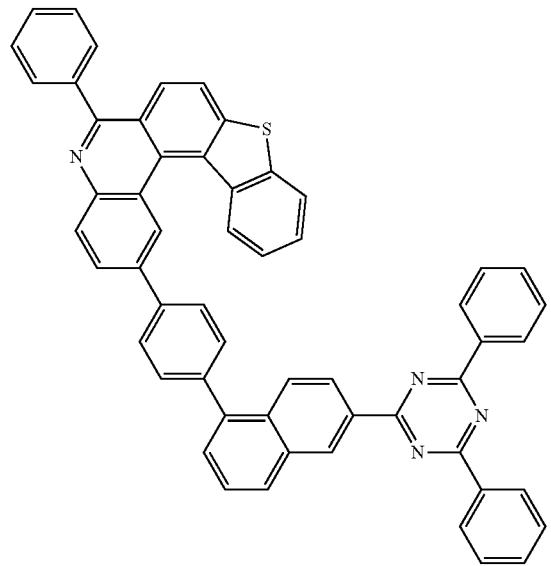
740
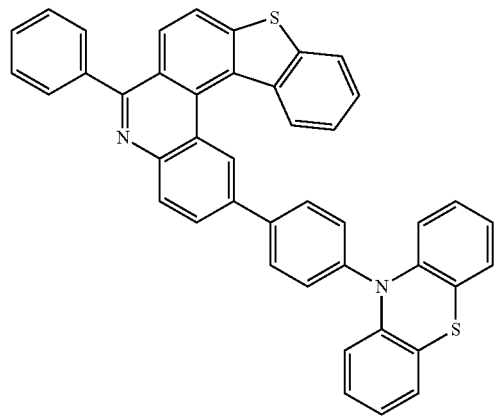

-continued
741
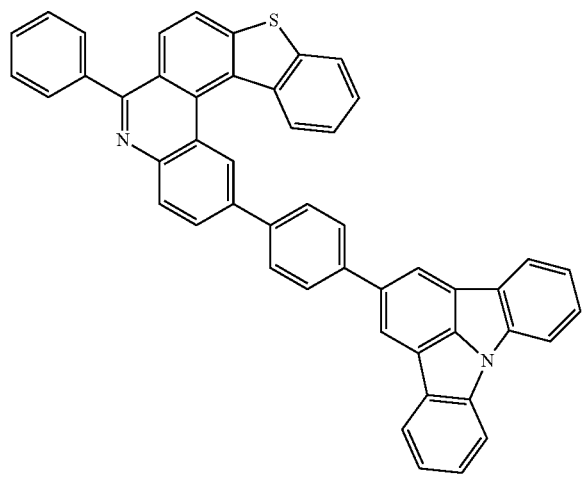
742
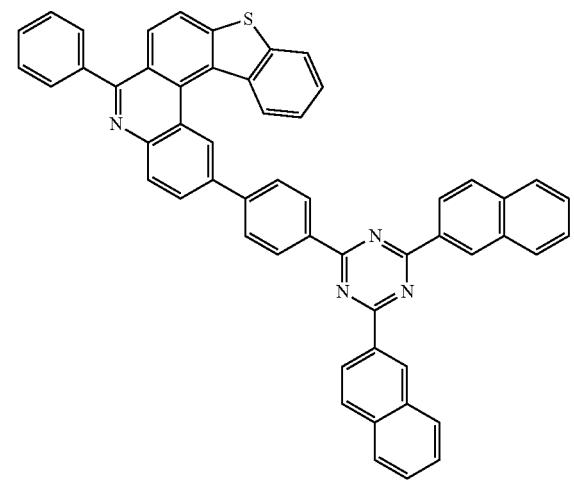
743
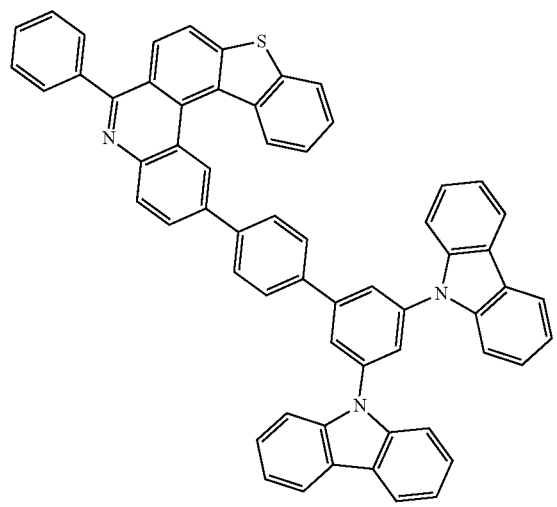
744
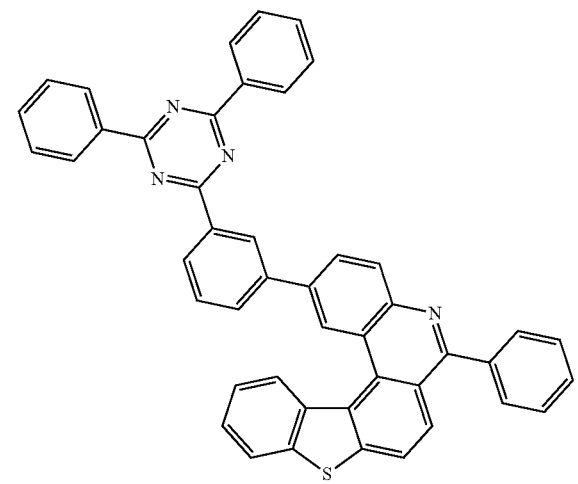
745
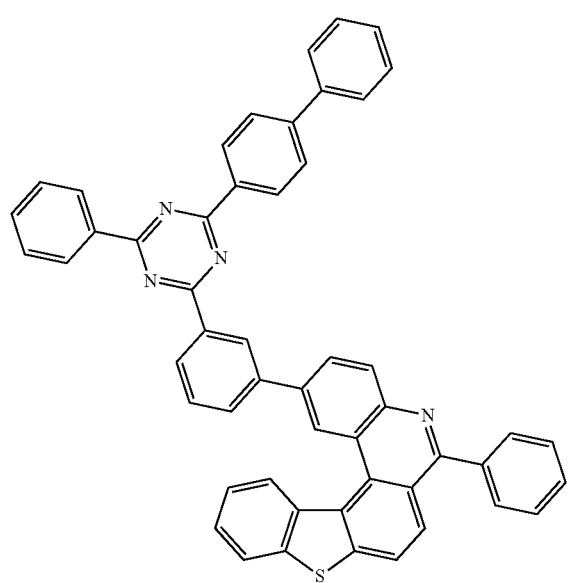
746
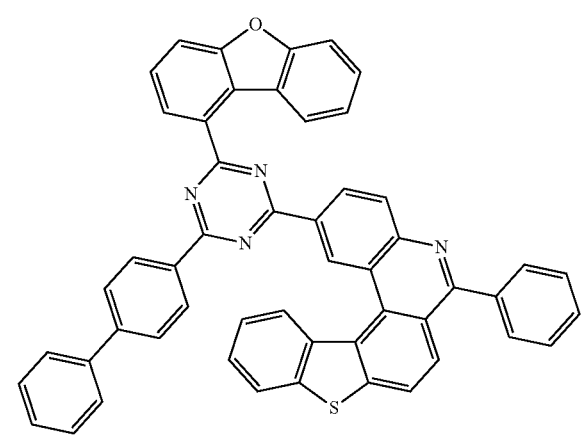

747
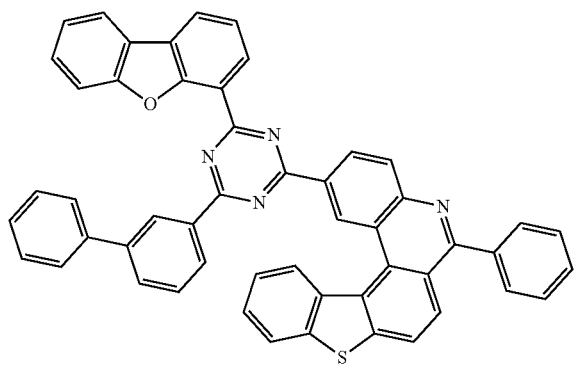
748
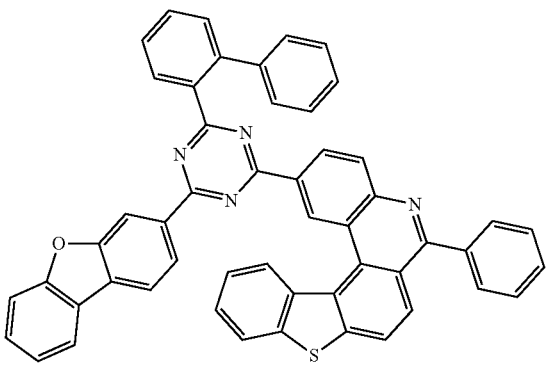
749
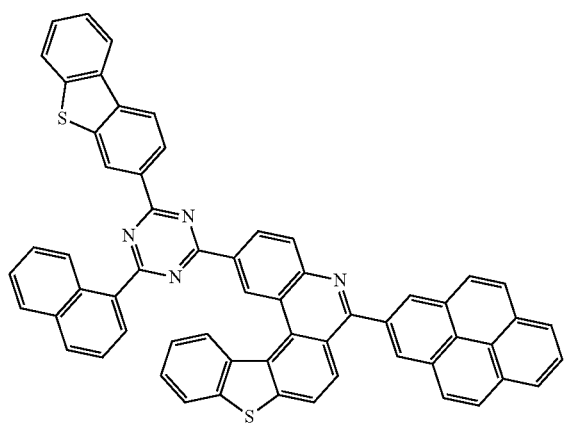
750
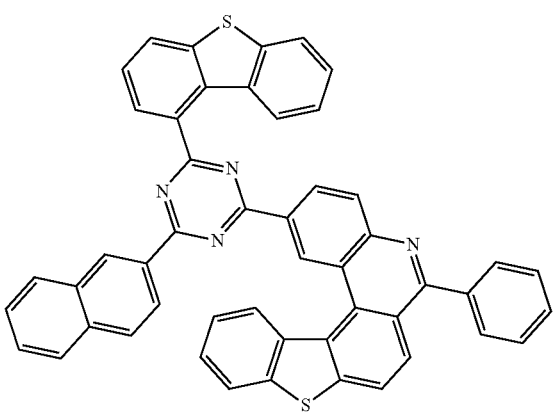
751
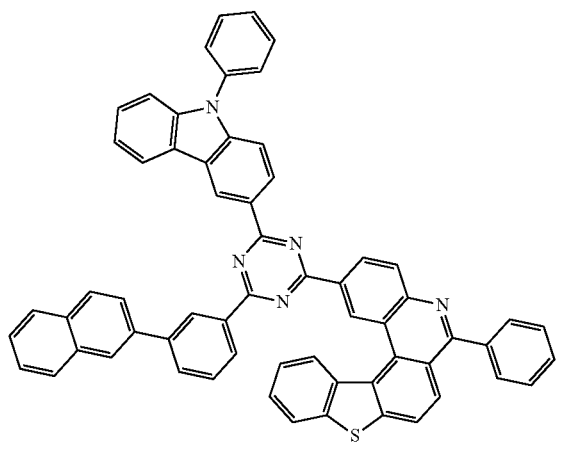
752
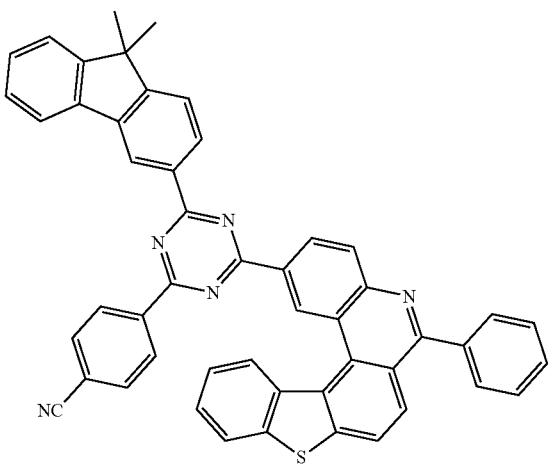

753
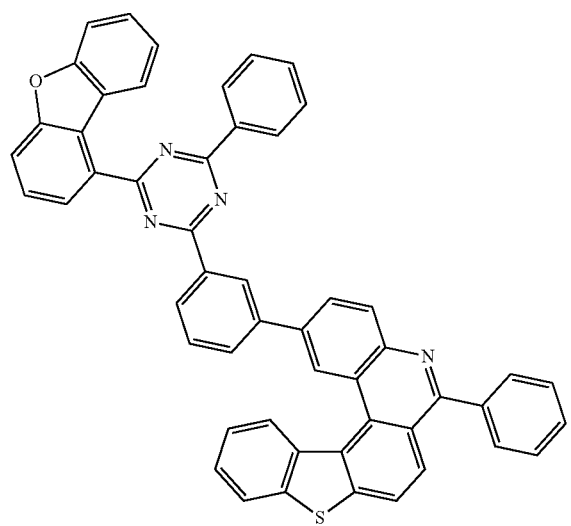
754
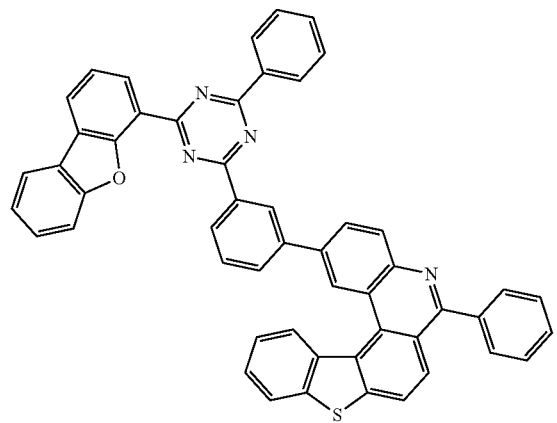
755
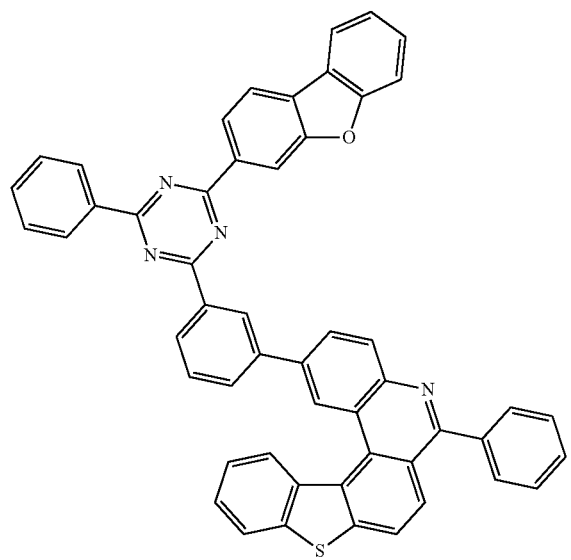
756
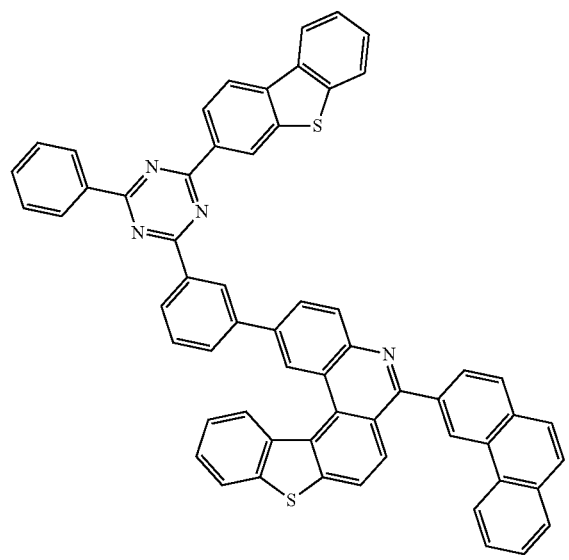

-continued
757
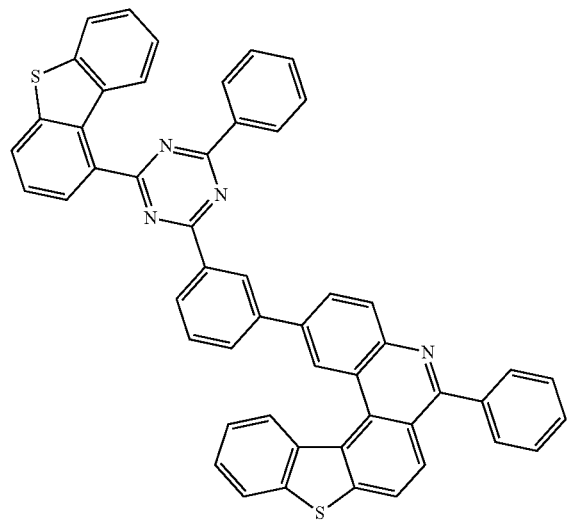
758
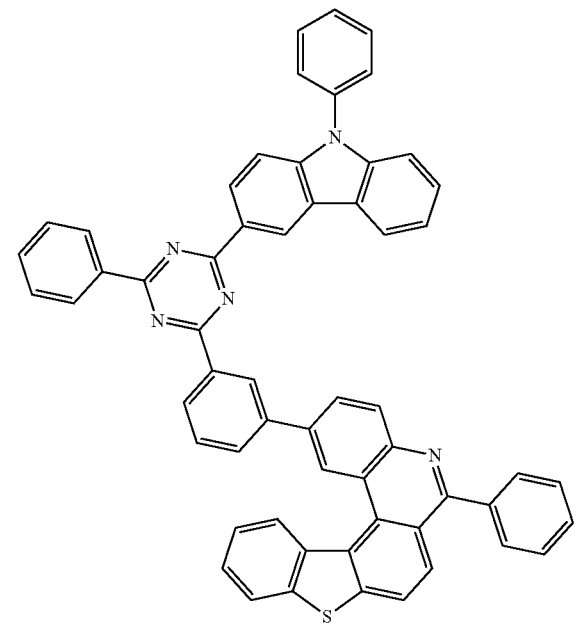
759
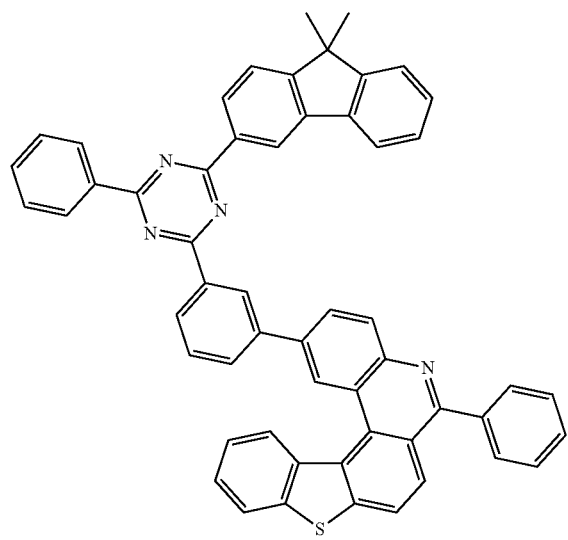
760
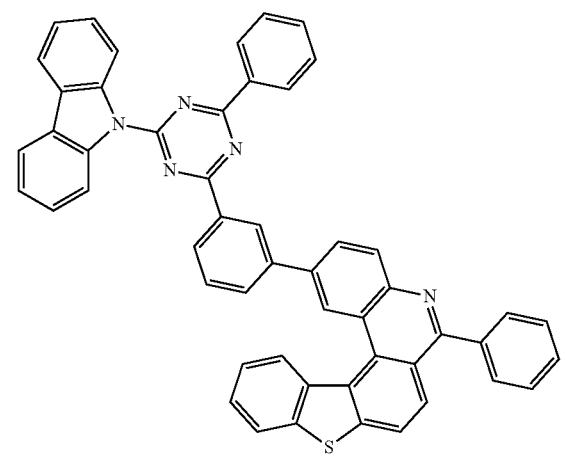
761
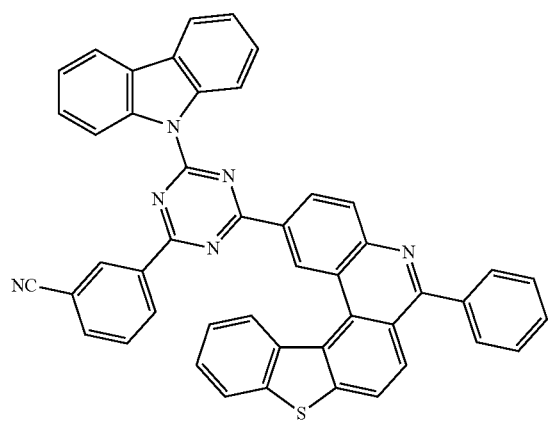
762
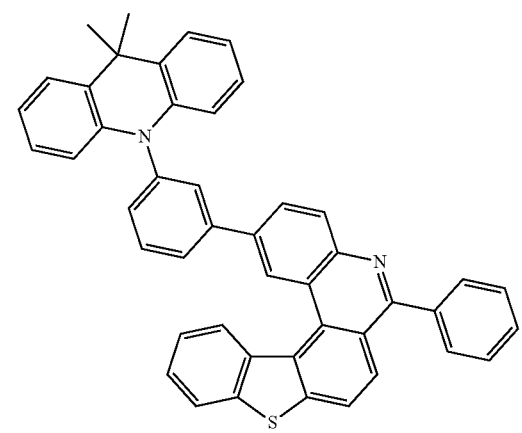

-continued
763
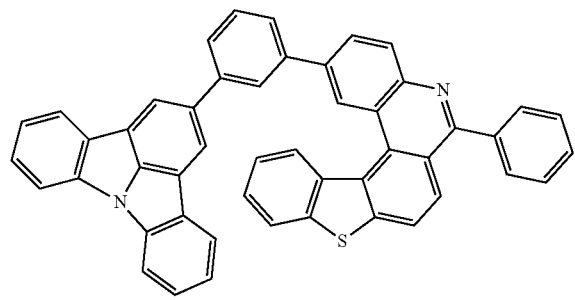
764
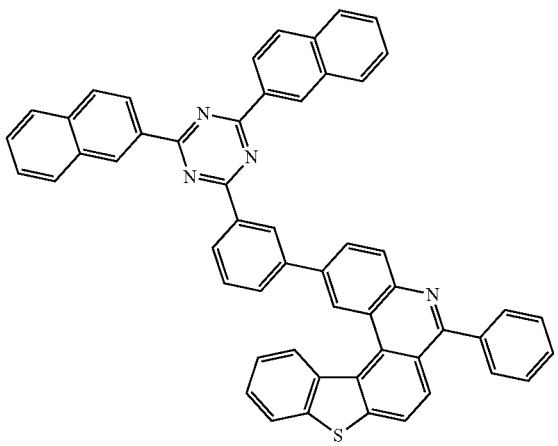
765
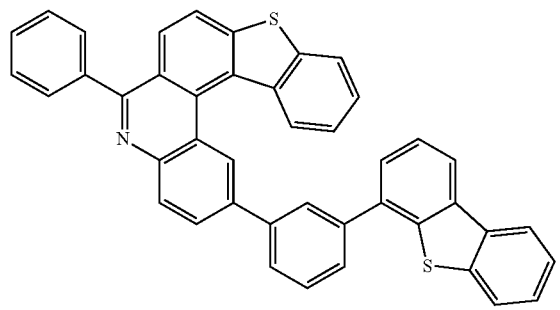
766
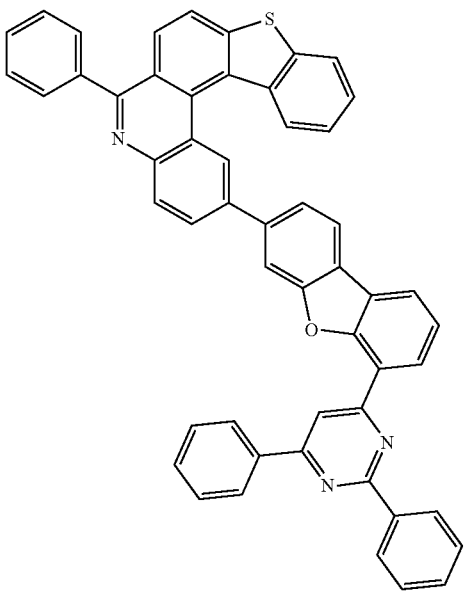
767
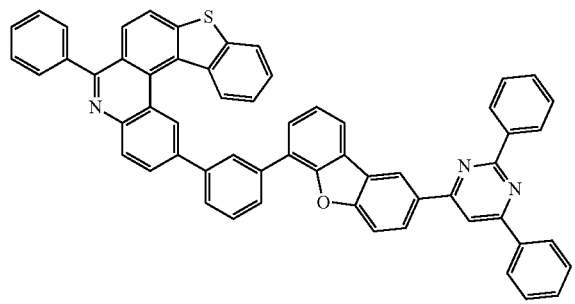
768
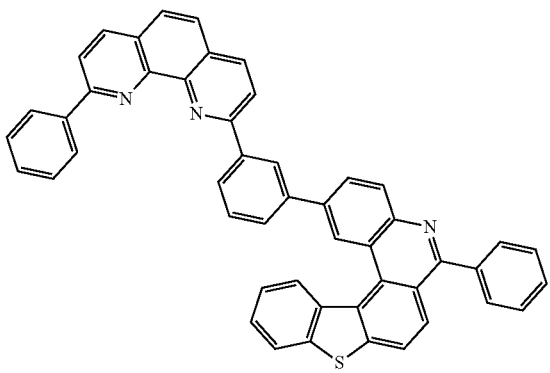

-continued
769
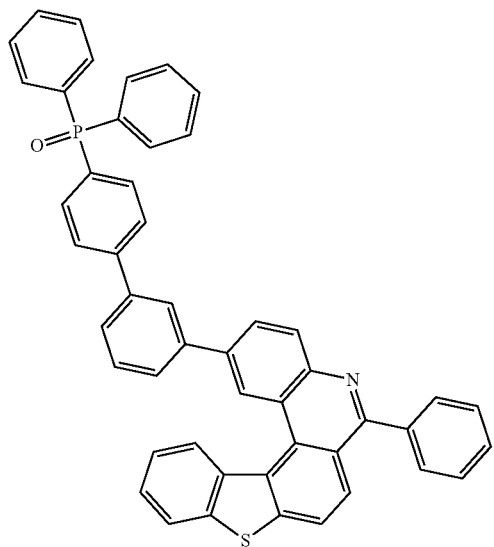
770
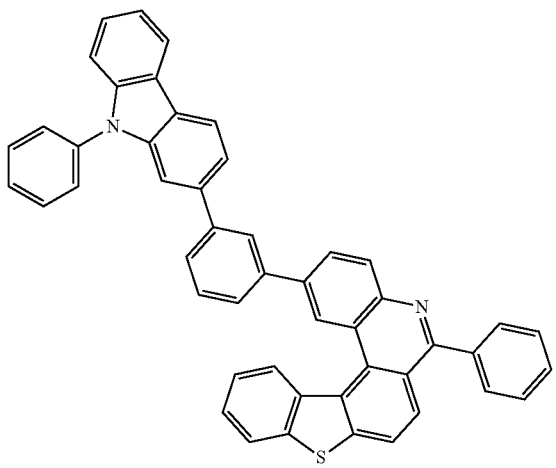
771
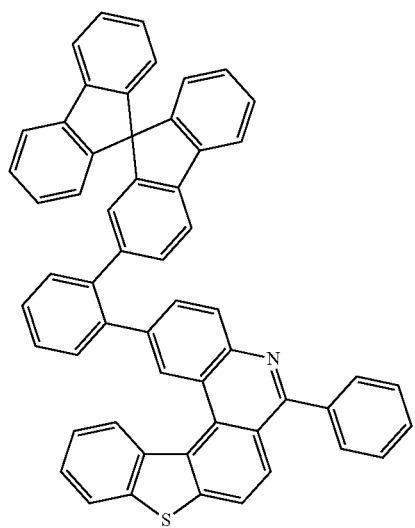
772
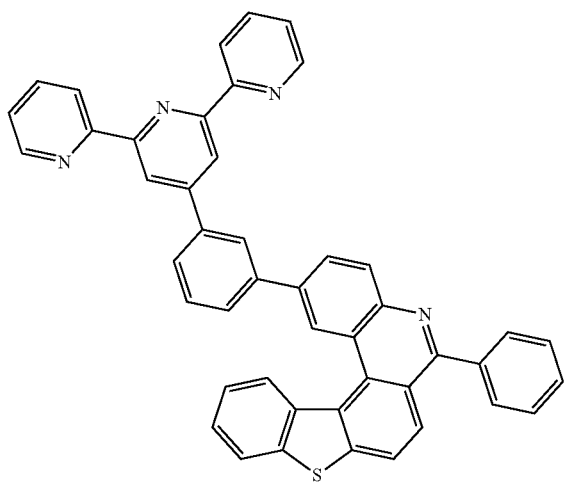
773
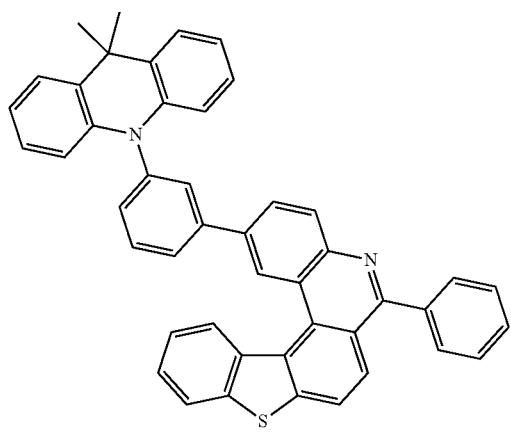
774
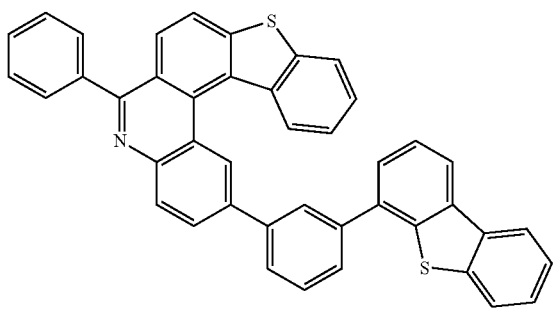

305 306
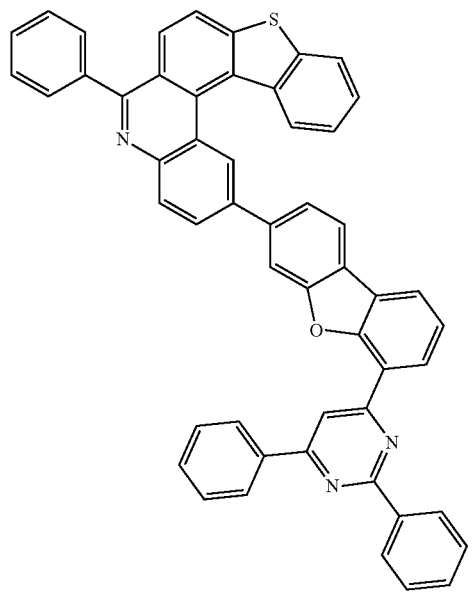
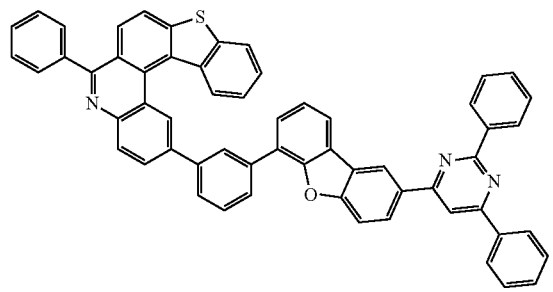
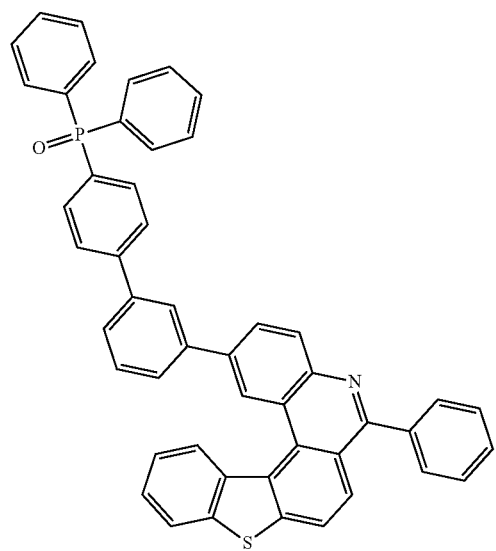

779
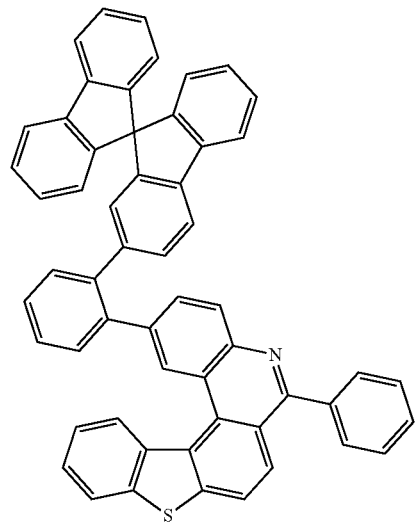
780
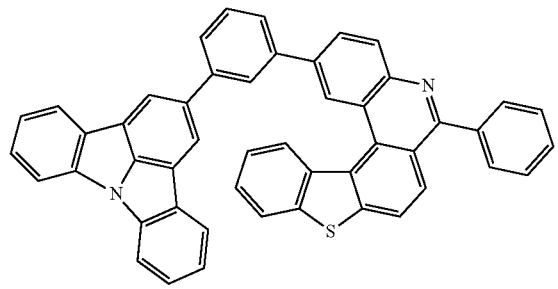
781
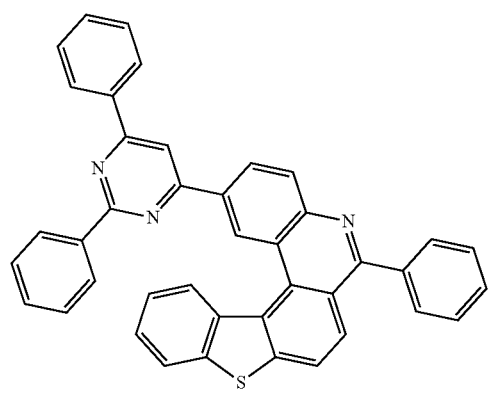
782
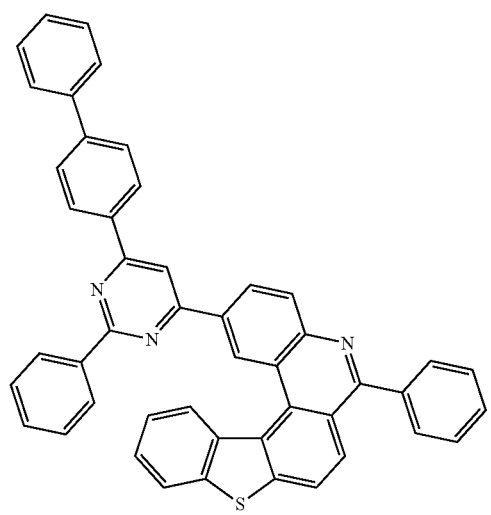
783
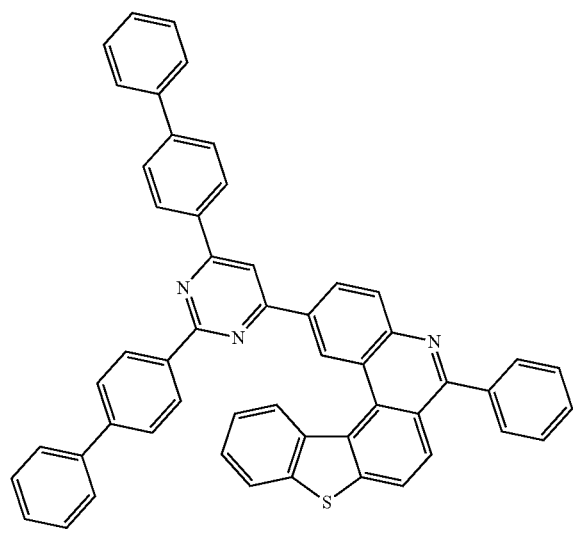
784
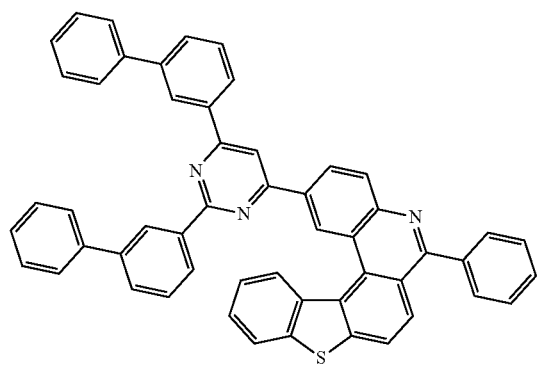

785
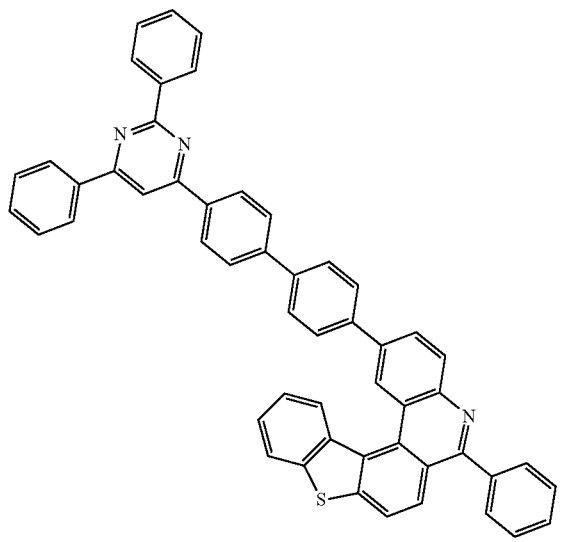
786
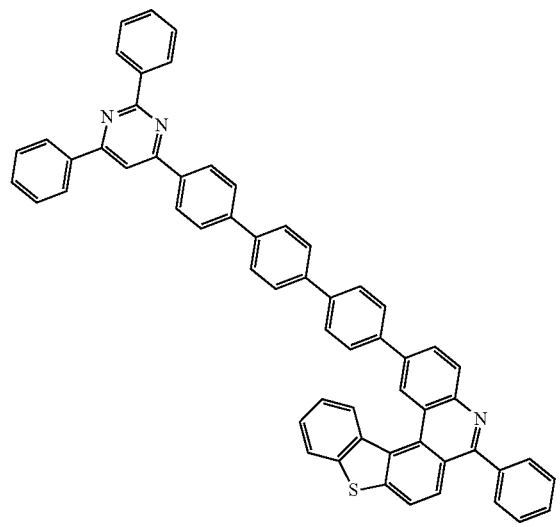
787
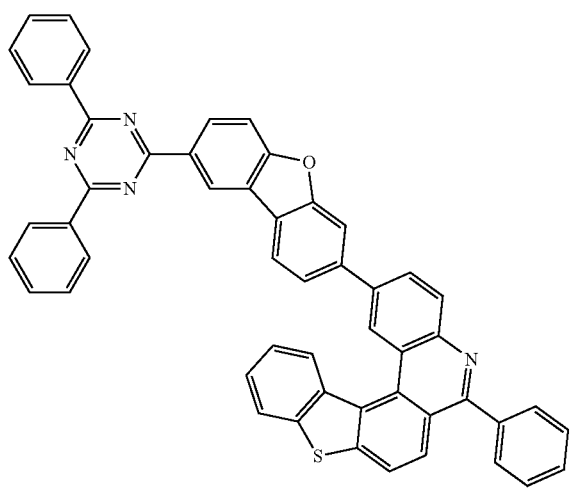
788
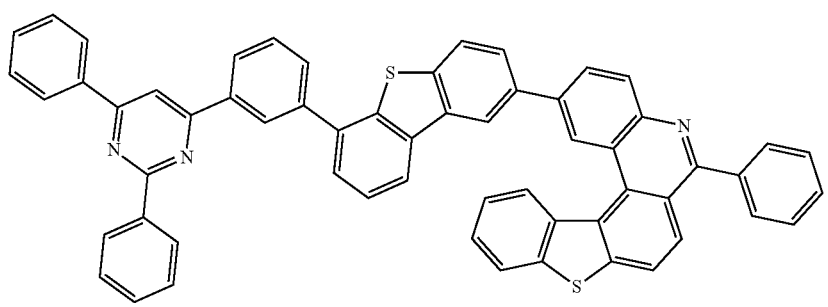

789
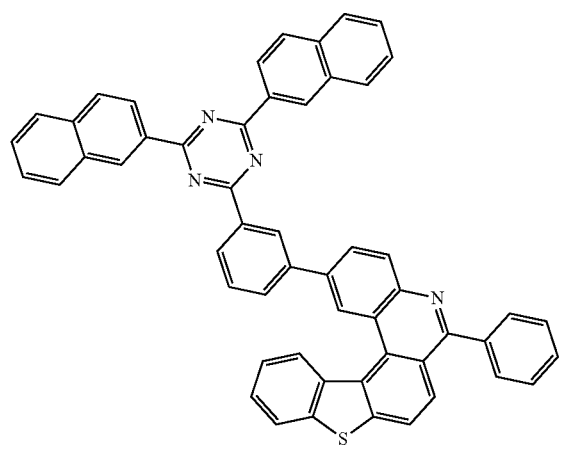
790
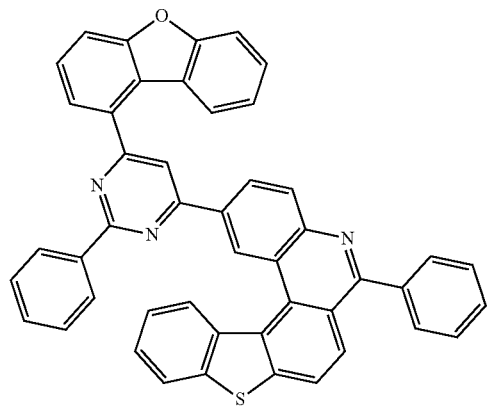
791
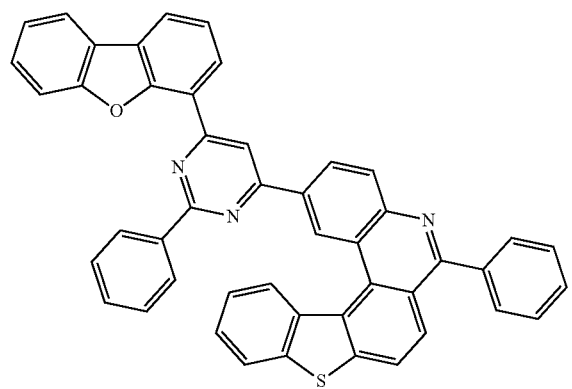
792
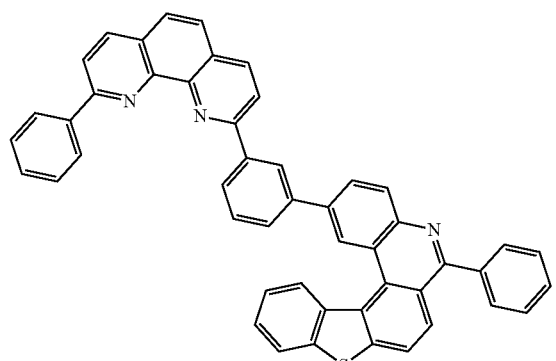
793
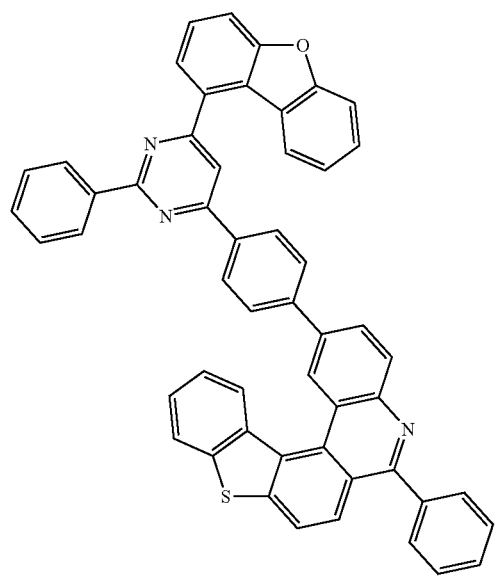
794
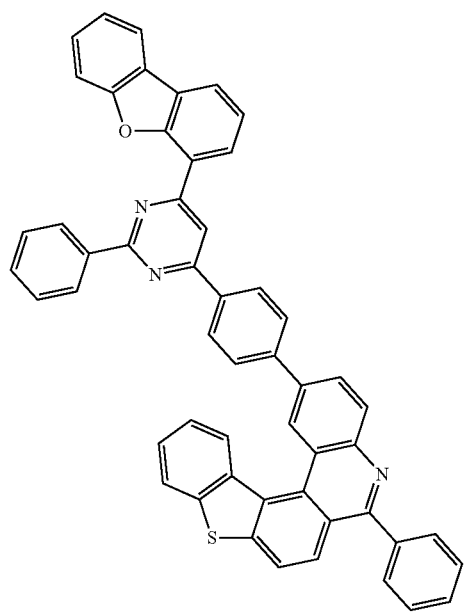

-continued
795
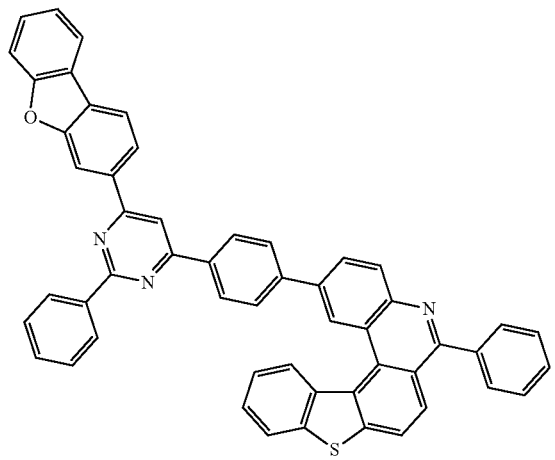
796
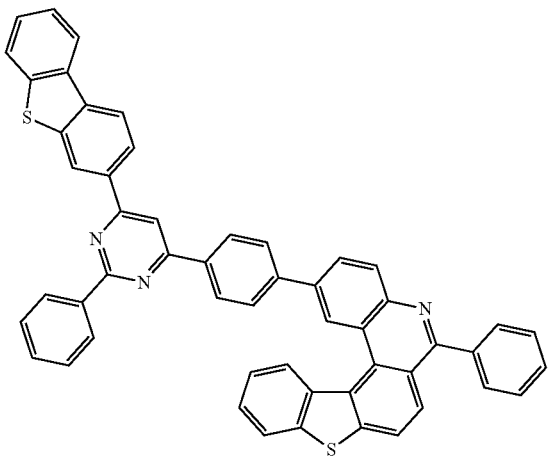
797
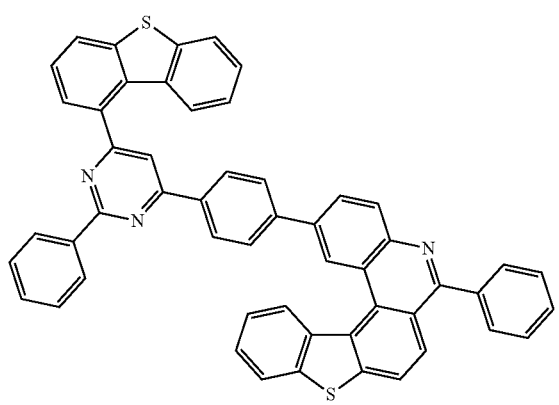
798
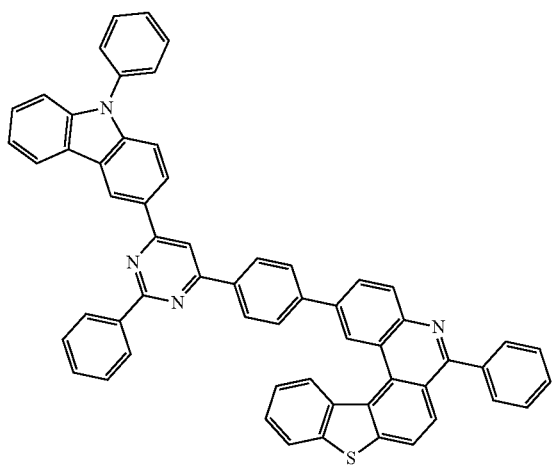
799
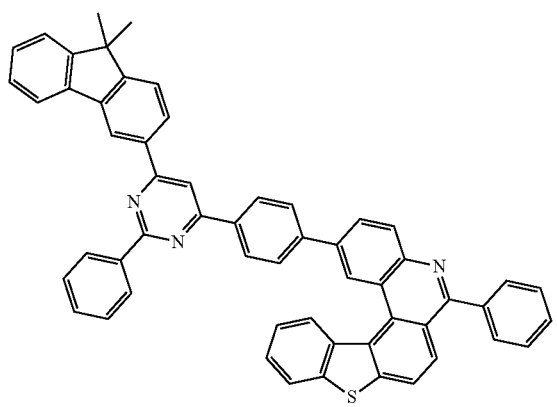
800
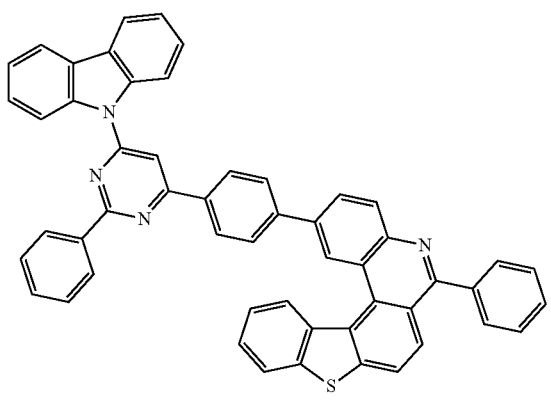

-continued
801
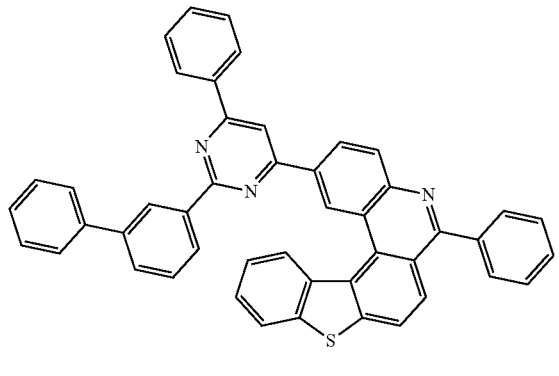
802
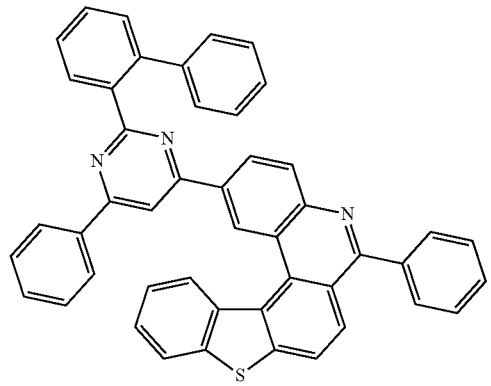
803
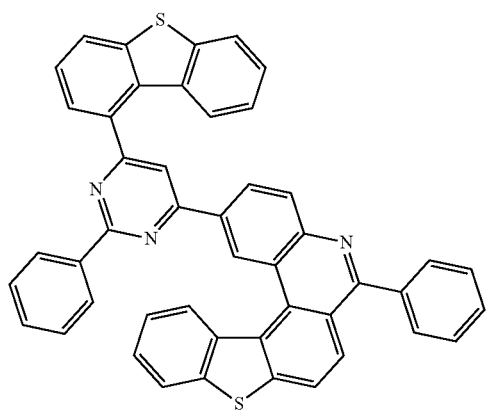
804
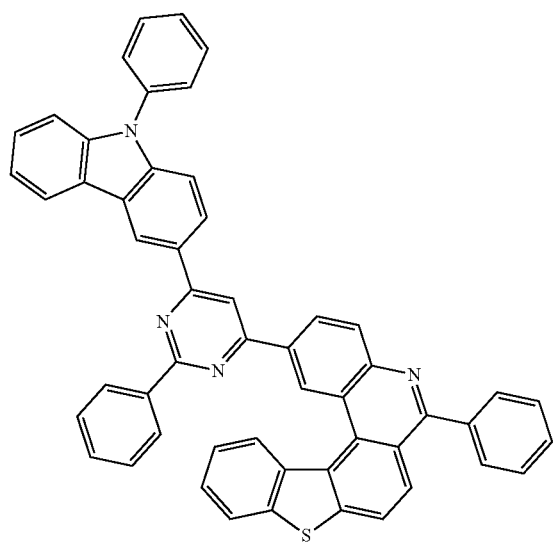
805
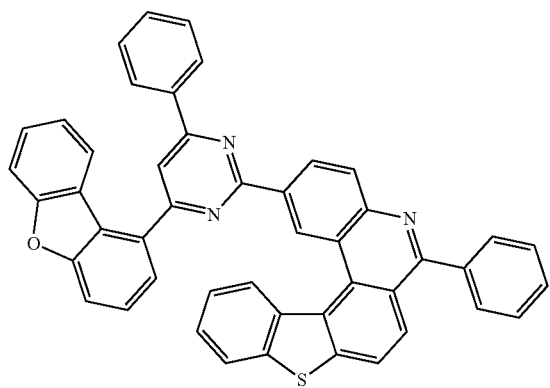
806
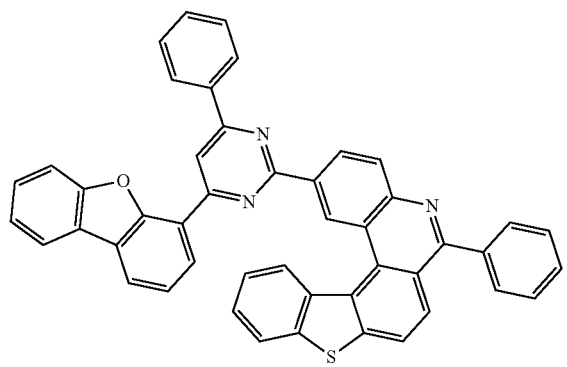

-continued
807
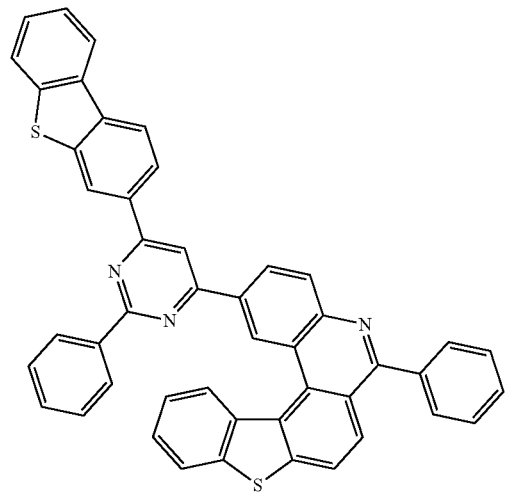
808
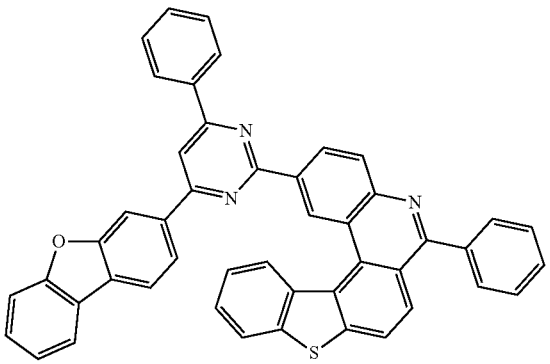
809
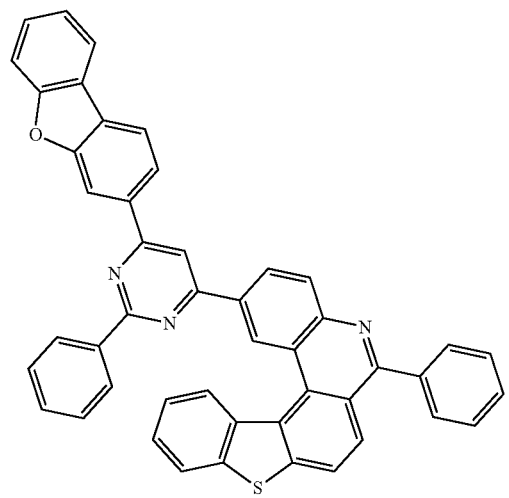
810
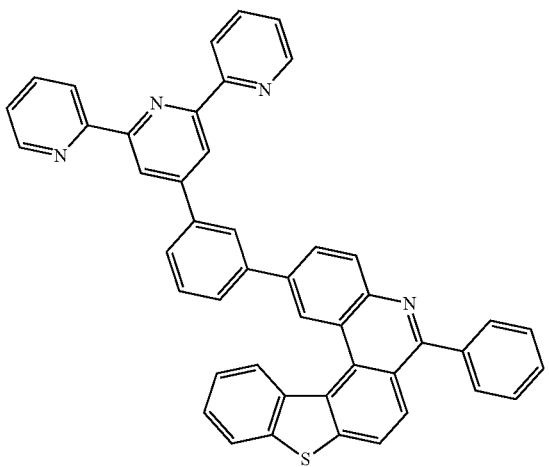
811
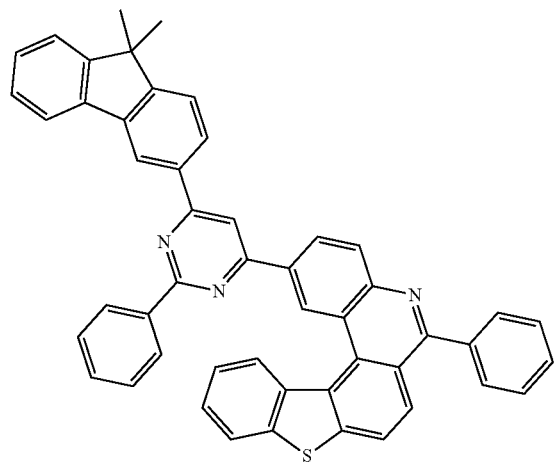
812
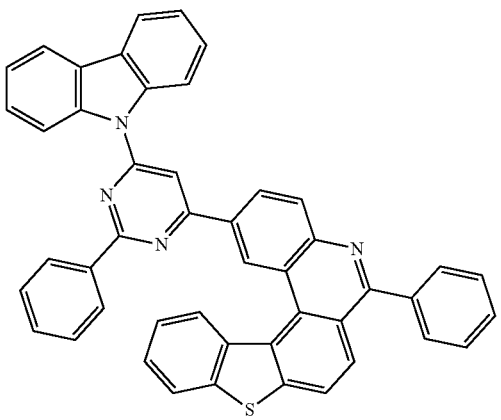

-continued
813
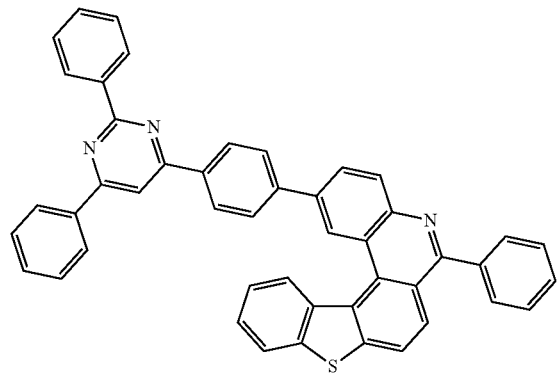
814
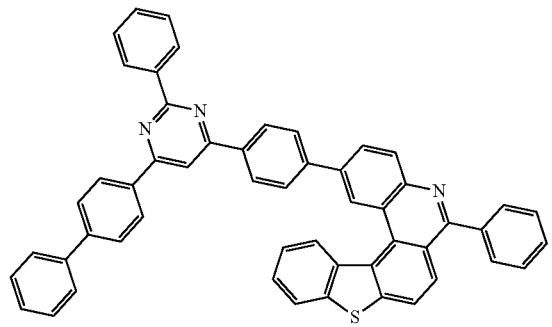
815
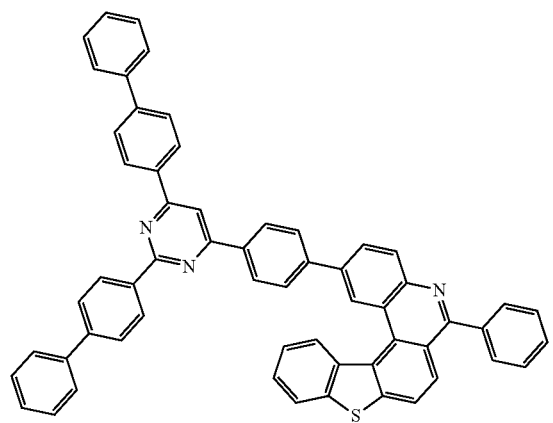
816
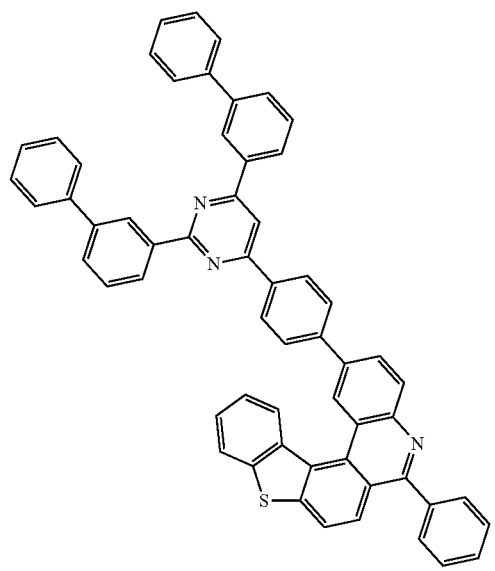
817
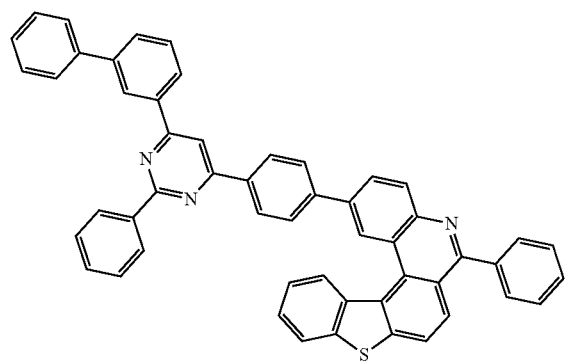
818
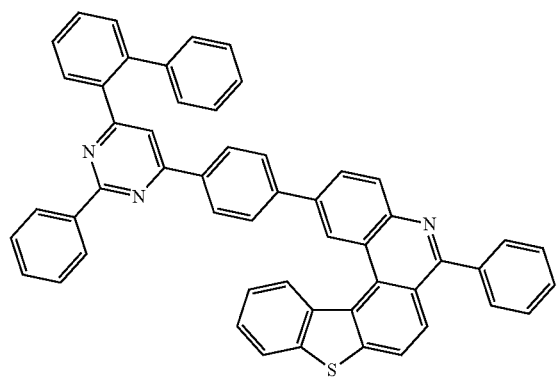

-continued
819
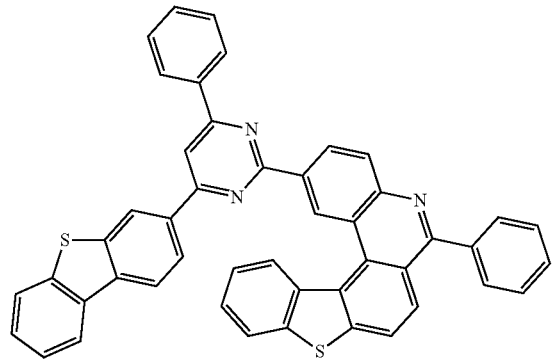
820
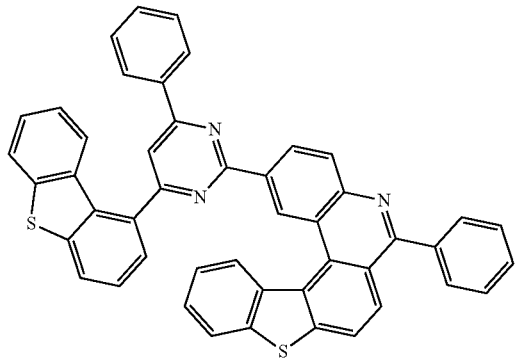
821
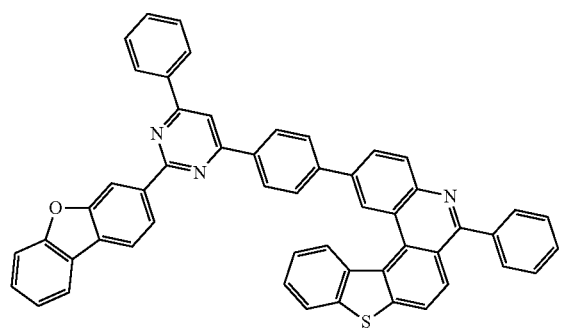
822
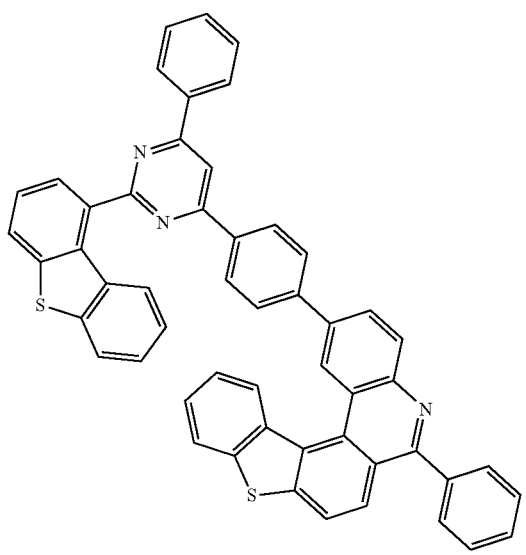
823
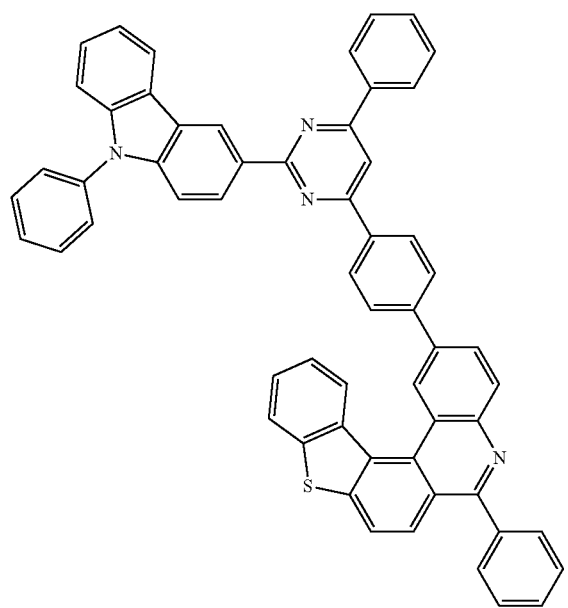
824
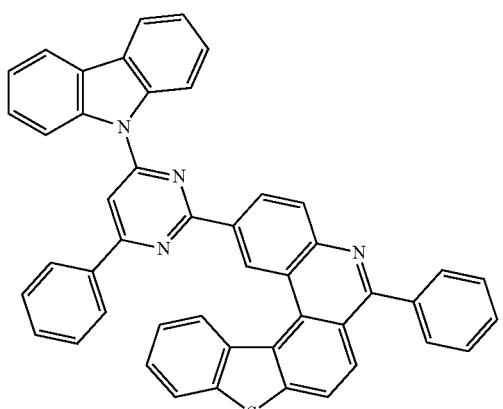

-continued
825
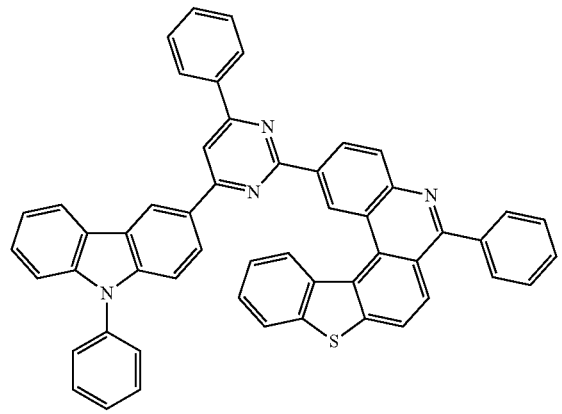
826
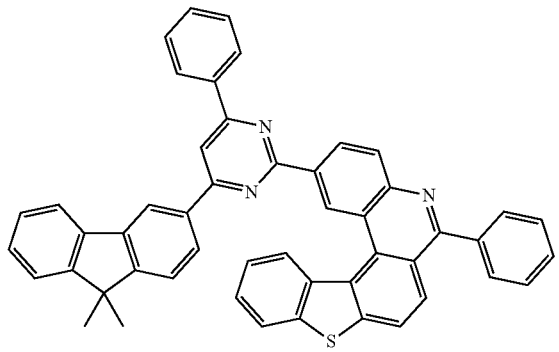
827
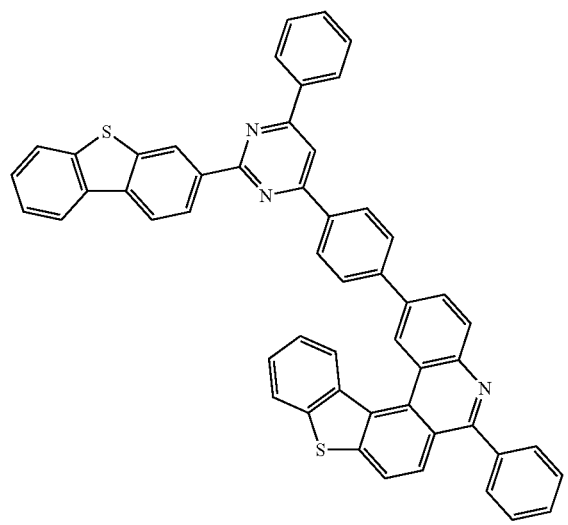
828
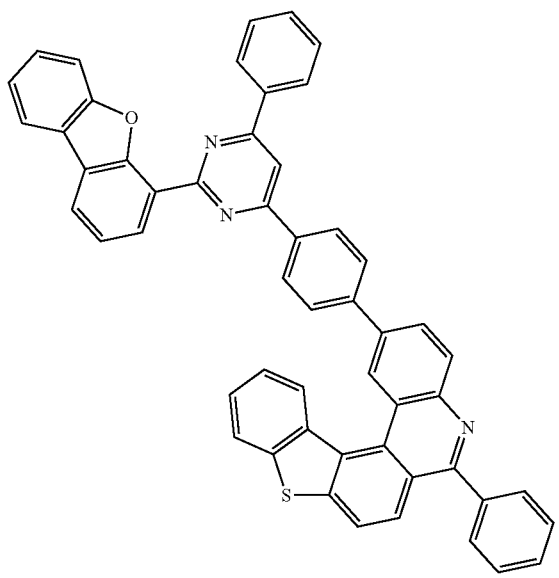
829
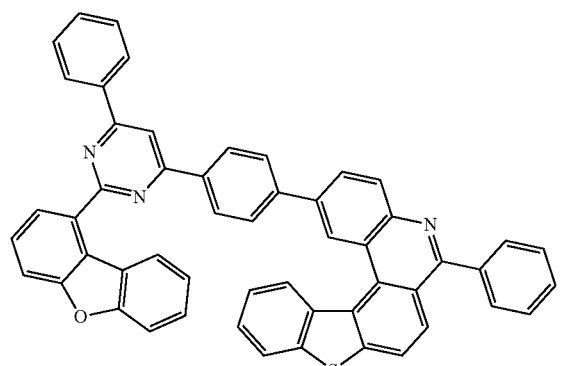
830
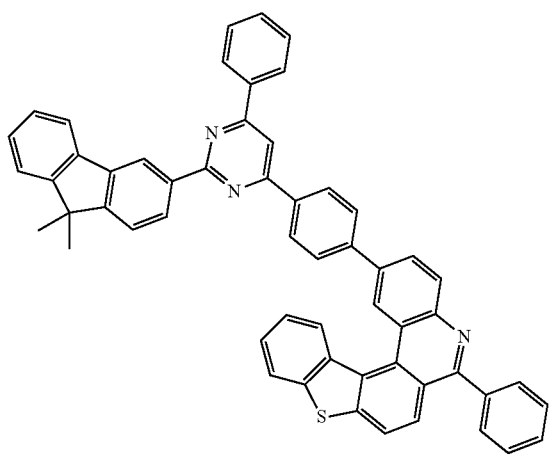

-continued
831
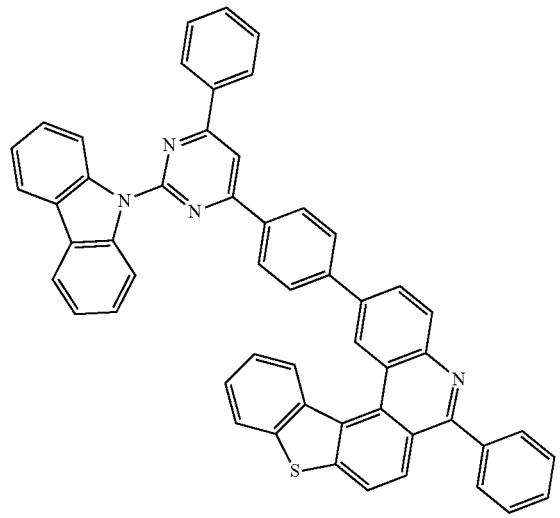
832
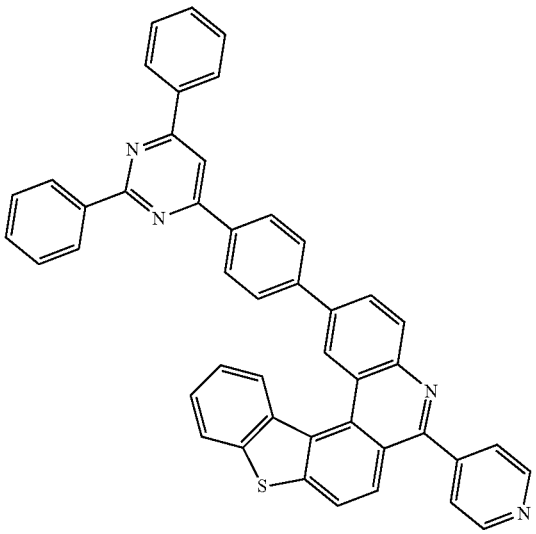
833
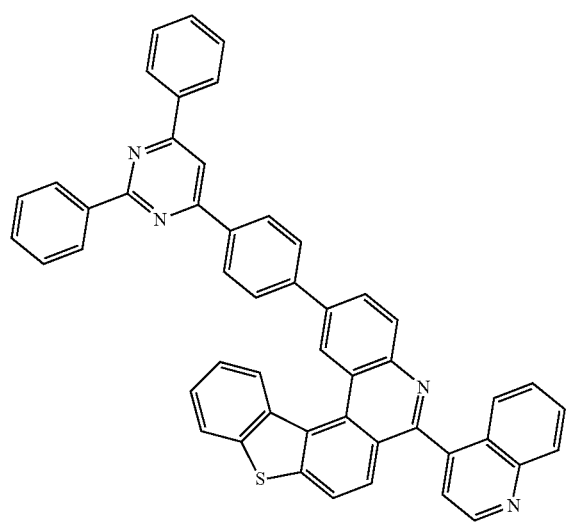
834
835
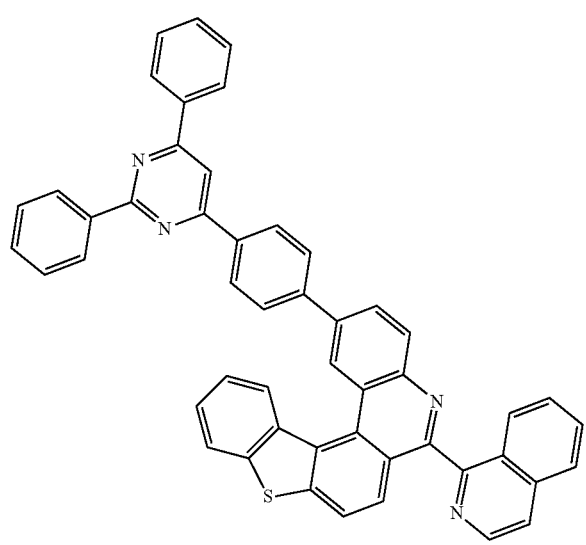

In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized. In addition, the energy band gap may be finely controlled, and with a high T1 value obtained therefrom, an organic light emitting device with superior efficiency may be provided. Herein, the T1 value means an energy level value in a triplet state.

In addition, by introducing various substituents with different properties to the structure of Chemical Formula 1, efficiency may increase through controlling HOMO and LUMO, and interfacial properties may be improved through controlling the molecular weight.

One embodiment of the present specification provides an organic light emitting device including a first electrode; a second electrode; and an organic material layer provided between the first electrode and the second electrode, wherein the organic material layer includes the heterocyclic compound represented by Chemical Formula 1.

In one embodiment of the present specification, the first electrode may be an anode, and the second electrode may be a cathode.

In another embodiment of the present specification, the first electrode may be a cathode, and the second electrode may be an anode.

In one embodiment of the present specification, the organic light emitting device may be a blue organic light emitting device, and the heterocyclic compound according to Chemical Formula 1 may be used as a material of the blue organic light emitting device. For example, the heterocyclic compound according to Chemical Formula 1 may be included in a charge generation layer or an electron transfer layer of the blue organic light emitting device.

In another embodiment of the present specification, the organic light emitting device may be a green organic light emitting device, and the heterocyclic compound according to Chemical Formula 1 may be used as a material of the green organic light emitting device. For example, the heterocyclic compound according to Chemical Formula 1 may be included in a charge generation layer or an electron transfer layer of the green organic light emitting device.

In another embodiment of the present specification, the organic light emitting device may be a red organic light emitting device, and the heterocyclic compound according to Chemical Formula 1 may be used as a material of the red organic light emitting device. For example, the heterocyclic compound according to Chemical Formula 1 may be included in a charge generation layer or an electron transfer layer of the red organic light emitting device.

Specific descriptions on the heterocyclic compound represented by Chemical Formula 1 are the same as the descriptions provided above.

The organic light emitting device of the present specification may be manufactured using common organic light emitting device manufacturing methods and materials except that one or more of the organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present specification may be formed in a single layer structure, but may be formed in a multilayer structure in which two or more organic material layers are laminated. For example, the organic light emitting device of the present disclosure may have a structure including a hole injection layer, a hole transfer layer, a light emitting layer, an electron transfer layer, an electron injection layer and the like as the organic material layer. However, the structure of the organic light emitting device is not limited thereto, and may include a smaller number of organic material layers.

In the organic light emitting device of the present specification, the organic material layer includes a charge generation layer, and the charge generation layer may include the heterocyclic compound of Chemical Formula 1. When including the heterocyclic compound in the charge generation layer, the band gap may be readily controlled facilitating carrier migration, and thermal properties may be improved by increasing the molecular weight.

In the organic light emitting device of the present specification, the organic material layer includes an electron transfer layer, and the electron transfer layer may include the heterocyclic compound of Chemical Formula 1. When using the heterocyclic compound as an electron transfer material, HOMO and LUMO may be controlled depending on the substituent position, and electron transfer efficiency is superior. In addition, a higher T1 is obtained compared to existing electron transfer materials leading to a low light emitter loss, and by preventing electrons from migrating in a reverse direction, excellent device efficiency is obtained.

The organic light emitting device of the present disclosure may further include one, two or more layers selected from the group consisting of a light emitting layer, a hole injection layer, a hole transfer layer. an electron injection layer, an electron transfer layer, an electron blocking layer and a hole blocking layer.

FIG. 1 to FIG. 5 illustrate a lamination order of electrodes and organic material layers of an organic light emitting device according to one embodiment of the present specification. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 and FIG. 4 illustrate cases of the organic material layer being a multilayer. The organic light emitting device according to FIG. 3 includes a hole injection layer (301), a hole transfer layer (302), a light emitting layer (303), an electron transfer layer (304) and a charge generation layer (306), and the organic light emitting device according to FIG. 4 includes a hole injection layer (301), a hole transfer layer (302), a light emitting layer (303), an electron transfer layer (304) and an electron injection layer (305). However, the scope of the present application is not limited to such a lamination structure, and as necessary, layers other than the light emitting layer may not be included, and other necessary functional layers may be further added.

The organic material layer including the heterocyclic compound represented by Chemical Formula 1 may further include other materials as necessary.

The organic light emitting device according to one embodiment of the present specification includes a first electrode; a first stack provided on the first electrode and including a first light emitting layer; a charge generation layer provided on the first stack; a second stack provided on the charge generation layer and including a second light emitting layer; and a second electrode provided on the second stack, wherein the charge generation layer may include the heterocyclic compound represented by Chemical Formula 1.

The organic light emitting device according to one embodiment of the present specification includes a first electrode; a second electrode; and an organic material layer provided between the first electrode and the second electrode, wherein the organic material layer includes two or more stacks, and the two or more stacks each independently include a light emitting layer, a charge generation layer is included between the two or more stacks, and the charge generation layer may include the heterocyclic compound represented by Chemical Formula 1.

The organic light emitting device according to one embodiment of the present specification includes a first electrode; a second electrode; and an organic material layer provided between the first electrode and the second electrode, wherein the organic material layer includes a first stack including a first light emitting layer; a charge generation layer provided on the first stack; and a second stack including a second light emitting layer, and the charge generation layer may include the heterocyclic compound represented by Chemical Formula 1.

In addition, the organic light emitting device according to one embodiment of the present specification includes an anode, a cathode, and two or more stacks provided between the anode and the cathode, the two or more stacks each independently include a light emitting layer, a charge generation layer is included between the two or more stacks, and the charge generation layer includes the heterocyclic compound represented by Chemical Formula 1.

In addition, the organic light emitting device according to one embodiment of the present specification includes an anode, a first stack provided on the anode and including a first light emitting layer, a charge generation layer provided on the first stack, a second stack provided on the charge generation layer and including a second light emitting layer, and a cathode provided on the second stack. Herein, the charge generation layer may include the heterocyclic compound represented by Chemical Formula 1. When the heterocyclic compound is included in the charge generation layer and used, superior efficiency is obtained as a charge generation layer material due to an electron-friendly substituent structure and a fused structure of quinoline-dibenzofuran or quinoline-dibenzothiophene friendly for hole migration.

Specifically, in the charge generation layer, controlling an energy level is important for an electron transfer layer and a hole transfer layer to favorably receive electrons and holes, respectively. By properly mixing a moiety with ET properties and a moiety with HT properties, the compound of the present disclosure is capable of controlling an energy level through properly controlling a substituent to have a deep LUMO level or a shallow HOMO level, and high efficiency as a charge generation layer may be obtained therethrough.

In addition, the first stack and the second stack may each independently further include one or more types of the hole injection layer, the hole transfer layer, the hole blocking layer, the electron transfer layer, the electron injection layer and the like described above.

The charge generation layer includes an N-type charge generation layer, and the N-type charge generation layer includes the heterocyclic compound represented by Chemical Formula 1 and, in addition to the compound, may further include a dopant known in the art.

As the organic light emitting device according to one embodiment of the present specification, an organic light emitting device having a 2-stack tandem structure is illustrated in FIG. 5.

Herein, the first electron blocking layer, the first hole blocking layer, the second hole blocking layer and the like described in FIG. 5 may not be included in some cases.

In the organic light emitting device according to one embodiment of the present specification, materials other than the heterocyclic compound represented by Chemical Formula 1 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as $ZnO:Al$ or $SnO_2:Sb$; conductive polymers such as poly(3-methylthiophene), poly[3,4-(ethylene-1,2-dioxy)thiophene](PEDOT), polypyrrole and polyaniline, and the like, but are not limited thereto.

As the cathode material, materials having relatively small work function may be used, and metals, metal oxides, conductive polymers or the like may be used. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrenesulfonate), polyaniline/camphor sulfonic acid or polyaniline/poly(4-styrenesulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used in addition to the heterocyclic compound, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involving in light emission together may also be used.

When mixing light emitting material hosts, same series hosts may be mixed, or different series hosts may be mixed. For example, any two or more types of materials among n-type host materials or p-type host materials may be selected and used as a host material of a light emitting layer.

The organic light emitting device according to one embodiment of the present specification may be a top-emission type, a bottom-emission type or a dual-emission type depending on the materials used.

The heterocyclic compound according to one embodiment of the present specification may also be used in an organic electronic device including an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

<Preparation Example 1> Preparation of Compound 1

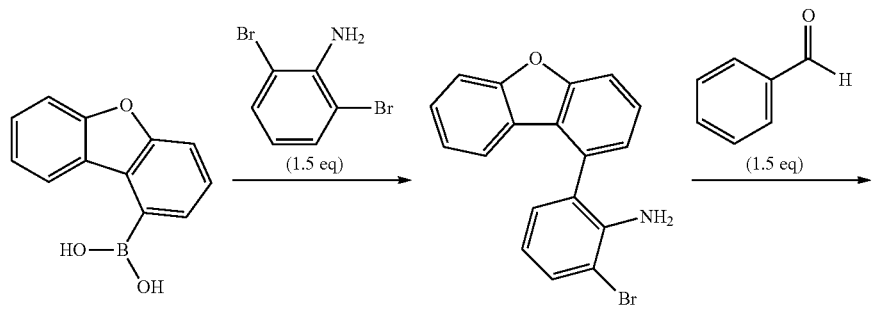

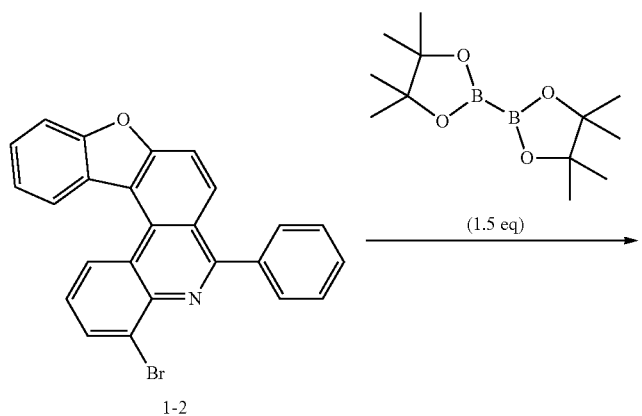

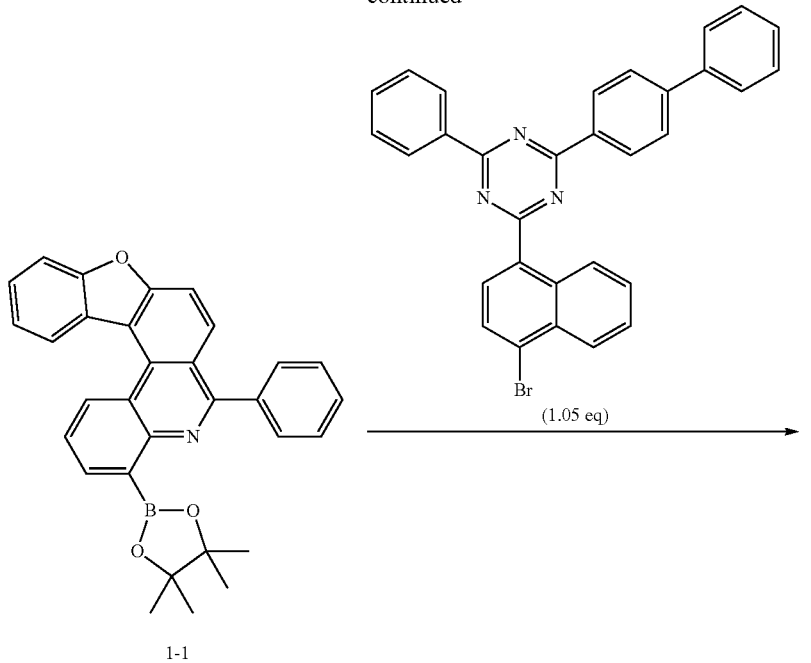

1-1

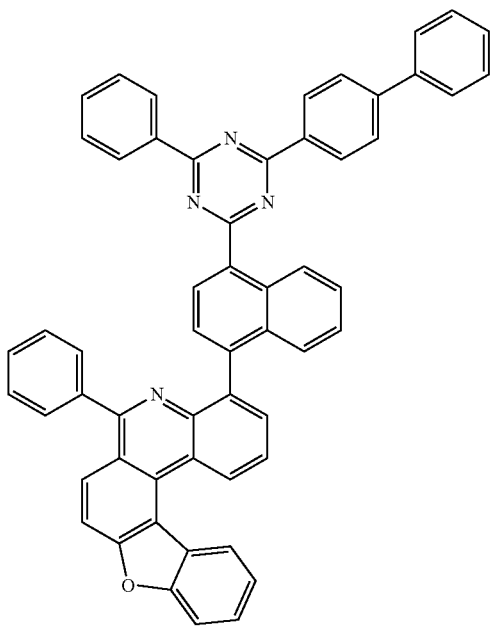

1

1) Preparation of Compound 1-3

After dissolving dibenzo[b,d]furan-1-ylboronic acid (30 g, 0.14 mol, 1 eq.) and 2,6-dibromoaniline (52.5 g, 0.21 mol, 1.5 eq.) in 1,4-dioxane (300 ml) and H$_2$O (90 ml), Pd(PPh$_3$)$_4$ (8 g, 0.007 mol, 0.05 eq.) and K$_3$PO$_4$ (89 g, 0.42 mol, 3 eq.) were introduced thereto, and the result was stirred for 4 hours under reflux.

The reaction solution was concentrated, then dissolved by introducing methylene chloride (MC) thereto, and then extracted with water, and the organic layer was dried with anhydrous Na$_2$SO$_4$. The solution was concentrated and dissolved again in methylene chloride, and after adsorbing the result to silica gel (250 ml), an MC/hexane column was performed to obtain Compound 1-3 (36 g).

2) Preparation of Compound 1-2

After dissolving Compound 1-3 (36 g, 0.11 mol, 1 eq.) and benzaldehyde (17.5 g, 0.17 mol, 1.5 eq.) in 1,2-dichlorobenzene (360 ml) and trifluoromethanesulfonic acid (20 ml), the result was stirred for 3 hours under reflux.

NaHCO₃ dissolved in H₂O was introduced to the reaction solution for neutralization. The solution was concentrated and dissolved in a small amount of MC, and then MC/methanol (MeOH) slurried and filtered. Compound 1-2 (28 g) was obtained in a 60% yield.

3) Preparation of Compound 1-1

After dissolving Compound 1-2 (28 g, 0.066 mol, 1 eq.) and bis(pinacolato)diboron (25 g, 0.099 mol, 1.5 eq.) in 1,4-dioxane (300 ml), Pd(dppf)Cl₂ (2.4 g, 0.033 mol, 0.05 eq.) and KOAc (19 g, 0.198 mol, 3 eq.) were introduced thereto, and the result was stirred for 4 hours under reflux. After the reaction was completed, the result was extracted with MC and water, and then the organic layer was dried with anhydrous MgSO₄ and then silica gel filtered. The result was precipitated with MC/MeOH and the precipitates were filtered to obtain Intermediate 1-1 (25 g) in a 81% yield.

4) Preparation of Compound 1

After dissolving Compound 1-1 (11 g, 0.0235 mol, 1 eq.) and 2-([1,1'-biphenyl]-4-yl)-4-(4-bromonaphthalen-1-yl)-6-phenyl-1,3,5-triazine (12.8 g, 0.025 mol, 1.05 eq.) in 1,4-dioxane (100 ml) and H₂O (30 ml), Pd(PPh₃)₄ (1.4 g, 0.00118 mol, 0.05 eq.) and K₃PO₄ (15 g, 0.71 mol, 3 eq.) were introduced thereto, and the result was stirred for 4 hours under reflux.

The reaction solution was cooled, then MeOH slurried to precipitate solids, and filtered. The solids were dissolved in 1,2-dichlorobenzene and silica gel filtered. The organic solution was concentrated, MC/MeOH slurried, and then filtered to obtain Compound 1 (12 g) in a 67% yield.

Compound P was synthesized in the same manner as in Preparation Example 1 except that Intermediate A of the following Table 1 was used instead of 2-([1,1'-biphenyl]-4-yl)-4-(4-bromonaphthalen-1-yl)-6-phenyl-1,3,5-triazine.

TABLE 1

| Compound Number | Intermediate A | Compound P | Yield |
|---|---|---|---|
| 1 | | | 67% |
| 4 | | | 78% |

TABLE 1-continued
| Compound Number | Intermediate A | Compound P | Yield |
|---|---|---|---|
| 7 | 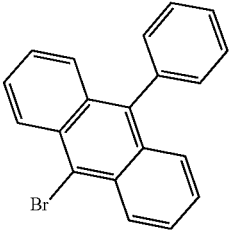 [SMILES: Brc1c2ccccc2c(-c2ccccc2)c2ccccc12] | 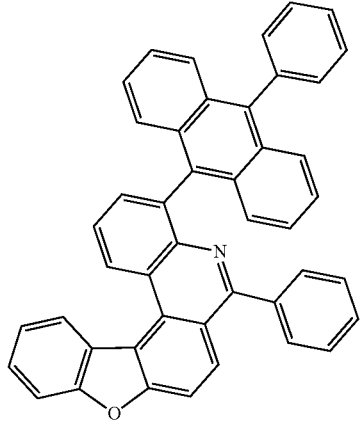 [SMILES: c1ccc(-c2c3ccccc3c(-c3cccc4c3nc(-c3ccccc3)c3ccc5oc6ccccc6c5c34)c3ccccc23)cc1] | 72% |
| 8 | 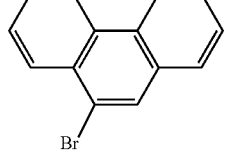 | 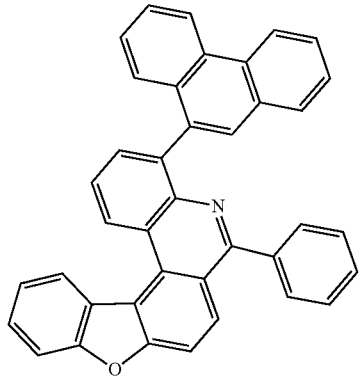 [SMILES: c1ccc(-c2nc3c(-c4cc5ccccc5c5ccccc45)cccc3c3c2ccc2oc4ccccc4c23)cc1] | 79% |
| 15 | 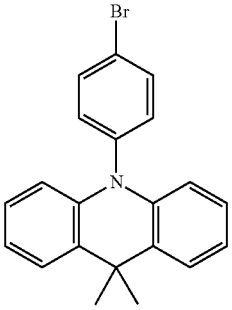 [SMILES: CC1(C)c2ccccc2N(c2ccc(Br)cc2)c2ccccc21] | 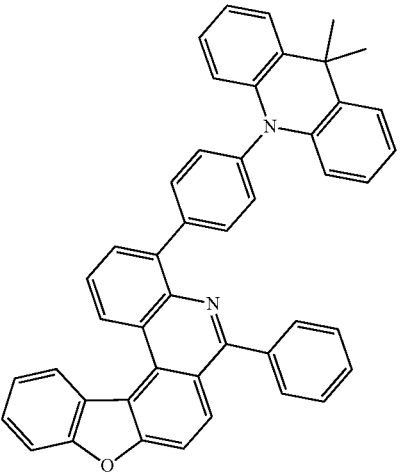 [SMILES: CC1(C)c2ccccc2N(c2ccc(-c3cccc4c3nc(-c3ccccc3)c3ccc5oc6ccccc6c5c34)cc2)c2ccccc21] | 79% |

TABLE 1-continued

| Compound Number | Intermediate A | Compound P | Yield |
|---|---|---|---|
| 18 | | | 85% |
| 21 | | | 82% |
| 32 | | | 91% |

TABLE 1-continued

| Compound Number | Intermediate A | Compound P | Yield |
|---|---|---|---|
| 35 | | | 78% |
| 38 | | | 82% |

TABLE 1-continued
| Compound Number | Intermediate A | Compound P | Yield |
|---|---|---|---|
| 41 | 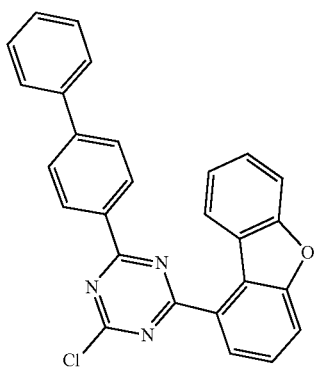 [SMILES: Clc1nc(-c2ccc(-c3ccccc3)cc2)nc(-c2cccc3oc4ccccc4c23)n1] | 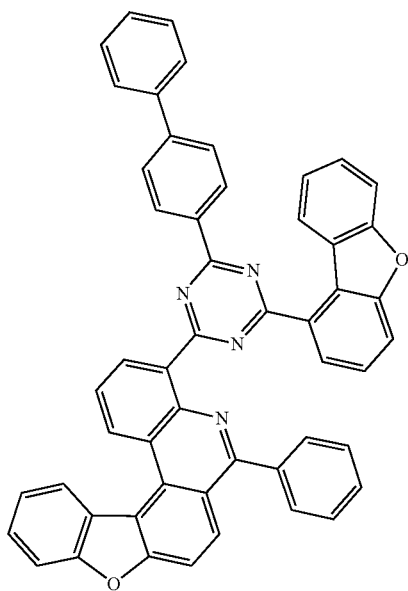 [SMILES: c1ccc(-c2ccc(-c3nc(-c4cccc5c4nc(-c4ccccc4)c4ccc6oc7ccccc7c6c45)nc(-c4cccc5oc6ccccc6c45)n3)cc2)cc1] | 78% |
| 44 | 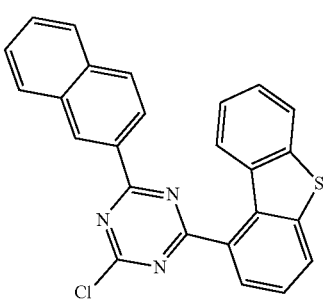 [SMILES: Clc1nc(-c2ccc3ccccc3c2)nc(-c2cccc3sc4ccccc4c23)n1] | 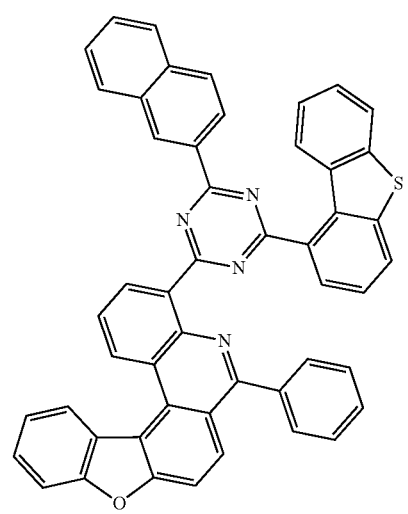 [SMILES: c1ccc(-c2nc3c(-c4nc(-c5ccc6ccccc6c5)nc(-c5cccc6sc7ccccc7c56)n4)cccc3c3c2ccc2oc4ccccc4c23)cc1] | 81% |

TABLE 1-continued
| Compound Number | Intermediate A | Compound P | Yield |
|---|---|---|---|
| 47 | 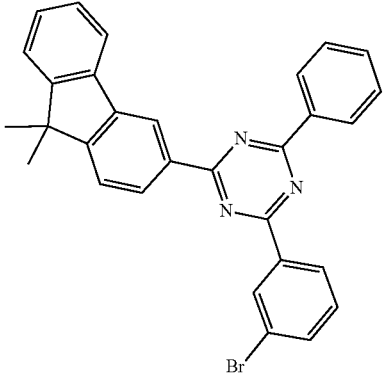 [SMILES: CC1(C)c2ccccc2-c2cc(-c3nc(-c4ccccc4)nc(-c4cccc(Br)c4)n3)ccc21] | 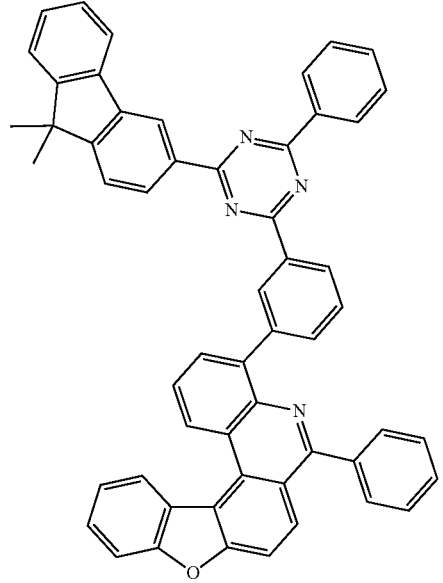 [SMILES: CC1(C)c2ccccc2-c2cc(-c3nc(-c4ccccc4)nc(-c4cccc(-c5cccc6c5nc(-c5ccccc5)c5ccc7oc8ccccc8c7c56)c4)n3)ccc21] | 92% |
| 50 | 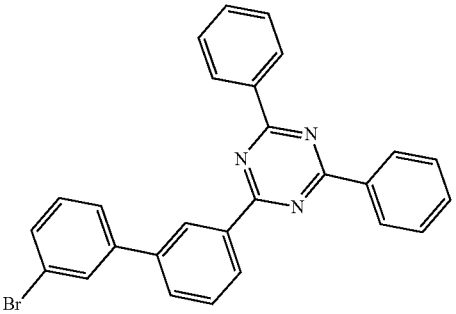 [SMILES: Brc1cccc(-c2cccc(-c3nc(-c4ccccc4)nc(-c4ccccc4)n3)c2)c1] | 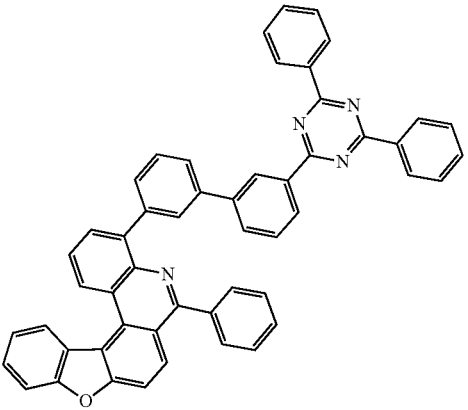 [SMILES: c1ccc(-c2nc(-c3ccccc3)nc(-c3cccc(-c4cccc(-c5cccc6c5nc(-c5ccccc5)c5ccc7oc8ccccc8c7c56)c4)c3)n2)cc1] | 88% |
| 53 | 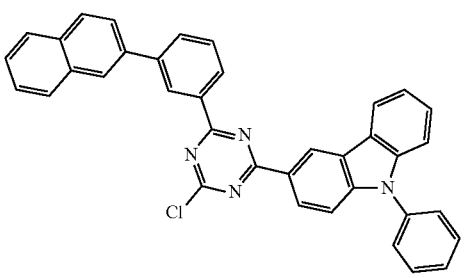 [SMILES: Clc1nc(-c2cccc(-c3ccc4ccccc4c3)c2)nc(-c2ccc3c(c2)c2ccccc2n3-c2ccccc2)n1] | 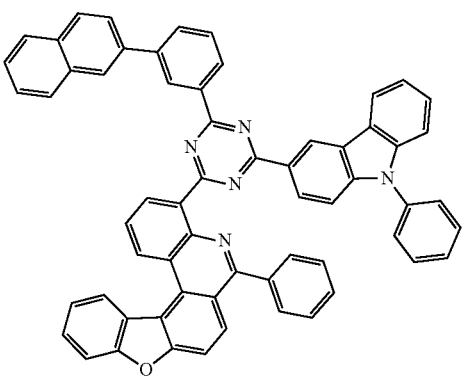 [SMILES: c1ccc(-c2nc3c(-c4nc(-c5cccc(-c6ccc7ccccc7c6)c5)nc(-c5ccc6c(c5)c5ccccc5n6-c5ccccc5)n4)cccc3c3c2ccc2oc4ccccc4c23)cc1] | 89% |

TABLE 1-continued

| Compound Number | Intermediate A | Compound P | Yield |
|---|---|---|---|
| 58 | | | 78% |
| 61 | | | 82% |
| 63 | | | 95% |

TABLE 1-continued

| Compound Number | Intermediate A | Compound P | Yield |
|---|---|---|---|
| 67 | | | 92% |
| 73 | | | 90% |
| 76 | | | 89% |

TABLE 1-continued

| Compound Number | Intermediate A | Compound P | Yield |
|---|---|---|---|
| 78 | | | 86% |
| 81 | | | 96% |
| 83 | | | 93% |

TABLE 1-continued

| Compound Number | Intermediate A | Compound P | Yield |
|---|---|---|---|
| 86 | | | 88% |
| 90 | | | 81% |
| 92 | | | 92% |

TABLE 1-continued

| Compound Number | Intermediate A | Compound P | Yield |
|---|---|---|---|
| 95 | | | 89% |
| 101 | | | 90% |
| 103 | | | 92% |

TABLE 1-continued
| Compound Number | Intermediate A | Compound P | Yield |
|---|---|---|---|
| 107 | 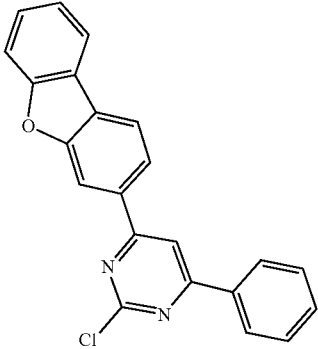 [SMILES: Clc1nc(-c2ccccc2)cc(-c2ccc3c(c2)oc2ccccc23)n1] | 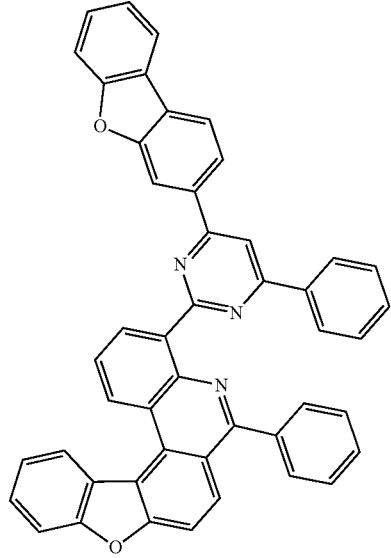 [SMILES: c1ccc(-c2cc(-c3ccc4c(c3)oc3ccccc34)nc(-c3cccc4c3nc(-c3ccccc3)c3ccc5oc6ccccc6c5c34)n2)cc1] | 95% |
| 110 | 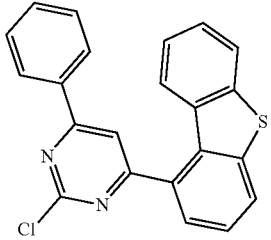 [SMILES: Clc1nc(-c2ccccc2)cc(-c2cccc3sc4ccccc4c23)n1] | 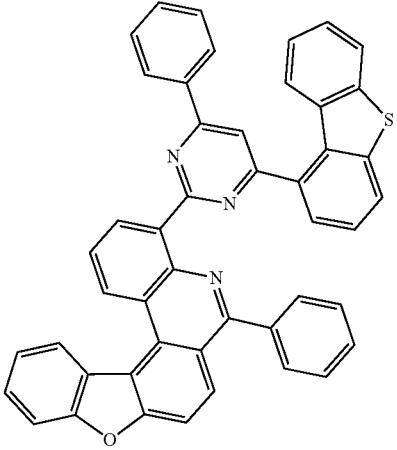 [SMILES: c1ccc(-c2cc(-c3cccc4sc5ccccc5c34)nc(-c3cccc4c3nc(-c3ccccc3)c3ccc5oc6ccccc6c5c34)n2)cc1] | 87% |

TABLE 1-continued
| Compound Number | Intermediate A | Compound P | Yield |
|---|---|---|---|
| 113 | 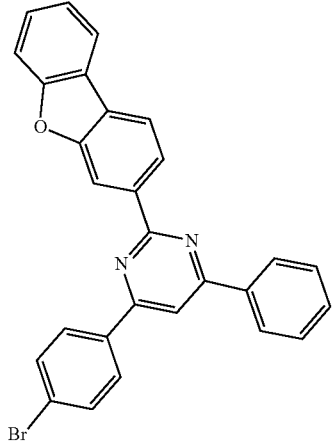 [SMILES: Brc1ccc(-c2cc(-c3ccccc3)nc(-c3ccc4c(c3)oc3ccccc34)n2)cc1] | 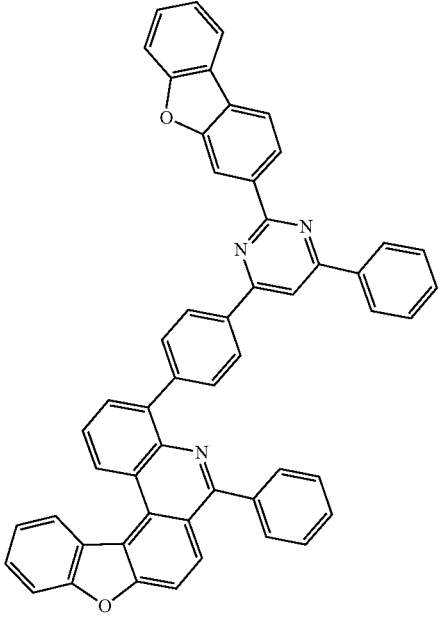 [SMILES: c1ccc(-c2cc(-c3ccc(-c4cccc5c4nc(-c4ccccc4)c4ccc6oc7ccccc7c6c45)cc3)nc(-c3ccc4c(c3)oc3ccccc34)n2)cc1] | 86% |
| 115 | 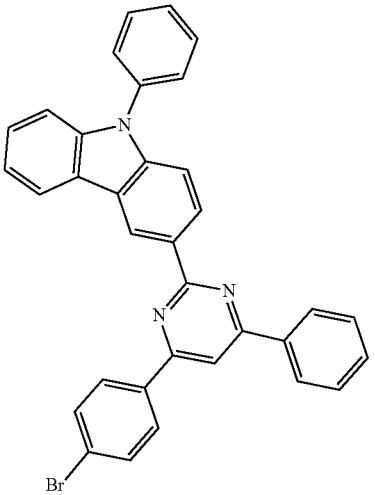 [SMILES: Brc1ccc(-c2cc(-c3ccccc3)nc(-c3ccc4c(c3)c3ccccc3n4-c3ccccc3)n2)cc1] | 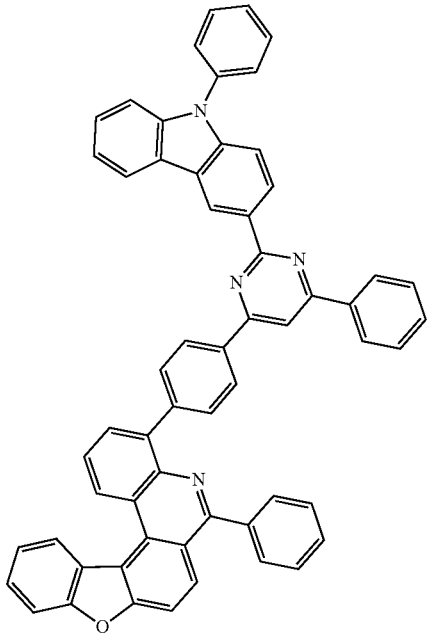 [SMILES: c1ccc(-c2cc(-c3ccc(-c4cccc5c4nc(-c4ccccc4)c4ccc6oc7ccccc7c6c45)cc3)nc(-c3ccc4c(c3)c3ccccc3n4-c3ccccc3)n2)cc1] | 82% |

<Preparation Example 2> Preparation of Compound 122

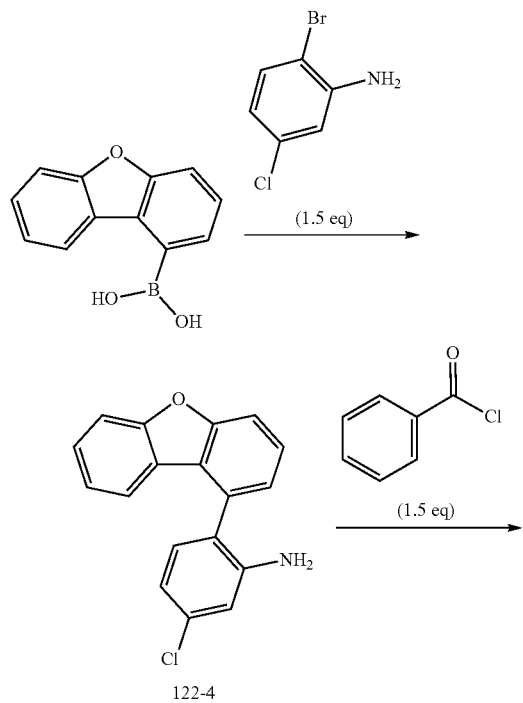

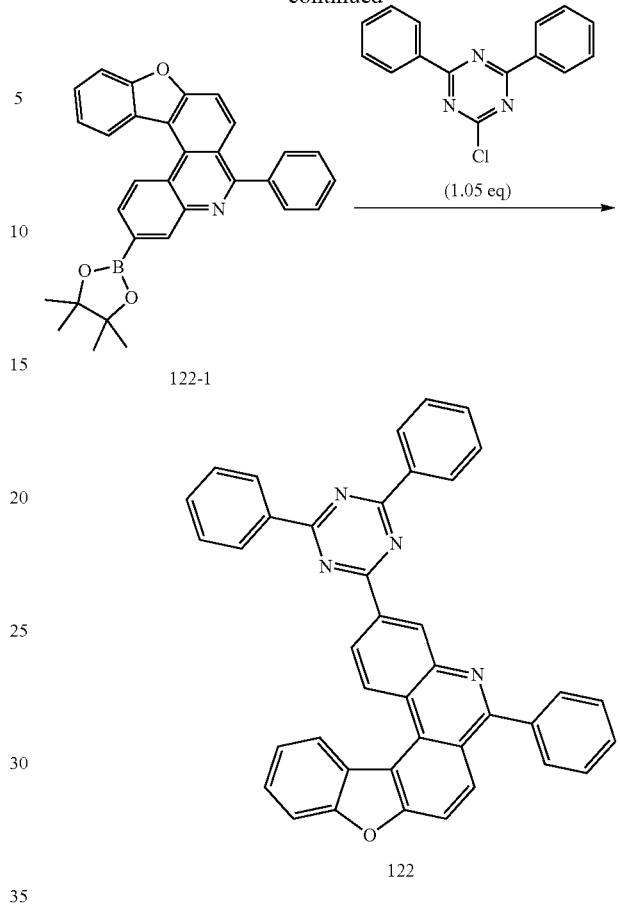

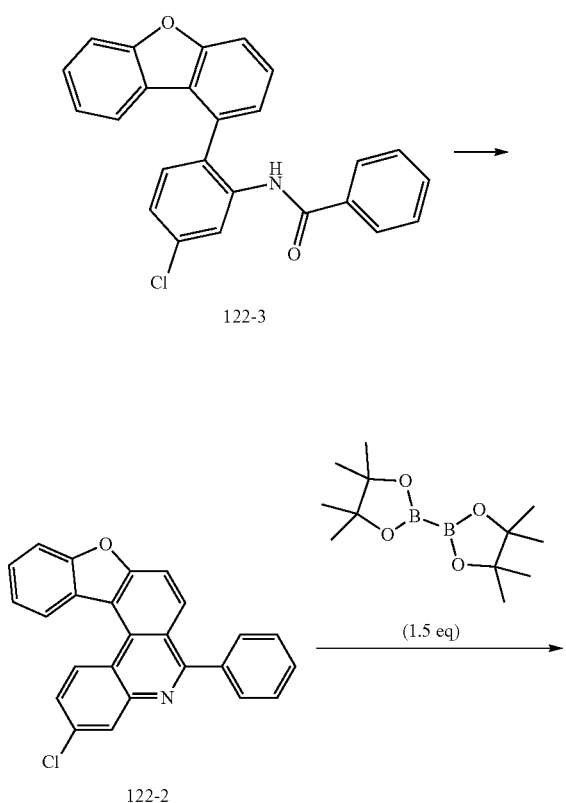

1) Preparation of Compound 122-4

Compound 122-4 (38 g, 92% yield) was obtained in the same manner as in Preparation Example 1 except that 2-bromo-5-chloroaniline was used instead of 2,6-dibromoaniline. 2) Preparation of Compound 122-3

After dissolving Compound 122-4 (38 g, 0.129 mol, 1 eq.) in tetrahydrofuran (THF), triethylamine (TEA) (0.516 mol) and benzoyl chloride (0.194 mol) were added thereto at 0° C., and then the result was stirred for 1 hour at room temperature. After the reaction was finished, the result was extracted with distilled water and ethyl acetate (EA). The organic layer was dried with $MgSO_4$, then filtered, and concentrated. The result was adsorbed to silica gel, and purified by column chromatography using dichloromethane and hexane as a developing solvent to obtain Compound 122-3 (48.5 g) in a 95% yield.

3) Preparation of Compound 122-2

After dissolving Compound 122-3 (48.5 g, 0.121 mol, 1 eq.) in nitrobenzene, $POCl_3$ (0.182 mol) was added thereto, and the result was stirred for 17 hours at 150° C. After the reaction was finished, the result was neutralized at room temperature, and then extracted with distilled water and dichloromethane. The organic layer was dried with $MgSO_4$, then filtered, and concentrated. The concentrated residue was slurried with MeOH, and then filtered to obtain Compound 122-2 (26 g) in a 56% yield.

4) Preparation of Compound 122-1

After adding 4,4,4',4',5,5,5',5'-octamethyl-2,2'-bi(1,3,2-dioxaborolane) (0.102 mol), Pd(dba)$_2$ (0.0068 mol), XPhos (0.0136 mol), KoAc (0.204 mol) and 1,4-dioxane to Compound 122-2 (26 g, 0.068 mol, 1 eq.), the result was stirred for 5 hours at 110° C. After the reaction was completed, the result was base filtered, and then washed with dichloromethane. The organic solution was concentrated, and then dissolved in a small amount of chloroform, and passed through silica gel. The solution was concentrated, and then MC/MeOH slurried to obtain Compound 122-1 (31 g) in a 97% yield.

5) Preparation of Compound 122

After dissolving Compound 122-1 (10 g, 0.039 mol, 1 eq.) and 2-chloro-4,6-diphenyl-1,3,5-triazine (0.041 mol, 1.05 eq.) in 1,4-dioxane (100 ml) and H$_2$O (30 ml), Pd(PPh$_3$)$_4$ (0.0019 mol, 0.05 eq.) and K$_3$PO$_4$ (0.117 mol, 3 eq.) were introduced thereto, and the result was stirred for 4 hours under reflux.

The reaction solution was cooled, then MeOH slurried to precipitate solids, and then filtered. The solids were dissolved in 1,2-dichlorobenzene and silica gel filtered. The organic solution was concentrated, MC/MeOH slurried, and then filtered to obtain Compound 122 (20 g) in a 78% yield.

Compound P was synthesized in the same manner as in Preparation Example 2 except that Intermediate A of the following Table 2 was used instead of 2-([1,1'-biphenyl]-4-yl)-4-chloro-6-phenyl-1,3,5-triazine.

TABLE 2

| Compound Number | Intermediate A | Compound P | Yield |
|---|---|---|---|
| 122 | 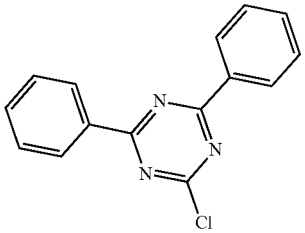 [SMILES: Clc1nc(-c2ccccc2)nc(-c2ccccc2)n1] | 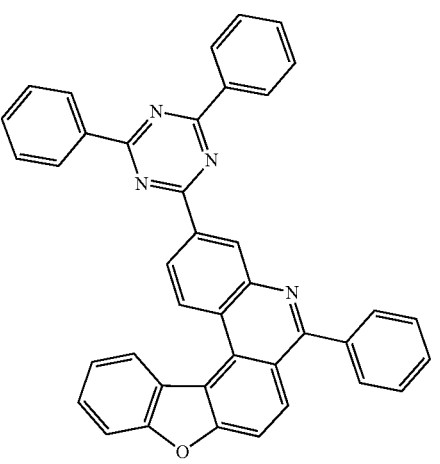 [SMILES: c1ccc(-c2nc(-c3ccccc3)nc(-c3ccc4c(c3)nc(-c3ccccc3)c3ccc5oc6ccccc6c5c34)n2)cc1] | 78% |
| 124 | 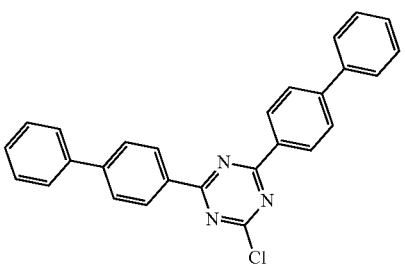 [SMILES: Clc1nc(-c2ccc(-c3ccccc3)cc2)nc(-c2ccc(-c3ccccc3)cc2)n1] | 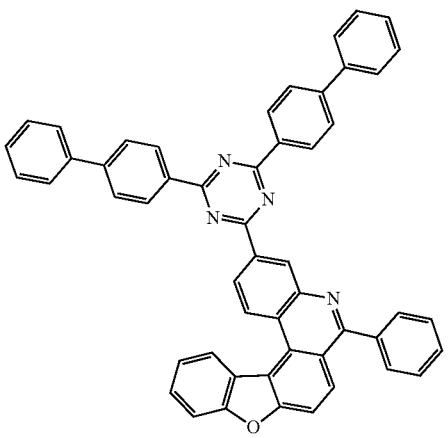 [SMILES: c1ccc(-c2ccc(-c3nc(-c4ccc(-c5ccccc5)cc4)nc(-c4ccc5c(c4)nc(-c4ccccc4)c4ccc6oc7ccccc7c6c45)n3)cc2)cc1] | 78% |

TABLE 2-continued
| Compound Number | Intermediate A | Compound P | Yield |
|---|---|---|---|
| 126 | 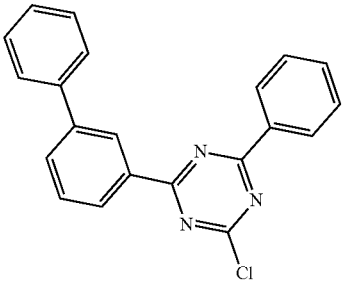 [SMILES: Clc1nc(-c2ccccc2)nc(-c2cccc(-c3ccccc3)c2)n1] | 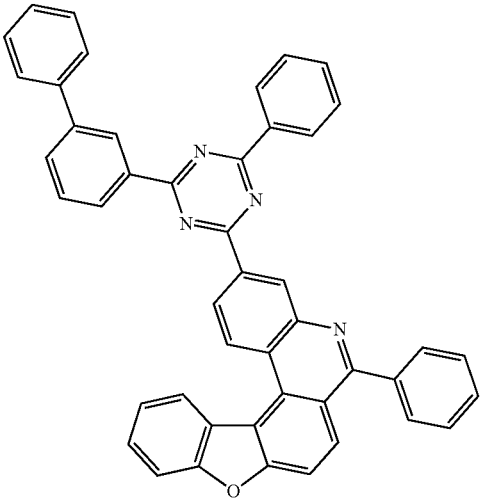 [SMILES: c1ccc(-c2cccc(-c3nc(-c4ccccc4)nc(-c4ccc5c(c4)nc(-c4ccccc4)c4ccc6oc7ccccc7c6c45)n3)c2)cc1] | 72% |
| 130 | 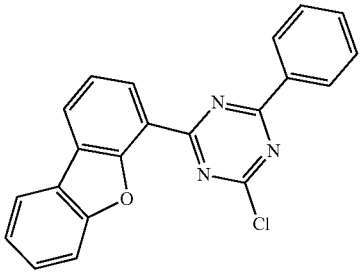 [SMILES: Clc1nc(-c2ccccc2)nc(-c2cccc3c2oc2ccccc23)n1] | 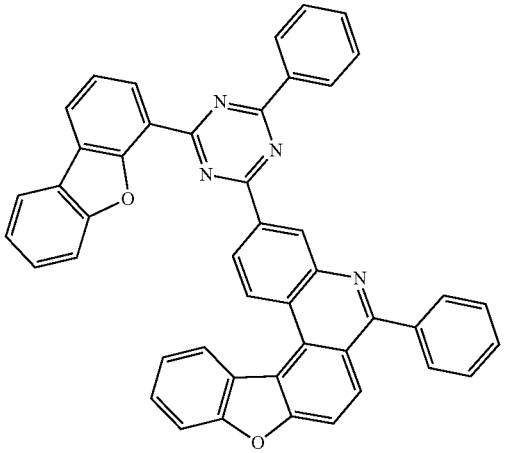 [SMILES: c1ccc(-c2nc(-c3ccc4c(c3)nc(-c3ccccc3)c3ccc5oc6ccccc6c5c34)nc(-c3cccc4c3oc3ccccc34)n2)cc1] | 79% |
| 135 | 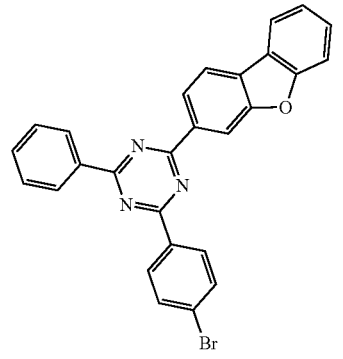 [SMILES: Brc1ccc(-c2nc(-c3ccccc3)nc(-c3ccc4c(c3)oc3ccccc34)n2)cc1] | 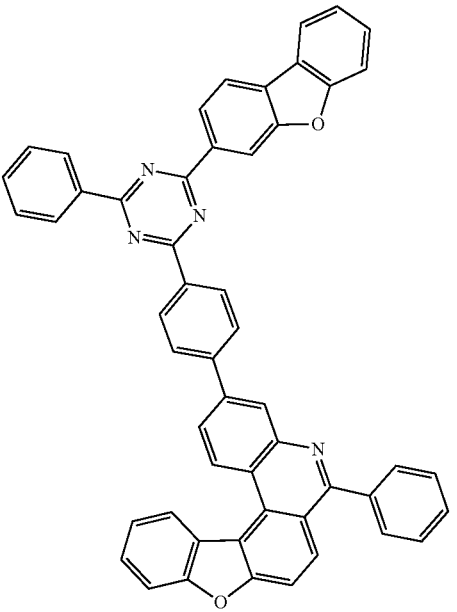 [SMILES: c1ccc(-c2nc(-c3ccc(-c4ccc5c(c4)nc(-c4ccccc4)c4ccc6oc7ccccc7c6c45)cc3)nc(-c3ccc4c(c3)oc3ccccc34)n2)cc1] | 79% |

TABLE 2-continued

| Compound Number | Intermediate A | Compound P | Yield |
|---|---|---|---|
| 138 | | | 69% |
| 147 | | | 82% |
| 149 | | | 84% |

TABLE 2-continued

| Compound Number | Intermediate A | Compound P | Yield |
|---|---|---|---|
| 152 | | | 78% |
| 155 | | | 82% |
| 161 | | | 82% |

TABLE 2-continued

| Compound Number | Intermediate A | Compound P | Yield |
|---|---|---|---|
| 164 | | | 81% |
| 168 | | | 92% |

TABLE 2-continued

| Compound Number | Intermediate A | Compound P | Yield |
|---|---|---|---|
| 172 | | | 93% |
| 178 | | | 95% |
| 181 | | | 96% |

TABLE 2-continued

| Compound Number | Intermediate A | Compound P | Yield |
|---|---|---|---|
| 186 | | | 87% |
| 190 | | | 83% |
| 194 | | | 75% |

TABLE 2-continued

| Compound Number | Intermediate A | Compound P | Yield |
|---|---|---|---|
| 198 | | | 84% |
| 202 | | | 79% |
| 206 | | | 80% |

TABLE 2-continued
| Compound Number | Intermediate A | Compound P | Yield |
|---|---|---|---|
| 210 | 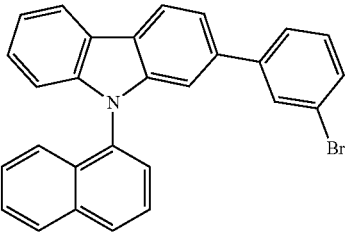 [SMILES: Brc1cccc(-c2ccc3c4ccccc4n(-c4cccc5ccccc45)c3c2)c1] | 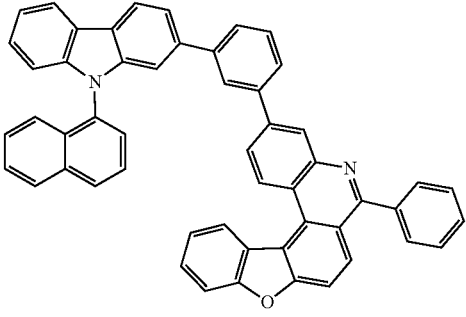 [SMILES: c1ccc(-c2nc3cc(-c4cccc(-c5ccc6c7ccccc7n(-c7cccc8ccccc78)c6c5)c4)ccc3c3c2ccc2oc4ccccc4c23)cc1] | 86% |
| 214 | 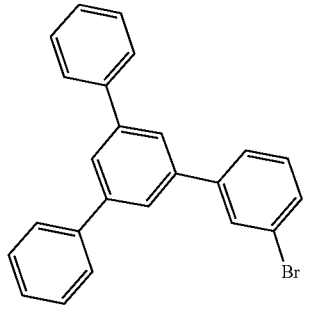 [SMILES: Brc1cccc(-c2cc(-c3ccccc3)cc(-c3ccccc3)c2)c1] | 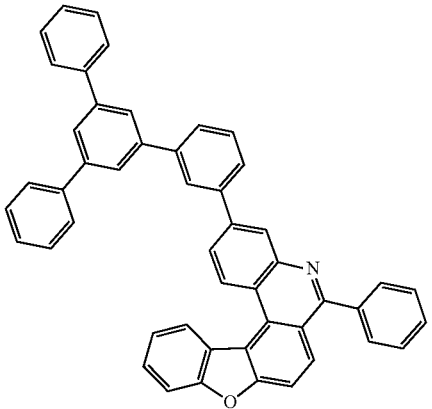 [SMILES: c1ccc(-c2cc(-c3ccccc3)cc(-c3cccc(-c4ccc5c(c4)nc(-c4ccccc4)c4ccc6oc7ccccc7c6c45)c3)c2)cc1] | 88% |
| 218 | 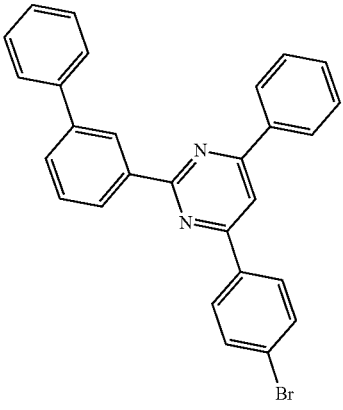 [SMILES: Brc1ccc(-c2cc(-c3ccccc3)nc(-c3cccc(-c4ccccc4)c3)n2)cc1] | 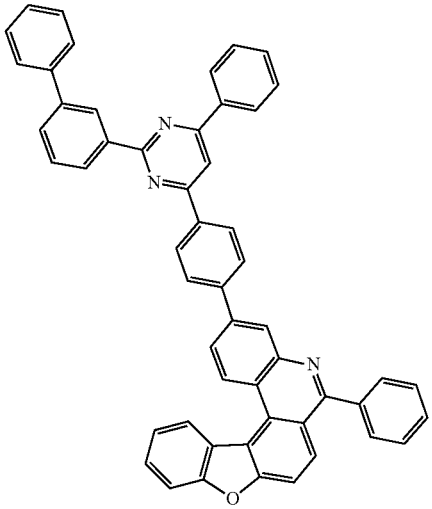 [SMILES: c1ccc(-c2cccc(-c3nc(-c4ccccc4)cc(-c4ccc(-c5ccc6c(c5)nc(-c5ccccc5)c5ccc7oc8ccccc8c7c56)cc4)n3)c2)cc1] | 89% |

TABLE 2-continued

| Compound Number | Intermediate A | Compound P | Yield |
|---|---|---|---|
| 222 | | | 91% |
| 226 | | | 82% |
| 230 | | | 83% |

TABLE 2-continued
| Compound Number | Intermediate A | Compound P | Yield |
|---|---|---|---|
| 234 | 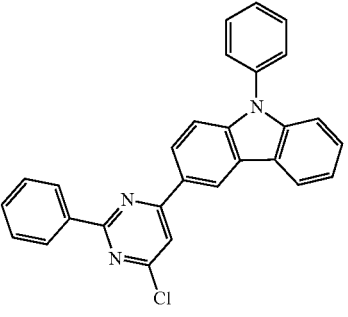 [SMILES: Clc1cc(-c2ccc3c(c2)c2ccccc2n3-c2ccccc2)nc(-c2ccccc2)n1] | 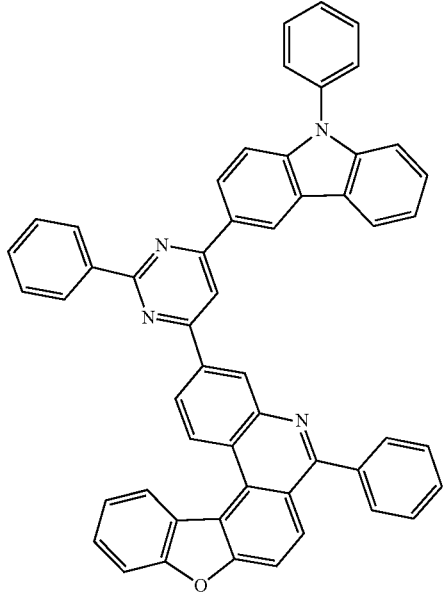 [SMILES: c1ccc(-c2nc(-c3ccc4c(c3)nc(-c3ccccc3)c3ccc5oc6ccccc6c5c34)cc(-c3ccc4c(c3)c3ccccc3n4-c3ccccc3)n2)cc1] | 93% |
| 238 | 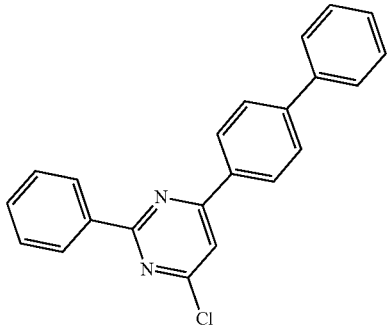 [SMILES: Clc1cc(-c2ccc(-c3ccccc3)cc2)nc(-c2ccccc2)n1] | 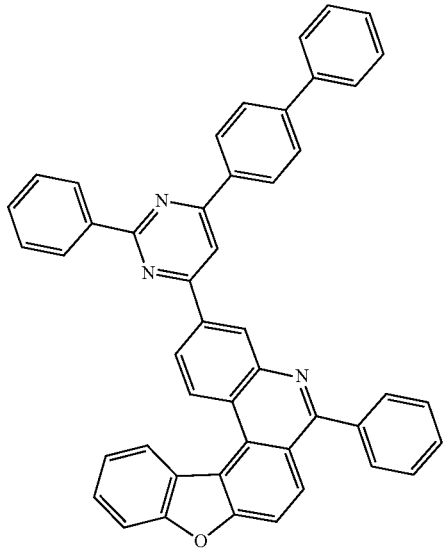 [SMILES: c1ccc(-c2ccc(-c3cc(-c4ccc5c(c4)nc(-c4ccccc4)c4ccc6oc7ccccc7c6c45)nc(-c4ccccc4)n3)cc2)cc1] | 94% |

TABLE 2-continued

| Compound Number | Intermediate A | Compound P | Yield |
|---|---|---|---|
| 242 | | | 89% |
| 246 | | | 78% |

TABLE 2-continued

| Compound Number | Intermediate A | Compound P | Yield |
|---|---|---|---|
| 250 | | | 79% |
| 254 | | | 75% |

TABLE 2-continued
| Compound Number | Intermediate A | Compound P | Yield |
|---|---|---|---|
| 258 | 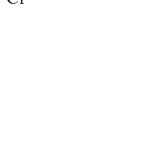 | 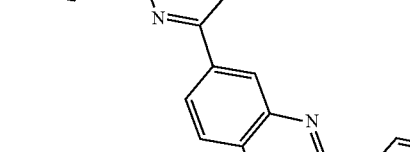 | 81% |
| 262 | 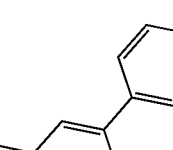 | 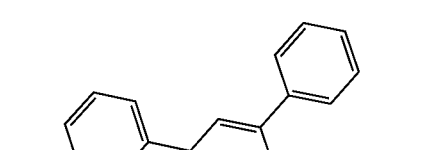 | 82% |
| 266 |  | 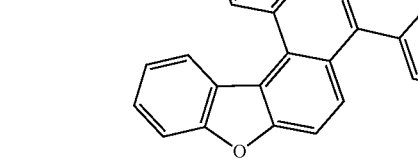 | 91% |

TABLE 2-continued

| Compound Number | Intermediate A | Compound P | Yield |
|---|---|---|---|
| 270 | | | 92% |
| 274 | | | 86% |
| 278 | | | 87% |

Compound P was obtained in the same manner as in Preparation Example 2 except that 4-chloro-2-(dibenzo[b,d]furan-1-yl)aniline was synthesized instead of Compound 122-4 using 2-bromo-4-chloroaniline instead of 2-bromo-5-chloroaniline, and Intermediate A of the following Table 3 was used instead of 2-([1,1'-biphenyl]-4-yl)-4-chloro-6-phenyl-1,3,5-triazine.

TABLE 3

| Compound Number | Intermediate A | Compound P | Yield |
|---|---|---|---|
| 282 | | | 82% |
| 286 | | | 81% |
| 290 | | | 92% |

TABLE 3-continued

| Compound Number | Intermediate A | Compound P | Yield |
|---|---|---|---|
| 294 | | | 78% |
| 298 | | | 93% |

TABLE 3-continued

| Compound Number | Intermediate A | Compound P | Yield |
|---|---|---|---|
| 302 | | | 72% |
| 306 | | | 79% |
| 310 | | | 79% |
| 314 | | | 69% |

TABLE 3-continued
| Compound Number | Intermediate A | Compound P | Yield |
|---|---|---|---|
| 318 | 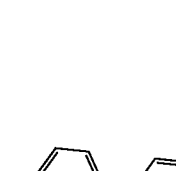 | 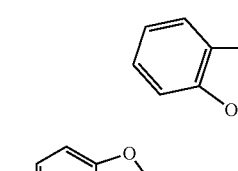 | 82% |
| 326 | 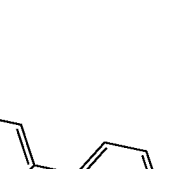 | 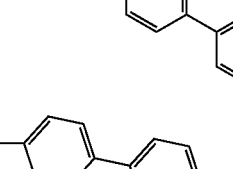 | 84% |
| 330 |  |  | 78% |
| 334 | 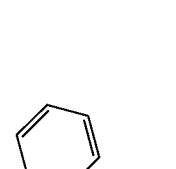 | 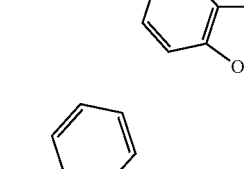 | 82% |
| 338 |  | 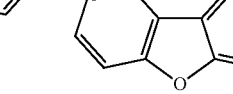 | 81% |

TABLE 3-continued
| Compound Number | Intermediate A | Compound P | Yield |
|---|---|---|---|
| 342 | 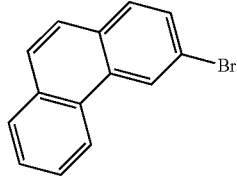 | 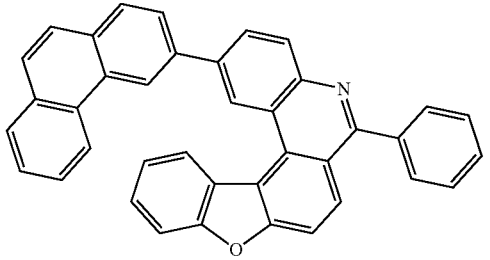 [SMILES: c1ccc(-c2nc3ccc(-c4ccc5ccc6ccccc6c5c4)cc3c3c2ccc2oc4ccccc4c23)cc1] | 82% |
| 346 | 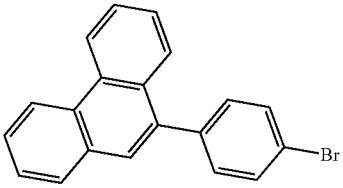 [SMILES: Brc1ccc(-c2cc3ccccc3c3ccccc23)cc1] | 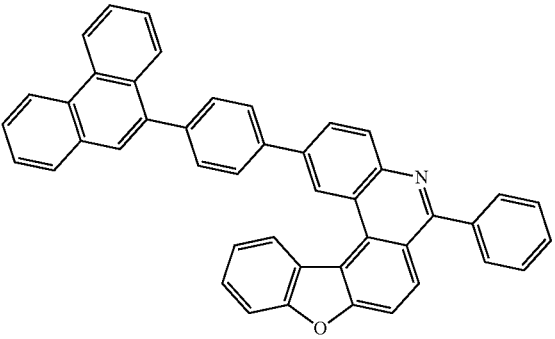 [SMILES: c1ccc(-c2nc3ccc(-c4ccc(-c5cc6ccccc6c6ccccc56)cc4)cc3c3c2ccc2oc4ccccc4c23)cc1] | 92% |
| 350 | 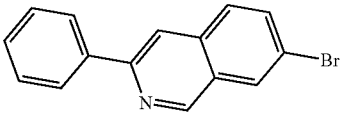 [SMILES: Brc1ccc2cc(-c3ccccc3)ncc2c1] | 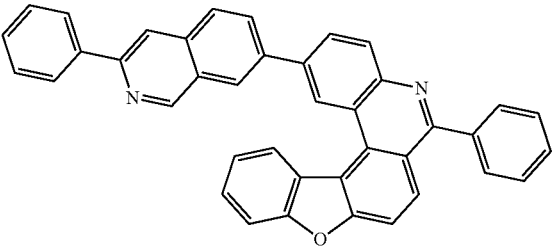 [SMILES: c1ccc(-c2cc3ccc(-c4ccc5nc(-c6ccccc6)c6ccc7oc8ccccc8c7c6c5c4)cc3cn2)cc1] | 93% |
| 358 | 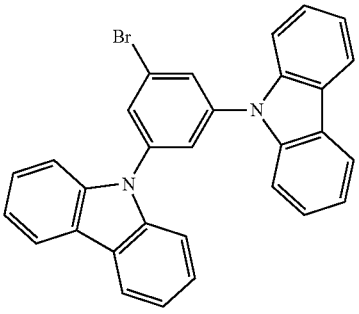 | 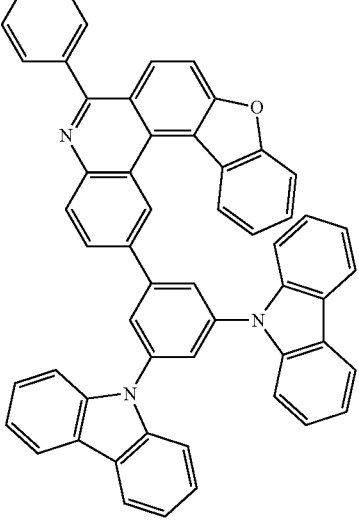 | 88% |

TABLE 3-continued

| Compound Number | Intermediate A | Compound P | Yield |
|---|---|---|---|
| 366 | | | 91% |
| 370 | | | 92% |
| 374 | | | 87% |

TABLE 3-continued

| Compound Number | Intermediate A | Compound P | Yield |
|---|---|---|---|
| 378 | | | 75% |
| 382 | | | 79% |
| 386 | | | 81% |

TABLE 3-continued

| Compound Number | Intermediate A | Compound P | Yield |
|---|---|---|---|
| 390 | | | 92% |
| 394 | | | 88% |
| 398 | | | 78% |

TABLE 3-continued

| Compound Number | Intermediate A | Compound P | Yield |
|---|---|---|---|
| 402 | | | 79% |
| 406 | | | 82% |

TABLE 3-continued

| Compound Number | Intermediate A | Compound P | Yield |
|---|---|---|---|
| 410 | | | 86% |
| 414 | | | 89% |
| 418 | | | 92% |

TABLE 3-continued
| Compound Number | Intermediate A | Compound P | Yield |
|---|---|---|---|
| 422 | 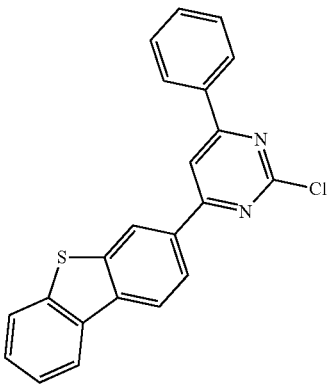 | 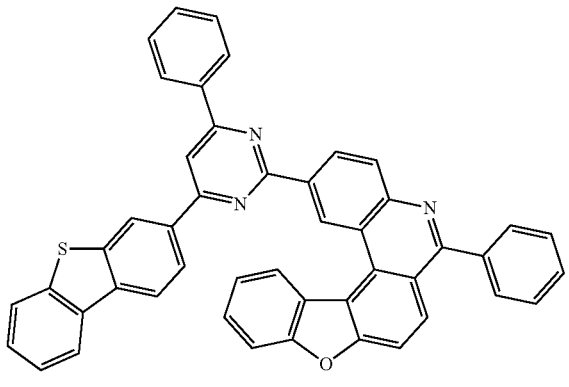 | 93% |
| 426 | 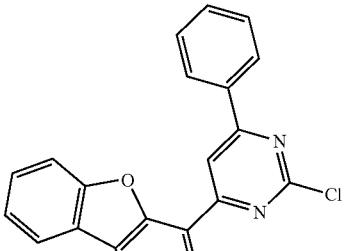 | 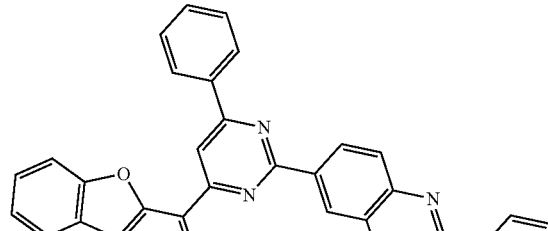 | 83% |

TABLE 3-continued

| Compound Number | Intermediate A | Compound P | Yield |
|---|---|---|---|
| 430 | | | 78% |
| 434 | | | 72% |
| 438 | | | 81% |

Compound P was synthesized in the same manner as in Preparation Example 1 except that dibenzo[b,d]thiophen-1-ylboronic acid was used instead of dibenzo[b,d]furan-1-ylboronic acid, and Intermediate A of the following Table 4 was used instead of 2-([1,1'-biphenyl]-4-yl)-4-(4-bromonaphthalen-1-yl)-6-phenyl-1,3,5-triazine.

TABLE 4

| Compound Number | Intermediate A | Compound P | Yield |
|---|---|---|---|
| 442 | | | 81% |
| 446 | | | 78% |
| 450 | | | 75% |

TABLE 4-continued

| Compound Number | Intermediate A | Compound P | Yield |
|---|---|---|---|
| 454 | | | 81% |
| 458 | | | 78% |
| 462 | | | 72% |

TABLE 4-continued
| Compound Number | Intermediate A | Compound P | Yield |
|---|---|---|---|
| 466 | 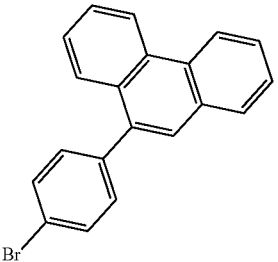 | 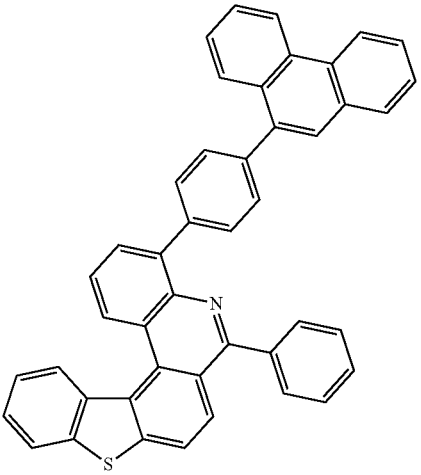 | 79% |
| 470 | 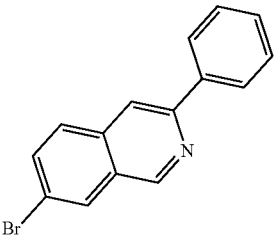 | 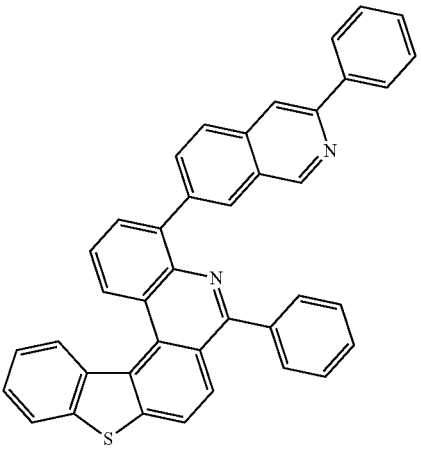 | 79% |
| 474 | 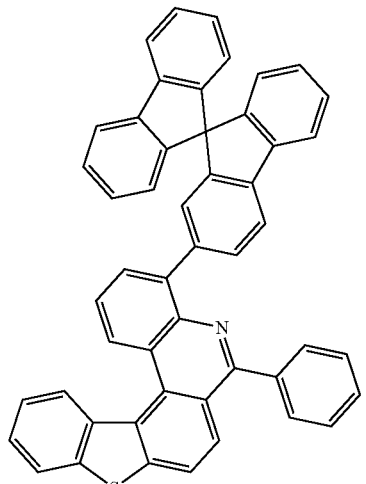 | 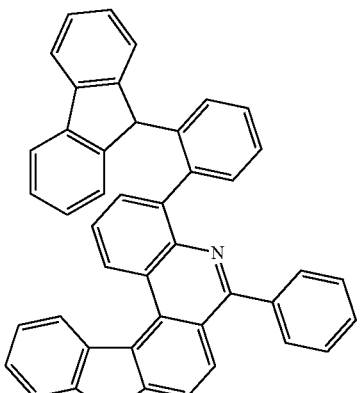 | 69% |

TABLE 4-continued
| Compound Number | Intermediate A | Compound P | Yield |
|---|---|---|---|
| 478 | 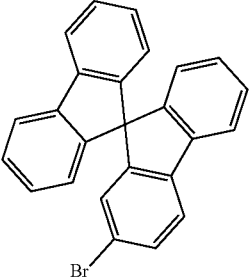 | 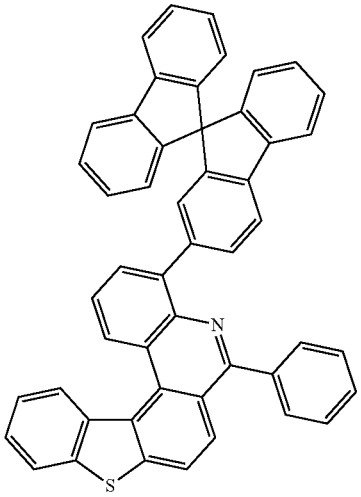 | 82% |
| 482 | 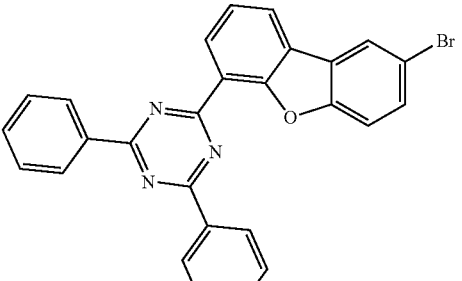 | 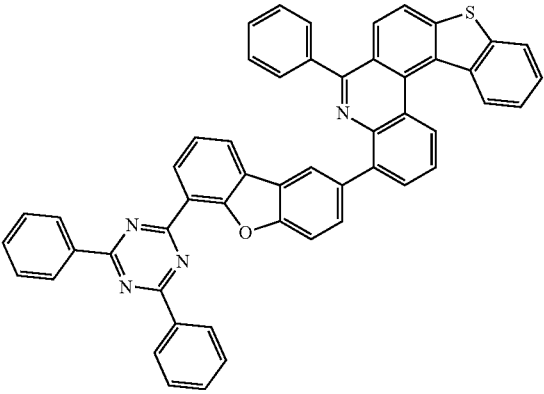 | 84% |
| 486 | 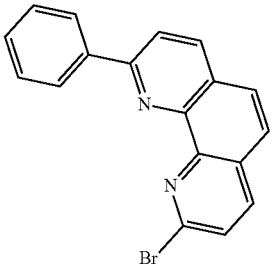 | 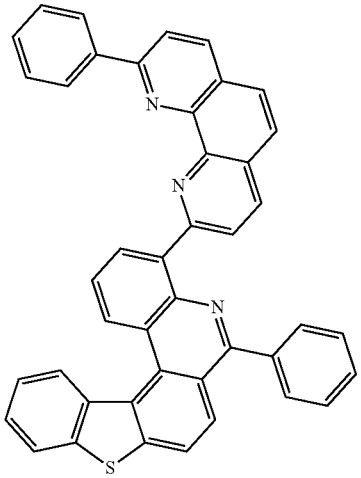 | 82% |

TABLE 4-continued

| Compound Number | Intermediate A | Compound P | Yield |
|---|---|---|---|
| 490 | | | 78% |
| 498 | | | 82% |
| 502 | | | 75% |

TABLE 4-continued

| Compound Number | Intermediate A | Compound P | Yield |
|---|---|---|---|
| 506 | | | 82% |
| 510 | | | 72% |

TABLE 4-continued
| Compound Number | Intermediate A | Compound P | Yield |
|---|---|---|---|
| 514 | 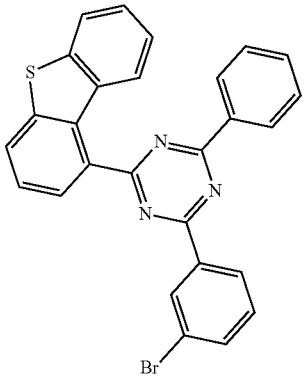 | 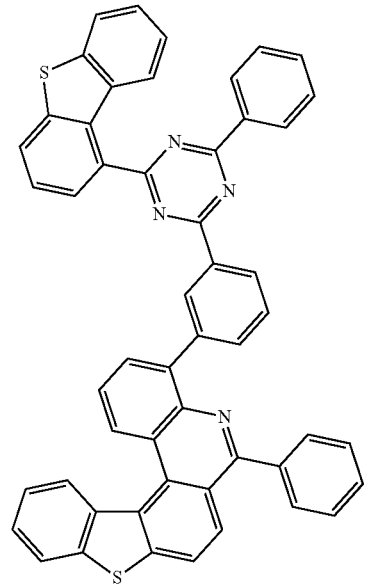 | 81% |
| 518 | 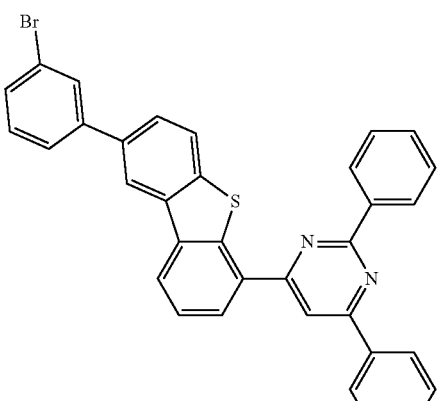 | 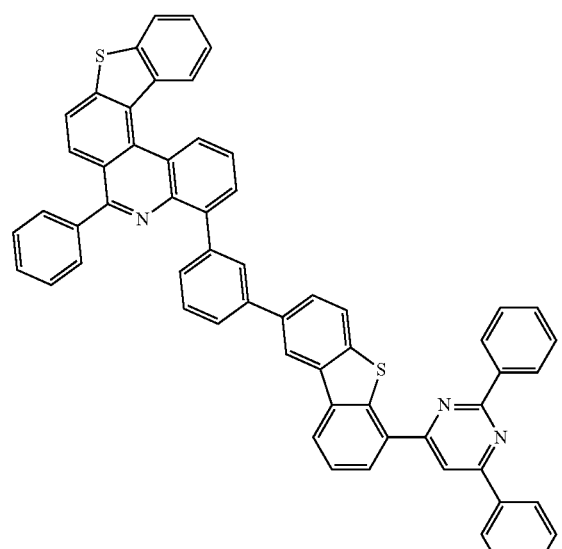 | 83% |

TABLE 4-continued

| Compound Number | Intermediate A | Compound P | Yield |
|---|---|---|---|
| 522 | | | 82% |
| 526 | | | 78% |
| 530 | | | 72% |

TABLE 4-continued

| Compound Number | Intermediate A | Compound P | Yield |
|---|---|---|---|
| 534 | | | 81% |
| 538 | | | 85% |
| 542 | | | 91% |

TABLE 4-continued
| Compound Number | Intermediate A | Compound P | Yield |
|---|---|---|---|
| 546 | 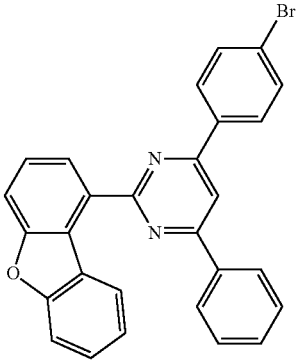 | 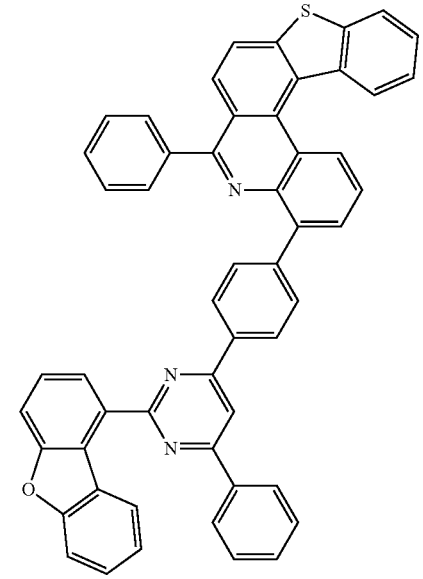 | 88% |
| 550 | 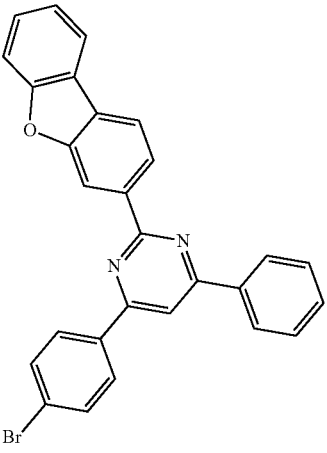 | 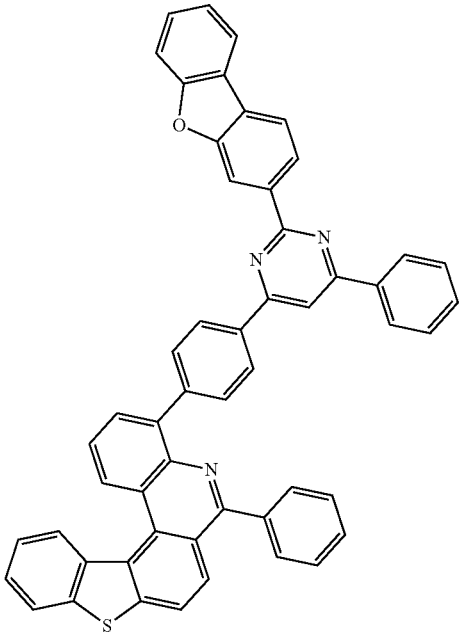 | 84% |

TABLE 4-continued

| Compound Number | Intermediate A | Compound P | Yield |
|---|---|---|---|
| 554 | | | 92% |
| 558 | | | 87% |

Compound P was synthesized in the same manner as in Preparation Example 2 except that 5-chloro-2-(dibenzo[b,d]thiophen-1-yl)aniline was obtained instead of Compound 122-4 using dibenzo[b,d]thiophen-1-ylboronic acid instead of dibenzo[b,d]furan-1-ylboronic acid, and Intermediate B of the following Table 5 was used instead of 2-chloro-4,6-diphenyl-1,3,5-triazine.

TABLE 5

| Compound Number | Intermediate B | Compound P | Yield |
|---|---|---|---|
| 562 | | | 82% |
| 566 | | | 81% |
| 570 | | | 78% |

TABLE 5-continued

| Compound Number | Intermediate B | Compound P | Yield |
|---|---|---|---|
| 574 | | | 78% |
| 578 | | | 72% |
| 582 | | | 71% |

TABLE 5-continued
| Compound Number | Intermediate B | Compound P | Yield |
|---|---|---|---|
| 586 | 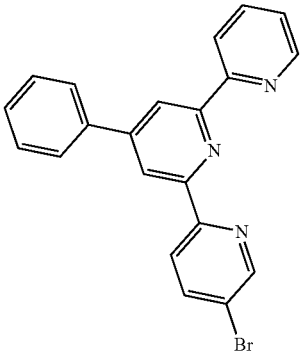 | 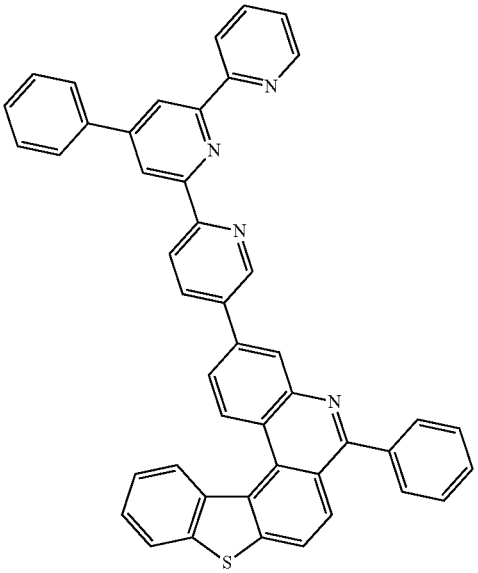 | 79% |
| 590 | 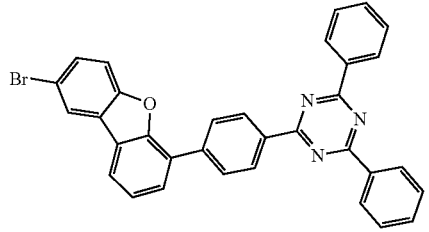 | 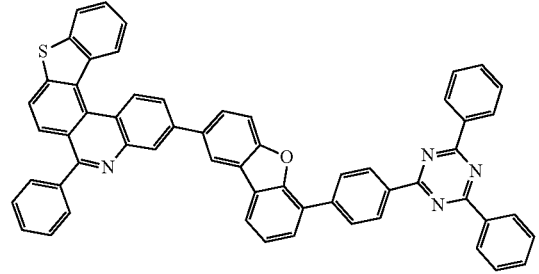 | 79% |
| 594 | 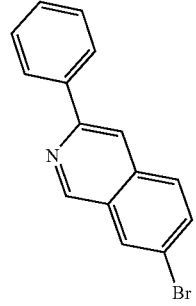 | 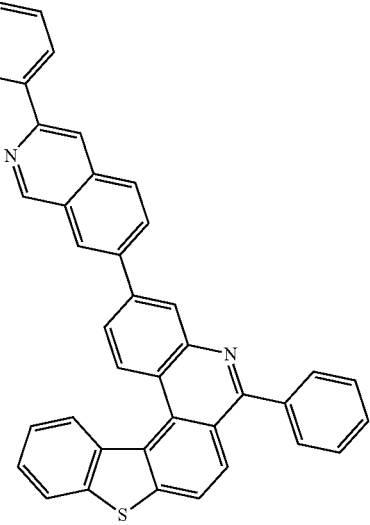 | 69% |

TABLE 5-continued
| Compound Number | Intermediate B | Compound P | Yield |
|---|---|---|---|
| 598 | 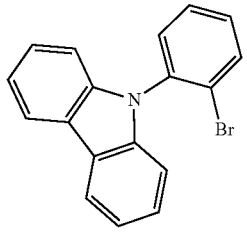 | 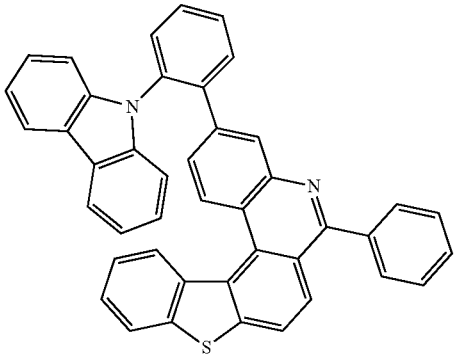 | 82% |
| 602 | 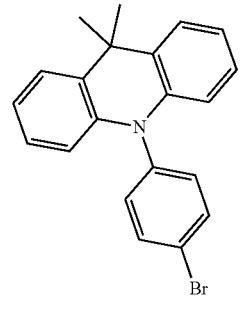 | 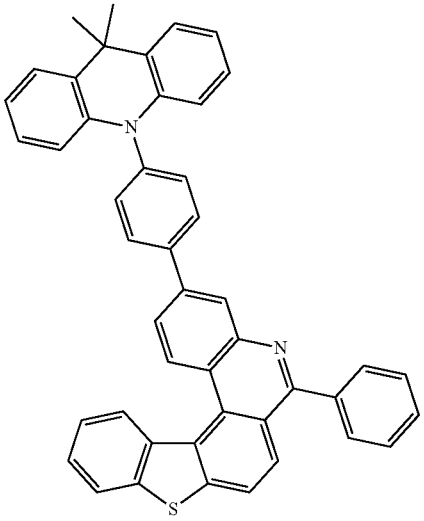 | 84% |
| 606 | 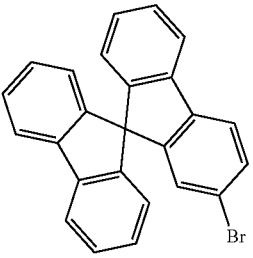 | 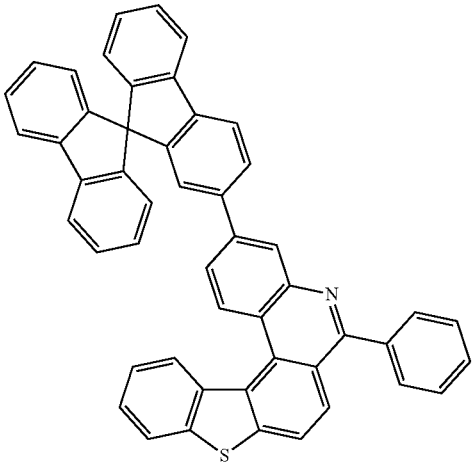 | 78% |

TABLE 5-continued

| Compound Number | Intermediate B | Compound P | Yield |
|---|---|---|---|
| 610 | | | 82% |
| 614 | | | 71% |
| 618 | | | 82% |

TABLE 5-continued

| Compound Number | Intermediate B | Compound P | Yield |
|---|---|---|---|
| 622 | | | 72% |
| 626 | | | 68% |
| 630 | | | 91% |

TABLE 5-continued

| Compound Number | Intermediate B | Compound P | Yield |
|---|---|---|---|
| 634 | | | 72% |
| 638 | | | 75% |
| 642 | | | 89% |
| 646 | | | 69% |

TABLE 5-continued
| Compound Number | Intermediate B | Compound P | Yield |
|---|---|---|---|
| 650 | 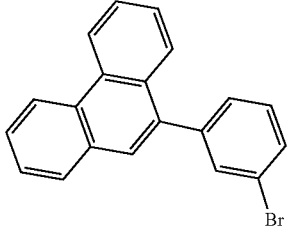 | 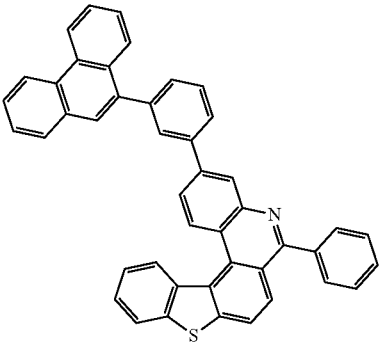 | 75% |
| 654 | 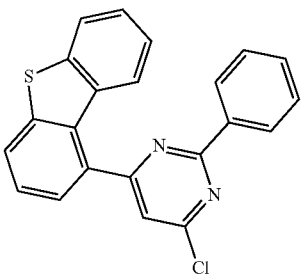 | 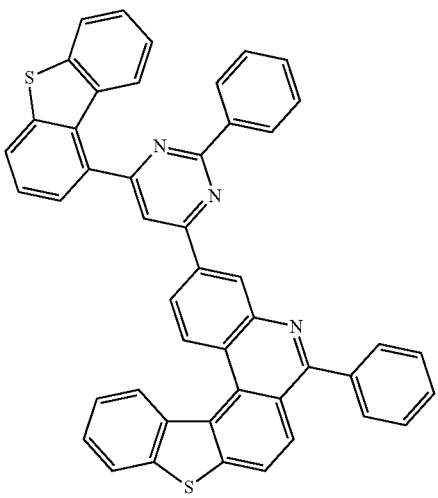 | 78% |
| 658 | 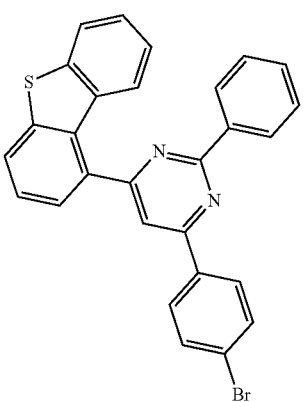 | 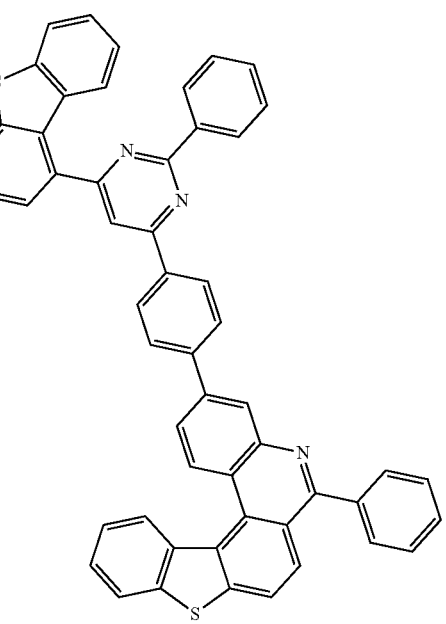 | 81% |

TABLE 5-continued

| Compound Number | Intermediate B | Compound P | Yield |
|---|---|---|---|
| 662 | | | 91% |
| 666 | | | 89% |
| 670 | | | 82% |

TABLE 5-continued

| Compound Number | Intermediate B | Compound P | Yield |
|---|---|---|---|
| 674 | | | 81% |
| 678 | | | 78% |
| 682 | | | 77% |

TABLE 5-continued

| Compound Number | Intermediate B | Compound P | Yield |
|---|---|---|---|
| 686 | | | 82% |
| 690 | | | 91% |
| 694 | | | 68% |

TABLE 5-continued

| Compound Number | Intermediate B | Compound P | Yield |
|---|---|---|---|
| 698 | | | 71% |

Compound P was obtained in the same manner as in Preparation Example 2 except that 4-chloro-2-(dibenzo[b,d]thiophen-1-yl) aniline was synthesized using dibenzo[b,d]thiophen-1-ylboronic acid instead of dibenzo [b,d]furan-1-ylboronic acid and 2-bromo-4-chloroaniline instead of 2-bromo-5-chloroaniline, and Intermediate A of the following Table 6 was used instead of 2-chloro-4,6-diphenyl-1,3,5-triazine.

TABLE 6

| Compound Number | Intermediate A | Compound P | Yield |
|---|---|---|---|
| 702 | | | 81% |
| 706 | | | 72% |

TABLE 6-continued

| Compound Number | Intermediate A | Compound P | Yield |
|---|---|---|---|
| 710 | | | 78% |
| 714 | | | 72% |
| 718 | | | 86% |
| 722 | | | 79% |

TABLE 6-continued

| Compound Number | Intermediate A | Compound P | Yield |
| --- | --- | --- | --- |
| 726 | | | 79% |
| 730 | | | 69% |
| 734 | | | 82% |
| 742 | | | 78% |

TABLE 6-continued

| Compound Number | Intermediate A | Compound P | Yield |
|---|---|---|---|
| 750 | | | 69% |
| 754 | | | 82% |
| 758 | | | 82% |

TABLE 6-continued

| Compound Number | Intermediate A | Compound P | Yield |
|---|---|---|---|
| 762 | | | 68% |
| 766 | | | 71% |
| 770 | | | 72% |

TABLE 6-continued
| Compound Number | Intermediate A | Compound P | Yield |
|---|---|---|---|
| 774 | 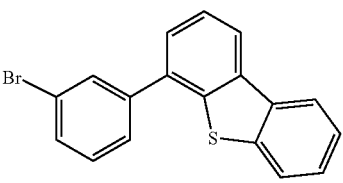 | 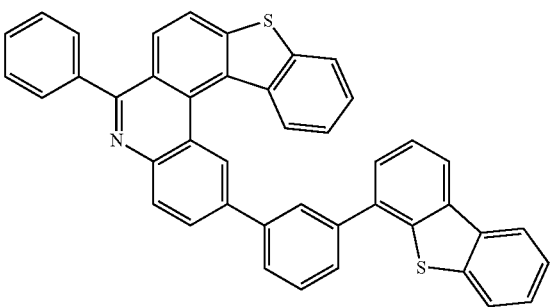 | 82% |
| 778 | 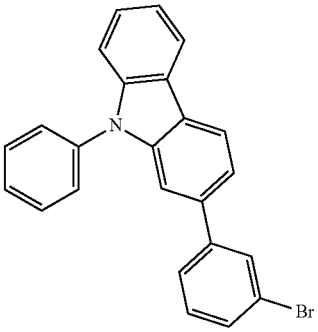 | 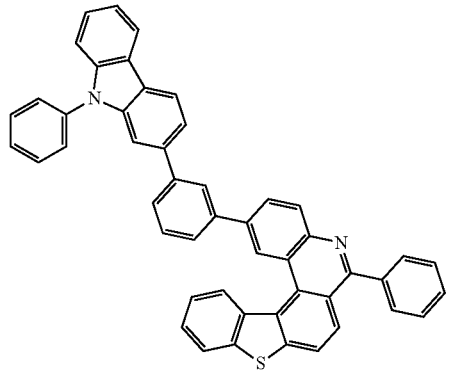 | 89% |
| 782 | 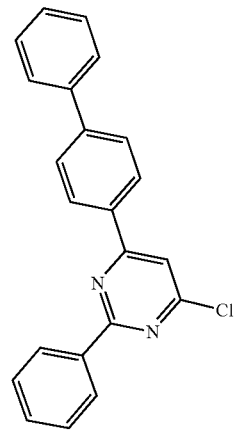 | 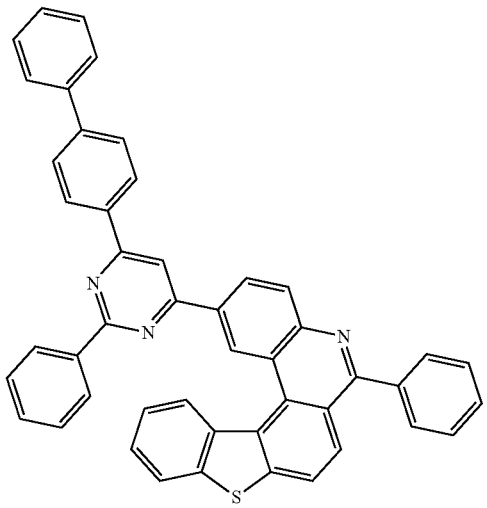 | 82% |

TABLE 6-continued
| Compound Number | Intermediate A | Compound P | Yield |
|---|---|---|---|
| 786 | 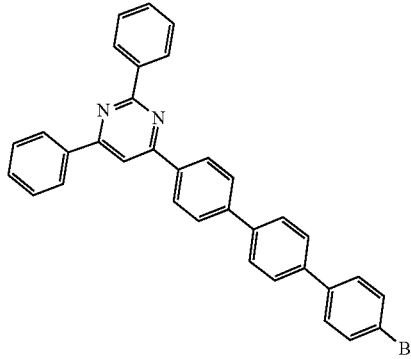 | 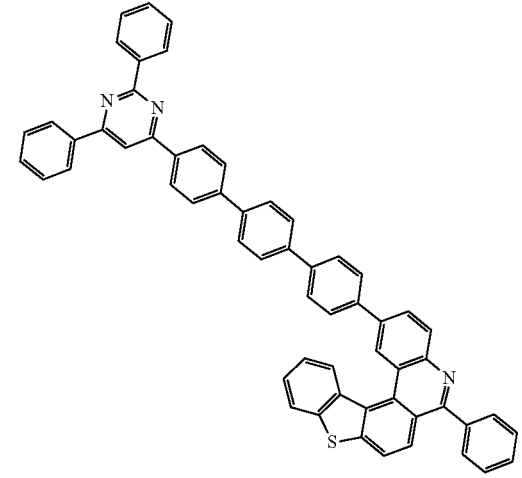 | 89% |
| 790 | 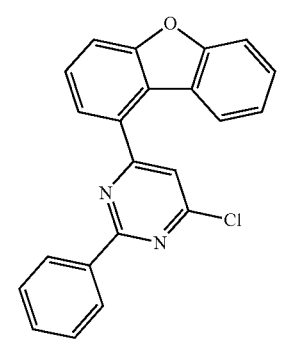 | 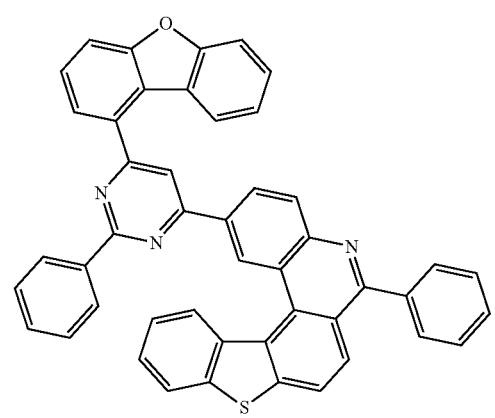 | 82% |
| 794 | 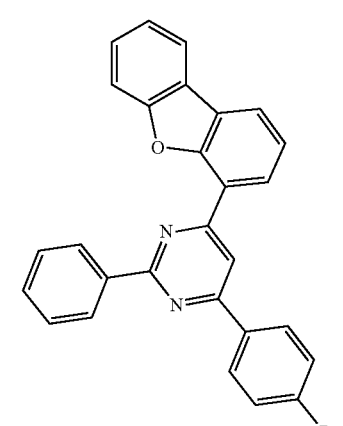 | 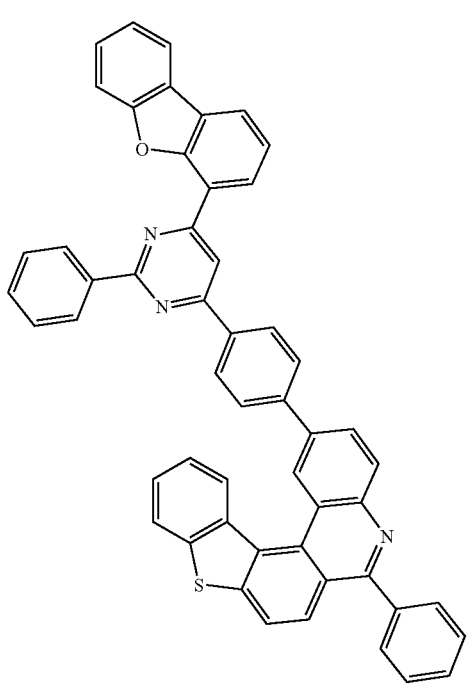 | 83% |

TABLE 6-continued

| Compound Number | Intermediate A | Compound P | Yield |
|---|---|---|---|
| 798 | | | 78% |
| 802 | | | 79% |
| 806 | | | 69% |

TABLE 6-continued

| Compound Number | Intermediate A | Compound P | Yield |
|---|---|---|---|
| 810 | | | 71% |
| 814 | | | 77% |
| 818 | | | 82% |

TABLE 6-continued

| Compound Number | Intermediate A | Compound P | Yield |
|---|---|---|---|
| 822 | | | 85% |
| 826 | | | 69% |
| 830 | | | 67% |

Compounds were prepared in the same manner as in the preparation examples, and the synthesis identification results are shown in the following Table 7.

TABLE 7

| Compound | FD-MS |
|---|---|
| 1 | m/z = 778.90 (C56H34N4O = 778.27) |
| 4 | m/z = 571.66 (C43H25NO = 571.19) |
| 8 | m/z = 521.61 (C39H23NO = 521.18) |
| 12 | m/z = 597.70 (C45H27NO = 597.21) |
| 15 | m/z = 628.76 (C46H32N2O = 628.25) |
| 18 | m/z = 599.68 (C43H25N3O = 599.20) |
| 21 | m/z = 725.83 (C53H31N3O = 725.25) |
| 25 | m/z = 736.86 (C55H32N2O = 736.25) |
| 28 | m/z = 702.80 (C51H30N2O2 = 702.23) |
| 32 | m/z = 676.76 (C48H28N4O = 676.23) |
| 35 | m/z = 652.74 (C46H28N4O = 652.23) |
| 38 | m/z = 742.82 (C52H30N4O2 = 742.24) |
| 41 | m/z = 742.82 (C52H30N4O2 = 742.24) |
| 44 | m/z = 732.85 (C50H28N4OS = 732.20) |
| 47 | m/z = 768.90 (C55H36N4O = 768.29) |
| 50 | m/z = 728.84 (C52H32N4O = 728.2) |
| 53 | m/z = 867.99 (C62H37N5O = 867.30) |
| 58 | m/z = 884.05 (C63H37N5O = 883.27) |
| 61 | m/z = 697.76 (C49H32NO2P = 697.22) |
| 63 | m/z = 597.70 (C45H27NO = 597.21) |
| 67 | m/z = 785.93 (C60H35NO = 785.27) |
| 73 | m/z = 651.75 (C47H29N3O = 651.23) |
| 76 | m/z = 665.74 (C47H27N3O2 = 665.21) |
| 78 | m/z = 741.83 (C53H31N3O2 = 741.24) |
| 81 | m/z = 665.74 (C47H27N3O2 = 665.21) |
| 83 | m/z = 681.80 (C47H27N3OS = 681.19) |
| 86 | m/z = 816.94 (C59H36N4O = 816.29) |
| 90 | m/z = 664.75 (C47H28N4O = 664.23) |
| 92 | m/z = 727.85 (C53H33N3O = 727.26) |
| 95 | m/z = 575.66 (C41H25N3O = 575.20) |
| 101 | m/z = 651.75 (C47H29N3O = 651.23) |
| 103 | m/z = 803.94 (C59H37N3O = 803.29) |
| 107 | m/z = 665.74 (C47H27N3O2 = 665.21) |
| 110 | m/z = 681.80 (C47H27N3OS = 681.19) |
| 113 | m/z = 741.83 (C53H31N3O2 = 741.24) |
| 115 | m/z = 816.94 (C59H36N4O = 816.29) |
| 122 | m/z = 576.64 (C40H24N4O = 576.20) |
| 124 | m/z = 728.84 (C52H32N4O = 728.26) |
| 126 | m/z = 652.74 (C46H28N4O = 652.23) |
| 130 | m/z = 666.72 (C46H26N4O2 = 666.21) |
| 135 | m/z = 742.82 (C52H30N4O2 = 742.24) |
| 138 | m/z = 817.93 (C58H35N5O = 817.28) |
| 142 | m/z = 692.80 (C49H32N4O = 692.26) |
| 144 | m/z = 804.93 (C58H36N4O = 804.29) |
| 147 | m/z = 521.61 (C39H23NO = 521.18) |
| 149 | m/z = 571.66 (C43H25NO = 571.19) |
| 152 | m/z = 649.78 (C49H31NO = 649.24) |
| 155 | m/z = 548.63 (C40H24N2O = 548.19) |
| 161 | m/z = 573.68 (C43H27NO = 573.21) |
| 164 | m/z = 603.73 (C43H25NOS = 603.17) |
| 168 | m/z = 752.90 (C56H36N2O = 752.28) |
| 172 | m/z = 652.74 (C46H28N4O = 652.23) |
| 174 | m/z = 634.72 (C47H26N2O = 634.20) |
| 178 | m/z = 751.87 (C55H33N3O = 751.26) |
| 181 | m/z = 758.89 (C52H30N4OS = 758.21) |
| 186 | m/z = 742.82 (C52H30N4O2 = 742.24) |
| 190 | m/z = 742.82 (C52H30N4O2 = 742.24) |
| 194 | m/z = 732.85 (C50H28N4OS = 732.20) |
| 198 | m/z = 690.75 (C47H26N6O = 690.22) |
| 201 | m/z = 618.74 (C43H26N2OS = 618.18) |
| 202 | m/z = 660.76 (C49H28N2O = 660.22) |
| 206 | m/z = 741.83 (C53H31N3O2 = 741.24) |
| 210 | m/z = 712.83 (C53H32N2 = 712.25) |
| 214 | m/z = 649.78 (C49H31NO = 649.24) |
| 218 | m/z = 727.85 (C53H33N3O = 727.26) |
| 221 | m/z = 665.74 (C47H27N3O2 = 665.21) |
| 222 | m/z = 665.74 (C47H27N3O2 = 665.21) |
| 226 | m/z = 741.83 (C53H31N3O2 = 741.24) |
| 230 | m/z = 816.94 (C59H36N4O = 816.29) |
| 234 | m/z = 740.85 (C53H32N4O = 740.26) |
| 238 | m/z = 651.75 (C47H29N3O = 651.23) |
| 241 | m/z = 727.85 (C53H33N3O = 727.26) |
| 242 | m/z = 727.85 (C53H33N3O = 727.26) |
| 246 | m/z = 665.74 (C47H27N3O2 = 665.21) |
| 250 | m/z = 741.83 (C53H31N3O2 = 741.24) |
| 254 | m/z = 816.94 (C59H36N4O = 816.29) |
| 258 | m/z = 740.85 (C53H32N4O = 740.26) |
| 261 | m/z = 651.75 (C47H29N3O = 651.23) |
| 262 | m/z = 665.74 (C47H27N3O2 = 665.21) |
| 266 | m/z = 681.80 (C47H27N3OS = 681.19) |
| 270 | m/z = 791.89 (C57H33N3O2 = 791.26) |
| 274 | m/z = 816.94 (C59H36N4O = 816.29) |
| 278 | m/z = 691.82 (C50H33N3O = 691.26) |
| 280 | m/z = 652.74 (C46H28N4O = 652.23) |
| 282 | m/z = 728.84 (C52H32N4O = 728.26) |
| 286 | m/z = 728.84 (C52H32N4O = 728.26) |
| 290 | m/z = 666.72 (C46H26N4O2 = 666.21) |
| 294 | m/z = 742.82 (C52H30N4O2 = 742.24) |
| 298 | m/z = 741.84 (C52H31N5O = 741.25) |
| 301 | m/z = 778.90 (C56H34N4O = 778.27) |
| 302 | m/z = 728.84 (C52H32N4O = 728.26) |
| 306 | m/z = 741.84 (C52H31N5O = 741.25) |
| 310 | m/z = 521.61 (C39H23NO = 521.18) |
| 314 | m/z = 597.70 (C45H27NO = 597.21) |
| 318 | m/z = 548.63 (C40H24N2O = 548.19) |
| 321 | m/z = 527.63 (C37H21NOS = 527.13) |
| 322 | m/z = 552.66 (C40H28N2O = 552.22) |
| 326 | m/z = 663.76 (C49H29NO2 = 663.22) |
| 330 | m/z = 662.78 (C49H30N2O = 662.24) |
| 334 | m/z = 652.74 (C46H28N4O = 652.23) |
| 338 | m/z = 549.62 (C39H23N3O = 549.18) |
| 341 | m/z = 571.66 (C43H25NO = 571.19) |
| 342 | m/z = 521.61 (C39H23NO = 521.18) |
| 346 | m/z = 597.70 (C45H27NO = 597.21) |
| 350 | m/z = 548.63 (C40H24N2O = 548.19) |
| 354 | m/z = 676.80 (C50H32N2O = 676.25) |
| 358 | m/z = 751.87 (C55H33N3O = 751.26) |
| 361 | m/z = 602.68 (C43H26N2O2 = 602.20) |
| 362 | m/z = 742.88 (C53H30N2OS = 742.21) |
| 366 | m/z = 728.84 (C52H32N4O = 728.26) |
| 370 | m/z = 742.82 (C52H30N4O2 = 742.24) |
| 374 | m/z = 742.82 (C52H30N4O2 = 742.24) |
| 378 | m/z = 867.99 (C62H37N5O = 867.30) |
| 381 | m/z = 628.76 (C46H32N2O = 628.25) |
| 382 | m/z = 602.68 (C43H26N2O2 = 602.20) |
| 386 | m/z = 675.77 (C49H29N3O = 675.23) |
| 390 | m/z = 713.82 (C53H31NO2 = 713.24) |
| 394 | m/z = 662.78 (C49H30N2O = 662.24) |
| 398 | m/z = 649.78 (C49H31NO = 649.24) |
| 401 | m/z = 727.85 (C53H33N3O = 727.26) |
| 402 | m/z = 727.85 (C53H33N3O = 727.26) |
| 406 | m/z = 665.74 (C47H27N3O2 = 665.21) |
| 410 | m/z = 741.83 (C53H31N3O2 = 741.24) |
| 414 | m/z = 816.94 (C59H36N4O = 816.29) |
| 418 | m/z = 664.75 (C47H28N4O = 664.23) |
| 421 | m/z = 803.94 (C59H37N3O = 803.29) |
| 422 | m/z = 681.80 (C47H27N3OS = 681.19) |
| 426 | m/z = 665.74 (C47H27N3O2 = 665.21) |
| 430 | m/z = 741.83 (C53H31N3O2 = 741.24) |
| 434 | m/z = 757.90 (C53H31N3OS = 757.22) |
| 438 | m/z = 664.75 (C47H28N4O = 664.23) |
| 441 | m/z = 744.90 (C52H32N4S = 744.23) |
| 442 | m/z = 682.79 (C46H26N4OS = 682.18) |
| 446 | m/z = 682.79 (C46H26N4OS = 682.18) |
| 450 | m/z = 757.90 (C52H31N5S = 757.23) |
| 454 | m/z = 784.97 (C55H36N4S = 784.27) |
| 458 | m/z = 758.89 (C52H30N4OS = 758.21) |
| 461 | m/z = 587.73 (C43H25NS = 587.17) |
| 462 | m/z = 537.67 (C39H23NS = 537.16) |
| 466 | m/z = 613.77 (C45H27NS = 613.19) |
| 470 | m/z = 564.70 (C40H24N2S = 564.17) |
| 474 | m/z = 602.74 (C43H26N2S = 602.18) |
| 478 | m/z = 675.84 (C50H29NS = 675.20) |
| 480 | m/z = 644.82 (C46H32N2S = 644.23) |
| 481 | m/z = 543.70 (C37H21NS2 = 543.11) |
| 482 | m/z = 543.70 (C37H21NS2 = 543.11) |
| 486 | m/z = 758.89 (C52H30N4OS = 758.21) |
| 490 | m/z = 615.74 (C43H25N3S = 615.18) |
| 494 | m/z = 845.02 (C60H36N4S = 844.27) |
| 498 | m/z = 758.89 (C52H30N4OS = 758.21) |
| 501 | m/z = 758.89 (C52H30N4OS = 758.21) |

TABLE 7-continued

| Compound | FD-MS |
|---|---|
| 502 | m/z = 884.06 (C62H37N5S = 883.28) |
| 506 | m/z = 821.00 (C58H36N4S = 820.27) |
| 510 | m/z = 744.90 (C52H32N4S = 744.23) |
| 514 | m/z = 774.95 (C52H30N4S2 = 774.19) |
| 518 | m/z = 850.06 (C59H35N3S2 = 849.23) |
| 521 | m/z = 697.87 (C47H27N3S = 697.16) |
| 522 | m/z = 756.91 (C53H32N4S = 756.23) |
| 526 | m/z = 743.91 (C53H33N3S = 743.24) |
| 530 | m/z = 743.91 (C53H33N3S = 743.24) |
| 534 | m/z = 833.01 (C59H36N4S = 832.27) |
| 538 | m/z = 681.80 (C47H27N3OS = 681.19) |
| 541 | m/z = 870.07 (C63H39N3S = 869.29) |
| 542 | m/z = 591.72 (C41H25N3S = 591.18) |
| 546 | m/z = 757.90 (C53H31N3OS = 757.22) |
| 550 | m/z = 757.90 (C53H31N3OS = 757.22) |
| 554 | m/z = 668.81 (C46H28N4S = 668.20) |
| 558 | m/z = 773.96 (C53H31N3S2 = 773.20) |
| 561 | m/z = 682.79 (C46H26N4OS = 682.18) |
| 562 | m/z = 682.79 (C46H26N4OS = 682.18) |
| 566 | m/z = 758.89 (C52H30N4OS = 758.21) |
| 570 | m/z = 774.95 (C52H30N4S2 = 774.19) |
| 574 | m/z = 681.81 (C46H27N5S = 681.20) |
| 578 | m/z = 587.73 (C43H25NS = 587.17) |
| 581 | m/z = 589.75 (C43H27NS = 589.19) |
| 582 | m/z = 543.70 (C37H21NS2 = 543.11) |
| 586 | m/z = 668.81 (C46H28N4S = 668.20) |
| 590 | m/z = 834.98 (C58H34N4S2 = 834.25) |
| 594 | m/z = 564.70 (C40H24N2S = 564.17) |
| 598 | m/z = 602.74 (C43H26N2S = 602.18) |
| 601 | m/z = 568.73 (C40H28N2S = 568.20) |
| 602 | m/z = 644.82 (C46H32N2S = 644.23) |
| 606 | m/z = 675.84 (C50H29NS = 675.20) |
| 610 | m/z = 869.04 (C62H36N4S = 868.27) |
| 614 | m/z = 884.06 (C62H37N5S = 883.28) |
| 618 | m/z = 834.00 (C58H35N5S = 833.26) |
| 621 | m/z = 744.90 (C52H32N4S = 744.23) |
| 622 | m/z = 821.00 (C58H36N4S = 820.27) |
| 626 | m/z = 758.89 (C52H30N4OS = 758.21) |
| 630 | m/z = 901.11 (C62H36N4S2 = 900.24) |
| 634 | m/z = 758.89 (C52H30N4OS = 758.21) |
| 638 | m/z = 678.84 (C49H30N2S = 678.21) |
| 641 | m/z = 644.82 (C46H32N2S = 644.23) |
| 642 | m/z = 618.74 (C43H26N2OS = 618.18) |
| 646 | m/z = 691.84 (C49H29N3S = 691.21) |
| 650 | m/z = 613.77 (C45H27NS = 613.19) |
| 654 | m/z = 697.87 (C47H27N3S2 = 697.16) |
| 658 | m/z = 773.96 (C53H31N3S2 = 773.20) |
| 661 | m/z = 591.72 (C41H25N3S = 591.18) |
| 662 | m/z = 667.82 (C47H29N3S = 667.21) |
| 666 | m/z = 743.91 (C53H33N3S = 743.24) |
| 670 | m/z = 681.80 (C47H27N3OS = 681.19) |
| 674 | m/z = 681.80 (C47H27N3OS = 681.19) |
| 678 | m/z = 756.91 (C53H32N4S = 756.23) |
| 681 | m/z = 820.01 (C59H37N3S = 819.27) |
| 682 | m/z = 667.82 (C47H29N3S = 667.21) |
| 686 | m/z = 681.80 (C47H27N3OS = 681.19) |
| 670 | m/z = 757.90 (C53H31N3OS = 757.22) |
| 674 | m/z = 743.91 (C53H33N3S = 743.24) |
| 678 | m/z = 783.98 (C56H37N3S = 783.27) |
| 681 | m/z = 820.01 (C59H37N3S = 819.27) |
| 682 | m/z = 667.82 (C47H29N3S = 667.21) |
| 686 | m/z = 681.80 (C47H27N3OS = 681.19) |
| 690 | m/z = 757.90 (C53H31N3OS = 757.22) |
| 694 | m/z = 743.91 (C53H33N3S = 743.24) |
| 698 | m/z = 783.98 (C56H37N3S = 783.27) |
| 701 | m/z = 592.71 (C40H24N4S = 592.17) |
| 702 | m/z = 668.81 (C46H28N4S = 668.20) |
| 706 | m/z = 682.79 (C46H26N4OS = 682.18) |
| 710 | m/z = 758.89 (C52H30N4OS = 758.21) |
| 714 | m/z = 834.00 (C58H35N5S = 833.26) |
| 718 | m/z = 681.81 (C46H27N5S = 681.20) |
| 721 | m/z = 613.77 (C45H27NS = 613.19) |
| 722 | m/z = 665.84 (C49H31NS = 665.22) |
| 726 | m/z = 539.65 (C37H21N3S = 539.15) |
| 730 | m/z = 564.70 (C40H24N2S = 564.17) |
| 734 | m/z = 678.84 (C49H30N2S = 678.21) |
| 738 | m/z = 692.87 (C50H32N2S = 692.23) |
| 741 | m/z = 676.83 (C49H28N2S = 676.20) |
| 742 | m/z = 768.92 (C54H32N4S = 768.23) |
| 746 | m/z = 758.89 (C52H30N4OS = 758.21) |
| 750 | m/z = 748.91 (C50H28N4S2 = 748.18) |
| 754 | m/z = 758.89 (C52H30N4OS = 758.21) |
| 758 | m/z = 834.00 (C58H35N5S = 833.26) |
| 761 | m/z = 706.81 (C47H26N6S = 706.19) |
| 762 | m/z = 644.82 (C46H32N2S = 644.23) |
| 766 | m/z = 757.90 (C53H31N3OS = 757.22) |
| 770 | m/z = 678.84 (C49H30N2S = 678.21) |
| 774 | m/z = 619.80 (C43H25NS2 = 619.14) |
| 778 | m/z = 678.84 (C49H30N2S = 678.21) |
| 781 | m/z = 591.72 (C41H25N3S = 591.18) |
| 782 | m/z = 667.82 (C47H29N3S = 667.21) |
| 786 | m/z = 820.01 (C59H37N3S = 819.27) |
| 790 | m/z = 681.80 (C47H27N3OS = 681.19) |
| 794 | m/z = 757.90 (C53H31N3OS = 757.22) |
| 798 | m/z = 833.01 (C59H36N4S = 832.27) |
| 801 | m/z = 667.82 (C47H29N3S = 667.21) |
| 802 | m/z = 667.82 (C47H29N3S = 667.21) |
| 806 | m/z = 681.80 (C47H27N3OS = 681.19) |
| 810 | m/z = 668.81 (C46H28N4S = 668.20) |
| 814 | m/z = 743.91 (C53H33N3S = 743.24) |
| 818 | m/z = 743.91 (C53H33N3S = 743.24) |
| 821 | m/z = 757.90 (C53H31N3OS = 757.22) |
| 823 | m/z = 833.01 (C59H36N4S = 832.27) |
| 826 | m/z = 707.88 (C50H33N3S = 707.24) |
| 828 | m/z = 757.90 (C53H31N3OS = 757.22) |
| 830 | m/z = 783.98 (C56H37N3S = 783.27) |
| 831 | m/z = 756.91 (C53H32N4S = 756.23) |

TABLE 8

| NO | $^1$H NMR (CDCl$_3$, 300 Mz) |
|---|---|
| 1 | δ = 8.55(t, 2H), 8.30~8.21(m, 5H), 8.02~8.01(m, 3H), 7.85~7.90(m, 4H), 7.66(m, 2H), 7.54~7.25(m, 18H) |
| 4 | δ = 9.15(s, 1H), 8.93(t, 2H), 8.30~8.02(m, 8H), 7.92~7.82(m, 6H), 7.66(m, 2H), 7.54-7.32(m, 6H) |
| 8 | δ = 8.93(m, 2H), 8.30(m, 2H), 8.21(m, 1H), 8.12(m, 2H), 8.02(t, 1H), 7.93~7.82(m, 7H), 7.66(m, 2H), 7.54~7.32(m, 6H) |
| 12 | δ = 8.93(t, 2H), 8.30(t, 2H), 8.21(d, 2H), 8.12(t, 2H), 8.02(d, 1H), 7.92~7.82(m, 7H), 7.66(m, 2H), 7.54~7.25(m, 10H) |
| 15 | δ = 8.30(t, 2H), 8.21(d, 1H), 8.02(d, 1H), 7.92~7.89(m, 2H), 7.66(m, 2H), 7.54~7.32(m, 8H), 7.05~7.02(m, 4H), 6.73~6.69(m, 4H), 6.55(m, 2H), 1.72(s, 2H) |
| 18 | δ = 8.88(m, 1H), 8.30(m, 4H), 8.10~8.06(m, 4H), 7.89~7.92(m, 2H), 7.81(m, 1H), 7.69-7.66(m, 2H), 7.54~7.32(m, 11H) |
| 21 | δ = 8.55(m, 3H), 8.30(m, 4H), 8.21(d, 1H), 8.10~8.02(m, 5H), 7.92~7.89(m, 2H), 7.81(m, 1H), 7.66(m, 2H), 7.55~7.32(m, 13H) |
| 25 | δ = 9.66(d, 1H), 8.93(t, 2H), 8.55(t, 2H), 8.21~8.12(m, 5H), 7.89~7.79(m, 9H), 7.68~7.51(m, 8H), 7.38~7.29(m, 5H) |

TABLE 8-continued

| NO | ¹H NMR (CDCl₃, 300 Mz) |
|---|---|
| 28 | δ = 8.33(d, 1H), 8.21(d, 1H), 8.02(m, 1H), 7.91~7.89(m, 6H), 7.66(m, 2H), 7.54~7.50(m, 3H), 7.39~7.32(m, 6H), 6.92~6.89(m, 4H), 6.79~6.69(m, 4H), 6.59(m, 2H) |
| 32 | δ = 8.49(t, 2H), 8.30(t, 2H), 8.21(d, 1H), 8.02~7.89(m, 9H), 7.66~7.32(m, 12H) |
| 35 | δ = 8.30~8.21(m, 8H), 8.02(d, 1H), 7.92~7.89(m, 2H), 7.66~7.32(m, 17H) |
| 38 | δ = 8.30~8.21(m, 6H), 8.02(d, 1H), 7.92~7.81(m, 5H), 7.70~7.32(m, 18H), |
| 41 | δ = 8.30(m, 2H), 8.21(d, 1H), 8.02(d, 1H), 7.92~7.85(m, 5H), 7.75(m, 1H), 7.66~7.32(m, 20H) |
| 44 | δ = 9.09(d, 1H), 8.49~8.45(t, 2H), 8.30(t, 2H), 8.21(m, 1H), 8.02~7.92(m, 9H), 7.66~7.32(m, 13H) |
| 47 | δ = 8.30~8.21(m, 7H), 8.02(d, 1H), 7.92~7.85(m, 4H), 7.66~7.25(m, 20H) |
| 50 | δ = 8.30~8.21(m, 8H), 8.02(d, 1H), 7.92~7.89(m, 2H), 7.66~7.32(m, 21H) |
| 53 | δ = 8.55(d, 1H), 8.30~8.21(m, 4H), 8.00~7.89(m, 8H), 7.59~7.25(m, 24H) |
| 58 | δ = 8.55(m, 1H), 8.41(d, 1H), 8.30~8.20(m, 7H), 8.11~8.02(m, 4H), 7.89~7.76(m, 7H), 7.54~7.32(m, 17H) |
| 61 | δ = 8.30(t, 2H), 8.21(d, 1H), 8.02(d, 1H), 7.79~7.32(m, 28H) |
| 63 | δ = 8.93(t, 3H), 8.30(t, 2H), 8.21(m, 1H), 8.12~7.54(m, 2H), 8.02(d, 1H), 7.93~7.82(m, 7H), 7.57~7.38(m, 12H) |
| 67 | δ = 8.40(t, 2H), 8.30(t, 2H), 8.21(m, 1H), 8.00~7.75(m, 9H), 7.54~7.16(m, 21H) |
| 73 | δ = 8.30~8.21(m, 8H), 8.02(d, 1H), 7.92~7.89(m, 2H), 7.79(m, 2H), 7.66(m, 2H), 7.54~7.32(m, 14H) |
| 76 | δ = 8.37~8.28(m, 6H), 8.02(d, 1H), 7.92~7.85(m, 4H), 7.66~7.32(m, 16H) |
| 78 | δ = 8.30~8.21(m, 8H), 8.02(d, 1H), 7.92~7.85(m, 4H), 7.66~7.32(m, 18H) |
| 81 | δ = 8.37~8.28(m, 6H), 8.02~7.89(m, 5H), 7.66~7.75(m, 5H), 7.54~7.32(m, 11H) |
| 83 | δ = 8.45(d, 1H), 8.37~8.28(m, 6H), 8.02~7.82(m, 6H), 7.66(t, 2H), 7.54~7.32(m, 12H) |
| 86 | δ = 8.55(d, 1H), 8.30~8.21(m, 8H), 8.02(d, 1H), 7.94~7.87(m, 4H), 7.66~7.25(m, 21H) |
| 90 | δ = 8.55(d, 1H), 8.37~8.28(m, 5H), 8.12(d, 1H), 8.02(m, 1H), 7.94~7.89(m, 3H), 7.66~7.32(m, 17H) |
| 92 | δ = 8.30~8.23(m, 8H), 8.02(d, 1H), 7.92~7.79(m, 6H), 7.66(m, 2H), 7.51~7.25(m, 16H) |
| 95 | δ = 8.30(m, 2H), 8.23~8.21(m, 2H), 8.02(m, 1H), 7.92~7.89(m, 2H), 7.79(m, 3H), 7.66(m, 2H), 7.54~7.32(m, 12H) |
| 101 | δ = 8.30~8.21(m, 8H), 8.02(d, 1H), 7.92~7.89(m, 2H), 7.79(t, 2H), 7.66(m, 2H), 7.54~7.32(m, 14H) |
| 103 | δ = 8.30~8.21(m, 5H), 8.02(d, 1H), 7.92~7.89(m, 2H), 7.79~7.25(m, 28H) |
| 107 | δ = 8.30(m, 2H), 8.02~7.89(m, 5H), 7.79~7.66(m, 7H), 7.51~7.32(m, 11H) |
| 110 | δ = 8.45(d, 1H), 8.30(m, 2H), 8.23~8.21(m, 2H), 7.98~7.79(m, 8H), 7.66(m, 2H), 7.52~7.32(m, 12H) |
| 113 | δ = 8.30~8.21(m, 6H), 8.02~7.89(m, 5H), 7.75~7.64(m, 7H), 7.54~7.32(m, 13H) |
| 115 | δ = 8.55(d, 1H), 8.30~8.23(m, 6H), 8.02(d, 1H), 7.94~7.87(m, 4H), 7.79~7.77(m, 3H), 7.69~7.32(m, 21H) |
| 122 | δ = 8.30~8.28(m, 7H), 8.12(d, 1H), 8.30(d, 1H), 7.92~7.89(m, 2H), 7.66(m, 1H), 7.54~7.32(m, 12H) |
| 124 | δ = 8.30~8.27(m, 3H), 8.12(d, 1H), 8.03(d, 1H), 7.92~7.85(m, 6H), 7.66(d, 1H), 7.52~7.25(m, 20H) |
| 126 | δ = 8.30~8.24(m, 6H), 8.12(d, 1H), 8.03(d, 1H), 7.92~7.89(m, 2H), 7.70~7.66(m, 2H), 7.54~7.32(m, 16H) |
| 130 | δ = 8.30~8.27(m, 5H), 8.12(d, 1H), 8.03(d, 1H), 7.92~7.81(m, 5H), 7.66(m, 2H), 7.54~7.32(m, 12H) |
| 135 | δ = 8.30~8.27(m, 5H), 8.12(d, 1H), 8.03(d, 1H), 7.95~7.85(m, 5H), 7.75(d, 1H), 7.66~7.64(m, 3H), 7.54~7.25(m, 13H) |
| 138 | δ = 8.55(d, 1H), 8.30~8.27(m, 5H), 8.12(d, 1H), 8.03(m, 1H), 7.94~7.85(m, 6H), 7.77(d, 1H), 7.69~7.33(m, 20H) |
| 142 | δ = 8.30~8.28(m, 5H), 8.12(m, 1H), 8.06~8.03(m, 2H), 7.92~7.87(m, 3H), 7.54~7.28(m, 25H) |
| 144 | δ = 8.30~8.28(m, 7H), 8.12(d, 1H), 8.03(d, 1H), 7.92~7.85(m, 4H), 7.66(m, 1H), 7.54~7.25(m, 22H) |
| 147 | δ = 9.15(d, 1H), 8.93(d, 1H), 8.30~8.27(m, 5H), 8.18~8.03(m, 5H), 7.89~7.82(m, 4H), 7.71~7.66(m, 3H), 7.54~7.32(m, 6H) |
| 149 | δ = 9.15(d, 1H), 8.93(m, 2H), 8.30~8.27(m, 3H), 8.18~8.03(m, 6H), 7.92~7.82(m, 6H), 7.66(d, 1H), 7.54~7.32(m, 6H) |
| 152 | δ = 8.30~8.27(m, 3H), 8.12(d, 1H), 7.03(d, 1H), 7.92~7.89(m, 2H), 7.66(m, 4H), 7.54~7.32(m, 20H) |
| 155 | δ = 8.88(d, 1H), 8.30~8.27(m, 5H), 8.12~8.03(m, 3H), 7.89~7.82(m, 4H), 7.66(m, 2H), 7.54~7.32(m, 9H) |
| 161 | δ = 8.30~8.27(m, 3H), 8.12(d, 1H), 8.03(d, 1H), 7.92~7.89(m, 2H), 7.66(m, 4H), 7.54~7.41(m, 16H) |
| 164 | δ = 8.45~8.41(m, 2H), 8.30(m, 2H), 8.20(m, 1H), 8.72(m, 1H), 8.03~7.89(m, 3H), 7.58~7.25(m, 14H) |

TABLE 8-continued

| NO | $^1$H NMR (CDCl$_3$, 300 Mz) |
|---|---|
| 168 | δ = 8.30~8.27(m, 3H), 8.12(m, 1H), 8.03(m, 1H), 7.92~7.89(m, 2H), 7.66(m, 1H), 7.54~7.26(m, 14H), 7.11~6.98(m, 8H), 6.69(m, 4H), 6.51(t, 2H) |
| 172 | δ = 8.30~8.24(m, 8H), 8.12(d, 1H), 8.03(d, 1H), 7.92~7.89(t, 2H), 7.70~7.66(m, 2H), 7.57~7.32(m, 14H) |
| 174 | δ = 8.85(d, 1H), 8.38(d, 1H), 8.27(d, 1H), 8.12(m, 3H), 8.03~7.03(m, 6H), 7.66~7.50(m, 10H), 7.92~7.29(m, 4H) |
| 178 | δ = 8.55(m, 2H), 8.30~8.27(m, 3H), 8.12~8.03(m, 6H), 7.94~7.89(m, 4H), 7.66~7.25(m, 18H) |
| 181 | δ = 8.45(d, 1H), 8.30~8.24(m, 6H), 8.12(d, 1H), 8.03~7.98(m, 6H), 7.70~7.66(t, 2H), 7.57~7.32(m, 14H) |
| 186 | δ = 8.30~8.24(m, 4H), 8.12(d, 1H), 8.03(d, 1H), 7.92~7.81(m, 5H), 7.70~7.66(m, 3H), 7.57~7.32(m, 16H) |
| 190 | δ = 8.30~8.24(m, 6H), 8.12(d, 1H), 8.03(d, 1H), 7.92~7.85(m, 5H), 7.70~7.32(m, 17H) |
| 194 | δ = 9.09(d, 1H), 8.49~8.45(m, 2H), 8.30~8.27(m, 3H), 8.12(m, 1H), 8.00~7.89(m, 9H), 7.59~7.32(m, 12H) |
| 198 | δ = 8.56~8.55(m, 2H), 8.30~8.27(m, 3H), 8.12(m, 2H), 8.03(d, 1H), 7.94~7.88(m, 4H), 7.69~7.25(m, 14H) |
| 201 | δ = 8.30~8.27(m, 3H), 8.12(d, 1H), 8.03(d, 2H), 7.92~7.89(m, 2H), 7.66(m, 1H), 7.54~7.32(m, 7H), 7.21~7.16(m, 6H), 6.97~6.88(m, 4H), 6.59(d, 1H) |
| 202 | δ = 8.30~8.27(m, 3H), 8.12(m, 3H), 8.03(d, 1H), 7.92~7.89(m, 2H), 7.70~7.29(m, 19H) |
| 206 | δ = 8.27~8.23(m, 6H), 8.12(d, 1H), 8.03(d, 1H), 7.92~7.79(m, 7H), 7.66~7.32(m, 16H) |
| 210 | δ = 8.49(d, 1H), 8.30~8.27(m, 3H), 8.12~8.03(m, 7H), 7.92~7.89(m, 2H), 7.66~7.29(m, 18H) |
| 214 | δ = 8.30~8.27(m, 3H), 8.12(d, 1H), 8.03(d, 1H), 7.92~7.89(m, 2H), 7.70~7.66(m, 5H), 7.54~7.32(m, 19H) |
| 218 | δ = 8.30~8.24(m, 7H), 8.12(d, 1H), 8.03(d, 1H), 7.92~7.79(m, 6H), 7.70~7.66(m, 2H), 7.57~7.32(m, 16H) |
| 221 | δ = 8.30~8.23(m, 6H), 8.12(d, 1H), 8.03(d, 1H), 7.92~7.89(m, 3H), 7.75(d, 1H), 7.66~7.32(m, 15H) |
| 222 | δ = 8.30~8.23(m, 6H), 8.12(d, 1H), 8.03(m, 1H), 7.92~7.85(m, 4H), 7.66~7.32(m, 25H) |
| 226 | δ = 8.30~8.23(m, 8H), 8.12(d, 1H), 8.03(d, 1H), 7.92~7.85(m, 6H), 7.66~7.32(m, 15H) |
| 230 | δ = 8.55(d, 1H), 8.30~8.28(m, 8H), 8.12(d, 1H), 8.03(d, 1H), 7.94~7.85(m, 6H), 7.77(d, 1H), 7.69~7.25(m, 18H) |
| 234 | δ = 8.55(d, 1H), 8.30~8.23(m, 6H), 8.12(d, 1H), 8.03(m, 1H), 7.94~7.87(m, 4H), 7.77(d, 1H), 7.69~7.25(m, 18H) |
| 238 | δ = 8.30~8.23(m, 8H), 8.12(d, 1H), 8.03(d, 1H), 7.89~7.85(m, 4H), 7.66(d, 1H), 7.54~7.32(m, 14H) |
| 241 | δ = 8.30~8.23(m, 5H), 8.12(d, 1H), 8.03(d, 1H), 7.92~7.89(m, 2H), 7.75~7.66(m, 4H), 7.57~7.32(m, 20H) |
| 242 | δ = 8.30~8.23(m, 8H), 8.12(d, 1H), 8.03(m, 1H), 7.92~7.79(m, 6H), 7.66(d, 1H), 7.54~7.25(m, 16H) |
| 246 | δ = 8.30~8.23(m, 6H), 8.12(d, 1H), 8.03(d, 1H), 7.92~7.85(m, 4H), 7.66~7.32(m, 15H) |
| 250 | δ = 8.30~8.28(m, 8H), 8.12(d, 1H), 8.03(m, 1H), 7.89~7.85(m, 6H), 7.66~7.32(m, 15H) |
| 254 | δ = 8.55(d, 1H), 8.30~8.23(m, 8H), 8.12(d, 1H), 8.03(d, 1H), 7.94~7.85(m, 6H), 7.77(d, 1H), 7.66~7.25(m, 18H) |
| 258 | δ = 8.55(d, 1H), 8.30~8.28(m, 6H), 8.12(d, 1H), 8.03(d, 1H), 7.94~7.87(m, 4H), 7.77(d, 1H), 7.58~7.25(m, 18H) |
| 261 | δ = 8.30~8.23(m, 4H), 8.12(d, 1H), 8.03(d, 1H), 7.92~7.79(m, 8H), 7.66(m, 1H), 7.54~7.32(m, 14H) |
| 262 | δ = 8.30~8.23(m, 4H), 8.12(d, 1H), 8.03(d, 1H), 7.92~7.79(m, 6H), 7.66~7.32(m, 15H) |
| 266 | δ = 8.45(d, 1H), 8.30~8.23(m, 4H), 8.12~7.79(m, 10H), 7.66(m, 1H), 7.54~7.32(m, 11H) |
| 270 | δ = 2.34~8.23(m, 5H), 8.12(d, 1H), 8.03(d, 1H), 7.92~7.32(m, 13H), 7.54~7.32(m, 12H) |
| 274 | δ = 8.55(d, 1H), 8.30~8.23(m, 6H), 8.12(d, 1H), 8.03(d, 1H), 7.94~7.79(m, 9H), 7.66~7.25(m, 18H) |
| 278 | δ = 8.30~8.23(m, 4H), 8.12(d, 1H), 8.06~8.03(m, 2H), 7.92~7.87(m, 3H), 7.79(m, 2H), 7.66~7.28(m, 16H), 1.72(s, 2H) |
| 280 | δ = 8.30~8.28(m, 7H), 8.04(d, 1H), 7.92~7.89(m, 3H), 7.66(d, 1H), 7.54~7.41(m, 12H) |
| 282 | δ = 8.30(m, 2H), 8.21(d, 1H), 8.04(d, 1H), 7.92~7.85(m, 6H), 7.56(d, 1H), 7.54~7.25(m, 20H) |
| 286 | δ = 8.55(m, 2H), 8.45(d, 1H), 8.30~8.21(m, 5H), 8.01~7.82(m, 10H), 7.66(d, 1H), 7.55~7.41(m, 13H) |
| 290 | δ = 8.30~8.21(m, 5H), 8.04(d, 1H), 7.92~7.85(m, 7H), 7.66(d, 1H), 7.54~7.25(m, 18H) |
| 294 | δ = 8.30~8.21(m, 5H), 8.04(d, 1H), 7.90~7.81(m, 8H), 7.66(m, 2H), 7.54~7.25(m, 14H) |

TABLE 8-continued

| NO | ¹H NMR (CDCl₃, 300 Mz) |
|---|---|
| 298 | δ = 8.55(d, 1H), 8.30~8.21(m, 5H), 8.04(m, 1H), 7.94~7.87(m, 5H), 7.77(s, 1H), 7.66~7.25(m, 18H) |
| 301 | δ = 8.55(d, 1H), 8.42(d, 1H), 8.28~8.21(m, 5H), 8.08~8.04(m, 3H), 7.92~7.79(m, 7H), 7.66~7.41(m, 17H) |
| 302 | δ = 8.28~8.21(m, 6H), 8.04(d, 1H), 7.92~7.85(m, 5H), 7.70~7.66(m, 2H), 7.51~7.25(m, 18H) |
| 306 | δ = 8.55(d, 1H), 8.30~8.21(m, 5H), 8.12(d, 1H), 8.04(d, 1H), 7.94~7.85(m, 6H), 7.66~7.25(m, 17H) |
| 310 | δ = 8.30(m, 2H), 8.21~8.04(m, 5H), 7.92~7.82(m, 5H), 7.71~7.66(m, 3H), 7.54~7.32(m, 6H) |
| 314 | δ = 8.93(m, 2H), 8.30(m, 2H), 8.21(d, 1H), 8.12~8.04(m, 2H), 7.92~7.82(m, 8H), 7.66(m, 1H), 7.54~7.25(m, 10H) |
| 318 | δ = 8.30~8.21(m, 5H), 8.09~8.04(m, 2H), 7.92~7.82(m, 5H), 7.66(m, 2H), 7.54~7.32(m, 10H) |
| 321 | δ = 8.45(m, 1H), 8.30(m, 2H), 8.21(m, 1H), 8.11~7.98(m, 8H) |
| 322 | δ = 8.30(m, 2H), 7.92~7.82(m, 3H), 7.66(m, 1H), 7.54~7.02(m, 6H), 7.32~7.02(m, 4H), 6.80~6.73(m, 3H), 6.55(m, 2H). 1.72(m, 6H) |
| 326 | δ = 8.30(m, 2H), 8.21(m, 2H), 8.04(m, 1H), 7.92~7.81(m, 6H), 7.72~7.66(m, 3H), 7.54~7.25(m, 16H) |
| 330 | δ = 8.49(m, 1H), 8.30(m, 2H), 8.21(m, 1H), 8.12~8.04(m, 3H), 7.92~7.89(m, 3H), 7.58~7.25(m, 20H) |
| 334 | δ = 8.53(m, 2H), 8.30(m, 2H), 8.21(m, 1H), 8.04(m, 1H), 7.92~7.89(m, 3H), 7.70~7.66(m, 3H), 7.54~7.25(m, 10H), 7.14(m, 2H) |
| 338 | δ = 8.30~8.16(m, 6H), 8.04(m, 1H), 7.92~7.83(m, 5H), 7.66~7.41(m, 11H) |
| 341 | δ = 9.15(d, 1H), 8.92(m, 2H), 8.30(m, 2H), 8.21~8.04(m, 6H), 7.90~7.82(m, 7H), 7.66(m, 1H), 7.54~7.38(m, 6H) |
| 342 | δ = 9.15(d, 1H), 8.93(m, 1H), 8.30(m, 2H), 8.21~8.04(m, 5H), 7.92~7.82(m, 5H), 7.66~7.71(m, 3H), 7.54~7.32(m, 6H) |
| 346 | δ = 8.93(m, 2H), 8.30(m, 2H), 8.21(m, 1H), 8.12~8.04(m, 3H), 7.93~7.82(m, 8H), 7.66(m, 1H), 7.54~7.25(m, 10H) |
| 350 | δ = 8.88(s, 1H), 8.30~8.21(m, 5H), 8.09~8.04(m, 2H), 7.92~7.82(m, 5H), 7.66(m, 2H), 7.54~7.32(m, 9H) |
| 354 | δ = 8.30(m, 2H), 7.92~7.82(m, 3H), 7.66(m, 1H), 7.54~7.26(m, 12H), 7.11~7.02(m, 8H), 6.80(m, 1H), 6.69(m, 2H), 6.51(m, 2H) |
| 358 | δ = 8.55(m, 2H), 8.30(m, 2H), 8.21(m, 1H), 8.12~8.04(m, 4H), 7.94~7.90(m, 5H), 7.63~7.29(m, 18H) |
| 361 | δ = 8.30(m, 2H), 8.21(m, 1H), 8.04(m, 1H), 7.92~7.89(m, 3H), 7.66(m, 1H), 7.54~7.32(m, 8H), 6.92~6.89(m, 4H), 6.77~6.69(m, 4H) |
| 362 | δ = 8.55(d, 1H), 8.21(m, 2H), 8.12(m, 1H), 8.04(m, 1H), 7.92~7.82(m, 5H), 7.71(m, 5H), 7.54~7.50(m, 3H), 7.38~7.32(m, 2H), 7.21~7.16(m, 6H), 6.97(m, 2H), 6.69(m, 2H) |
| 366 | δ = 8.30~8.21(m, 6H), 8.04(d, 1H), 7.92~7.85(m, 5H), 7.70(m, 1H), 7.66~7.32(m, 18H) |
| 370 | δ = 8.30~8.21(m, 4H), 8.04(d, 1H), 7.92~7.85(m, 6H), 7.70~7.66(m, 3H), 7.54~7.32(m, 16H) |
| 374 | δ = 8.28~8.21(m, 6H), 8.04(d, 1H), 7.92~7.81(m, 6H), 7.66~7.32(m, 17H) |
| 378 | δ = 8.55(m, 1H), 8.30~8.21(m, 4H), 8.00~7.87(m, 9H), 7.66~7.25(m, 23H) |
| 381 | δ = 8.30(d, 2H), 8.21(d, 1H), 8.04(d, 1H), 7.92~7.89(m, 3H), 7.66(m, 1H), 7.54~7.32(m, 7H), 7.05~7.02(m, 4H), 6.89~6.88(m, 2H), 6.73(m, 2H), 6.59~6.55(m, 3H), 1.72(s, 6H) |
| 382 | δ = 8.30(m, 2H), 8.21(m, 1H), 8.04(d, 1H), 7.90~7.89(m, 3H), 7.66(m, 1H), 7.54~7.32(m, 7H), 6.92~6.88(m, 6H), 6.77(m, 2H), 6.59(m, 3H) |
| 386 | δ = 8.30~8.21(m, 7H), 8.10~8.06(m, 3H), 7.92~7.89(m, 3H), 7.81(d, 1H), 7.66~7.32(m, 14H) |
| 390 | δ = 8.55(m, 1H), 8.30(m, 2H), 8.21(d, 1H), 8.08~8.04(m, 2H), 7.92~7.81(m, 9H), 7.66(m, 1H), 7.55~7.32(m, 15H) |
| 394 | δ = 8.49(d, 1H), 8.30(m, 2H), 8.21(m, 1H), 8.12~8.04(m, 3H), 7.92~7.89(m, 3H), 7.57~7.29(m, 20H) |
| 398 | δ = 8.30(m, 2H), 8.21(d, 1H), 8.04(d, 1H), 7.92~7.89(m, 3H), 7.66(m, 3H), 7.57~7.32(m, 20H) |
| 401 | δ = 8.30~8.21(m, 6H), 8.04(m, 1H), 7.90~7.79(m, 11H), 7.66(m, 1H), 7.54~7.41(m, 14H) |
| 402 | δ = 8.30~8.21(m, 8H), 8.04(m, 1H), 7.90~7.79(m, 7H), 7.66(d, 1H), 7.54~7.25(m, 16H) |
| 406 | δ = 8.30~8.21(m, 6H), 8.04(d, 1H), 7.92~7.89(m, 5H), 7.66~7.32(m, 15H) |
| 410 | δ = 8.30~8.23(m, 8H), 8.04(d, 1H), 7.95~7.85(m, 7H), 7.75(m, 1H), 7.66~7.64(m, 3H), 7.54~7.32(m, 11H) |
| 414 | δ = 8.55(d, 1H), 8.30~8.21(m, 8H), 8.04(d, 1H), 7.94~7.87(m, 7H), 7.77(d, 1H), 7.66~7.25(m, 18H) |
| 418 | δ = 8.55(m, 1H), 8.30~8.21(m, 5H), 8.12(d, 1H), 8.04(d, 1H), 7.94~7.90(m, 4H), 7.66~7.25(m, 16H) |
| 421 | δ = 8.30~8.23(m, 5H), 8.04(d, 1H), 7.92~7.90(m, 3H), 7.79(m, 4H), 7.70~7.66(m, 2H), 7.57~7.25(m, 23H) |
| 422 | δ = 8.45(d, 1H), 8.30(m, 2H), 8.23~8.21(m, 2H), 8.08~7.82(m, 10H), 7.66(d, 1H), 7.54~7.41(m, 11H) |
| 426 | δ = 8.30~8.21(m, 4H), 8.04(d, 1H), 7.89~7.79(m, 7H), 7.66~7.32(m, 15H) |
| 430 | δ = 8.30~8.21(m, 6H), 8.04(d, 1H), 7.85~7.79(m, 10H), 7.66(m, 2H), 7.54~7.32(m, 10H) |

TABLE 8-continued

| NO | $^1$H NMR (CDCl$_3$, 300 Mz) |
|---|---|
| 446 | 8.45(m, 1H), 8.30(d, 2H), 8.21(d, 1H), 7.85(m, 8H), 7.66(t, 1H), 7.54~7.50(m, 16H), 7.25(m, 4H) |
| 450 | 8.55(d, 1H), 8.45(d, 1H), 8.30~8.21(m, 5H), 8.02~7.87(m, 5H), 7.77(d, 1H), 7.52~7.25(m, 18H) |
| 454 | 8.45(m, 1H), 8.30~8.21(m, 5H), 8.06~7.87(m, 7H), 7.61~7.41(m, 14H), 7.28~7.25(m, 3H) |
| 458 | 8.45(d, 1H), 8.30~8.21(m, 5H), 8.02~7.81(m, 8H), 7.66(m, 2H), 7.54~7.32(m, 24H) |
| 462 | 9.15(s, 1H), 8.93(d, 1H), 8.45(d, 1H), 8.30(m, 2H), 8.21~7.98(m, 9H), 8.12~7.82(m, 9H), 7.71~7.66(m, 3H), 7.54~7.47(m, 6H) |
| 466 | 8.93(d, 1H), 8.45(d, 1H), 8.30(m, 2H), 8.21(m, 1H), 8.12(d, 2H), 8.02~7.82(m, 8H), 7.66(s, 1H), 7.54~7.74(m, 6H), 7.25(s, 4H) |
| 470 | 8.88(s, 1H), 8.45(d, 1H), 8.30( ) |
| 474 | 8.88(s, 1H), 8.45(d, 1H), 8.30(m, 2H), 8.21(d, 1H), 8.09(s, 1H), 8.02~7.92(m, 2H), 7.84~7.82(m, 2H), 7.66(m, 2H), 7.54~7.47(m, 9H) |
| 478 | 8.45(d, 1H), 8.30(m, 2H), 8.21(d, 1H), 7.98~7.75(m, 7H), 7.66(m, 1H), 7.57~7.28(m, 16H) |
| 482 | 8.25(d, 1H), 8.30~8.28(m, 6H), 8.02~7.81(m, 6H), 7.72~7.66(m, 3H), 7.54~7.41(m, 13H) |
| 486 | 8.88(d, 1H), 8.45(d, 1H), 8.30(m, 4H), 8.10~8.06(m, 4H), 7.98~7.92(m, 2H), 7.81(m, 1H), 7.69(m, 1H), 7.54~7.47(m, 8H), 7.35(d, 2H) |
| 490 | 8.45(d, 1H), 8.30(m, 2H), 8.21(d, 1H), 8.12(m, 1H), 8.02~7.92(m, 3H), 7.63~7.50(m, 13H), 7.29(m, 2H) |
| 494 | 8.45(d, 1H), 8.30(m, 2H), 8.21(m, 2H), 8.12(m, 2H), 7.98 |
| 498 | 9.09(s, 1H), 8.49~8.45(m, 2H), 8.30~8.21(m, 7H), 8.04~7.92(m, 8H), 7.73(m, 3H), 7.58~7.41(m, 15H) |
| 502 | 8.55(d, 1H), 8.45(d, 1H), 8.30~8.21(m, 4H), 8.00~7.87(m, 8H), 7.77~7.45(m, 21H), 7.33~7.25(m, 2H) |
| 506 | 8.45(d, 1H), 8.30~8.21(m, 6H), 8.02~7.92(m, 3H), 7.70~7.41(m, 26H) |
| 510 | 8.45(d, 1H), 8.30~8.21(m, 8H), 8.02~7.92(m, 3H), 7.54~7.41(m, 16H), 7.25(s, 4H) |
| 514 | 8.45(d, 2H), 8.30~8.21(m, 6H), 8.02~7.94(m, 5H), 7.82(m, 1H), 7.66~7.41(m, 16H) |
| 518 | 8.45~8.41(m, 2H), 8.30~8.21(m, 6H), 8.00~7.86(m, 9H), 7.58~7.41(m, 18H) |
| 522 | 8.55(d, 1H), 8.45(d, 1H), 8.37~8.28(m, 6H), 8.02~7.87(m, 5H), 7.77(s, 1H), 7.69~7.33(m, 18H) |
| 526 | 8.45(d, 1H), 8.30~8.21(m, 6H), 8.02~7.92(m, 3H), 7.79~7.48(m, 20H), 7.25(s, 4H) |
| 530 | 8.45(d, 1H), 8.30~8.21(m, 6H), 8.02~7.92(m, 3H), 7.75~7.41(m, 19H), 7.25(s, 4H) |
| 534 | 8.55(d, 1H), 8.45(d, 1H), 8.30~8.21(m, 8H), 8.02~7.92(m, 5H), 7.77(s, 1H), 7.66~7.25(m, 20H) |
| 538 | 8.45(d, 1H), 8.30(m, 2H), 8.23~8.21(m, 2H), 8.02~7.79(m, 7H), 7.66~7.32(m, 15H) |
| 542 | 8.45(d, 1H), 8.30(m, 2H), 8.23~8.21(m, 2H), 8.02~7.92(m, 3H), 7.79(m, 4H), 7.66(m, 1H), 7.54~7.41(m, 12H) |
| 546 | 8.45(d, 1H), 8.30~8.21(m, 6H), 8.02~7.89(m, 4H), 7.79~7.75(m, 3H), 7.66~7.38(m, 17H) |
| 550 | 8.45(d, 1H), 8.30~8.21(m, 6H), 8.02~7.95(m, 5H), 7.79~7.75(m, 3H), 7.66~7.64(m, 2H), 7.54~7.32(m, 13H) |
| 554 | 8.45(d, 1H), 8.30~8.27(m, 5H), 8.12(d, 1H), 7.85~7.98(m, 5H), 7.52~7.41(m, 14H), 7.25(d, 2H) |
| 558 | 8.45(d, 2H), 8.30(m, 4H), 8.23~8.21(m, 2H), 8.02~7.92(m, 5H), 7.79~7.82(m, 3H), 7.66(m, 1H), 7.54~7.41(m, 12H), 7.25(m, 2H) |
| 562 | 8.45(s, 1H), 8.30~8.27(m, 5H), 8.12(m, 1H), 7.98~7.81(m, 6H), 7.66(m, 1H), 7.54~7.32(m, 12H) |
| 566 | 8.45(d, 1H), 8.30~8.27(m, 5H), 8.12(m, 1H), 8.03~7.81(m, 8H), 7.66(m, 1H), 7.54~7.32(m, 14H) |
| 570 | 8.45(d, 2H), 8.28~8.27(m, 5H), 8.12(d, 1H), 8.03~7.82(m, 8H), 7.56~7.41(m, 12H), 7.25(m, 2H) |
| 574 | 8.55(m, 1H), 8.45(m, 1H), 8.30~8.27(m, 5H), 8.12(m, 2H), 8.03~7.92(m, 4H), 7.63(m, 1H), 7.54~7.25(m, 13H) |
| 578 | 9.15(s, 1H), 8.93(m, 2H), 8.45(m, 1H), 8.30~8.27(m, 3H), 8.03~7.82(m, 12H), 7.54~7.41(m, 6H) |
| 582 | 8.45(m, 2H), 8.30(m, 2H), 8.11~7.98(m, 8H), 7.54~7.47(m, 8H) |
| 586 | 9.30(d, 1H), 9.15(s, 2H), 8.99(m, 1H), 8.81(s, 1H), 8.53(m, 1H), 8.45(m, 1H), 8.30~8.27(m, 3H), 8.12(m, 1H), 8.03~7.88(m, 4H), 7.70(m, 1H), 7.54~7.41(m, 11H), 7.14(m, 1H) |
| 590 | 8.45(m, 1H), 8.30~8.27(m, 7H), 8.12(m, 1H), 8.03~7.81(m, 8H), 7.71~7.72(m, 2H), 7.54~7.41(m, 13H) |
| 594 | 8.88(s, 1H), 8.45(d, 1H), 8.30~8.27(m, 5H), 8.12~7.98(m, 5H), 7.84~7.82(d, 2H), 7.66(s, 1H), 7.54~7.47(m, 9H) |
| 598 | 8.55(m, 1H), 8.43(d, 1H), 8.30~8.27(m, 3H), 8.12(m, 2H), 8.03~7.92(m, 4H), 7.79(m, 1H), 7.68~7.25(m, 11H), 7.52~7.29(m, 3H) |

TABLE 8-continued

| NO | $^1$H NMR (CDCl$_3$, 300 Mz) |
|---|---|
| 602 | 8.45(m, 1H), 8.30~8.27(m, 3H), 8.12(m, 1H), 8.03~7.98(m, 3H), 7.54~7.47(m, 8H), 7.05~7.02(m, 4H), 6.79~6.69(m, 4H), 6.55(m, 2H), 1.72(s, 2H) |
| 606 | 8.45(d, 1H), 8.27~8.30(m, 3H), 8.12(m, 1H), 7.98~7.75(m, 7H), 7.54~7.19(m, 16H) |
| 610 | 8.72(m, 1H), 8.57(m, 1H), 8.45~8.41(m, 2H), 8.30~8.22(m, 6H), 8.10~7.92(m, 10H), 7.81(m, 1H), 7.73(m, 2H), 7.58~7.50(m, 11H), 7.35(m, 2H) |
| 614 | 8.55(m, 1H), 8.45(m, 1H), 8.30~8.24(m, 4H), 8.12(m, 1H), 8.00~7.87(m, 8H), 7.77~7.69(m, 4H), 7.59~7.50(m, 16H), 7.33~7.25(m, 2H) |
| 618 | 8.55(m, 1H), 8.45(d, 1H), 8.30~8.24(m, 6H), 8.12(m, 1H), 8.03~7.92(m, 5H), 7.77(m, 1H), 7.70~7.69(m, 2H), 7.58~7.25(m, 18H) |
| 622 | 8.45(d, 1H), 8.30~8.24(m, 4H), 8.12(m, 1H), 7.85~7.98(m, 7H), 7.70(d, 1H), 7.57~7.41(m, 18H), 7.25(m, 4H) |
| 626 | 8.45(d, 1H), 8.27~8.24(m, 4H), 8.12(d, 1H), 8.03~7.81(m, 6H), 7.66(m, 2H), 7.57~7.32(m, 16H) |
| 630 | 8.55(d, 1H), 8.45~8.41(m, 2H), 8.30~8.28(m, 8H), 8.03~7.80(m, 10H), 7.55~7.41(m, 15H) |
| 634 | 8.45(m, 1H), 8.28~8.24(m, 6H), 8.12(d, 1H), 8.03~7.81(m, 6H), 7.70~7.66(m, 2H), 7.57~7.32(m, 15H) |
| 638 | 8.49~8.45(m, 2H), 8.30~8.27(m, 3H), 8.12~7.92(m, 6H), 7.70(m, 1H), 7.58~7.45(m, 17H), 7.29(m, 1H) |
| 642 | 8.45(d, 1H), 8.30~8.27(m, 3H), 8.12(m, 1H), 8.03~7.92(m, 3H), 7.54~7.44(m, 7H), 6.92~6.88(m, 6H), 6.77(m, 2H), 6.59(m, 3H) |
| 646 | 8.45(d, 1H), 8.30~8.26(m, 7H), 8.10~7.92(m, 7H), 7.81(m, 1H), .7.54~7.47(m, 11H) |
| 650 | 8.92(m, 2H), 8.45(d, 1H), 8.30~8.27(m, 3H), 8.12(m, 3H), 8.03~7..82(m, 8H), 7.70(d, 1H), 7.57~7.48(m, 9H) |
| 654 | 8.45(d, 2H), 8.28~8.23(m, 6H), 8.12(d, 1H), 8.03~7.92(m, 4H), 7.82(m, 1H), 7.52~7.41(m, 12H) |
| 658 | 8.45(m, 2H), 8.30~8.23(m, 8H), 8.12(m, 1H), 7.98~7.85(m, 8H), 7.56~7.41(m, 12H) |
| 662 | 8.45(m, 1H), 8.30~8.23(m, 8H), 8.12(d, 1H), 8.03~7.85(m, 5H), 7.54~7.41(m, 14H) |
| 666 | 8.45(d, 1H), 8.30~8.23(m, 8H), 8.12(m, 1H), 8.03~7.85(m, 7H), 7.54~7.47(m, 12H), 7.25(s, 4H) |
| 670 | 8.45(d, 1H), 8.30~8.23(m, 6H), 8.12(d, 1H), 8.03~7.92(m, 5H), 7.75(d, 1H), 7.66~7.64(m, 2H), 7.54~7.38(m, 11H) |
| 674 | 8.45(d, 1H), 8.30~8.23(m, 4H), 8.12(d, 1H), 8.03~7.79(m, 7H), 7.54~7.32(m, 15H) |
| 678 | 8.55(d, 1H), 8.45(d, 1H), 8.30~8.23(m, 4H), 8.12(d, 1H), 8.03~7.87(m, 5H), 7.79~7.77(m, 3H), 7.69(d, 1H), 7.58~7.41(m, 16H) |
| 682 | 8.45(d, 1H), 8.30~8.23(m, 8H), 8.12(d, 1H), 7.98~7.79(m, 7H), 7.54~7.41(m, 12H) |
| 686 | 8.45(d, 1H), 8.30~8.23(m, 4H), 8.12(d, 1H), 8.03~7.89(m, 4H), 7.79~7.75(m, 3H), 7.66~7.38(m, 15H) |
| 690 | 8.45(d, 1H), 8.30~8.23(m, 6H), 8.12(d, 1H), 7.92~7.79(m, 10H), 7.66(d, 1H), 7.54~7.32(m, 12H) |
| 694 | 8.45(d, 1H), 88.30~8.23(m, 9H), 8.12(d, 1H), 8.03~7.85(m, 5H), 7.75~7.70(m, 2H), 7.54~7.41(m, 16H) |
| 698 | 8.45(d, 1H), 8.30~8.23(m, 6H), 8.12(d, 1H), 8.06~7.79(m, 8H), 7.61~7.41(m, 13H), 7.28(m, 1H), 1.72(m, 6H) |
| 702 | 8.45(d, 1H), 8.30~8.21(m, 7H), 8.04~7.85(m, 6H), 7.54~7.41(m, 12H), 7.25(m, 2H) |
| 706 | 8.45(d, 1H), 8.30~8.21(m, 5H), 8.04~7.58(m, 7H), 7.66(d, 1H), 7.54~7.32(m, 15H) |
| 710 | 8.45(d, 1H), 8.30~8.21(m, 5H), 8.04~7.81(m, 9H), 7.66(m, 1H), 7.54~7.32(m, 15H) |
| 714 | 8.55(d, 1H), 8.45(m, 1H), 8.30~8.21(m, 5H), 8.04~7.85(m, 8H), 7.77(d, 1H), 7.69(d, 1H), 7.58~7.25(m, 18) |
| 718 | 8.55(d, 1H), 8.45(d, 1H), 8.30~8.21(m, 5H), 8.12(m, 1H), 8.04~7.92(m, 5H), 7.63(m, 1H), 7.54~7.25(m, 13H) |
| 722 | 8.45(d, 1H), 8.30(m, 2H), 8.21(m, 1H), 8.044~7.92(m, 4H), 7.66(s, 3H), 7.54~7.41(m, 16H), 7.25(d, 4H) |
| 726 | 8.83(m, 2H), 8.45~8.38(m, 4H), 8.21(m, 1H), 8.04~7.90(m, 4H), 7.58~7.47(m, 9H) |
| 730 | 8.88(s, 1H), 8.45(d, 1H), 8.30(m, 4H), 8.21(m, 1H), 7.90~7.82(m, 7H), 7.66(s, 1H), 7.54~7.47(m, 9H) |
| 734 | 8.49~8.45(m, 2H), 8.30(m, 2H), 8.21(m, 1H), 8.12~7.90(m, 6H), 7.63~7.45(m, 14H), 7.29~7.25(m, 5H) |
| 738 | 8.45(m, 2H), 8.30(m, 2H), 7.98~7.92(m, 2H), 7.54~7.47(m, 6H), 7.33~7.26(m, 6H), 7.11~6.98(m, 6H), 6.80(s, 1H), 6.69(m, 2H), 6.51(m, 2H) |
| 742 | 9.09(s, 2H), 8.49~8.45(m, 3H), 8.30(m, 2H), 8.21(m, 1H), 8.04~7.85(m, 12H), 7.59~7.54(m, 10H), 7.25(m, 2H) |
| 746 | 8.45(d, 1H), 8.30(m, 2H), 8.21(m, 1H), 8.04~7.85(m, 7H), 7.75(m, 1H), 7.66~7.25(m, 18H) |

TABLE 8-continued

| NO | $^1$H NMR (CDCl$_3$, 300 Mz) |
|---|---|
| 750 | 9.09(s, 1H), 8.49~8.45(m, 3H), 8.30(m, 2H), 8.21(m, 1H), 8.04~7.94(m, 9H), 7.82(m, 1H), 7.59~7.47(m, 11H) |
| 754 | 8.45(d, 1H), 8.30~8.21(m, 6H), 8.04~7.81(m, 7H), 7.70~7.66(m, 2H), 7.57~7.32(m, 14H) |
| 758 | 8.55(m, 1H), 8.45(m, 1H), 8.30~8.21(m, 6H), 8.04~7.87(m, 6H), 7.77(s, 1H), 7.70~7.69(m, 2H), 7.58~7.41(m, 18H) |
| 762 | 8.45(m, 1H), 8.30(m, 2H), 8.21(m, 1H), 8.04~7.92(m, 4H), 7.54~7.44(m, 7H), 7.05~7.02(m, 4H), 6.89~6.88(m, 2H), 6.73(m, 2H), 6.55(m, 2H) |
| 766 | 8.45(d, 1H), 8.30~8.28(m, 6H), 7.79~7.75(m, 8H), 7.54~7.41(m, 15H) |
| 770 | 8.49~8.45(m, 2H), 8.30(m, 2H), 8.21(m, 1H), 8.12~7.90(m, 6H), 7.70(s, 1H), 7.58~7.45(m, 17H), 7.29(m, 1H) |
| 774 | 8.45~8.41(m, 3H), 8.30(m, 2H), 8.21~8.20(m, 2H), 8.04~7.98(m, 4H), 7.70(m, 1H), 7.54~7.41(m, 12H) |
| 778 | 8.45(d, 1H), 8.30(m, 2H), 8.21(m, 1H), 8.12(m, 2H), 8.04~7.90(m, 4H), 7.70(s, 1H), 7.63~7.47(m, 15H), 7.29(m, 2H) |
| 782 | 8.45(d, 1H), 8.30~8.21(m, 5H), 8.04~7.92(m, 4H), 7.75~7.70(m, 3H), 7.57~7.41(m, 20H) |
| 786 | 8.41~8.54(m, 2H), 8.30~8.21(m, 6H), 8.04~7.75(m, 11H), 7.57~7.41(m, 15H) |
| 790 | 8.45(d, 1H), 8.30~8.21(m, 7H), 8.10~7.90(m, 7H), 7.81(d, 1H), 7.60~7.54(m, 11H) |
| 794 | 8.45(d, 1H), 8.30~8.21(m, 8H), 8.11~7.98(m, 10H), 7.54~7.41(m, 11H) |
| 898 | 8.55(m, 1H), 8.45(m, 1H), 8.30~8.21(m, 7H), 8.12(m, 1H), 8.04~7.92(m, 7H), 7.63(m, 1H), 7.54~7.25(m, 14H) |
| 802 | 8.55(m, 1H), 8.45(d, 1H), 8.30~8.21(m, 6H), 8.04~7.94(m, 6H), 7.77(s, 1H), 7.69(d, 1H), 7.58~7.25(m, 16H) |
| 806 | 8.45(d, 1H), 8.30(m, 2H), 8.23~8.21(m, 2H), 8.04~7.89(m, 6H), 7.79~7.75(m, 3H), 7.66~7.64(m, 2H), 7.54~7.38(m, 10H) |
| 810 | 8.55(d, 1H), 8.45(m, 1H), 8.30~8.21(m, 5H), 8.12(m, 1H), 8.04~7.92(m, 5H), 7.63(m, 1H), 7.54~7.25(m, 14H) |
| 814 | 8.45(d, 1H), 8.30~8.23(m, 7H), 8.04~7.85(m, 6H), 7.75~7.70(m, 3H), 7.57~7.41(m, 20H) |
| 818 | 8.45(d, 1H), 8.30(m, 2H), 8.23~8.21(m, 2H), 8.04~7.94(m, 6H), 7.82~7.79(m, 3H), 7.54~7.41(m, 12H) |
| 822 | 8.55(m, 1H), 8.45(d, 1H), 8.30(m, 2H), 8.21(m, 1H), 8.12(m, 1H), 8.04~7.90(m, 5H), 7.79(m, 2H), 7.63(m, 1H), 7.54~7.25(m, 14H) |
| 826 | 8.45(m, 1H), 8.300~8.21(m, 6H), 8.04~7.79(m, 11H), 7.66(m, 1H), 7.54~7.32(m, 12H) |
| 830 | 8.78(m, 2H), 8.50~8.45(m, 3H), 8.28~8.23(m, 6H), 7.85~7.79(m, 8H), 7.51~7.41(m, 10H) |

EXPERIMENTAL EXAMPLE

Experimental Example 1

1) Manufacture of Organic Light Emitting Device

A glass substrate on which indium tin oxide (ITO) was coated as a thin film to a thickness of 1,500 Å was cleaned with distilled water ultrasonic waves. After the cleaning with distilled water was finished, the substrate was ultrasonic cleaned with solvents such as acetone, methanol and isopropyl alcohol, then dried, and UVO treatment was conducted for 5 minutes using UV in a UV cleaner. After that, the substrate was transferred to a plasma cleaner (PT), and after conducting plasma treatment under vacuum for ITO work function and residual film removal, the substrate was transferred to a thermal deposition apparatus for organic deposition. On the transparent ITO electrode (anode), organic materials were formed in a single stack structure. The following HAT-CN was deposited to a thickness of 50 Å as a hole injection layer, and, as a hole transfer layer, DNTPD was doped to NPD by 10% or less and then deposited and formed to a thickness of 1500 Å, and TCTA was continuously deposited to a thickness of 200 Å. Subsequently, a light emitting layer including a t-Bu-perylene dopant in an ADN host was formed to a thickness of 250 Å. Then, Alq$_3$, an electron transfer layer, was formed as a film to a thickness of 250 Å, and as an N-type charge generation layer, a compound described in the following Table 9 was doped with lithium, an alkali metal, to be formed as a film to a thickness of 100 Å. Then, Al, a cathode, was formed as a film to a thickness of approximately 1,000 Å, and as a result, an organic light emitting device was manufactured.

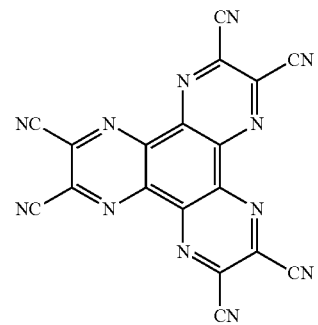

HAT-CN

-continued
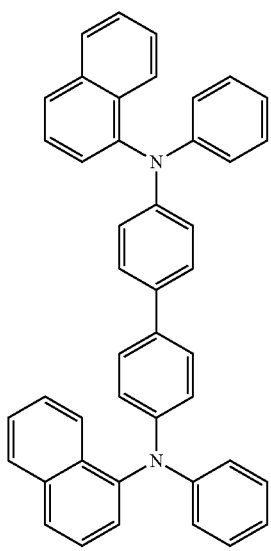
NPD
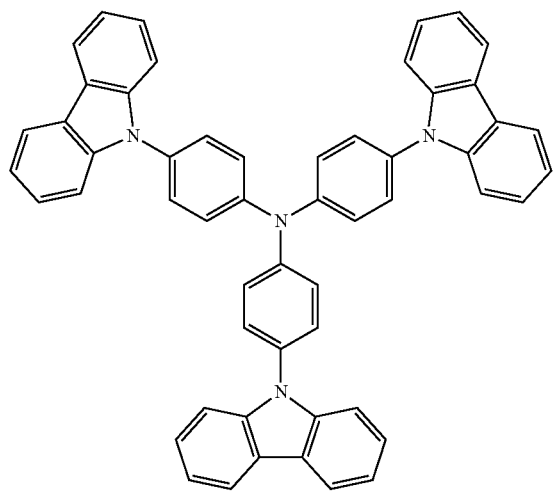
TCTA
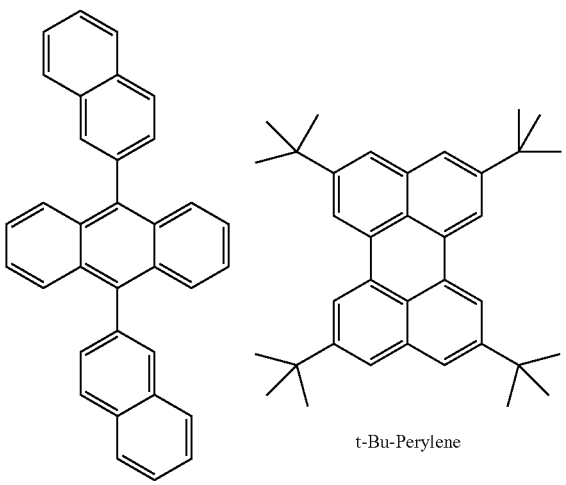
ADN
t-Bu-Perylene
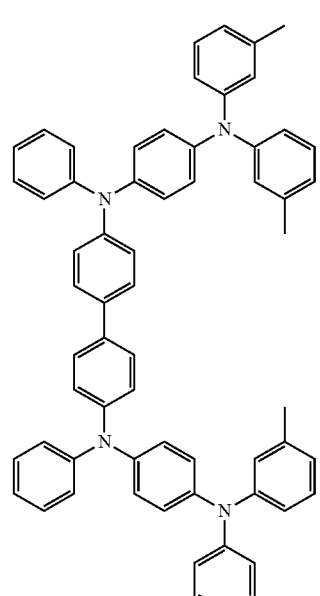
DNTPD
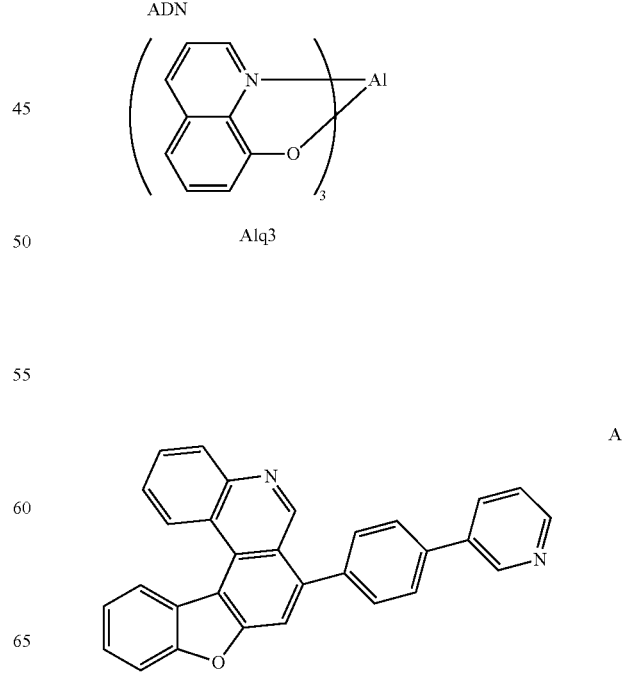
Alq3
A -continued

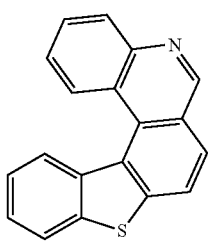

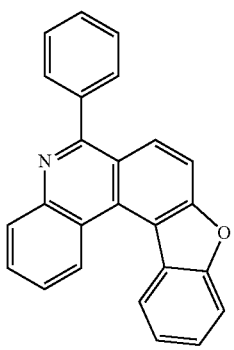

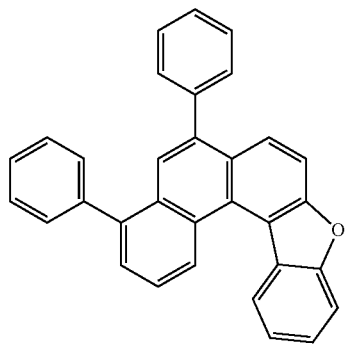

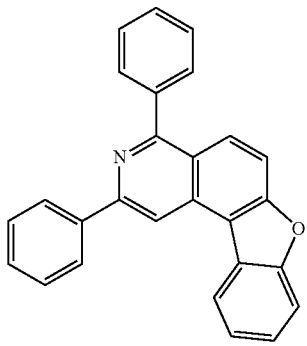

2) Driving Voltage and Light Emission Efficiency of Organic Light Emitting Device For each of the organic light emitting devices manufactured as above, electroluminescent (EL) properties were measured using M7000 manufactured by McScience Inc., and with the measurement results, $T_{95}$ was measured when standard luminance was 750 cd/m² through a lifetime measurement system (M6000) manufactured by McScience Inc. Results of measuring driving voltage, light emission efficiency, external quantum efficiency and color coordinate (CIE) of the white organic electroluminescent devices manufactured according to the present disclosure are as shown in Table 9.

TABLE 9

| | Compound | Driving Voltage (V) | Light Emission Efficiency (cd/A) | CIE (x, y) | Lifetime ($T_{95}$) |
|---|---|---|---|---|---|
| Example 1-1 | 1 | 4.53 | 7.21 | (0.134, 0.104) | 43 |
| Example 1-2 | 4 | 4.18 | 7.13 | (0.134, 0.104) | 45 |
| Example 1-3 | 8 | 4.27 | 7.30 | (0.134, 0.105) | 39 |
| Example 1-4 | 12 | 4.21 | 6.98 | (0.134, 0.103) | 41 |
| Example 1-5 | 15 | 4.97 | 6.56 | (0.134, 0.101) | 37 |
| Example 1-6 | 18 | 4.57 | 7.00 | (0.134, 0.101) | 44 |
| Example 1-7 | 21 | 5.12 | 6.48 | (0.133, 0.102) | 34 |
| Example 1-8 | 25 | 4.32 | 7.11 | (0.134, 0.100) | 42 |
| Example 1-9 | 28 | 5.11 | 6.42 | (0.133, 0.101) | 30 |
| Example 1-10 | 32 | 5.27 | 6.55 | (0.134, 0.101) | 28 |
| Example 1-11 | 35 | 5.68 | 6.42 | (0.134, 0.101) | 32 |
| Example 1-12 | 38 | 5.88 | 6.30 | (0.134, 0,101) | 30 |
| Example 1-13 | 41 | 5.14 | 6.51 | (0.133, 0.101) | 28 |
| Example 1-14 | 44 | 5.89 | 6.18 | (0.133, 0.102) | 80 |
| Example 1-15 | 47 | 5.90 | 6.11 | (0.134, 0.100) | 78 |
| Example 1-16 | 50 | 5.28 | 6.78 | (0.133, 0.101) | 27 |
| Example 1-17 | 53 | 5.44 | 6.37 | (0.134, 0.101) | 26 |
| Example 1-18 | 58 | 5.68 | 6.32 | (0.133, 0.100) | 37 |
| Example 1-19 | 61 | 5.40 | 6.48 | (0.134, 0.100) | 25 |
| Example 1-20 | 63 | 5.38 | 6.50 | (0.133, 0.101) | 28 |
| Example 1-21 | 67 | 5.33 | 6.48 | (0.134, 0.101) | 28 |
| Example 1-22 | 73 | 5.36 | 6.54 | (0.134, 0.099) | 27 |
| Example 1-23 | 76 | 5.34 | 6.55 | (0.134, 0.101) | 30 |
| Example 1-24 | 78 | 5.68 | 6.43 | (0.133, 0.101) | 31 |
| Example 1-25 | 81 | 5.44 | 6.40 | (0.134, 0.102) | 33 |
| Example 1-26 | 83 | 5.67 | 6.39 | (0.134, 0.101) | 35 |
| Example 1-27 | 86 | 4.87 | 5.99 | (0.132, 0.101) | 29 |
| Example 1-28 | 90 | 5.68 | 6.47 | (0.134, 0.103) | 31 |
| Example 1-29 | 92 | 5.68 | 6.50 | (0.134, 0.101) | 34 |
| Example 1-30 | 95 | 5.66 | 6.77 | (0.133, 0.102) | 29 |
| Example 1-31 | 101 | 5.73 | 6.41 | (0.133, 0.101) | 54 |
| Example 1-32 | 103 | 5.64 | 6.40 | (0.134, 0.100) | 32 |
| Example 1-33 | 107 | 5.71 | 6.52 | (0.134, 0,101) | 33 |
| Example 1-34 | 110 | 5.68 | 6.55 | (0.133, 0.100) | 30 |
| Example 1-35 | 113 | 5.70 | 6.40 | (0.133, 0.101) | 30 |
| Example 1-36 | 115 | 5.23 | 6.33 | (0.133, 0.101) | 31 |
| Example 1-37 | 122 | 5.78 | 6.44 | (0.133, 0.101) | 37 |
| Example 1-38 | 124 | 5.73 | 6.62 | (0.133, 0.099) | 31 |
| Example 1-39 | 126 | 5.22 | 6.38 | (0.134, 0.101) | 67 |
| Example 1-40 | 130 | 5.11 | 6.52 | (0.133, 0.101) | 30 |
| Example 1-41 | 135 | 5.27 | 6.55 | (0.134, 0.101) | 28 |
| Example 1-42 | 138 | 5.68 | 6.40 | (0.134, 0.101) | 36 |
| Example 1-43 | 142 | 5.88 | 6.34 | (0.134, 0,101) | 37 |
| Example 1-44 | 144 | 4.53 | 7.21 | (0.134, 0.104) | 43 |
| Example 1-45 | 147 | 4.18 | 7.13 | (0.134, 0.104) | 45 |
| Example 1-46 | 149 | 4.27 | 7.30 | (0.134, 0.105) | 39 |
| Example 1-47 | 152 | 4.21 | 6.98 | (0.134, 0.103) | 41 |
| Example 1-48 | 155 | 4.97 | 6.56 | (0.134, 0.101) | 37 |
| Example 1-49 | 161 | 4.57 | 7.00 | (0.134, 0.101) | 44 |
| Example 1-50 | 164 | 5.12 | 6.48 | (0.133, 0.102) | 34 |
| Example 1-51 | 168 | 4.32 | 7.11 | (0.134, 0.100) | 42 |
| Example 1-52 | 172 | 5.11 | 6.42 | (0.133, 0.101) | 30 |
| Example 1-53 | 174 | 5.27 | 6.55 | (0.134, 0.101) | 28 |
| Example 1-54 | 178 | 5.68 | 6.42 | (0.134, 0.101) | 32 |
| Example 1-55 | 181 | 5.88 | 6.30 | (0.134, 0,101) | 30 |
| Example 1-56 | 186 | 5.14 | 6.51 | (0.133, 0.101) | 28 |
| Example 1-57 | 190 | 5.89 | 6.18 | (0.133, 0.102) | 80 |

TABLE 9-continued

| Compound | Driving Voltage (V) | Light Emission Efficiency (cd/A) | CIE (x, y) | Lifetime ($T_{95}$) |
|---|---|---|---|---|
| Example 1-58 | 194 | 5.90 | 6.11 | (0.134, 0.100) | 78 |
| Example 1-59 | 198 | 5.28 | 6.78 | (0.133, 0.101) | 27 |
| Example 1-60 | 201 | 5.44 | 6.37 | (0.134, 0.101) | 26 |
| Example 1-61 | 202 | 5.68 | 6.32 | (0.133, 0.100) | 37 |
| Example 1-62 | 206 | 5.40 | 6.48 | (0.134, 0.100) | 25 |
| Example 1-63 | 210 | 5.38 | 6.50 | (0.133, 0.101) | 28 |
| Example 1-64 | 214 | 5.33 | 6.48 | (0.134, 0.101) | 28 |
| Example 1-65 | 218 | 5.36 | 6.54 | (0.134, 0.099) | 27 |
| Example 1-66 | 221 | 5.34 | 6.55 | (0.134, 0.101) | 30 |
| Example 1-67 | 222 | 5.68 | 6.43 | (0.133, 0.101) | 31 |
| Example 1-68 | 226 | 5.44 | 6.40 | (0.134, 0.102) | 33 |
| Example 1-69 | 230 | 5.67 | 6.39 | (0.134, 0.101) | 35 |
| Example 1-70 | 234 | 4.87 | 5.99 | (0.132, 0.101) | 29 |
| Example 1-71 | 238 | 5.68 | 6.47 | (0.134, 0.103) | 31 |
| Example 1-72 | 241 | 5.68 | 6.50 | (0.134, 0.101) | 34 |
| Example 1-73 | 242 | 5.66 | 6.77 | (0.133, 0.102) | 29 |
| Example 1-74 | 246 | 5.64 | 6.40 | (0.134, 0.100) | 32 |
| Example 1-75 | 250 | 5.71 | 6.52 | (0.134, 0.101) | 33 |
| Example 1-76 | 254 | 5.68 | 6.55 | (0.133, 0.100) | 30 |
| Example 1-77 | 258 | 5.70 | 6.40 | (0.133, 0.101) | 30 |
| Example 1-78 | 261 | 5.23 | 6.33 | (0.133, 0.101) | 31 |
| Example 1-79 | 262 | 5.78 | 6.44 | (0.133, 0.101) | 37 |
| Example 1-80 | 266 | 5.73 | 6.62 | (0.133, 0.099) | 31 |
| Example 1-81 | 270 | 5.22 | 6.38 | (0.134, 0.101) | 67 |
| Example 1-82 | 274 | 5.11 | 6.52 | (0.133, 0.101) | 30 |
| Example 1-83 | 278 | 5.27 | 6.55 | (0.134, 0.101) | 28 |
| Example 1-84 | 280 | 5.68 | 6.40 | (0.134, 0.101) | 36 |
| Example 1-85 | 282 | 5.88 | 6.34 | (0.134, 0.101) | 37 |
| Example 1-86 | 286 | 4.53 | 7.21 | (0.134, 0.104) | 43 |
| Example 1-87 | 290 | 4.18 | 7.13 | (0.134, 0.104) | 45 |
| Example 1-88 | 294 | 4.27 | 7.30 | (0.134, 0.105) | 39 |
| Example 1-89 | 298 | 5.68 | 6.43 | (0.133, 0.101) | 31 |
| Example 1-90 | 301 | 5.44 | 6.40 | (0.134, 0.102) | 33 |
| Example 1-91 | 302 | 5.67 | 6.39 | (0.134, 0.101) | 35 |
| Example 1-92 | 306 | 4.87 | 5.99 | (0.132, 0.101) | 29 |
| Example 1-93 | 310 | 5.68 | 6.47 | (0.134, 0.103) | 31 |
| Example 1-94 | 314 | 5.68 | 6.50 | (0.134, 0.101) | 34 |
| Example 1-95 | 318 | 5.66 | 6.77 | (0.133, 0.102) | 29 |
| Example 1-96 | 321 | 5.64 | 6.40 | (0.134, 0.100) | 32 |
| Example 1-97 | 322 | 5.71 | 6.52 | (0.134, 0.101) | 33 |
| Example 1-98 | 326 | 5.68 | 6.55 | (0.133, 0.100) | 30 |
| Example 1-99 | 330 | 5.70 | 6.40 | (0.133, 0.101) | 30 |
| Example 1-100 | 334 | 5.23 | 6.33 | (0.133, 0.101) | 31 |
| Example 1-101 | 338 | 5.78 | 6.44 | (0.133, 0.101) | 37 |
| Example 1-102 | 341 | 5.73 | 6.62 | (0.133, 0.099) | 31 |
| Example 1-103 | 342 | 5.22 | 6.38 | (0.134, 0.101) | 67 |
| Example 1-104 | 346 | 5.73 | 6.62 | (0.133, 0.099) | 31 |
| Example 1-105 | 350 | 5.22 | 6.38 | (0.134, 0.101) | 67 |
| Example 1-106 | 354 | 5.11 | 6.52 | (0.133, 0.101) | 30 |
| Example 1-107 | 358 | 5.27 | 6.55 | (0.134, 0.101) | 28 |
| Example 1-108 | 361 | 5.68 | 6.40 | (0.134, 0.101) | 36 |
| Example 1-109 | 362 | 5.88 | 6.34 | (0.134, 0,101) | 37 |
| Example 1-110 | 366 | 4.53 | 7.21 | (0.134, 0.104) | 43 |
| Example 1-111 | 370 | 4.18 | 7.13 | (0.134, 0.104) | 45 |
| Example 1-112 | 374 | 4.27 | 7.30 | (0.134, 0.105) | 39 |
| Example 1-113 | 378 | 4.21 | 6.98 | (0.134, 0.103) | 41 |
| Example 1-114 | 381 | 4.97 | 6.56 | (0.134, 0.101) | 37 |
| Example 1-115 | 382 | 4.57 | 7.00 | (0.134, 0.101) | 44 |
| Example 1-116 | 386 | 5.12 | 6.48 | (0.133, 0.102) | 34 |
| Example 1-117 | 390 | 4.32 | 7.11 | (0.134, 0.100) | 42 |
| Example 1-118 | 394 | 5.68 | 6.42 | (0.134, 0.101) | 32 |
| Example 1-119 | 398 | 5.88 | 6.30 | (0.134, 0.101) | 30 |
| Example 1-120 | 401 | 5.14 | 6.51 | (0.133, 0.101) | 28 |
| Example 1-121 | 402 | 5.89 | 6.18 | (0.133, 0.102) | 80 |
| Example 1-122 | 406 | 5.90 | 6.11 | (0.134, 0.100) | 78 |
| Example 1-123 | 410 | 5.28 | 6.78 | (0.133, 0.101) | 27 |
| Example 1-124 | 414 | 5.44 | 6.37 | (0.134, 0.101) | 26 |
| Example 1-125 | 418 | 5.68 | 6.32 | (0.133, 0.100) | 37 |
| Example 1-126 | 421 | 5.40 | 6.48 | (0.134, 0.100) | 25 |
| Example 1-127 | 422 | 5.38 | 6.50 | (0.133, 0.101) | 28 |
| Example 1-128 | 426 | 5.33 | 6.48 | (0.134, 0.101) | 28 |
| Example 1-129 | 430 | 5.36 | 6.54 | (0.134, 0.099) | 27 |
| Example 1-130 | 446 | 5.34 | 6.55 | (0.134, 0.101) | 30 |
| Example 1-131 | 450 | 5.68 | 6.43 | (0.133, 0.101) | 31 |
| Example 1-132 | 454 | 5.44 | 6.40 | (0.134, 0.102) | 33 |
| Example 1-133 | 458 | 5.67 | 6.39 | (0.134, 0.101) | 35 |
| Example 1-134 | 462 | 4.87 | 5.99 | (0.132, 0.101) | 29 |
| Example 1-135 | 466 | 5.68 | 6.47 | (0.134, 0.103) | 31 |
| Example 1-136 | 470 | 5.68 | 6.50 | (0.134, 0.101) | 34 |
| Example 1-137 | 474 | 5.66 | 6.77 | (0.133, 0.102) | 29 |
| Example 1-138 | 478 | 5.73 | 6.41 | (0.133, 0.101) | 54 |
| Example 1-139 | 482 | 5.64 | 6.40 | (0.134, 0.100) | 32 |
| Example 1-140 | 486 | 5.71 | 6.52 | (0.134, 0.101) | 33 |
| Example 1-141 | 490 | 5.68 | 6.55 | (0.133, 0.100) | 30 |
| Example 1-142 | 494 | 5.70 | 6.40 | (0.133, 0.101) | 30 |
| Example 1-143 | 498 | 5.23 | 6.33 | (0.133, 0.101) | 31 |
| Example 1-144 | 502 | 5.78 | 6.44 | (0.133, 0.101) | 37 |
| Example 1-145 | 506 | 5.73 | 6.62 | (0.133, 0.099) | 31 |
| Example 1-146 | 510 | 5.22 | 6.38 | (0.134, 0.101) | 67 |
| Example 1-147 | 514 | 5.11 | 6.52 | (0.133, 0.101) | 30 |
| Example 1-148 | 518 | 5.27 | 6.55 | (0.134, 0.101) | 28 |
| Example 1-149 | 522 | 5.68 | 6.40 | (0.134, 0.101) | 36 |
| Example 1-150 | 526 | 5.88 | 6.34 | (0.134, 0,101) | 37 |
| Example 1-151 | 530 | 4.53 | 7.21 | (0.134, 0.104) | 43 |
| Example 1-152 | 534 | 4.18 | 7.13 | (0.134, 0.104) | 45 |
| Example 1-153 | 538 | 4.27 | 7.30 | (0.134, 0.105) | 39 |
| Example 1-154 | 542 | 4.21 | 6.98 | (0.134, 0.103) | 41 |
| Example 1-155 | 546 | 4.97 | 6.56 | (0.134, 0.101) | 37 |
| Example 1-156 | 550 | 4.57 | 7.00 | (0.134, 0.101) | 44 |
| Example 1-157 | 554 | 5.12 | 6.48 | (0.133, 0.102) | 34 |
| Example 1-158 | 558 | 4.32 | 7.11 | (0.134, 0.100) | 42 |
| Example 1-159 | 562 | 5.11 | 6.42 | (0.133, 0.101) | 30 |
| Example 1-160 | 566 | 5.27 | 6.55 | (0.134, 0.101) | 28 |
| Example 1-161 | 570 | 5.68 | 6.42 | (0.134, 0.101) | 32 |
| Example 1-162 | 574 | 5.73 | 6.62 | (0.133, 0.099) | 31 |
| Example 1-163 | 578 | 5.22 | 6.38 | (0.134, 0.101) | 67 |
| Example 1-164 | 582 | 5.73 | 6.62 | (0.133, 0.099) | 31 |
| Example 1-165 | 586 | 5.22 | 6.38 | (0.134, 0.101) | 67 |
| Example 1-166 | 590 | 5.11 | 6.52 | (0.133, 0.101) | 30 |
| Example 1-167 | 594 | 5.27 | 6.55 | (0.134, 0.101) | 28 |
| Example 1-168 | 598 | 5.68 | 6.40 | (0.134, 0.101) | 36 |
| Example 1-169 | 602 | 5.88 | 6.34 | (0.134, 0.101) | 37 |
| Example 1-170 | 606 | 4.53 | 7.21 | (0.134, 0.104) | 43 |
| Example 1-171 | 610 | 5.89 | 6.18 | (0.133, 0.102) | 80 |
| Example 1-172 | 614 | 5.90 | 6.11 | (0.134, 0.100) | 78 |
| Example 1-173 | 618 | 5.28 | 6.78 | (0.133, 0.101) | 27 |
| Example 1-174 | 622 | 5.44 | 6.37 | (0.134, 0.101) | 26 |
| Example 1-175 | 626 | 5.68 | 6.32 | (0.133, 0.100) | 37 |
| Example 1-176 | 630 | 5.40 | 6.48 | (0.134, 0.100) | 25 |
| Example 1-177 | 634 | 5.38 | 6.50 | (0.133, 0.101) | 28 |
| Example 1-178 | 638 | 5.33 | 6.48 | (0.134, 0.101) | 28 |
| Example 1-179 | 642 | 5.36 | 6.54 | (0.134, 0.099) | 27 |
| Example 1-180 | 646 | 5.34 | 6.55 | (0.134, 0.101) | 30 |
| Example 1-181 | 650 | 5.68 | 6.43 | (0.133, 0.101) | 31 |
| Example 1-182 | 654 | 5.44 | 6.40 | (0.134, 0.102) | 33 |
| Example 1-183 | 658 | 5.67 | 6.39 | (0.134, 0.101) | 35 |
| Example 1-184 | 662 | 4.87 | 5.99 | (0.132, 0.101) | 29 |
| Example 1-185 | 666 | 5.68 | 6.47 | (0.134, 0.103) | 31 |
| Example 1-186 | 670 | 5.68 | 6.50 | (0.134, 0.101) | 34 |
| Example 1-187 | 674 | 5.66 | 6.77 | (0.133, 0.102) | 29 |
| Example 1-188 | 678 | 5.73 | 6.41 | (0.133, 0.101) | 54 |
| Example 1-189 | 682 | 5.64 | 6.40 | (0.134, 0.100) | 32 |
| Example 1-190 | 686 | 5.71 | 6.52 | (0.134, 0.101) | 33 |
| Example 1-191 | 690 | 5.68 | 6.55 | (0.133, 0.100) | 30 |
| Example 1-192 | 694 | 5.70 | 6.40 | (0.133, 0.101) | 30 |
| Example 1-193 | 698 | 5.23 | 6.33 | (0.133, 0.101) | 31 |
| Example 1-194 | 702 | 5.78 | 6.44 | (0.133, 0.101) | 37 |
| Example 1-195 | 706 | 5.73 | 6.62 | (0.133, 0.099) | 31 |
| Example 1-196 | 710 | 5.22 | 6.38 | (0.134, 0.101) | 67 |
| Example 1-197 | 714 | 5.11 | 6.52 | (0.133, 0.101) | 30 |
| Example 1-198 | 718 | 5.27 | 6.55 | (0.134, 0.101) | 28 |
| Example 1-199 | 722 | 5.68 | 6.40 | (0.134, 0.101) | 36 |
| Example 1-200 | 726 | 5.88 | 6.34 | (0.134, 0.101) | 37 |
| Example 1-201 | 730 | 4.53 | 7.21 | (0.134, 0.104) | 43 |
| Example 1-202 | 734 | 4.18 | 7.13 | (0.134, 0.104) | 45 |
| Example 1-203 | 738 | 4.27 | 7.30 | (0.134, 0.105) | 39 |
| Example 1-204 | 742 | 4.21 | 6.98 | (0.134, 0.103) | 41 |
| Example 1-205 | 746 | 4.97 | 6.56 | (0.134, 0.101) | 37 |
| Example 1-206 | 750 | 4.57 | 7.00 | (0.134, 0.101) | 44 |
| Example 1-207 | 754 | 5.12 | 6.48 | (0.133, 0.102) | 34 |

TABLE 9-continued

| Compound | Driving Voltage (V) | Light Emission Efficiency (cd/A) | CIE (x, y) | Lifetime ($T_{95}$) |
|---|---|---|---|---|
| Example 1-208 | 758 | 4.32 | 7.11 | (0.134, 0.100) | 42 |
| Example 1-209 | 762 | 5.11 | 6.42 | (0.133, 0.101) | 30 |
| Example 1-210 | 766 | 5.27 | 6.55 | (0.134, 0.101) | 28 |
| Example 1-211 | 770 | 5.68 | 6.42 | (0.134, 0.101) | 32 |
| Example 1-212 | 774 | 4.57 | 7.00 | (0.134, 0.101) | 44 |
| Example 1-213 | 778 | 5.68 | 6.47 | (0.134, 0.103) | 31 |
| Example 1-214 | 782 | 5.68 | 6.50 | (0.134, 0.101) | 34 |
| Example 1-215 | 786 | 5.66 | 6.77 | (0.133, 0.102) | 29 |
| Example 1-216 | 790 | 5.73 | 6.41 | (0.133, 0.101) | 54 |
| Example 1-217 | 794 | 5.64 | 6.40 | (0.134, 0.100) | 32 |
| Example 1-218 | 898 | 5.71 | 6.52 | (0.134, 0,101) | 33 |
| Example 1-219 | 802 | 5.68 | 6.55 | (0.133, 0.100) | 30 |
| Example 1-220 | 806 | 5.70 | 6.40 | (0.133, 0.101) | 30 |
| Example 1-221 | 810 | 5.23 | 6.33 | (0.133, 0.101) | 31 |
| Example 1-222 | 814 | 5.78 | 6.44 | (0.133, 0.101) | 37 |
| Example 1-223 | 818 | 5.73 | 6.62 | (0.133, 0.099) | 31 |
| Example 1-224 | 822 | 5.70 | 6.40 | (0.133, 0.101) | 30 |
| Example 1-225 | 826 | 5.88 | 6.34 | (0.134, 0,101) | 37 |
| Example 1-226 | 830 | 4.27 | 7.30 | (0.134, 0.105) | 39 |
| Comparative Example 1-1 | A | 5.82 | 2.23 | (0.134, 0.110) | 27 |
| Comparative Example 1-2 | B | 5.80 | 3.32 | (0.134, 0.111) | 29 |
| Comparative Example 1-3 | C | 5.84 | 2.39 | (0.134, 0.111) | 25 |
| Comparative Example 1-4 | D | 8.60 | 1.23 | (0.134, 0.100) | 21 |
| Comparative Example 1-5 | E | 7.81 | 3.23 | (0.128, 0.111) | 10 |
| Comparative Example 1-6 | F | 6.87 | 2.30 | (0.125, 0.097) | 12 |

As seen from the results of Table 9, the organic light emitting device using the charge generation layer material of the white organic light emitting device of the present disclosure had lower driving voltage and improved light emission efficiency compared to Comparative Examples 1-1 to 1-6.

Such a result is considered to be due to the fact that the compound of the present disclosure used as an N-type charge generation layer formed with the disclosed skeleton having proper length and strength, and flatness and a proper hetero-compound capable of binding to metals forms a gap state in the N-type charge generation layer by doping an alkali metal or an alkaline earth metal thereto, and electrons produced from a P-type charge generation layer are readily injected into an electron transfer layer through the gap state produced in the N-type charge generation layer. Accordingly, the P-type charge generation layer may favorably inject and transfer electrons to the N-type charge generation layer, and as a result, driving voltage was lowered, and efficiency and lifetime were improved in the organic light emitting device.

Experimental Example 2

1) Manufacture of Organic Light Emitting Device

A glass substrate on which indium tin oxide (ITO) was coated as a thin film to a thickness of 1,500 Å was cleaned with distilled water ultrasonic waves. After the cleaning with distilled water was finished, the substrate was ultrasonic cleaned with solvents such as acetone, methanol and isopropyl alcohol, then dried, and UVO treatment was conducted for 5 minutes using UV in a UV cleaner. After that, the substrate was transferred to a plasma cleaner (PT), and after conducting plasma treatment under vacuum for ITO work function and residual film removal, the substrate was transferred to a thermal deposition apparatus for organic deposition.

On the transparent ITO electrode (anode), organic materials were formed in a 2-stack white organic light emitting device (WOLED) structure. As for the first stack, TAPC was thermal vacuum deposited first to a thickness of 300 Å to form a hole transfer layer. After forming the hole transfer layer, a light emitting layer was thermal vacuum deposited thereon as follows. As the light emitting layer, TCz1, a host, was 8% doped with FIrpic, a blue phosphorescent dopant, and deposited to 300 Å. After forming an electron transfer layer to 400 Å using TmPyPB, a compound described in the following Table 10 was 20% doped with $Cs_2CO_3$ and formed to 100 Å as a charge generation layer.

As for the second stack, $MoO_3$ was thermal vacuum deposited first to a thickness of 50 Å to form a hole injection layer. A hole transfer layer, a common layer, was formed to 100 Å by 20% doping $MoO_3$ to TAPC, and then depositing the TAPC to 300 Å. A light emitting layer was formed thereon by 8% doping $Ir(ppy)_3$, a green phosphorescent dopant, to TCz1, a host, and depositing the result to 300 Å, and then an electron transfer layer was formed to 600 Å using TmPyPB. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic light emitting device was manufactured.

Meanwhile, all the organic compounds required to manufacture the OLED were vacuum sublimation purified under $10^{-8}$ torr to $10^{-6}$ torr for each material to be used in the OLED manufacture.

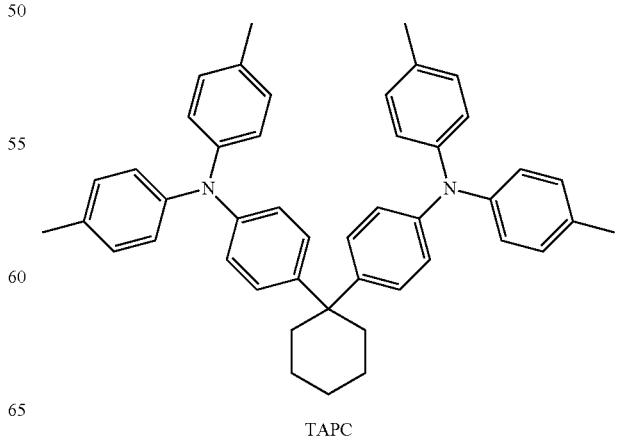

TAPC

505
-continued
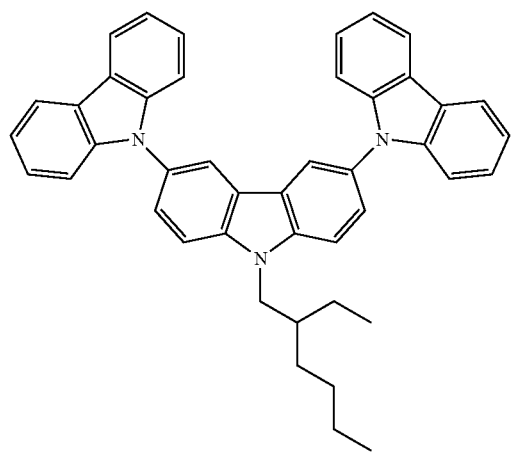
TCz1
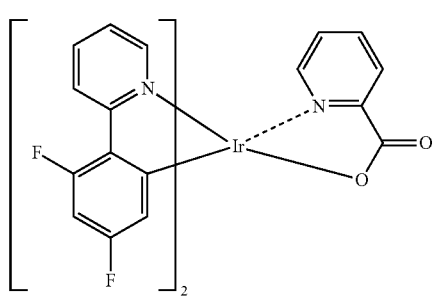
FIrpic
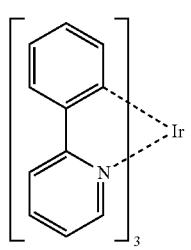
Ir(ppy)3
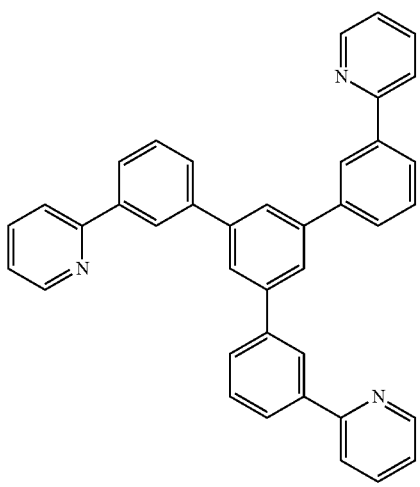
TmPyPB
506
-continued
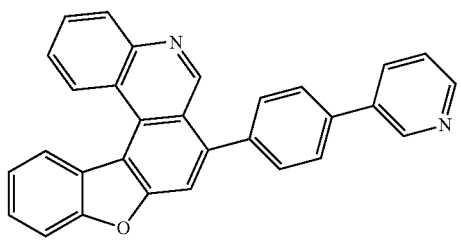
A
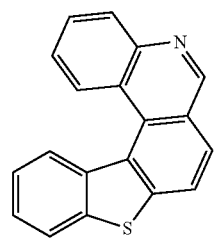
B
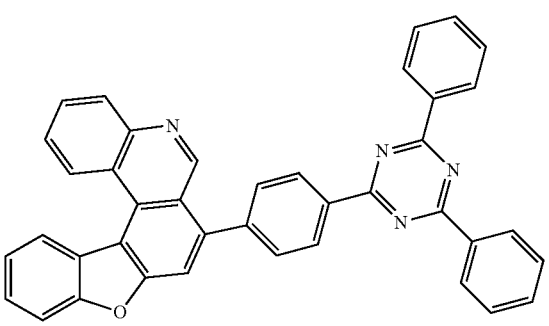
C
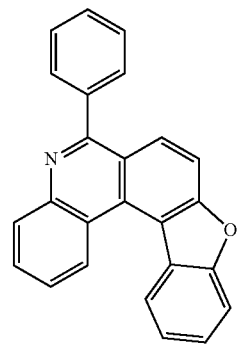
D
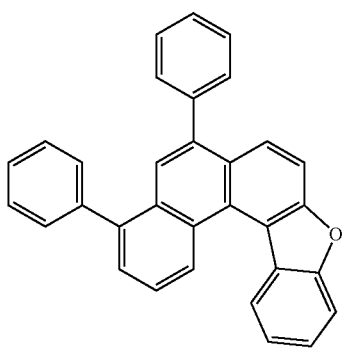
E

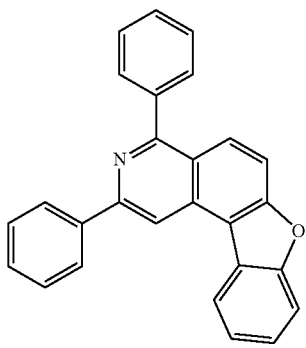

2) Driving Voltage and Light Emission Efficiency of Organic Light Emitting Device For each of the organic light emitting devices manufactured as above, electroluminescent (EL) properties were measured using M7000 manufactured by McScience Inc., and with the measurement results, $T_{95}$ was measured when standard luminance was 3,500 cd/m$^2$ through a lifetime measurement system (M6000) manufactured by McScience Inc. Results of measuring driving voltage, light emission efficiency, external quantum efficiency and color coordinate (CIE) of the white organic light emitting devices manufactured according to the present disclosure are as shown in the following Table 10.

TABLE 10

| | Compound | Driving Voltage (V) | Light Emission Efficiency (cd/A) | CIE (x, y) | Lifetime ($T_{95}$) |
|---|---|---|---|---|---|
| Example 2-1 | 1 | 7.23 | 68.95 | (0.218, 0.427) | 35 |
| Example 2-2 | 4 | 7.02 | 69.45 | (0.220, 0.431) | 49 |
| Example 2-3 | 8 | 7.07 | 64.88 | (0.200, 0.421) | 32 |
| Example 2-4 | 12 | 7.11 | 67.23 | (0.205, 0.411) | 40 |
| Example 2-5 | 15 | 7.65 | 63.21 | (0.221, 0.434) | 33 |
| Example 2-6 | 18 | 7.01 | 69.82 | (0.220, 0.440) | 43 |
| Example 2-7 | 21 | 7.67 | 58.98 | (0.219, 0.411) | 35 |
| Example 2-8 | 25 | 7.10 | 69.45 | (0.219, 0.429) | 40 |
| Example 2-9 | 28 | 7.66 | 59.22 | (0.215, 0.411) | 30 |
| Example 2-10 | 32 | 7.77 | 60.94 | (0.211, 0.419) | 32 |
| Example 2-11 | 35 | 8.24 | 58.26 | (0.209, 0.419) | 31 |
| Example 2-12 | 38 | 8.01 | 59.11 | (0.207, 0.409) | 33 |
| Example 2-13 | 41 | 7.40 | 63.66 | (0,208, 0.415) | 29 |
| Example 2-14 | 44 | 8.06 | 58.03 | (0.208, 0.412) | 52 |
| Example 2-15 | 47 | 8.24 | 57.98 | (0.208, 0.411) | 56 |
| Example 2-16 | 50 | 7.96 | 60.77 | (0.208, 0.412) | 27 |
| Example 2-17 | 53 | 7.88 | 61.29 | (0.209, 0.412) | 30 |
| Example 2-18 | 58 | 8.13 | 59.01 | (0.207, 0.411) | 49 |
| Example 2-19 | 61 | 8.00 | 59.13 | (0.231, 0.440) | 34 |
| Example 2-20 | 63 | 7.82 | 63.22 | (0.232, 0.422) | 26 |
| Example 2-21 | 67 | 7.99 | 63.88 | (0.230, 0.420) | 30 |
| Example 2-22 | 73 | 8.25 | 61.12 | (0.223, 0.433) | 36 |
| Example 2-23 | 76 | 7.76 | 63.47 | (0.222, 0.435) | 31 |
| Example 2-24 | 78 | 8.22 | 60.84 | (0.218, 0.421) | 30 |
| Example 2-25 | 81 | 8.37 | 59.91 | (0.220, 0.421) | 30 |
| Example 2-26 | 83 | 8.25 | 62.56 | (0.224, 0.429) | 32 |
| Example 2-27 | 86 | 7.55 | 60.99 | (0.215, 0.422) | 27 |
| Example 2-28 | 90 | 8.33 | 61.11 | (0.214, 0.420) | 33 |
| Example 2-29 | 92 | 7.74 | 63.32 | (0.230, 0.439) | 37 |
| Example 2-30 | 95 | 7.71 | 65.97 | (0.208, 0.412) | 29 |
| Example 2-31 | 101 | 8.52 | 57.04 | (0.231, 0.418) | 70 |
| Example 2-32 | 103 | 7.78 | 60.01 | (0.208, 0.412) | 32 |
| Example 2-33 | 107 | 8.01 | 59.97 | (0.209, 0.411) | 41 |
| Example 2-34 | 110 | 7.71 | 64.37 | (0.208, 0.412) | 30 |
| Example 2-35 | 113 | 7.82 | 54.67 | (0.233, 0.419) | 30 |
| Example 2-36 | 115 | 7.54 | 63.58 | (0.208, 0.412) | 31 |
| Example 2-37 | 122 | 7.88 | 59.36 | (0.207, 0.417) | 37 |
| Example 2-38 | 124 | 7.71 | 62.03 | (0.220, 0.412) | 29 |
| Example 2-39 | 126 | 8.38 | 59.80 | (0.231, 0.423) | 71 |
| Example 2-40 | 130 | 7.91 | 60.22 | (0.215, 0.411) | 28 |
| Example 2-41 | 135 | 7.97 | 60.94 | (0.211, 0.419) | 31 |
| Example 2-42 | 138 | 8.24 | 58.26 | (0.209, 0.419) | 35 |
| Example 2-43 | 142 | 8.01 | 59.11 | (0.207, 0.409) | 37 |
| Example 2-44 | 144 | 7.23 | 68.95 | (0.218, 0.427) | 35 |
| Example 2-45 | 147 | 7.02 | 69.45 | (0.220, 0.431) | 49 |
| Example 2-46 | 149 | 7.07 | 64.88 | (0.200, 0.421) | 32 |
| Example 2-47 | 152 | 7.11 | 67.23 | (0.205, 0.411) | 40 |
| Example 2-48 | 155 | 7.65 | 63.21 | (0.221, 0.434) | 33 |
| Example 2-49 | 161 | 7.01 | 69.82 | (0.220, 0.440) | 43 |
| Example 2-50 | 164 | 7.67 | 58.98 | (0.219, 0.411) | 35 |
| Example 2-51 | 168 | 7.10 | 69.45 | (0.219, 0.429) | 40 |
| Example 2-52 | 172 | 7.66 | 59.22 | (0.215, 0.411) | 30 |
| Example 2-53 | 174 | 7.77 | 60.94 | (0.211, 0.419) | 32 |
| Example 2-54 | 178 | 8.24 | 58.26 | (0.209, 0.419) | 31 |
| Example 2-55 | 181 | 8.01 | 59.11 | (0.207, 0.409) | 33 |
| Example 2-56 | 186 | 7.40 | 63.66 | (0,208, 0.415) | 29 |
| Example 2-57 | 190 | 8.06 | 58.03 | (0.208, 0.412) | 52 |
| Example 2-58 | 194 | 8.24 | 57.98 | (0.208, 0.411) | 56 |
| Example 2-59 | 198 | 7.96 | 60.77 | (0.208, 0.412) | 27 |
| Example 2-60 | 201 | 7.88 | 61.29 | (0.209, 0.412) | 30 |
| Example 2-61 | 202 | 8.13 | 59.01 | (0.207, 0.411) | 49 |
| Example 2-62 | 206 | 8.00 | 59.13 | (0.231, 0.440) | 34 |
| Example 2-63 | 210 | 7.82 | 63.22 | (0.232, 0.422) | 26 |
| Example 2-64 | 214 | 7.40 | 63.66 | (0,208, 0.415) | 29 |
| Example 2-65 | 218 | 8.06 | 58.03 | (0.208, 0.412) | 52 |
| Example 2-66 | 221 | 8.24 | 57.98 | (0.208, 0.411) | 56 |
| Example 2-67 | 222 | 7.96 | 60.77 | (0.208, 0.412) | 27 |
| Example 2-68 | 226 | 7.88 | 61.29 | (0.209, 0.412) | 30 |
| Example 2-69 | 230 | 8.13 | 59.01 | (0.207, 0.411) | 49 |
| Example 2-70 | 234 | 8.00 | 59.13 | (0.231, 0.440) | 34 |
| Example 2-71 | 238 | 7.82 | 63.22 | (0.232, 0.422) | 26 |
| Example 2-72 | 241 | 7.99 | 63.88 | (0.230, 0.420) | 30 |
| Example 2-73 | 242 | 8.25 | 61.12 | (0.223, 0.433) | 36 |
| Example 2-74 | 246 | 7.76 | 63.47 | (0.222, 0.435) | 31 |
| Example 2-75 | 250 | 8.22 | 60.84 | (0.218, 0.421) | 30 |
| Example 2-76 | 254 | 8.37 | 59.91 | (0.220, 0.421) | 30 |
| Example 2-77 | 258 | 8.25 | 62.56 | (0.224, 0.429) | 32 |
| Example 2-78 | 261 | 7.55 | 60.99 | (0.215, 0.422) | 27 |
| Example 2-79 | 262 | 7.66 | 59.22 | (0.215, 0.411) | 30 |
| Example 2-80 | 266 | 7.77 | 60.94 | (0.211, 0.419) | 32 |
| Example 2-81 | 270 | 8.24 | 58.26 | (0.209, 0.419) | 31 |
| Example 2-82 | 274 | 8.01 | 59.11 | (0.207, 0.409) | 33 |
| Example 2-83 | 278 | 7.40 | 63.66 | (0,208, 0.415) | 29 |
| Example 2-84 | 280 | 8.06 | 58.03 | (0.208, 0.412) | 52 |
| Example 2-85 | 282 | 8.24 | 57.98 | (0.208, 0.411) | 56 |
| Example 2-86 | 286 | 7.96 | 60.77 | (0.208, 0.412) | 27 |
| Example 2-87 | 290 | 7.88 | 61.29 | (0.209, 0.412) | 30 |
| Example 2-88 | 294 | 8.13 | 59.01 | (0.207, 0.411) | 49 |
| Example 2-89 | 298 | 8.00 | 59.13 | (0.231, 0.440) | 34 |
| Example 2-90 | 301 | 7.82 | 63.22 | (0.232, 0.422) | 26 |
| Example 2-91 | 302 | 7.40 | 63.66 | (0,208, 0.415) | 29 |
| Example 2-92 | 306 | 7.74 | 63.32 | (0.230, 0.439) | 37 |
| Example 2-93 | 310 | 7.71 | 65.97 | (0.208, 0.412) | 29 |
| Example 2-94 | 314 | 8.52 | 57.04 | (0.231, 0.418) | 70 |
| Example 2-95 | 318 | 7.78 | 60.01 | (0.208, 0.412) | 32 |
| Example 2-96 | 321 | 8.01 | 59.97 | (0.209, 0.411) | 41 |
| Example 2-97 | 322 | 7.71 | 64.37 | (0.208, 0.412) | 30 |
| Example 2-98 | 326 | 7.82 | 54.67 | (0.233, 0.419) | 30 |
| Example 2-99 | 330 | 7.54 | 63.58 | (0.208, 0.412) | 31 |
| Example 2-100 | 334 | 7.88 | 59.36 | (0.207, 0.417) | 37 |
| Example 2-101 | 338 | 7.71 | 62.03 | (0.220, 0.412) | 29 |
| Example 2-102 | 341 | 8.38 | 59.80 | (0.231, 0.423) | 71 |
| Example 2-103 | 342 | 7.91 | 60.22 | (0.215, 0.411) | 28 |
| Example 2-104 | 346 | 7.97 | 60.94 | (0.211, 0.419) | 31 |
| Example 2-105 | 350 | 8.24 | 58.26 | (0.209, 0.419) | 35 |
| Example 2-106 | 354 | 7.88 | 61.29 | (0.209, 0.412) | 30 |
| Example 2-107 | 358 | 8.13 | 59.01 | (0.207, 0.411) | 49 |
| Example 2-108 | 361 | 8.00 | 59.13 | (0.231, 0.440) | 34 |
| Example 2-109 | 362 | 7.82 | 63.22 | (0.232, 0.422) | 26 |
| Example 2-110 | 366 | 7.40 | 63.66 | (0,208, 0.415) | 29 |
| Example 2-111 | 370 | 7.74 | 63.32 | (0.230, 0.439) | 37 |
| Example 2-112 | 374 | 7.71 | 65.97 | (0.208, 0.412) | 29 |

TABLE 10-continued

| Com-pound | Driving Voltage (V) | Light Emission Efficiency (cd/A) | CIE (x, y) | Lifetime ($T_{95}$) |
|---|---|---|---|---|
| Example 2-113 | 378 | 8.52 | 57.04 | (0.231, 0.418) | 70 |
| Example 2-114 | 381 | 7.78 | 60.01 | (0.208, 0.412) | 32 |
| Example 2-115 | 382 | 8.01 | 59.97 | (0.209, 0.411) | 41 |
| Example 2-116 | 386 | 7.71 | 64.37 | (0.208, 0.412) | 30 |
| Example 2-117 | 390 | 7.82 | 54.67 | (0.233, 0.419) | 30 |
| Example 2-118 | 394 | 7.54 | 63.58 | (0.208, 0.412) | 31 |
| Example 2-119 | 398 | 7.11 | 67.23 | (0.205, 0.411) | 40 |
| Example 2-120 | 401 | 7.65 | 63.21 | (0.221, 0.434) | 33 |
| Example 2-121 | 402 | 7.01 | 69.82 | (0.220, 0.440) | 43 |
| Example 2-122 | 406 | 7.67 | 58.98 | (0.219, 0.411) | 35 |
| Example 2-123 | 410 | 7.10 | 69.45 | (0.219, 0.429) | 40 |
| Example 2-124 | 414 | 7.66 | 59.22 | (0.215, 0.411) | 30 |
| Example 2-125 | 418 | 7.77 | 60.94 | (0.211, 0.419) | 32 |
| Example 2-126 | 421 | 8.24 | 58.26 | (0.209, 0.419) | 31 |
| Example 2-127 | 422 | 8.01 | 59.11 | (0.207, 0.409) | 33 |
| Example 2-128 | 426 | 7.40 | 63.66 | (0.208, 0.415) | 29 |
| Example 2-129 | 430 | 8.06 | 58.03 | (0.208, 0.412) | 52 |
| Example 2-130 | 446 | 8.24 | 57.98 | (0.208, 0.411) | 56 |
| Example 2-131 | 450 | 7.96 | 60.77 | (0.208, 0.412) | 27 |
| Example 2-132 | 454 | 7.88 | 61.29 | (0.209, 0.412) | 30 |
| Example 2-133 | 458 | 8.13 | 59.01 | (0.207, 0.411) | 49 |
| Example 2-134 | 462 | 8.00 | 59.13 | (0.231, 0.440) | 34 |
| Example 2-135 | 466 | 7.82 | 63.22 | (0.232, 0.422) | 26 |
| Example 2-136 | 470 | 7.78 | 60.01 | (0.208, 0.412) | 32 |
| Example 2-137 | 474 | 8.01 | 59.97 | (0.209, 0.411) | 41 |
| Example 2-138 | 478 | 7.71 | 64.37 | (0.208, 0.412) | 30 |
| Example 2-139 | 482 | 7.82 | 54.67 | (0.233, 0.419) | 30 |
| Example 2-140 | 486 | 7.54 | 63.58 | (0.208, 0.412) | 31 |
| Example 2-141 | 490 | 7.11 | 67.23 | (0.205, 0.411) | 40 |
| Example 2-142 | 494 | 7.65 | 63.21 | (0.221, 0.434) | 33 |
| Example 2-143 | 498 | 7.01 | 69.82 | (0.220, 0.440) | 43 |
| Example 2-144 | 502 | 7.67 | 58.98 | (0.219, 0.411) | 35 |
| Example 2-145 | 506 | 7.10 | 69.45 | (0.219, 0.429) | 40 |
| Example 2-146 | 510 | 7.66 | 59.22 | (0.215, 0.411) | 30 |
| Example 2-147 | 514 | 7.77 | 60.94 | (0.211, 0.419) | 32 |
| Example 2-148 | 518 | 8.24 | 58.26 | (0.209, 0.419) | 31 |
| Example 2-149 | 522 | 8.01 | 59.11 | (0.207, 0.409) | 33 |
| Example 2-150 | 526 | 7.55 | 60.99 | (0.215, 0.422) | 27 |
| Example 2-151 | 530 | 7.66 | 59.22 | (0.215, 0.411) | 30 |
| Example 2-152 | 534 | 7.77 | 60.94 | (0.211, 0.419) | 32 |
| Example 2-153 | 538 | 8.24 | 58.26 | (0.209, 0.419) | 31 |
| Example 2-154 | 542 | 8.01 | 59.11 | (0.207, 0.409) | 33 |
| Example 2-155 | 546 | 7.40 | 63.66 | (0.208, 0.415) | 29 |
| Example 2-156 | 550 | 8.06 | 58.03 | (0.208, 0.412) | 52 |
| Example 2-157 | 554 | 8.24 | 57.98 | (0.208, 0.411) | 56 |
| Example 2-158 | 558 | 7.96 | 60.77 | (0.208, 0.412) | 27 |
| Example 2-159 | 562 | 7.88 | 61.29 | (0.209, 0.412) | 30 |
| Example 2-160 | 566 | 8.13 | 59.01 | (0.207, 0.411) | 49 |
| Example 2-161 | 570 | 8.00 | 59.13 | (0.231, 0.440) | 34 |
| Example 2-162 | 574 | 7.82 | 63.22 | (0.232, 0.422) | 26 |
| Example 2-163 | 578 | 7.40 | 63.66 | (0.208, 0.415) | 29 |
| Example 2-164 | 582 | 7.74 | 63.32 | (0.230, 0.439) | 37 |
| Example 2-165 | 586 | 7.71 | 65.97 | (0.208, 0.412) | 29 |
| Example 2-166 | 590 | 8.52 | 57.04 | (0.231, 0.418) | 70 |
| Example 2-167 | 594 | 7.78 | 60.01 | (0.208, 0.412) | 32 |
| Example 2-168 | 598 | 8.01 | 59.97 | (0.209, 0.411) | 41 |
| Example 2-169 | 602 | 7.71 | 64.37 | (0.208, 0.412) | 30 |
| Example 2-170 | 606 | 7.82 | 54.67 | (0.233, 0.419) | 30 |
| Example 2-171 | 610 | 7.54 | 63.58 | (0.208, 0.412) | 31 |
| Example 2-172 | 614 | 7.88 | 59.36 | (0.207, 0.417) | 37 |
| Example 2-173 | 618 | 7.71 | 62.03 | (0.220, 0.412) | 29 |
| Example 2-174 | 622 | 7.82 | 63.22 | (0.232, 0.422) | 26 |
| Example 2-175 | 626 | 7.40 | 63.66 | (0.208, 0.415) | 29 |
| Example 2-176 | 630 | 7.74 | 63.32 | (0.230, 0.439) | 37 |
| Example 2-177 | 634 | 7.71 | 65.97 | (0.208, 0.412) | 29 |
| Example 2-178 | 638 | 8.52 | 57.04 | (0.231, 0.418) | 70 |
| Example 2-179 | 642 | 7.78 | 60.01 | (0.208, 0.412) | 32 |
| Example 2-180 | 646 | 8.01 | 59.97 | (0.209, 0.411) | 41 |
| Example 2-181 | 650 | 7.71 | 64.37 | (0.208, 0.412) | 30 |
| Example 2-182 | 654 | 7.82 | 54.67 | (0.233, 0.419) | 30 |
| Example 2-183 | 658 | 7.54 | 63.58 | (0.208, 0.412) | 31 |
| Example 2-184 | 662 | 7.88 | 59.36 | (0.207, 0.417) | 37 |
| Example 2-185 | 666 | 7.71 | 62.03 | (0.220, 0.412) | 29 |
| Example 2-186 | 670 | 7.66 | 59.22 | (0.215, 0.411) | 30 |
| Example 2-187 | 674 | 7.77 | 60.94 | (0.211, 0.419) | 32 |
| Example 2-188 | 678 | 8.24 | 58.26 | (0.209, 0.419) | 31 |
| Example 2-189 | 682 | 8.01 | 59.11 | (0.207, 0.409) | 33 |
| Example 2-190 | 686 | 7.55 | 60.99 | (0.215, 0.422) | 27 |
| Example 2-191 | 690 | 7.66 | 59.22 | (0.215, 0.411) | 30 |
| Example 2-192 | 694 | 7.77 | 60.94 | (0.211, 0.419) | 32 |
| Example 2-193 | 698 | 7.45 | 71.80 | (0.210, 0.418) | 35 |
| Example 2-194 | 702 | 7.11 | 67.23 | (0.205, 0.411) | 40 |
| Example 2-195 | 706 | 7.65 | 63.21 | (0.221, 0.434) | 33 |
| Example 2-196 | 710 | 7.01 | 69.82 | (0.220, 0.440) | 43 |
| Example 2-197 | 714 | 7.67 | 58.98 | (0.219, 0.411) | 35 |
| Example 2-198 | 718 | 7.10 | 69.45 | (0.219, 0.429) | 40 |
| Example 2-199 | 722 | 7.66 | 59.22 | (0.215, 0.411) | 30 |
| Example 2-200 | 726 | 7.77 | 60.94 | (0.211, 0.419) | 32 |
| Example 2-201 | 730 | 8.24 | 58.26 | (0.209, 0.419) | 31 |
| Example 2-202 | 734 | 8.01 | 59.11 | (0.207, 0.409) | 33 |
| Example 2-203 | 738 | 7.40 | 63.66 | (0.208, 0.415) | 29 |
| Example 2-204 | 742 | 8.06 | 58.03 | (0.208, 0.412) | 52 |
| Example 2-205 | 746 | 8.24 | 57.98 | (0.208, 0.411) | 56 |
| Example 2-206 | 750 | 7.96 | 60.77 | (0.208, 0.412) | 27 |
| Example 2-207 | 754 | 7.88 | 61.29 | (0.209, 0.412) | 30 |
| Example 2-208 | 758 | 8.13 | 59.01 | (0.207, 0.411) | 49 |
| Example 2-209 | 762 | 8.00 | 59.13 | (0.231, 0.440) | 34 |
| Example 2-210 | 766 | 7.82 | 63.22 | (0.232, 0.422) | 26 |
| Example 2-211 | 770 | 7.66 | 59.22 | (0.215, 0.411) | 30 |
| Example 2-212 | 774 | 7.77 | 60.94 | (0.211, 0.419) | 32 |
| Example 2-213 | 778 | 8.24 | 58.26 | (0.209, 0.419) | 31 |
| Example 2-214 | 782 | 8.01 | 59.11 | (0.207, 0.409) | 33 |
| Example 2-215 | 786 | 7.40 | 63.66 | (0.208, 0.415) | 29 |
| Example 2-216 | 790 | 8.06 | 58.03 | (0.208, 0.412) | 52 |
| Example 2-217 | 794 | 8.24 | 57.98 | (0.208, 0.411) | 56 |
| Example 2-218 | 898 | 7.96 | 60.77 | (0.208, 0.412) | 27 |
| Example 2-219 | 802 | 7.88 | 61.29 | (0.209, 0.412) | 30 |
| Example 2-220 | 806 | 8.13 | 59.01 | (0.207, 0.411) | 49 |
| Example 2-221 | 810 | 7.71 | 64.37 | (0.208, 0.412) | 30 |
| Example 2-222 | 814 | 7.82 | 54.67 | (0.233, 0.419) | 30 |
| Example 2-223 | 818 | 7.54 | 63.58 | (0.208, 0.412) | 31 |
| Example 2-224 | 822 | 7.88 | 59.36 | (0.207, 0.417) | 37 |
| Example 2-225 | 826 | 7.71 | 62.03 | (0.220, 0.412) | 29 |
| Example 2-226 | 830 | 7.82 | 63.22 | (0.232, 0.422) | 26 |
| Comparative Example 2-1 | A | 2.82 | 23.23 | (0.134, 0.110) | 21 |
| Comparative Example 2-2 | B | 3.80 | 32.32 | (0.134, 0.111) | 19 |
| Comparative Example 2-3 | C | 5.64 | 15.65 | (0.128, 0.099) | 8 |
| Comparative Example 2-4 | D | 3.20 | 18.22 | (0.119, 0.100) | 11 |
| Comparative Example 2-5 | E | 6.54 | 10.88 | (0.128, 0.111) | 9 |
| Comparative Example 2-6 | F | 2.34 | 9.86 | (0.125, 0.097) | 15 |

As seen from the results of Table 10, the organic light emitting device using the charge generation layer material of the 2-stack white organic light emitting device of the present disclosure had improved light emission efficiency and lifetime compared to Comparative Examples 2-1 to 2-6.

Such a result is considered to be due to the fact that the compound of the present disclosure used as an N-type charge generation layer formed with the disclosed skeleton having proper length and strength, and flatness and a proper hetero-compound capable of binding to metals forms a gap state in the N-type charge generation layer by doping an alkali metal or an alkaline earth metal thereto, and electrons produced from a P-type charge generation layer are readily injected into an electron transfer layer through the gap state produced in the N-type charge generation layer. Accordingly, the P-type charge generation layer may favorably inject and transfer electrons to the N-type charge generation layer, and as a result, driving voltage was lowered, and efficiency and lifetime were improved in the organic light emitting device.

Experimental Example 3

1) Manufacture of Organic Light Emitting Device

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

Next, the ITO substrate was installed in a substrate folder of a vacuum deposition apparatus, and the following 4,4',4''-tris(N,N-(2-naphthyl)-phenylamino)triphenylamine (2-TNATA) was introduced to a cell in the vacuum deposition apparatus.

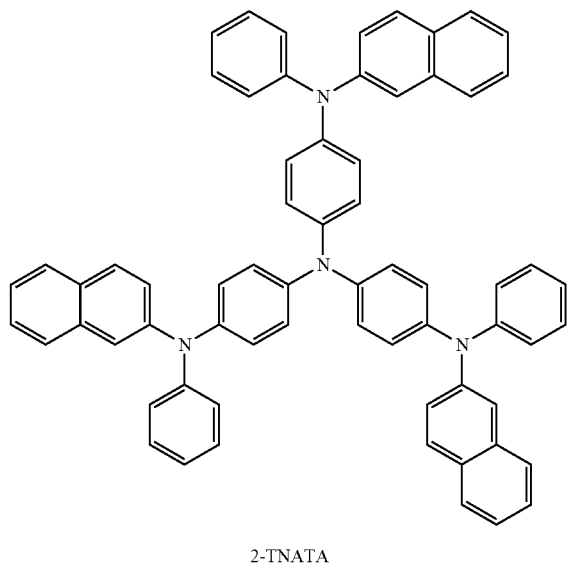

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell in the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

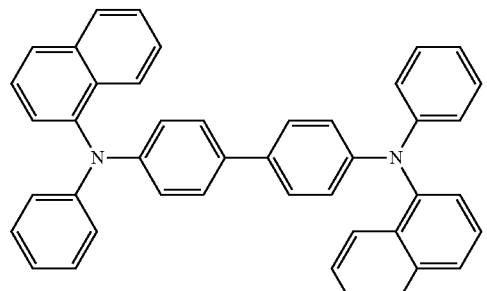

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

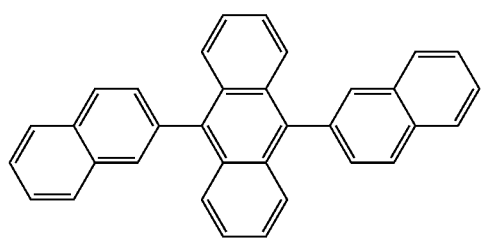

H1

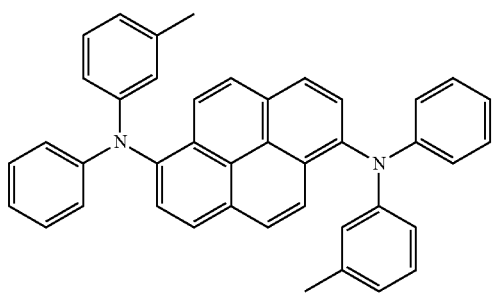

D1

Subsequently, a compound of the following Table 11 was deposited to a thickness of 300 Å as an electron transfer layer.

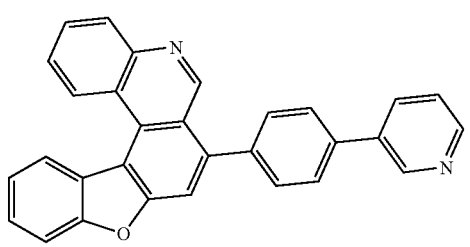

A

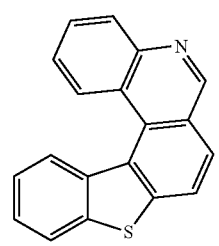

B

-continued

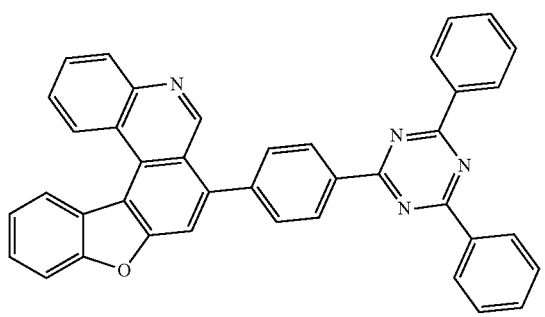

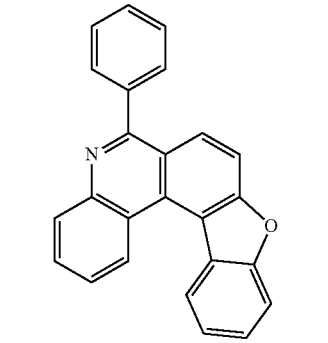

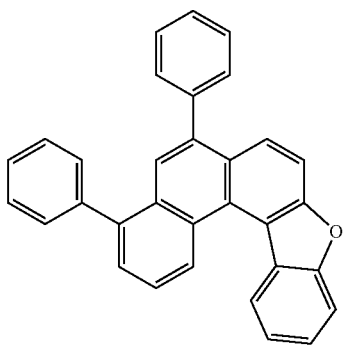

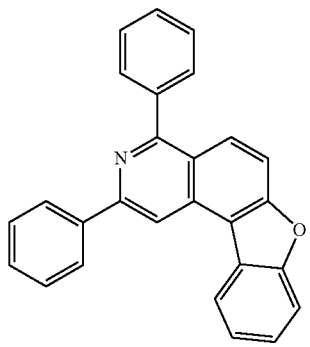

As an electron injection layer, lithium fluoride (LiF) was deposited to a thickness of 10 Å, and an Al cathode was employed to a thickness of 1,000 Å, and as a result, an OLED was manufactured.

Meanwhile, all the organic compounds required to manufacture the OLED were vacuum sublimation purified under $10^{-8}$ torr to $10^{-6}$ torr by each material to be used in the OLED manufacture.

2) Driving Voltage and Light Emission Efficiency of Organic Light Emitting Device For each of the organic light emitting devices manufactured as above, electroluminescent (EL) properties were measured using M7000 manufactured by McScience Inc., and with the measurement results, $T_{95}$ was measured when standard luminance was 700 cd/m² through a lifetime measurement system (M6000) manufactured by McScience Inc. Results of measuring driving voltage, light emission efficiency, external quantum efficiency and color coordinate (CIE) of the white organic light emitting devices manufactured according to the present disclosure are as shown in Table 11.

TABLE 11

| | Compound | Driving Voltage (V) | Light Emission Efficiency (cd/A) | CIE (x, y) | Lifetime ($T_{95}$) |
|---|---|---|---|---|---|
| Example 3-1 | 1 | 5.50 | 6.32 | (0.134, 0.101) | 33 |
| Example 3-2 | 4 | 5.44 | 6.44 | (0.134, 0.102) | 32 |
| Example 3-3 | 8 | 5.34 | 6.38 | (0.134, 0.101) | 31 |
| Example 3-4 | 12 | 5.38 | 6.20 | (0.134, 0.103) | 35 |
| Example 3-5 | 15 | 5.60 | 6.12 | (0.134, 0.102) | 34 |
| Example 3-6 | 18 | 5.45 | 6.01 | (0.134, 0.101) | 33 |
| Example 3-7 | 21 | 5.44 | 6.22 | (0.134, 0.102) | 30 |
| Example 3-8 | 25 | 5.46 | 6.18 | (0.134, 0.101) | 29 |
| Example 3-9 | 28 | 5.40 | 6.13 | (0.134, 0.101) | 31 |
| Example 3-10 | 32 | 5.44 | 6.30 | (0.134, 0.100) | 32 |
| Example 3-11 | 35 | 5.37 | 6.35 | (0.134, 0.101) | 32 |
| Example 3-12 | 38 | 5.38 | 6.41 | (0.134, 0.100) | 30 |
| Example 3-13 | 41 | 4.81 | 6.93 | (0.134, 0.100) | 30 |
| Example 3-14 | 44 | 5.48 | 6.21 | (0.134, 0.100) | 87 |
| Example 3-15 | 47 | 5.47 | 6.28 | (0.134, 0.100) | 79 |
| Example 3-16 | 50 | 4.45 | 6.98 | (0.134, 0.100) | 42 |
| Example 3-17 | 53 | 4.52 | 6.63 | (0.134, 0.102) | 44 |
| Example 3-18 | 58 | 5.12 | 6.20 | (0.134, 0.101) | 40 |
| Example 3-19 | 61 | 4.39 | 6.87 | (0.134, 0.102) | 43 |
| Example 3-20 | 63 | 4.71 | 6.48 | (0.134, 0.100) | 34 |
| Example 3-21 | 67 | 4.38 | 7.00 | (0.134, 0.103) | 39 |
| Example 3-22 | 73 | 5.34 | 6.31 | (0.134, 0.100) | 36 |
| Example 3-23 | 76 | 5.40 | 6.36 | (0.134, 0.102) | 32 |
| Example 3-24 | 78 | 5.42 | 6.26 | (0.134, 0.101) | 32 |
| Example 3-25 | 81 | 5.39 | 6.19 | (0.134, 0.100) | 31 |
| Example 3-26 | 83 | 5.55 | 6.27 | (0.134, 0.102) | 31 |
| Example 3-27 | 86 | 4.98 | 6.20 | (0.134, 0.103) | 30 |
| Example 3-28 | 90 | 5.41 | 6.19 | (0.134, 0.100) | 32 |
| Example 3-29 | 92 | 5.22 | 6.28 | (0.134, 0.103) | 36 |
| Example 3-30 | 95 | 5.19 | 6.41 | (0.134, 0.102) | 33 |
| Example 3-31 | 101 | 5.43 | 6.17 | (0.134, 0.100) | 62 |
| Example 3-32 | 103 | 4.94 | 6.85 | (0.134, 0.099) | 40 |
| Example 3-33 | 107 | 4.51 | 6.97 | (0.134, 0.102) | 42 |
| Example 3-34 | 110 | 4.45 | 7.03 | (0.134, 0.100) | 39 |
| Example 3-35 | 113 | 5.00 | 6.21 | (0.134, 0.103) | 32 |
| Example 3-36 | 115 | 4.93 | 6.35 | (0.134, 0.101) | 35 |
| Example 3-37 | 122 | 4.50 | 6.92 | (0.134, 0.104) | 41 |
| Example 3-38 | 124 | 5.03 | 6.27 | (0.134, 0.100) | 35 |
| Example 3-39 | 126 | 5.11 | 6.22 | (0.134, 0.103) | 36 |
| Example 3-40 | 130 | 5.01 | 6.98 | (0.134, 0.100) | 31 |
| Example 3-41 | 135 | 4.98 | 7.10 | (0.134, 0.103) | 33 |
| Example 3-42 | 138 | 5.34 | 6.21 | (0.134, 0.100) | 36 |
| Example 3-43 | 142 | 5.40 | 6.36 | (0.134, 0.102) | 39 |
| Example 3-44 | 144 | 5.42 | 6.26 | (0.134, 0.101) | 32 |
| Example 3-45 | 147 | 5.39 | 6.19 | (0.134, 0.100) | 31 |
| Example 3-46 | 149 | 5.55 | 6.27 | (0.134, 0.102) | 31 |
| Example 3-47 | 152 | 4.98 | 6.20 | (0.134, 0.103) | 30 |
| Example 3-48 | 155 | 5.41 | 6.19 | (0.134, 0.100) | 32 |
| Example 3-49 | 161 | 5.22 | 6.28 | (0.134, 0.103) | 36 |
| Example 3-50 | 164 | 5.19 | 6.41 | (0.134, 0.102) | 33 |
| Example 3-51 | 168 | 5.43 | 6.17 | (0.134, 0.100) | 62 |
| Example 3-52 | 172 | 4.94 | 6.85 | (0.134, 0.099) | 40 |
| Example 3-53 | 174 | 4.51 | 6.97 | (0.134, 0.102) | 42 |
| Example 3-54 | 178 | 4.45 | 7.03 | (0.134, 0.100) | 39 |
| Example 3-55 | 181 | 5.00 | 6.21 | (0.134, 0.103) | 32 |
| Example 3-56 | 186 | 5.43 | 6.17 | (0.134, 0.100) | 62 |
| Example 3-57 | 190 | 4.94 | 6.85 | (0.134, 0.099) | 40 |

TABLE 11-continued

| Compound | Driving Voltage (V) | Light Emission Efficiency (cd/A) | CIE (x, y) | Lifetime ($T_{95}$) |
|---|---|---|---|---|
| Example 3-58 | 194 | 4.51 | 6.97 | (0.134, 0.102) | 42 |
| Example 3-59 | 198 | 4.45 | 7.03 | (0.134, 0.100) | 39 |
| Example 3-60 | 201 | 5.00 | 6.21 | (0.134, 0.103) | 32 |
| Example 3-61 | 202 | 4.93 | 6.35 | (0.134, 0.101) | 35 |
| Example 3-62 | 206 | 4.50 | 6.92 | (0.134, 0.104) | 41 |
| Example 3-63 | 210 | 5.03 | 6.27 | (0.134, 0.100) | 35 |
| Example 3-64 | 214 | 5.11 | 6.22 | (0.134, 0.103) | 36 |
| Example 3-65 | 218 | 5.01 | 6.98 | (0.134, 0.100) | 31 |
| Example 3-66 | 221 | 4.98 | 7.10 | (0.134, 0.103) | 33 |
| Example 3-67 | 222 | 5.34 | 6.21 | (0.134, 0.100) | 36 |
| Example 3-68 | 226 | 5.40 | 6.36 | (0.134, 0.102) | 39 |
| Example 3-69 | 230 | 5.42 | 6.26 | (0.134, 0.101) | 32 |
| Example 3-70 | 234 | 5.22 | 6.28 | (0.134, 0.103) | 36 |
| Example 3-71 | 238 | 5.19 | 6.41 | (0.134, 0.102) | 33 |
| Example 3-72 | 241 | 5.43 | 6.17 | (0.134, 0.100) | 62 |
| Example 3-73 | 242 | 4.94 | 6.85 | (0.134, 0.099) | 40 |
| Example 3-74 | 246 | 4.51 | 6.97 | (0.134, 0.102) | 42 |
| Example 3-75 | 250 | 4.45 | 7.03 | (0.134, 0.100) | 39 |
| Example 3-76 | 254 | 5.00 | 6.21 | (0.134, 0.103) | 32 |
| Example 3-77 | 258 | 5.43 | 6.17 | (0.134, 0.100) | 62 |
| Example 3-78 | 261 | 4.94 | 6.85 | (0.134, 0.099) | 40 |
| Example 3-79 | 262 | 4.51 | 6.97 | (0.134, 0.102) | 42 |
| Example 3-80 | 266 | 4.45 | 7.03 | (0.134, 0.100) | 39 |
| Example 3-81 | 270 | 5.00 | 6.21 | (0.134, 0.103) | 32 |
| Example 3-82 | 274 | 4.93 | 6.35 | (0.134, 0.101) | 35 |
| Example 3-83 | 278 | 4.94 | 6.85 | (0.134, 0.099) | 40 |
| Example 3-84 | 280 | 4.51 | 6.97 | (0.134, 0.102) | 42 |
| Example 3-85 | 282 | 4.45 | 7.03 | (0.134, 0.100) | 39 |
| Example 3-86 | 286 | 5.00 | 6.21 | (0.134, 0.103) | 32 |
| Example 3-87 | 290 | 4.93 | 6.35 | (0.134, 0.101) | 35 |
| Example 3-88 | 294 | 4.50 | 6.92 | (0.134, 0.104) | 41 |
| Example 3-89 | 298 | 5.03 | 6.27 | (0.134, 0.100) | 35 |
| Example 3-90 | 301 | 5.11 | 6.22 | (0.134, 0.103) | 36 |
| Example 3-91 | 302 | 5.01 | 6.98 | (0.134, 0.100) | 31 |
| Example 3-92 | 306 | 4.98 | 7.10 | (0.134, 0.103) | 33 |
| Example 3-93 | 310 | 5.01 | 6.98 | (0.134, 0.100) | 31 |
| Example 3-94 | 314 | 4.98 | 7.10 | (0.134, 0.103) | 33 |
| Example 3-95 | 318 | 5.34 | 6.21 | (0.134, 0.100) | 36 |
| Example 3-96 | 321 | 5.40 | 6.36 | (0.134, 0.102) | 39 |
| Example 3-97 | 322 | 5.42 | 6.26 | (0.134, 0.101) | 32 |
| Example 3-98 | 326 | 5.22 | 6.28 | (0.134, 0.103) | 36 |
| Example 3-99 | 330 | 5.19 | 6.41 | (0.134, 0.102) | 33 |
| Example 3-100 | 334 | 5.43 | 6.17 | (0.134, 0.100) | 62 |
| Example 3-101 | 338 | 4.94 | 6.85 | (0.134, 0.099) | 40 |
| Example 3-102 | 341 | 4.51 | 6.97 | (0.134, 0.102) | 42 |
| Example 3-103 | 342 | 4.45 | 7.03 | (0.134, 0.100) | 39 |
| Example 3-104 | 346 | 5.00 | 6.21 | (0.134, 0.103) | 32 |
| Example 3-105 | 350 | 5.43 | 6.17 | (0.134, 0.100) | 62 |
| Example 3-106 | 354 | 5.22 | 6.28 | (0.134, 0.103) | 36 |
| Example 3-107 | 358 | 5.19 | 6.41 | (0.134, 0.102) | 33 |
| Example 3-108 | 361 | 5.43 | 6.17 | (0.134, 0.100) | 62 |
| Example 3-109 | 362 | 4.94 | 6.85 | (0.134, 0.099) | 40 |
| Example 3-110 | 366 | 4.51 | 6.97 | (0.134, 0.102) | 42 |
| Example 3-111 | 370 | 4.45 | 7.03 | (0.134, 0.100) | 39 |
| Example 3-112 | 374 | 5.00 | 6.21 | (0.134, 0.103) | 32 |
| Example 3-113 | 378 | 5.43 | 6.17 | (0.134, 0.100) | 62 |
| Example 3-114 | 381 | 4.94 | 6.85 | (0.134, 0.099) | 40 |
| Example 3-115 | 382 | 4.51 | 6.97 | (0.134, 0.102) | 42 |
| Example 3-116 | 386 | 4.45 | 7.03 | (0.134, 0.100) | 39 |
| Example 3-117 | 390 | 5.00 | 6.21 | (0.134, 0.103) | 32 |
| Example 3-118 | 394 | 4.93 | 6.35 | (0.134, 0.101) | 35 |
| Example 3-119 | 398 | 4.50 | 6.92 | (0.134, 0.104) | 41 |
| Example 3-120 | 401 | 5.03 | 6.27 | (0.134, 0.100) | 35 |
| Example 3-121 | 402 | 5.48 | 6.21 | (0.134, 0.100) | 87 |
| Example 3-122 | 406 | 5.47 | 6.28 | (0.134, 0.100) | 79 |
| Example 3-123 | 410 | 4.45 | 6.98 | (0.134, 0.100) | 42 |
| Example 3-124 | 414 | 4.52 | 6.63 | (0.134, 0.102) | 44 |
| Example 3-125 | 418 | 5.12 | 6.20 | (0.134, 0.101) | 40 |
| Example 3-126 | 421 | 4.39 | 6.87 | (0.134, 0.102) | 43 |
| Example 3-127 | 422 | 4.71 | 6.48 | (0.134, 0.100) | 34 |
| Example 3-128 | 426 | 4.38 | 7.00 | (0.134, 0.103) | 39 |
| Example 3-129 | 430 | 5.34 | 6.31 | (0.134, 0.100) | 36 |
| Example 3-130 | 446 | 5.40 | 6.36 | (0.134, 0.102) | 32 |
| Example 3-131 | 450 | 5.42 | 6.26 | (0.134, 0.101) | 32 |
| Example 3-132 | 454 | 5.39 | 6.19 | (0.134, 0.100) | 31 |
| Example 3-133 | 458 | 5.55 | 6.27 | (0.134, 0.102) | 31 |
| Example 3-134 | 462 | 4.98 | 6.20 | (0.134, 0.103) | 30 |
| Example 3-135 | 466 | 5.41 | 6.19 | (0.134, 0.100) | 32 |
| Example 3-136 | 470 | 5.22 | 6.28 | (0.134, 0.103) | 36 |
| Example 3-137 | 474 | 5.19 | 6.41 | (0.134, 0.102) | 33 |
| Example 3-138 | 478 | 5.43 | 6.17 | (0.134, 0.100) | 62 |
| Example 3-139 | 482 | 4.94 | 6.85 | (0.134, 0.099) | 40 |
| Example 3-140 | 486 | 4.51 | 6.97 | (0.134, 0.102) | 42 |
| Example 3-141 | 490 | 4.45 | 7.03 | (0.134, 0.100) | 39 |
| Example 3-142 | 494 | 5.00 | 6.21 | (0.134, 0.103) | 32 |
| Example 3-143 | 498 | 4.93 | 6.35 | (0.134, 0.101) | 35 |
| Example 3-144 | 502 | 4.50 | 6.92 | (0.134, 0.104) | 41 |
| Example 3-145 | 506 | 5.03 | 6.27 | (0.134, 0.100) | 35 |
| Example 3-146 | 510 | 5.11 | 6.22 | (0.134, 0.103) | 36 |
| Example 3-147 | 514 | 5.01 | 6.98 | (0.134, 0.100) | 31 |
| Example 3-148 | 518 | 4.98 | 7.10 | (0.134, 0.103) | 33 |
| Example 3-149 | 522 | 5.34 | 6.21 | (0.134, 0.100) | 36 |
| Example 3-150 | 526 | 5.40 | 6.36 | (0.134, 0.102) | 39 |
| Example 3-151 | 530 | 5.42 | 6.26 | (0.134, 0.101) | 32 |
| Example 3-152 | 534 | 5.39 | 6.19 | (0.134, 0.100) | 31 |
| Example 3-153 | 538 | 5.55 | 6.27 | (0.134, 0.102) | 31 |
| Example 3-154 | 542 | 4.98 | 6.20 | (0.134, 0.103) | 30 |
| Example 3-155 | 546 | 5.41 | 6.19 | (0.134, 0.100) | 32 |
| Example 3-156 | 550 | 5.22 | 6.28 | (0.134, 0.103) | 36 |
| Example 3-157 | 554 | 5.19 | 6.41 | (0.134, 0.102) | 33 |
| Example 3-158 | 558 | 5.43 | 6.17 | (0.134, 0.100) | 62 |
| Example 3-159 | 562 | 4.94 | 6.85 | (0.134, 0.099) | 40 |
| Example 3-160 | 566 | 4.51 | 6.97 | (0.134, 0.102) | 42 |
| Example 3-161 | 570 | 4.45 | 7.03 | (0.134, 0.100) | 39 |
| Example 3-162 | 574 | 5.00 | 6.21 | (0.134, 0.103) | 32 |
| Example 3-163 | 578 | 5.43 | 6.17 | (0.134, 0.100) | 62 |
| Example 3-164 | 582 | 4.94 | 6.85 | (0.134, 0.099) | 40 |
| Example 3-165 | 586 | 5.43 | 6.17 | (0.134, 0.100) | 62 |
| Example 3-166 | 590 | 4.94 | 6.85 | (0.134, 0.099) | 40 |
| Example 3-167 | 594 | 4.51 | 6.97 | (0.134, 0.102) | 42 |
| Example 3-168 | 598 | 4.45 | 7.03 | (0.134, 0.100) | 39 |
| Example 3-169 | 602 | 5.00 | 6.21 | (0.134, 0.103) | 32 |
| Example 3-170 | 606 | 5.43 | 6.17 | (0.134, 0.100) | 62 |
| Example 3-171 | 610 | 4.94 | 6.85 | (0.134, 0.099) | 40 |
| Example 3-172 | 614 | 4.51 | 6.97 | (0.134, 0.102) | 42 |
| Example 3-173 | 618 | 4.45 | 7.03 | (0.134, 0.100) | 39 |
| Example 3-174 | 622 | 5.00 | 6.21 | (0.134, 0.103) | 32 |
| Example 3-175 | 626 | 4.93 | 6.35 | (0.134, 0.101) | 35 |
| Example 3-176 | 630 | 4.50 | 6.92 | (0.134, 0.104) | 41 |
| Example 3-177 | 634 | 5.03 | 6.27 | (0.134, 0.100) | 35 |
| Example 3-178 | 638 | 5.48 | 6.21 | (0.134, 0.100) | 87 |
| Example 3-179 | 642 | 5.47 | 6.28 | (0.134, 0.100) | 79 |
| Example 3-180 | 646 | 4.45 | 6.98 | (0.134, 0.100) | 42 |
| Example 3-181 | 650 | 4.52 | 6.63 | (0.134, 0.102) | 44 |
| Example 3-182 | 654 | 5.12 | 6.20 | (0.134, 0.101) | 40 |
| Example 3-183 | 658 | 4.39 | 6.87 | (0.134, 0.102) | 43 |
| Example 3-184 | 662 | 4.71 | 6.48 | (0.134, 0.100) | 34 |
| Example 3-185 | 666 | 5.22 | 6.28 | (0.134, 0.103) | 36 |
| Example 3-186 | 670 | 5.19 | 6.41 | (0.134, 0.102) | 33 |
| Example 3-187 | 674 | 5.43 | 6.17 | (0.134, 0.100) | 62 |
| Example 3-188 | 678 | 4.94 | 6.85 | (0.134, 0.099) | 40 |
| Example 3-189 | 682 | 4.51 | 6.97 | (0.134, 0.102) | 42 |
| Example 3-190 | 686 | 4.45 | 7.03 | (0.134, 0.100) | 39 |
| Example 3-191 | 690 | 5.00 | 6.21 | (0.134, 0.103) | 32 |
| Example 3-192 | 694 | 5.43 | 6.17 | (0.134, 0.100) | 62 |
| Example 3-193 | 698 | 4.94 | 6.85 | (0.134, 0.099) | 40 |
| Example 3-194 | 702 | 5.43 | 6.17 | (0.134, 0.100) | 62 |
| Example 3-195 | 706 | 4.94 | 6.85 | (0.134, 0.099) | 40 |
| Example 3-196 | 710 | 4.51 | 6.97 | (0.134, 0.102) | 42 |
| Example 3-197 | 714 | 5.01 | 6.98 | (0.134, 0.100) | 31 |
| Example 3-198 | 718 | 4.98 | 7.10 | (0.134, 0.103) | 33 |
| Example 3-199 | 722 | 5.34 | 6.21 | (0.134, 0.100) | 36 |
| Example 3-200 | 726 | 5.40 | 6.36 | (0.134, 0.102) | 39 |
| Example 3-201 | 730 | 5.42 | 6.26 | (0.134, 0.101) | 32 |
| Example 3-202 | 734 | 5.39 | 6.19 | (0.134, 0.100) | 31 |
| Example 3-203 | 738 | 5.55 | 6.27 | (0.134, 0.102) | 31 |
| Example 3-204 | 742 | 4.98 | 6.20 | (0.134, 0.103) | 30 |
| Example 3-205 | 746 | 5.41 | 6.19 | (0.134, 0.100) | 32 |
| Example 3-206 | 750 | 5.22 | 6.28 | (0.134, 0.103) | 36 |
| Example 3-207 | 754 | 4.51 | 6.97 | (0.134, 0.102) | 42 |

TABLE 11-continued

| Compound | Driving Voltage (V) | Light Emission Efficiency (cd/A) | CIE (x, y) | Lifetime ($T_{95}$) |
|---|---|---|---|---|
| Example 3-208 | 758 | 4.45 | 7.03 | (0.134, 0.100) | 39 |
| Example 3-209 | 762 | 5.00 | 6.21 | (0.134, 0.103) | 32 |
| Example 3-210 | 766 | 4.93 | 6.35 | (0.134, 0.101) | 35 |
| Example 3-211 | 770 | 4.50 | 6.92 | (0.134, 0.104) | 41 |
| Example 3-212 | 774 | 5.03 | 6.27 | (0.134, 0.100) | 35 |
| Example 3-213 | 778 | 5.11 | 6.22 | (0.134, 0.103) | 36 |
| Example 3-214 | 782 | 5.01 | 6.98 | (0.134, 0.100) | 31 |
| Example 3-215 | 786 | 4.98 | 7.10 | (0.134, 0.103) | 33 |
| Example 3-216 | 790 | 5.01 | 6.98 | (0.134, 0.100) | 31 |
| Example 3-217 | 794 | 4.98 | 7.10 | (0.134, 0.103) | 33 |
| Example 3-218 | 898 | 5.34 | 6.21 | (0.134, 0.100) | 36 |
| Example 3-219 | 802 | 5.22 | 6.28 | (0.134, 0.103) | 36 |
| Example 3-220 | 806 | 5.19 | 6.41 | (0.134, 0.102) | 33 |
| Example 3-221 | 810 | 5.43 | 6.17 | (0.134, 0.100) | 62 |
| Example 3-222 | 814 | 4.94 | 6.85 | (0.134, 0.099) | 40 |
| Example 3-223 | 818 | 4.51 | 6.97 | (0.134, 0.102) | 42 |
| Example 3-224 | 822 | 4.50 | 6.92 | (0.134, 0.104) | 41 |
| Example 3-225 | 826 | 5.43 | 6.17 | (0.134, 0.100) | 62 |
| Example 3-226 | 830 | 4.94 | 6.85 | (0.134, 0.099) | 40 |
| Comparative Example 3-1 | A | 2.82 | 2.23 | (0.134, 0.110) | 15 |
| Comparative Example 3-2 | B | 3.80 | 4.32 | (0.134, 0.111) | 20 |
| Comparative Example 3-3 | C | 1.78 | 3.39 | (0.128, 0.099) | 11 |
| Comparative Example 3-4 | D | 3.56 | 1.23 | (0.119, 0.100) | 9 |
| Comparative Example 3-5 | E | 1.89 | 2.23 | (0.128, 0.111) | 10 |
| Comparative Example 3-6 | F | 2.13 | 1.30 | (0.125, 0.097) | 11 |

As seen from the results of Table 11, the organic light emitting device using the electron transfer layer material of the white organic light emitting device of the present disclosure had significantly improved light emission efficiency and lifetime compared to Comparative Examples 3-1 to 3-6.

Such a result is considered to be due to the fact that, when using the disclosed compound having proper length and strength, and flatness as an electron transfer layer, a compound in an excited state is made by receiving electrons under a specific condition, and particularly when an excited state is formed in the hetero-skeleton site of the compound, excited energy moves to a stable state before the excited hetero-skeleton site goes through other reactions, and as a result, the relatively stabilized compound is capable of efficiently transferring electrons without the compound being decomposed or destroyed. For reference, those that are stable when excited are considered to be aryl or acene-based compounds or polycyclic hetero-compounds.

Accordingly, it is considered that the compound of the present disclosure brought excellence in all aspects of driving, efficiency and lifetime by enhancing improved electron-transfer properties or improved stability.

The invention claimed is:

1. A heterocyclic compound represented by the following Chemical Formula 1:

[Chemical Formula 1]

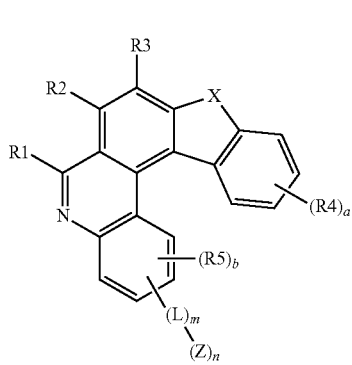

wherein, in Chemical Formula 1,

X is O or S,

L is a direct bond; a substituted or unsubstituted C6 to C30 arylene group; or a substituted or unsubstituted C2 to C30 heteroarylene group, Z is a substituted or unsubstituted C6 to C30 aryl group; a substituted or unsubstituted C2 to C30 heteroaryl group or a substituted or unsubstituted phosphine oxide group, R1 is a substituted or unsubstituted C6 to C30 aryl group; or a substituted or unsubstituted C2 to C30 heteroaryl group, R2 to R5 are each independently hydrogen or deuterium, a is an integer of 1 to 4, b is an integer of 1 to 3, m and n are each an integer of 1 to 5, and when a, b, m and n are each 2 or greater, substituents in the parentheses are the same as or different from each other.

2. The heterocyclic compound of claim 1, wherein Chemical Formula 1 is represented by the following Chemical Formula 2 or 3:

[Chemical Formula 2]

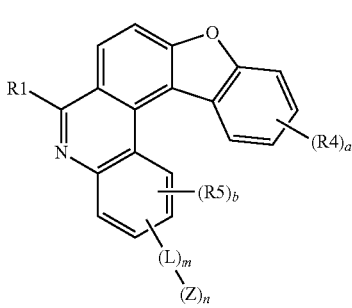

-continued

[Chemical Formula 3]

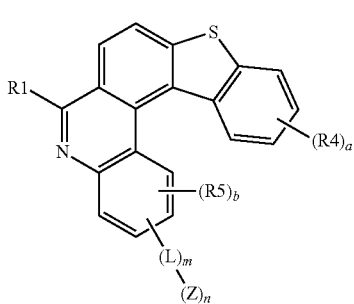

in Chemical Formulae 2 and 3,

L, Z, R1, R4, R5, a, b, m and n have the same definitions as in Chemical Formula 1.

3. The heterocyclic compound of claim 1, wherein Chemical Formula 1 is represented by any one of the following Chemical Formulae 4 to 6:

[Chemical Formula 4]

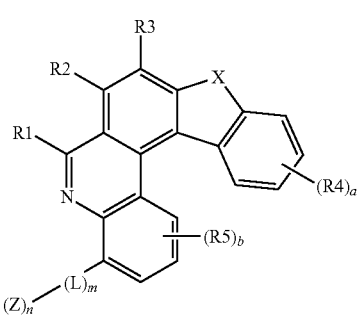

[Chemical Formula 5]

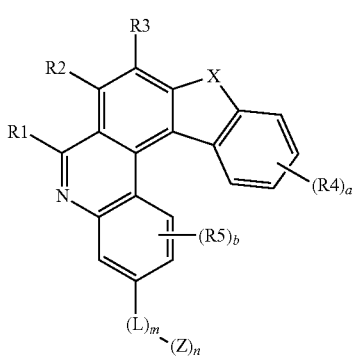

[Chemical Formula 6]

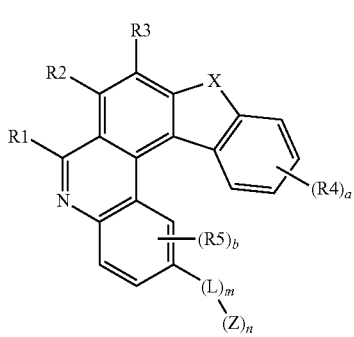

in Chemical Formulae 4 to 6,

X, L, Z, R1 to R5, a, b, m and n have the same definitions as in Chemical Formula 1.

4. The heterocyclic compound of claim 1, wherein R1 is a substituted or unsubstituted C6 to C30 aryl group.

5. The heterocyclic compound of claim 1, wherein L is a direct bond; a phenylene group; a biphenylene group; a terphenylene group; a naphthylene group; an anthracenylene group; a triphenylenylene group; or a phenanthrenylene group.

6. The heterocyclic compound of claim 1, wherein Z is a substituted or unsubstituted phenyl group; a biphenyl group; a terphenyl group; a naphthyl group; a triphenylenyl group; a phenanthrenyl group; an anthracenyl group; a dimethylfluorenyl group; a diphenylfluorenyl group; a spirobifluorenyl group; an isoquinolinyl group; a quinazolinyl group; a phenoxazinyl group; a phenothiazinyl group; an indolocarbazole group; a benzonaphthothiophene group; a substituted or unsubstituted pyrazole group; a substituted or unsubstituted pyridine group; a substituted or unsubstituted pyrimidine group; a substituted or unsubstituted triazine group; a substituted or unsubstituted carbazole group; a substituted or unsubstituted phenanthrolinyl group; a substituted or unsubstituted dibenzofuran group; a substituted or unsubstituted dibenzothiophene group; a substituted or unsubstituted dihydroacridine group; or a substituted or unsubstituted phosphine oxide group.

7. The heterocyclic compound of claim 1, wherein Chemical Formula 1 is represented by any one of the following compounds:

1

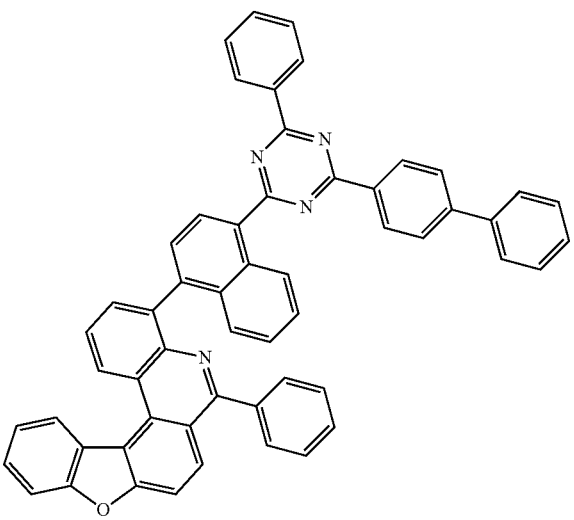

521
-continued
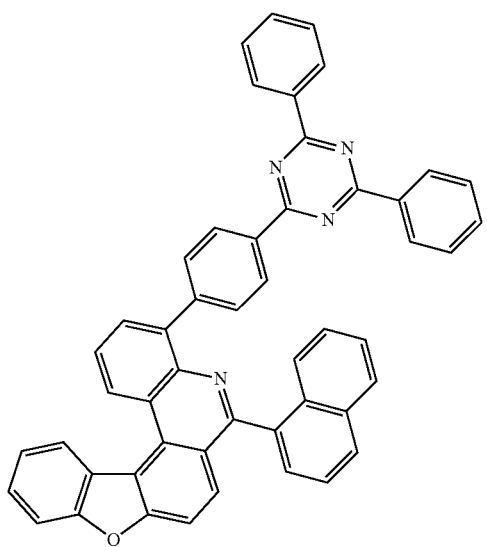
2
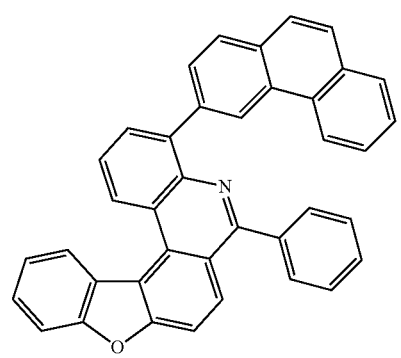
3
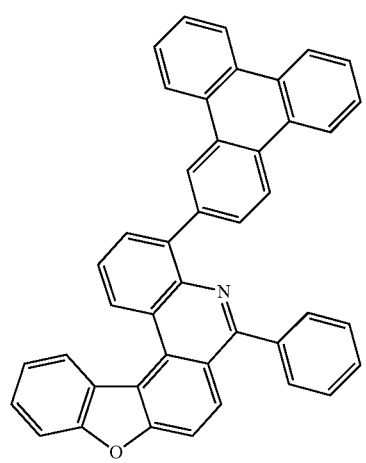
4
522
-continued
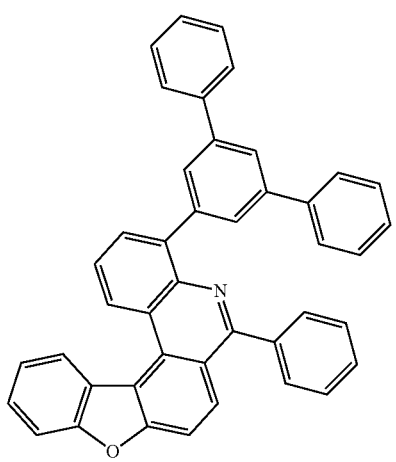
5
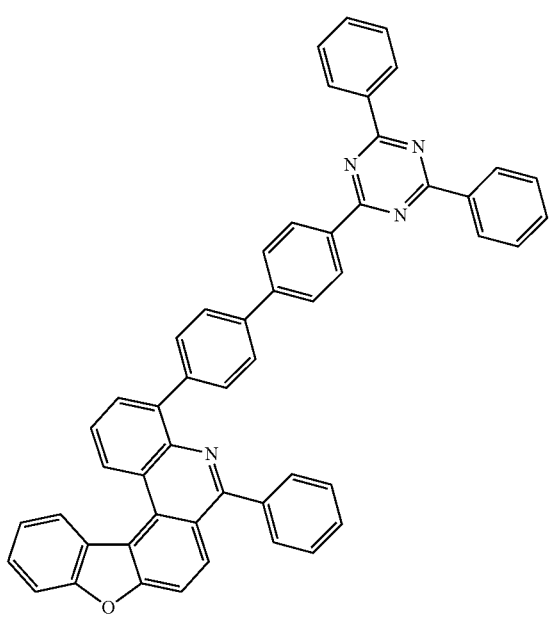
6
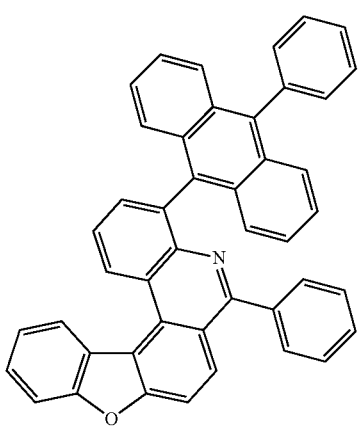
7

523
-continued
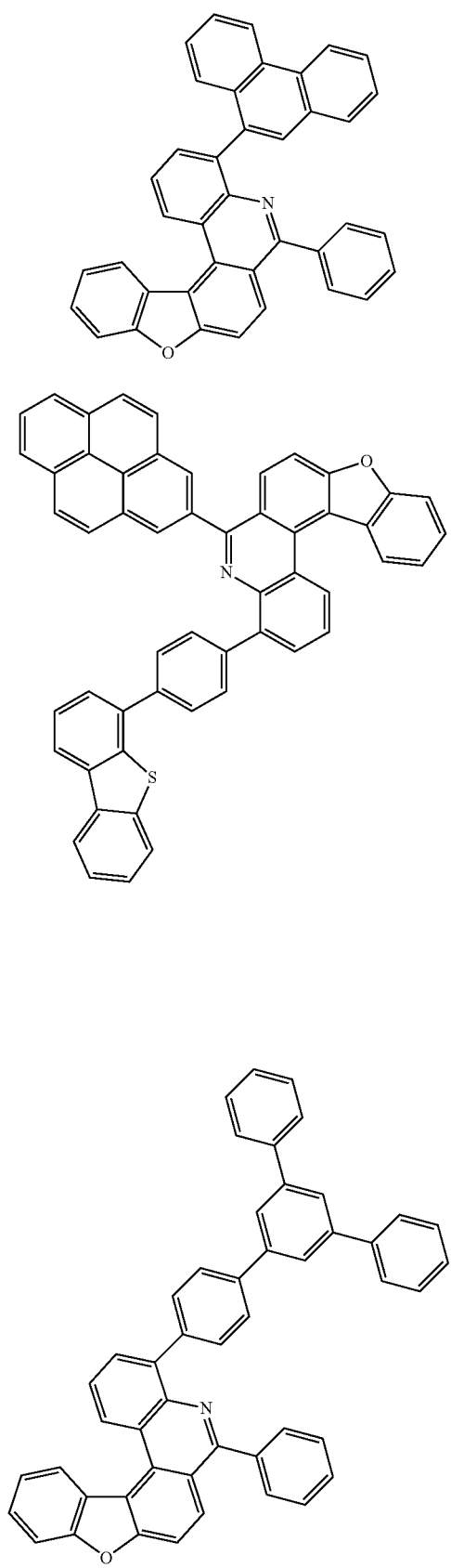
524
-continued
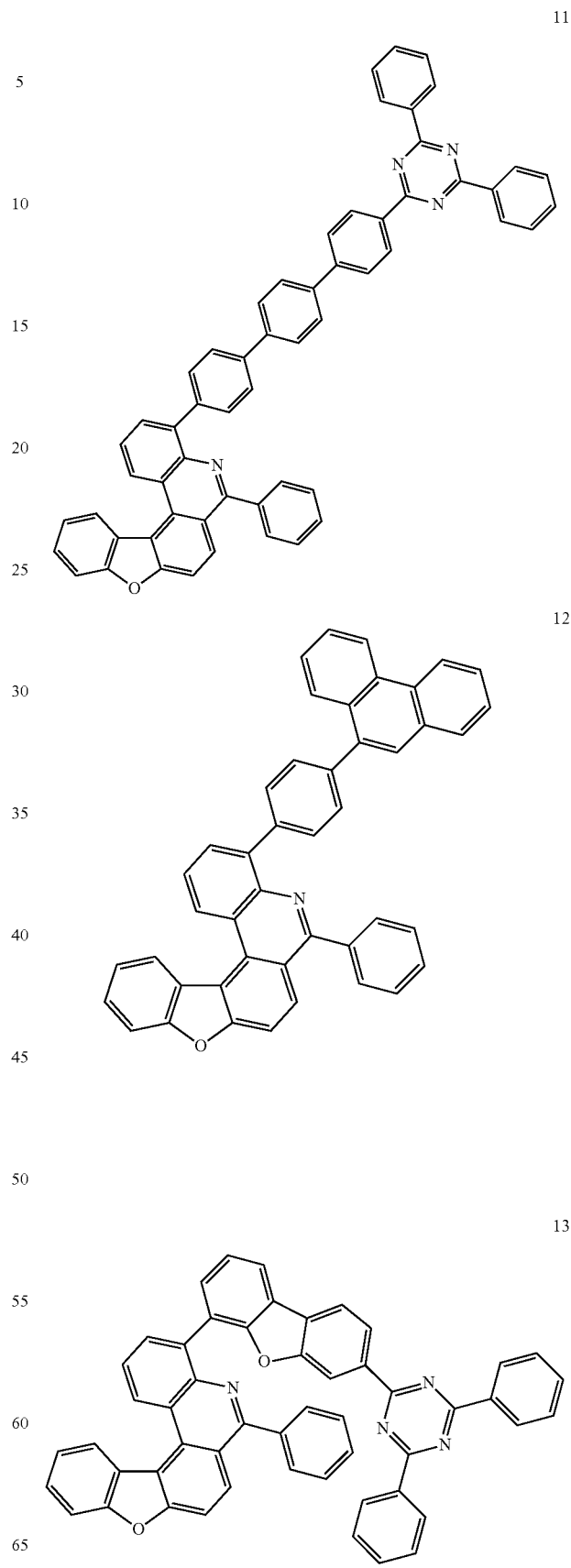

14
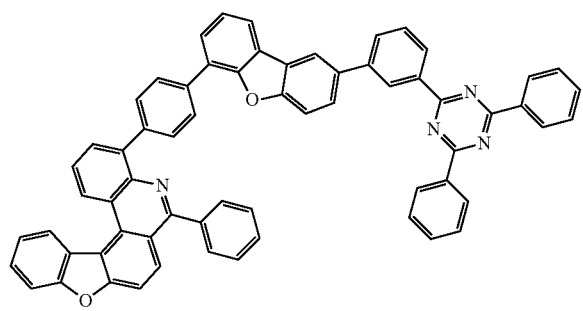
15
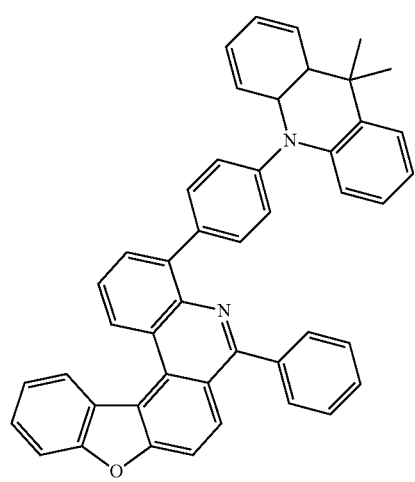
16
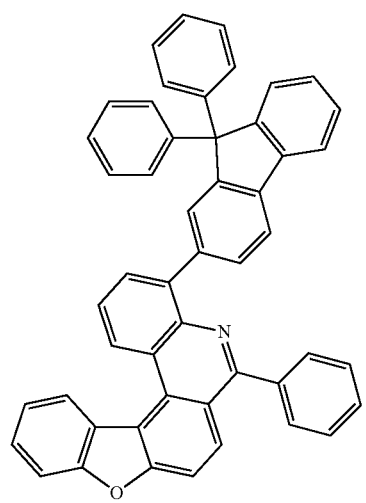
17
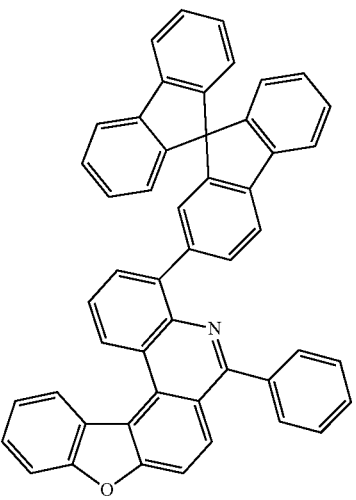
18
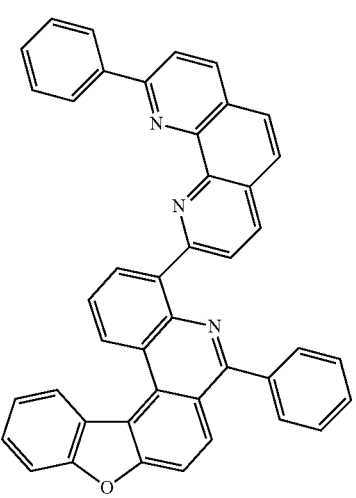
19
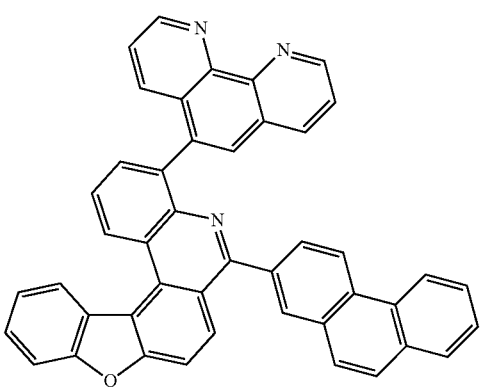

527
-continued
20
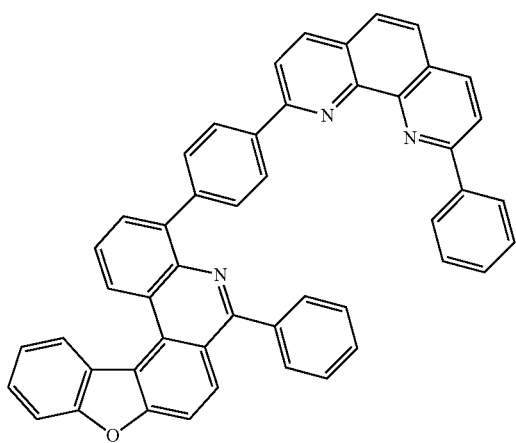
21
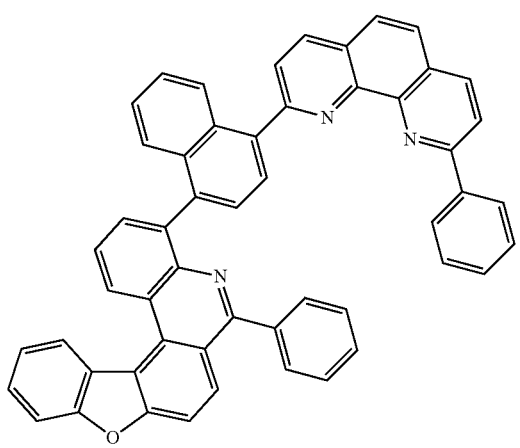
22
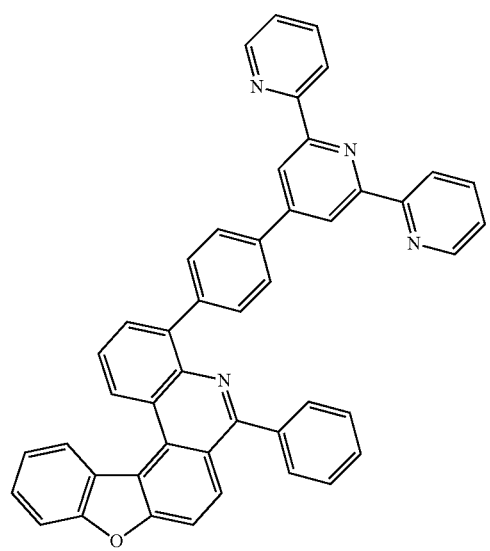
528
-continued
23
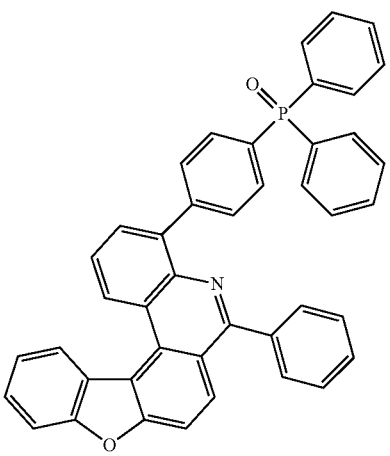
24
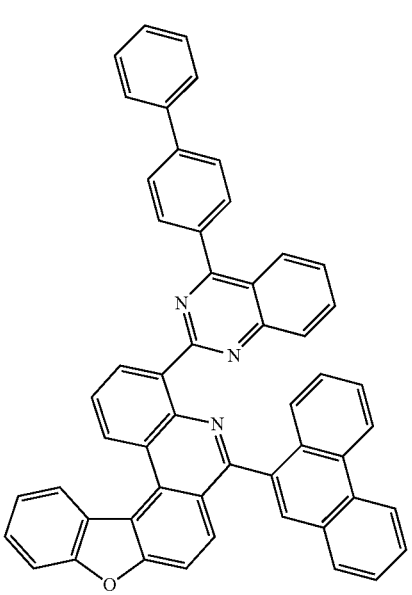
25
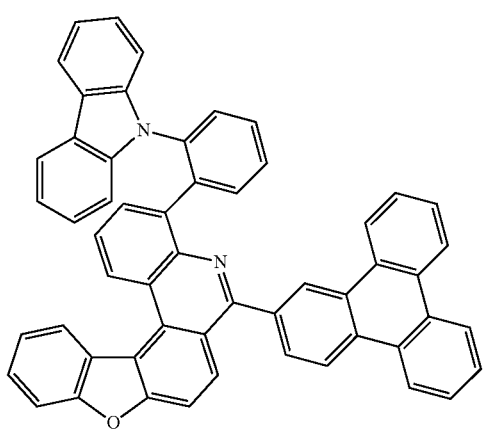

529 -continued
26
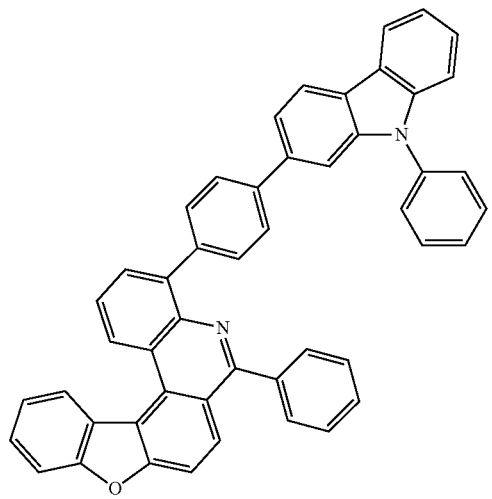
27
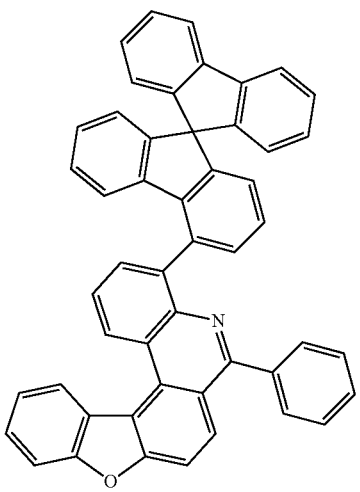
28
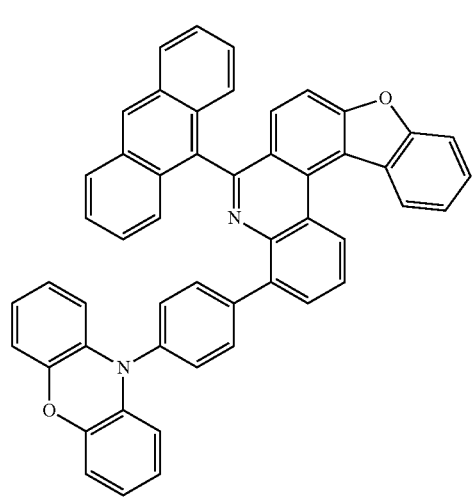
530 -continued
29
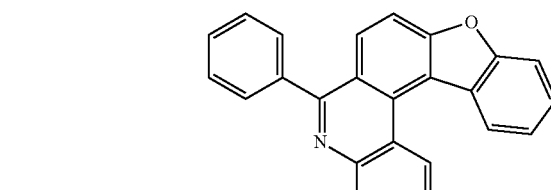
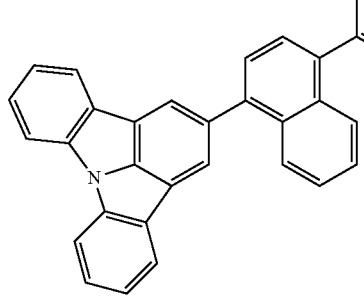
30
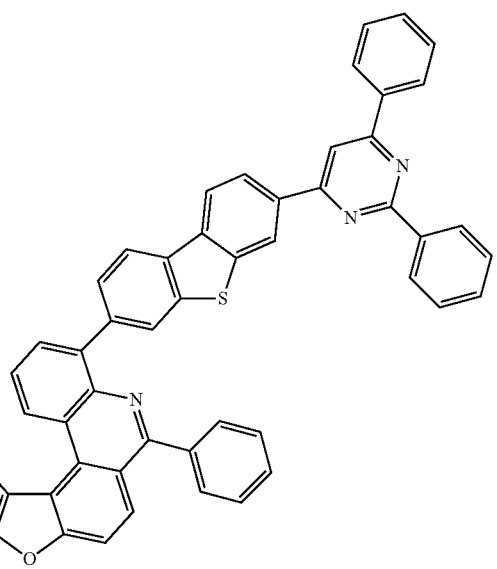
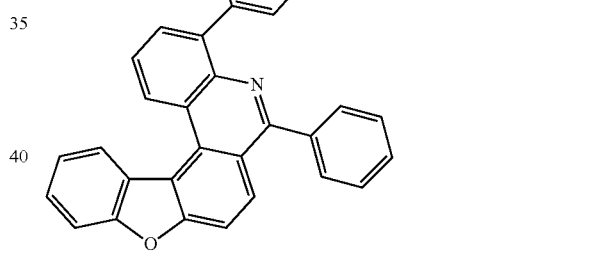
31
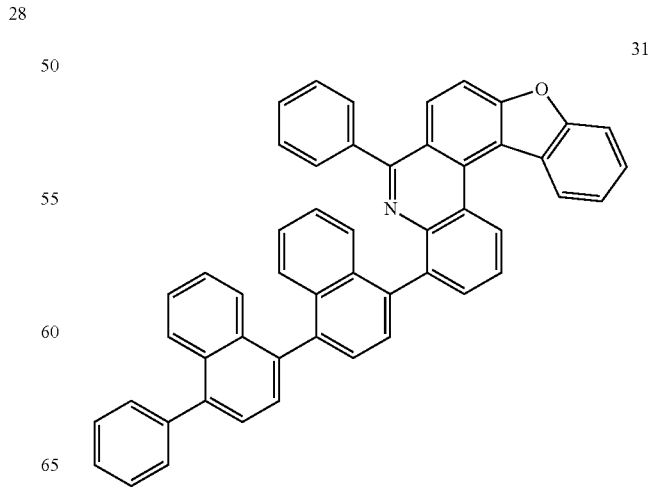

531
-continued
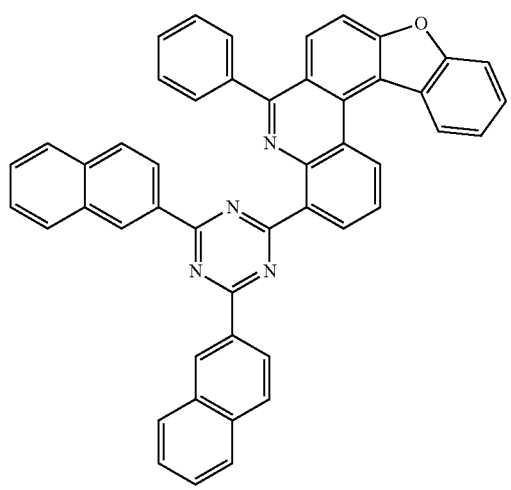
532
-continued
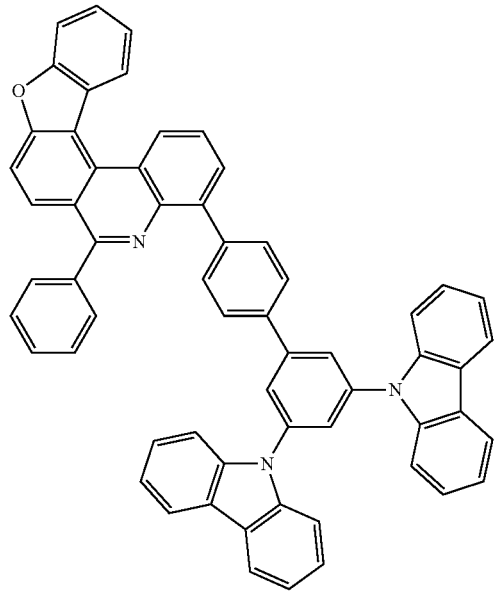
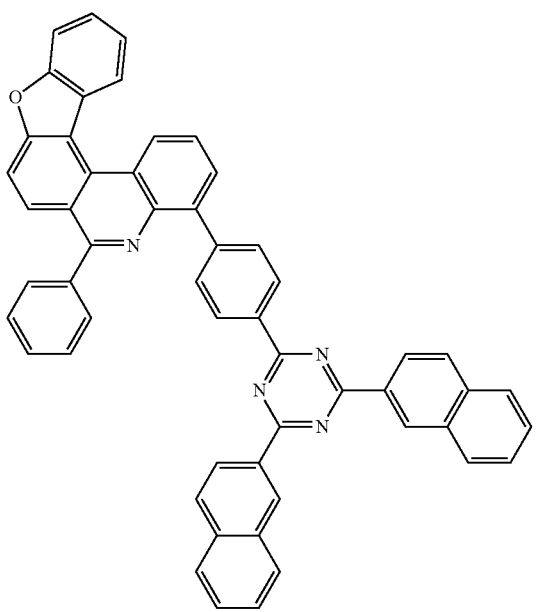
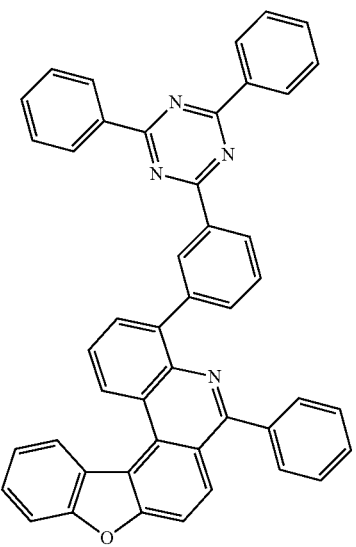

533
-continued
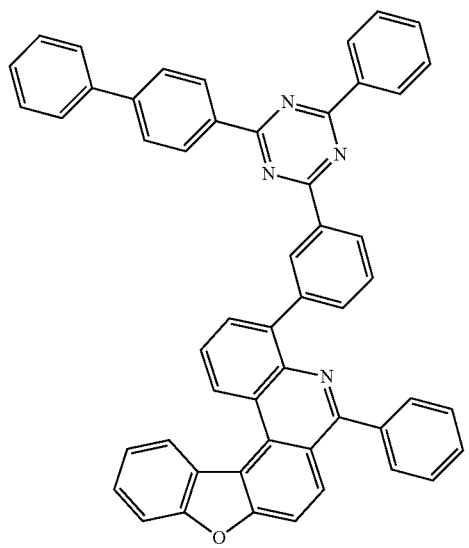
36
534
-continued
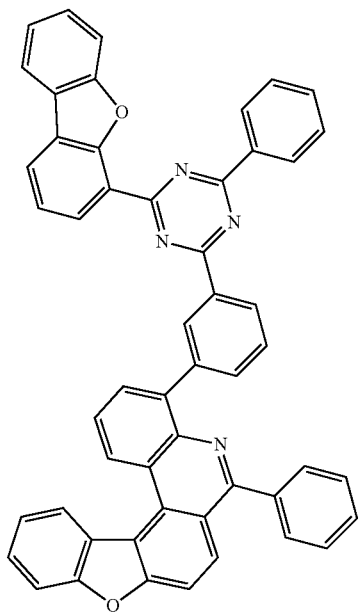
38
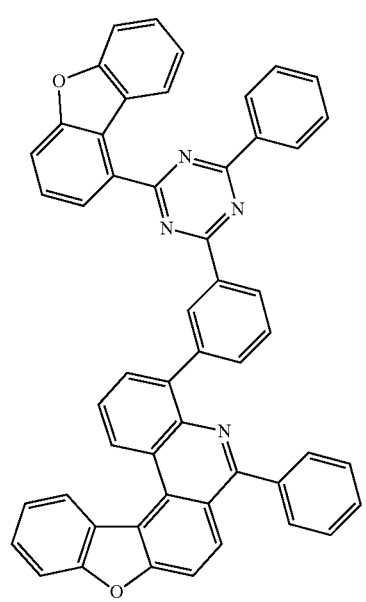
37
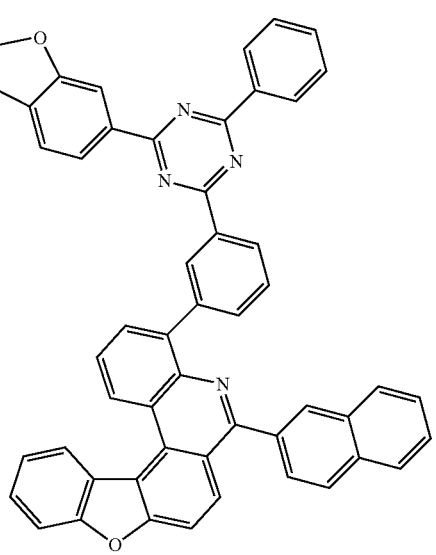
39

535
-continued
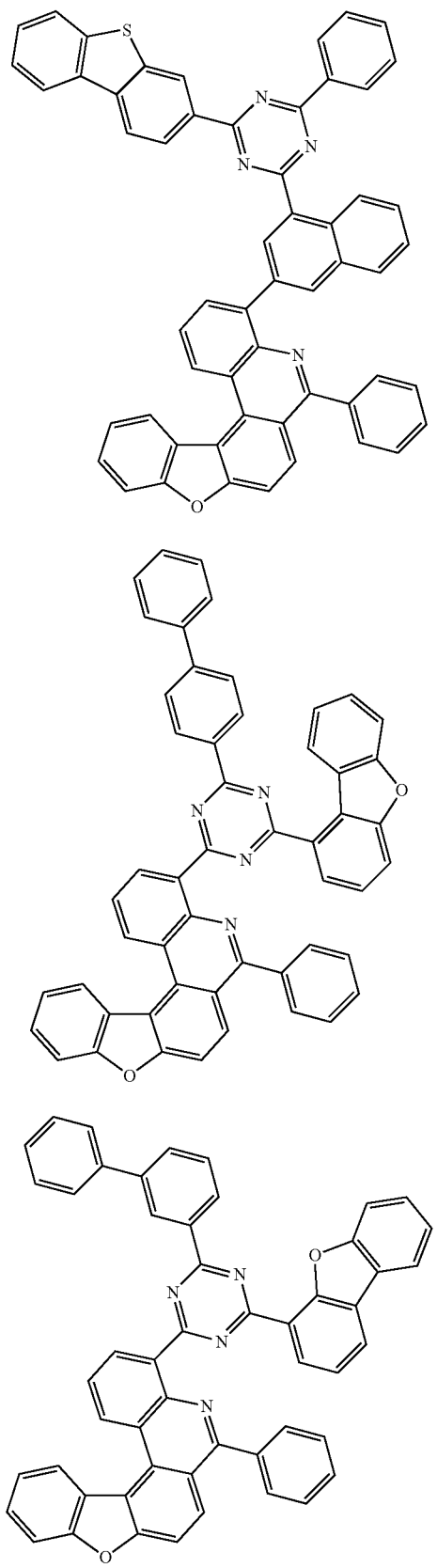
536
-continued
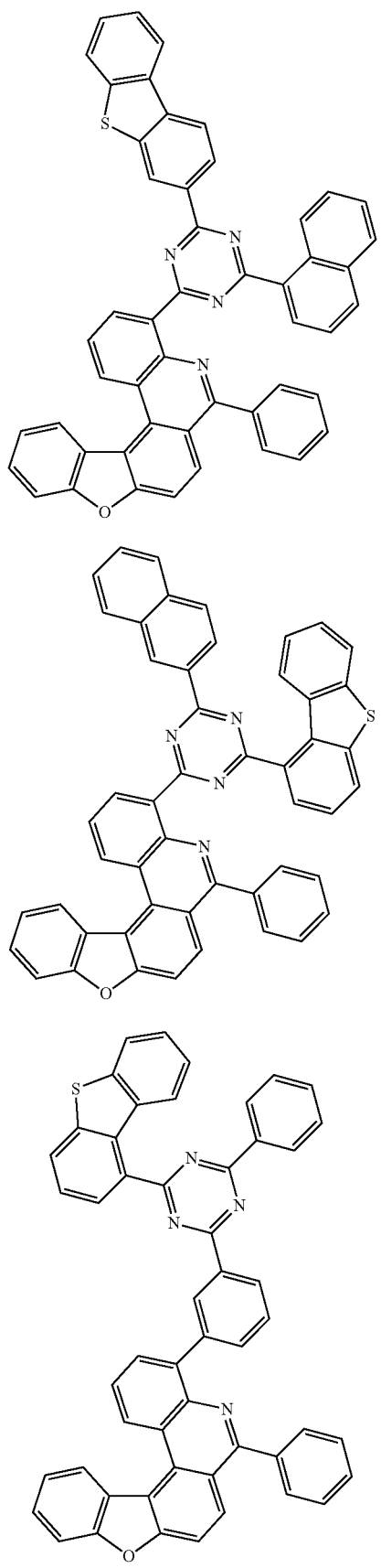

537
-continued
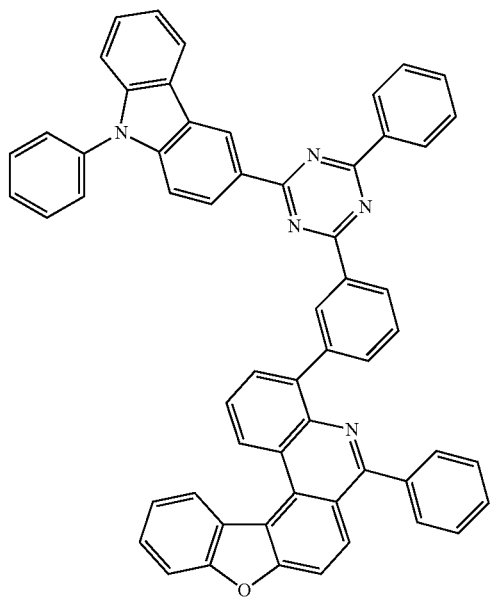
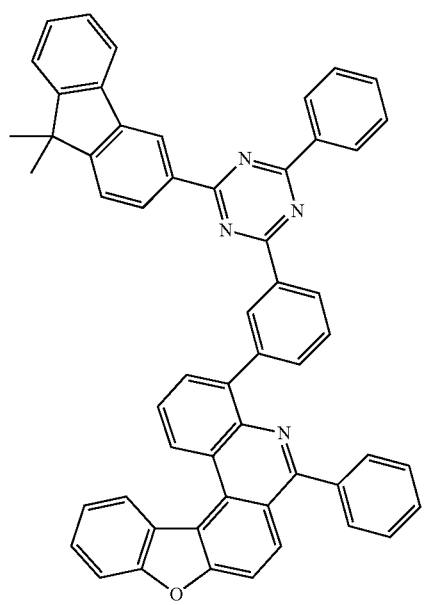
538
-continued
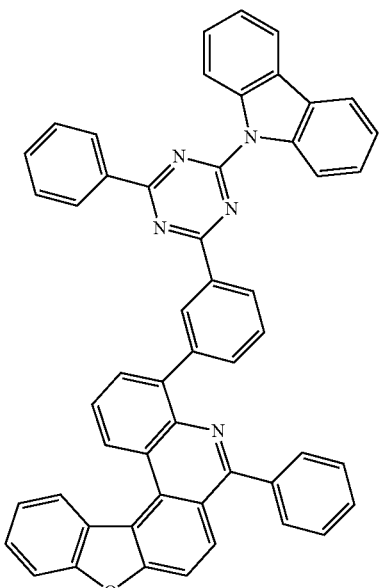
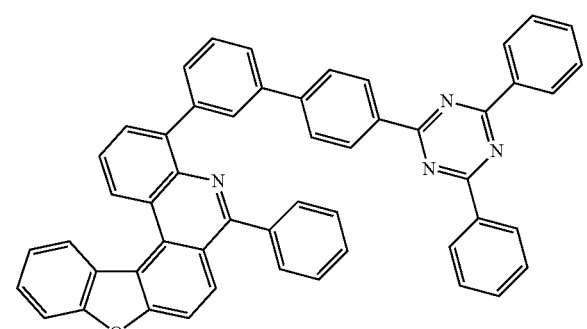
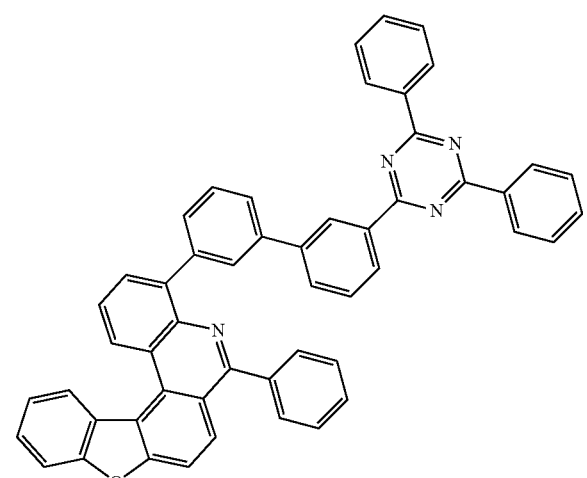

51
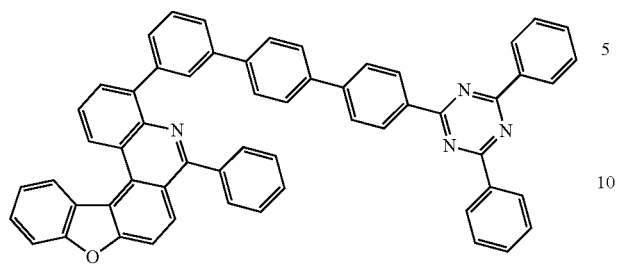
52
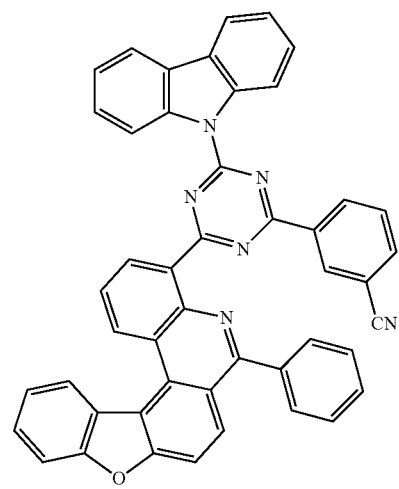
53
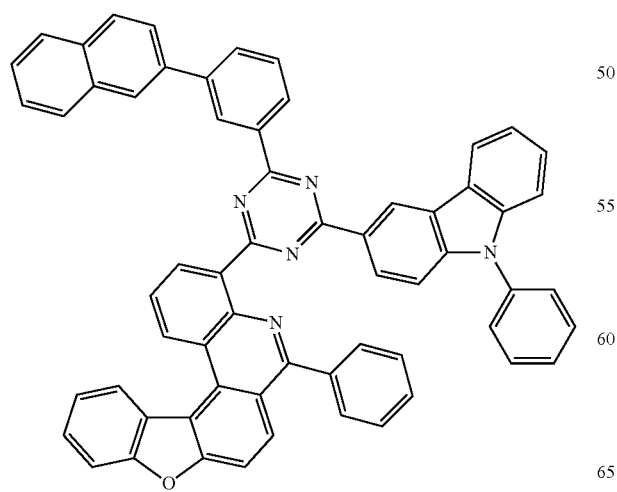
54
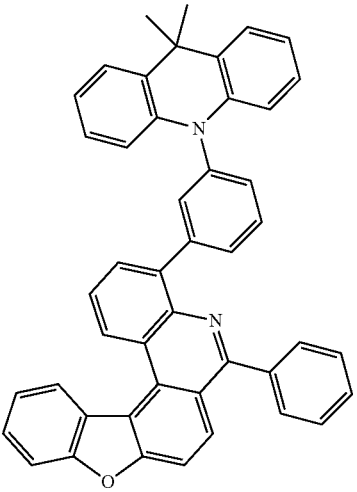
55
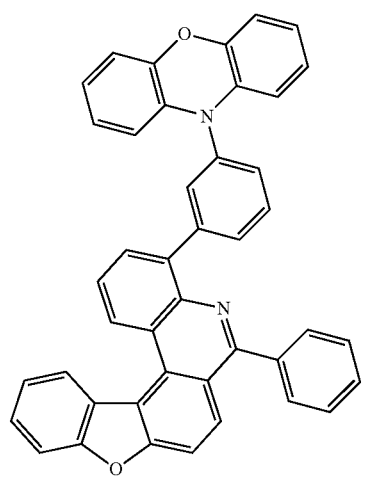
56
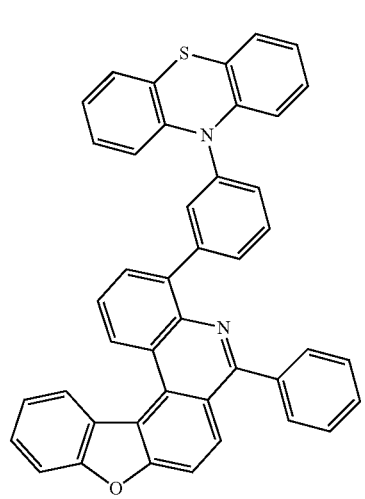

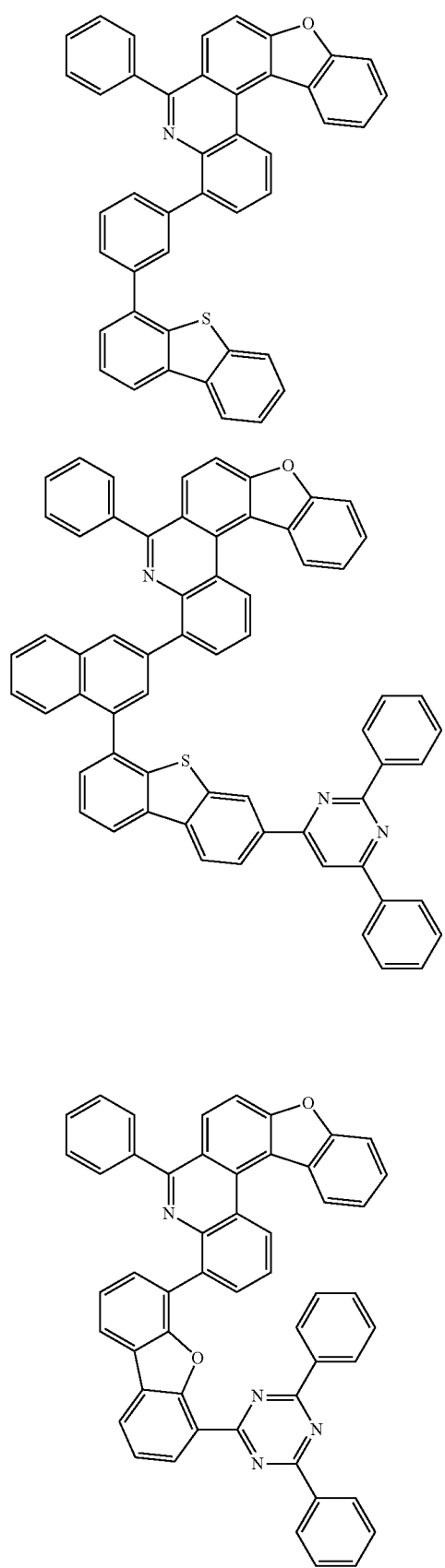

-continued
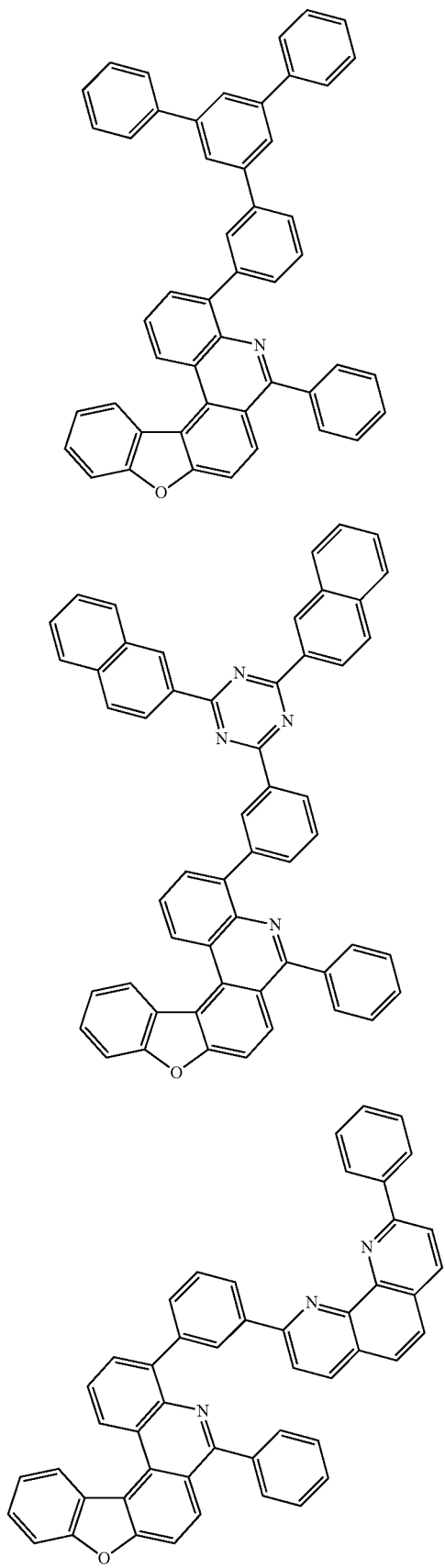
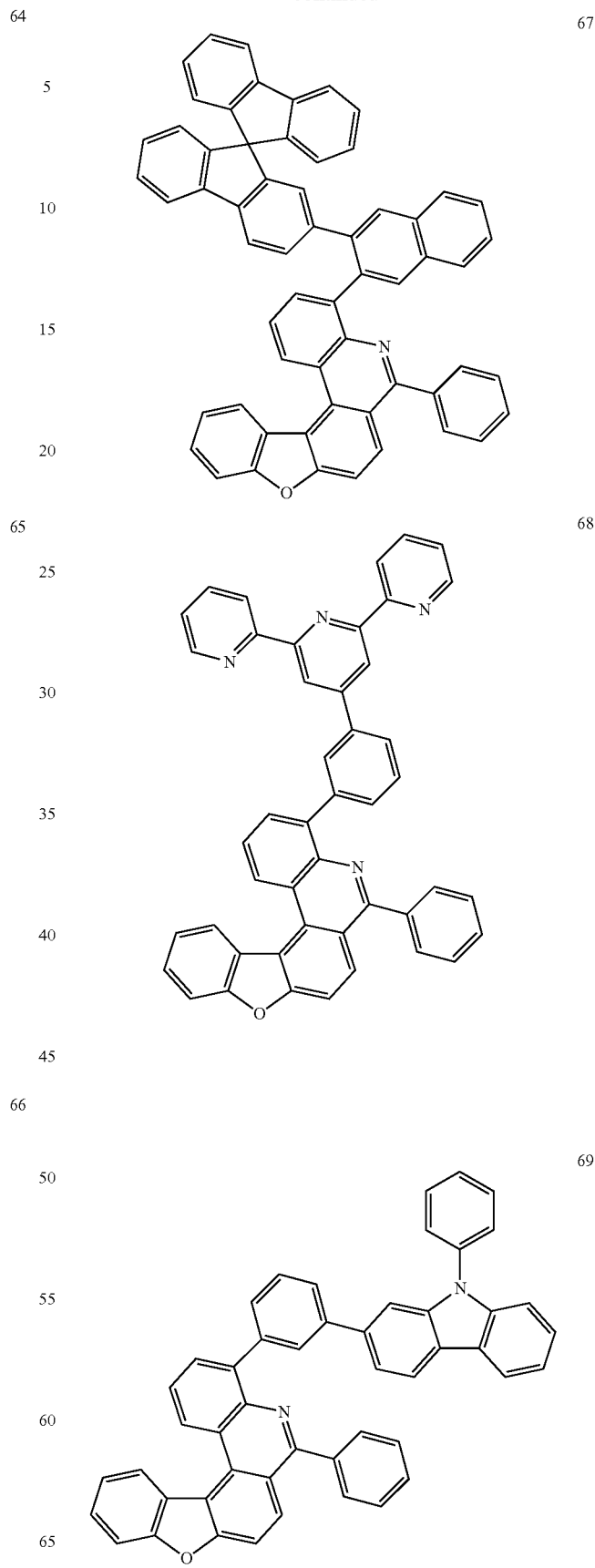

545
-continued
70
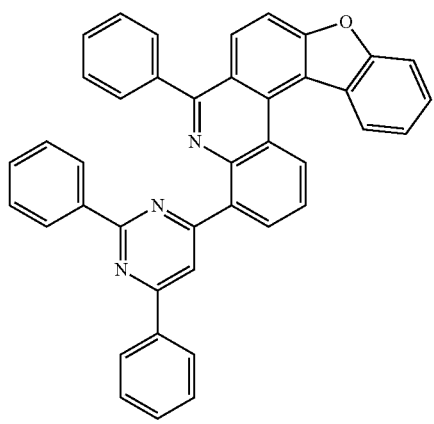
71
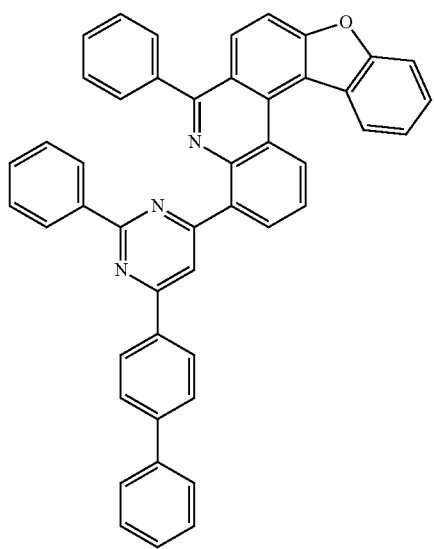
72
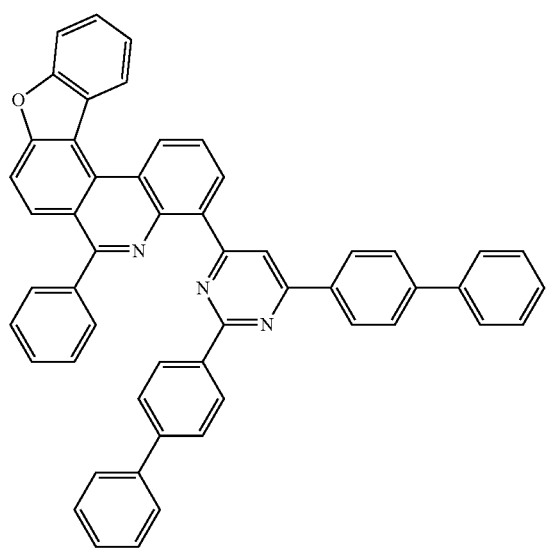
546
-continued
73
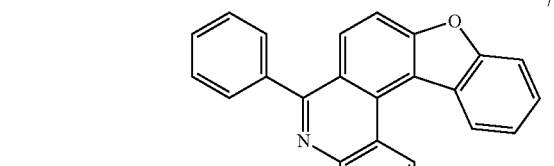
74
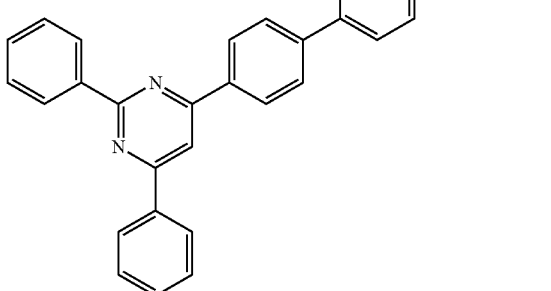
75
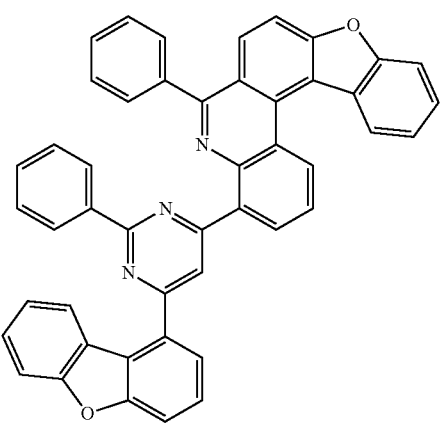

76
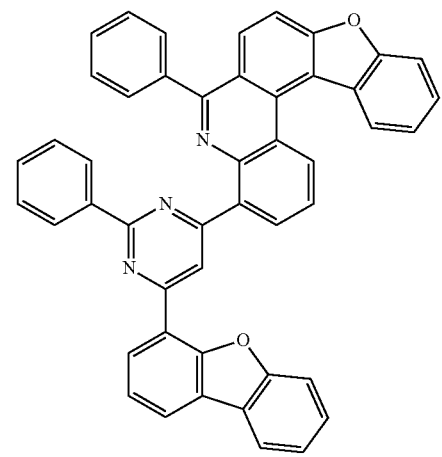
77
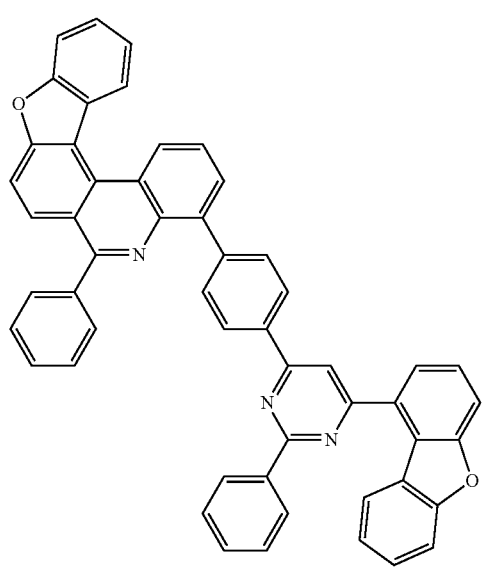
78
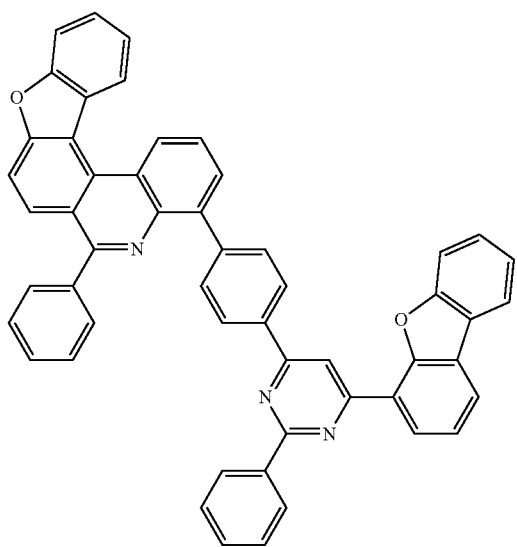
79
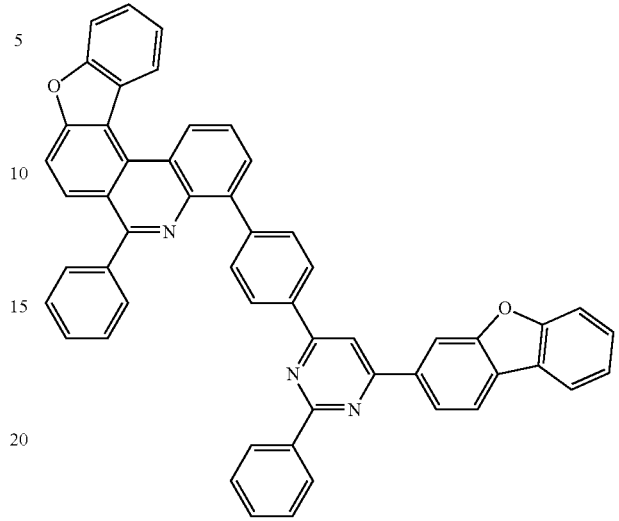
80
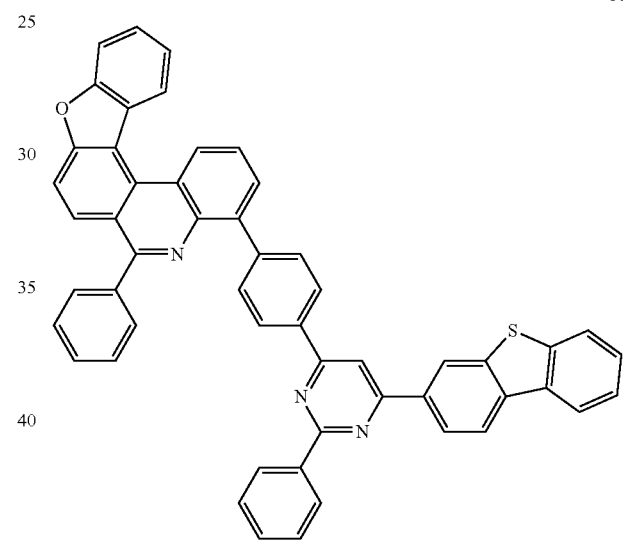
81
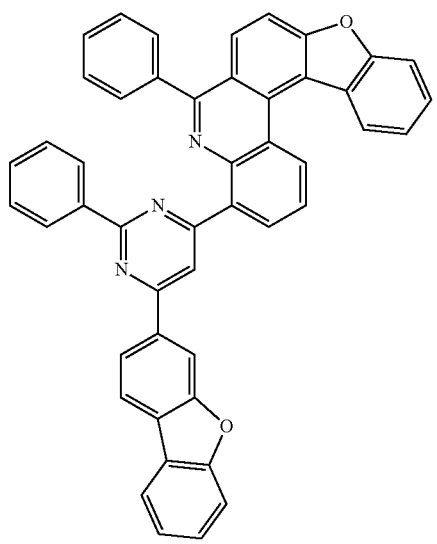

549
-continued
82
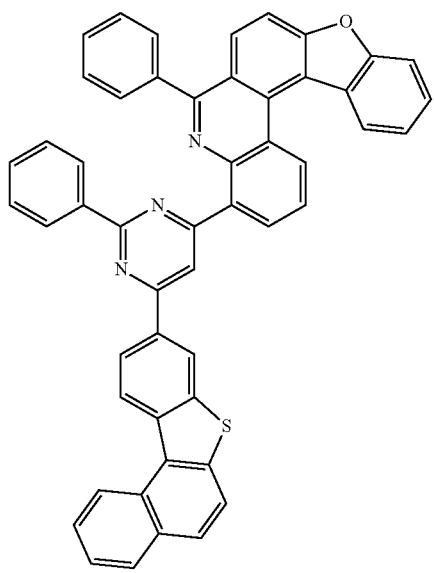
83
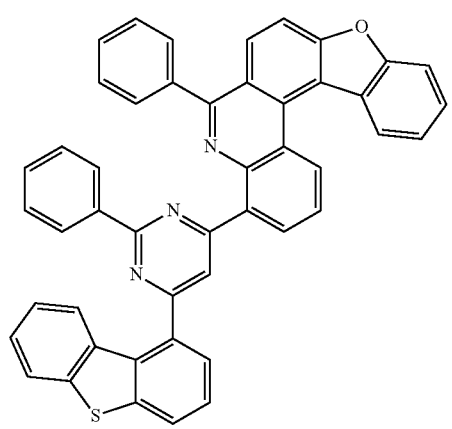
84
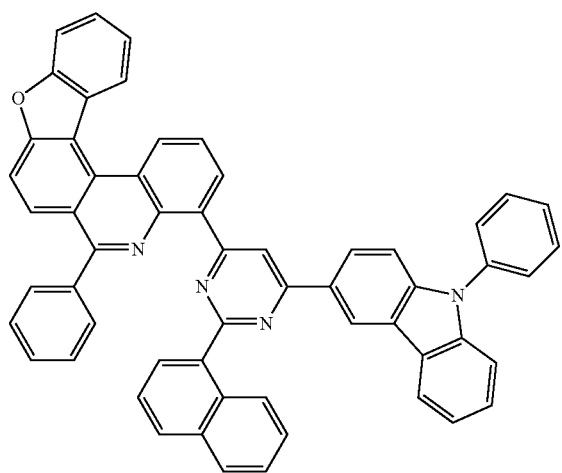
550
-continued
85
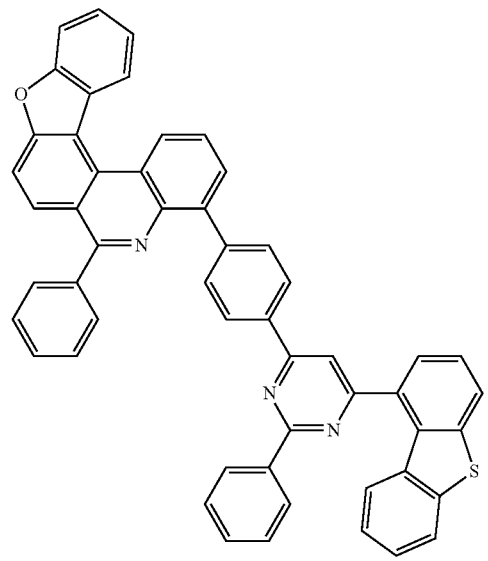
86
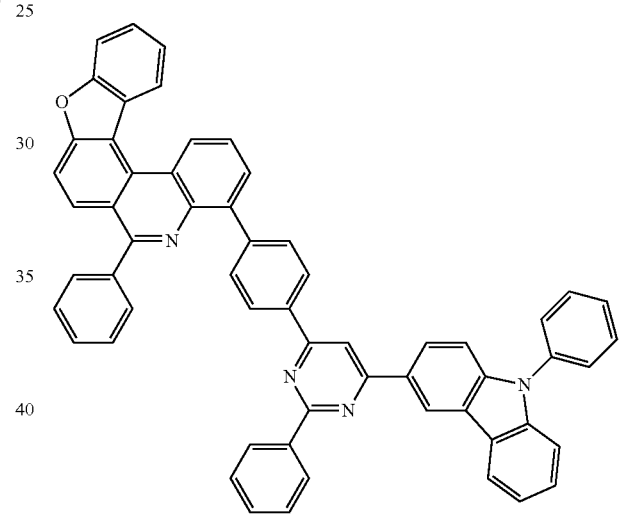
87
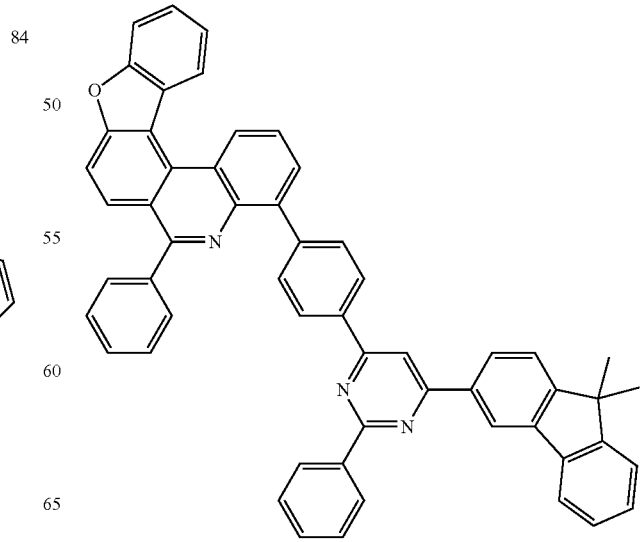

551
-continued
88
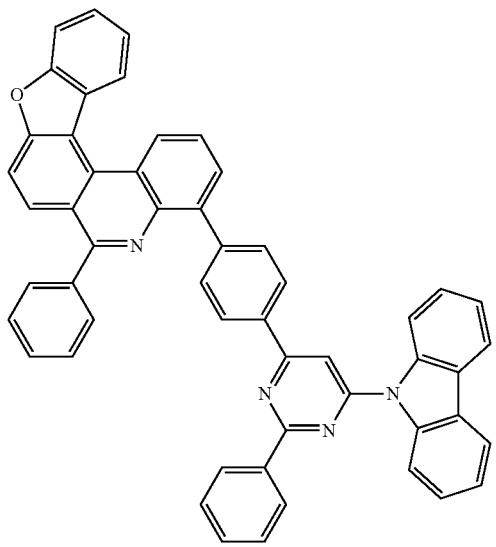
89
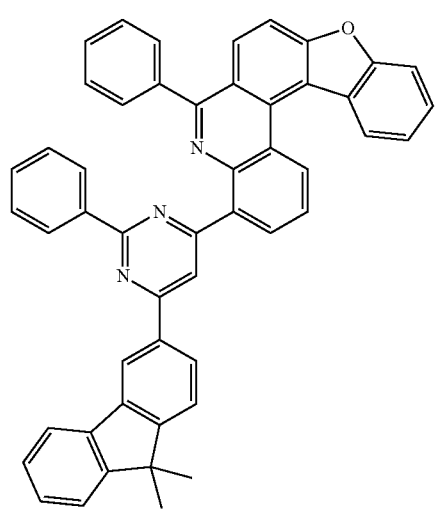
90
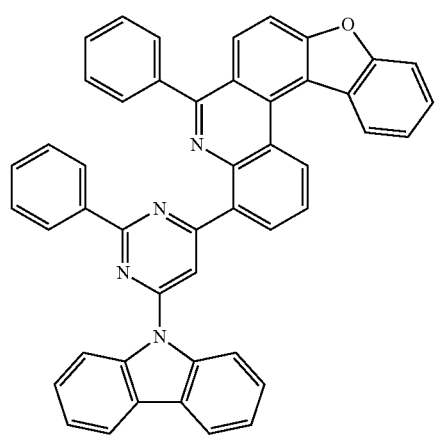
552
-continued
91
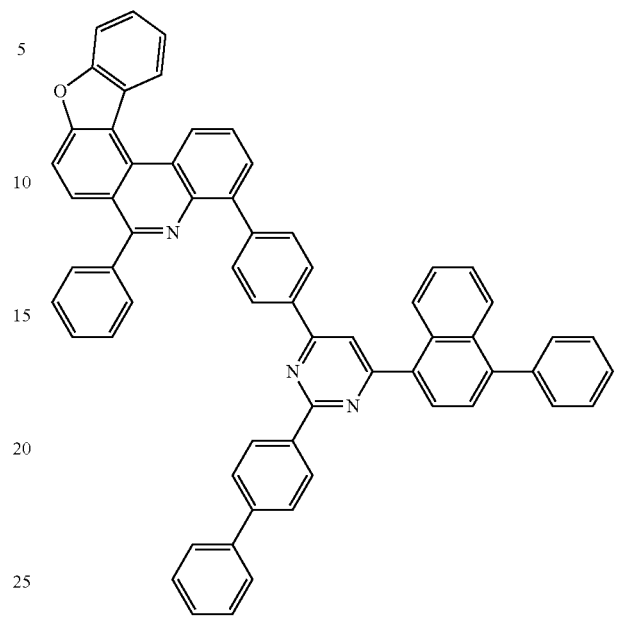
92
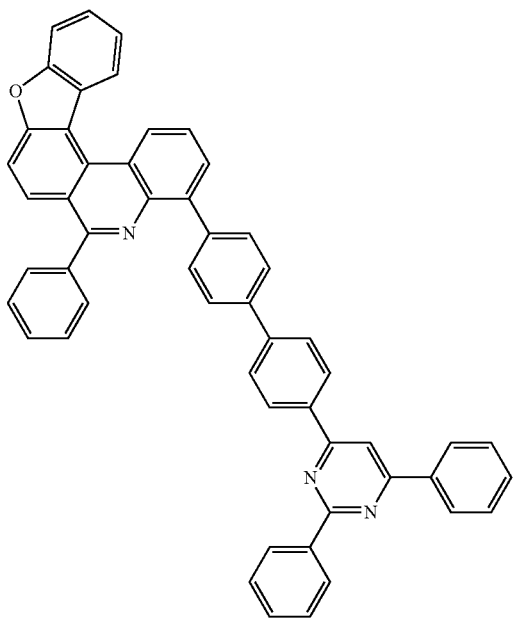

553
-continued
93
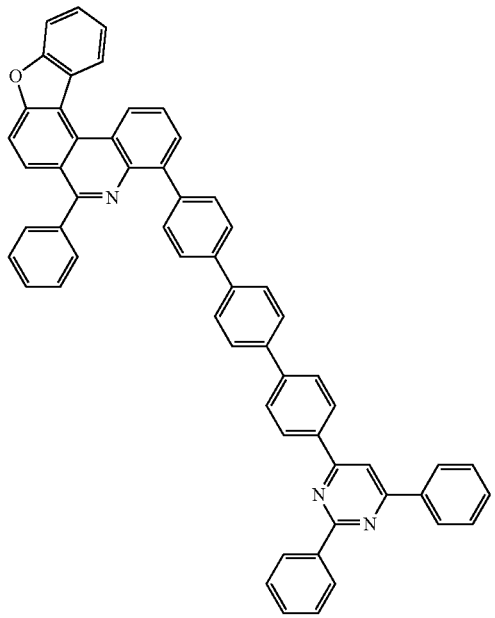
94
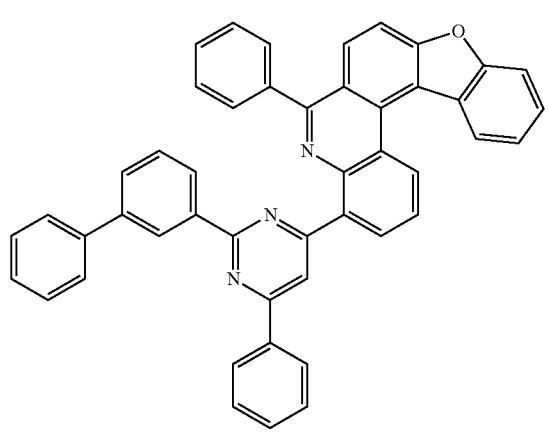
95
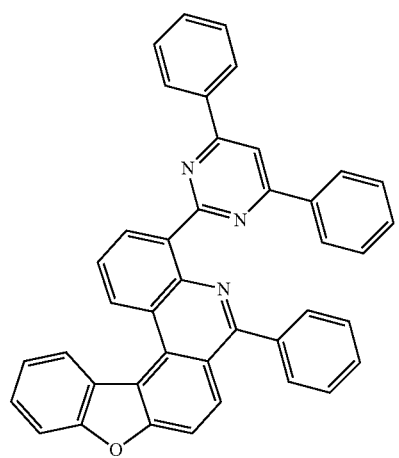
554
-continued
96
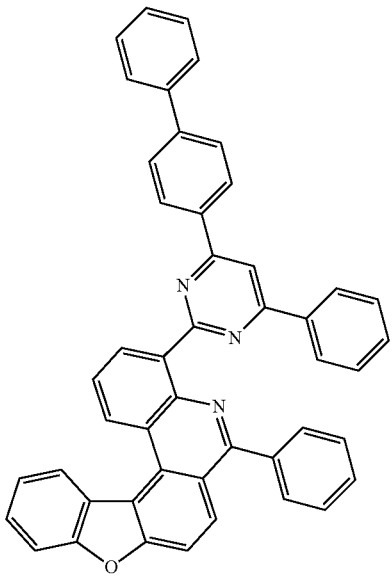
97
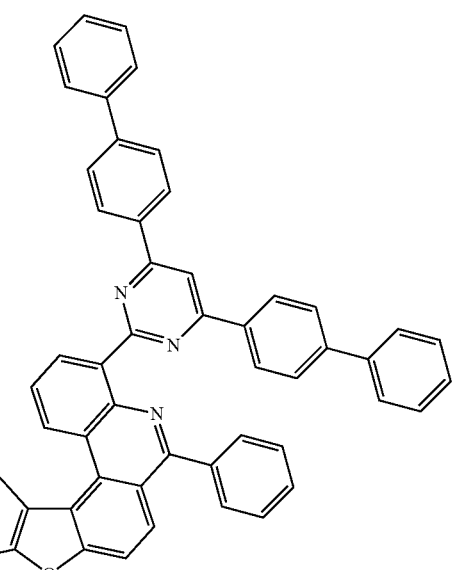
98
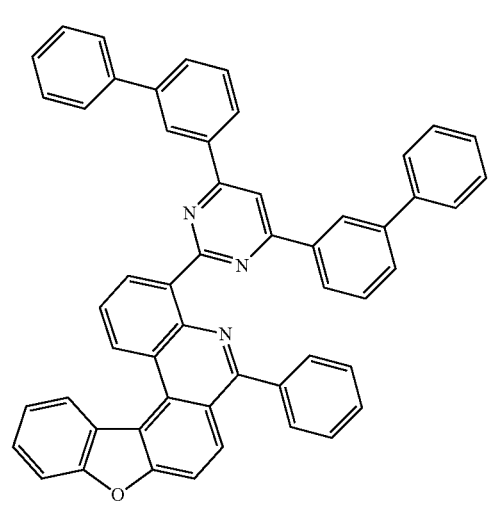

555
-continued
556
-continued
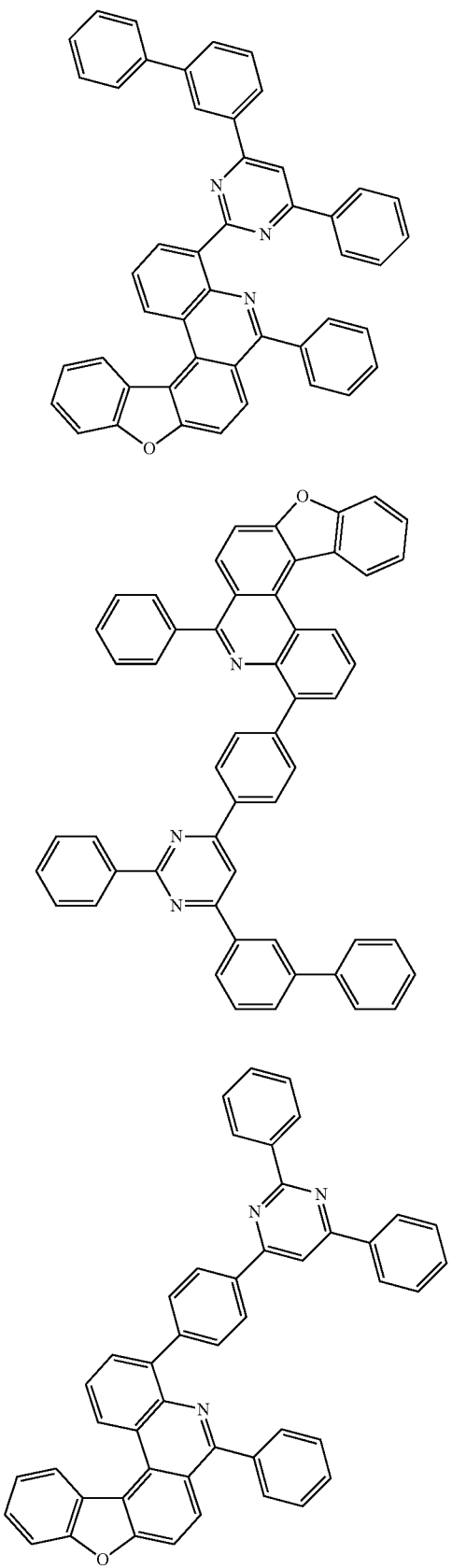
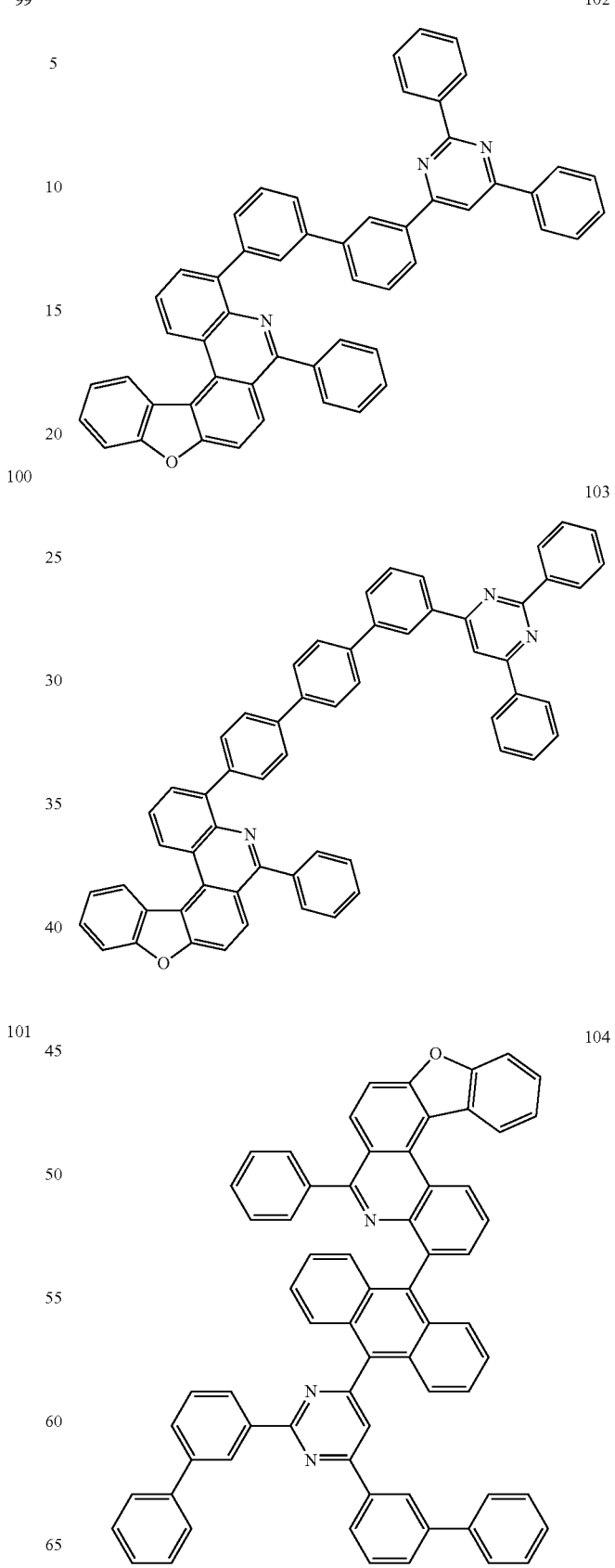

557
-continued
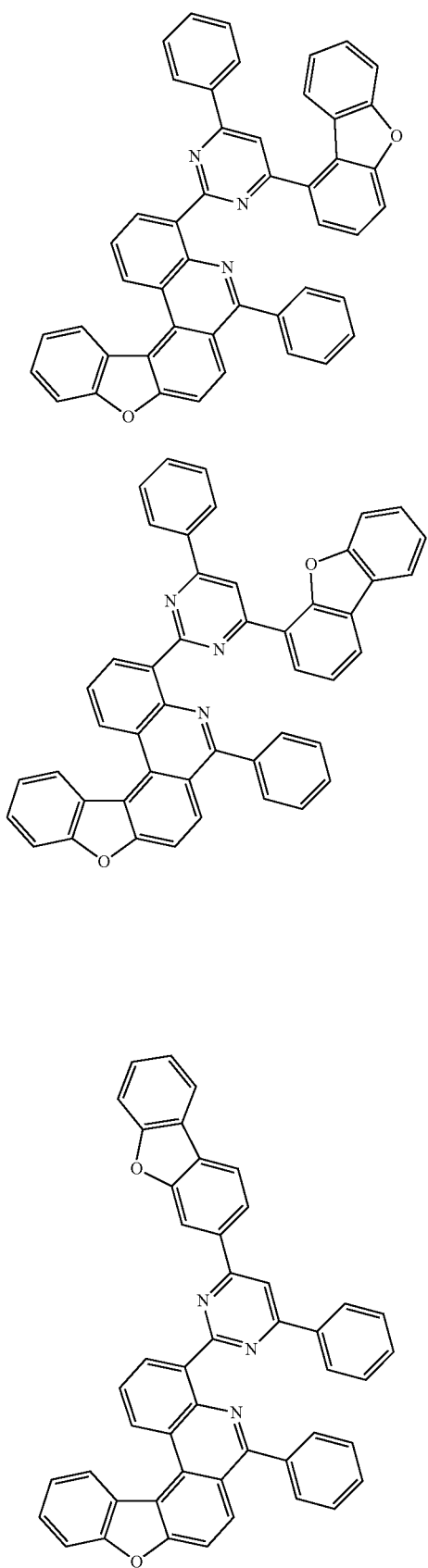
558
-continued
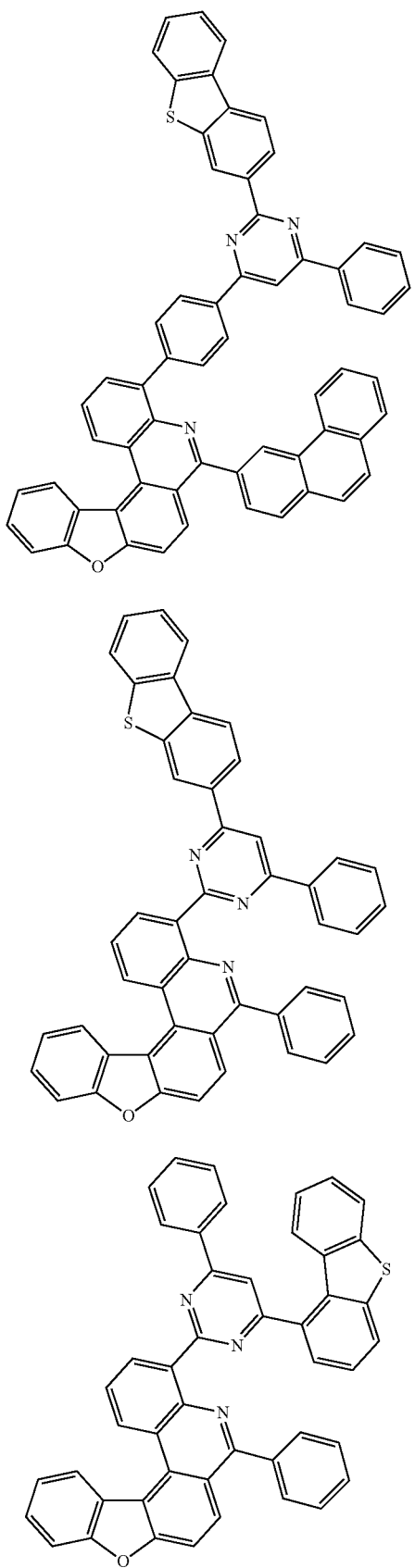

559
-continued
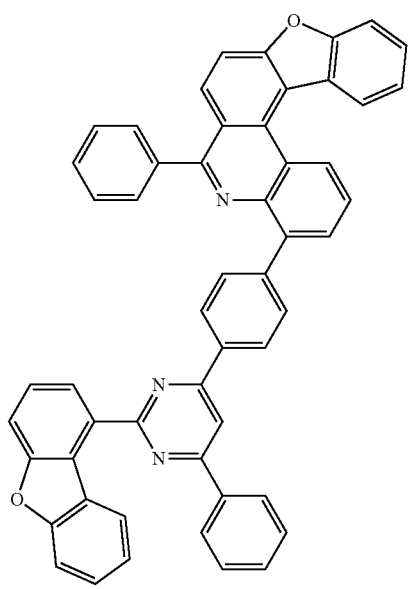
111
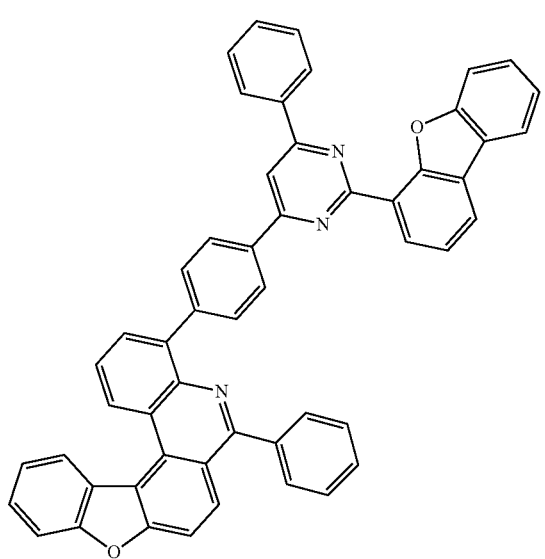
112
560
-continued
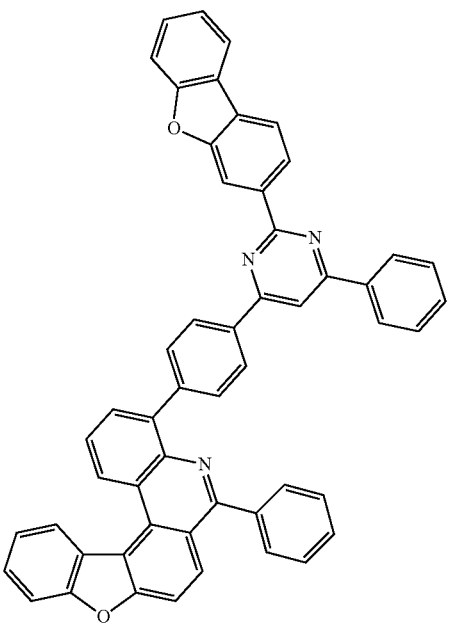
113
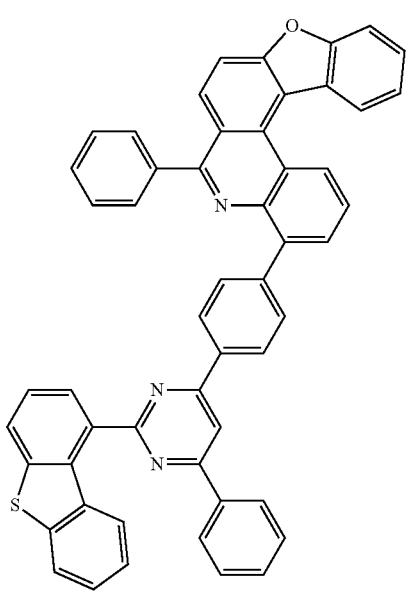
114

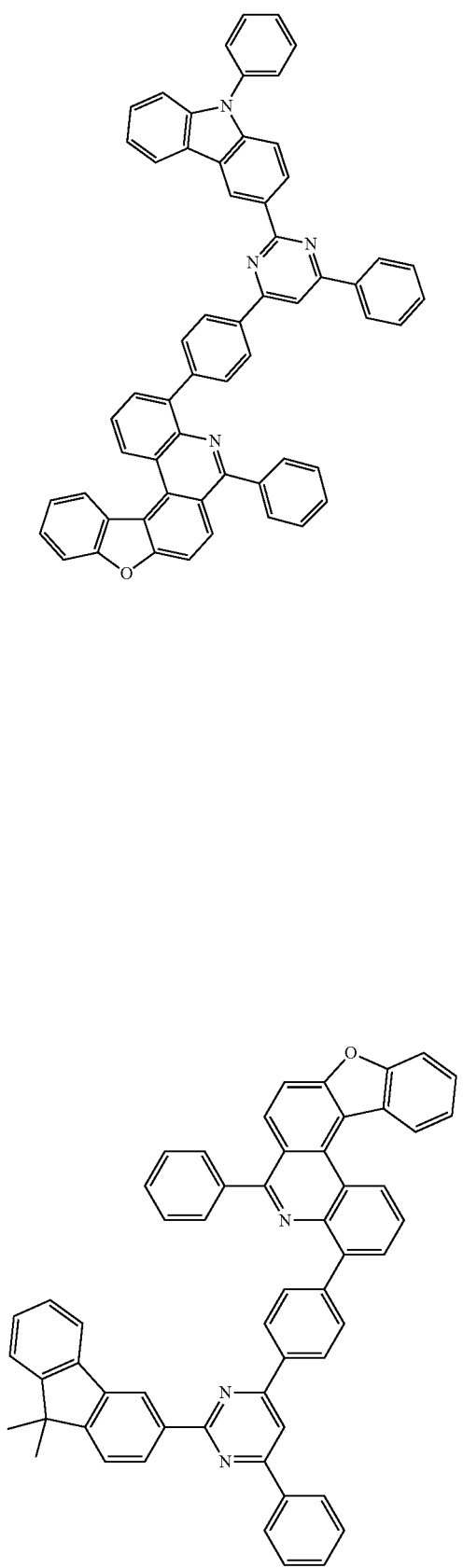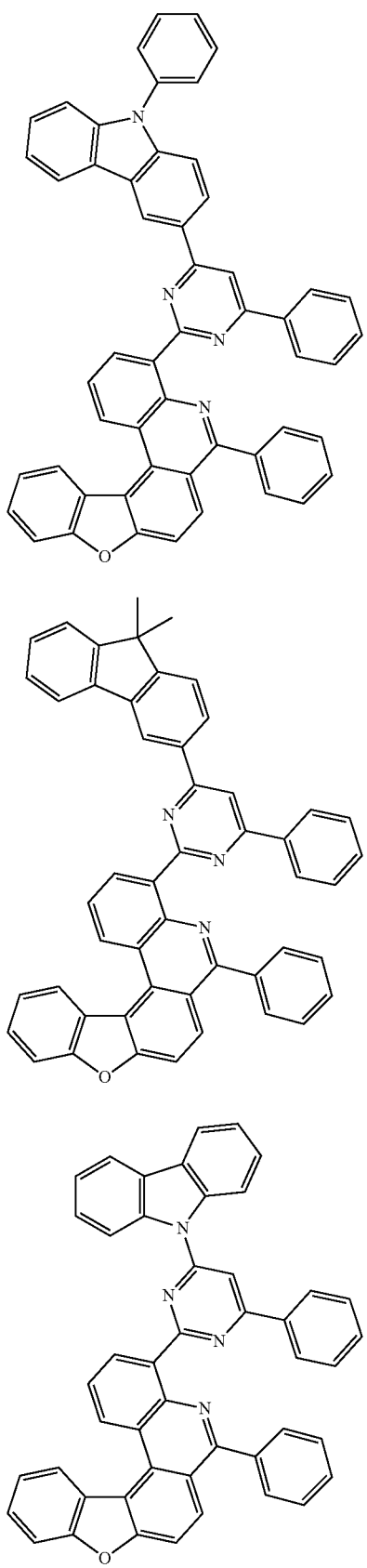

120
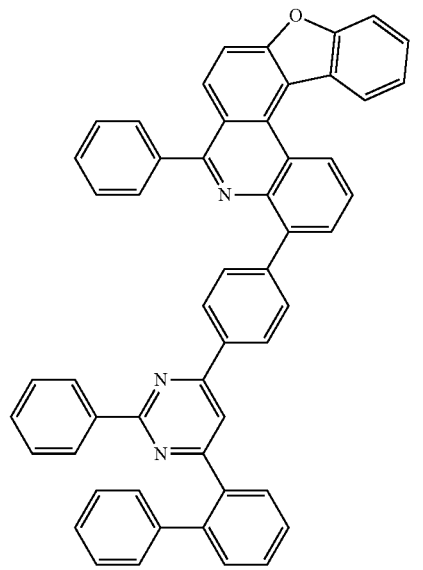
121
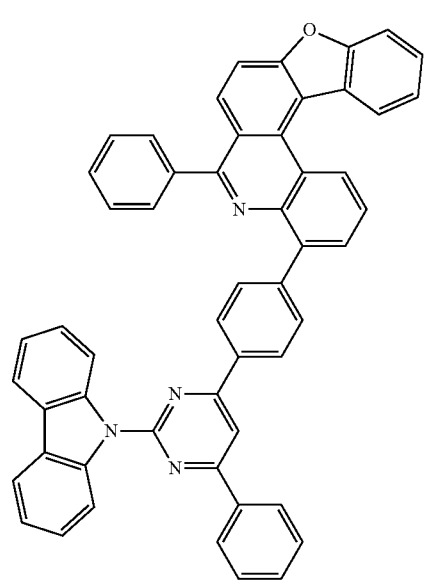
122
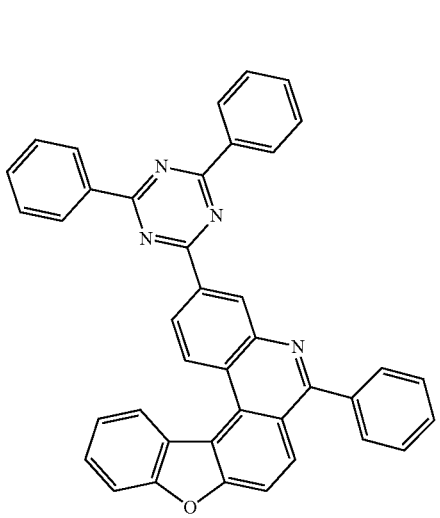
123
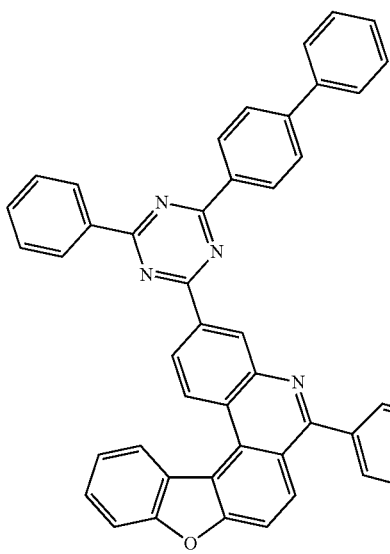
124
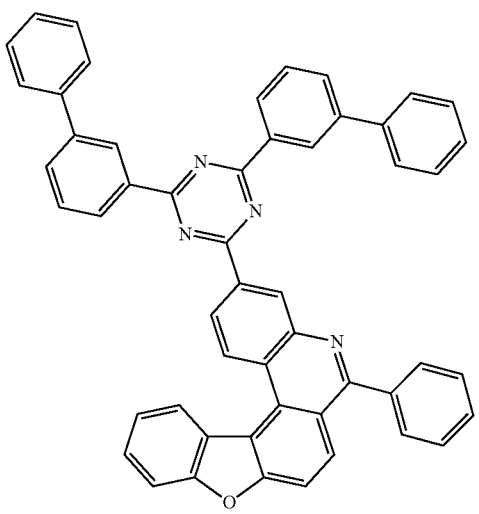
125

126
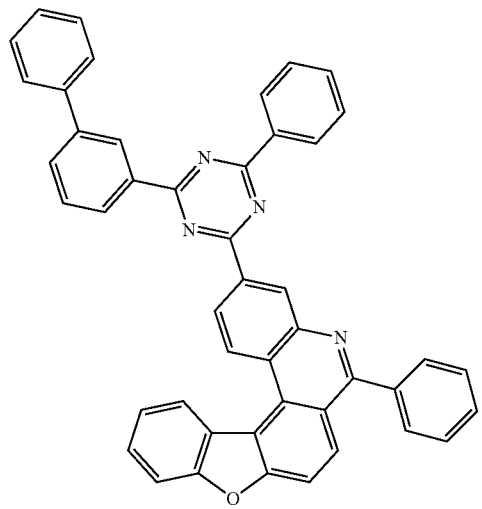
127
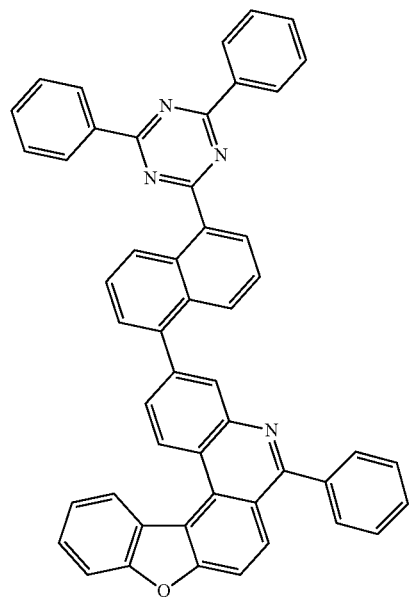
128
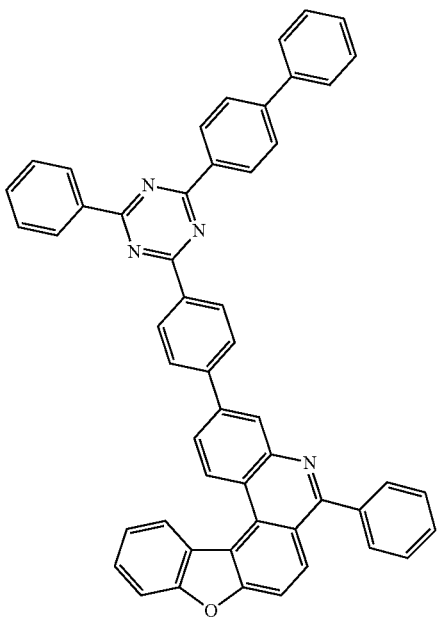
129
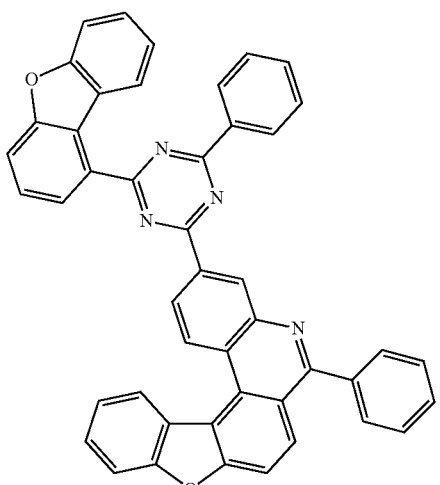
130
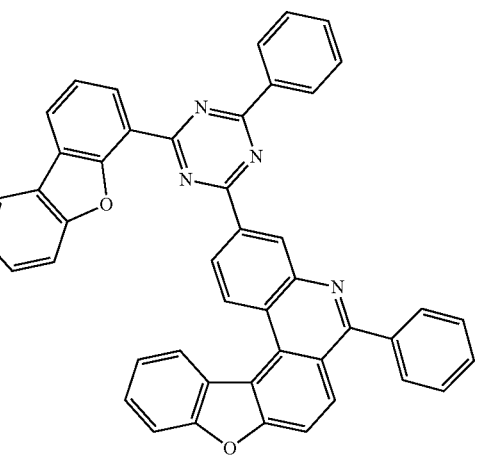

567
-continued
568
-continued
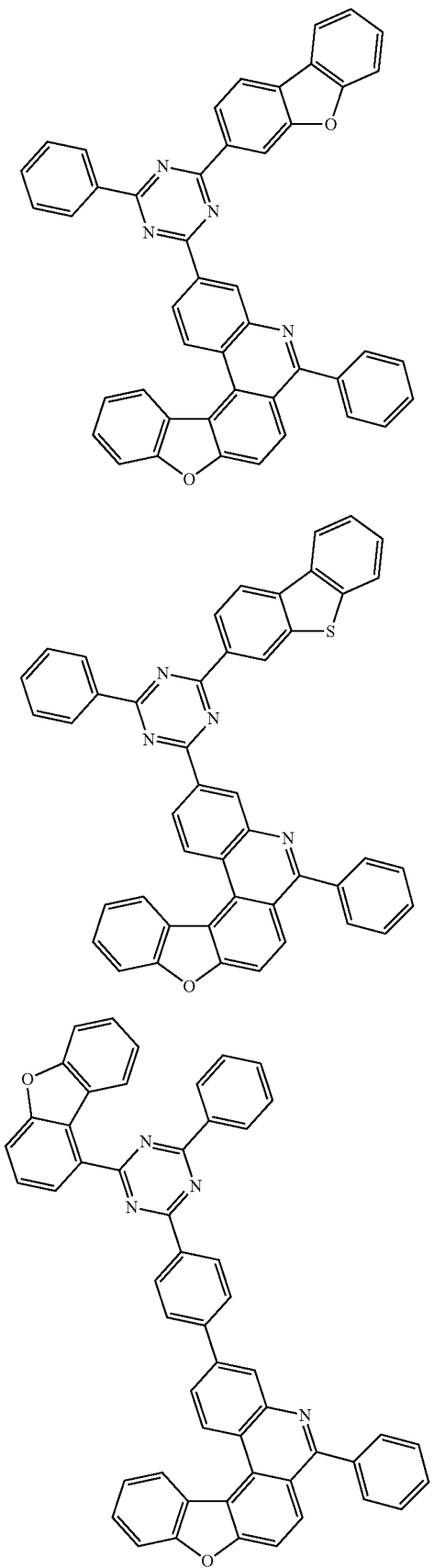
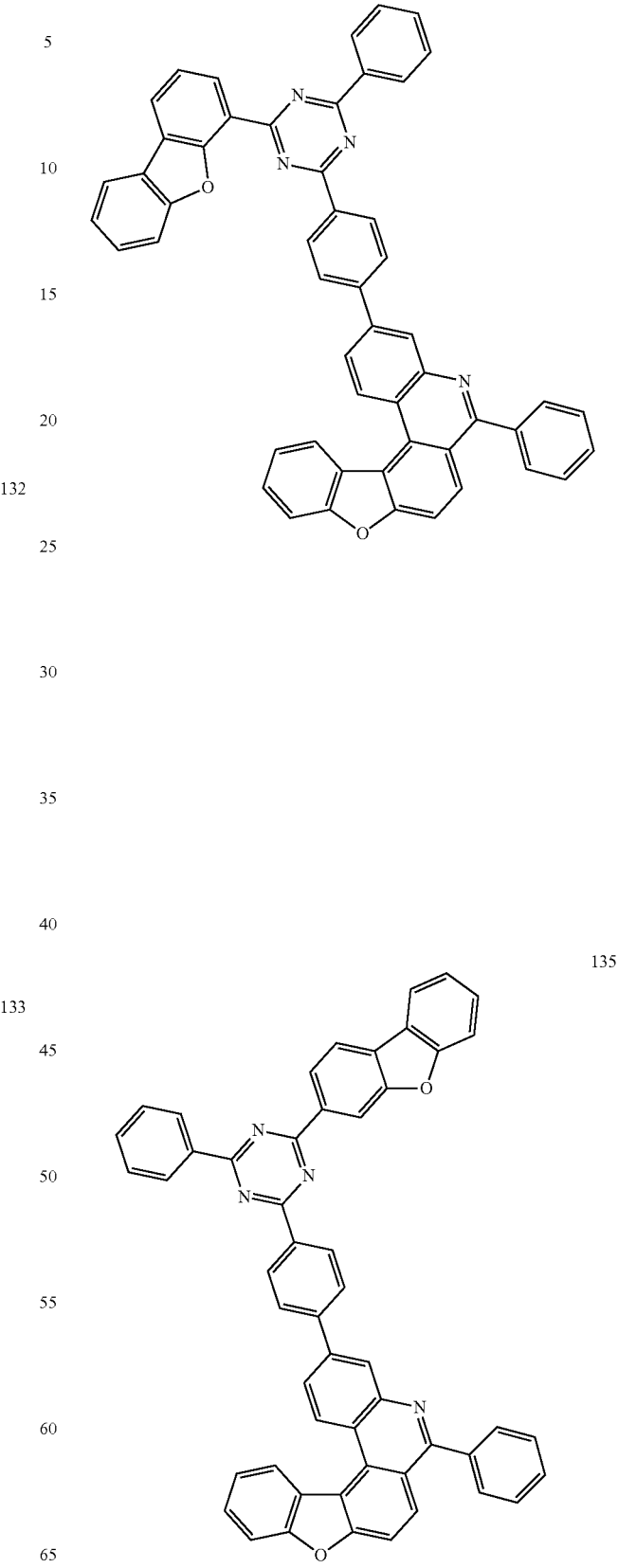

569
-continued
136
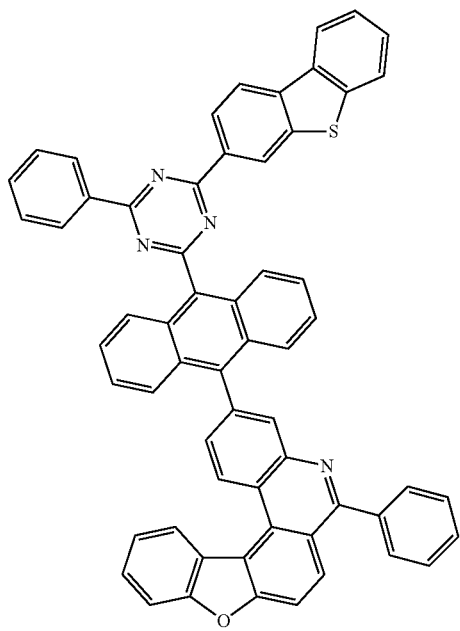
137
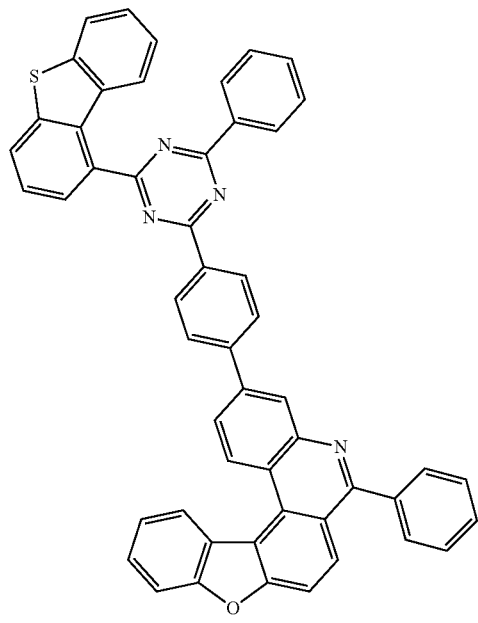
570
-continued
138
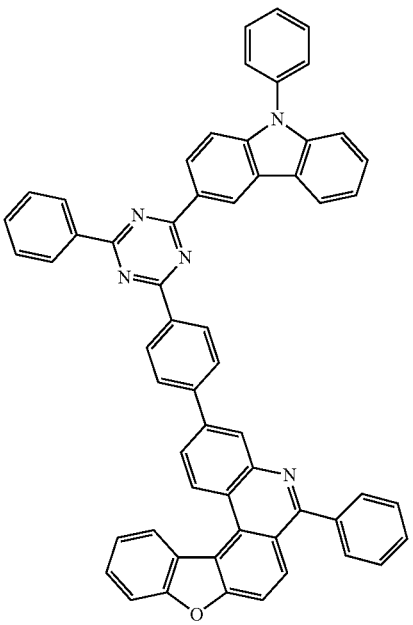
139
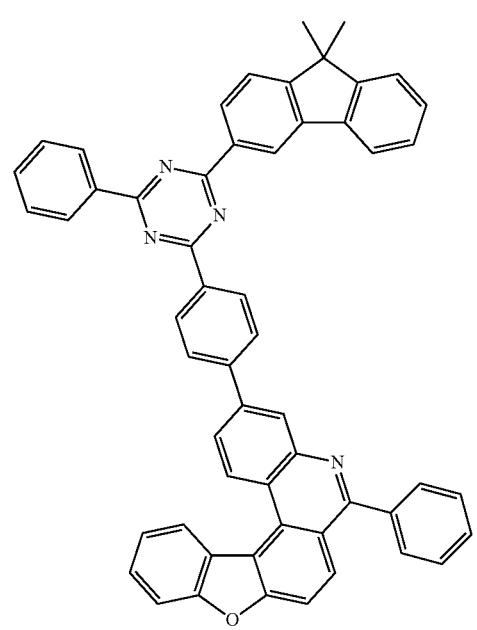

571
-continued
140
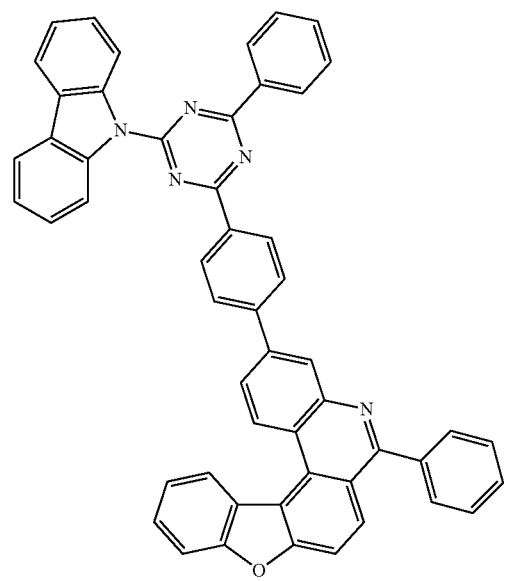
141
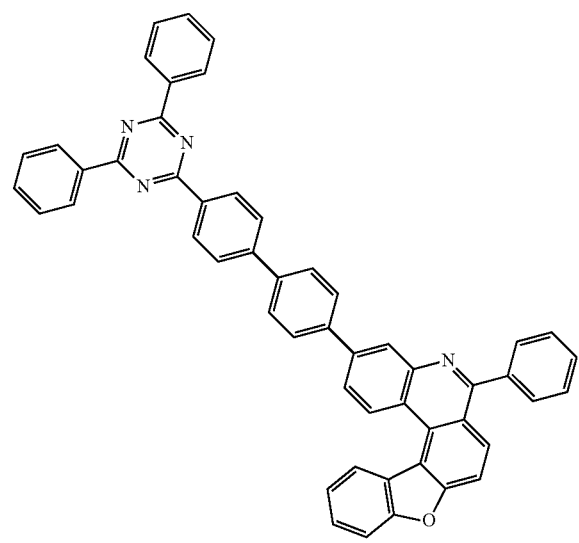
142
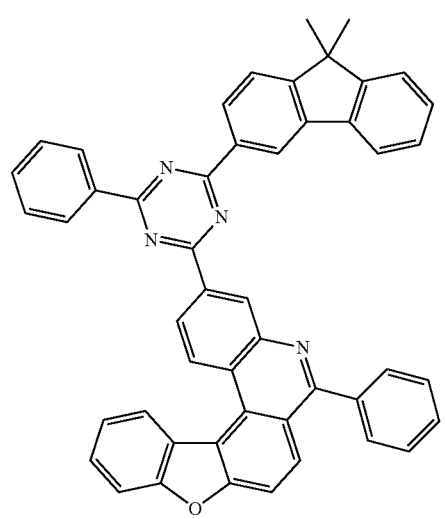
572
-continued
143
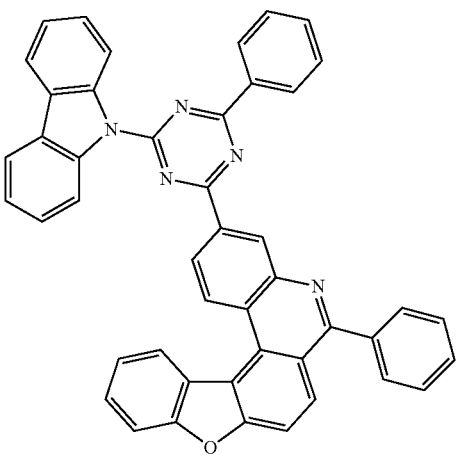
144
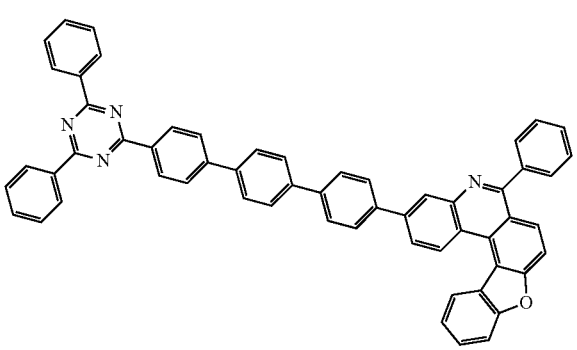
145
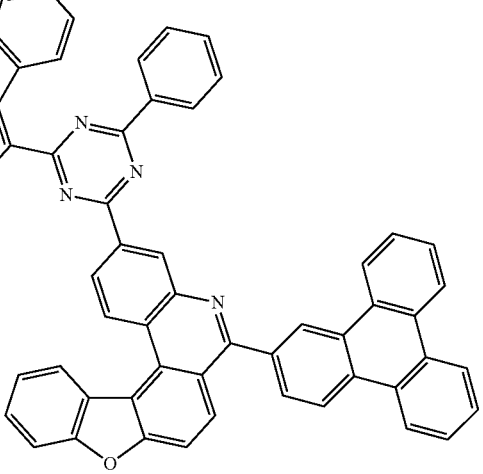

146
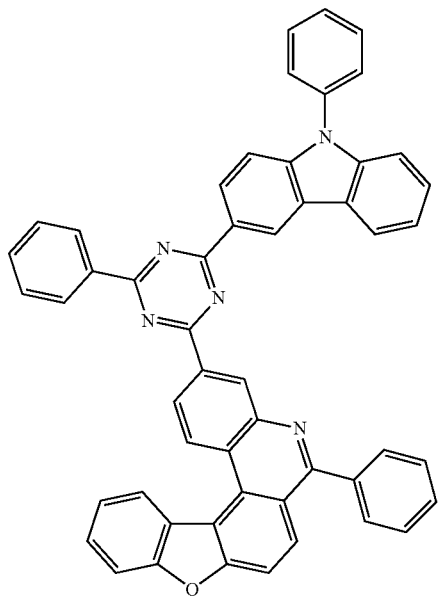
147
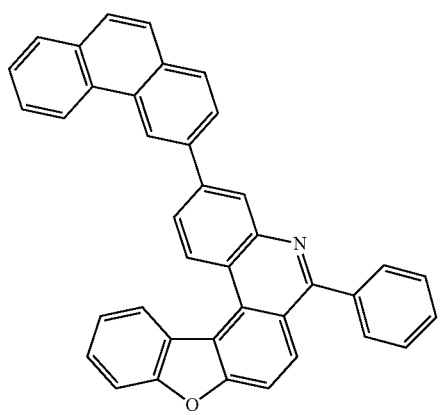
148
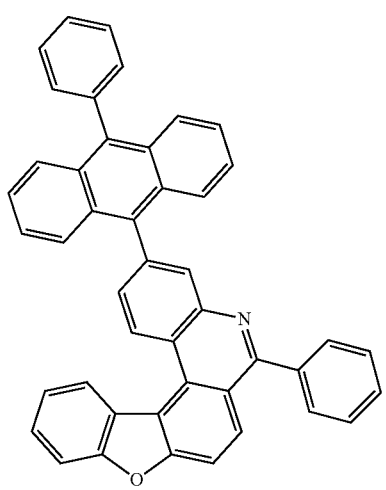
149
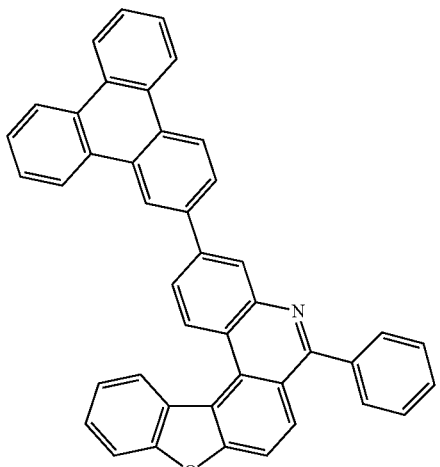
150
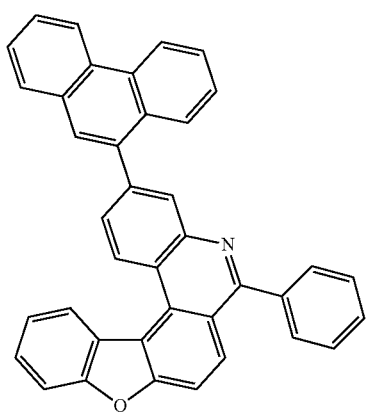
151
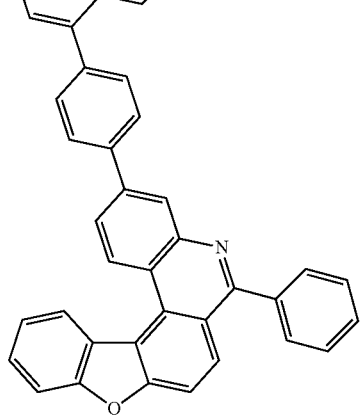

152
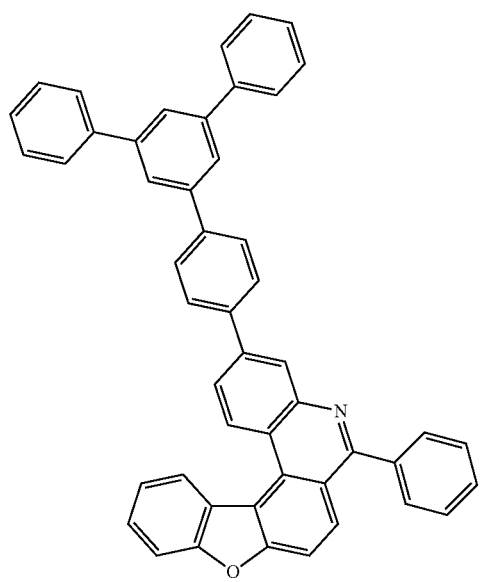
153
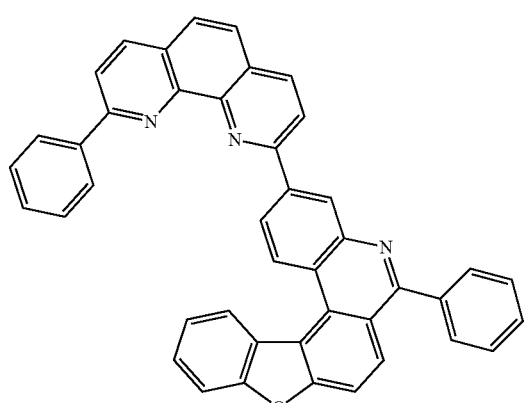
154
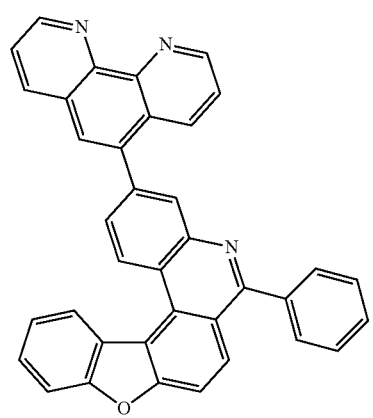
155
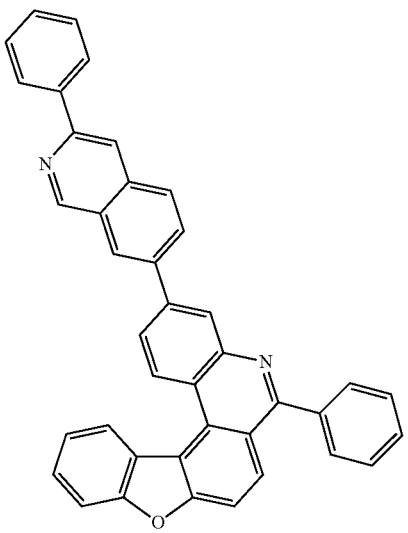
156
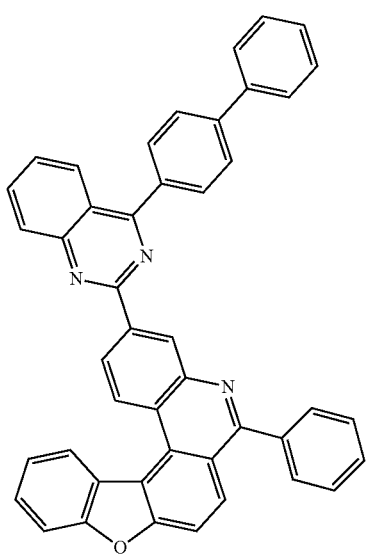
157
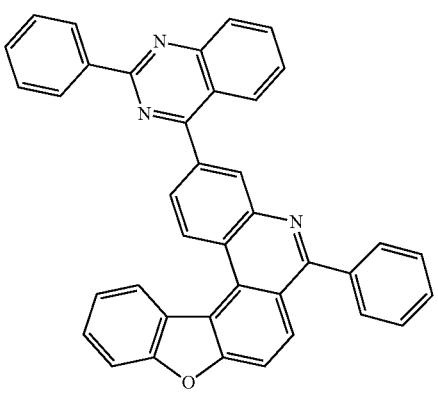

158
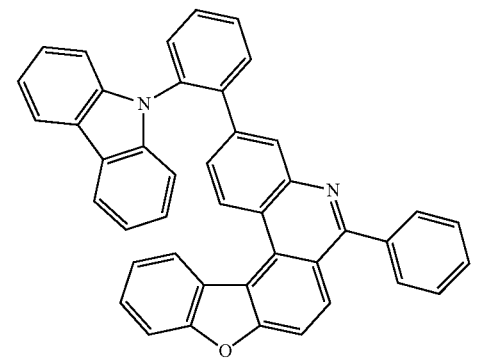
159
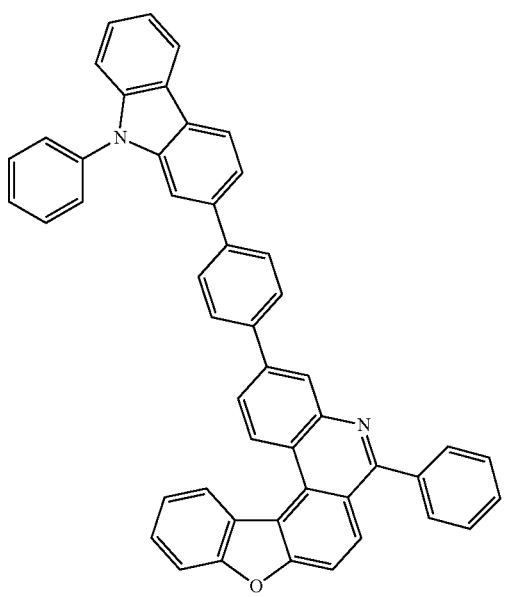
160
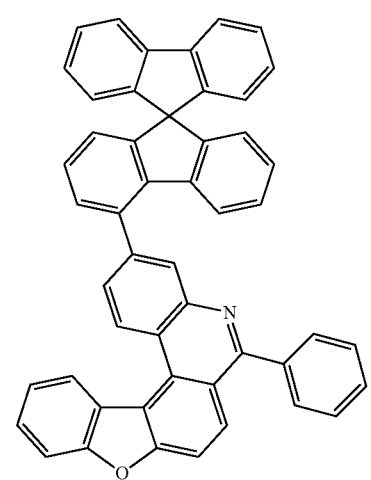
161

162
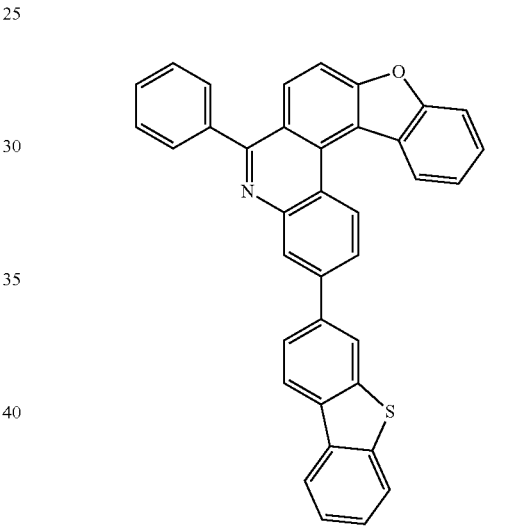
163
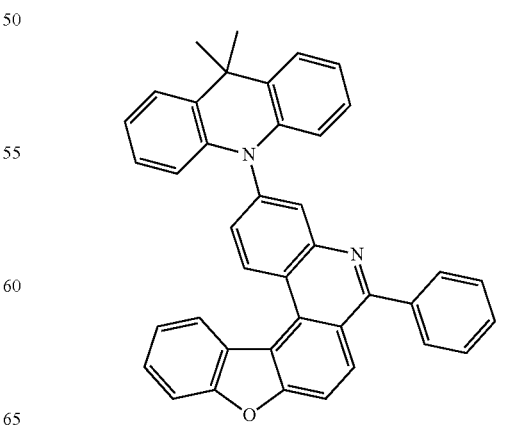

579
-continued
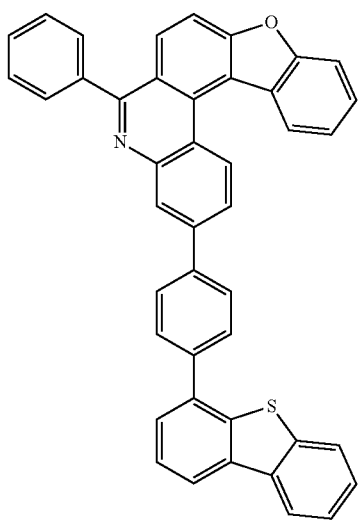
164
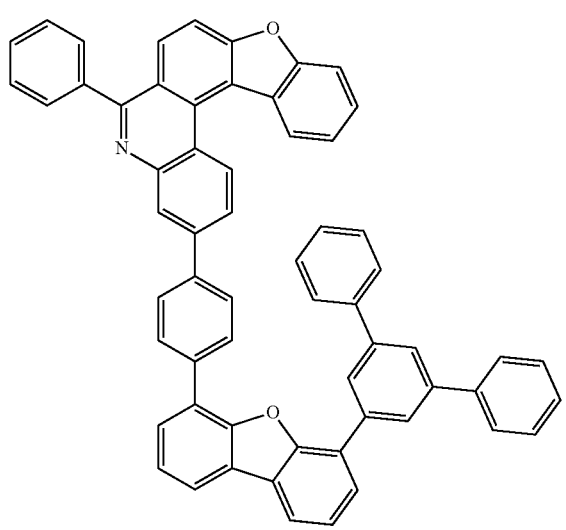
165
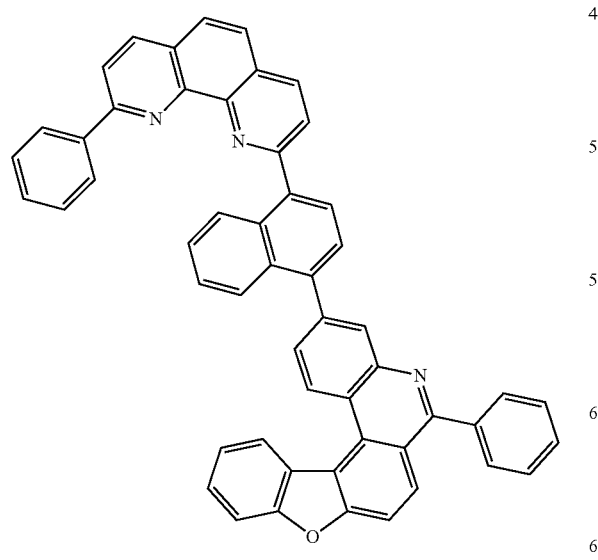
166
580
-continued
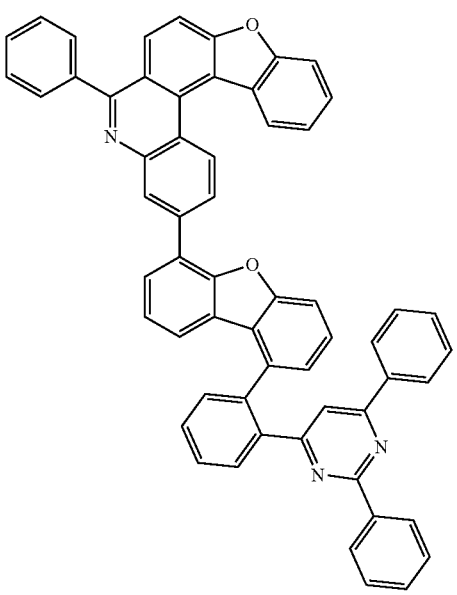
167
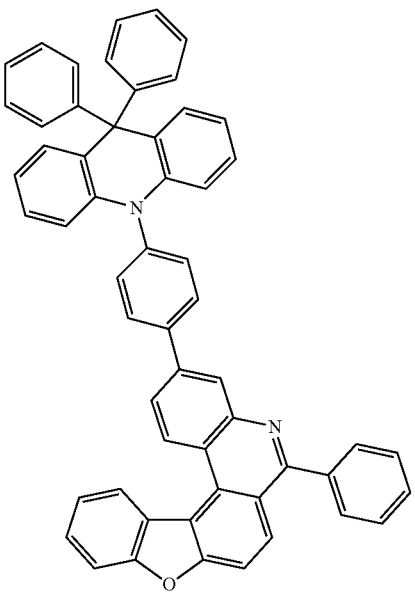
168

169
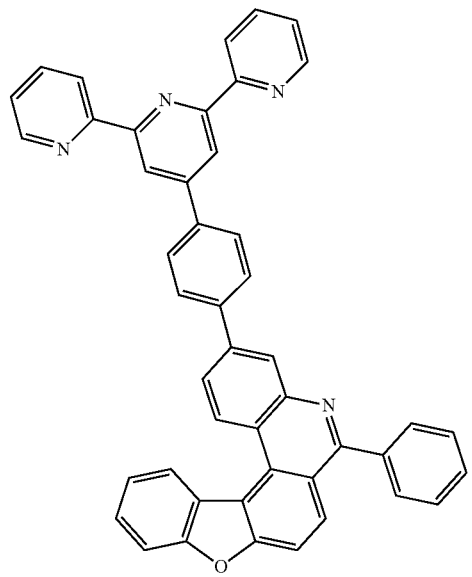
170
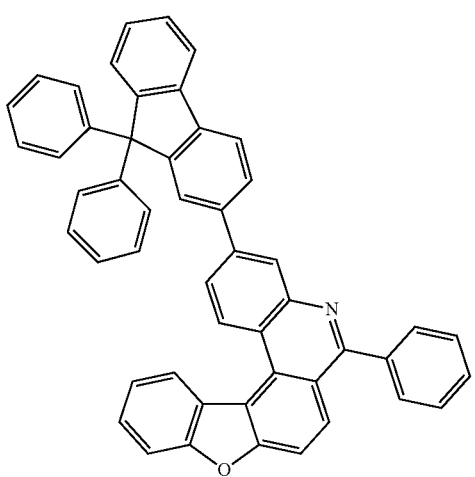
171
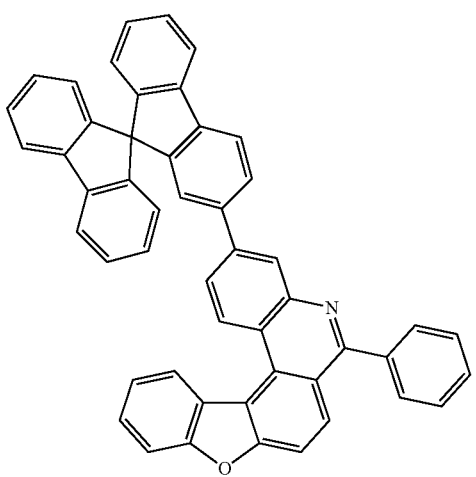
172
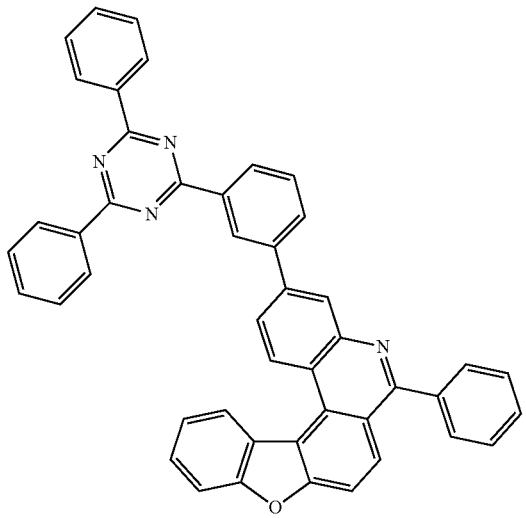
173
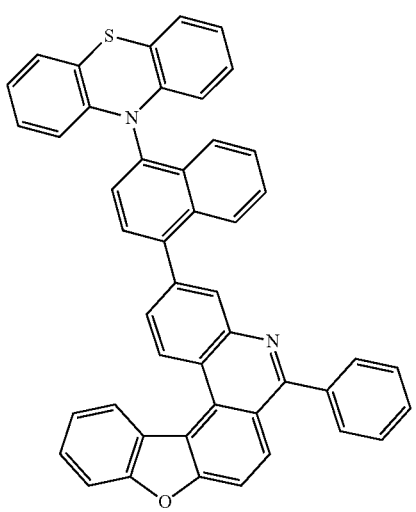
174
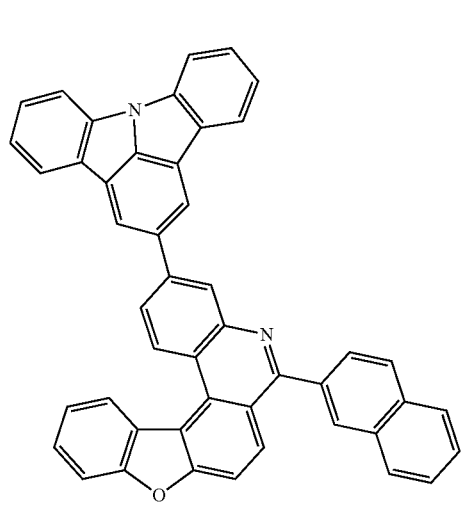

583
-continued
175
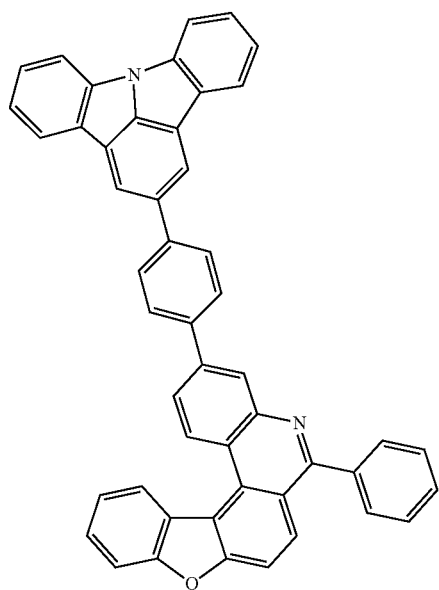
176
584
-continued
177
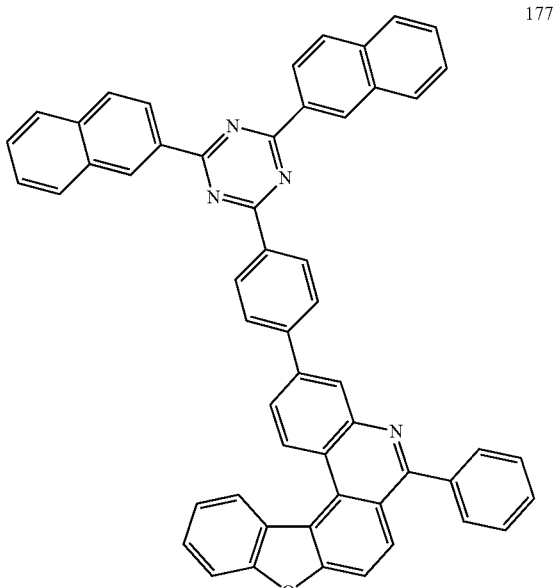
178

179
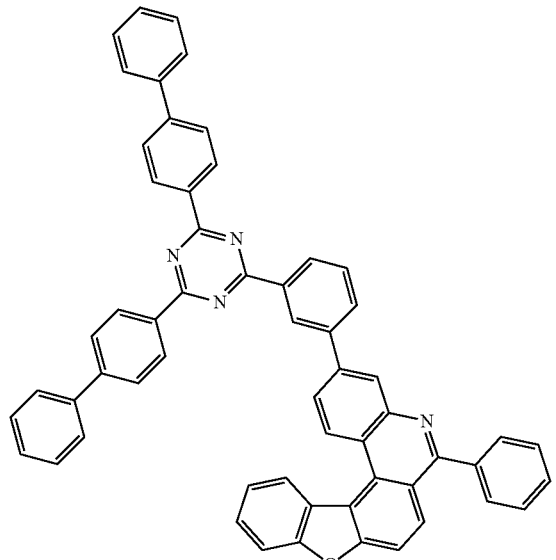
180
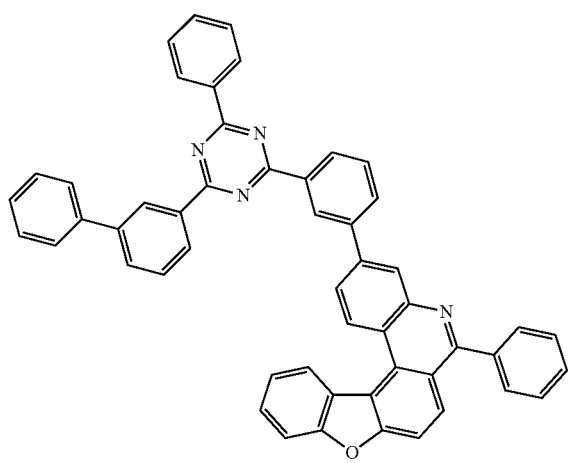
181
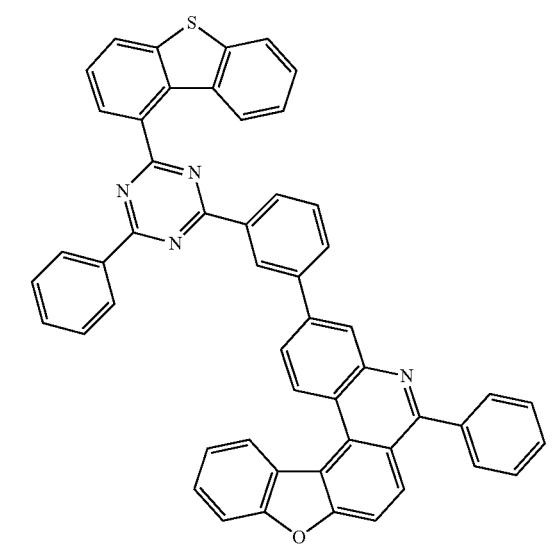
182
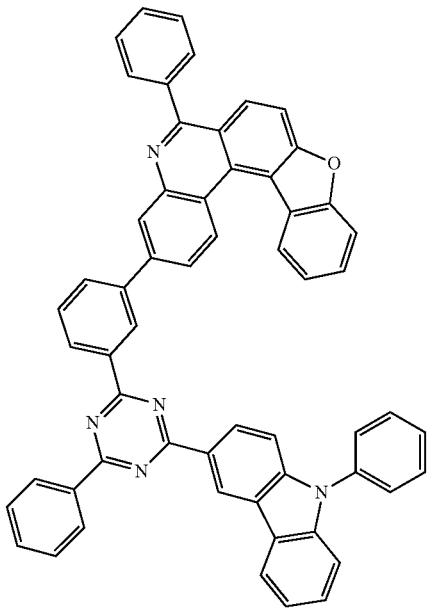
183
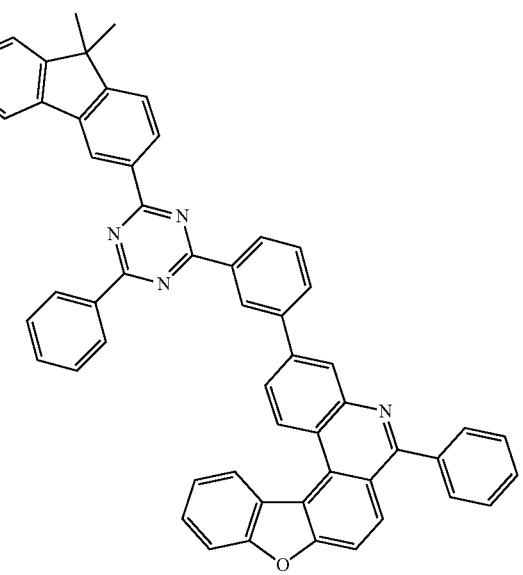

587
-continued
184
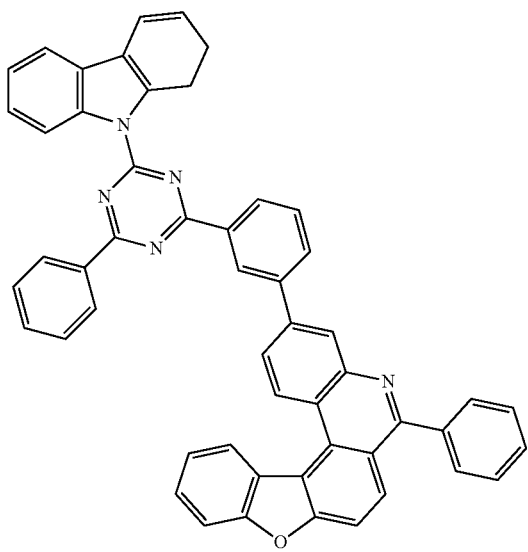
185
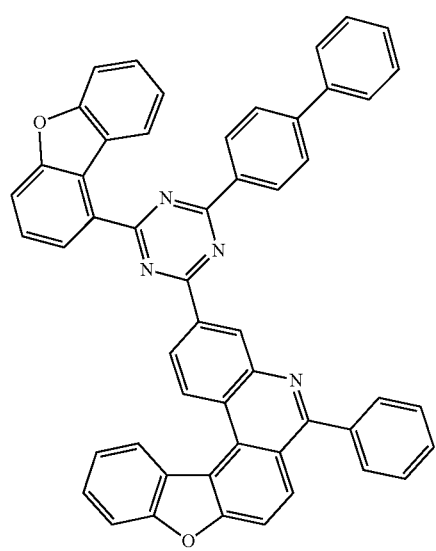
186
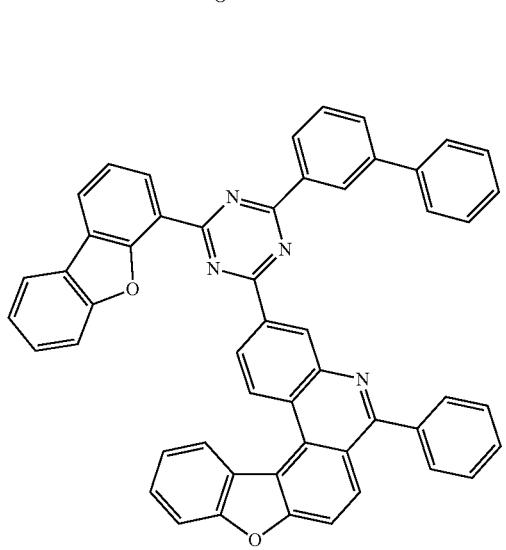
588
-continued
187
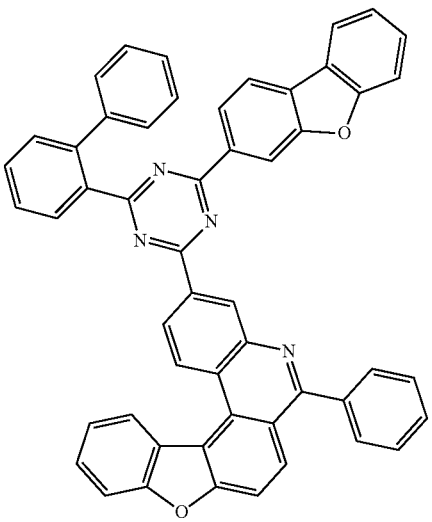
188
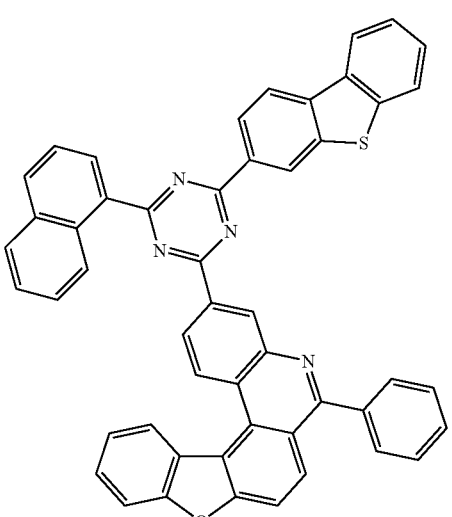
189
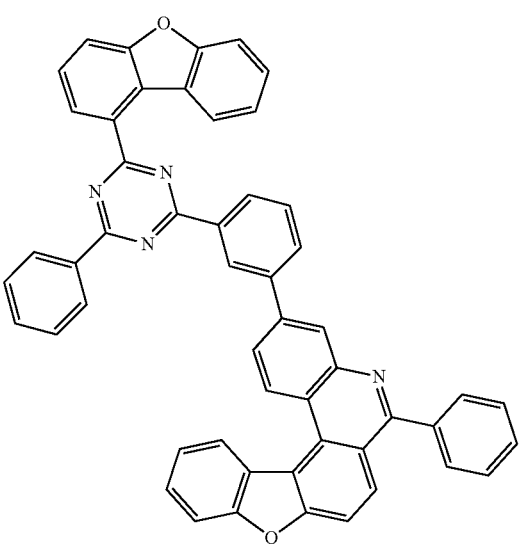

589
-continued
190
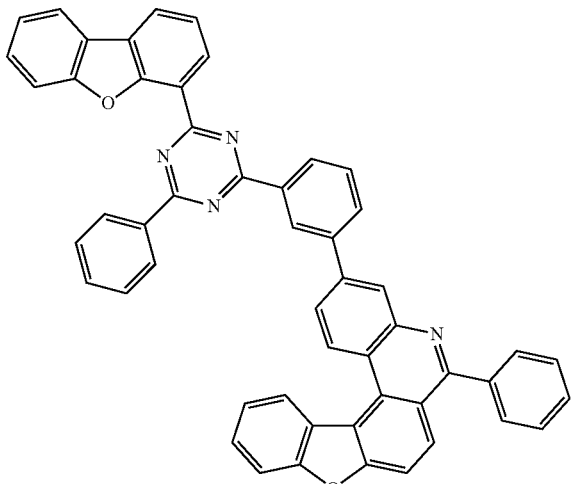
191
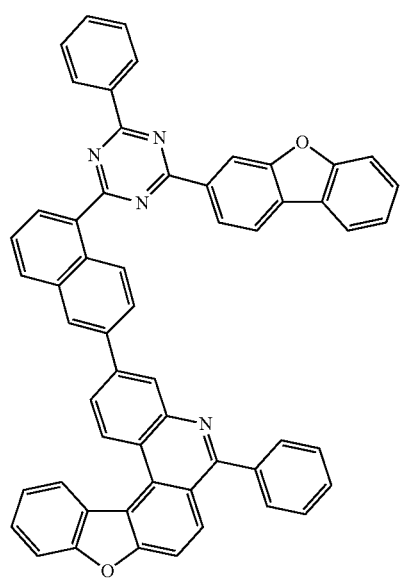
192
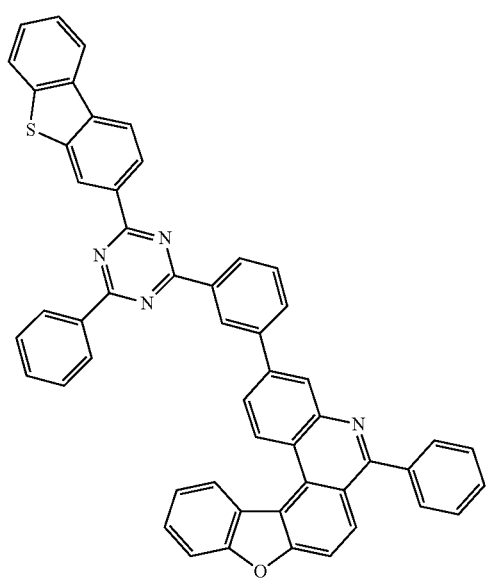
590
-continued
193
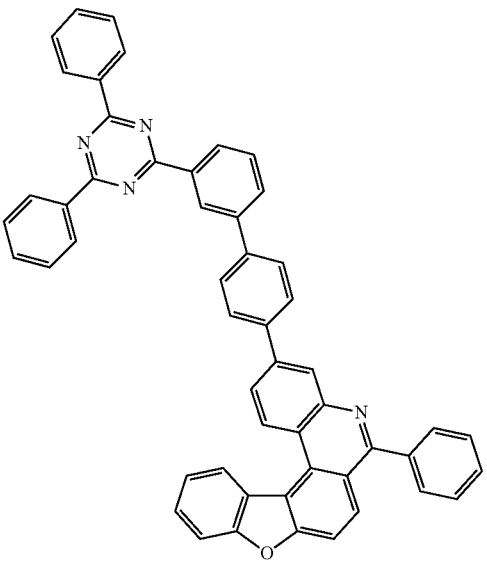
194
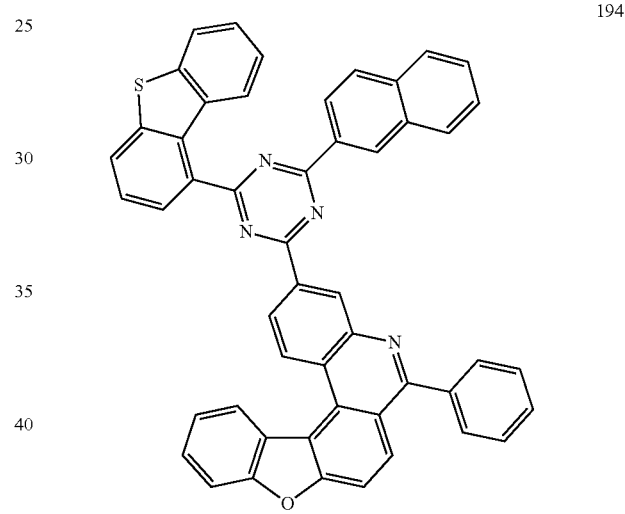
195
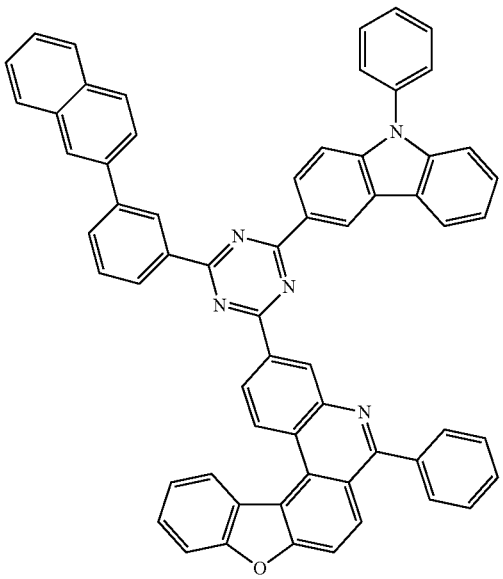

591
-continued
196
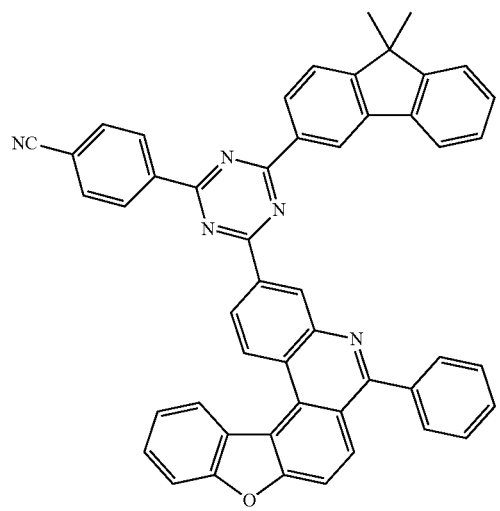
197
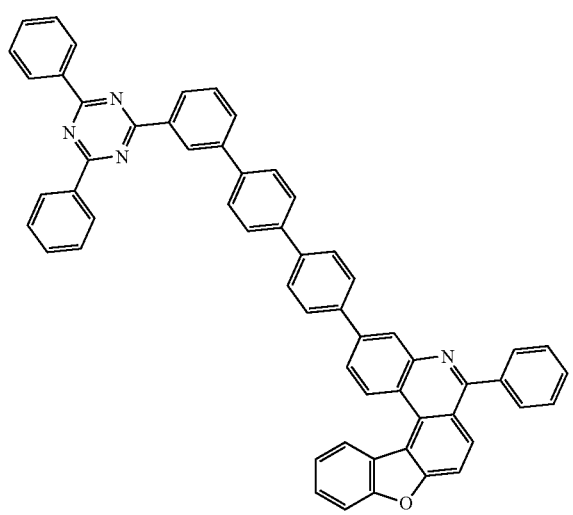
198
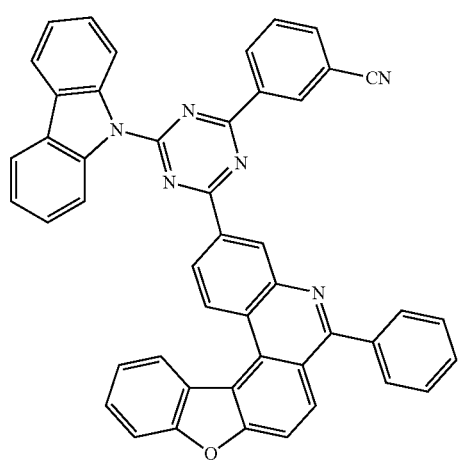
592
-continued
199
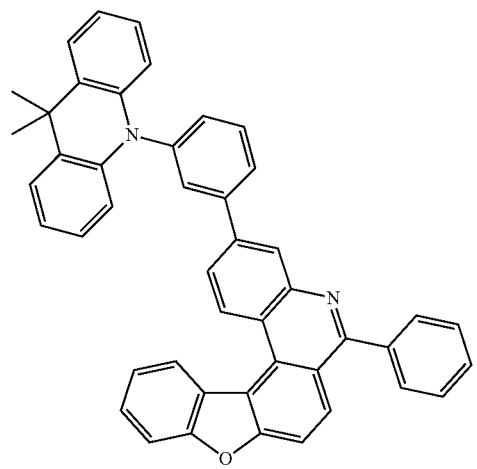
200
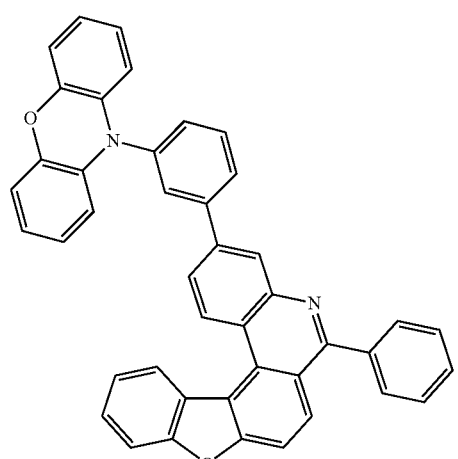
201
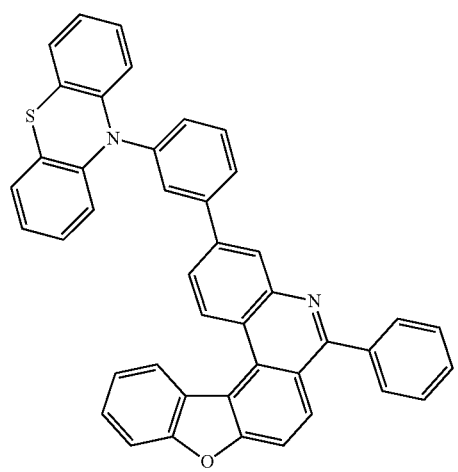

202
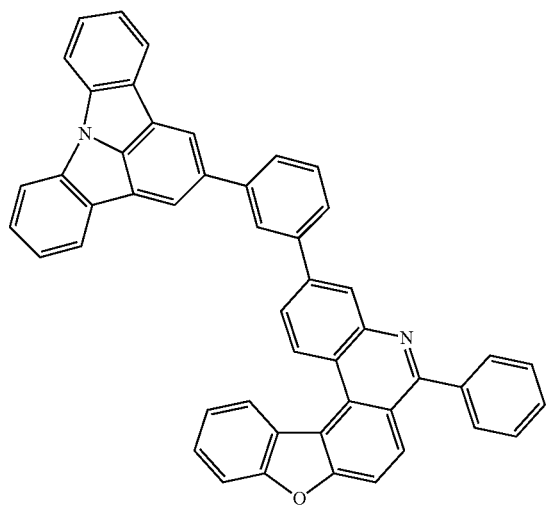
203
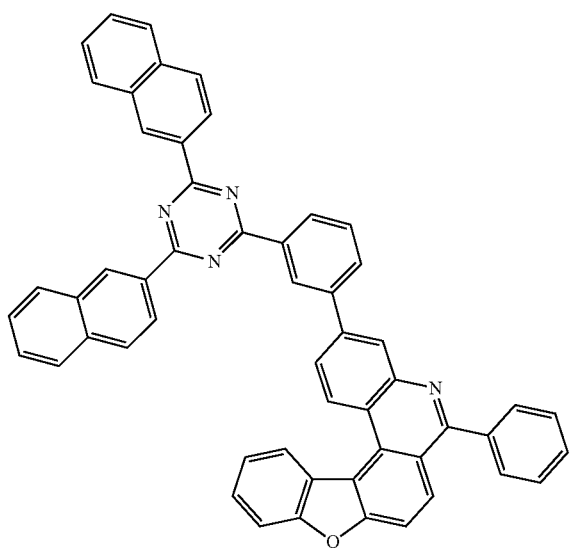
204
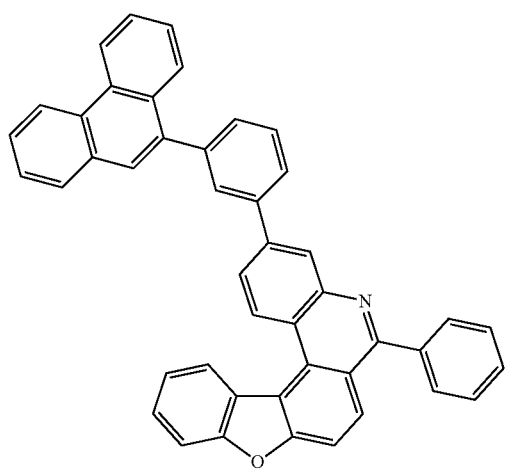
205
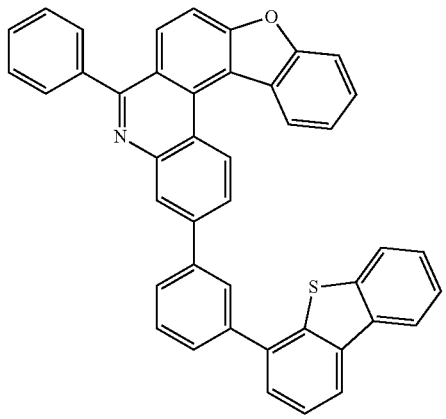
206
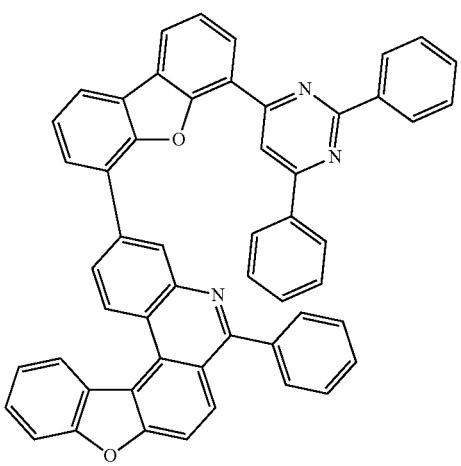
207
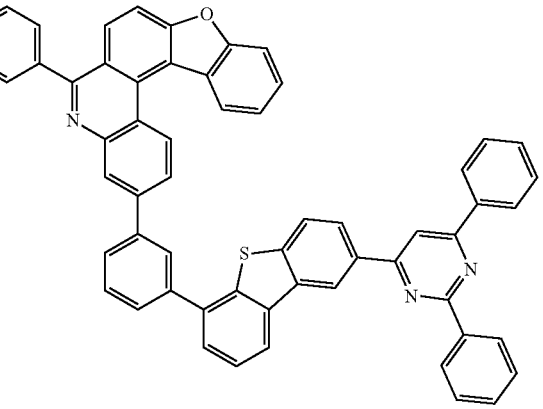

208
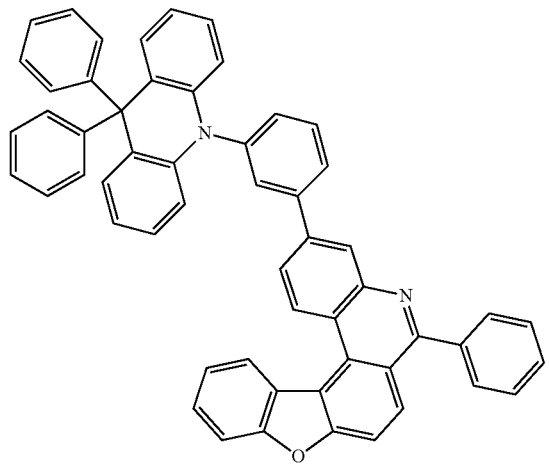
209
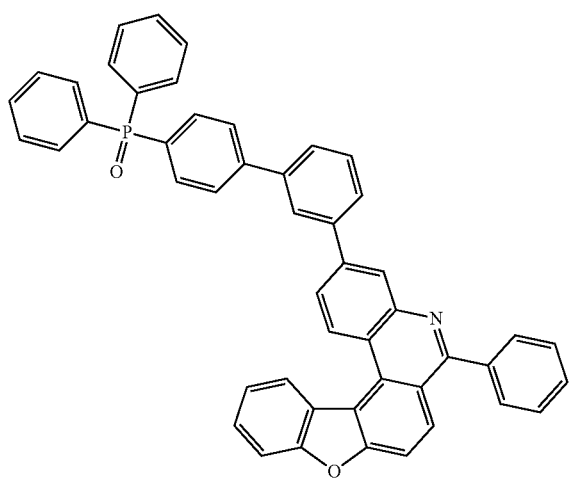
210
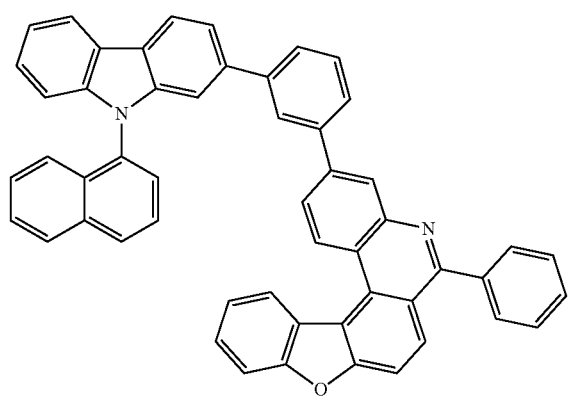
211
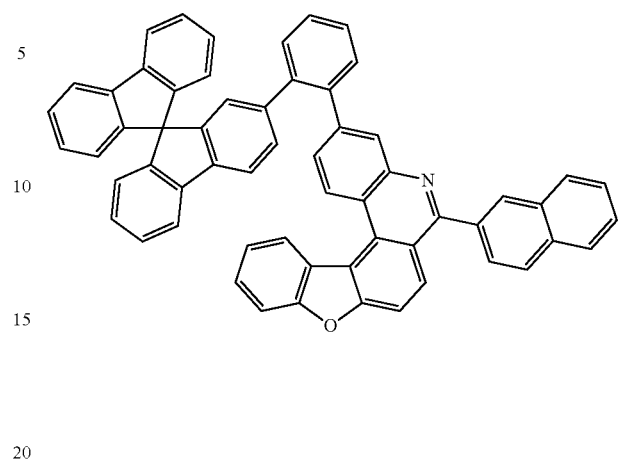
212
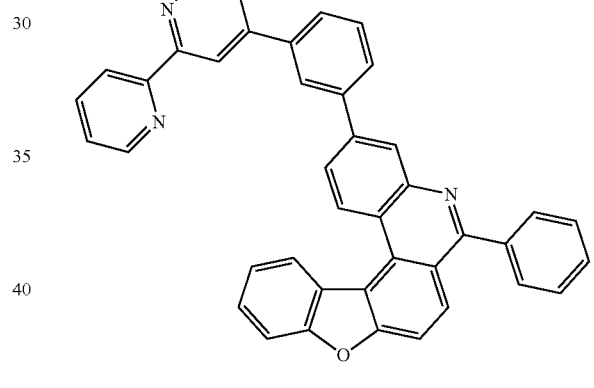
213
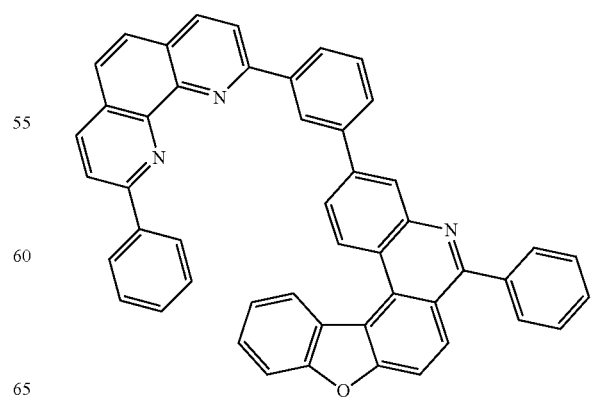

214
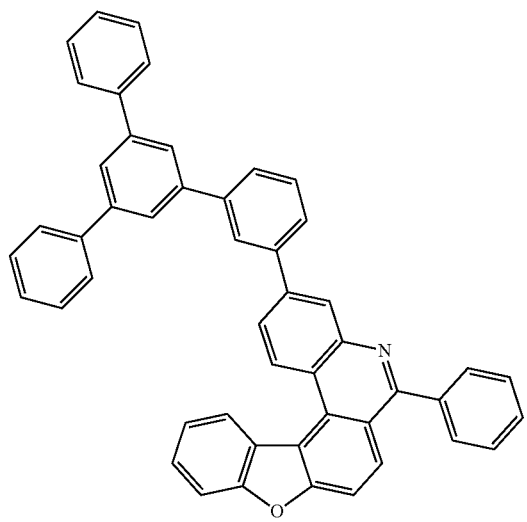
215
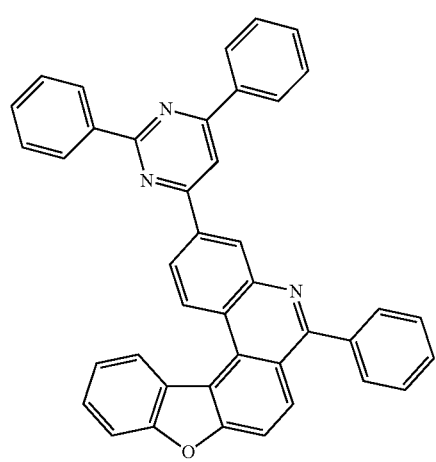
216
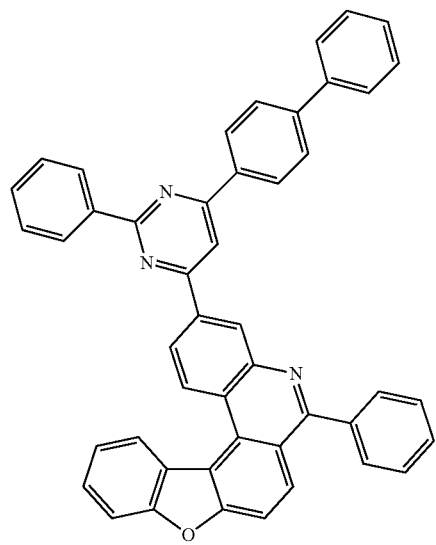
217
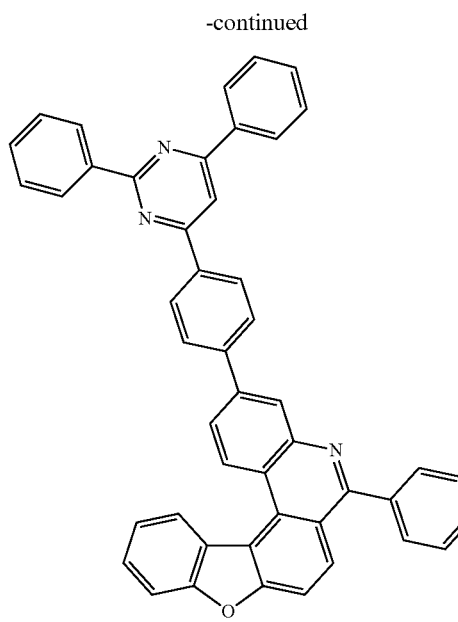
218
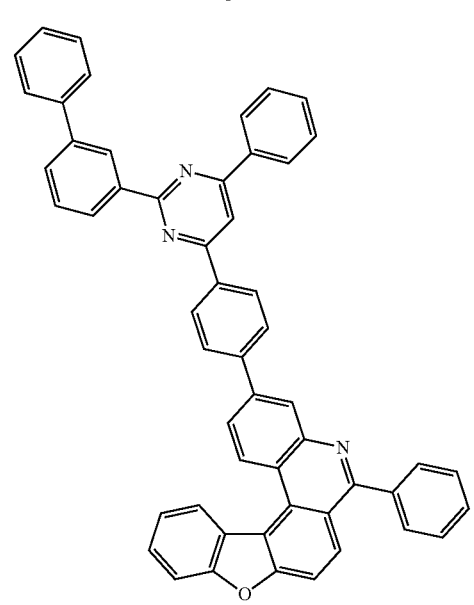
219
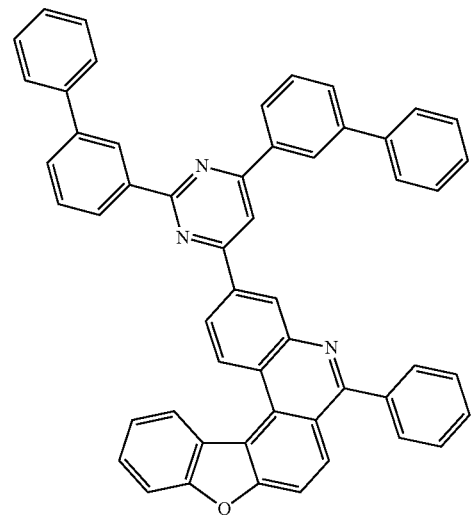

599
-continued
220
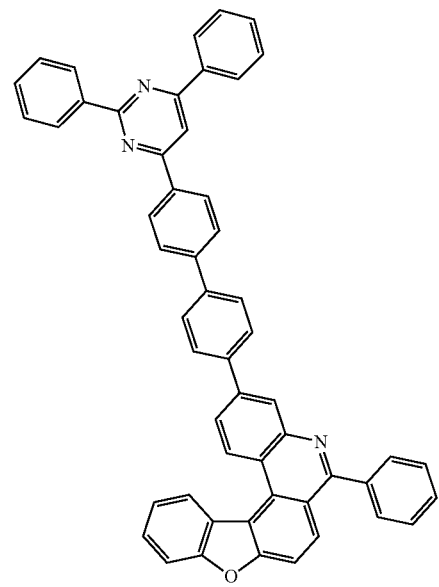
221
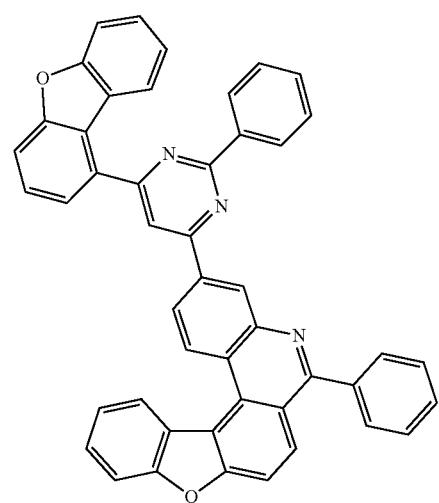
222
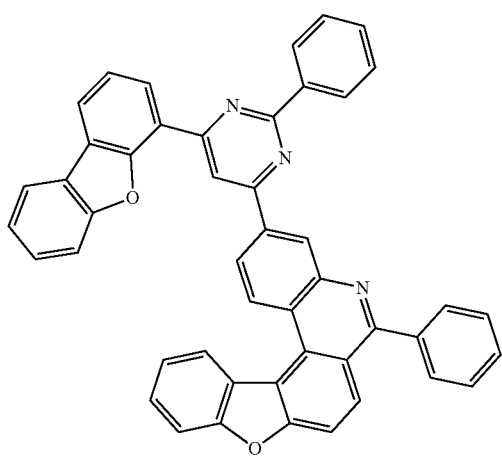
600
-continued
223
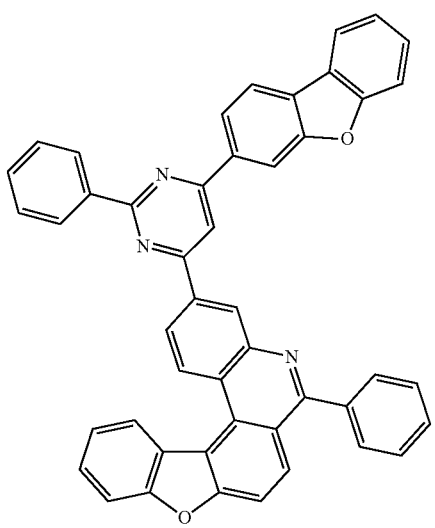
224
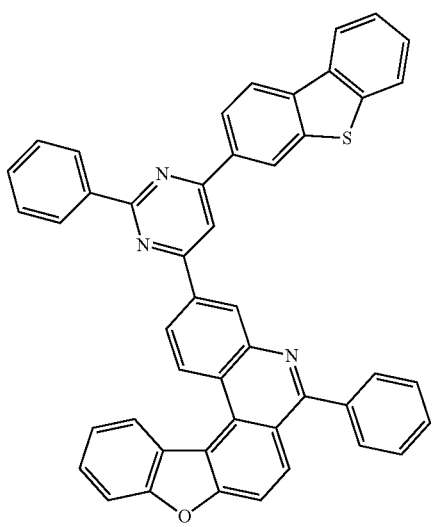
225
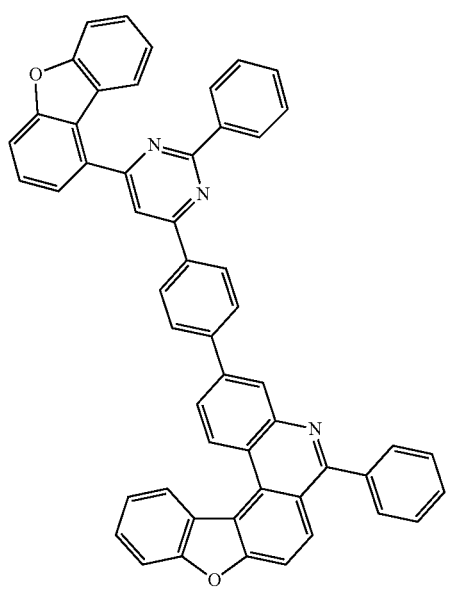

226
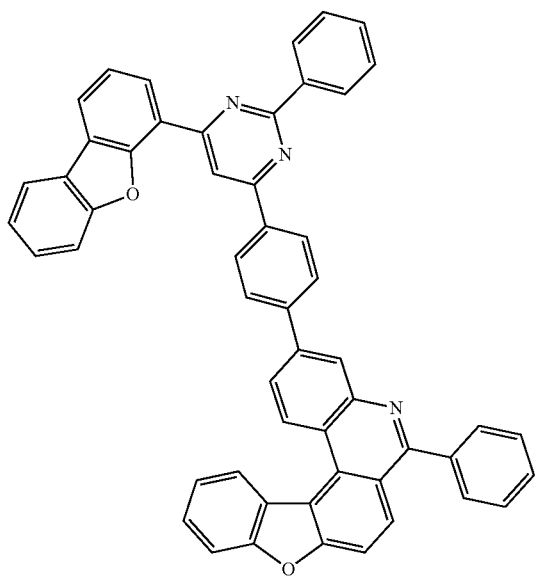
227
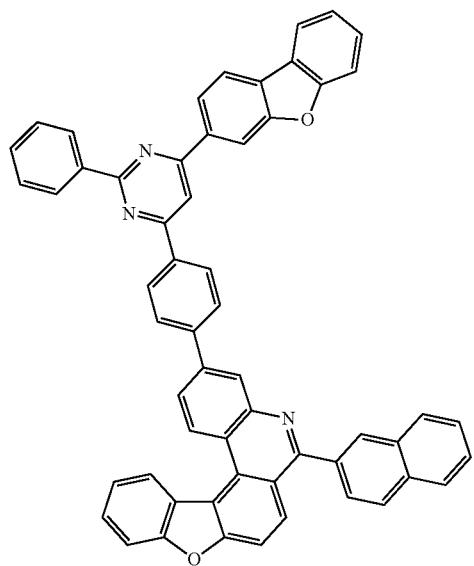
228
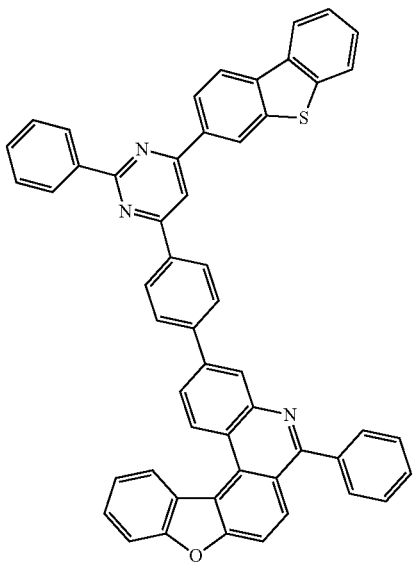
229
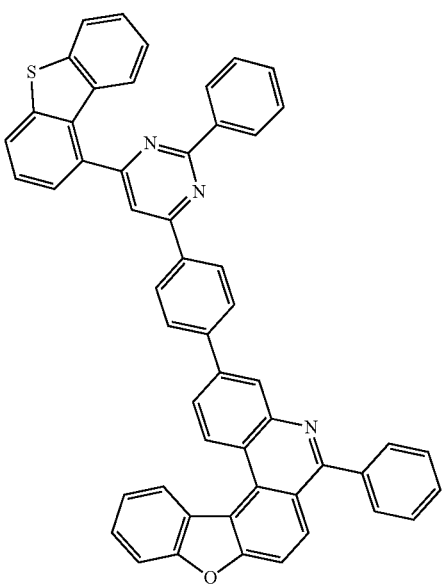

230
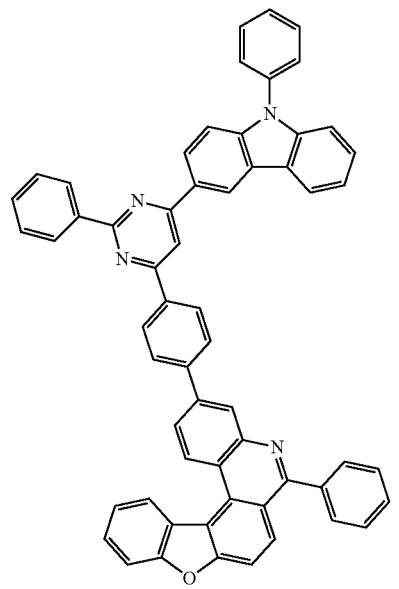
231
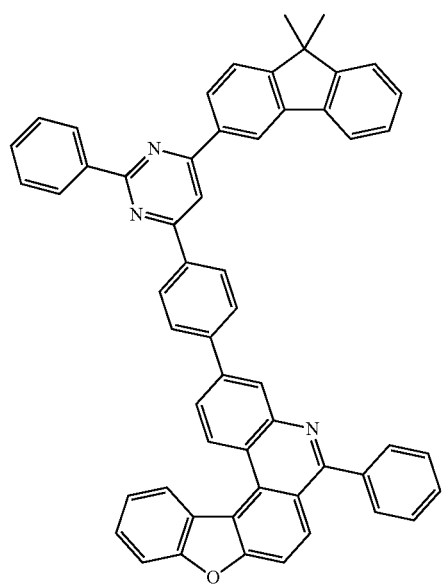
232
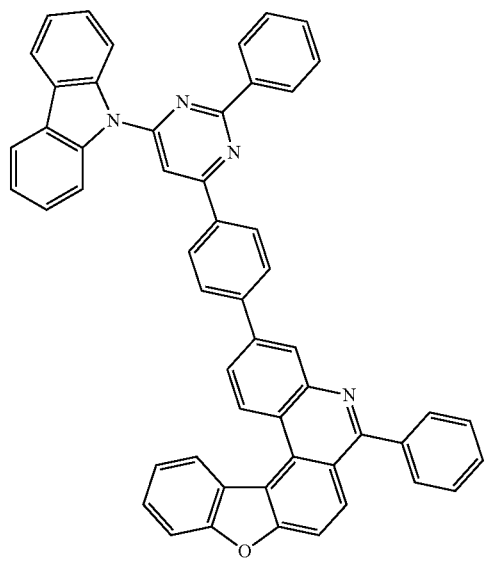
233
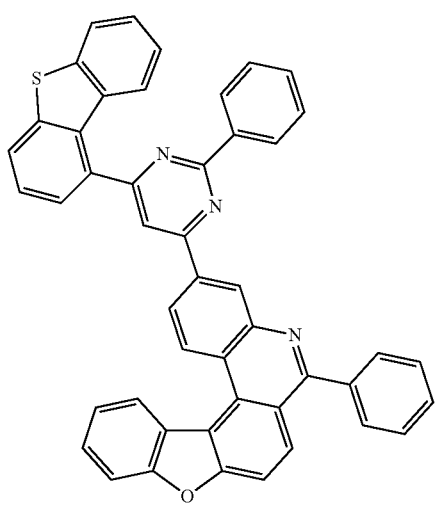
234
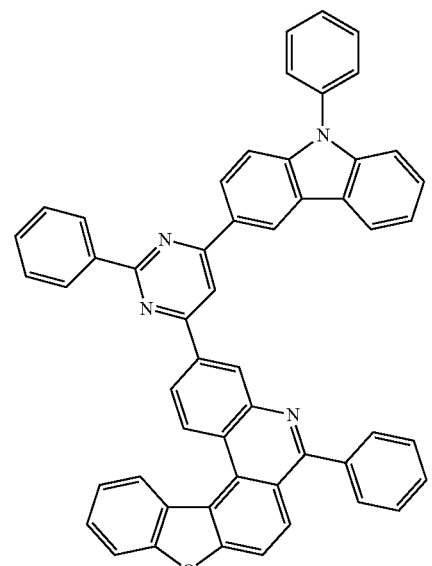

605
-continued
235
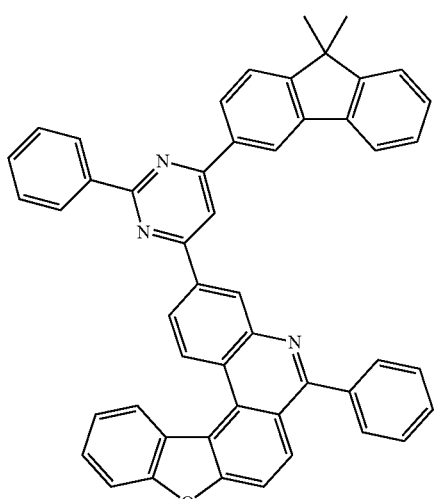
236
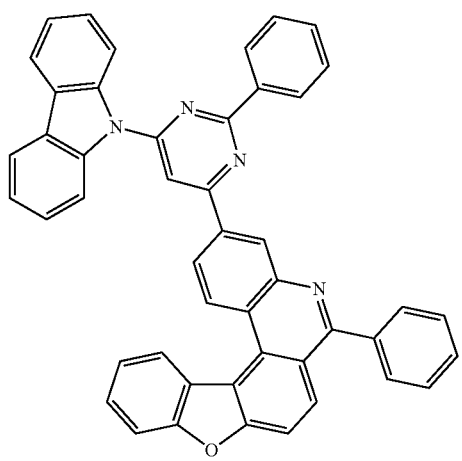
237
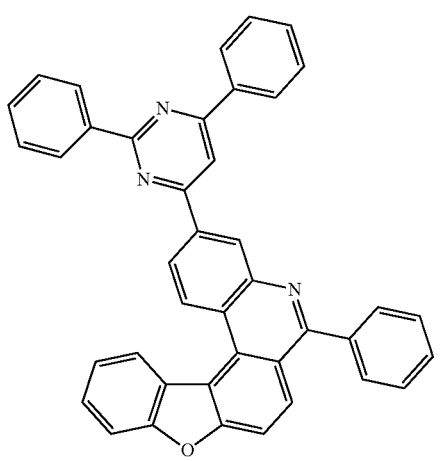
606
-continued
238
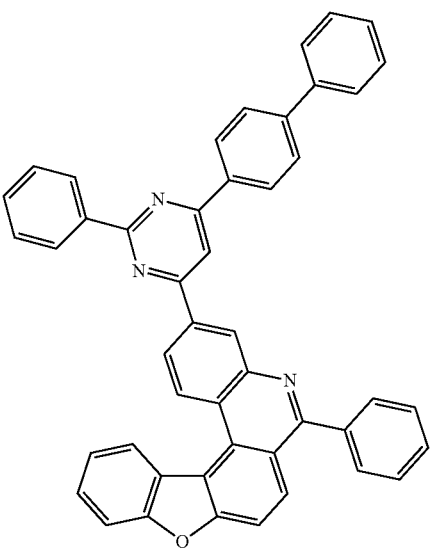
239
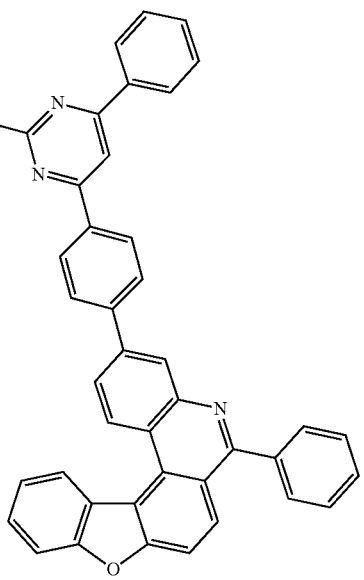

240
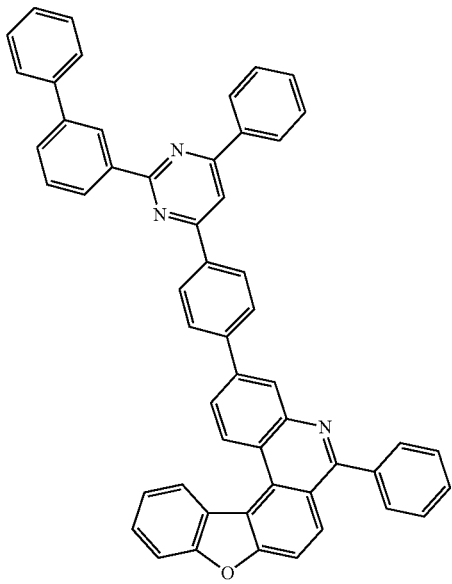
241
243
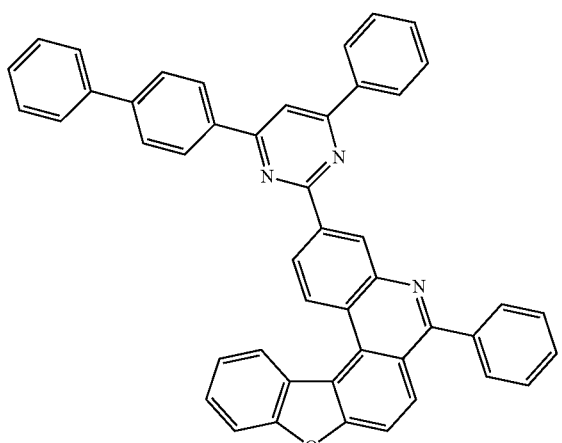
244
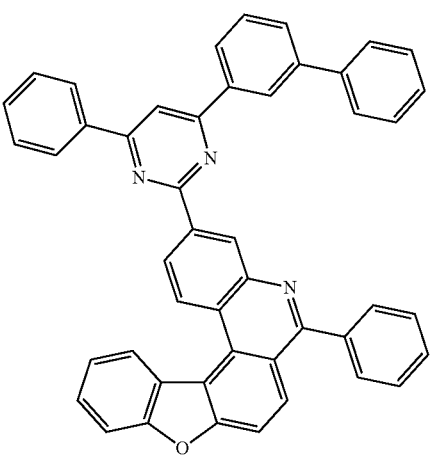
242
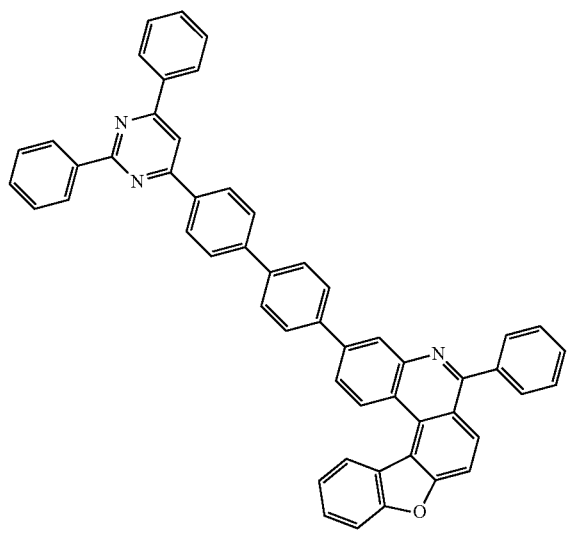
245
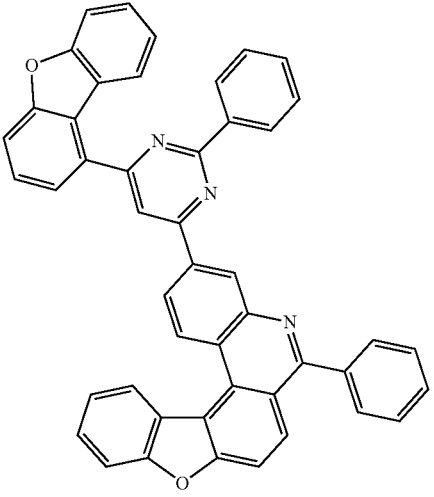

246
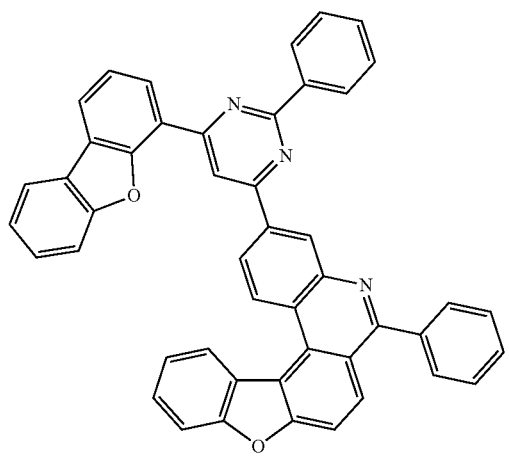
247
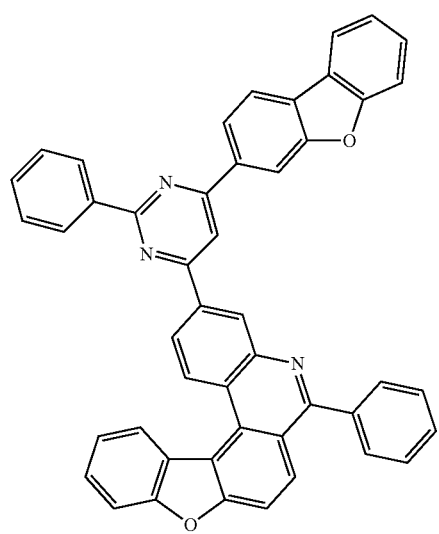
248
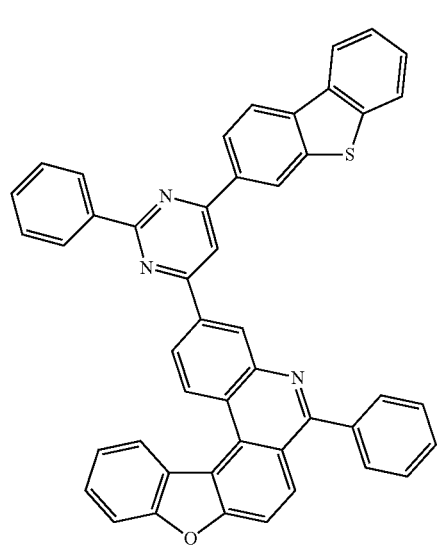
249
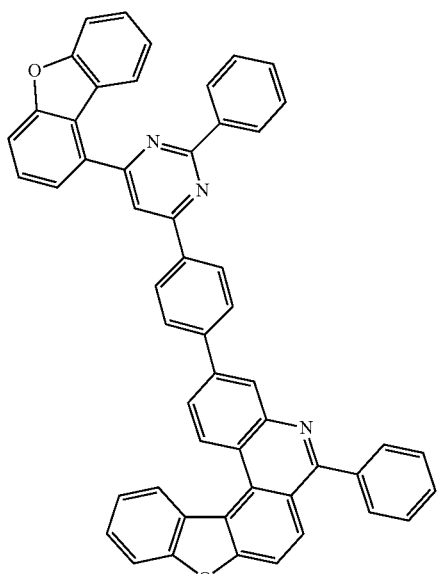
250
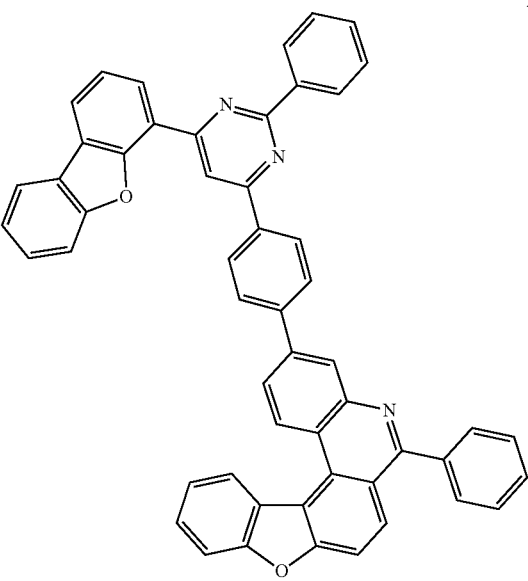

611
-continued
612
-continued
251
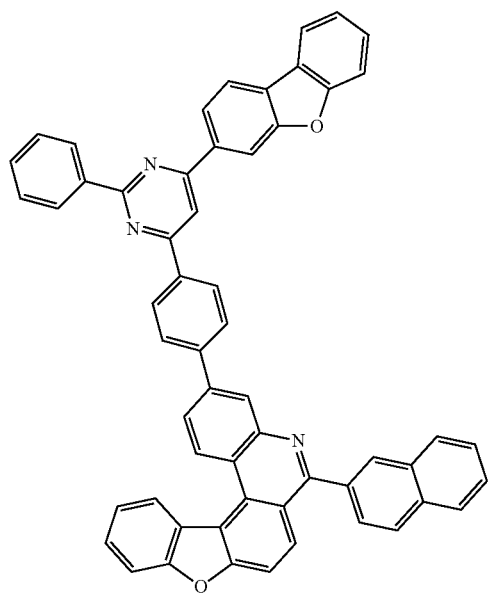
253
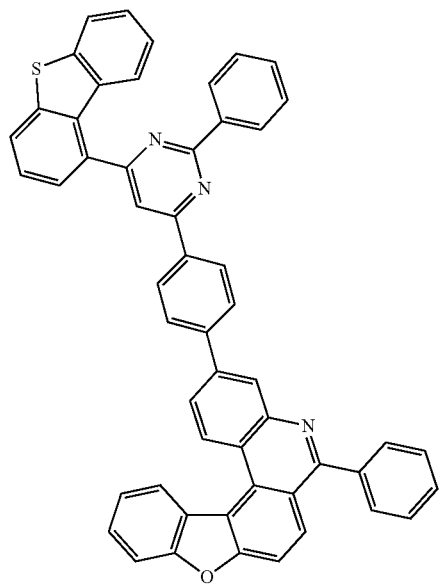
252
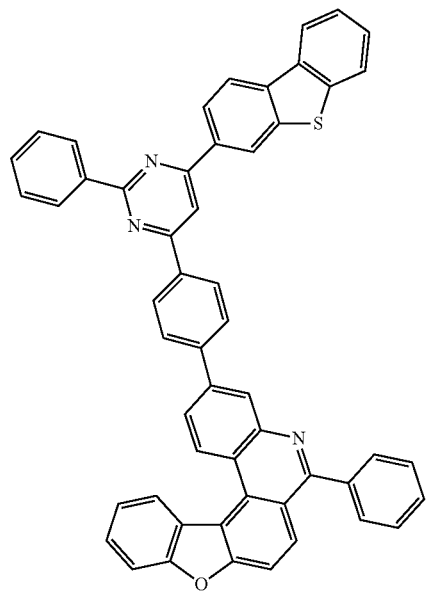
254
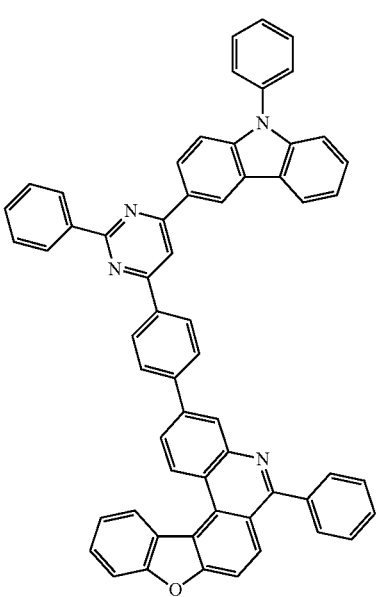

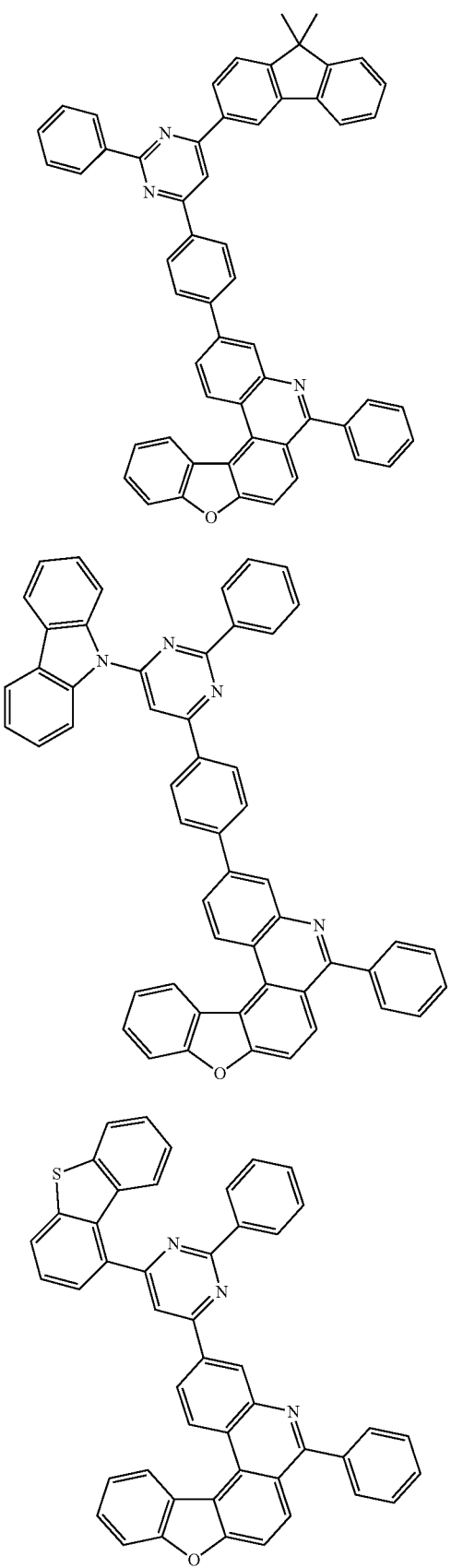
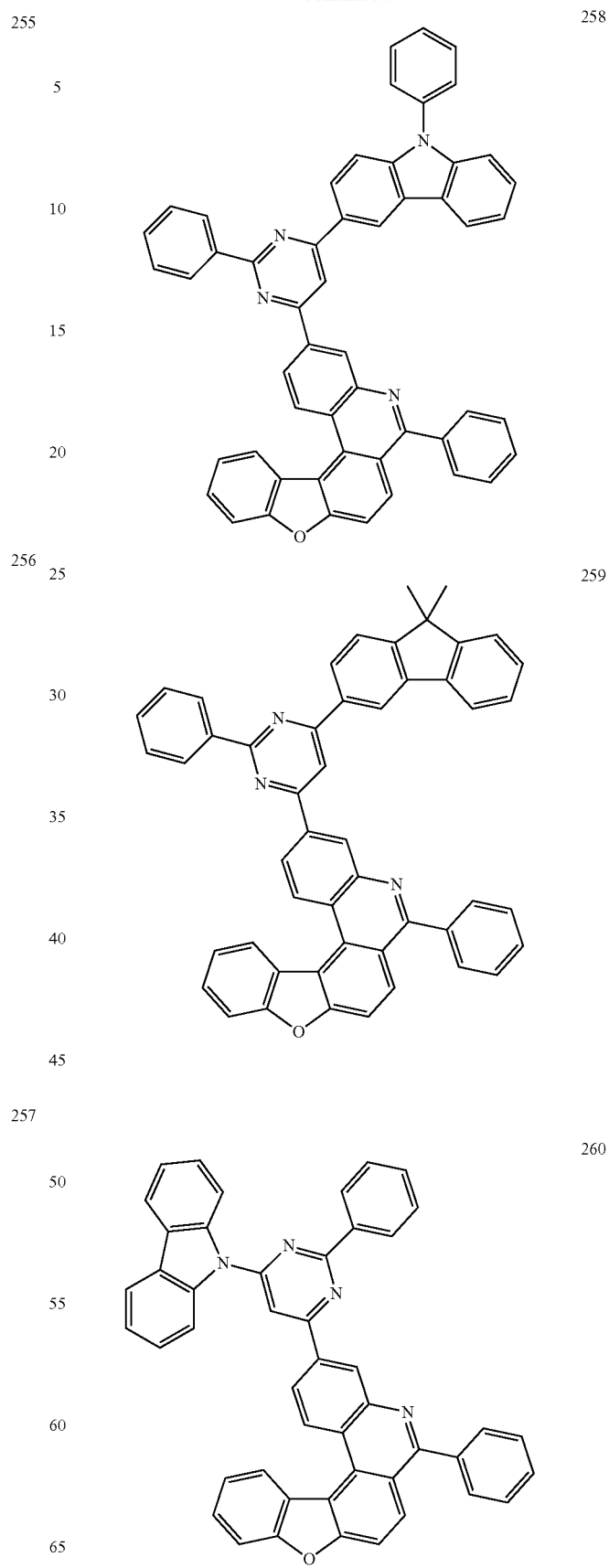

261
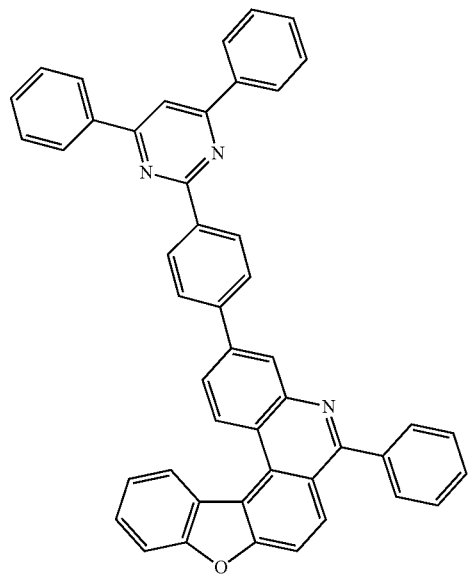
262
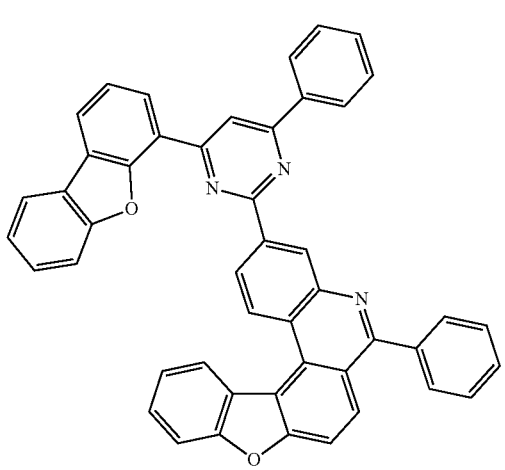
263
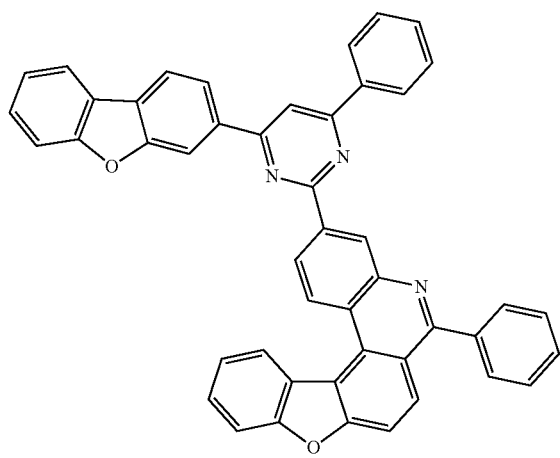
264
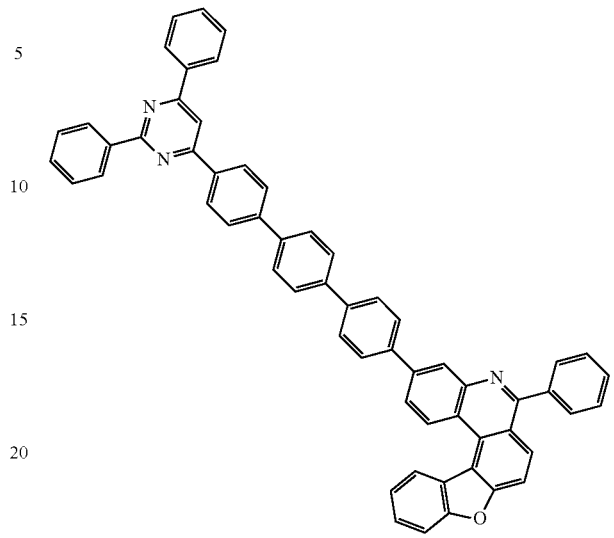
265
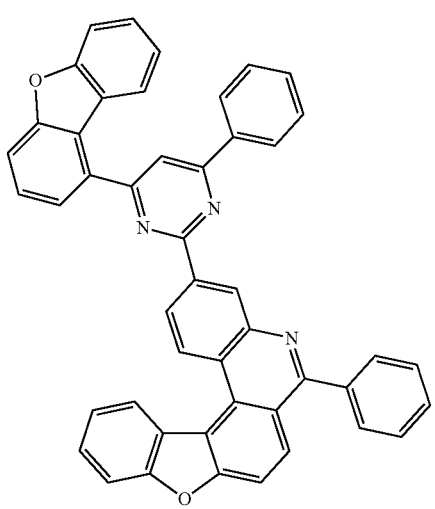
266
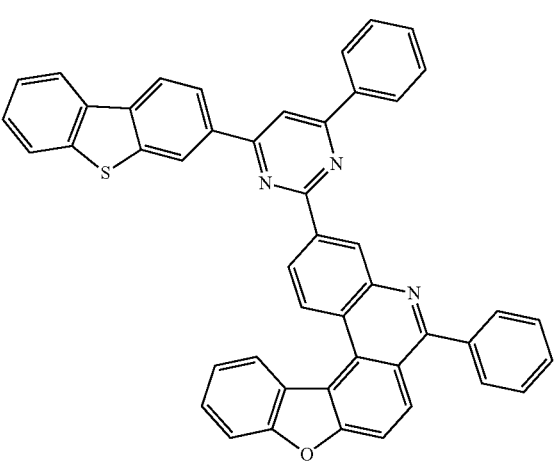

267
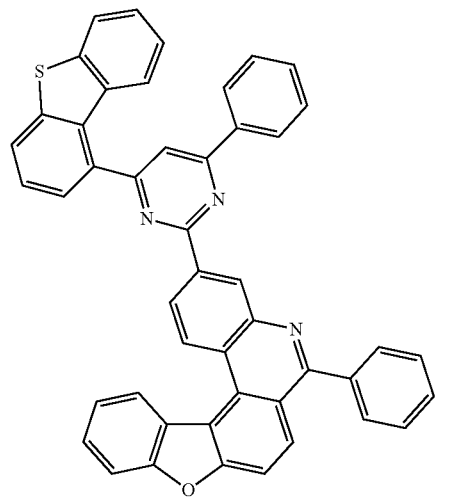
268
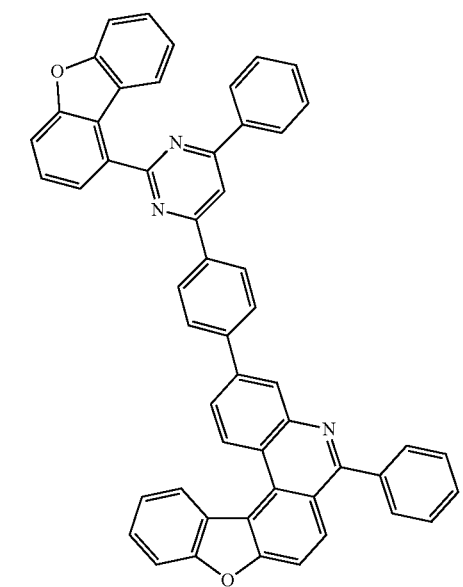
269
270
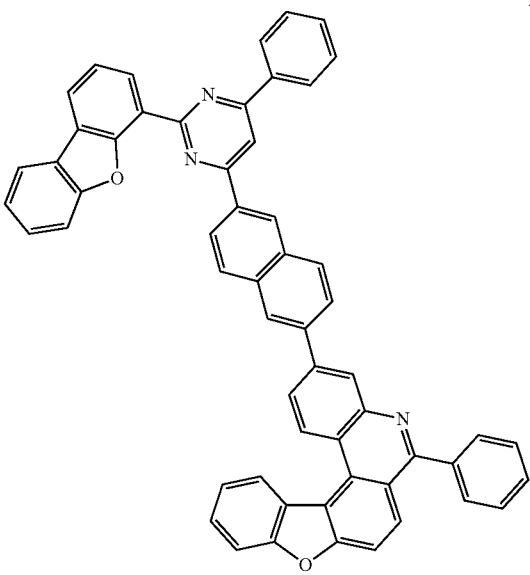
271
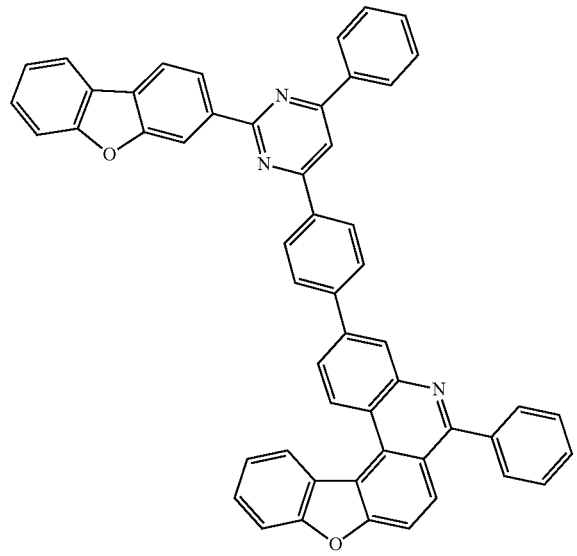

619
-continued
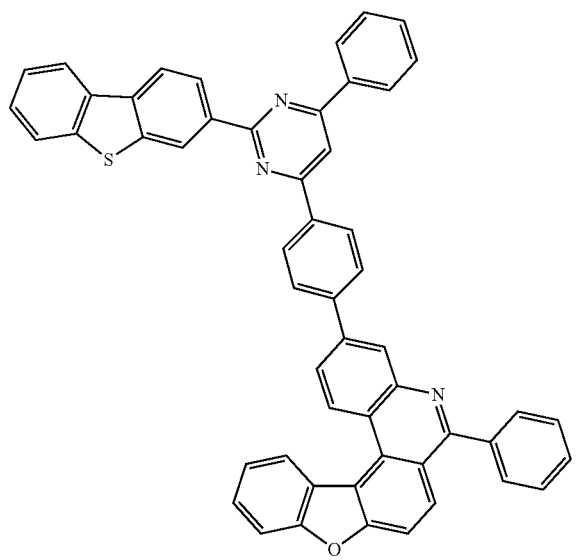
272
620
-continued
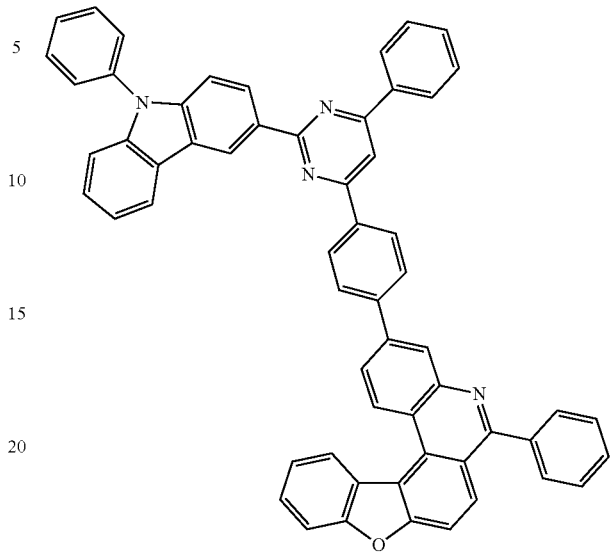
274
273
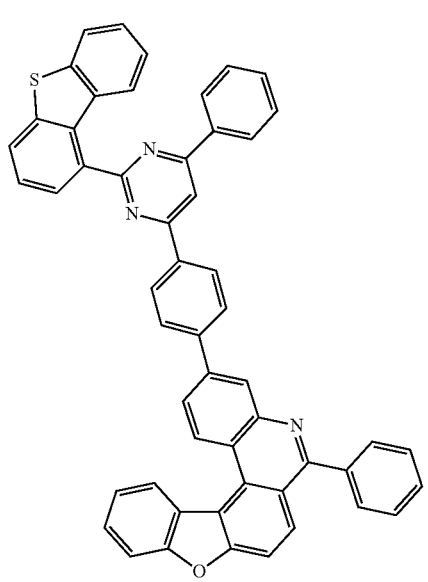
275
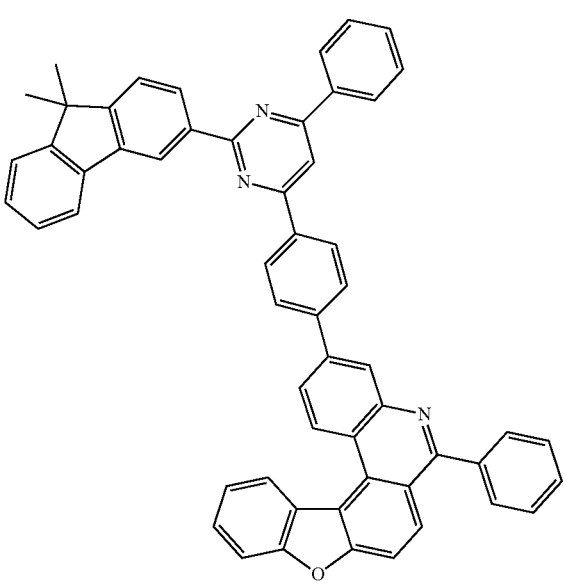

276
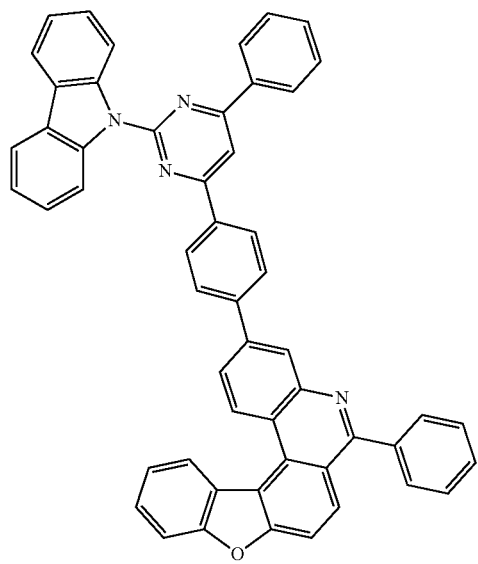
277
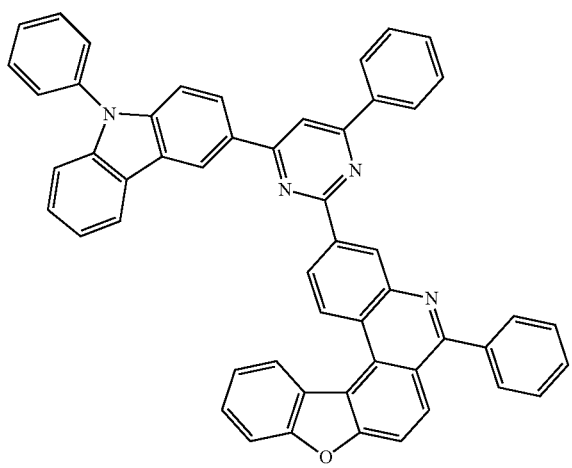
278
279
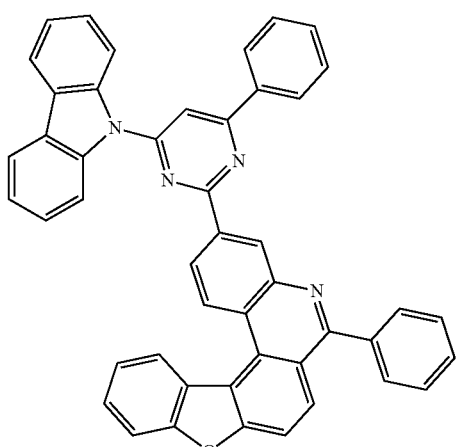
280
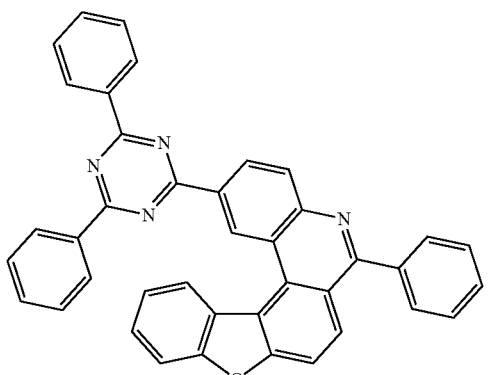
281
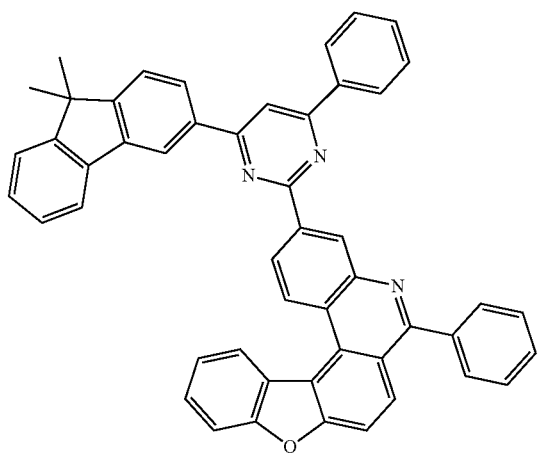
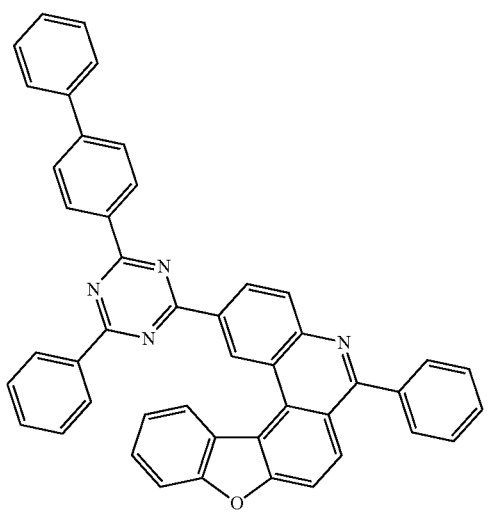

282
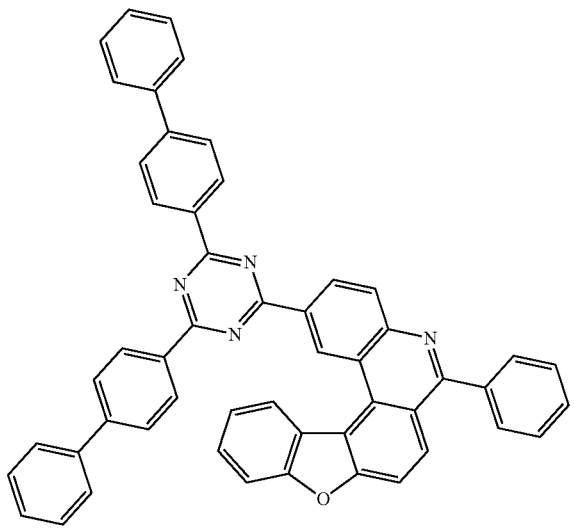
283
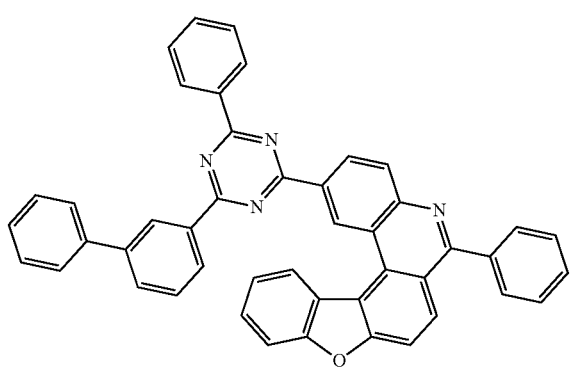
284
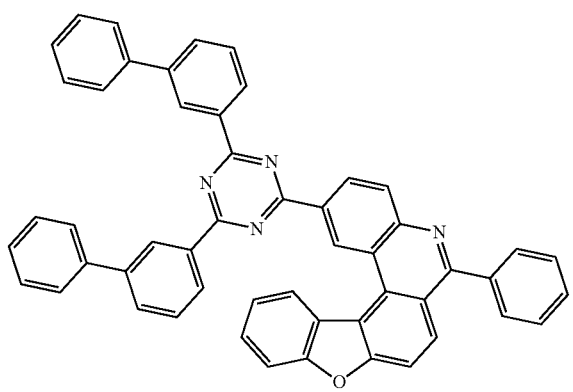
285
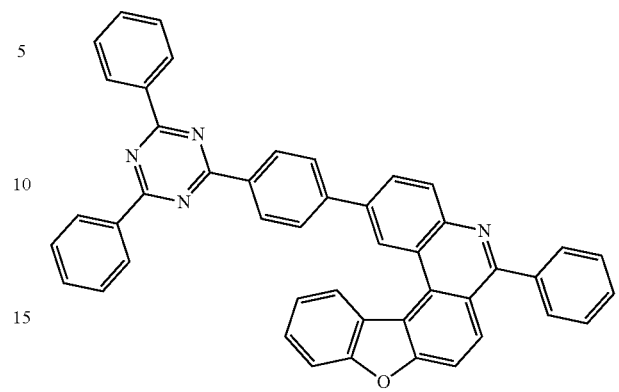
286
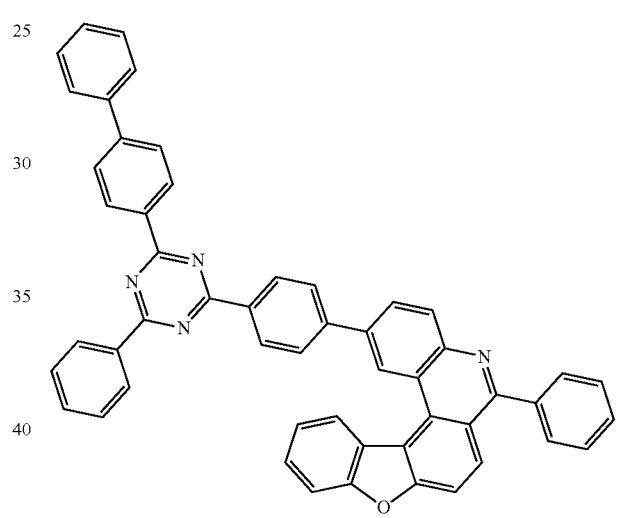
287
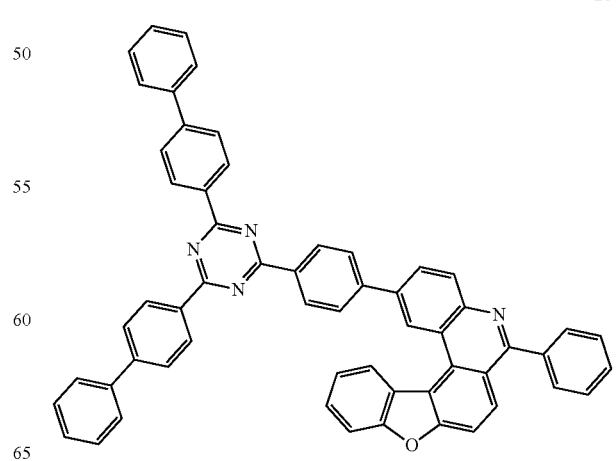

288
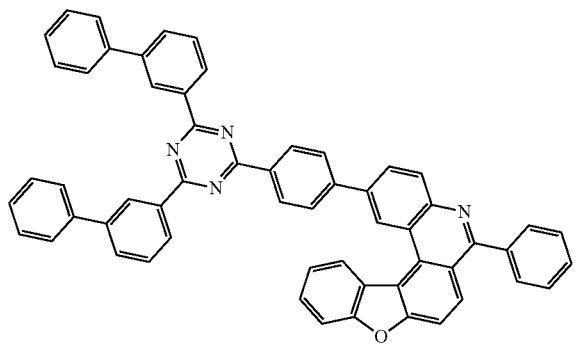
291
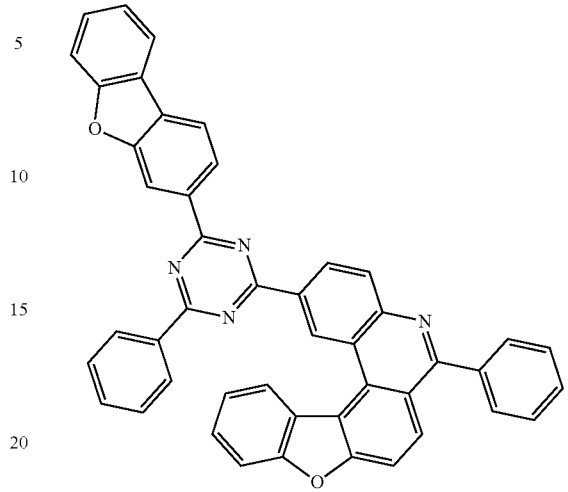
289
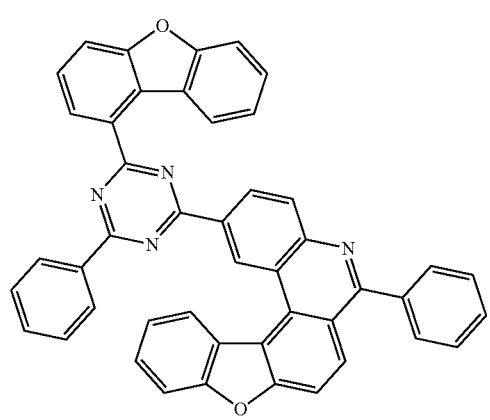
292
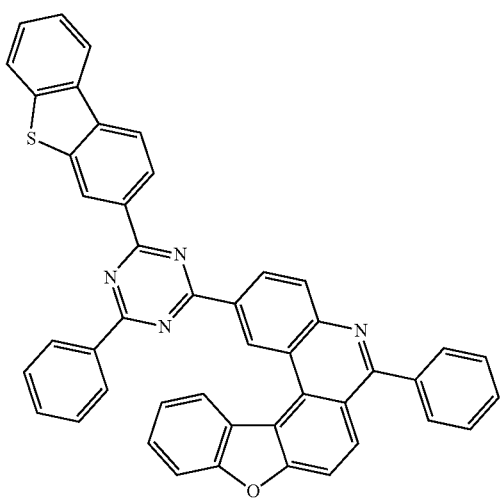
290
293
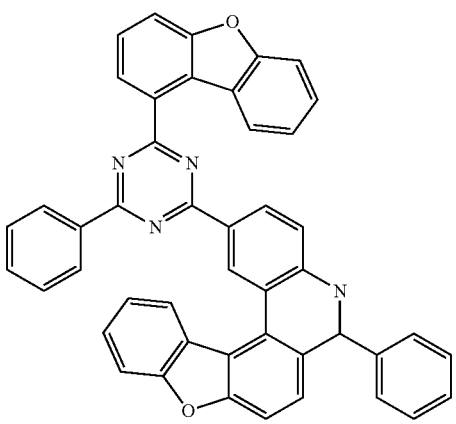

294
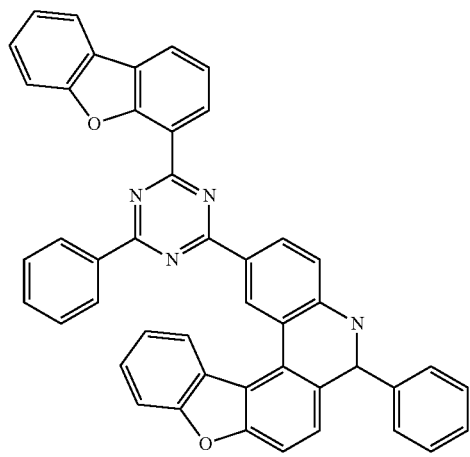
295
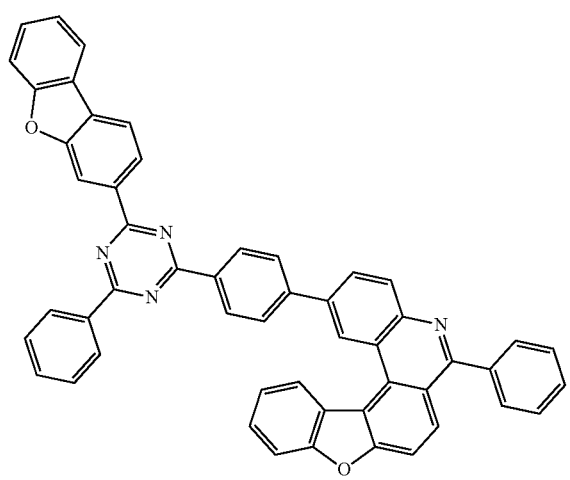
296
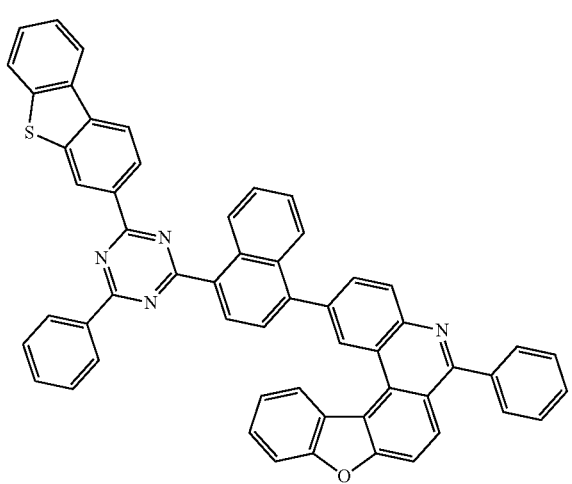
297
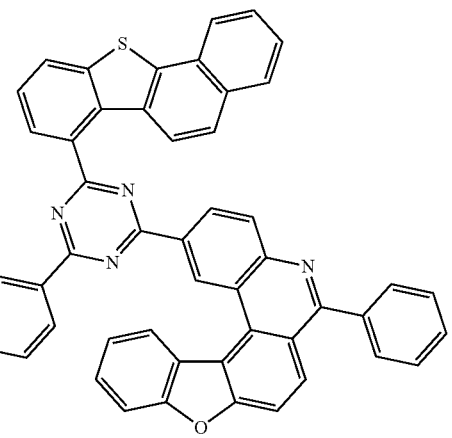
298
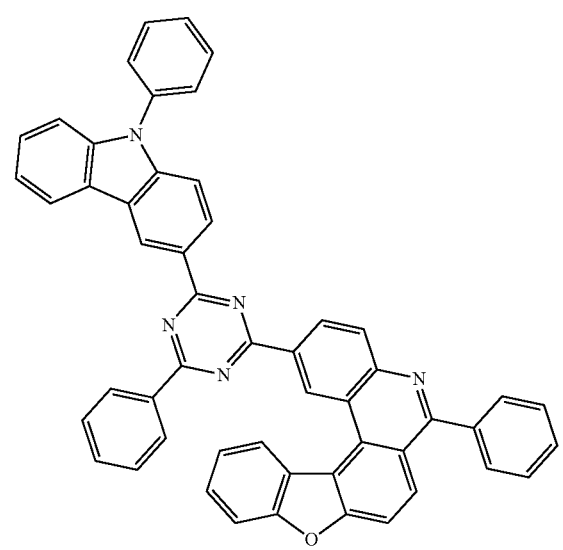
299
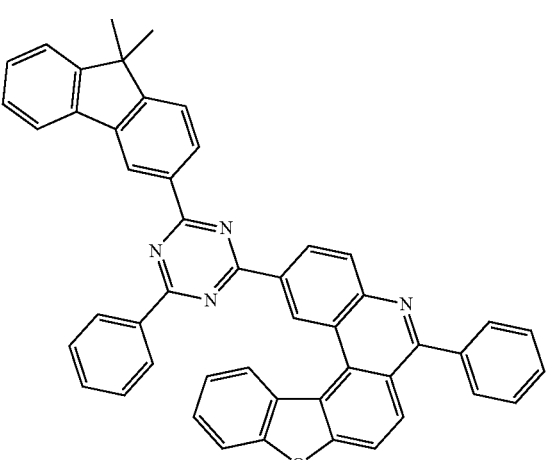

-continued
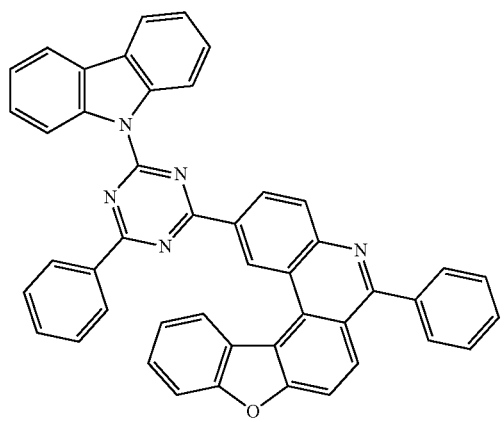
300
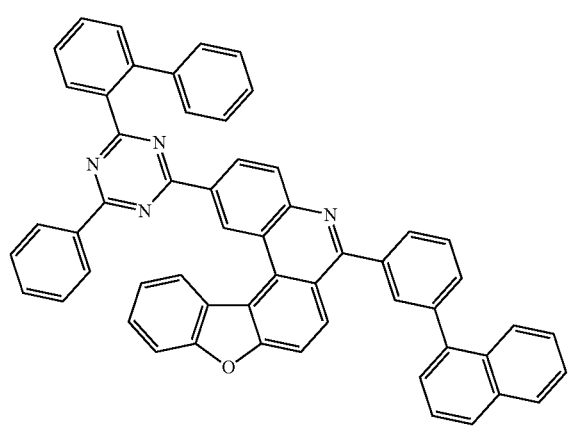
301
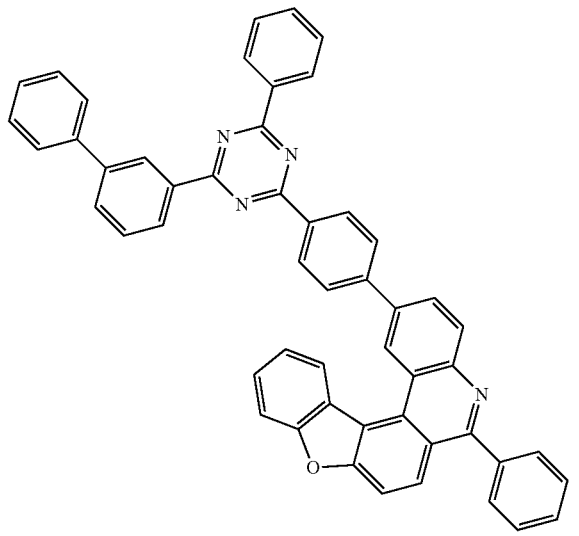
302
-continued
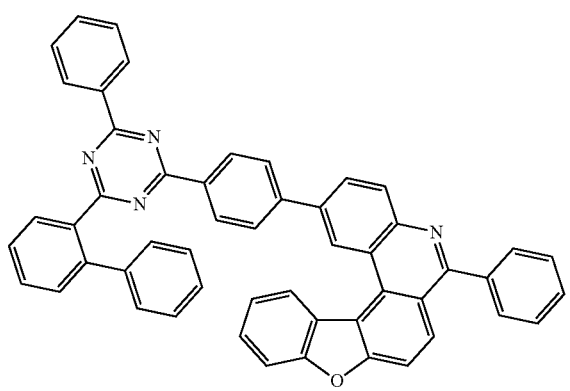
303
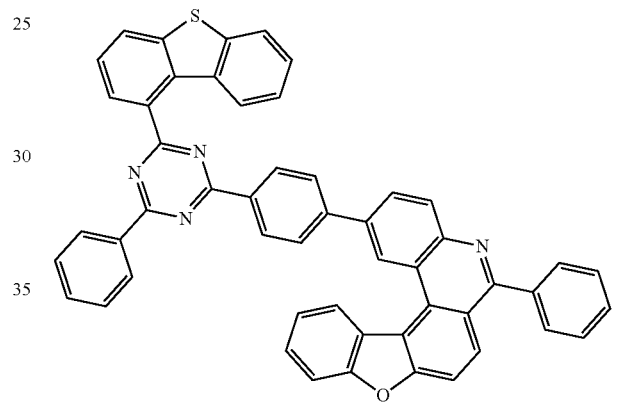
304
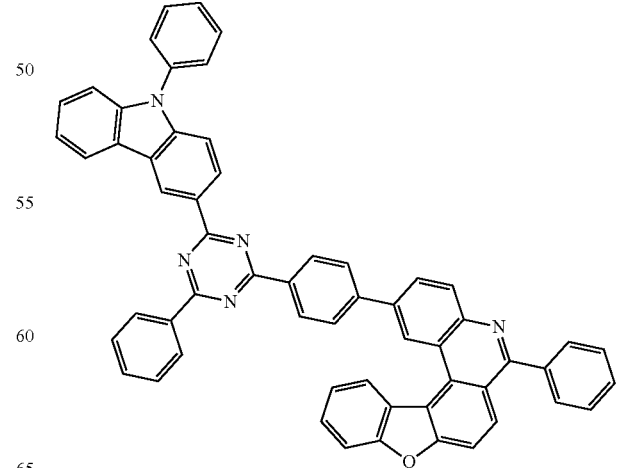
305

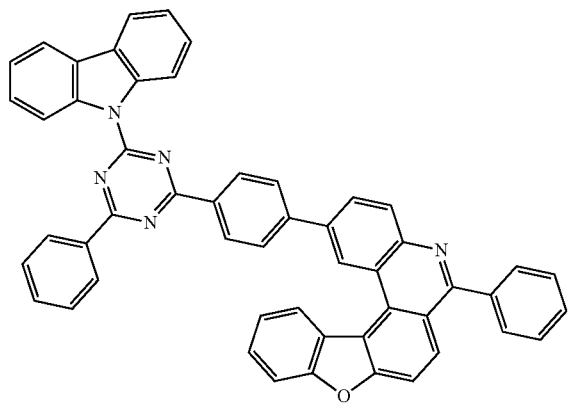
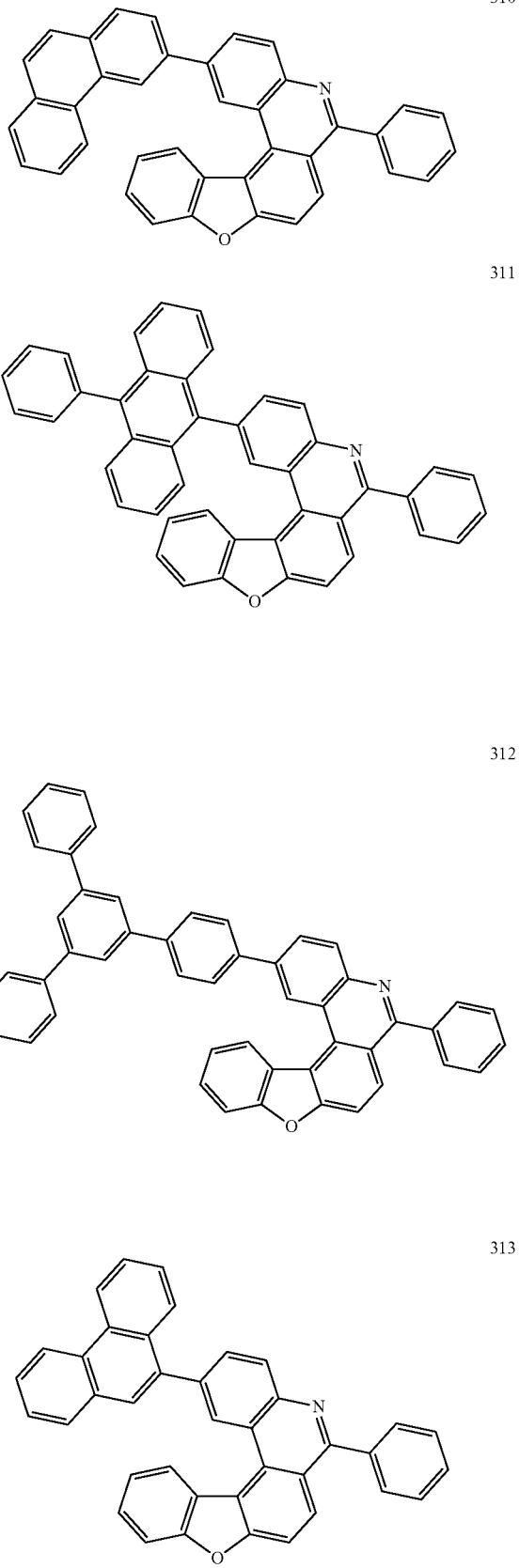

314
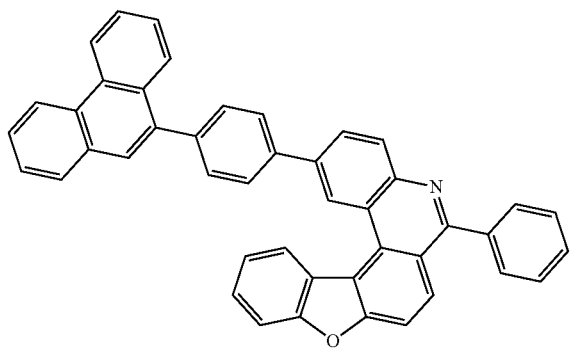
315
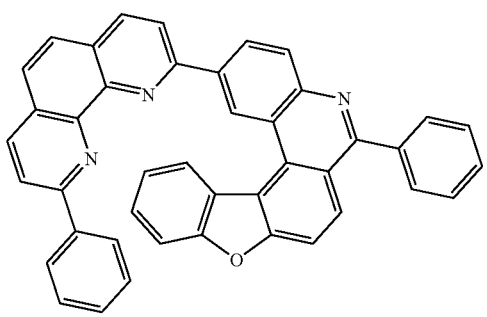
316
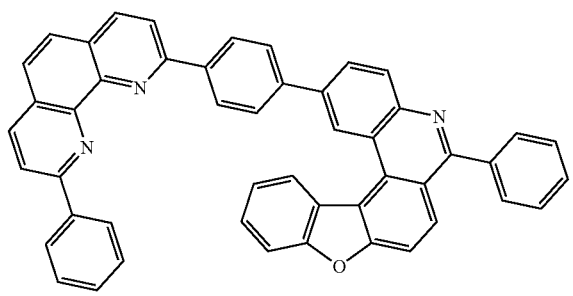
317
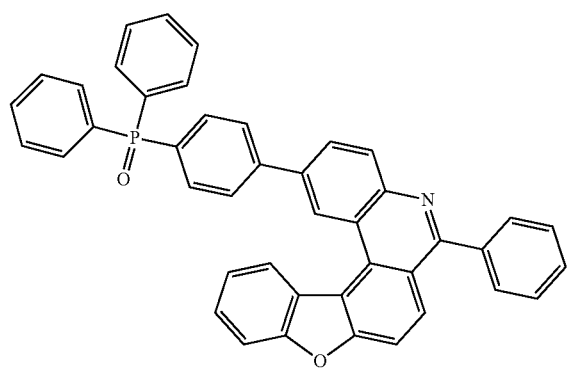
318
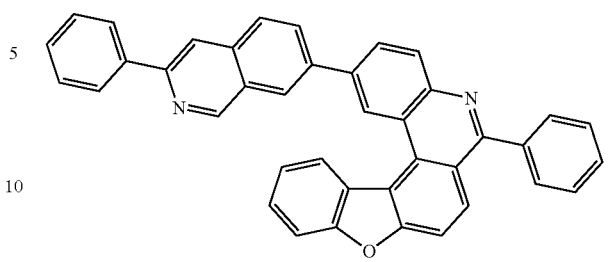
319
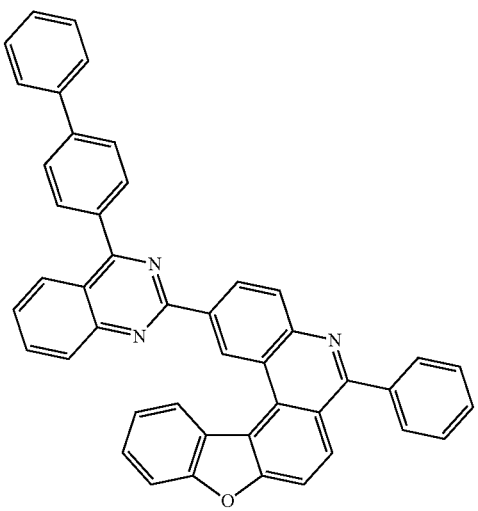
320
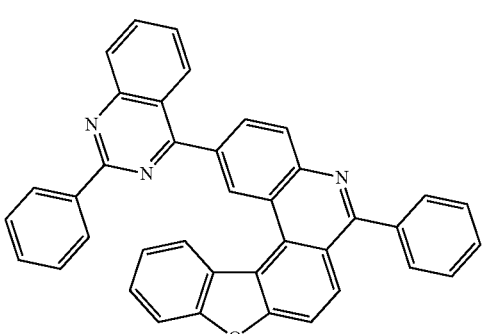

| 635 | 636 |
|---|---|
| 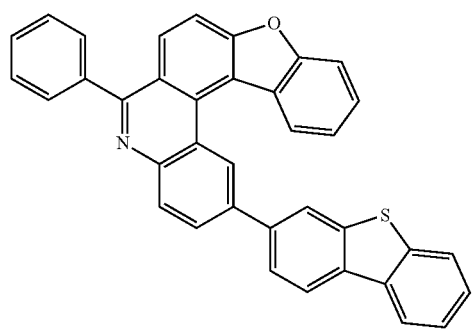 321 | 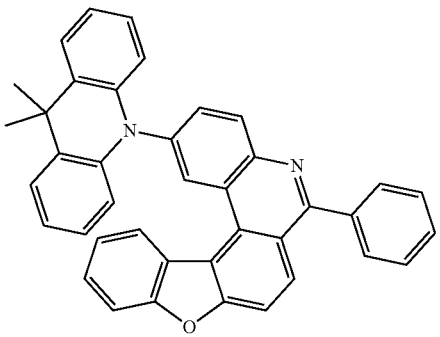 322 |
| 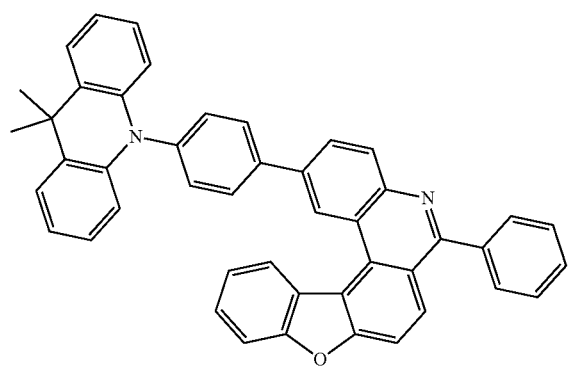 323 | 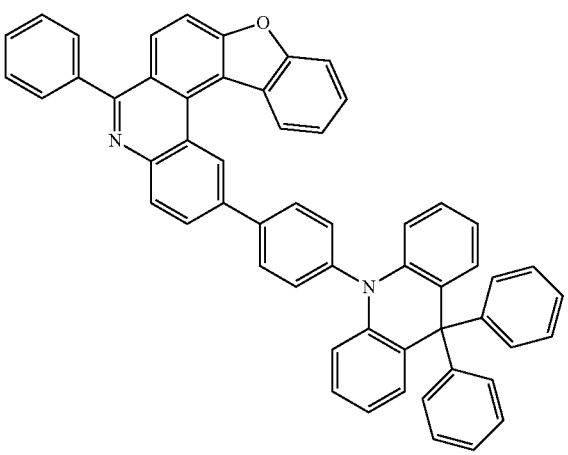 324 |
| 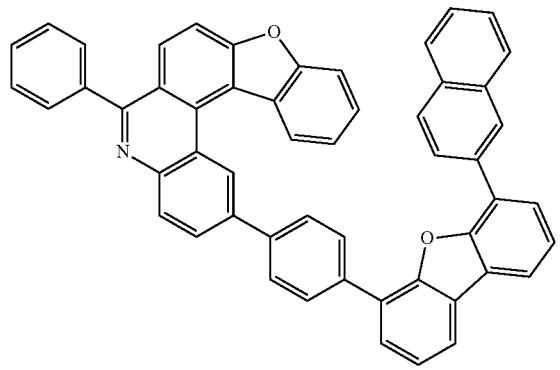 325 | 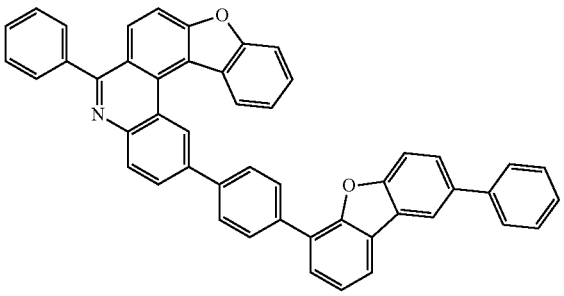 [SMILES: c1ccc(-c2ccc3oc4c(-c5ccc(-c6ccc7nc(-c8ccccc8)c8ccc9oc%10ccccc%10c9c8c7c6)cc5)cccc4c3c2)cc1] 326 |
| 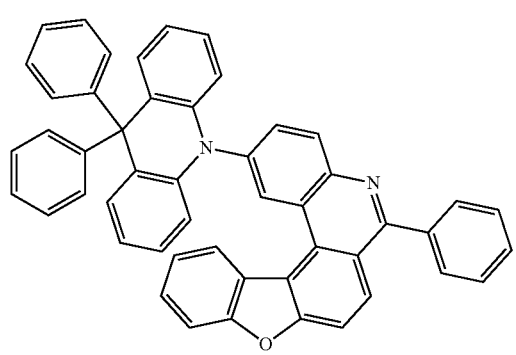 327 | 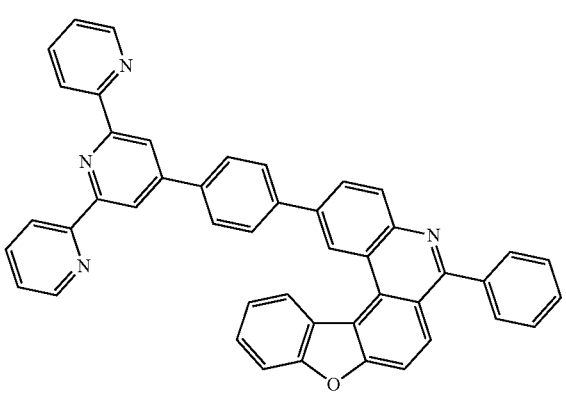 328 |

-continued
329
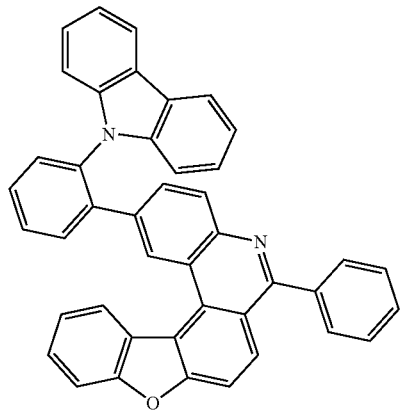
330
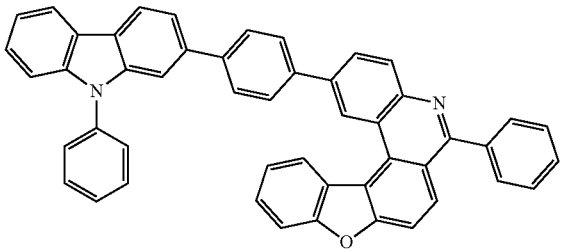 [SMILES: c1ccc(-c2nc3ccc(-c4ccc(-c5ccc6c7ccccc7n(-c7ccccc7)c6c5)cc4)cc3c3c2ccc2oc4ccccc4c23)cc1]
331
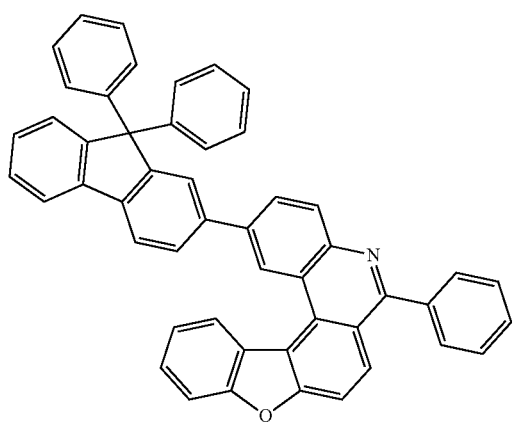
332
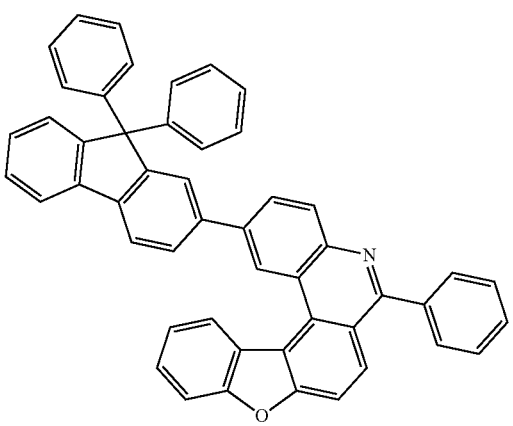
333
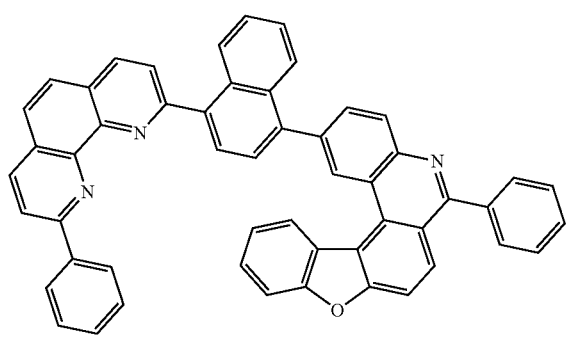
334
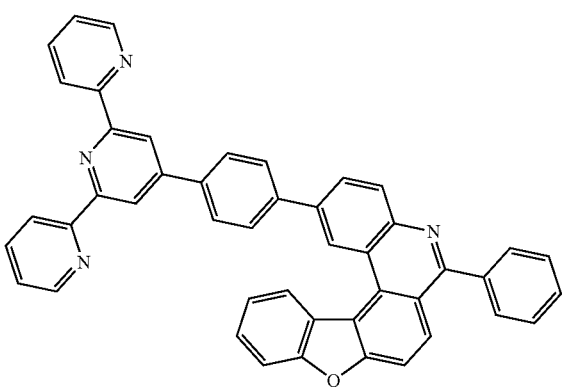 [SMILES: c1ccc(-c2nc3ccc(-c4ccc(-c5cc(-c6ccccn6)nc(-c6ccccn6)c5)cc4)cc3c3c2ccc2oc4ccccc4c23)cc1]
335
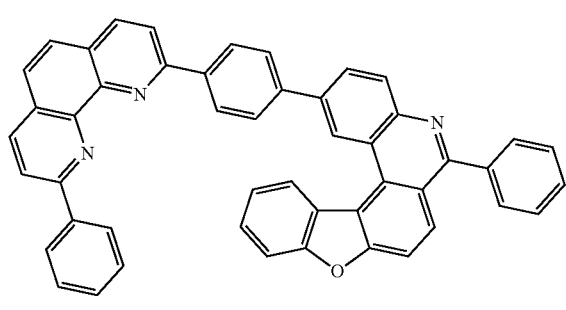
336
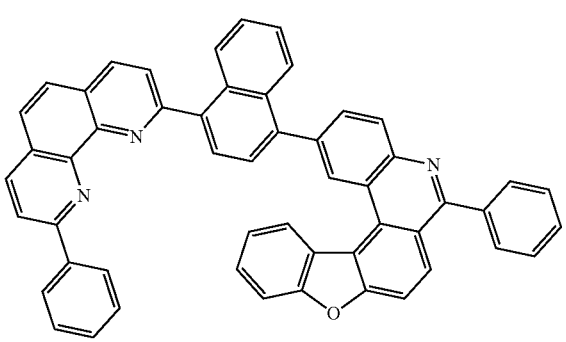

-continued
337
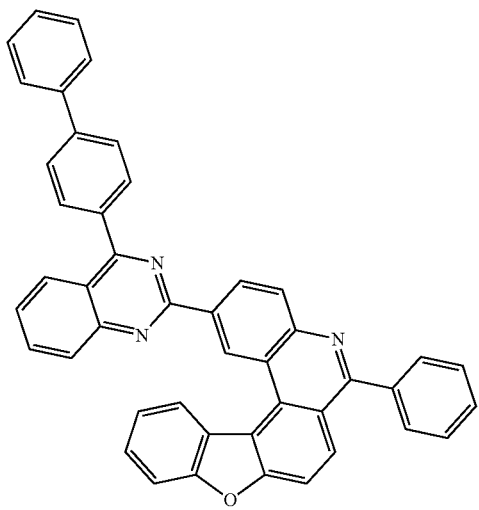
338
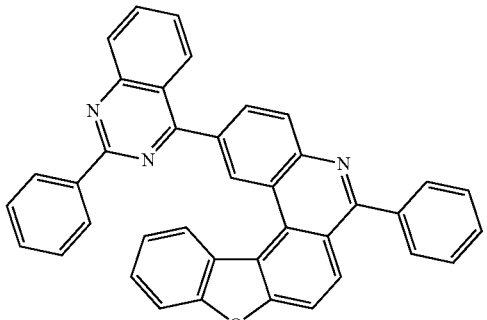
339
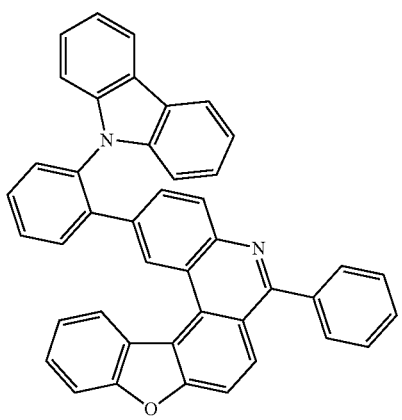
340
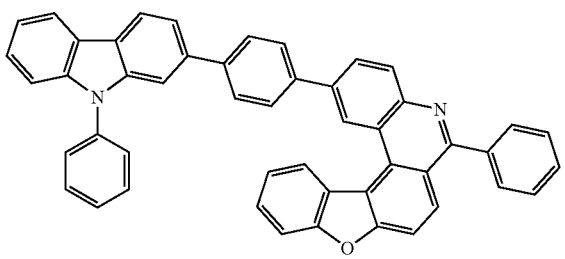
341
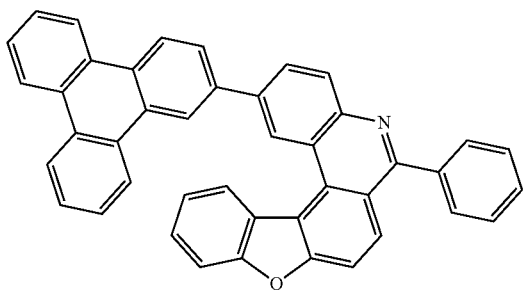
342
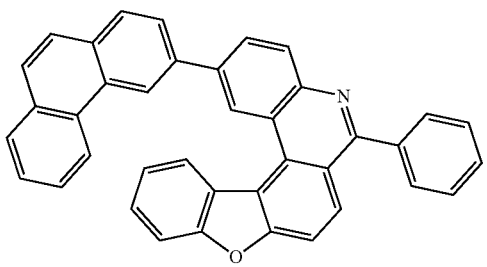 [SMILES: c1ccc(-c2nc3ccc(-c4ccc5ccc6ccccc6c5c4)cc3c3c2ccc2oc4ccccc4c23)cc1]
343
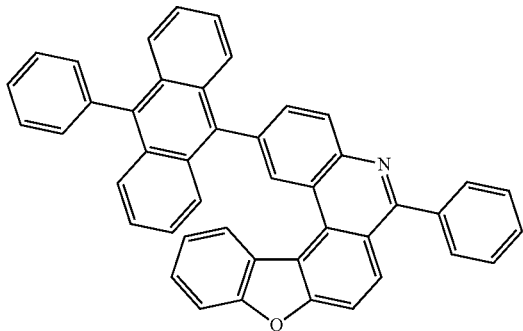
344
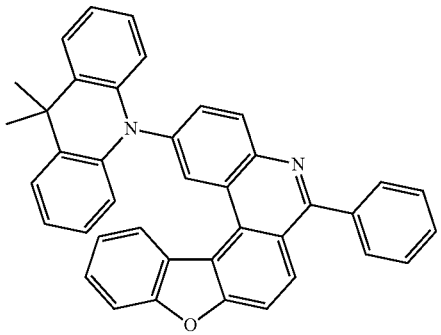

-continued
345
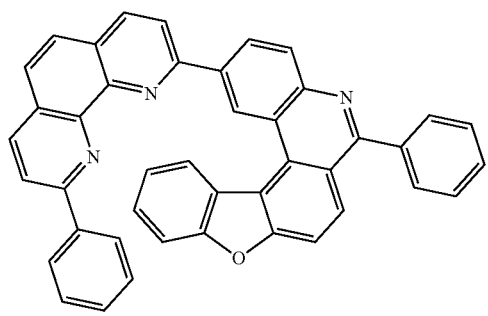
346
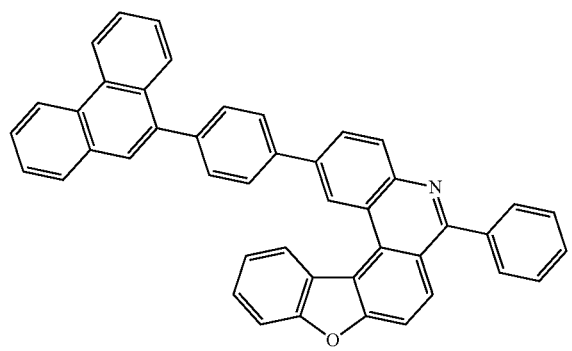 [SMILES: c1ccc(-c2nc3ccc(-c4ccc(-c5cc6ccccc6c6ccccc56)cc4)cc3c3c2ccc2oc4ccccc4c23)cc1]
347
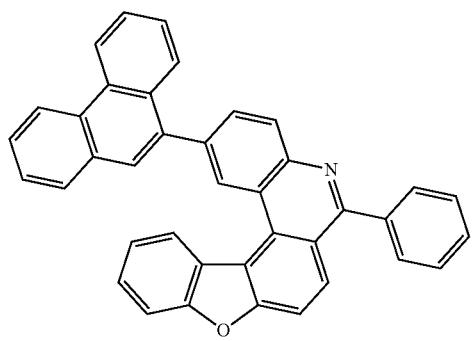
348
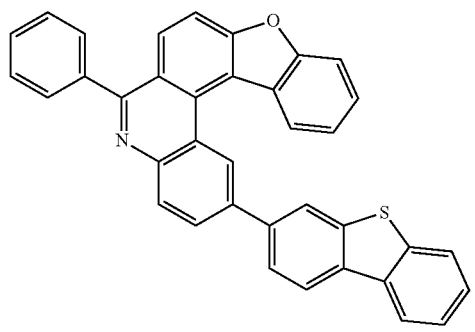
349
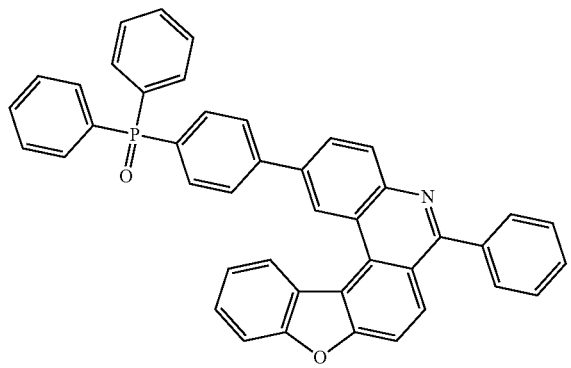
350
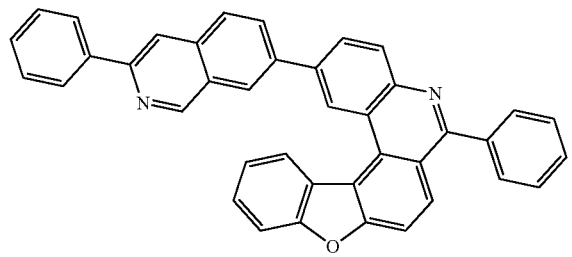 [SMILES: c1ccc(-c2cc3ccc(-c4ccc5nc(-c6ccccc6)c6ccc7oc8ccccc8c7c6c5c4)cc3cn2)cc1]
351
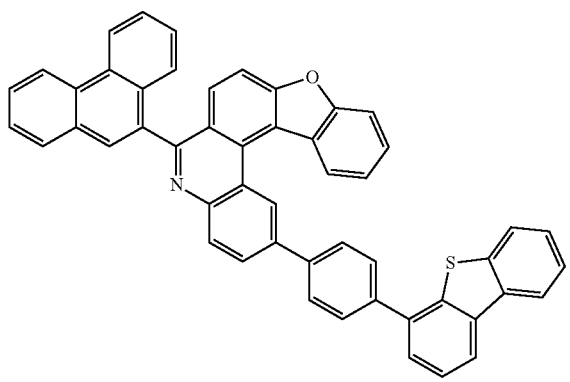
352
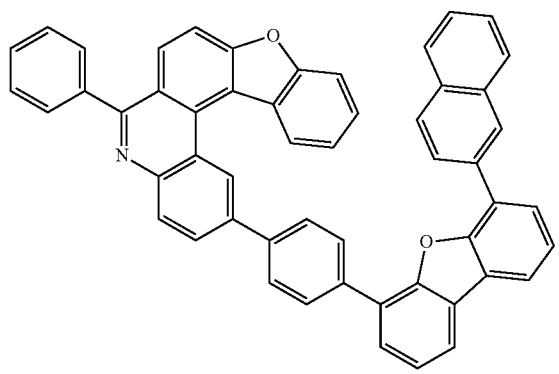

-continued
353
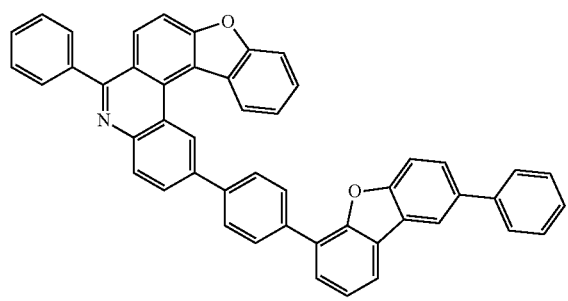
354
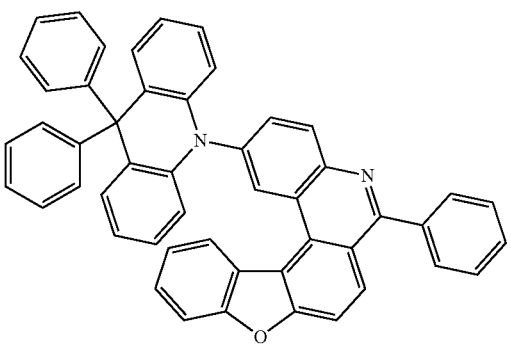
355
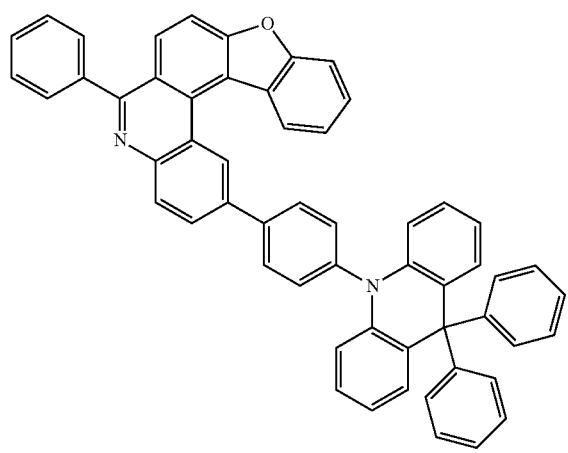
356
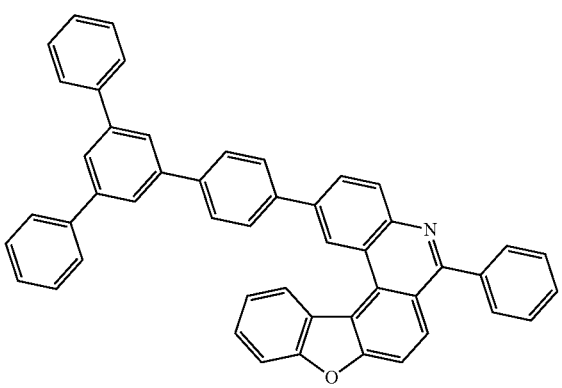
357
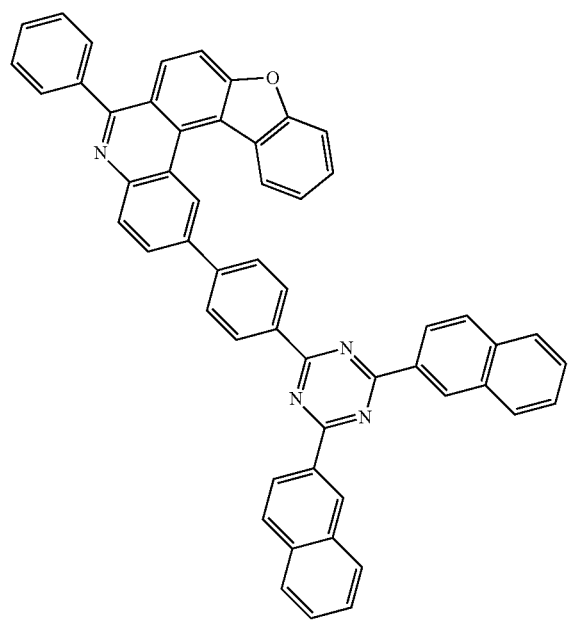
358
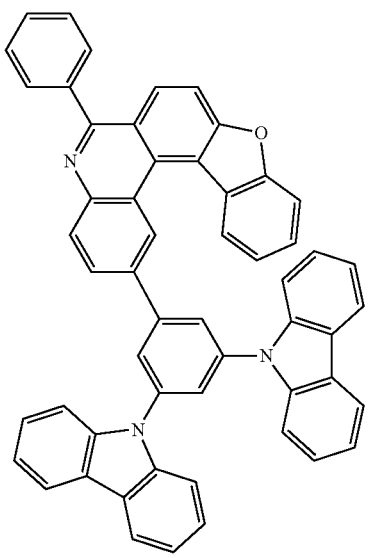

-continued
359
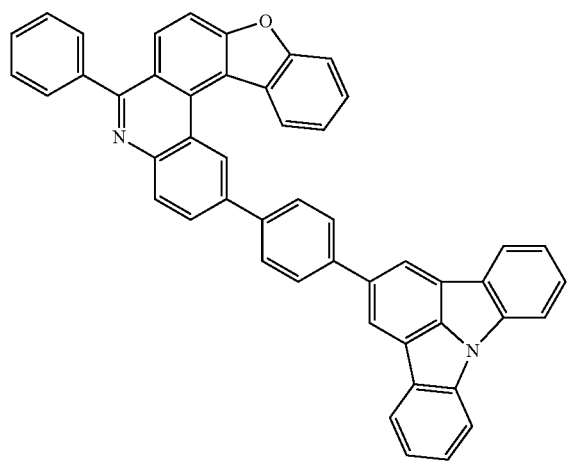
360
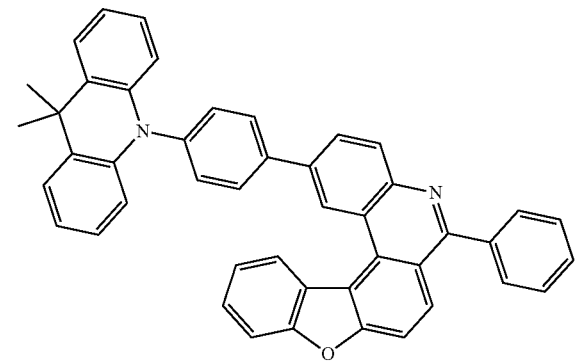
361
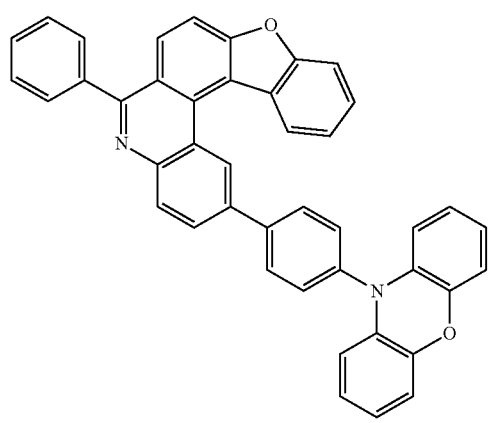
362
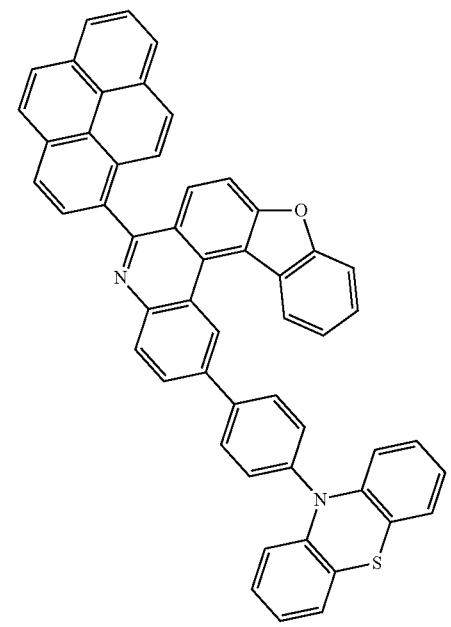
363
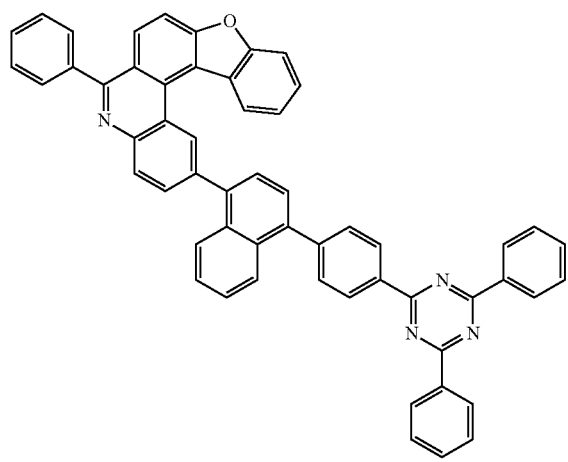
364
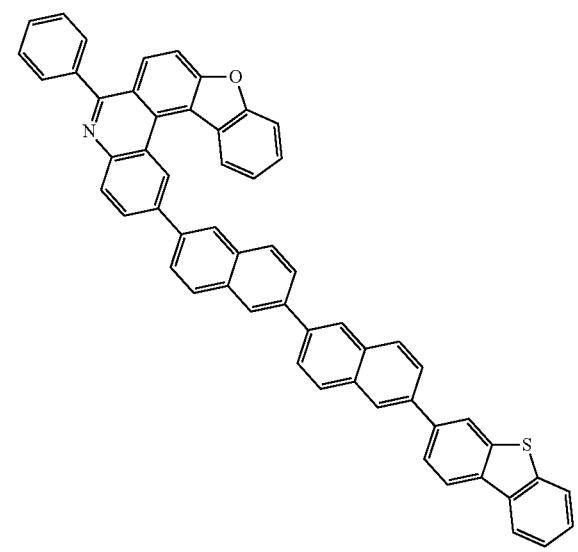

-continued
365
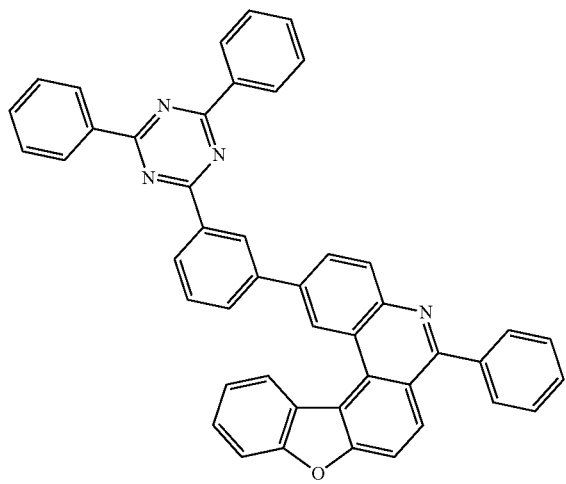
366
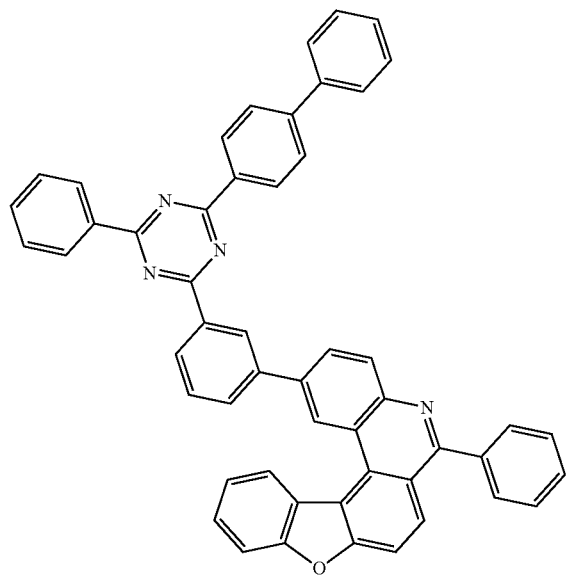 [SMILES: c1ccc(-c2ccc(-c3nc(-c4ccccc4)nc(-c4cccc(-c5ccc6nc(-c7ccccc7)c7ccc8oc9ccccc9c8c7c6c5)c4)n3)cc2)cc1]
367
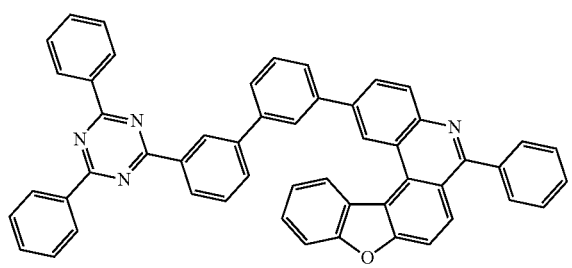
368
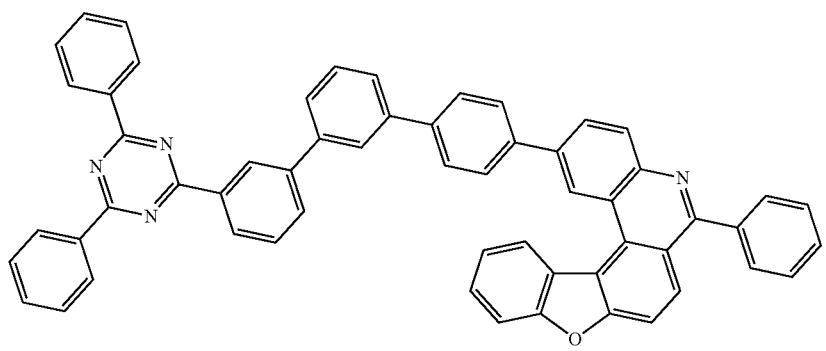
369
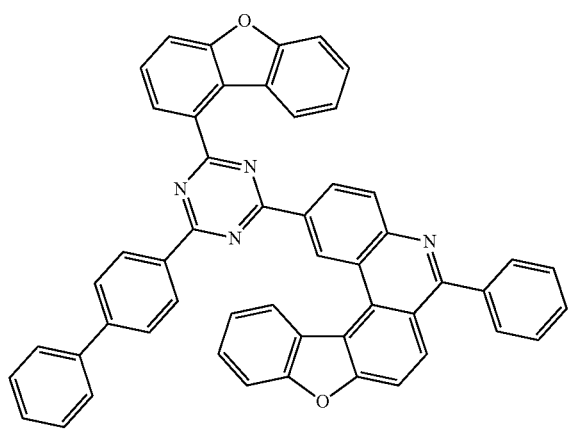
370
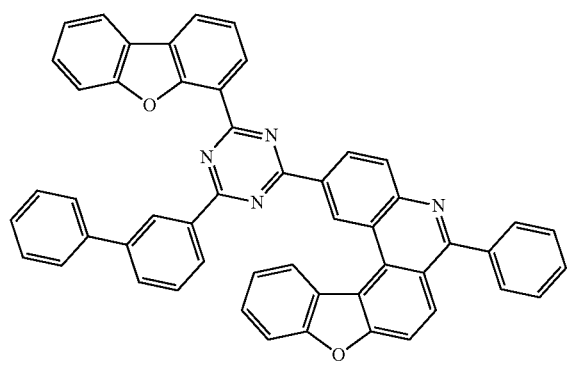 [SMILES: c1ccc(-c2cccc(-c3nc(-c4ccc5nc(-c6ccccc6)c6ccc7oc8ccccc8c7c6c5c4)nc(-c4cccc5c4oc4ccccc45)n3)c2)cc1]

-continued
371
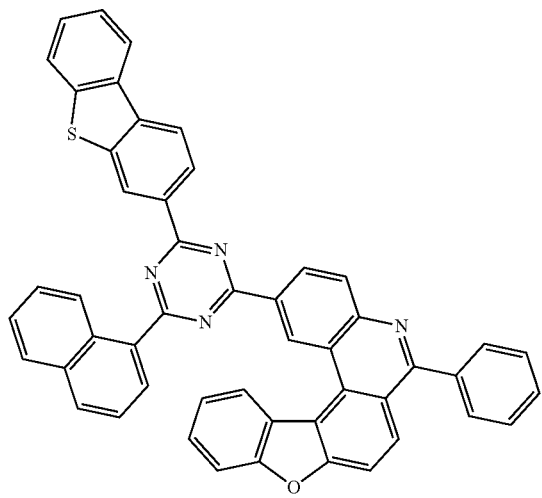
372
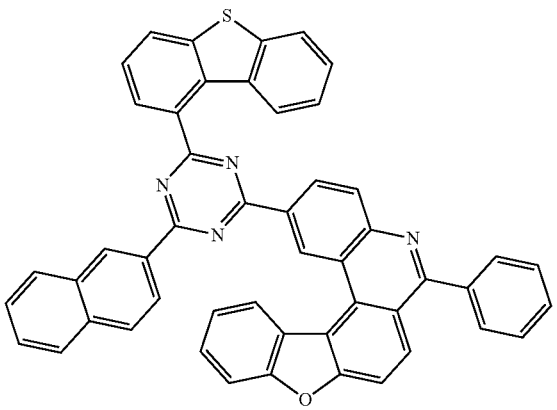
373
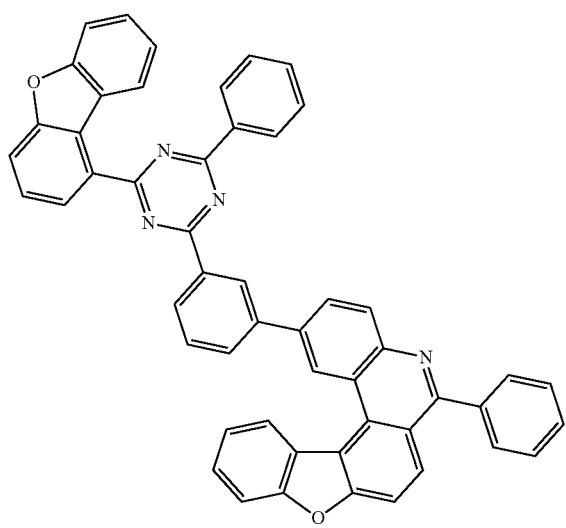
374
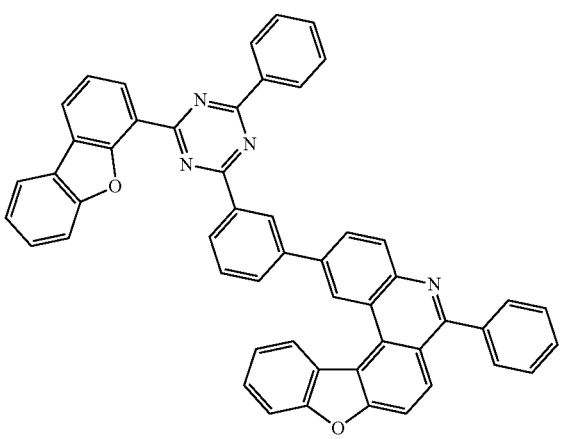 [SMILES: c1ccc(-c2nc(-c3cccc(-c4ccc5nc(-c6ccccc6)c6ccc7oc8ccccc8c7c6c5c4)c3)nc(-c3cccc4c3oc3ccccc34)n2)cc1]
375
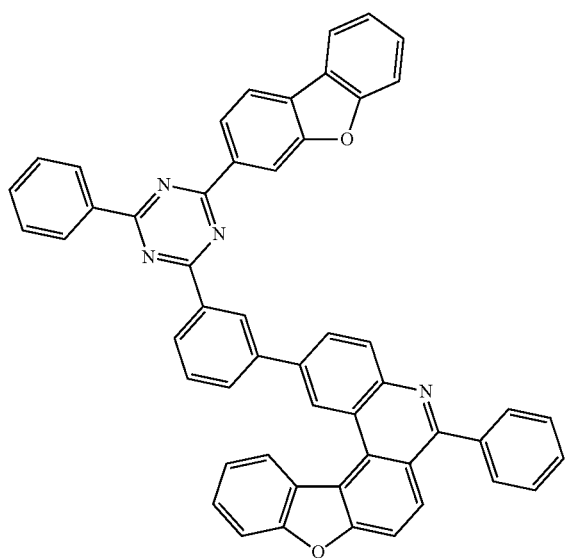
376
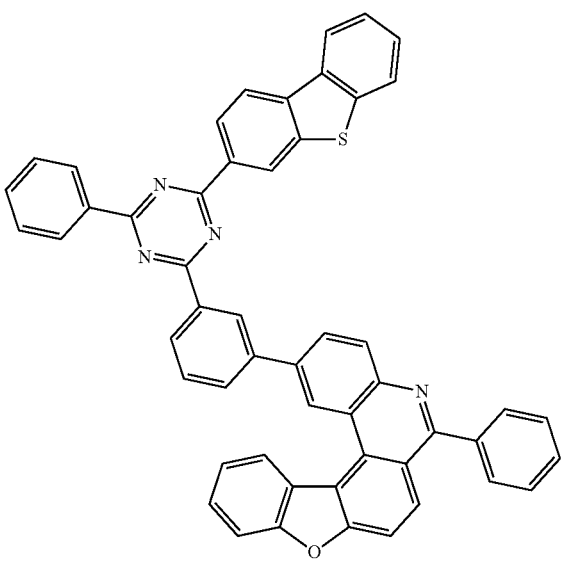

-continued
377
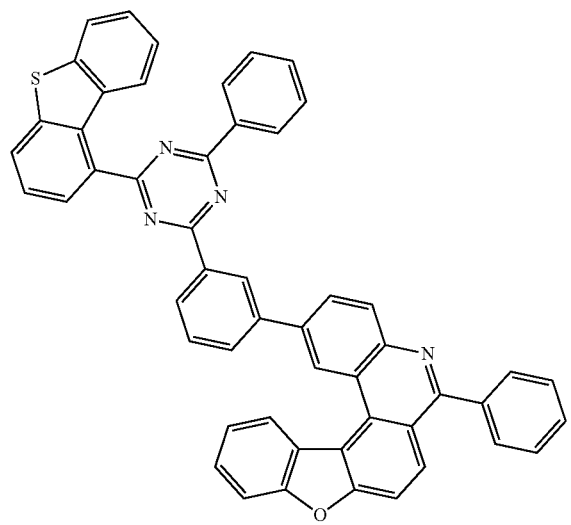
378
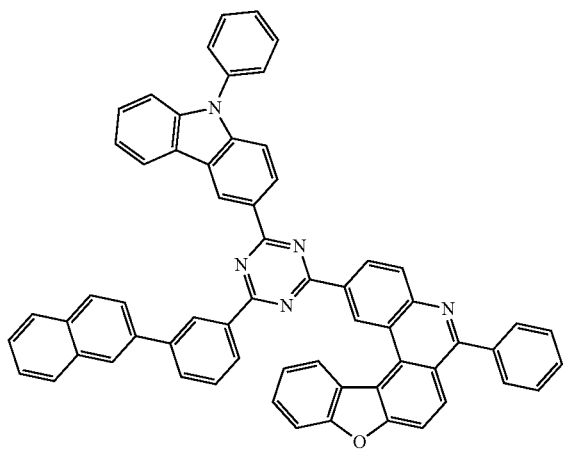 [SMILES: c1ccc(-c2nc3ccc(-c4nc(-c5cccc(-c6ccc7ccccc7c6)c5)nc(-c5ccc6c(c5)c5ccccc5n6-c5ccccc5)n4)cc3c3c2ccc2oc4ccccc4c23)cc1]
379
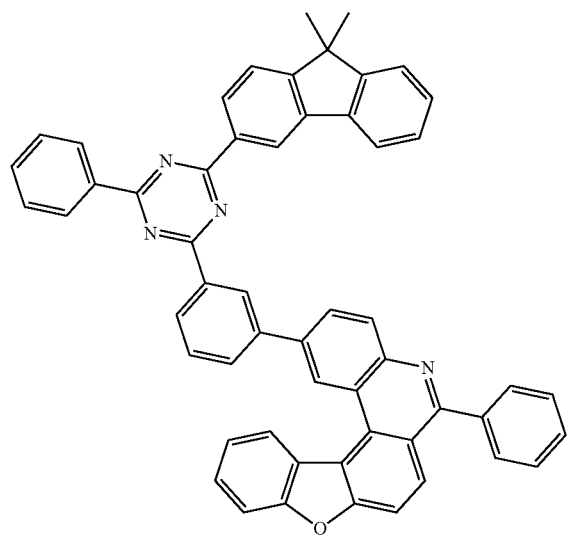
380
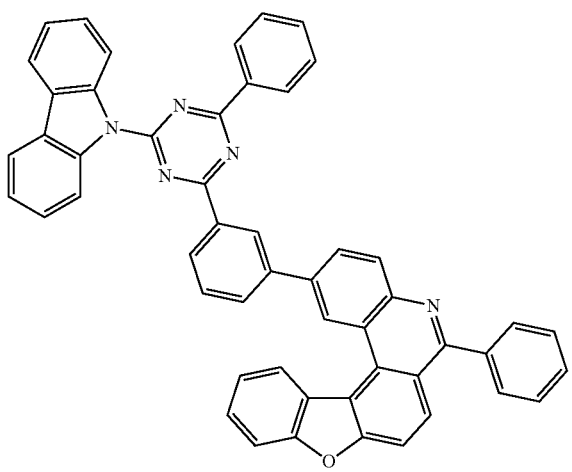
381
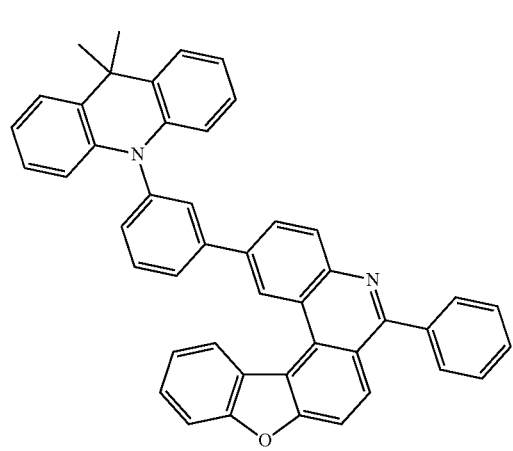
382
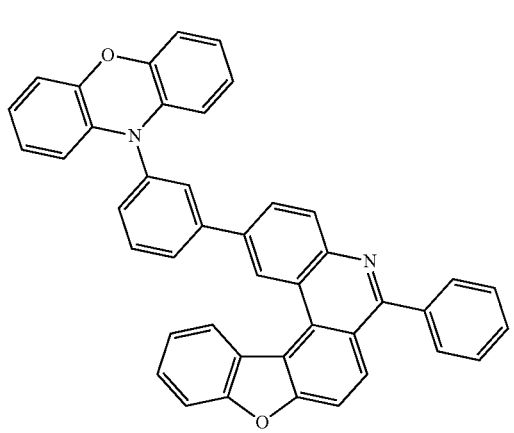

-continued
383
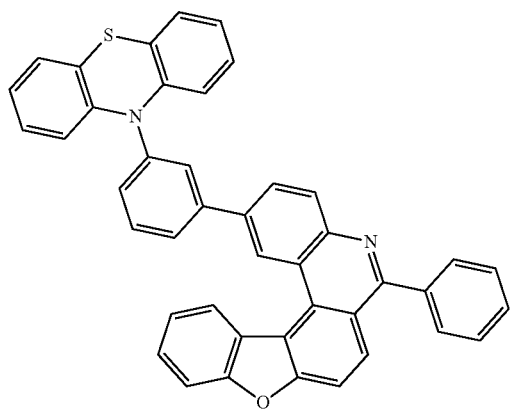 [SMILES: c1ccc(-c2nc3ccc(-c4cccc(N5c6ccccc6Oc6ccccc65)c4)cc3c3c2ccc2oc4ccccc4c23)cc1]
384
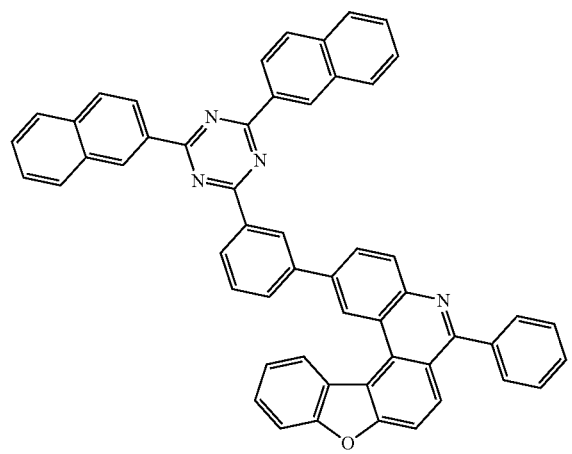
385
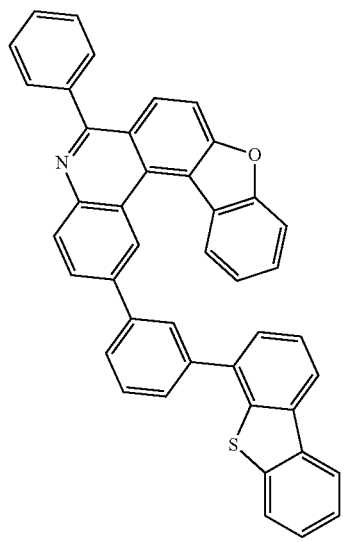
386
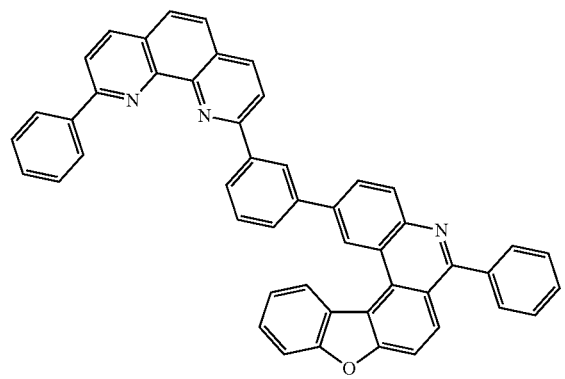 [SMILES: c1ccc(-c2ccc3ccc4ccc(-c5cccc(-c6ccc7nc(-c8ccccc8)c8ccc9oc%10ccccc%10c9c8c7c6)c5)nc4c3n2)cc1]
387
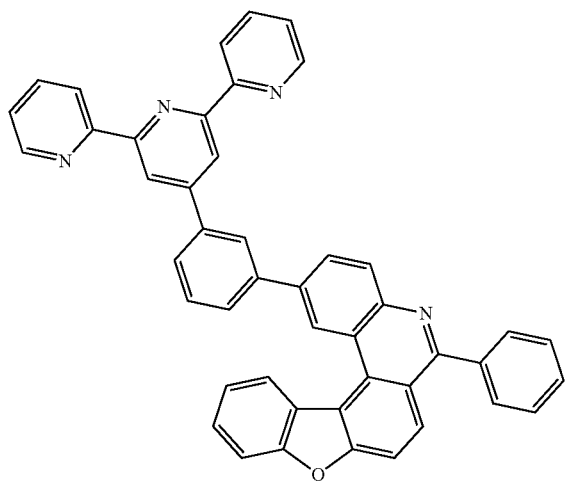
388
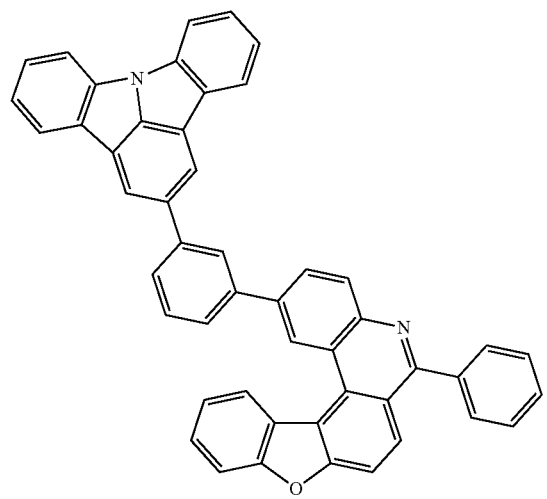

-continued
389
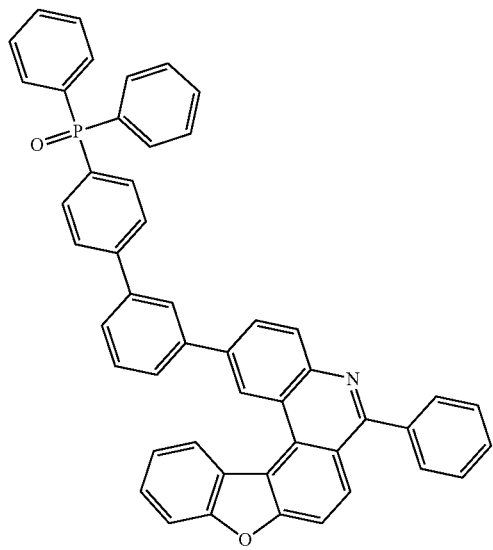
390
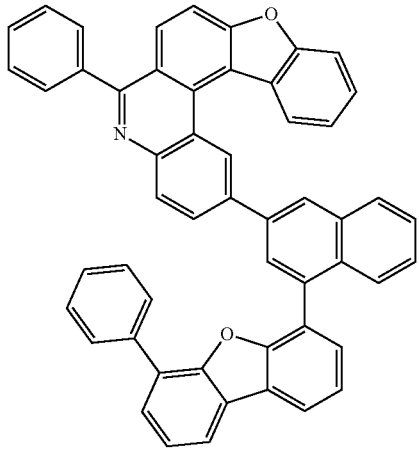 [SMILES: c1ccc(-c2nc3ccc(-c4cc(-c5cccc6c5oc5c(-c7ccccc7)cccc56)c5ccccc5c4)cc3c3c2ccc2oc4ccccc4c23)cc1]
391
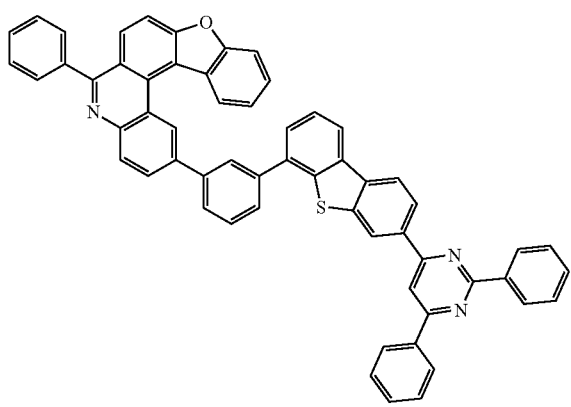
392
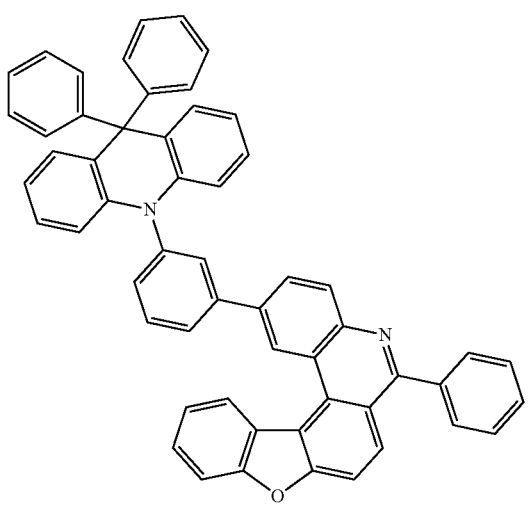
393
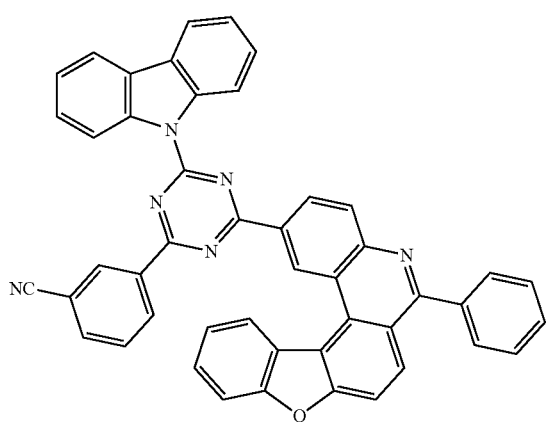
394
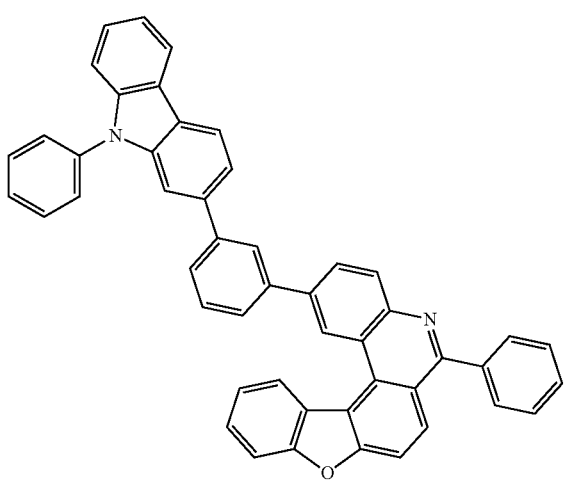 [SMILES: c1ccc(-c2nc3ccc(-c4cccc(-c5ccc6c7ccccc7n(-c7ccccc7)c6c5)c4)cc3c3c2ccc2oc4ccccc4c23)cc1]

-continued
395
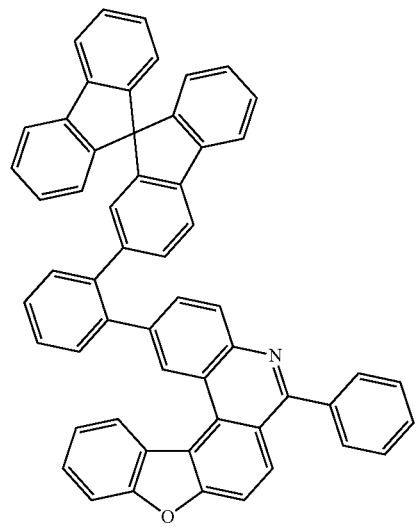
396
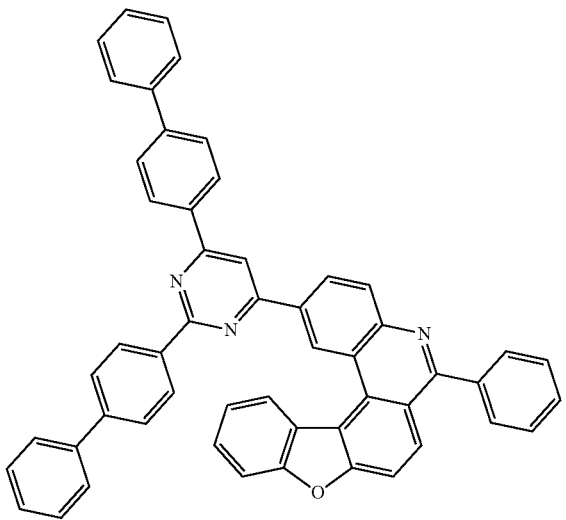
397
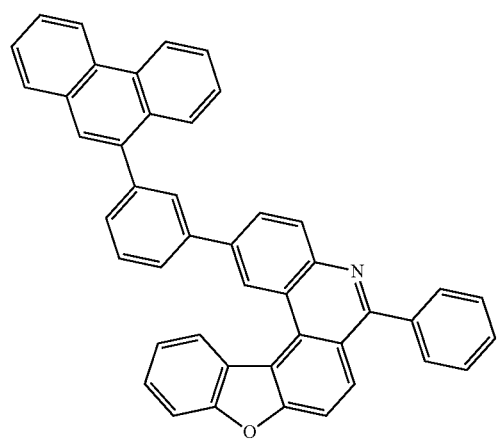
398
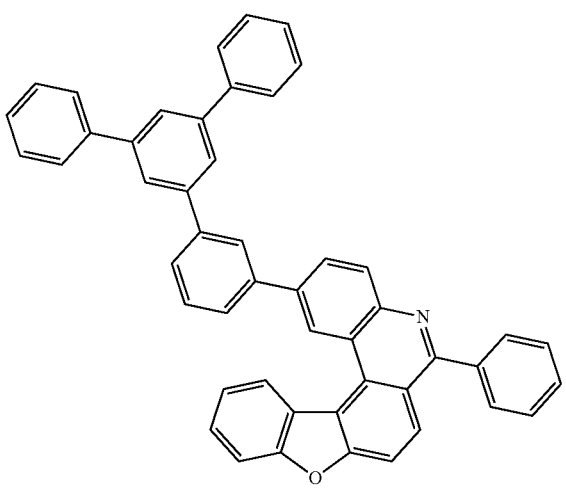 [SMILES: c1ccc(-c2cc(-c3ccccc3)cc(-c3cccc(-c4ccc5nc(-c6ccccc6)c6ccc7oc8ccccc8c7c6c5c4)c3)c2)cc1]
399
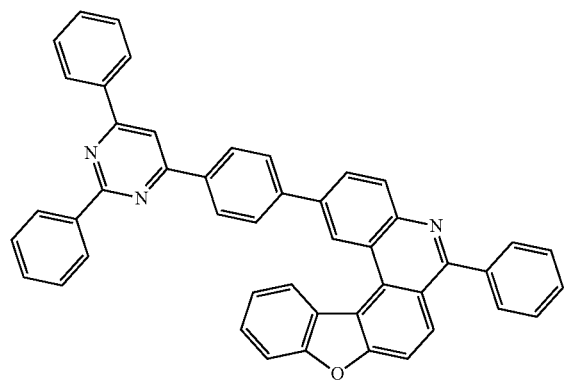
400
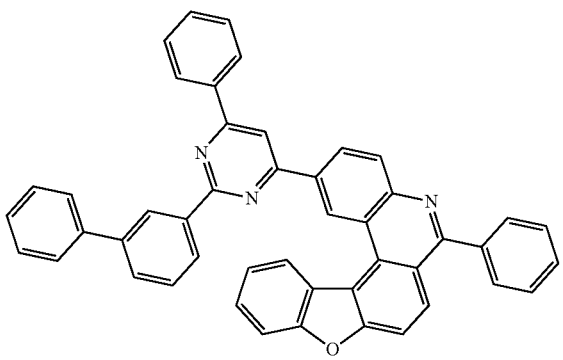

401
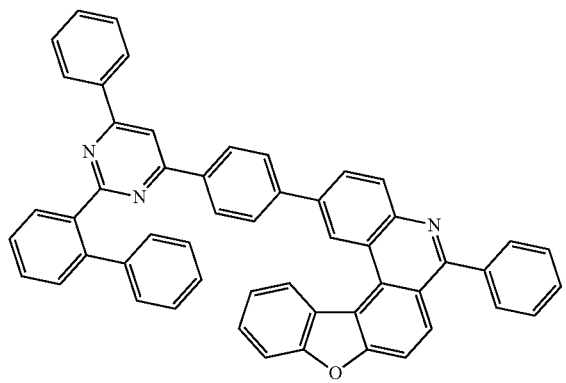
402
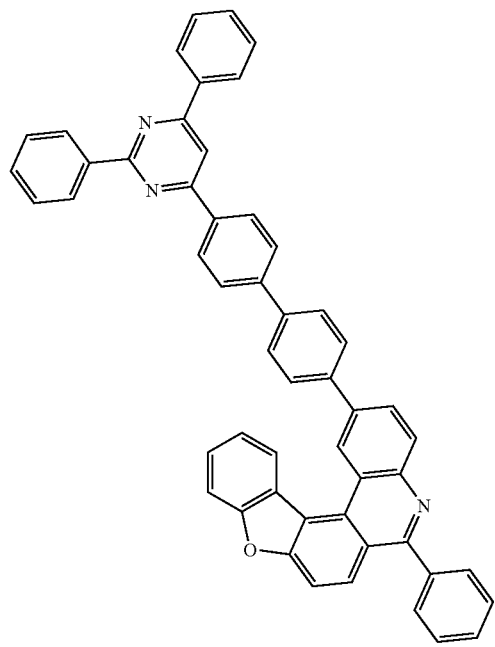 [SMILES: c1ccc(-c2cc(-c3ccc(-c4ccc(-c5ccc6nc(-c7ccccc7)c7ccc8oc9ccccc9c8c7c6c5)cc4)cc3)nc(-c3ccccc3)n2)cc1]
403
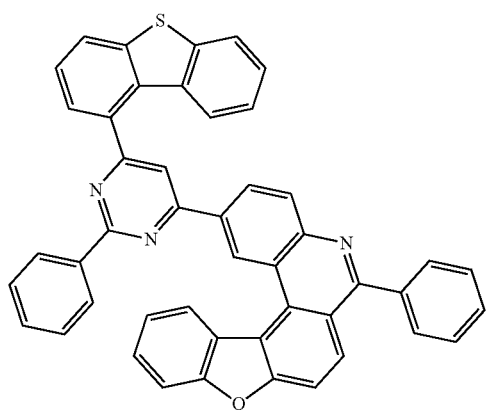
404
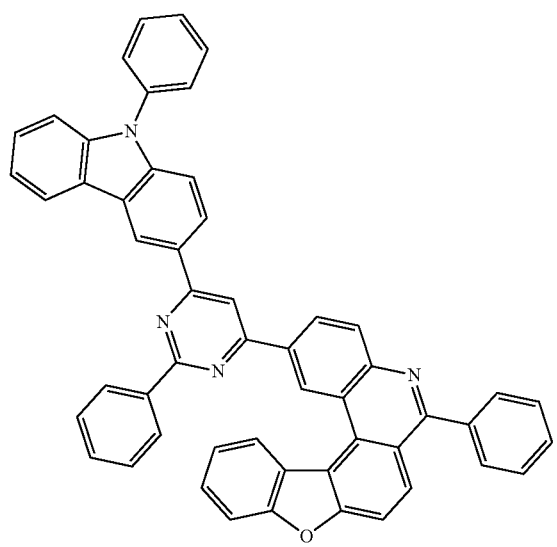
405
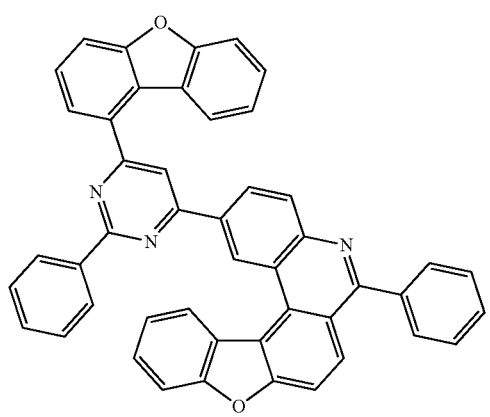
406
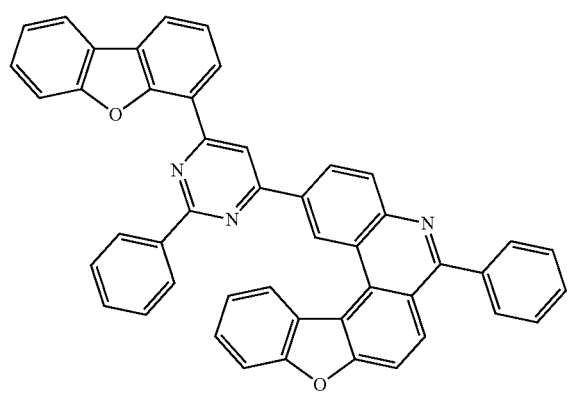 [SMILES: c1ccc(-c2nc(-c3ccc4nc(-c5ccccc5)c5ccc6oc7ccccc7c6c5c4c3)cc(-c3cccc4c3oc3ccccc34)n2)cc1]

661
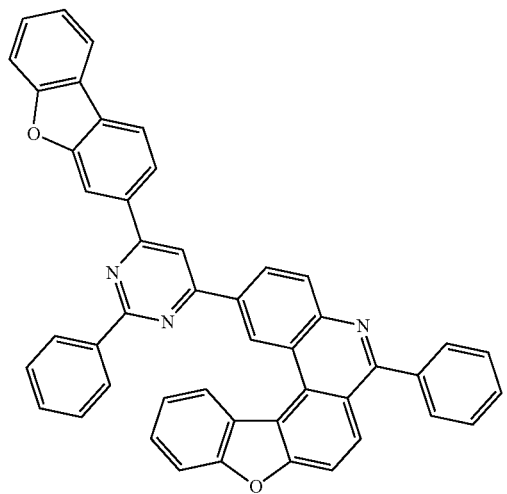
662
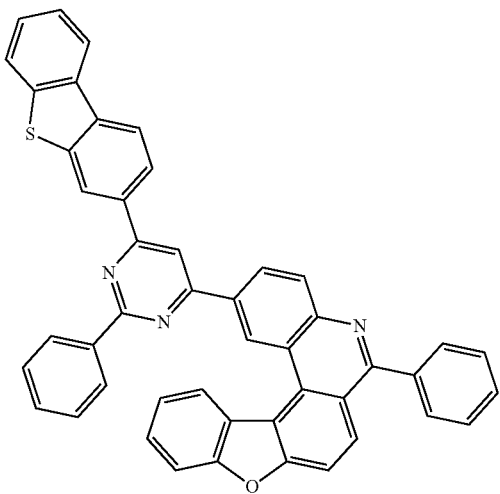
409
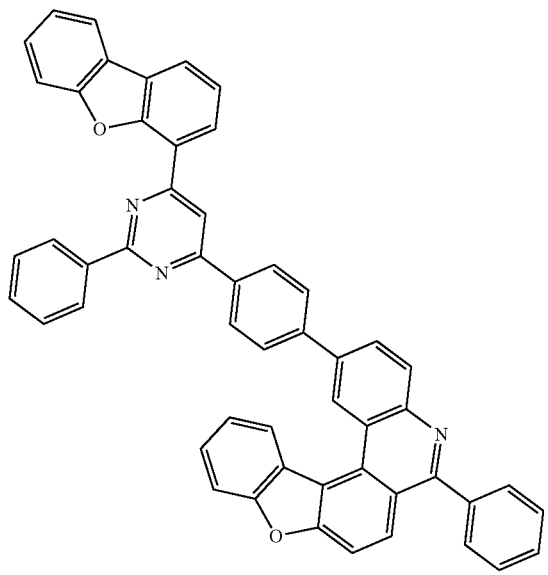
410
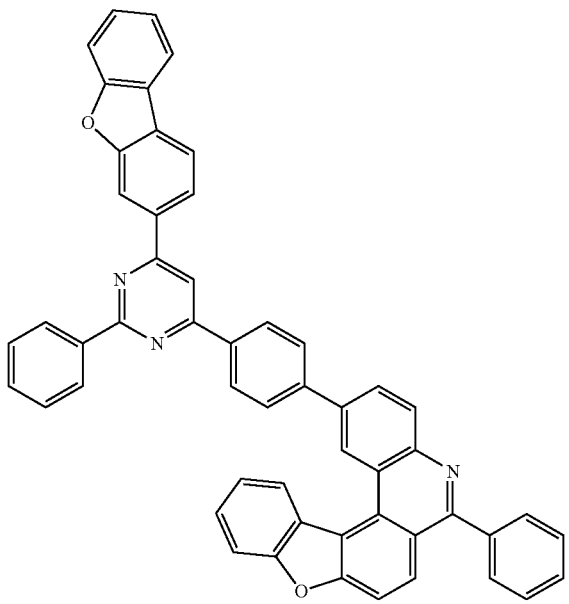 [SMILES: c1ccc(-c2nc(-c3ccc(-c4ccc5nc(-c6ccccc6)c6ccc7oc8ccccc8c7c6c5c4)cc3)cc(-c3ccc4c(c3)oc3ccccc34)n2)cc1]

-continued
411
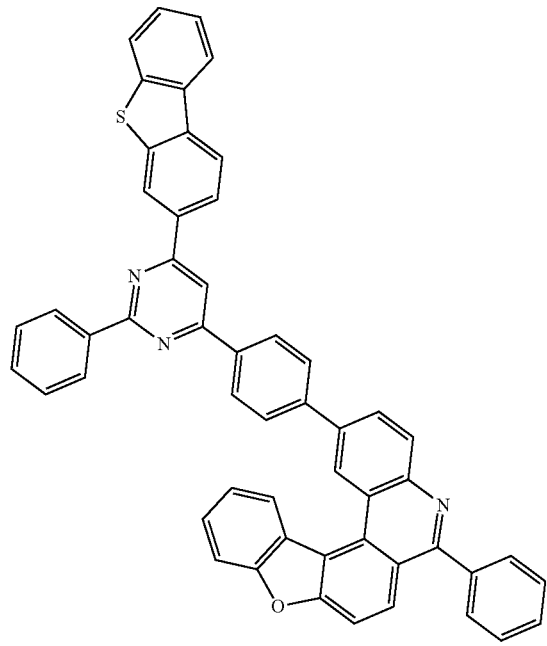
412
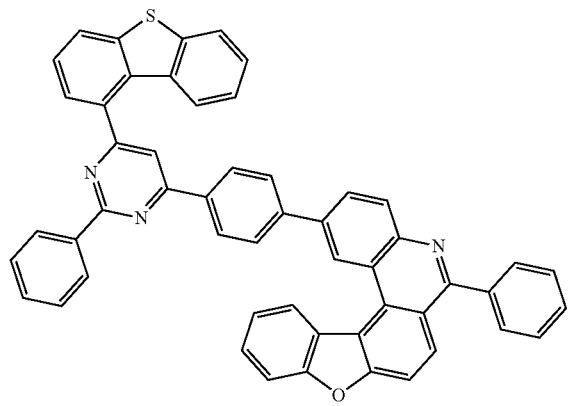
413
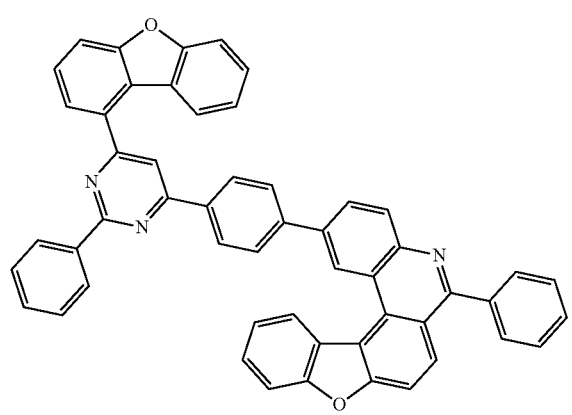
414
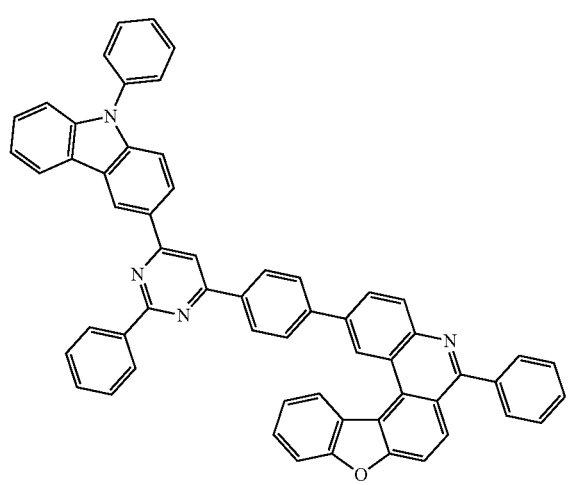 [SMILES: c1ccc(-c2nc(-c3ccc(-c4ccc5nc(-c6ccccc6)c6ccc7oc8ccccc8c7c6c5c4)cc3)cc(-c3ccc4c(c3)c3ccccc3n4-c3ccccc3)n2)cc1]
415
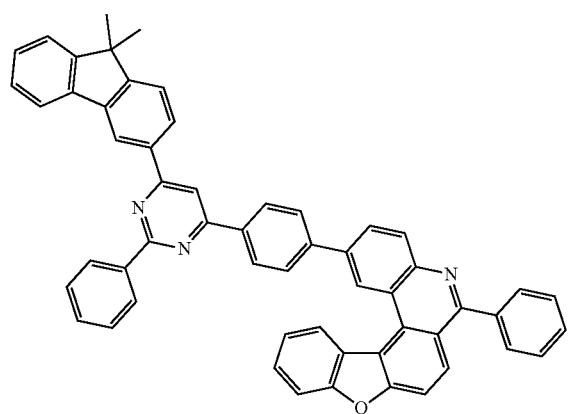
416
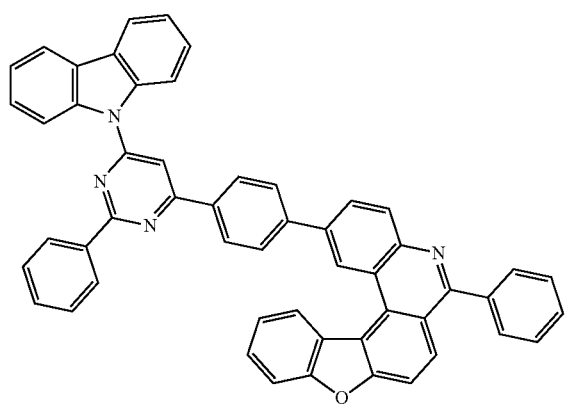

-continued
417
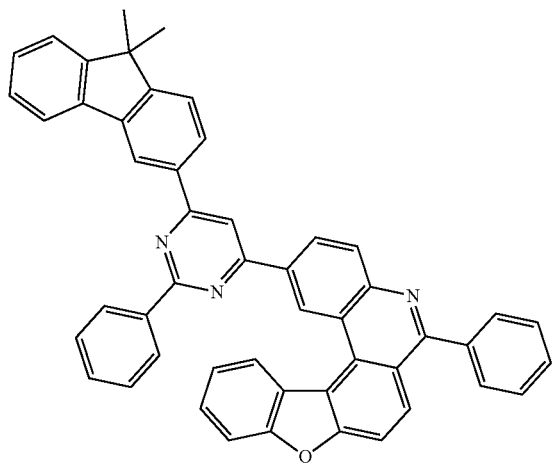
418
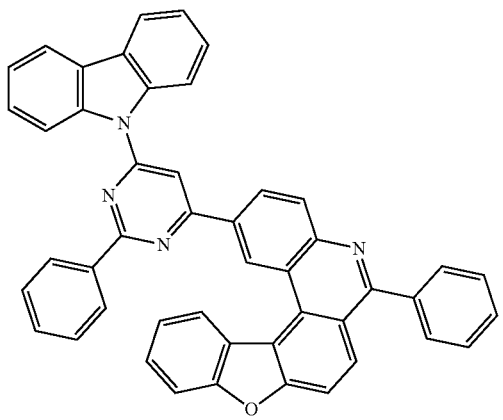 [SMILES: c1ccc(-c2nc(-c3ccc4nc(-c5ccccc5)c5ccc6oc7ccccc7c6c5c4c3)cc(-n3c4ccccc4c4ccccc43)n2)cc1]
419
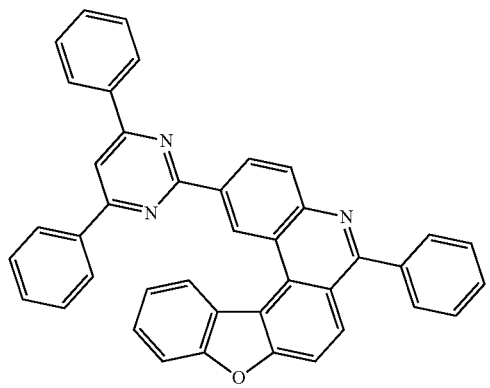
420
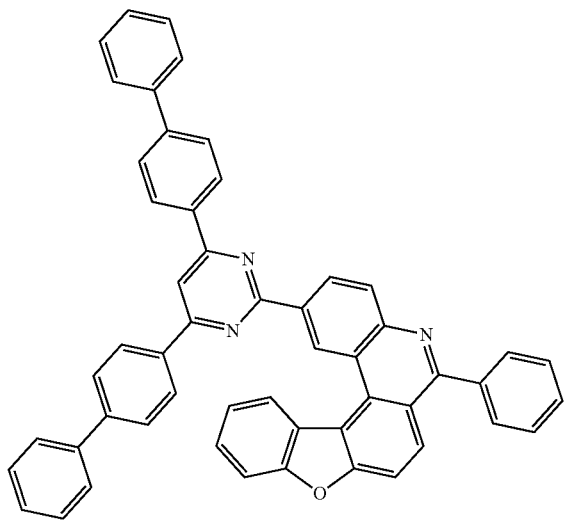
421
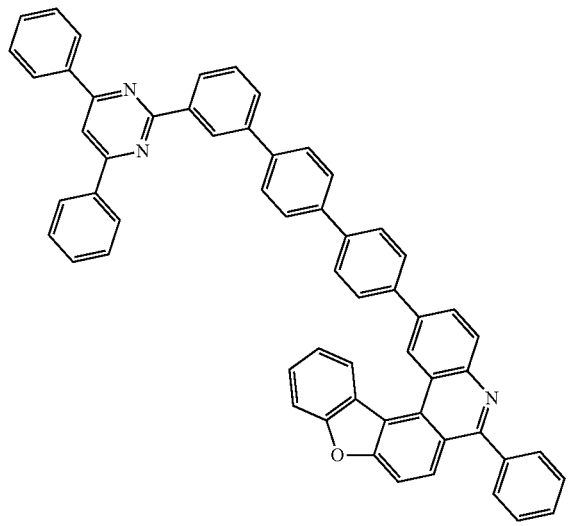
422
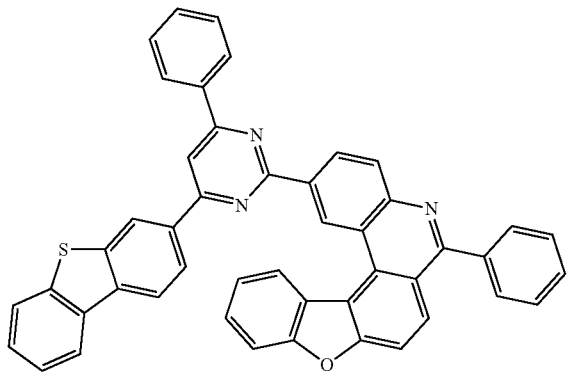 [SMILES: c1ccc(-c2cc(-c3ccc4c(c3)sc3ccccc34)nc(-c3ccc4nc(-c5ccccc5)c5ccc6oc7ccccc7c6c5c4c3)n2)cc1]

-continued
423
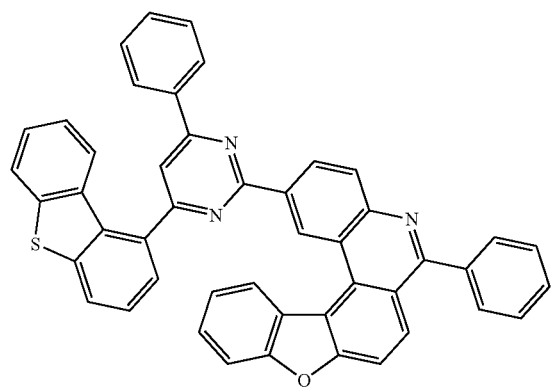
424
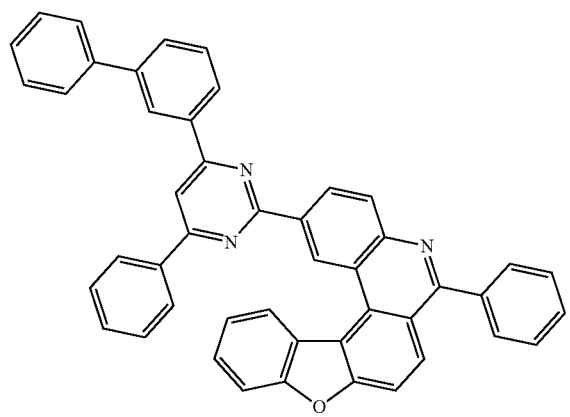
425
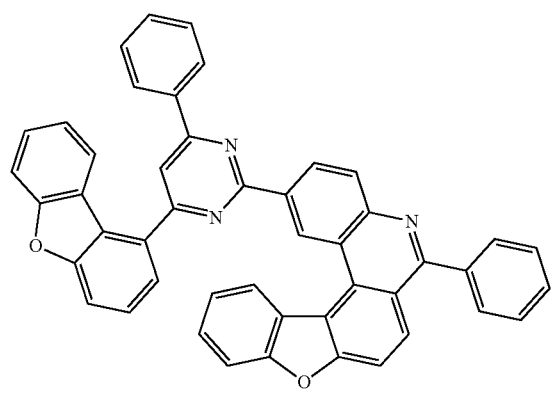
426
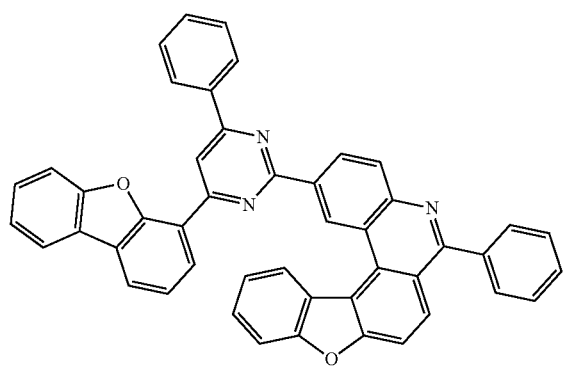 [SMILES: c1ccc(-c2cc(-c3cccc4c3oc3ccccc34)nc(-c3ccc4nc(-c5ccccc5)c5ccc6oc7ccccc7c6c5c4c3)n2)cc1]
427
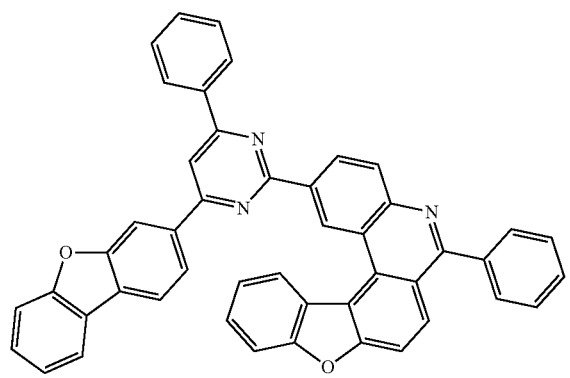
428
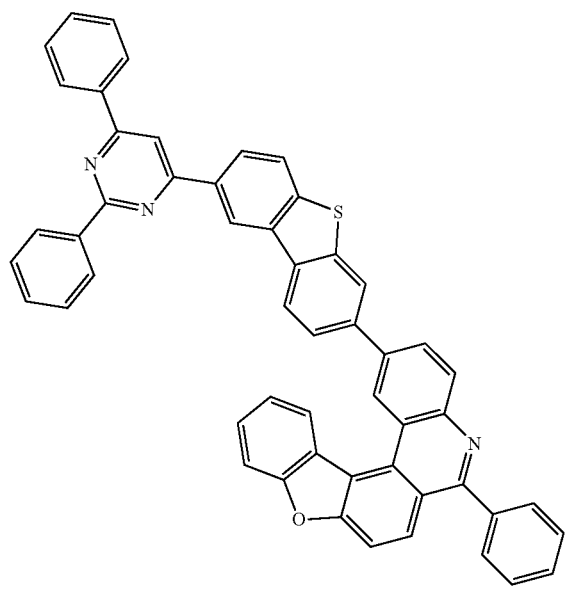

-continued
429
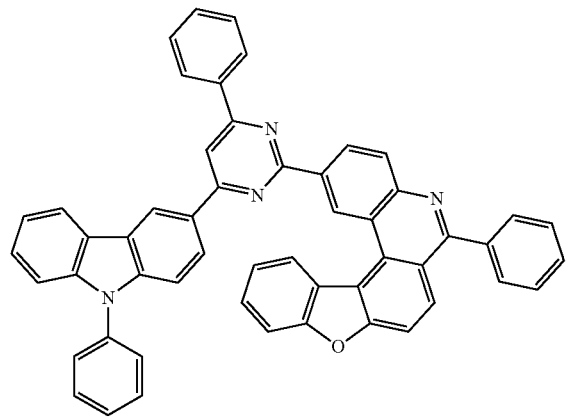
430
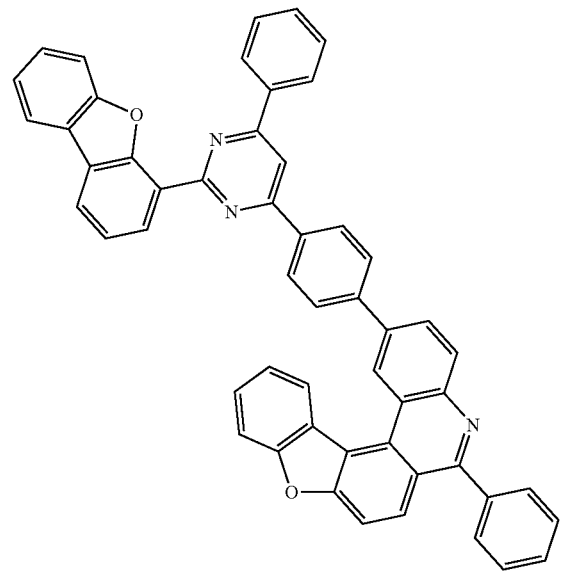
431
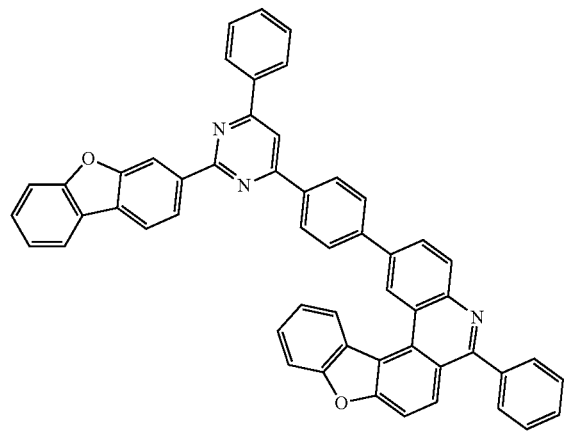
432
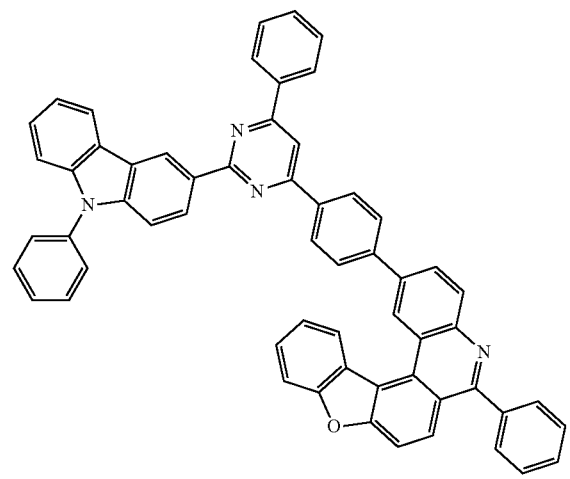

-continued
433
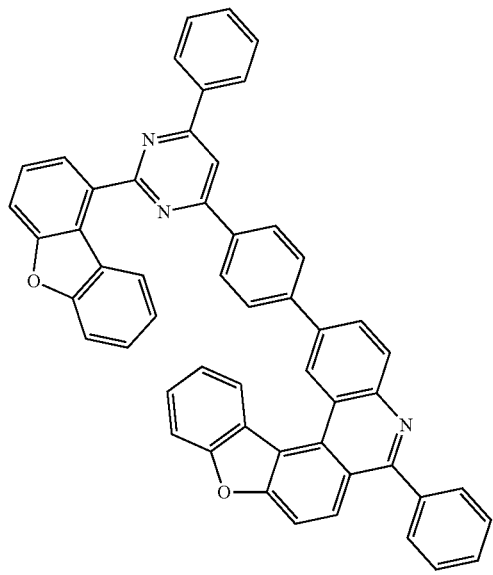
434
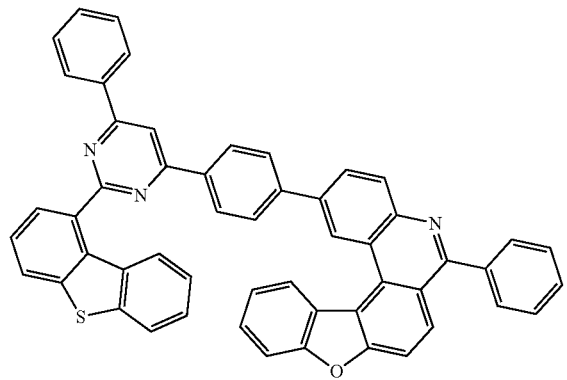 [SMILES: c1ccc(-c2cc(-c3ccc(-c4ccc5nc(-c6ccccc6)c6ccc7oc8ccccc8c7c6c5c4)cc3)nc(-c3cccc4sc5ccccc5c34)n2)cc1]
435
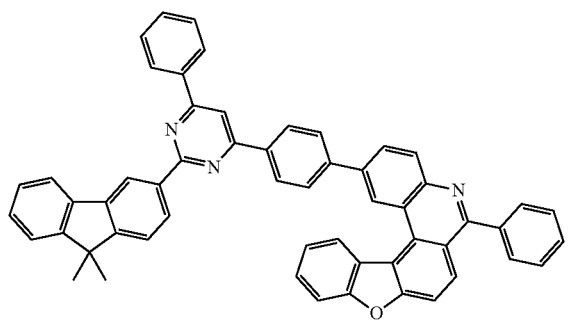
436
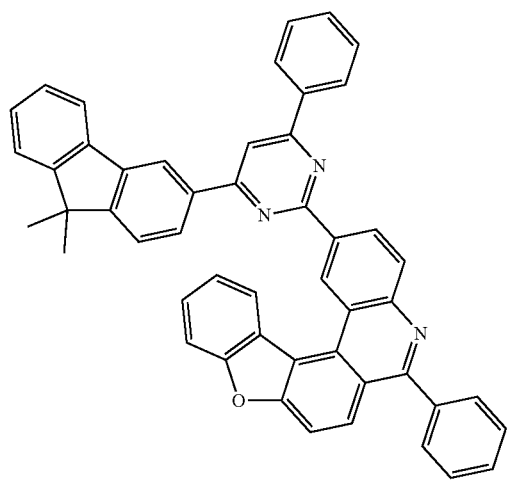
437
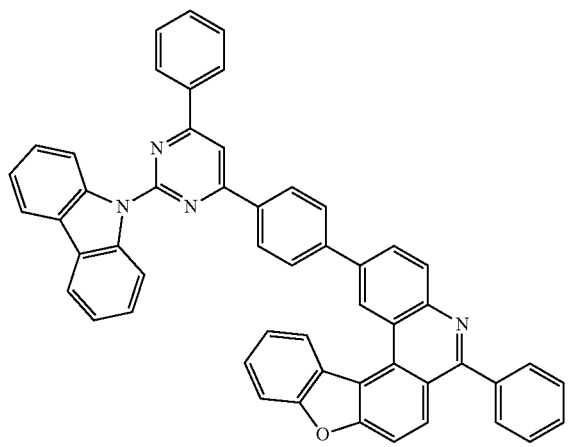
438
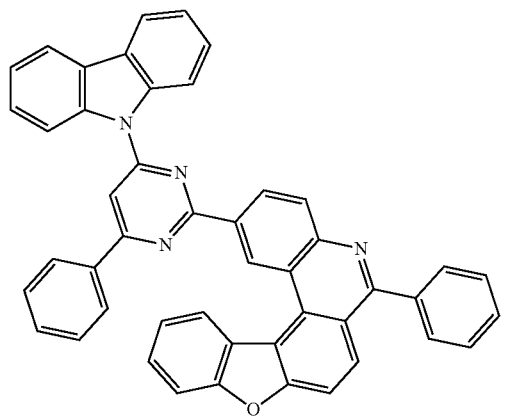 [SMILES: c1ccc(-c2cc(-n3c4ccccc4c4ccccc43)nc(-c3ccc4nc(-c5ccccc5)c5ccc6oc7ccccc7c6c5c4c3)n2)cc1]

-continued
673
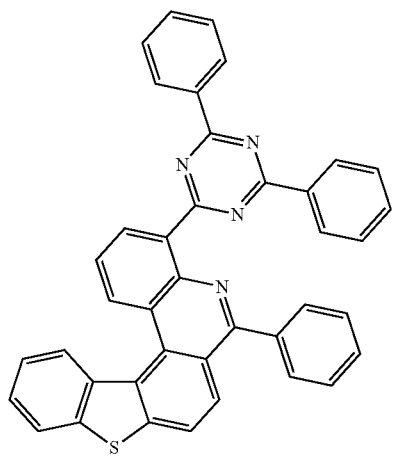
439
674
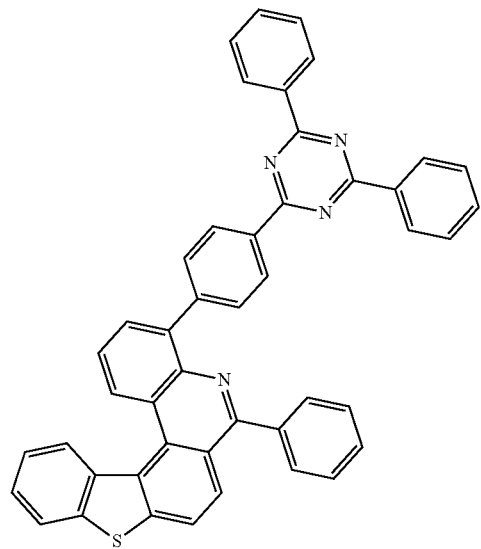
440
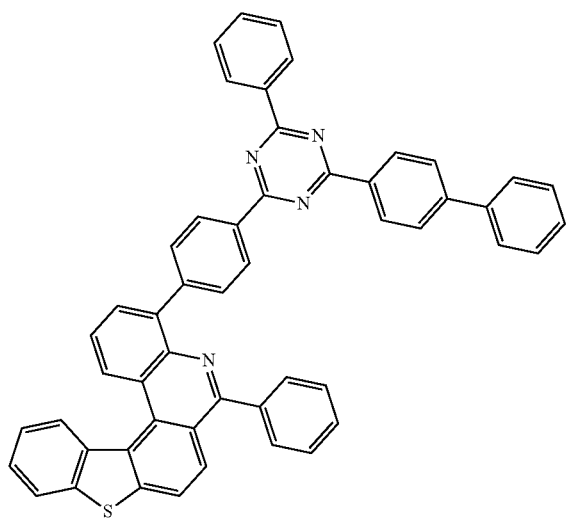
441
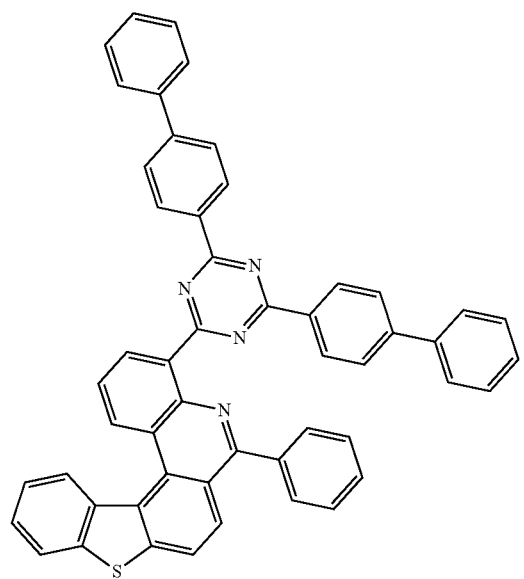 [SMILES: c1ccc(-c2ccc(-c3nc(-c4ccc(-c5ccccc5)cc4)nc(-c4cccc5c4nc(-c4ccccc4)c4ccc6sc7ccccc7c6c45)n3)cc2)cc1]
442
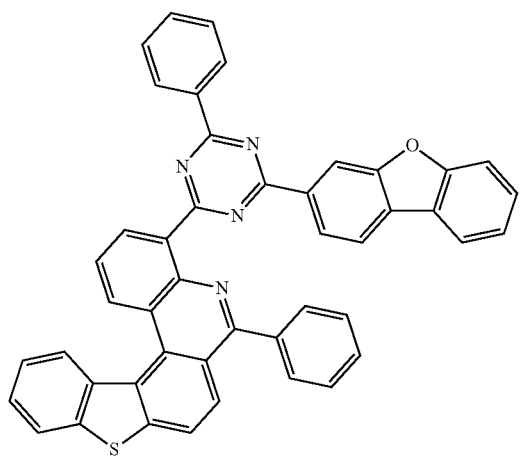
443
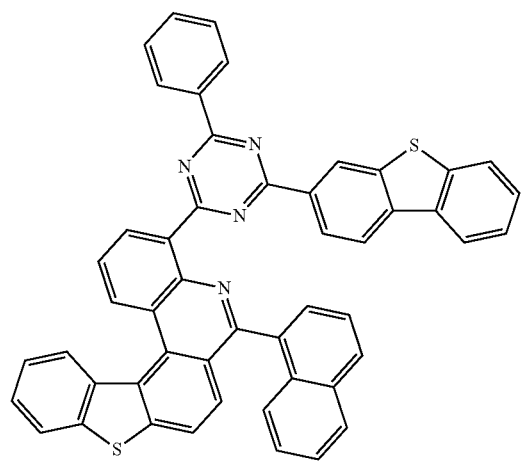
444

-continued
445
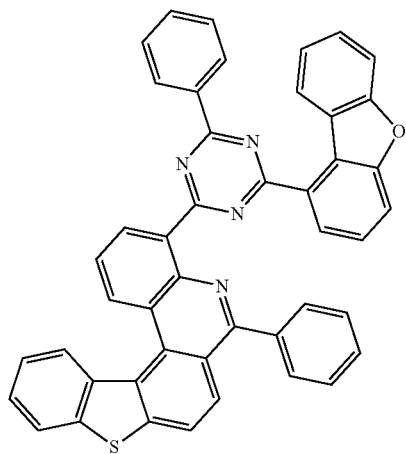
446
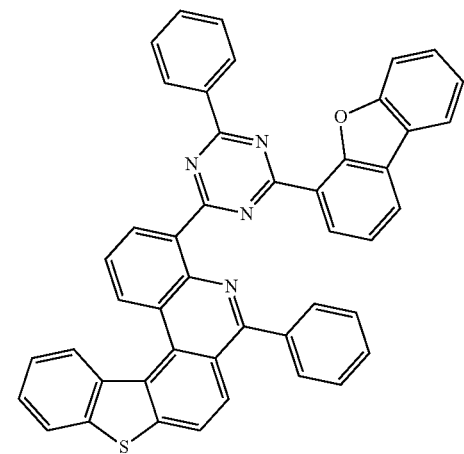
447
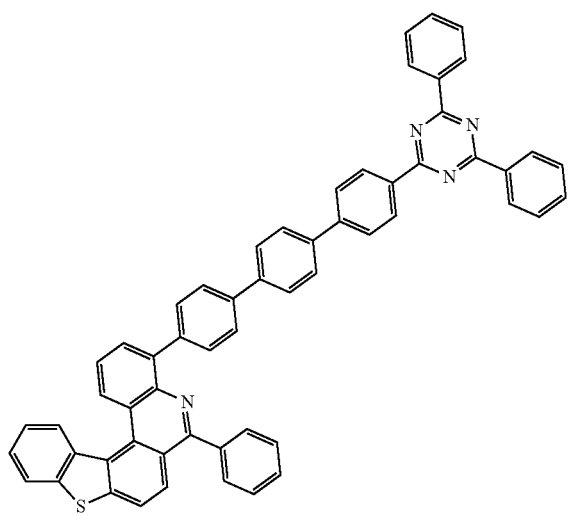
448
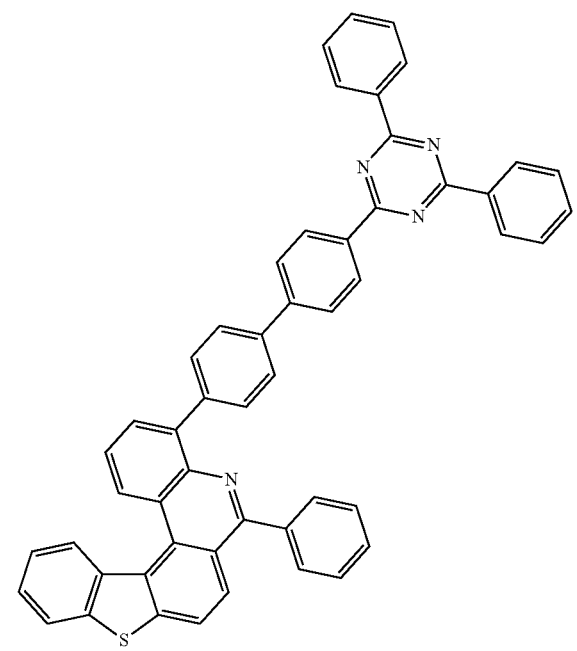
449
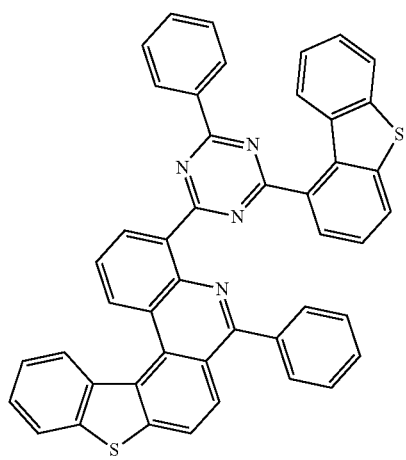
450
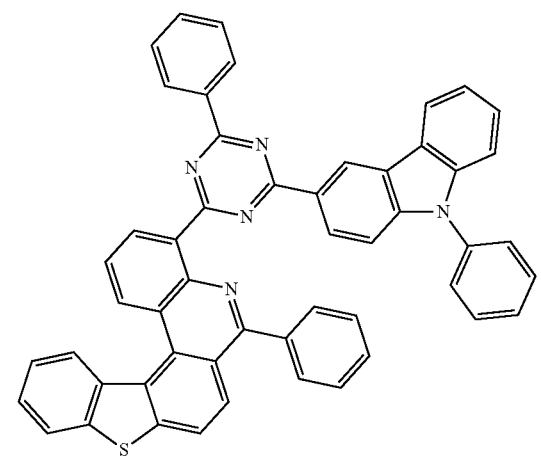 [SMILES: c1ccc(-c2nc(-c3ccc4c(c3)c3ccccc3n4-c3ccccc3)nc(-c3cccc4c3nc(-c3ccccc3)c3ccc5sc6ccccc6c5c34)n2)cc1]

-continued
451
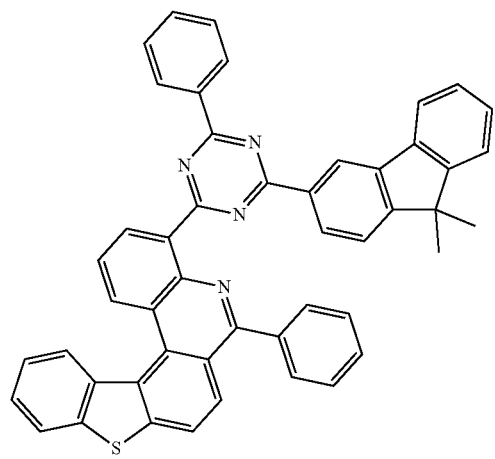
452
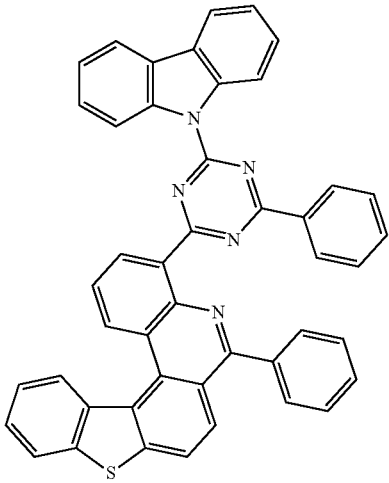
453
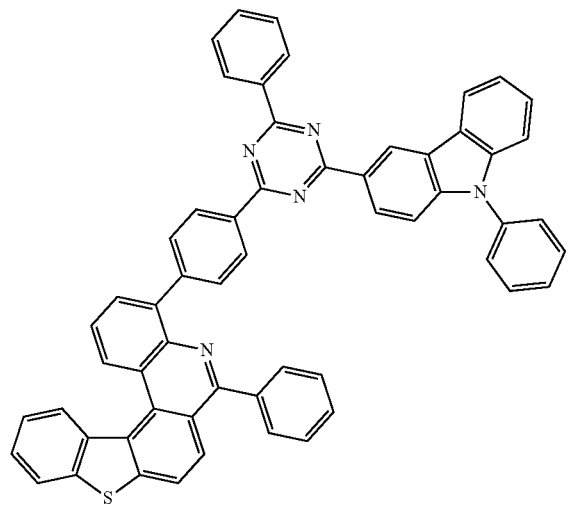
454
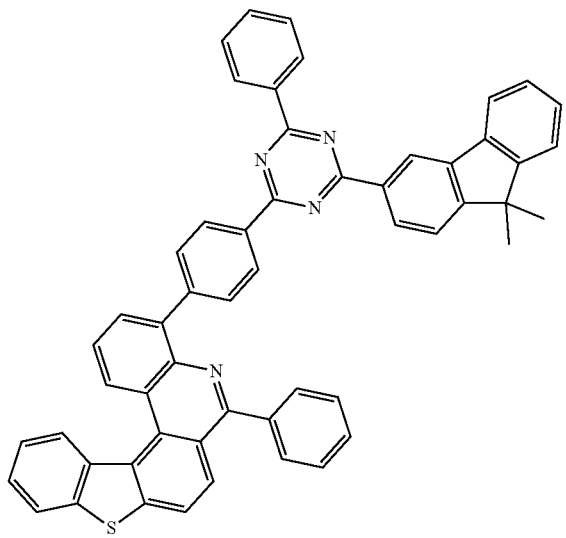 [SMILES: CC1(C)c2ccccc2-c2cc(-c3nc(-c4ccccc4)nc(-c4ccc(-c5cccc6c5nc(-c5ccccc5)c5ccc7sc8ccccc8c7c56)cc4)n3)ccc21]
455
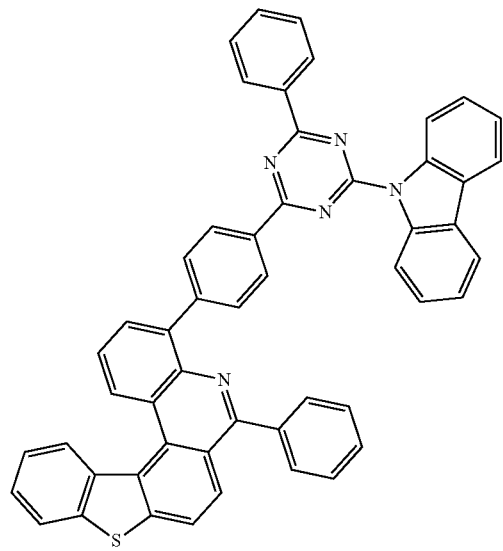
456
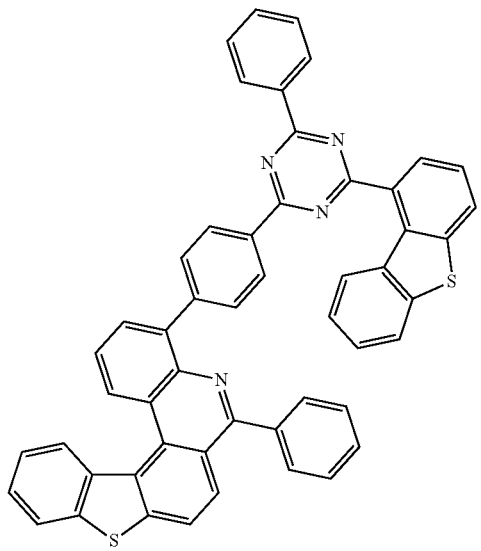

-continued
457
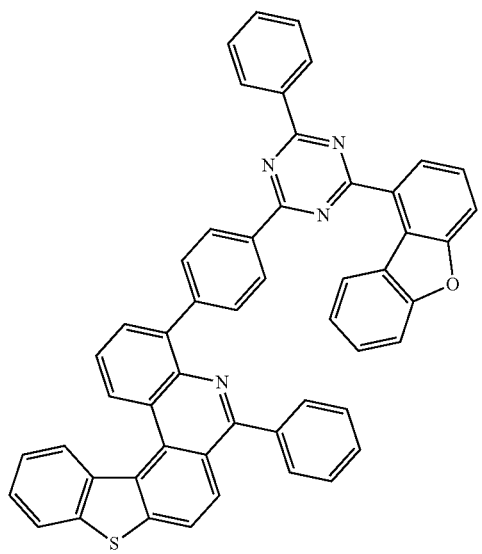
458
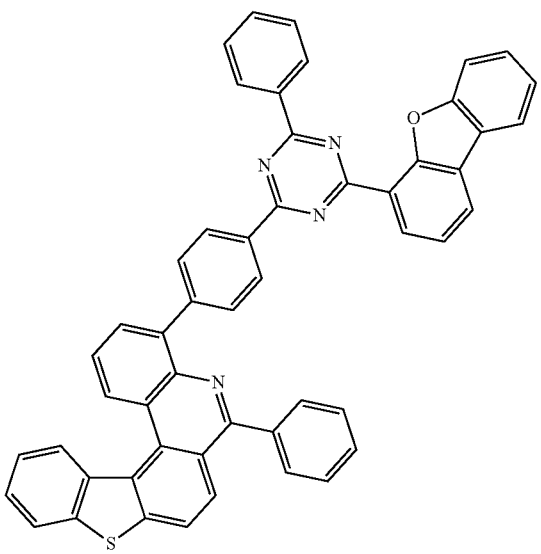 [SMILES: c1ccc(-c2nc(-c3ccc(-c4cccc5c4nc(-c4ccccc4)c4ccc6sc7ccccc7c6c45)cc3)nc(-c3cccc4c3oc3ccccc34)n2)cc1]
459
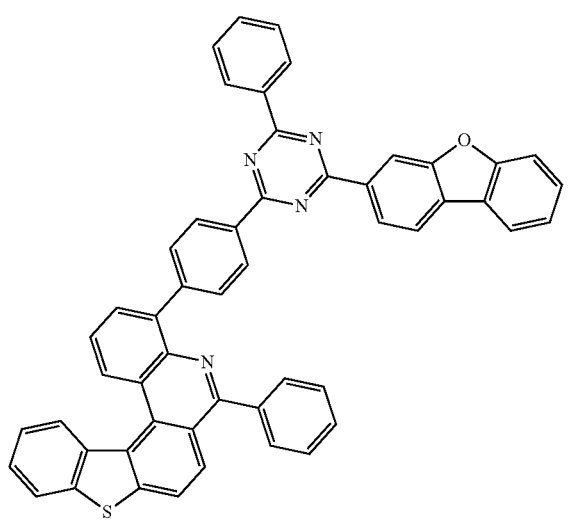
460
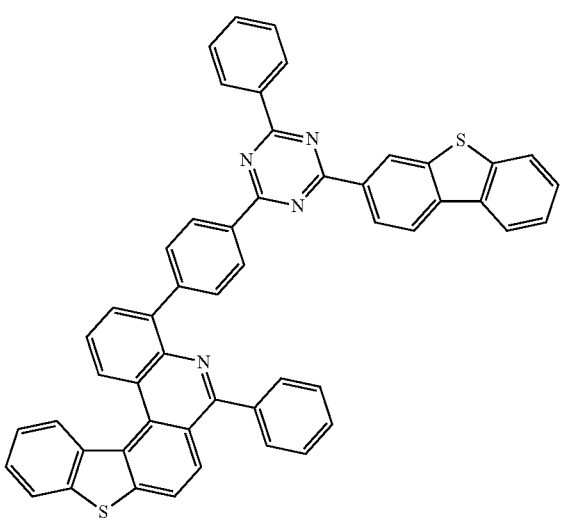
461
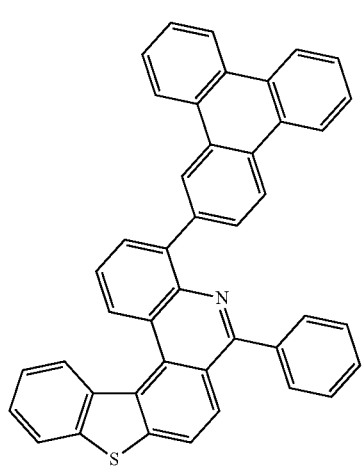
462
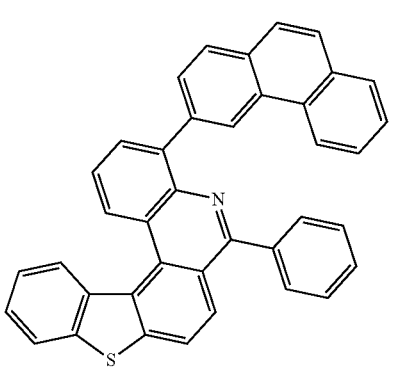 [SMILES: c1ccc(-c2nc3c(-c4ccc5ccc6ccccc6c5c4)cccc3c3c2ccc2sc4ccccc4c23)cc1]

-continued
463
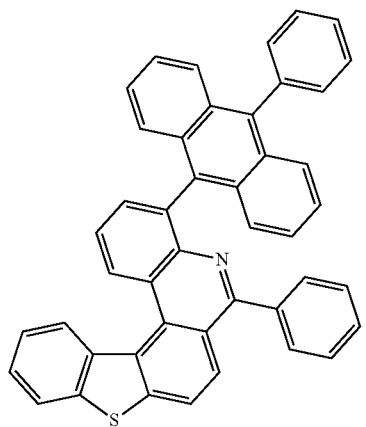
464
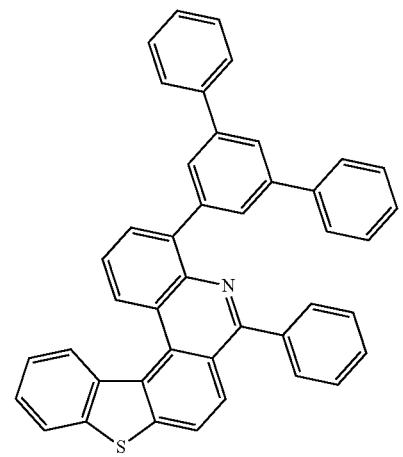
465
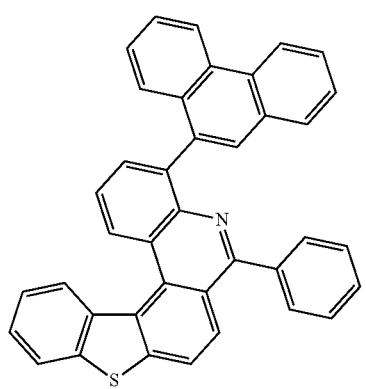
466
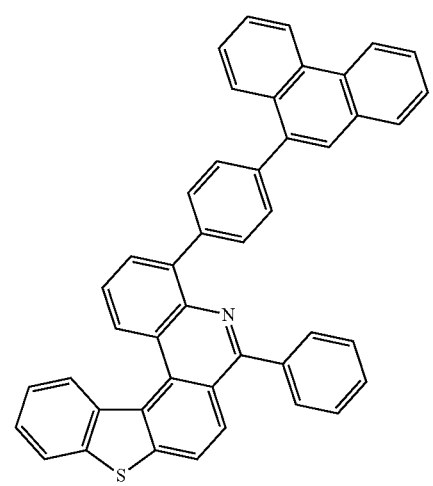 [SMILES: c1ccc(-c2nc3c(-c4ccc(-c5cc6ccccc6c6ccccc56)cc4)cccc3c3c2ccc2sc4ccccc4c23)cc1]
467
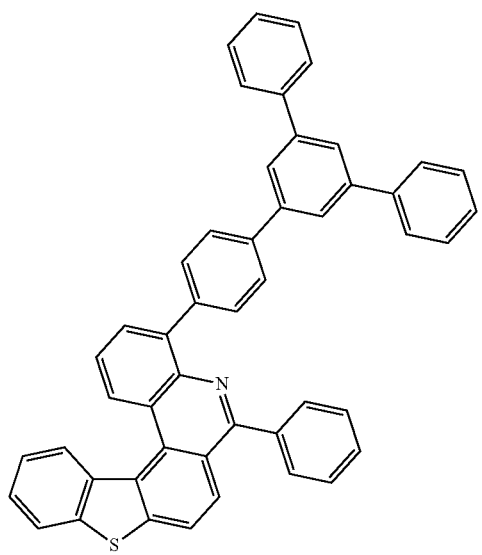
468
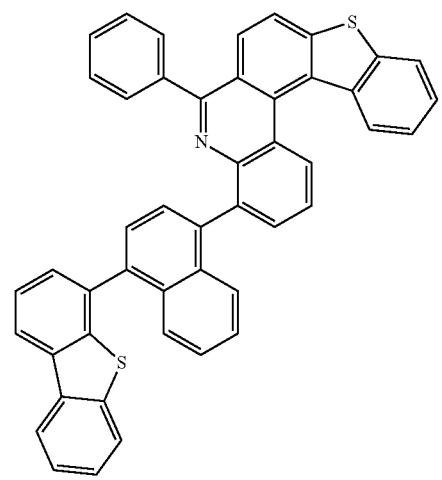

-continued
469
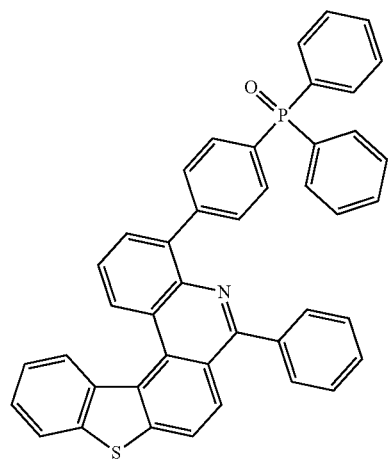
470
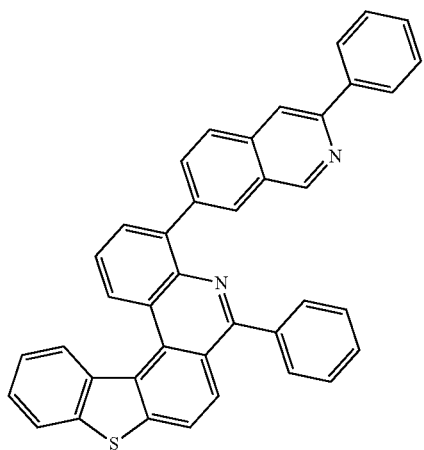 [SMILES: c1ccc(-c2cc3ccc(-c4cccc5c4nc(-c4ccccc4)c4ccc6sc7ccccc7c6c45)cc3cn2)cc1]
471
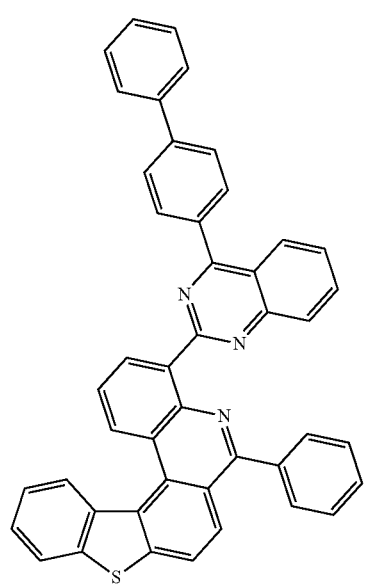
472
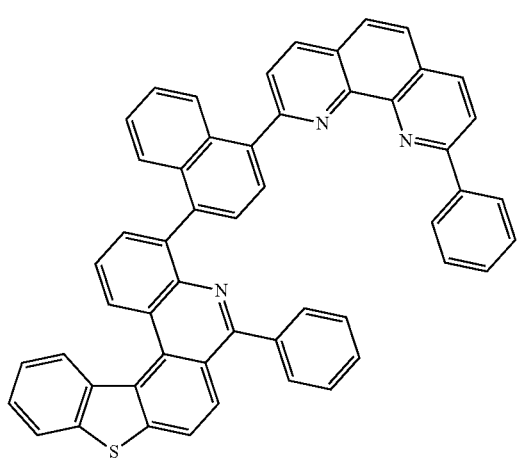
473
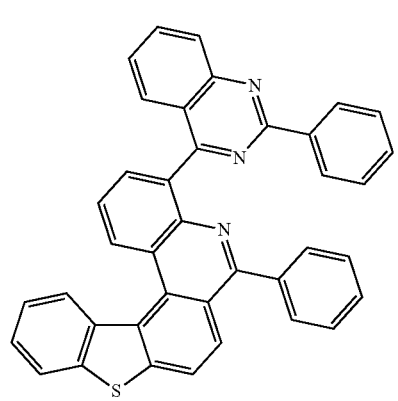
474
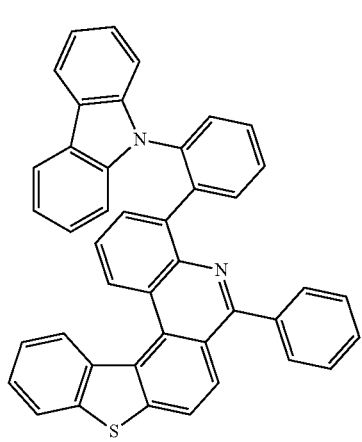 [SMILES: c1ccc(-c2nc3c(-c4ccccc4C4c5ccccc5-c5ccccc54)cccc3c3c2ccc2sc4ccccc4c23)cc1]

-continued
475 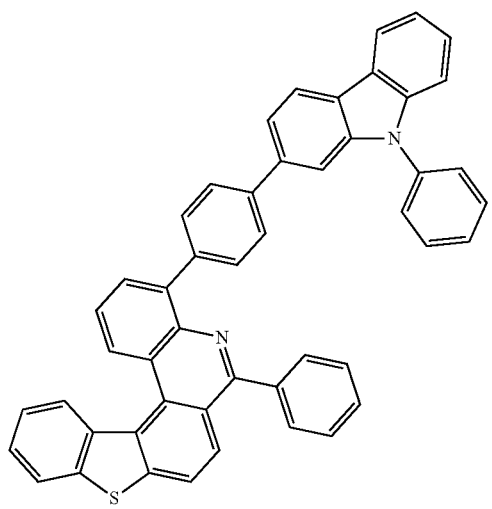
476 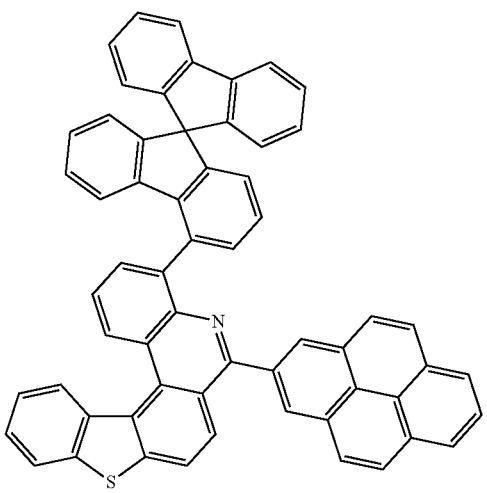
477 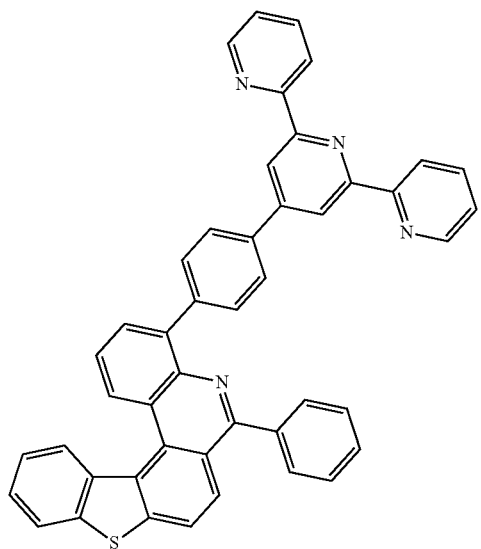
478 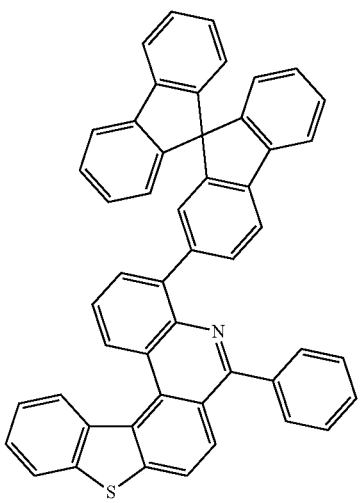 [SMILES: c1ccc(-c2nc3c(-c4ccc5c(c4)C4(c6ccccc6-c6ccccc64)c4ccccc4-5)cccc3c3c2ccc2sc4ccccc4c23)cc1]
479 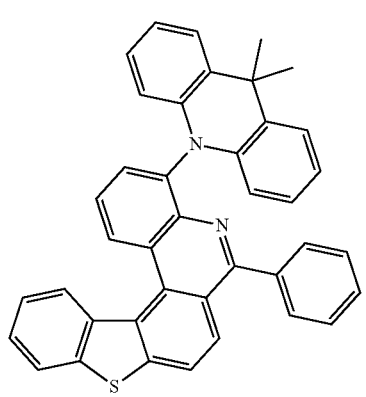
480 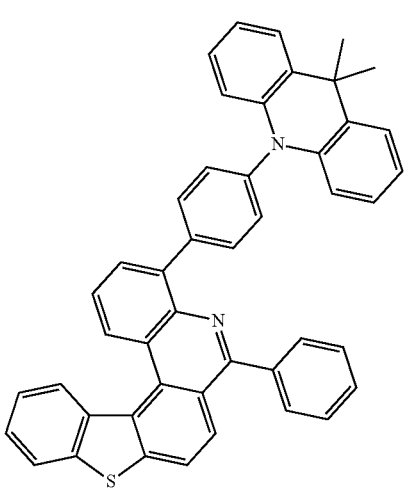

687           688
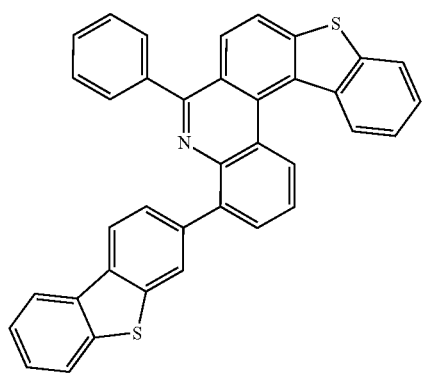   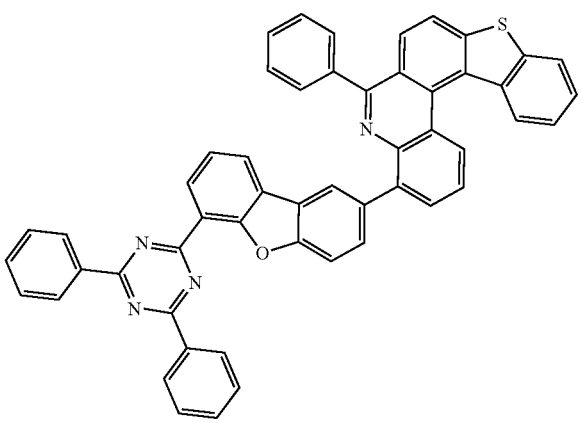
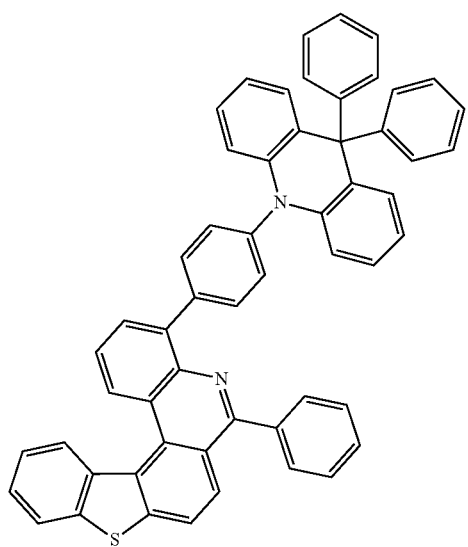
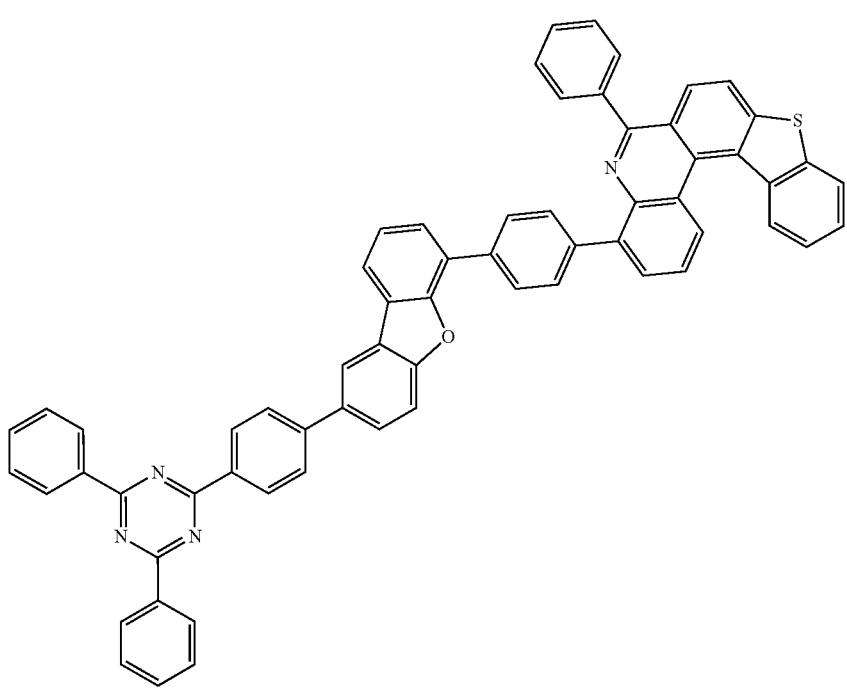

-continued
485
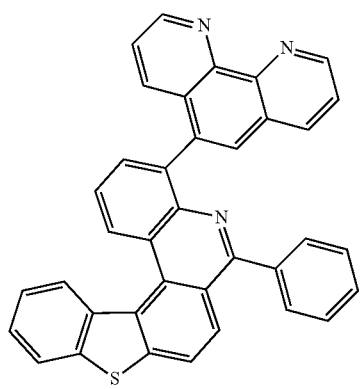
486
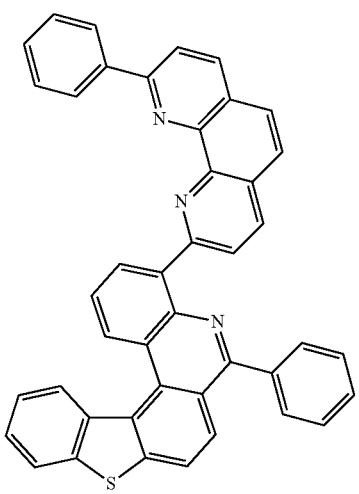
487
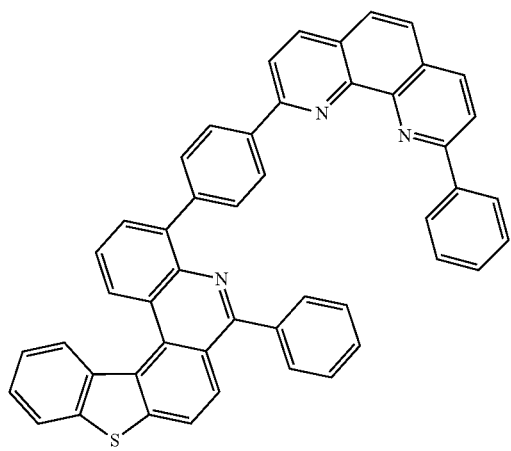
488
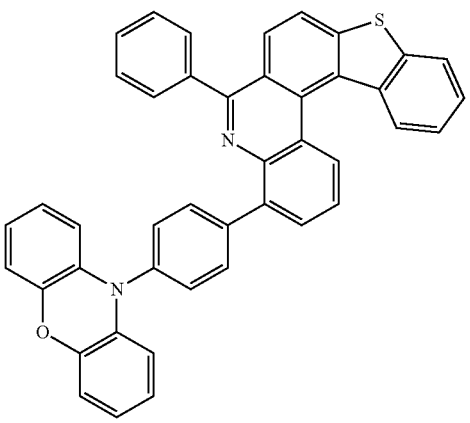
489
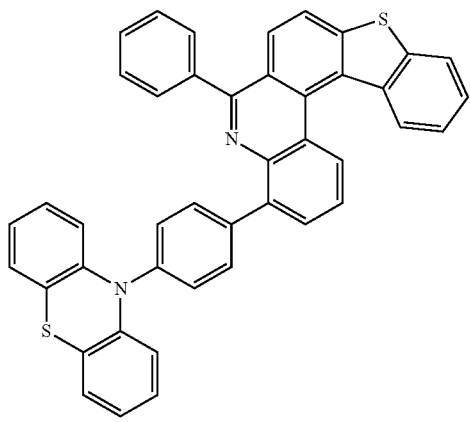
490
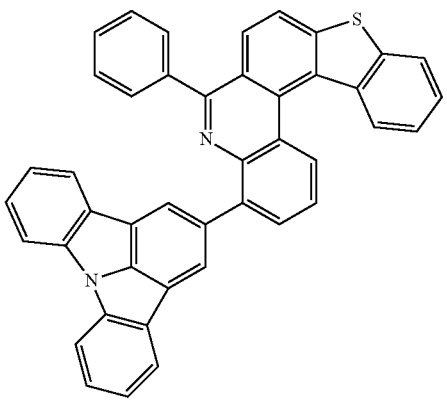 [SMILES: c1ccc(-c2nc3c(-c4cc5c6ccccc6n6c7ccccc7c(c4)c56)cccc3c3c2ccc2sc4ccccc4c23)cc1]

491
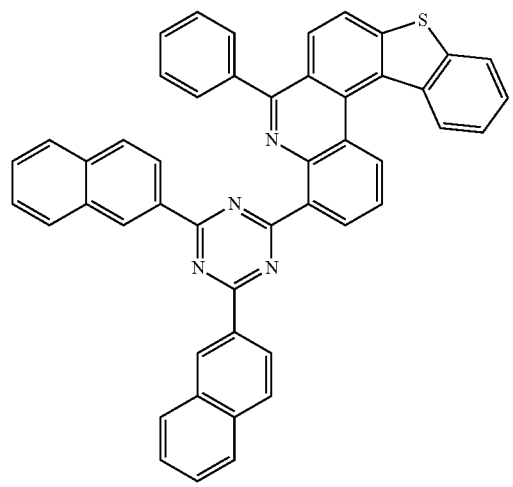
492
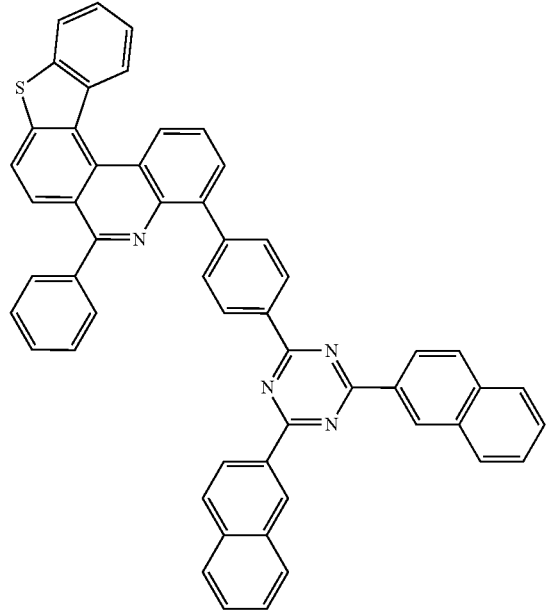
-continued
493
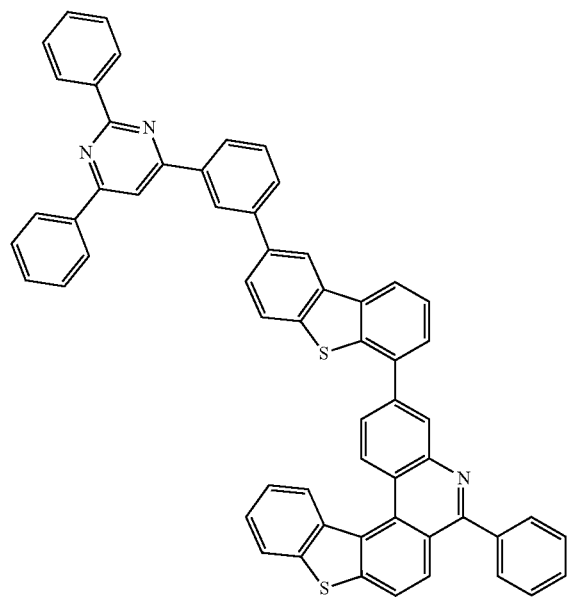
494
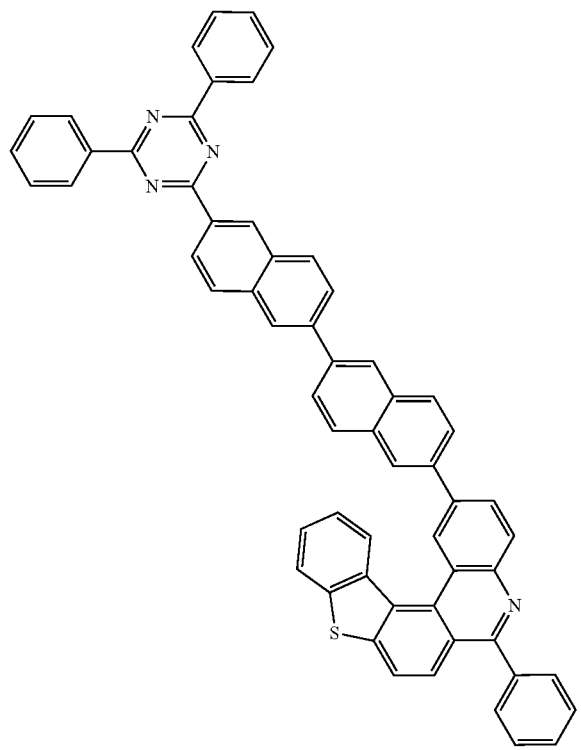

-continued
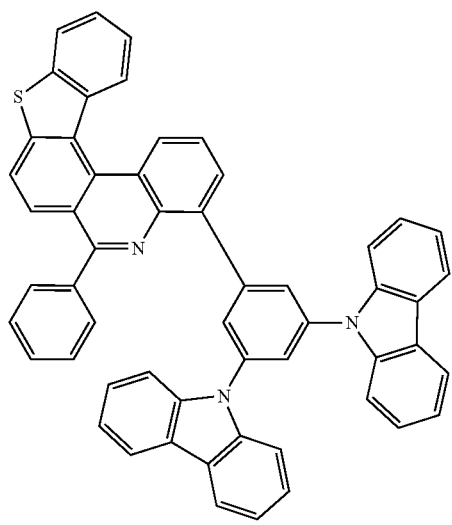
495
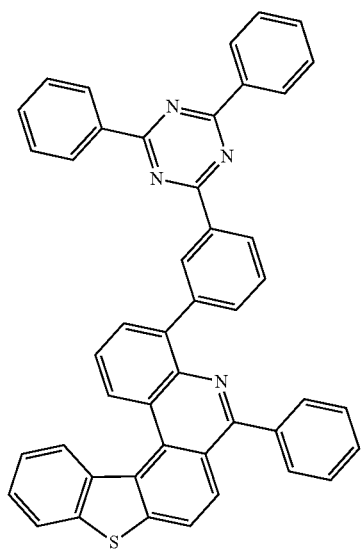
496
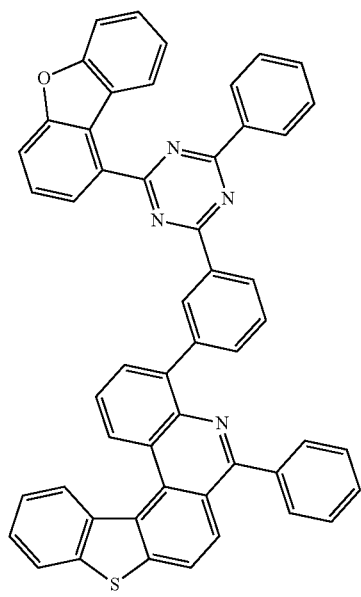
497
498

-continued
499
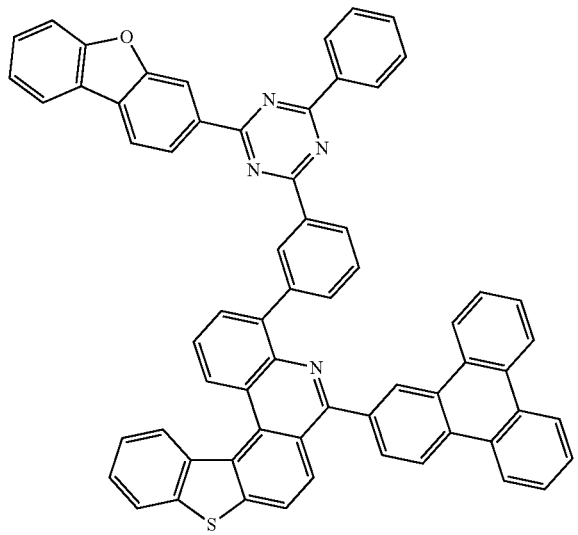
500
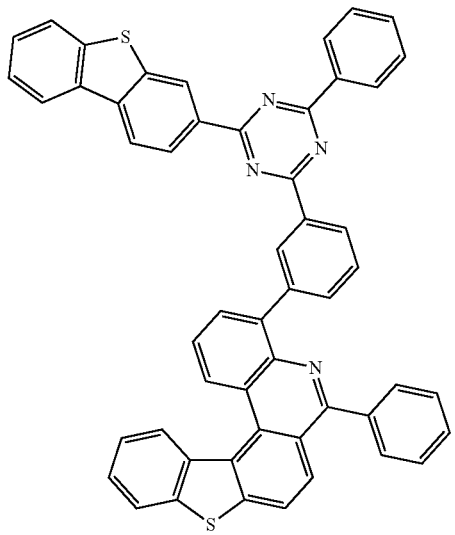
501
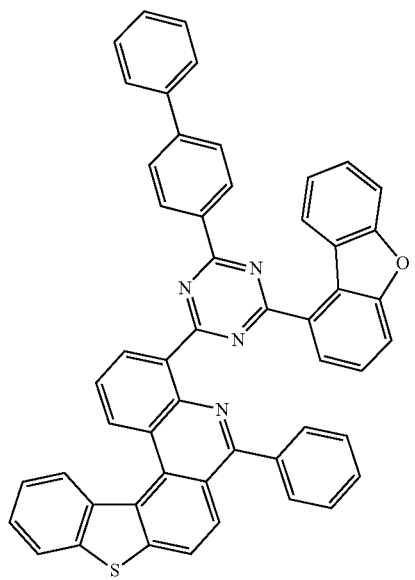
502
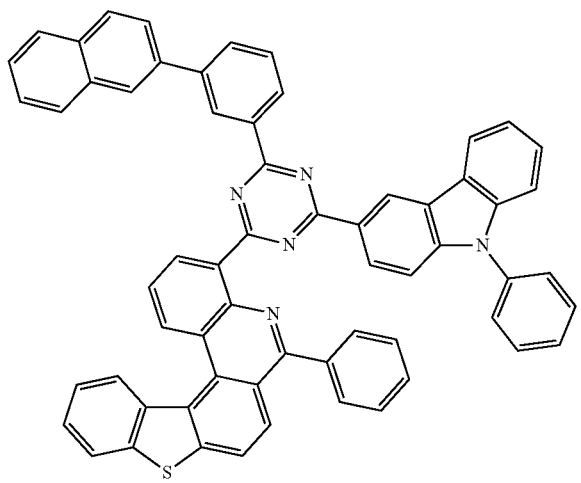
503
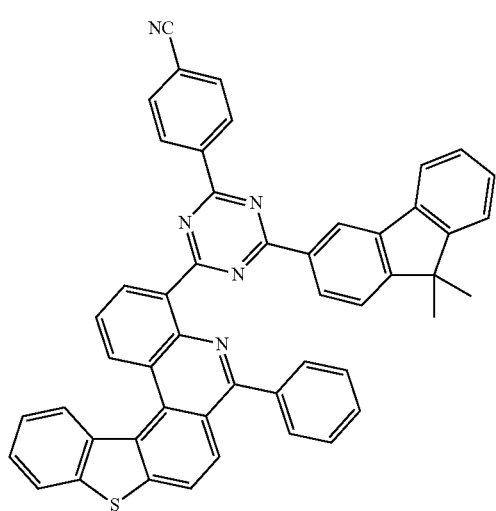
504
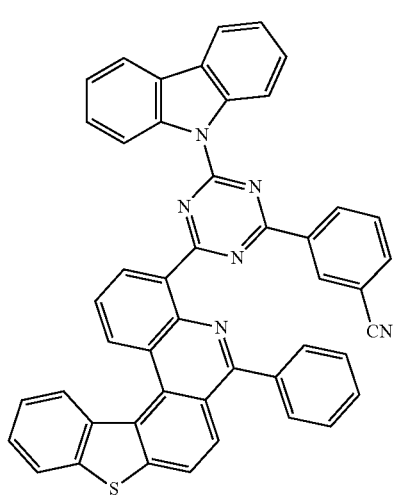

-continued
697
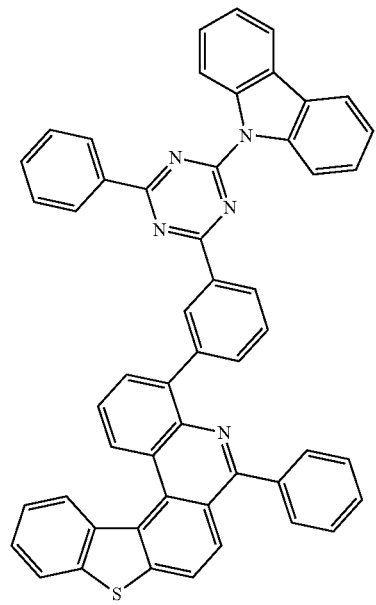
698
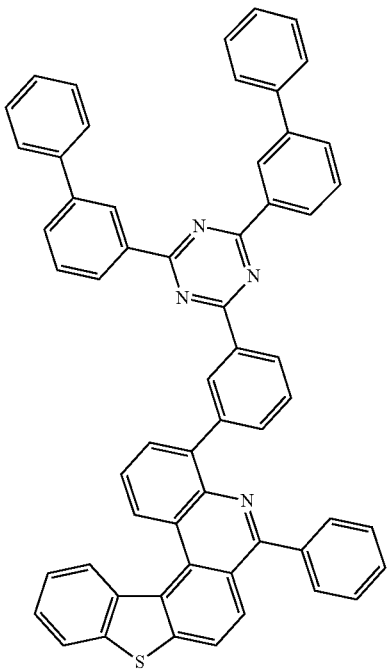 [SMILES: c1ccc(-c2cccc(-c3nc(-c4cccc(-c5ccccc5)c4)nc(-c4cccc(-c5cccc6c5nc(-c5ccccc5)c5ccc7sc8ccccc8c7c56)c4)n3)c2)cc1]
507
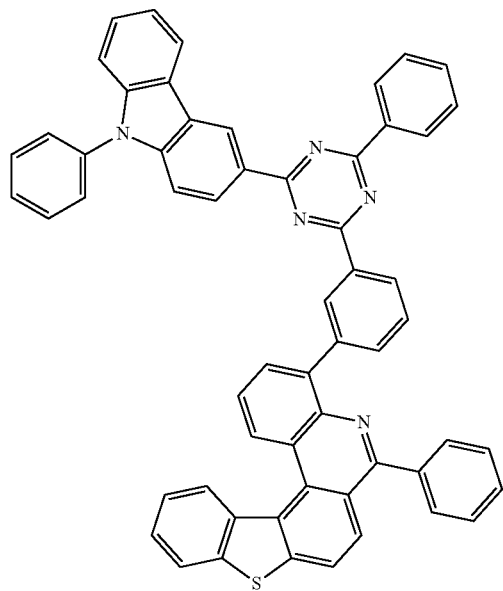
508
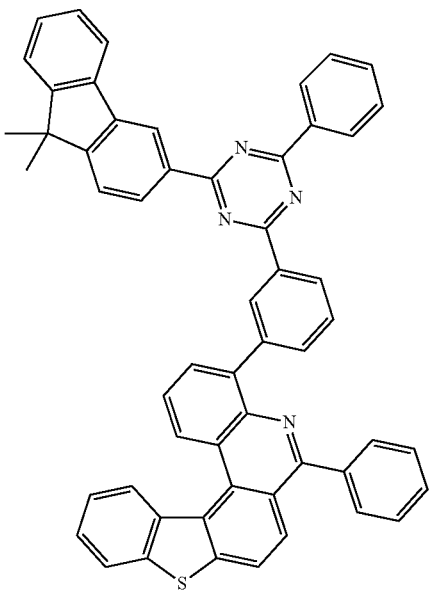

-continued
699
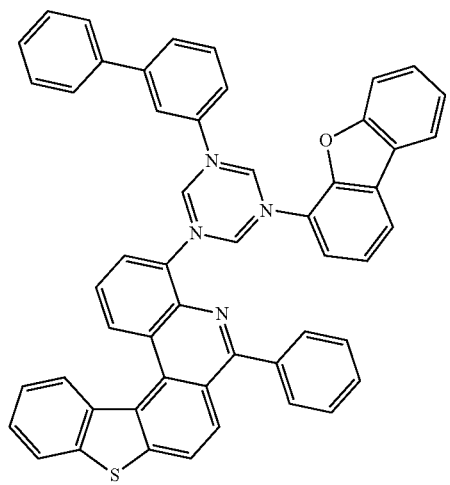
509
700
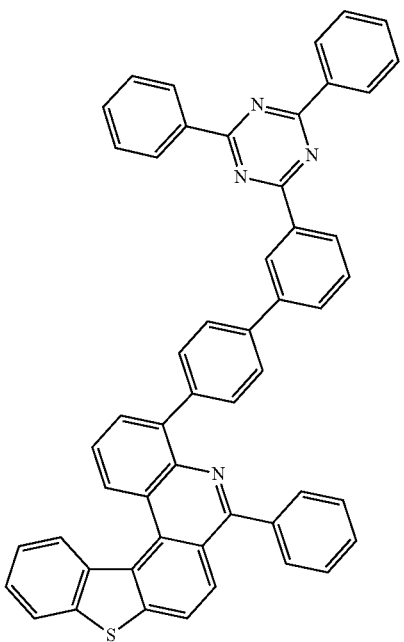 [SMILES: c1ccc(-c2nc(-c3ccccc3)nc(-c3cccc(-c4ccc(-c5cccc6c5nc(-c5ccccc5)c5ccc7sc8ccccc8c7c56)cc4)c3)n2)cc1]
510
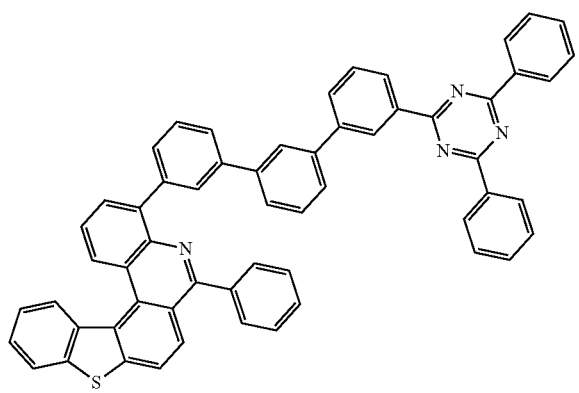
511
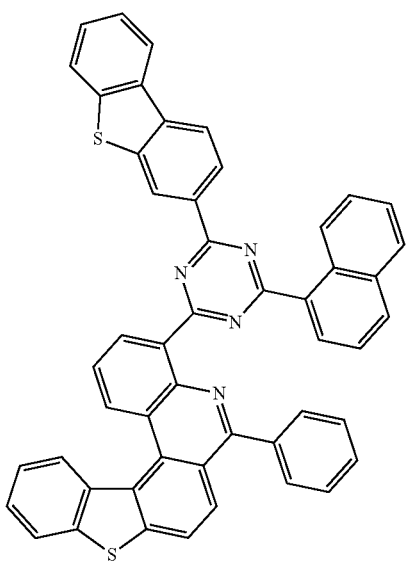
512

-continued
513
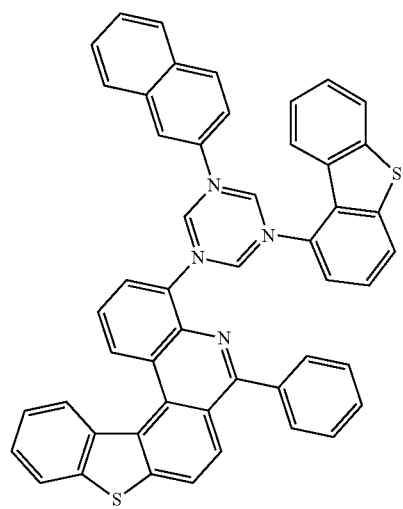
514
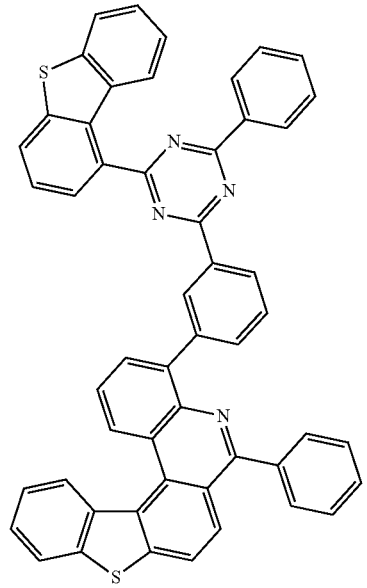
515
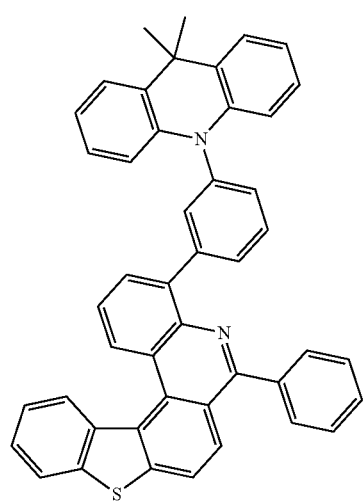
516
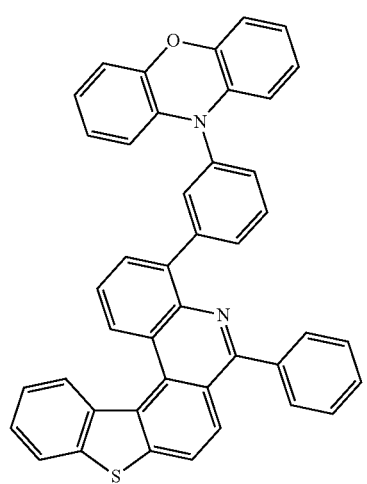

-continued
517
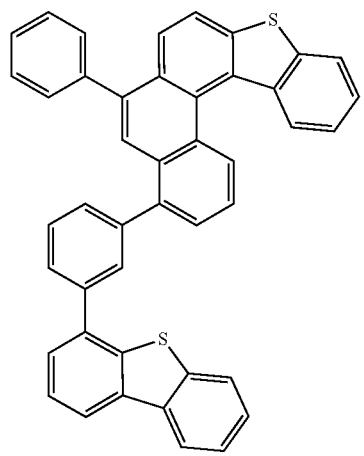
518
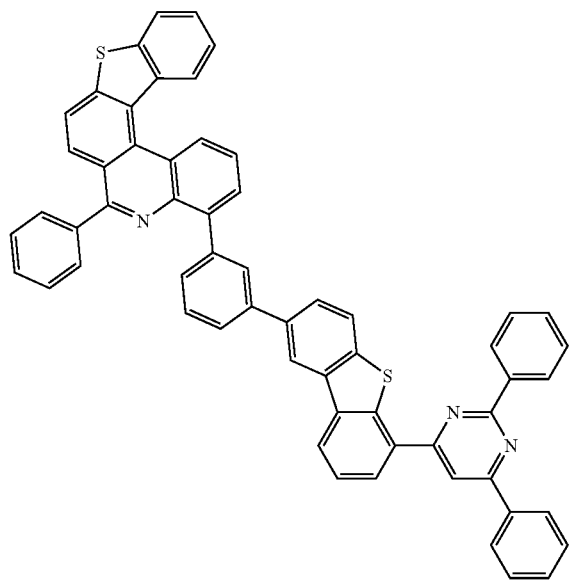 [SMILES: c1ccc(-c2cc(-c3cccc4c3sc3ccc(-c5cccc(-c6cccc7c6nc(-c6ccccc6)c6ccc8sc9ccccc9c8c67)c5)cc34)nc(-c3ccccc3)n2)cc1]
519
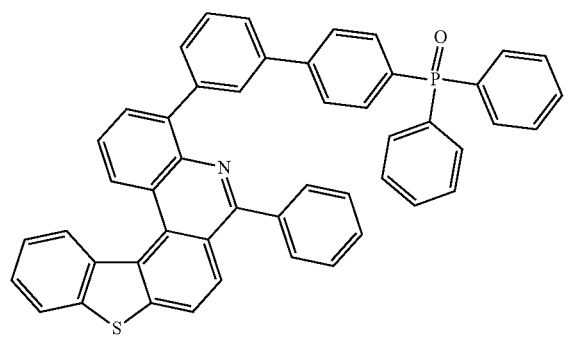
520
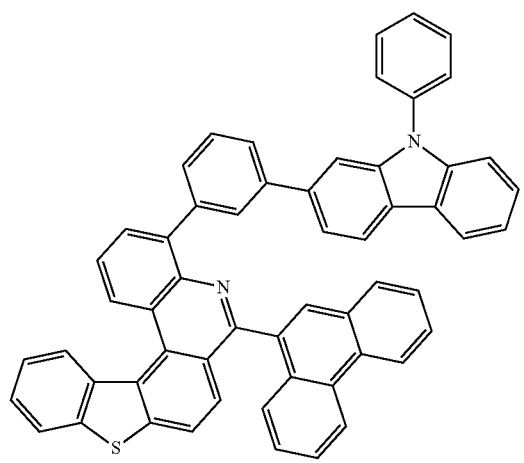
521
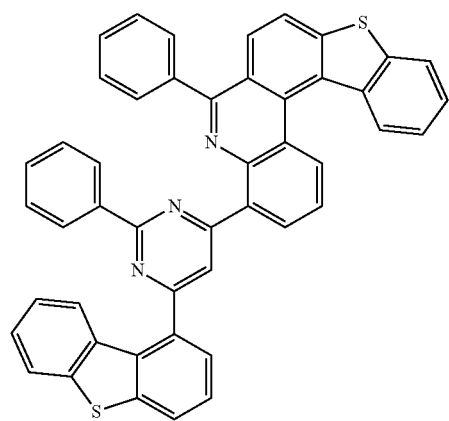
522
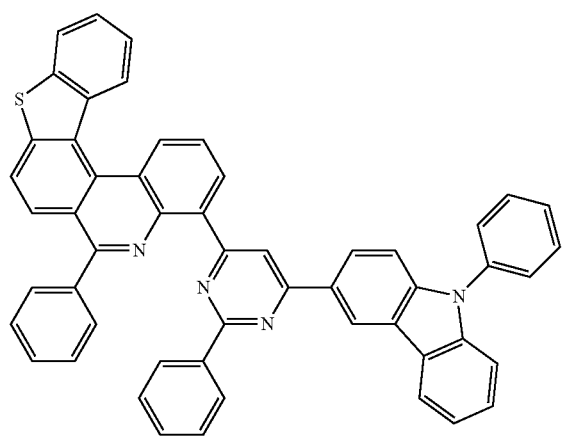 [SMILES: c1ccc(-c2nc(-c3ccc4c(c3)c3ccccc3n4-c3ccccc3)cc(-c3cccc4c3nc(-c3ccccc3)c3ccc5sc6ccccc6c5c34)n2)cc1]

-continued
705
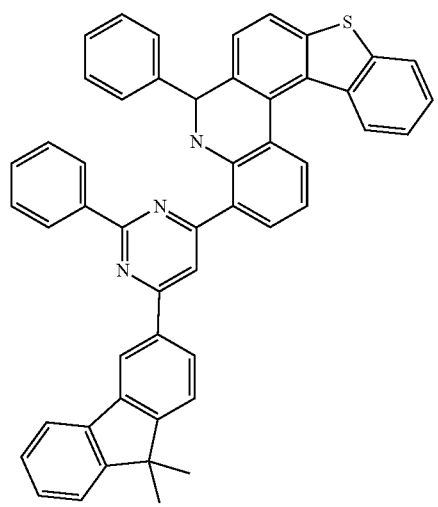
706
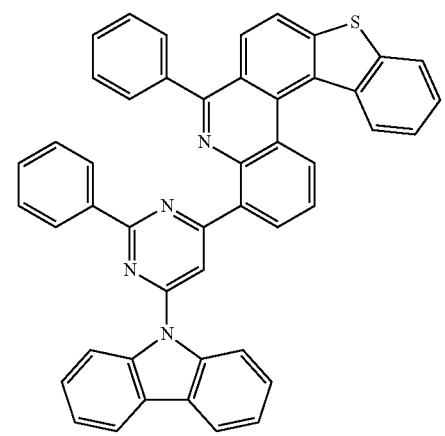
523
524
525
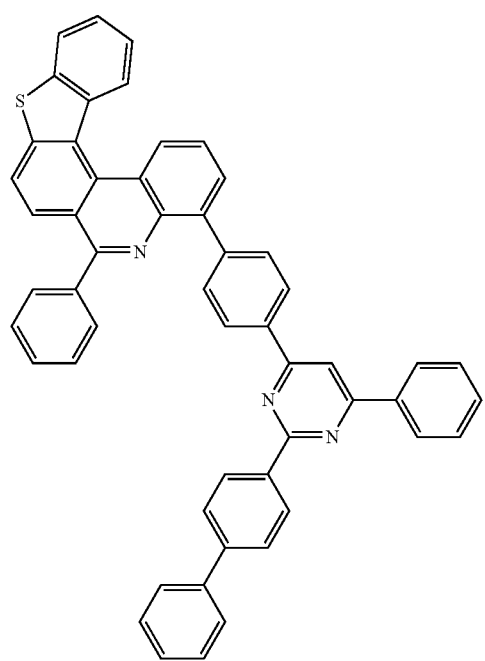
526
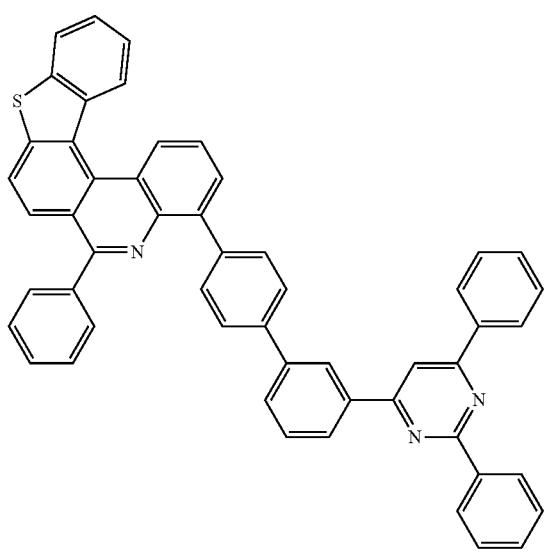 [SMILES: c1ccc(-c2cc(-c3cccc(-c4ccc(-c5cccc6c5nc(-c5ccccc5)c5ccc7sc8ccccc8c7c56)cc4)c3)nc(-c3ccccc3)n2)cc1]

-continued
527
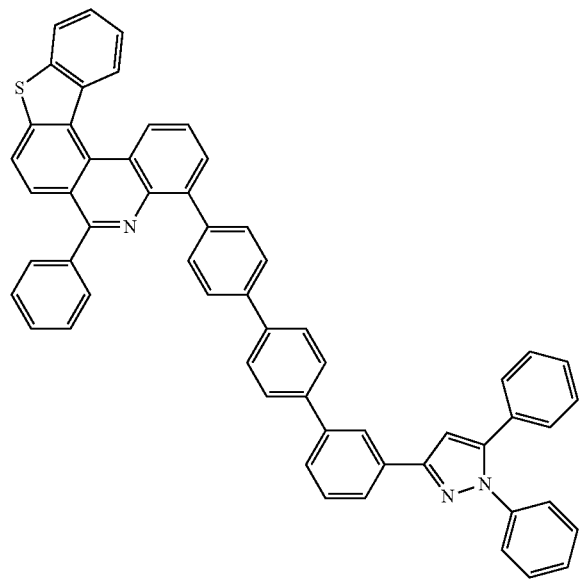
528
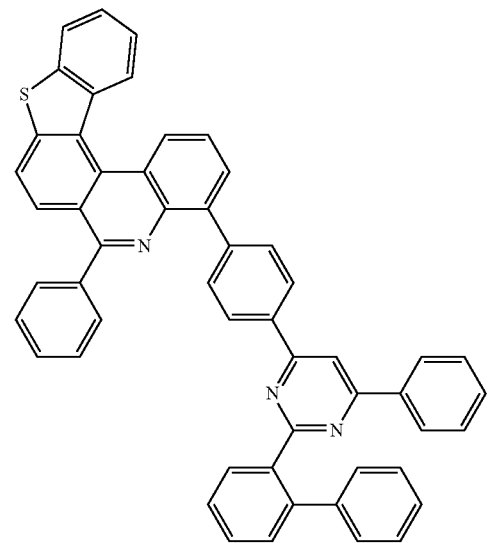
529
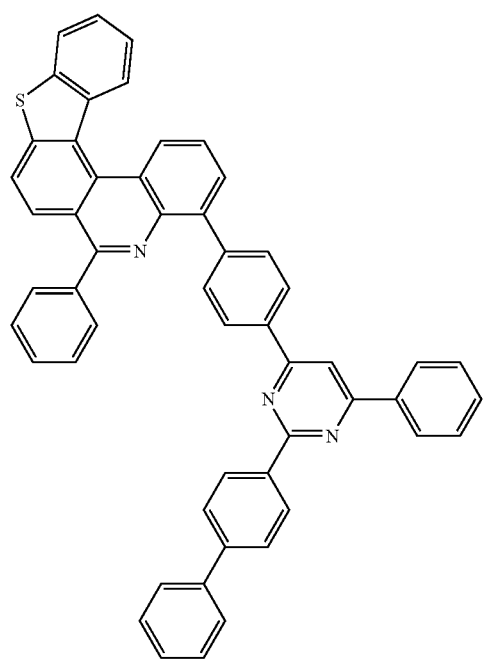
530
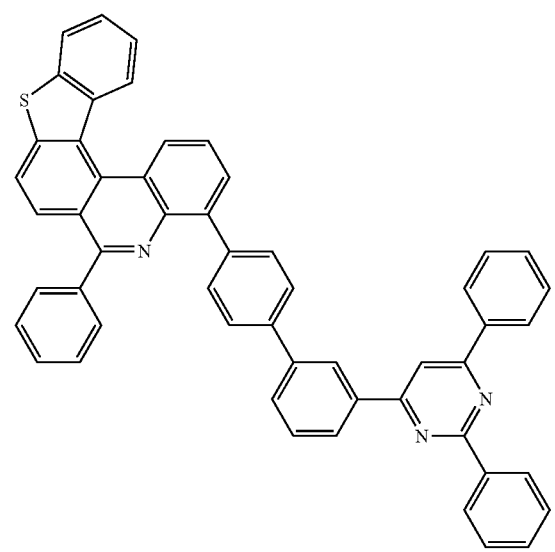 [SMILES: c1ccc(-c2cc(-c3cccc(-c4ccc(-c5cccc6c5nc(-c5ccccc5)c5ccc7sc8ccccc8c7c56)cc4)c3)nc(-c3ccccc3)n2)cc1]

-continued
531
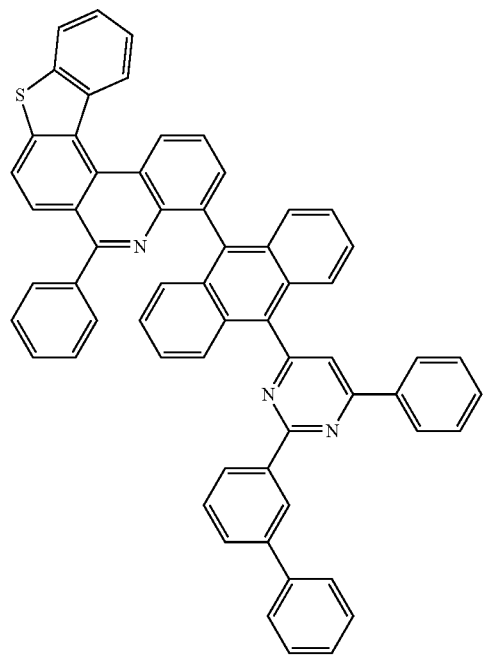
532
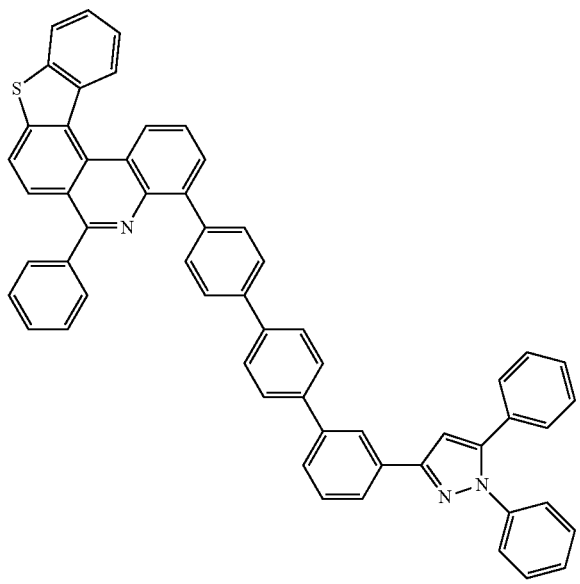
533
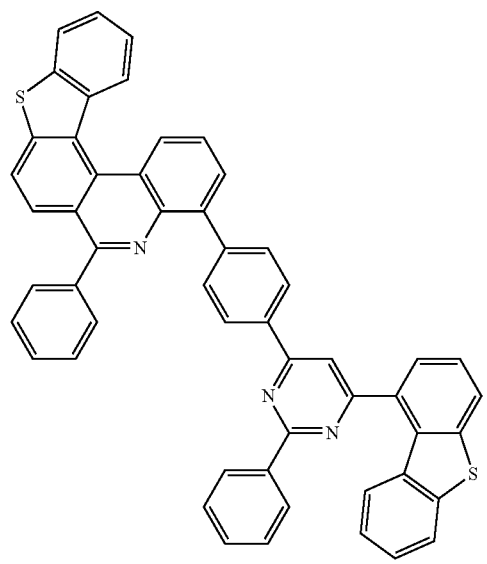
534
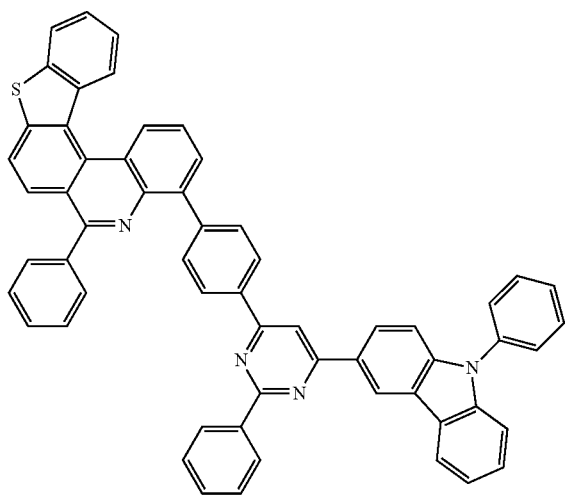 [SMILES: c1ccc(-c2nc(-c3ccc(-c4cccc5c4nc(-c4ccccc4)c4ccc6sc7ccccc7c6c45)cc3)cc(-c3ccc4c(c3)c3ccccc3n4-c3ccccc3)n2)cc1]

-continued
535
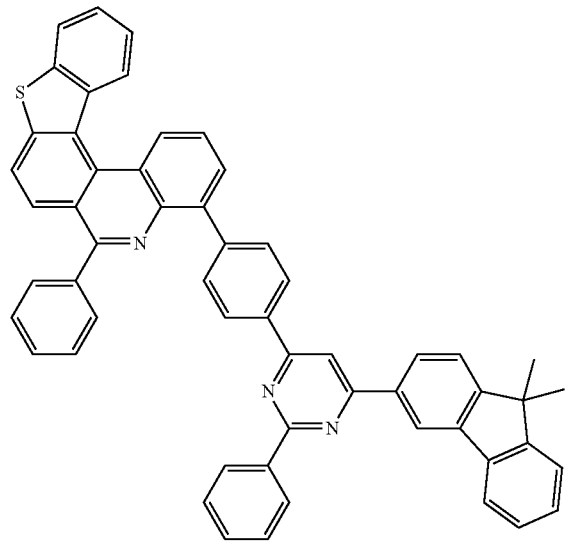
536
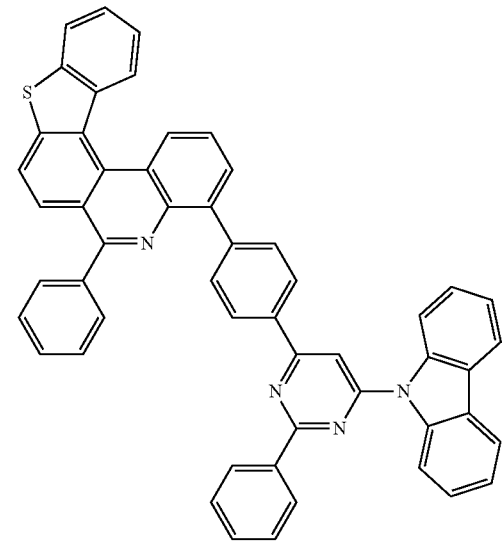
537
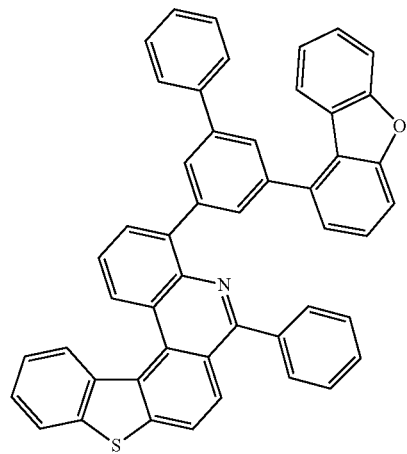
538
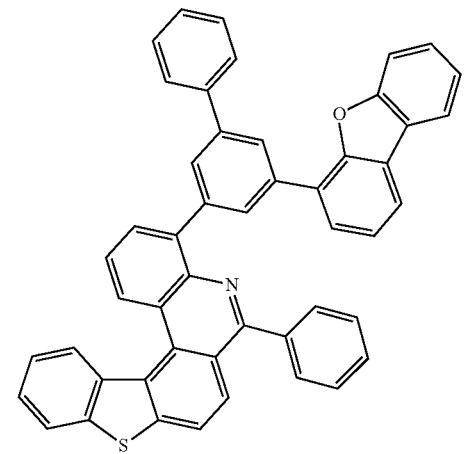
539
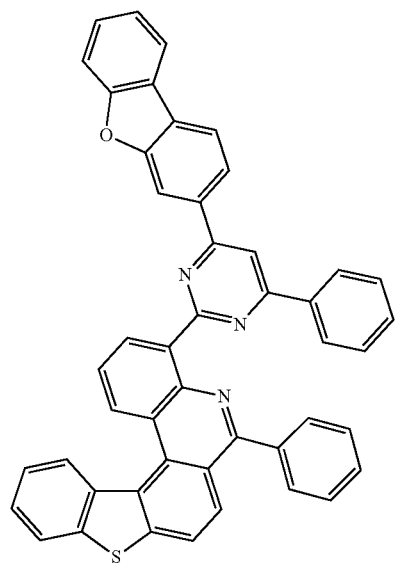
540
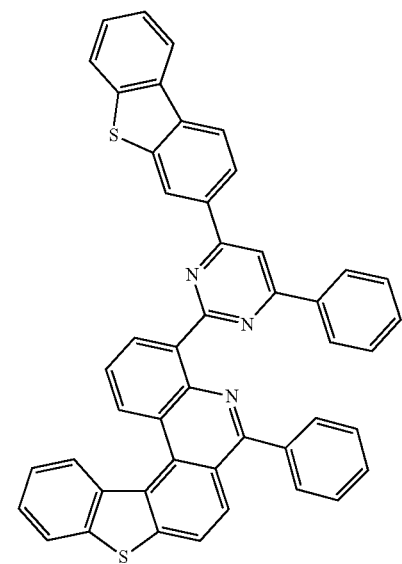

-continued
541
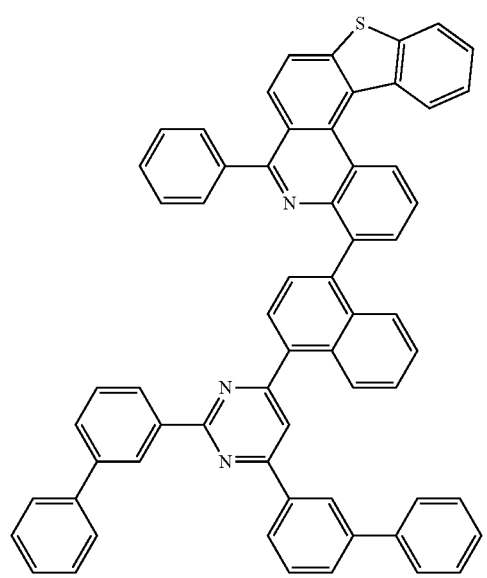
542
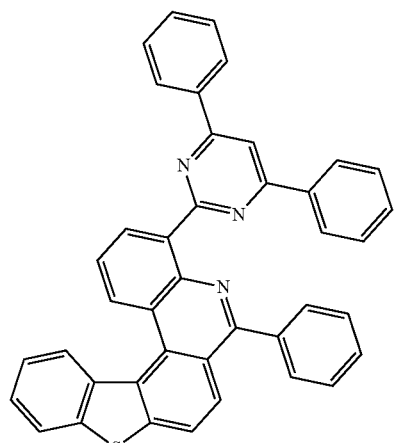
543
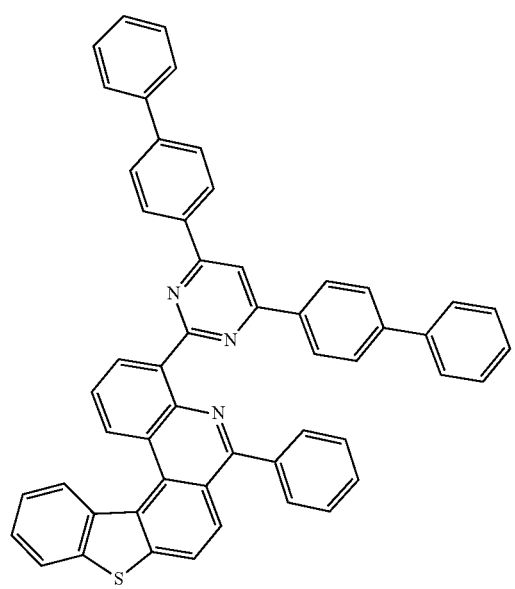
544
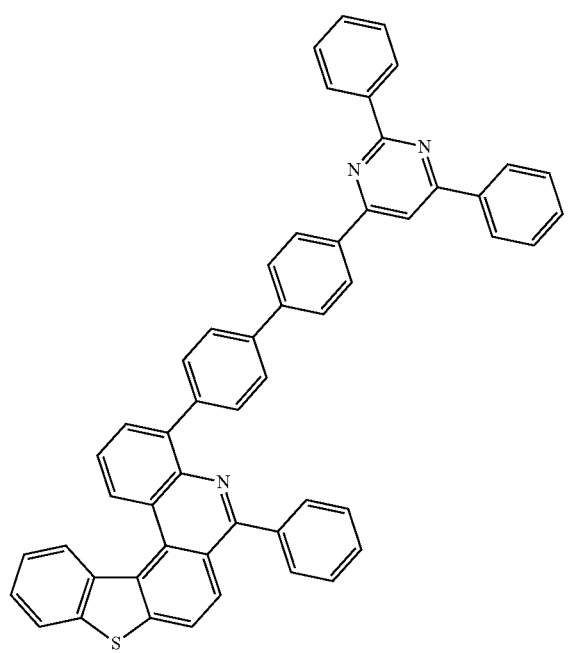

715 716
-continued
545 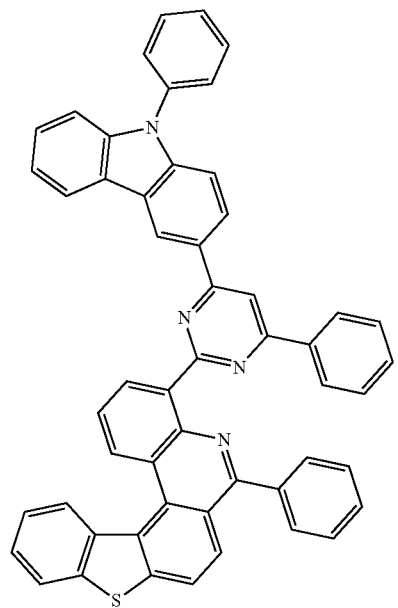 546 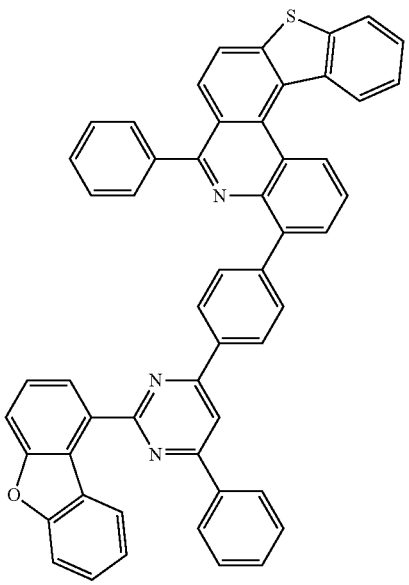 [SMILES: c1ccc(-c2cc(-c3ccc(-c4cccc5c4nc(-c4ccccc4)c4ccc6sc7ccccc7c6c45)cc3)nc(-c3cccc4oc5ccccc5c34)n2)cc1]
547 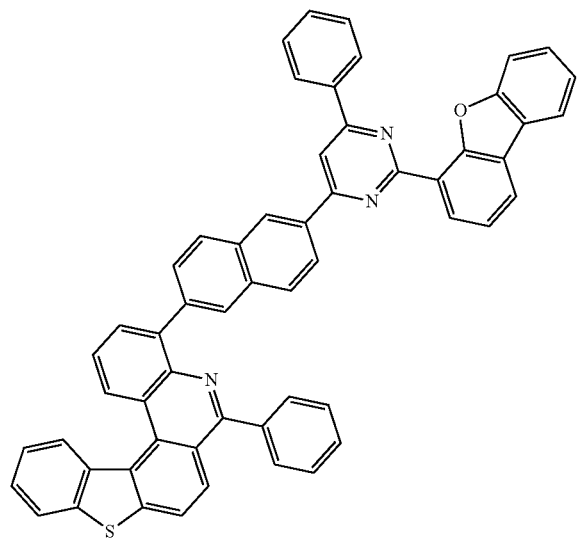 548 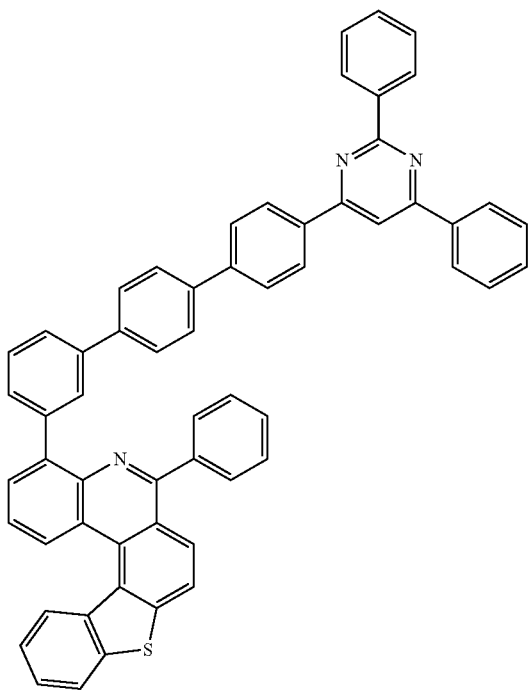

-continued
549
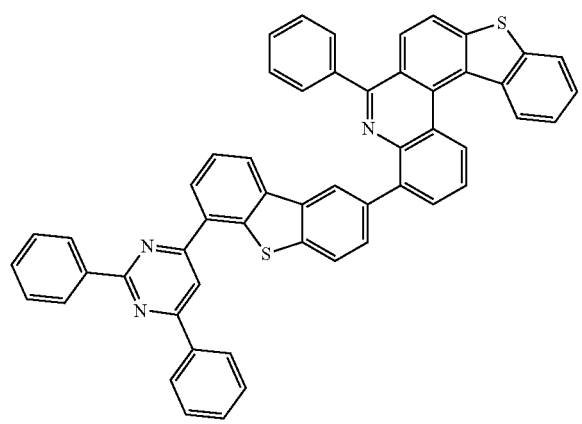
550
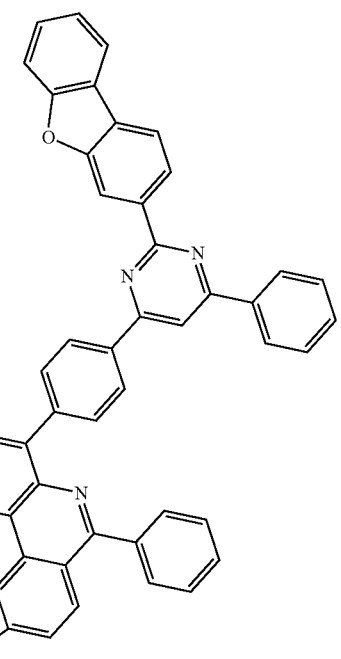
551
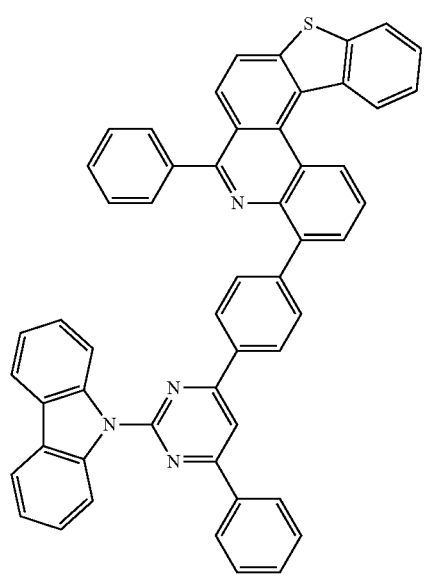

-continued
552
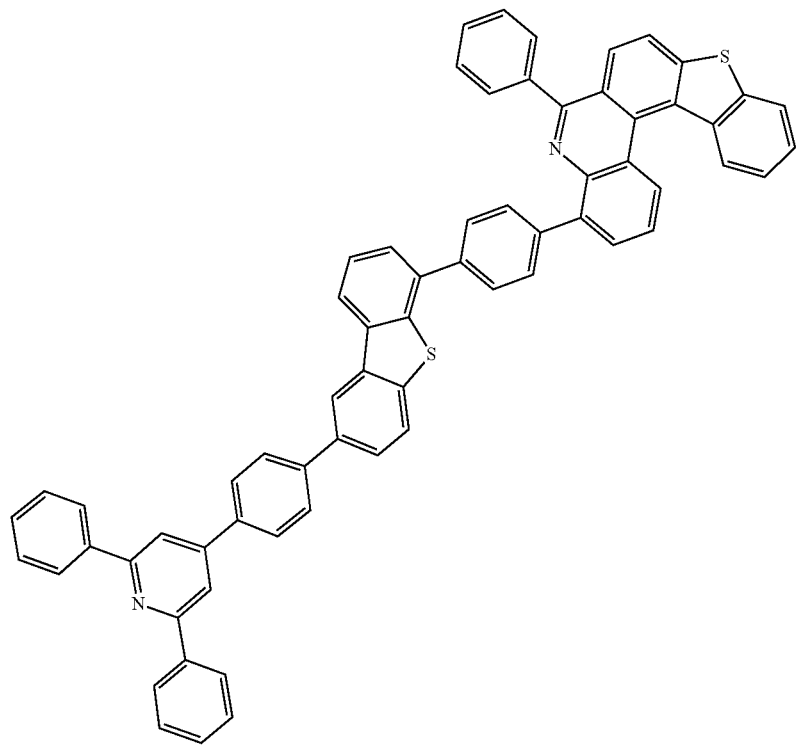
553
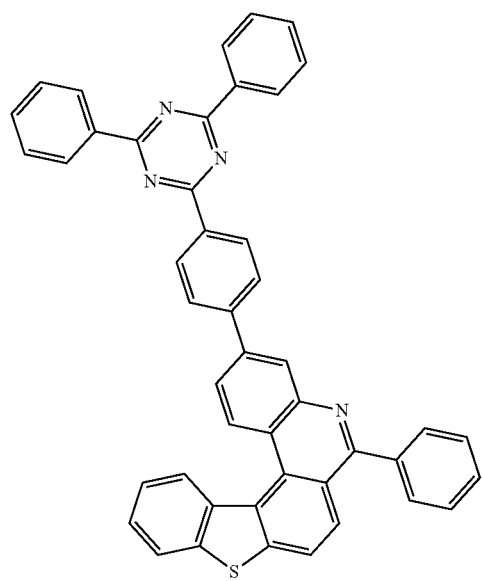
554

-continued
555
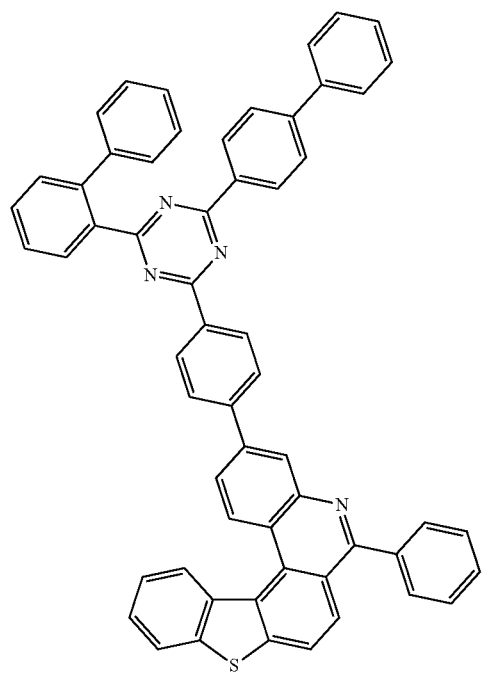
556
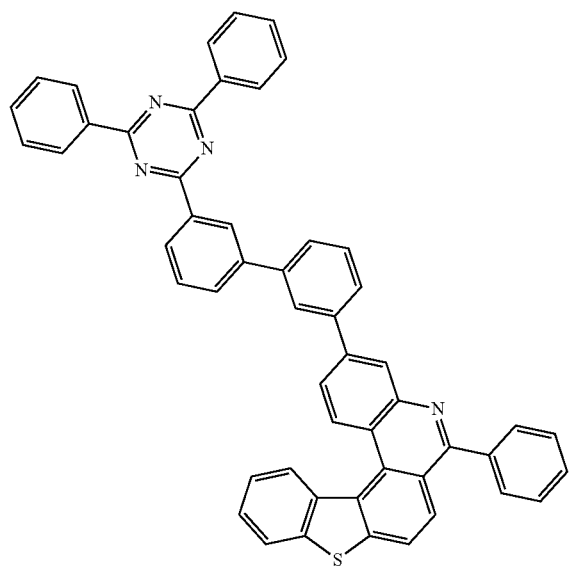
557
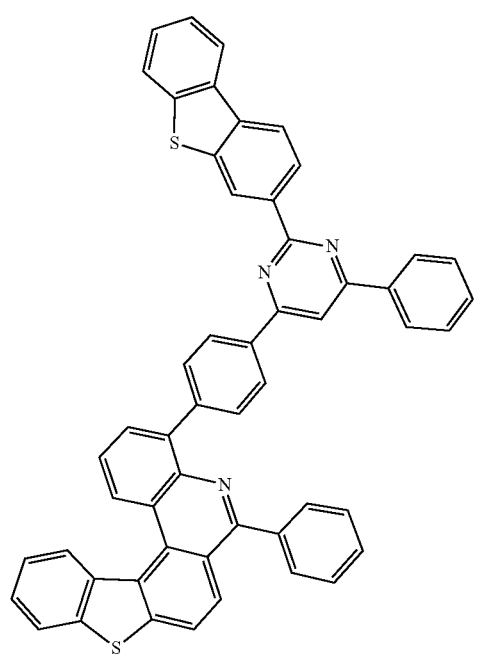
558
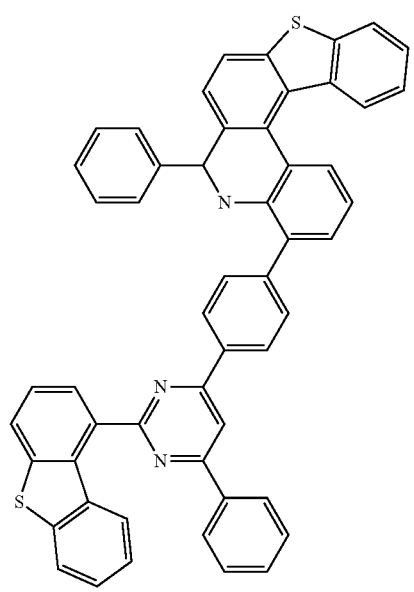 [SMILES: c1ccc(-c2cc(-c3ccc(-c4cccc5c4nc(-c4ccccc4)c4ccc6sc7ccccc7c6c45)cc3)nc(-c3cccc4sc5ccccc5c34)n2)cc1]

-continued
559 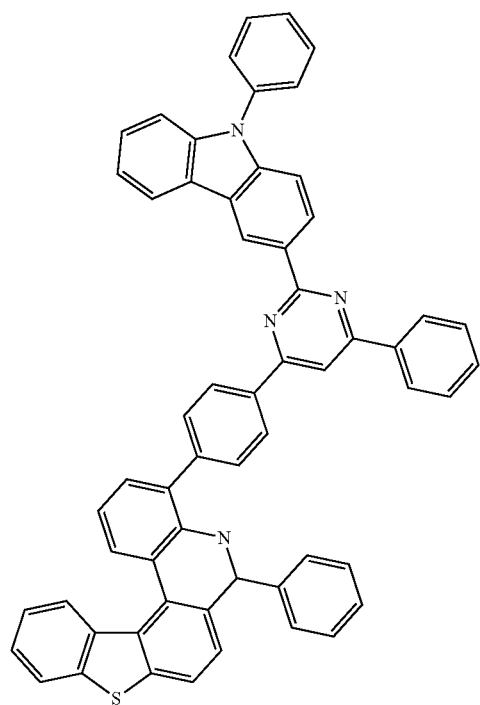
560 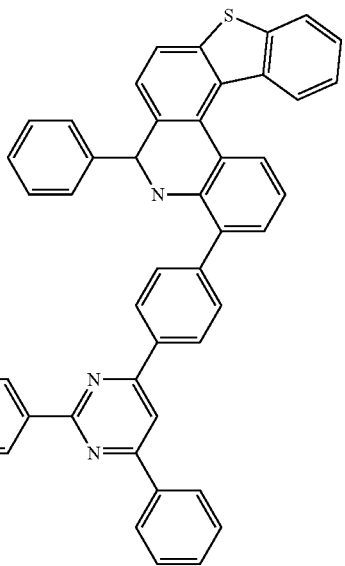
561 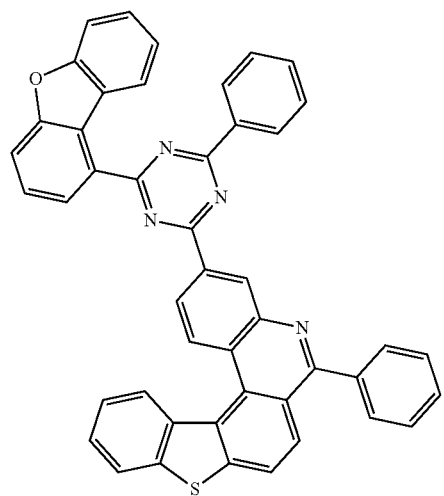
562 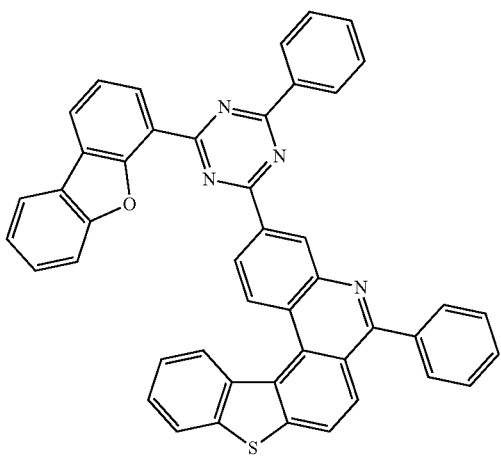 [SMILES: c1ccc(-c2nc(-c3ccc4c(c3)nc(-c3ccccc3)c3ccc5sc6ccccc6c5c34)nc(-c3cccc4c3oc3ccccc34)n2)cc1]

-continued
725
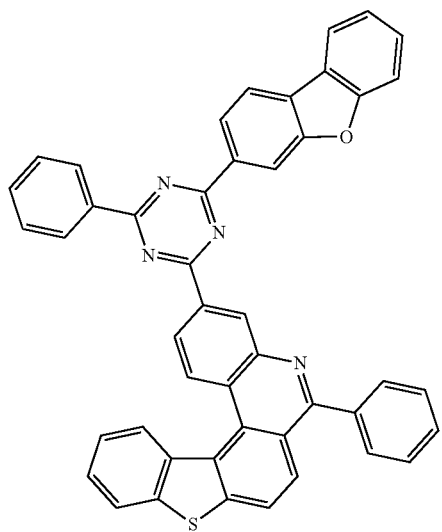
563
726
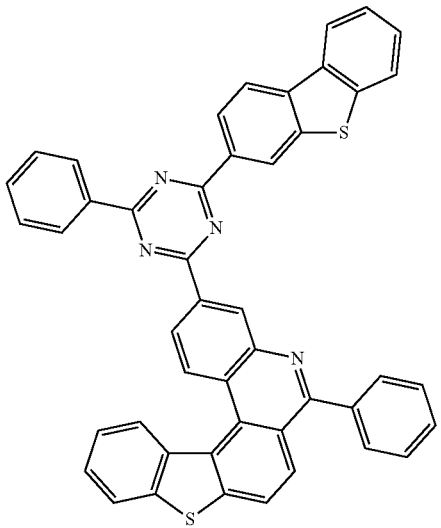
564
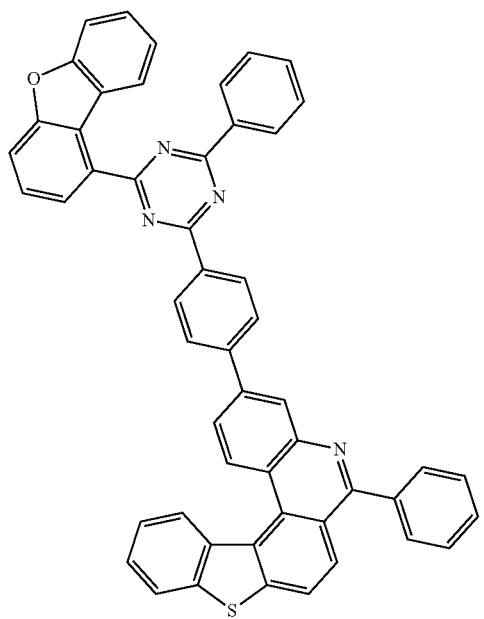
565
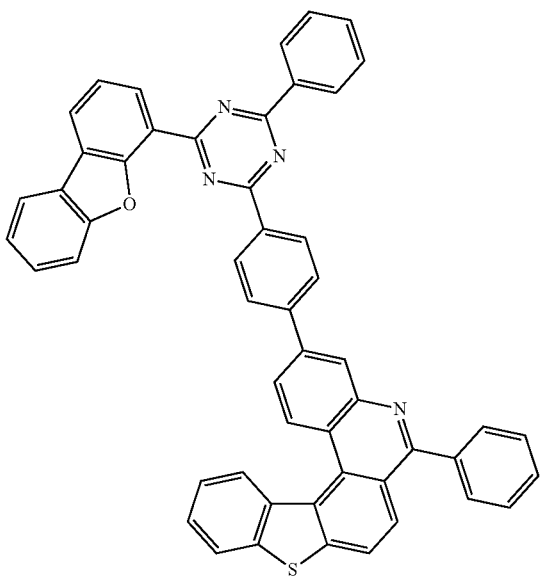
566

-continued
567
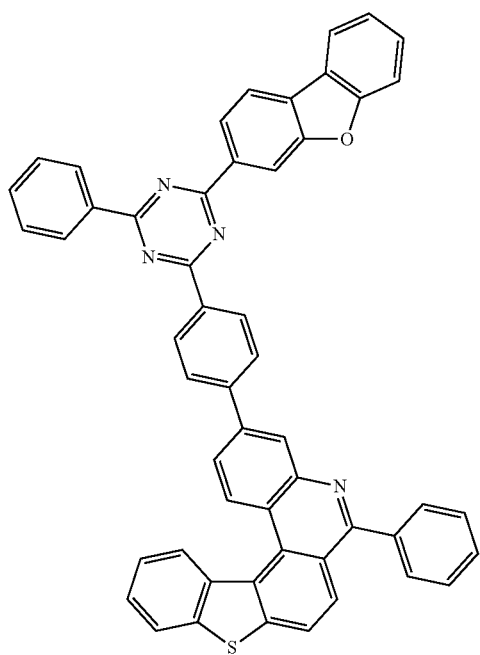
568
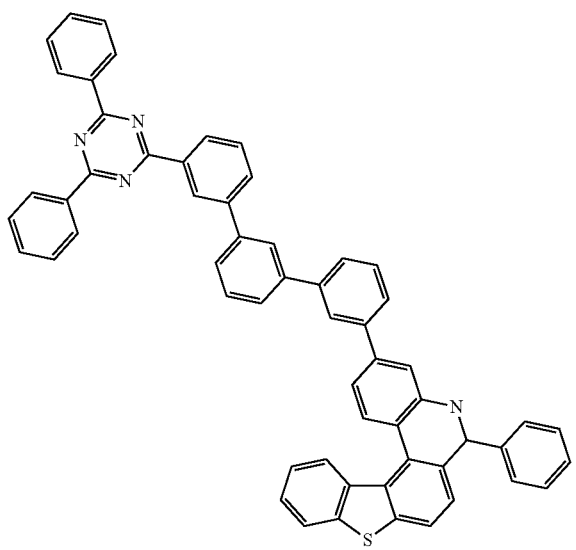
569
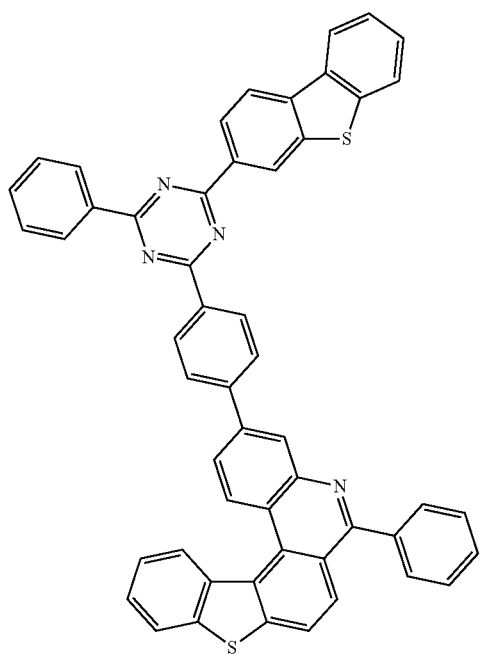
570
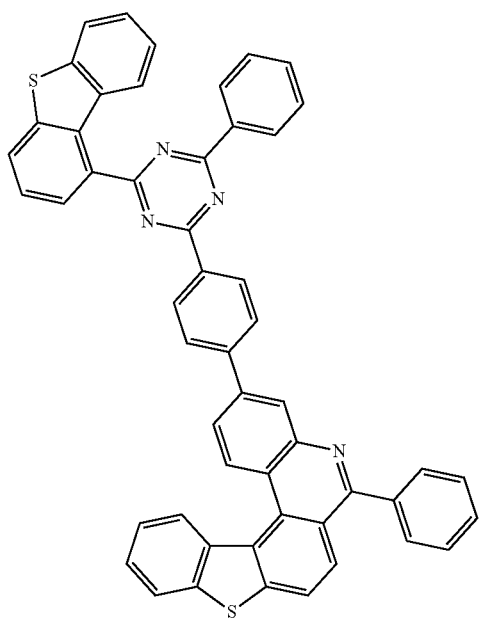 [SMILES: c1ccc(-c2nc(-c3ccc(-c4ccc5c(c4)nc(-c4ccccc4)c4ccc6sc7ccccc7c6c45)cc3)nc(-c3cccc4sc5ccccc5c34)n2)cc1]

-continued
729
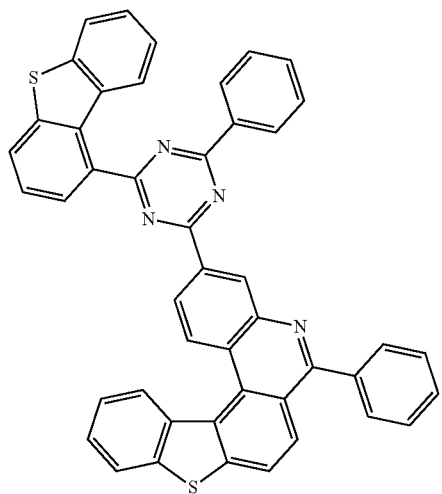
730
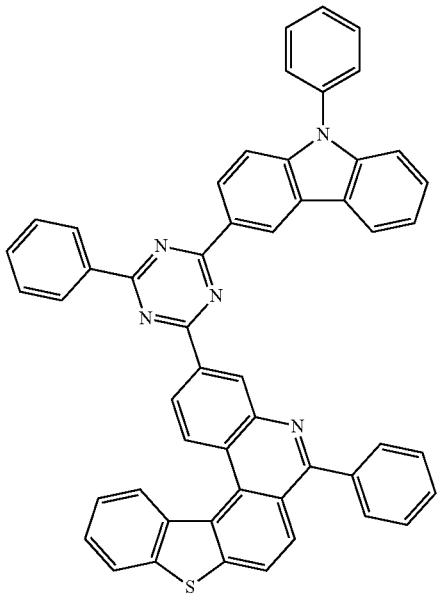
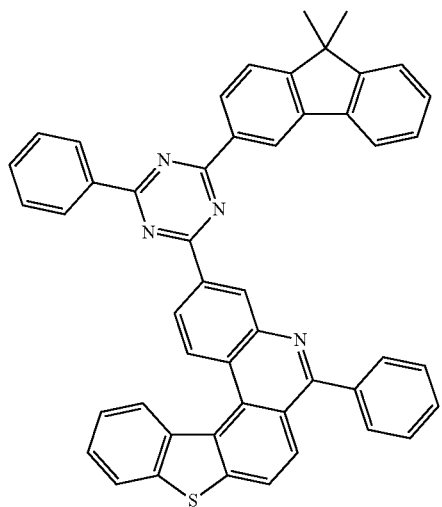
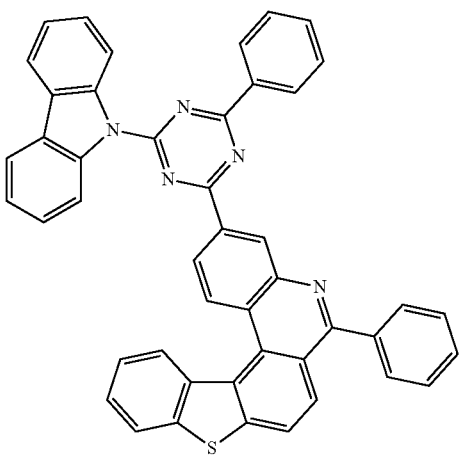 [SMILES: c1ccc(-c2nc(-c3ccc4c(c3)nc(-c3ccccc3)c3ccc5sc6ccccc6c5c34)nc(-n3c4ccccc4c4ccccc43)n2)cc1]

731
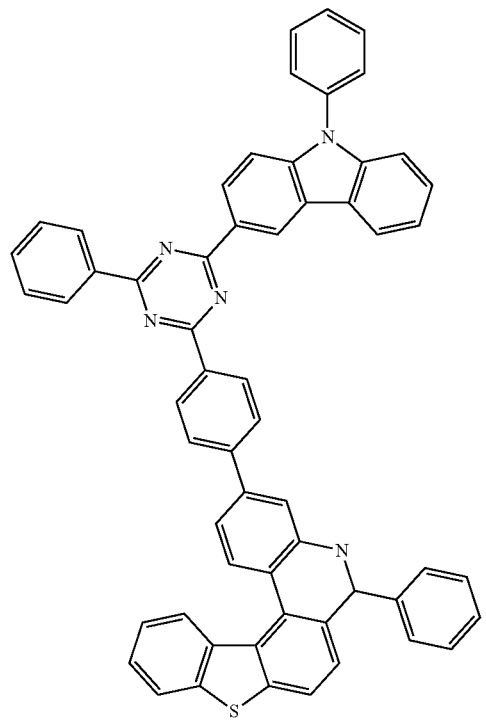
732
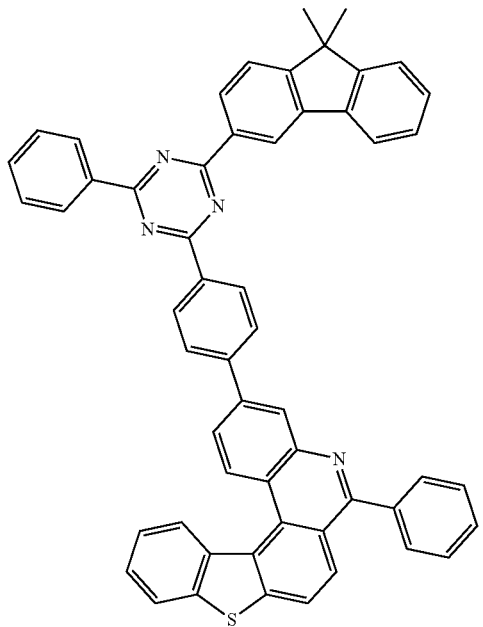
-continued
575
576
577
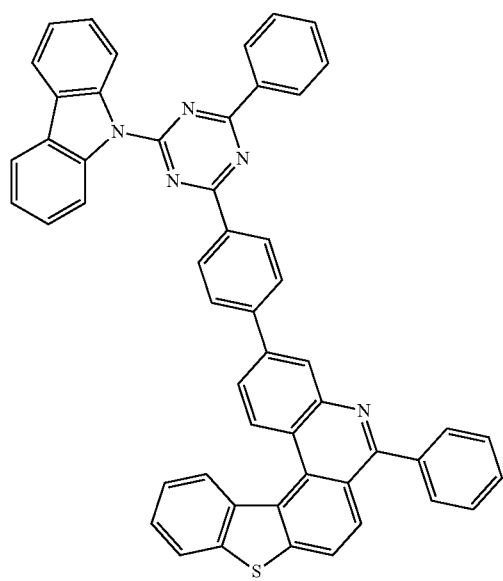
578
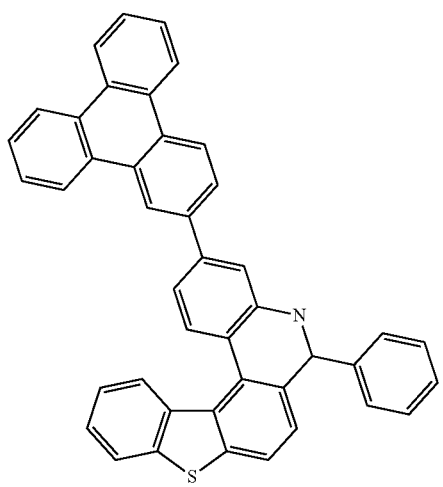 [SMILES: c1ccc(-c2nc3cc(-c4ccc5c6ccccc6c6ccccc6c5c4)ccc3c3c2ccc2sc4ccccc4c23)cc1]

-continued
579
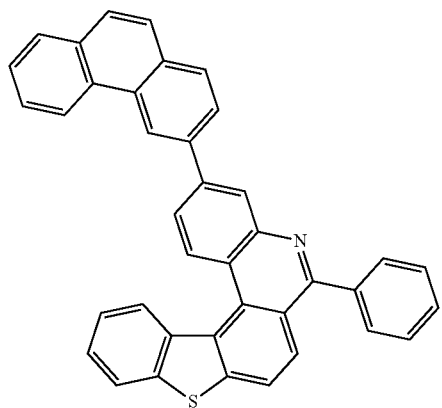
580
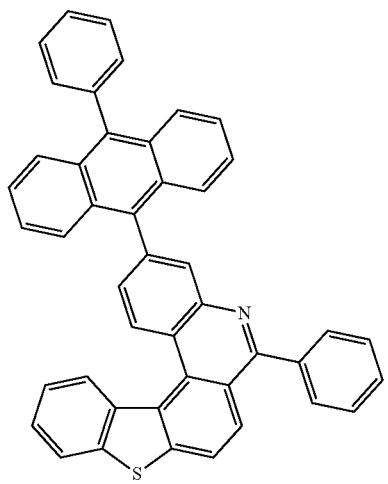
581
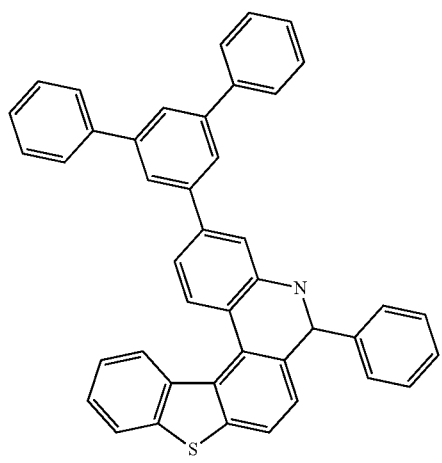
582
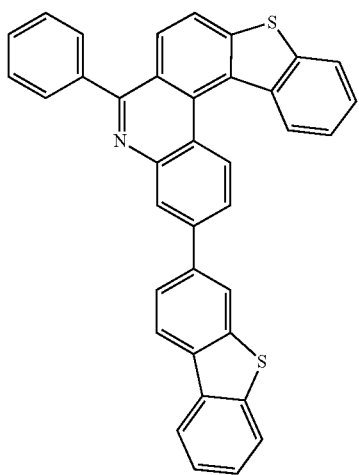 [SMILES: c1ccc(-c2nc3cc(-c4ccc5c(c4)sc4ccccc45)ccc3c3c2ccc2sc4ccccc4c23)cc1]
583
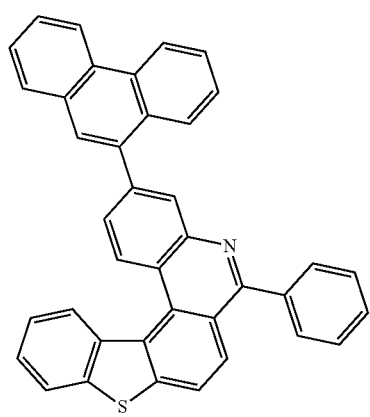
584
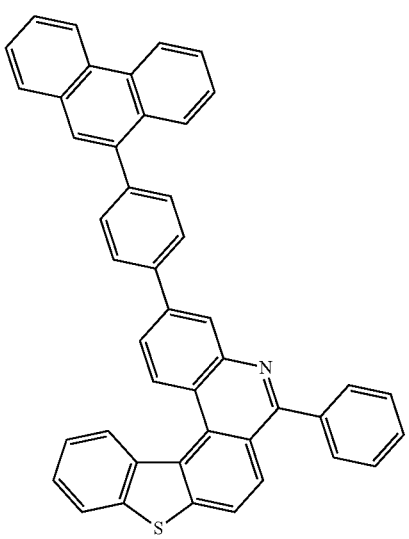

-continued
585
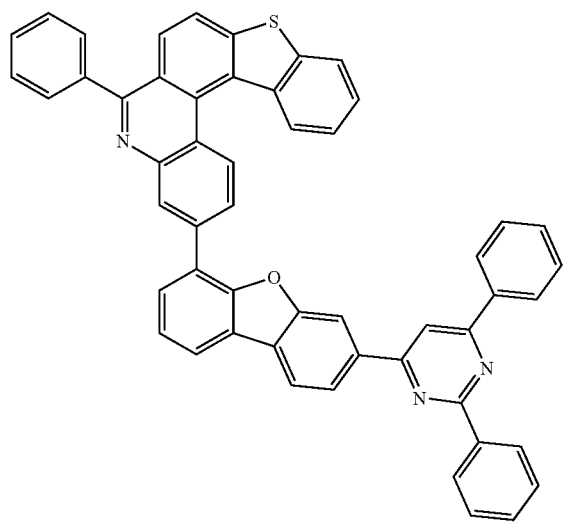
586
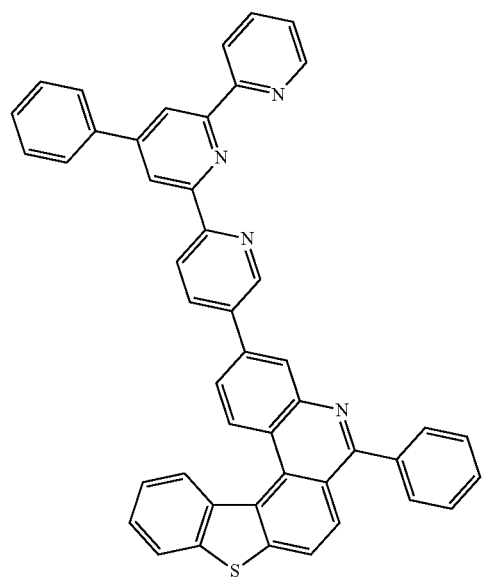 [SMILES: c1ccc(-c2cc(-c3ccccn3)nc(-c3ccc(-c4ccc5c(c4)nc(-c4ccccc4)c4ccc6sc7ccccc7c6c45)cn3)c2)cc1]
587
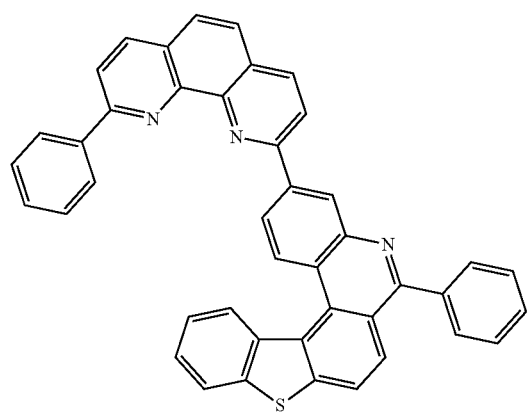
588
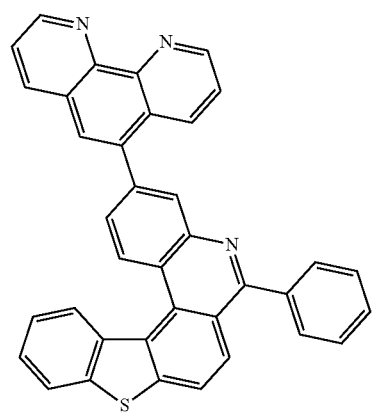
589
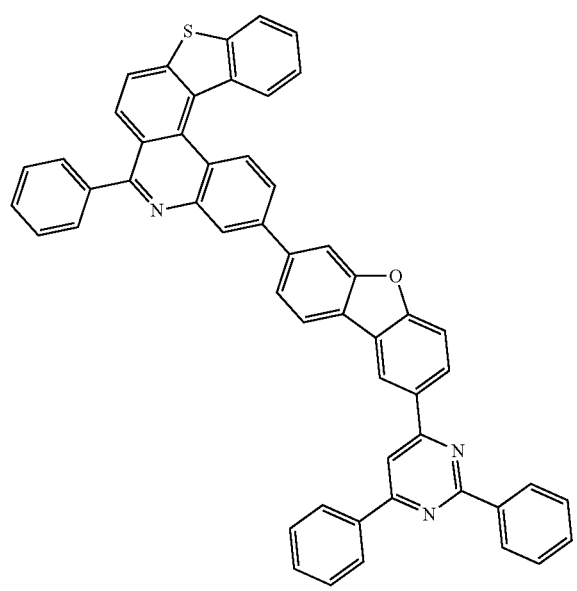
590
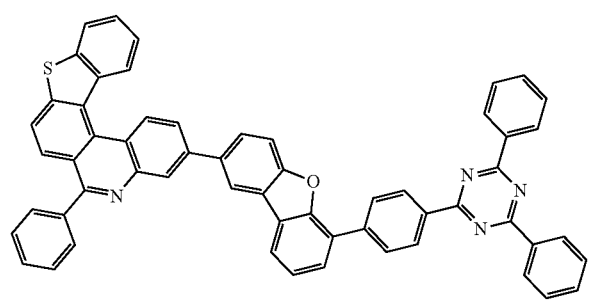

-continued
591 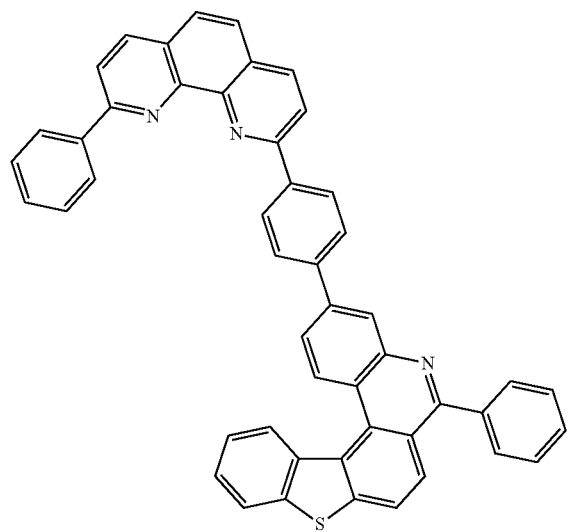
592 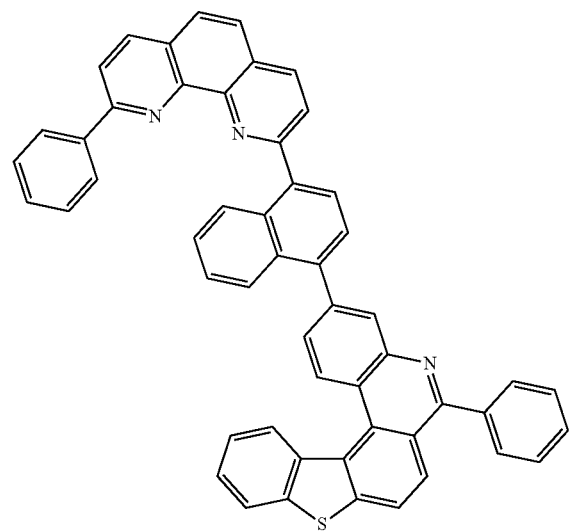
593 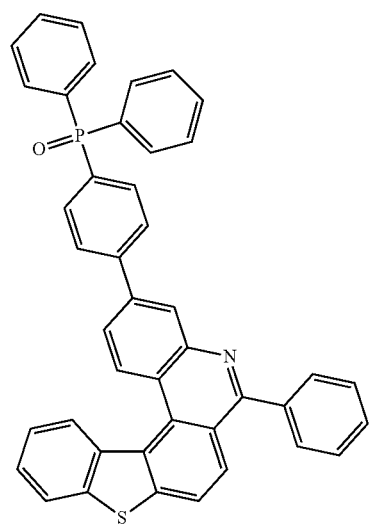
594 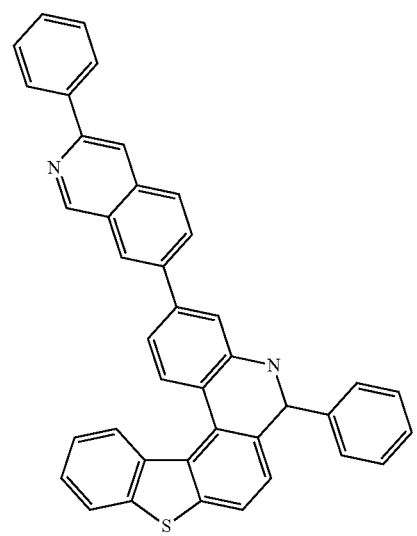 [SMILES: c1ccc(-c2cc3ccc(-c4ccc5c(c4)nc(-c4ccccc4)c4ccc6sc7ccccc7c6c45)cc3cn2)cc1]
595 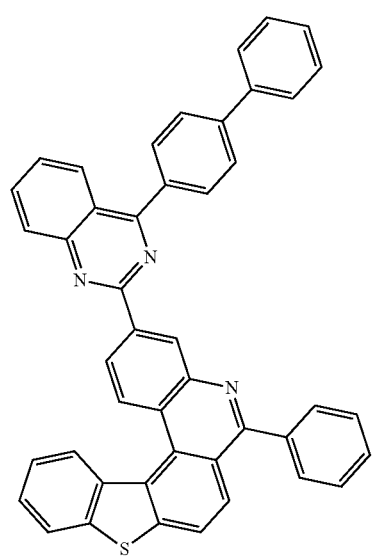
596 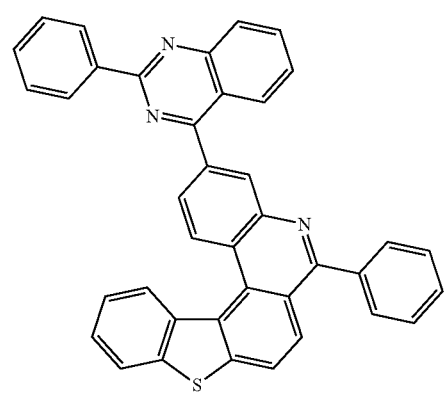

-continued
597
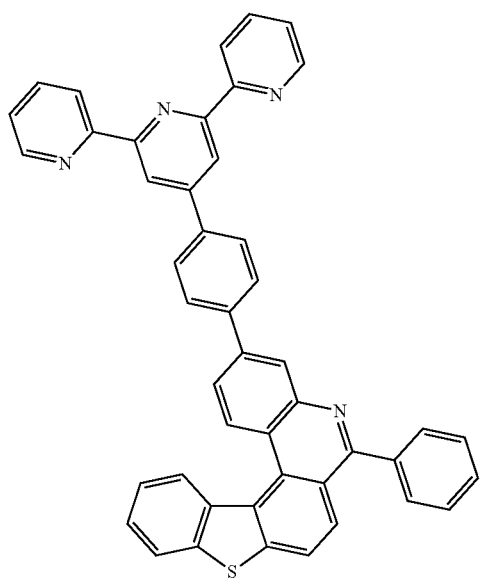
598
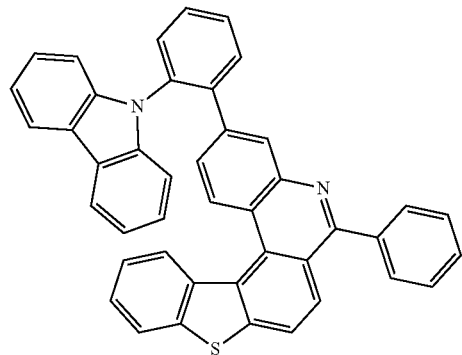
599
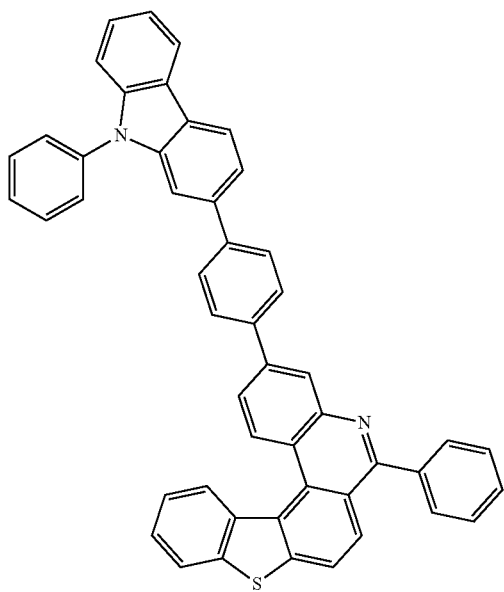
600
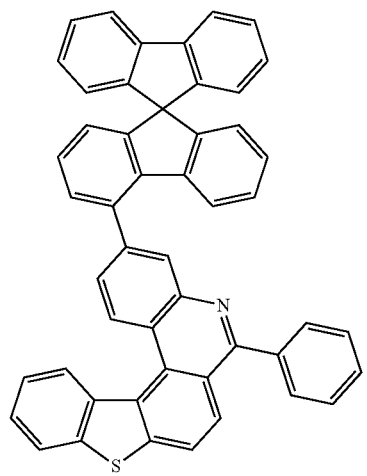

-continued
601 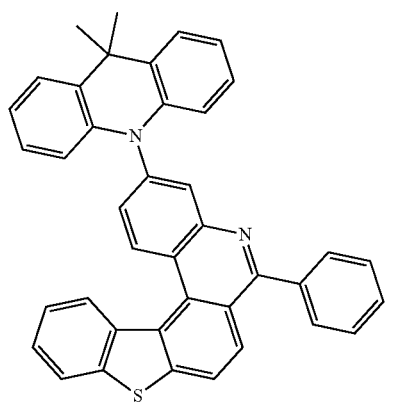
602 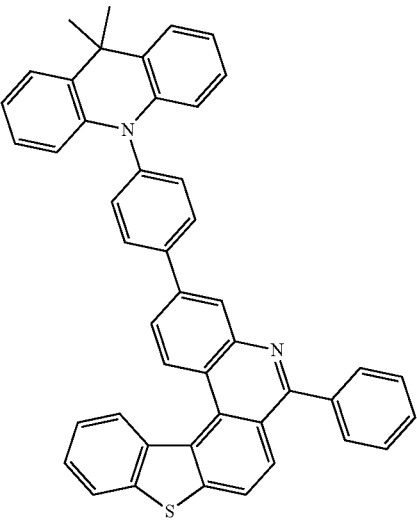 [SMILES: CC1(C)c2ccccc2N(c2ccc(-c3ccc4c(c3)nc(-c3ccccc3)c3ccc5sc6ccccc6c5c34)cc2)c2ccccc21]
603 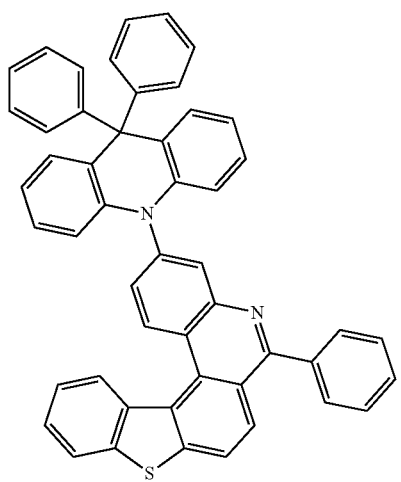
604 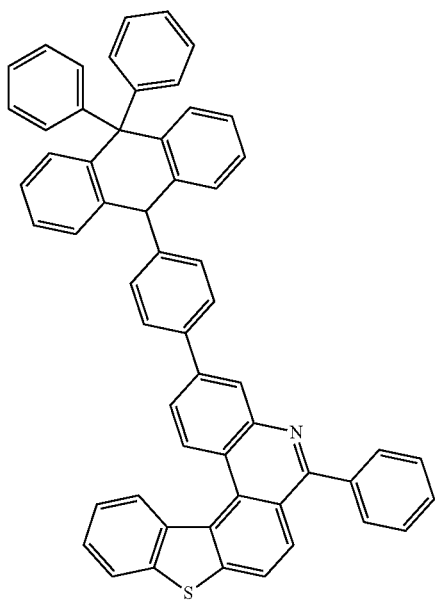
605 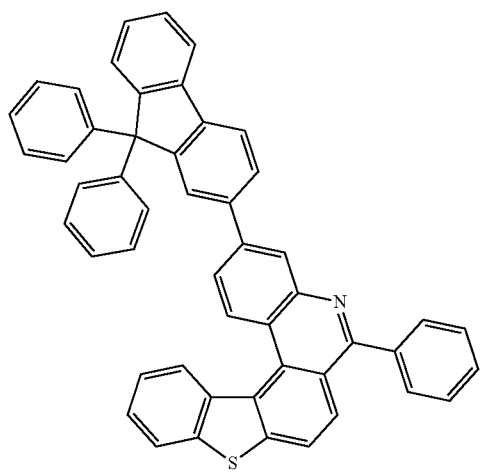
606 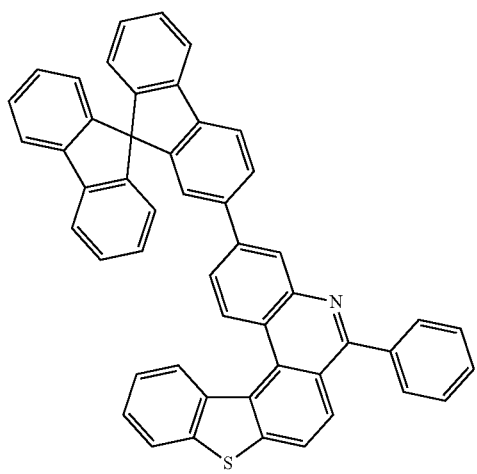 [SMILES: c1ccc(-c2nc3cc(-c4ccc5c(c4)C4(c6ccccc6-c6ccccc64)c4ccccc4-5)ccc3c3c2ccc2sc4ccccc4c23)cc1]

743
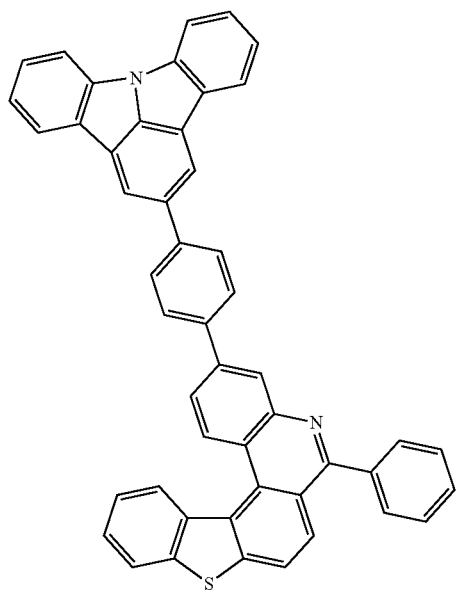
744
-continued
607
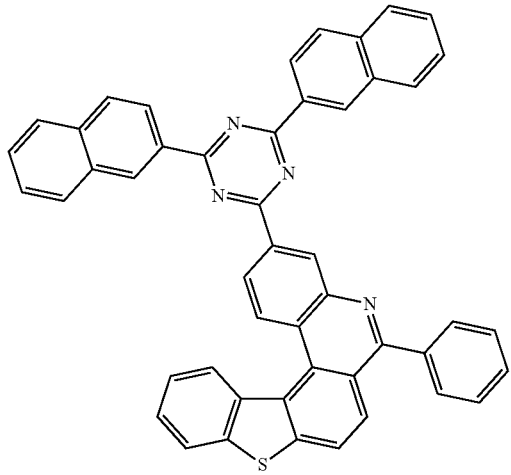
608
609
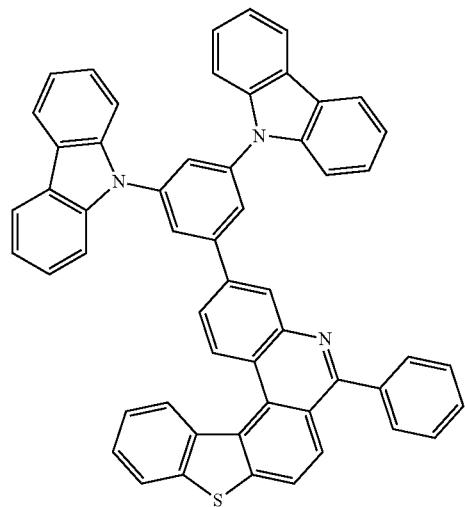
610
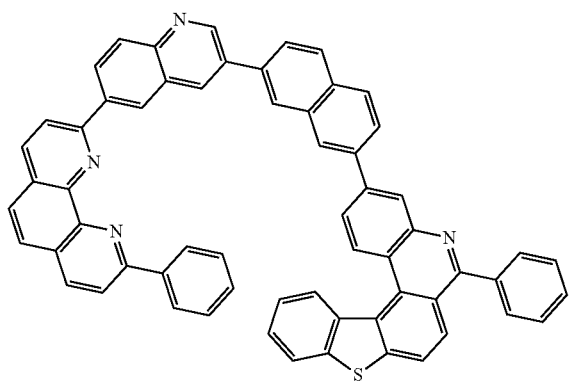 [SMILES: c1ccc(-c2ccc3ccc4ccc(-c5ccc6ncc(-c7ccc8ccc(-c9ccc%10c(c9)nc(-c9ccccc9)c9ccc%11sc%12ccccc%12c%11c9%10)cc8c7)cc6c5)nc4c3n2)cc1]

745 746
-continued
611
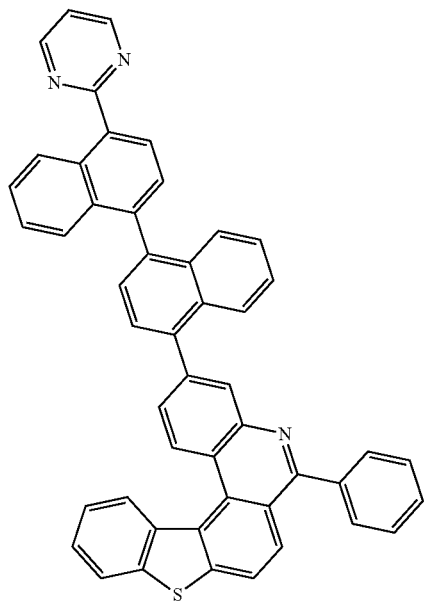
612
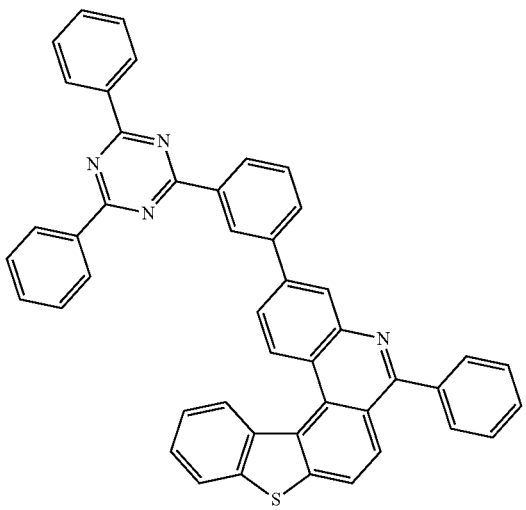
613
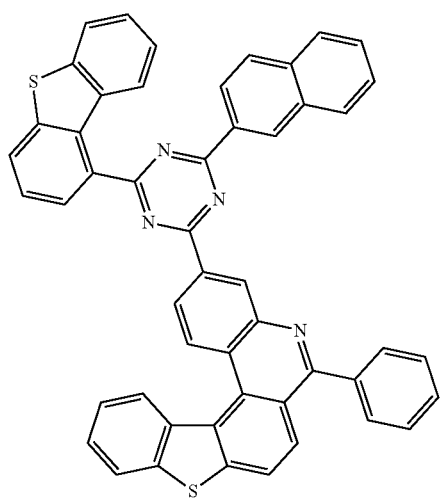
614
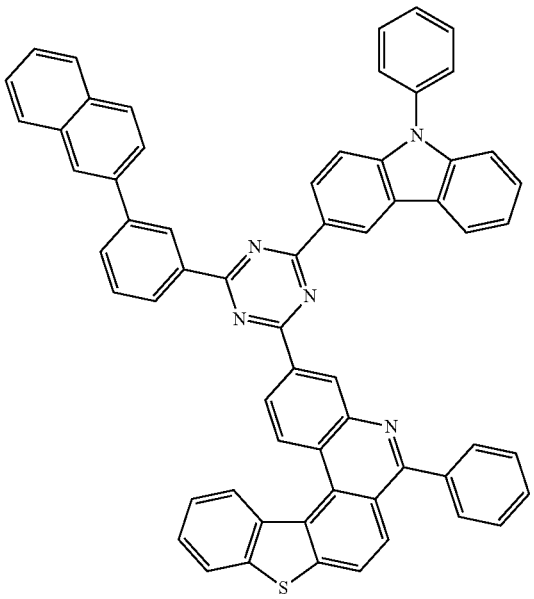 [SMILES: c1ccc(-c2nc3cc(-c4nc(-c5cccc(-c6ccc7ccccc7c6)c5)nc(-c5ccc6c(c5)c5ccccc5n6-c5ccccc5)n4)ccc3c3c2ccc2sc4ccccc4c23)cc1]

-continued
615
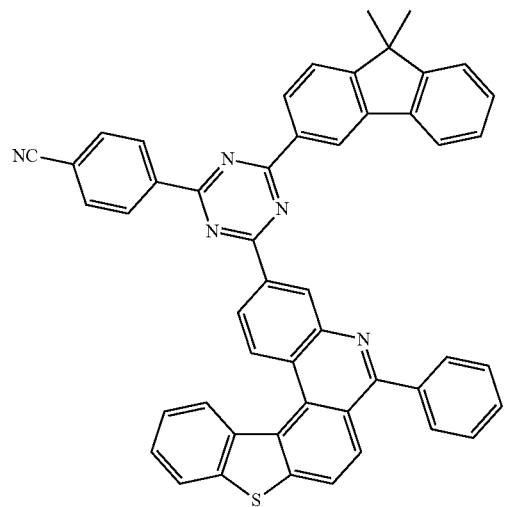
616
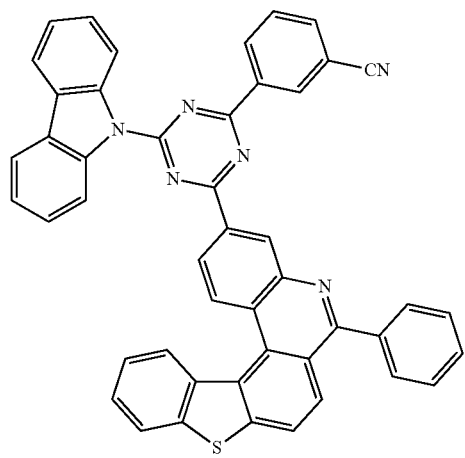
617
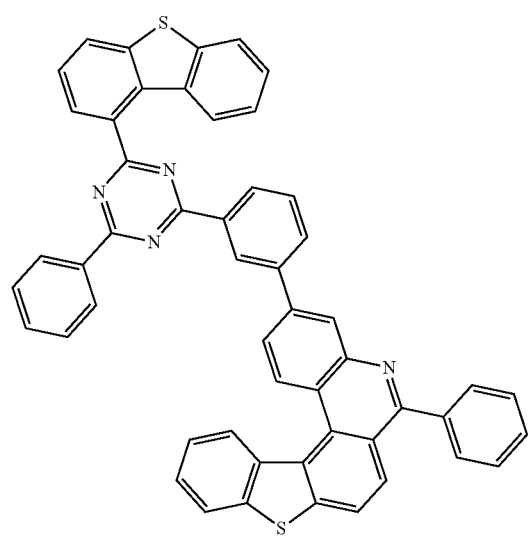
618
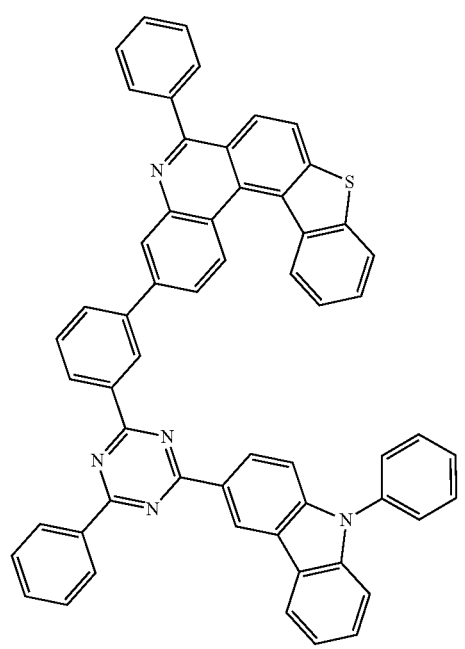

619
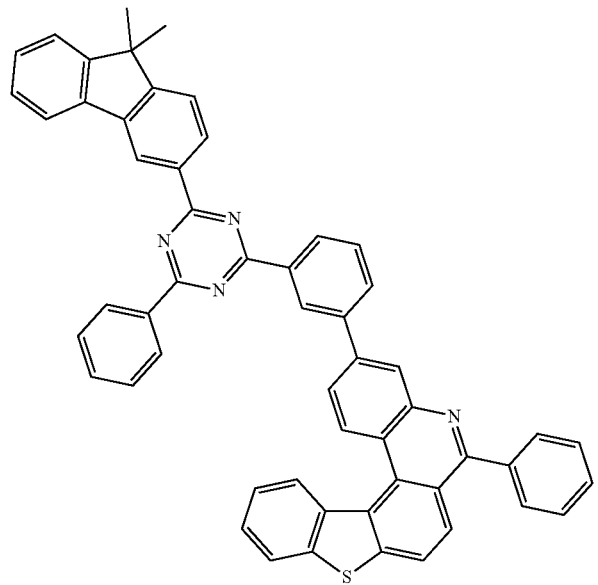
620
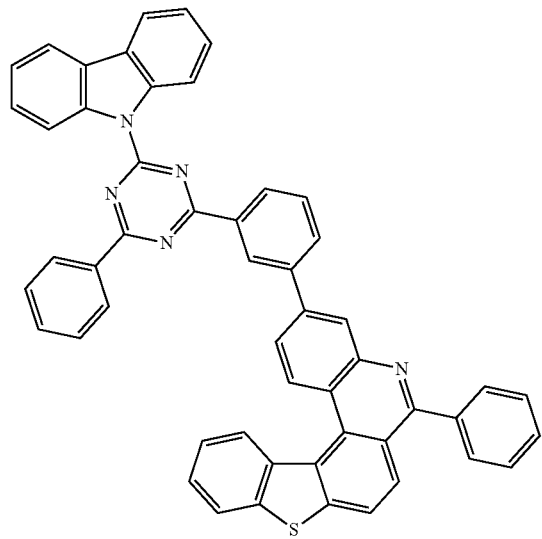
621
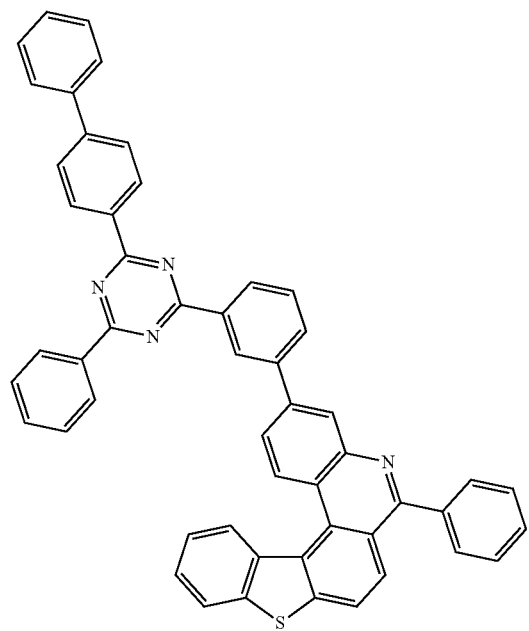
622
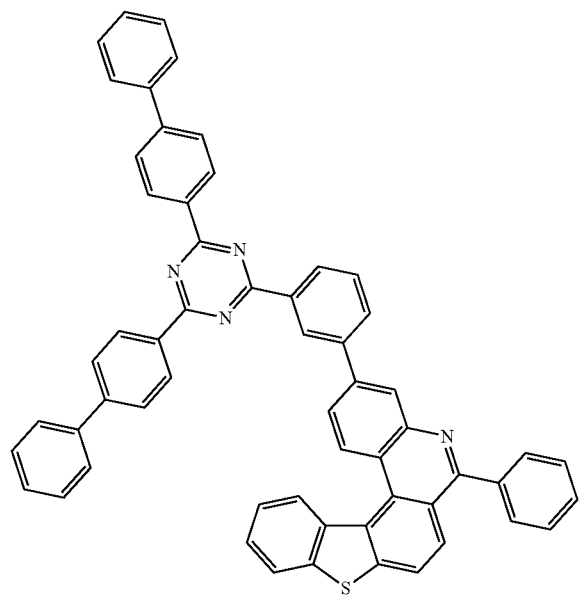 [SMILES: c1ccc(-c2ccc(-c3nc(-c4ccc(-c5ccccc5)cc4)nc(-c4cccc(-c5ccc6c(c5)nc(-c5ccccc5)c5ccc7sc8ccccc8c7c56)c4)n3)cc2)cc1]

-continued
623
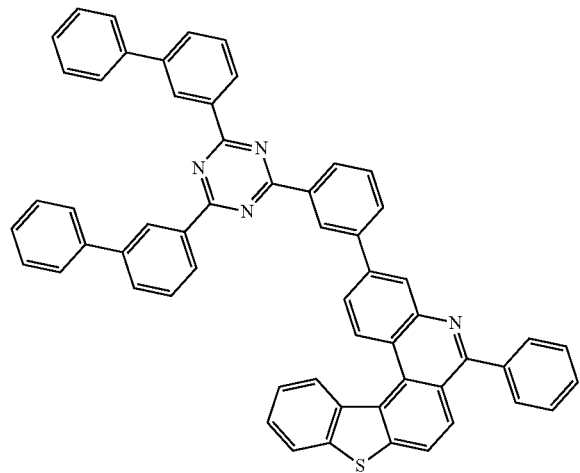
624
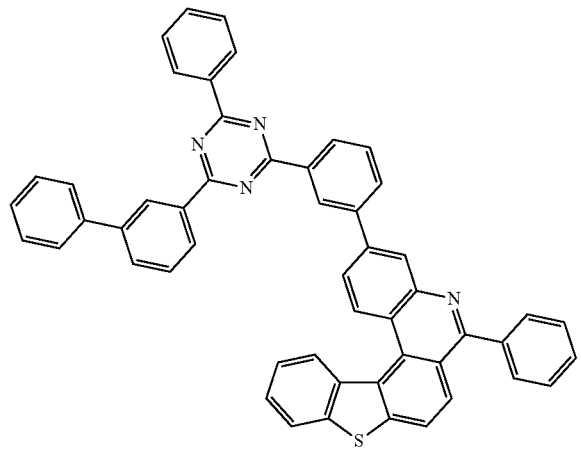
625
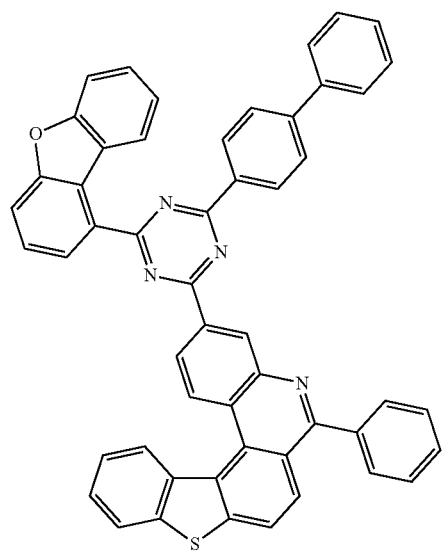
626
627
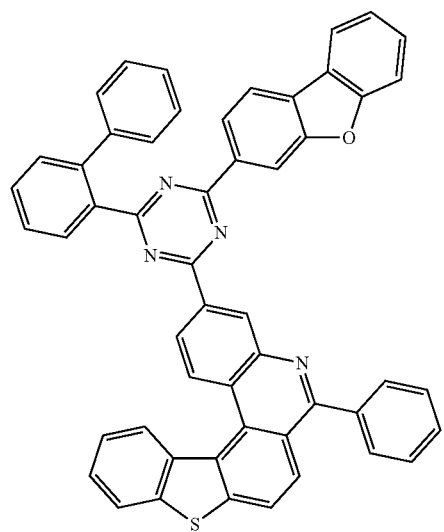
628
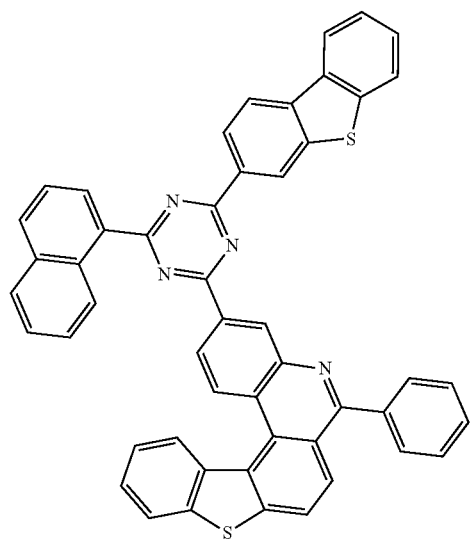

-continued
629
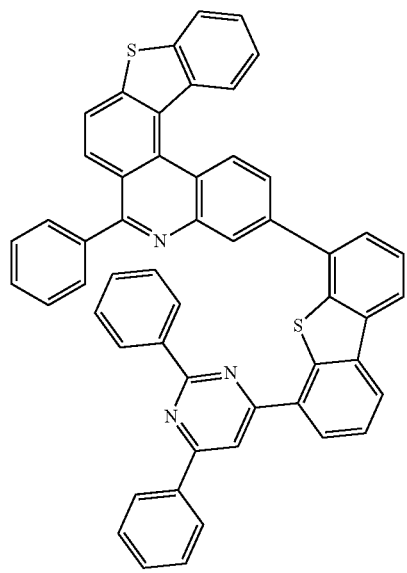
630
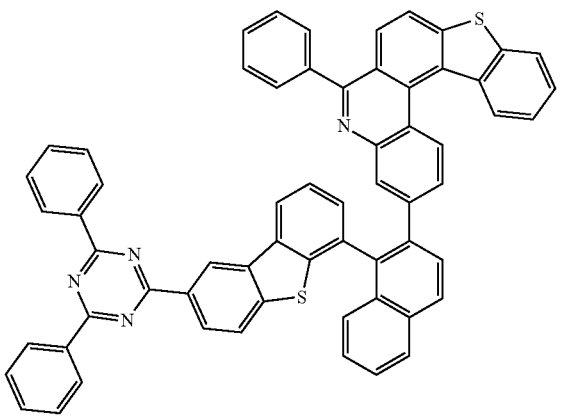 [SMILES: c1ccc(-c2nc(-c3ccccc3)nc(-c3ccc4sc5c(-c6c(-c7ccc8c(c7)nc(-c7ccccc7)c7ccc9sc%10ccccc%10c9c78)ccc7ccccc67)cccc5c4c3)n2)cc1]
631
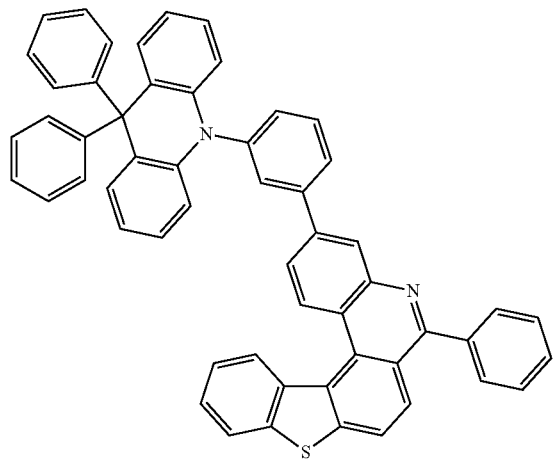
632
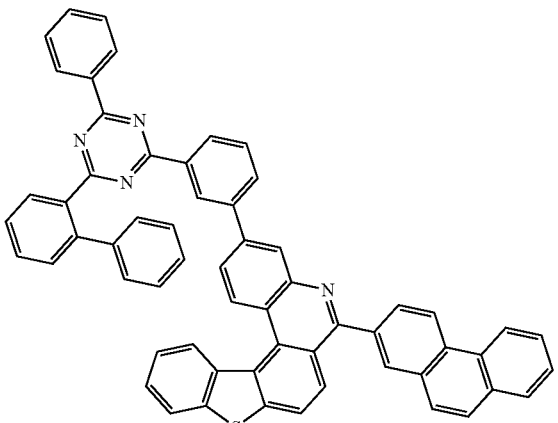
633
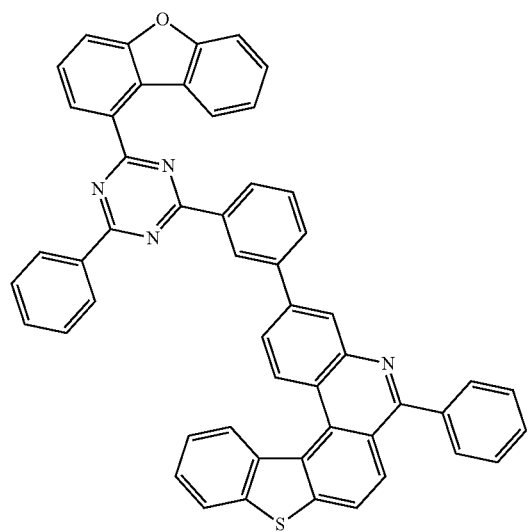
634
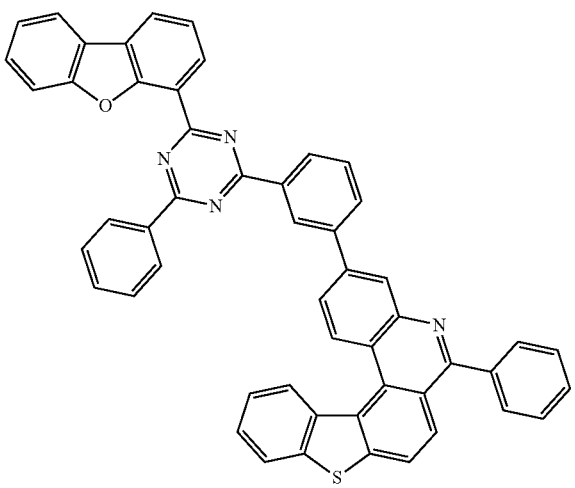 [SMILES: c1ccc(-c2nc(-c3cccc(-c4ccc5c(c4)nc(-c4ccccc4)c4ccc6sc7ccccc7c6c45)c3)nc(-c3cccc4c3oc3ccccc34)n2)cc1]

-continued
635
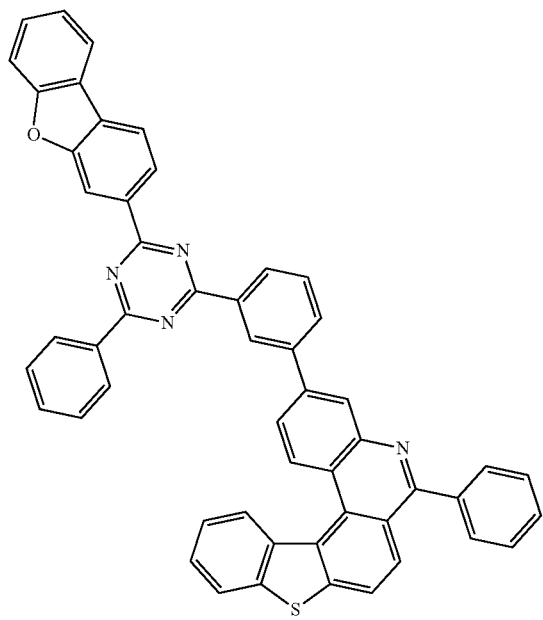
636
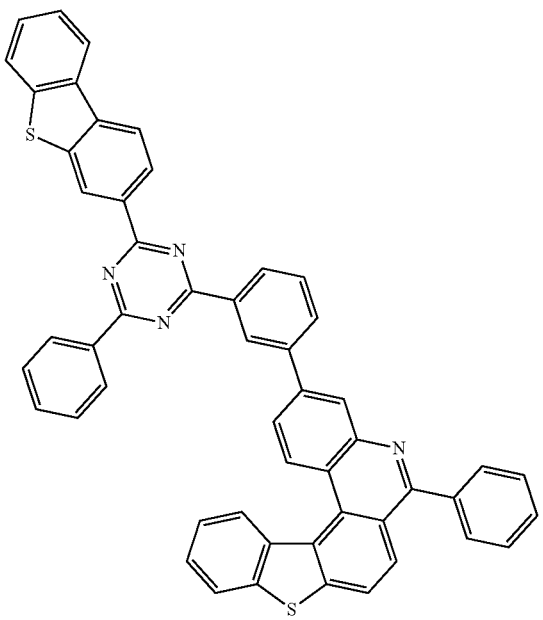
637
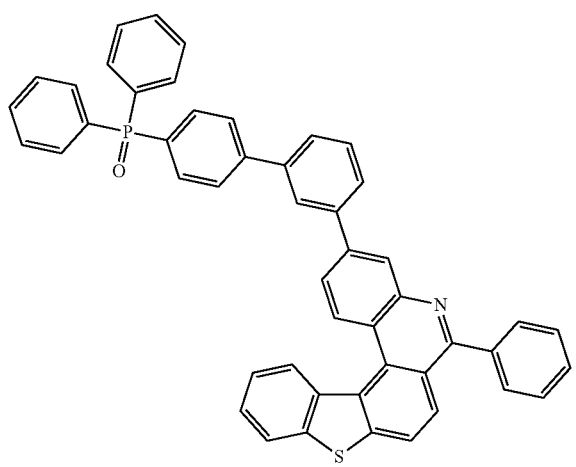
638
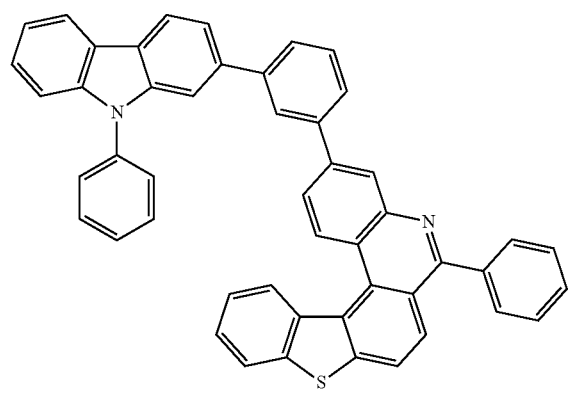 [SMILES: c1ccc(-c2nc3cc(-c4cccc(-c5ccc6c7ccccc7n(-c7ccccc7)c6c5)c4)ccc3c3c2ccc2sc4ccccc4c23)cc1]
639
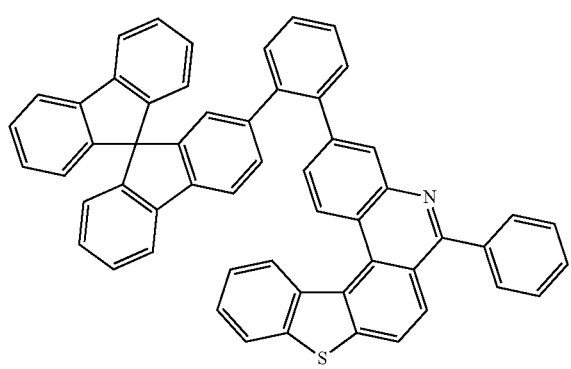
340
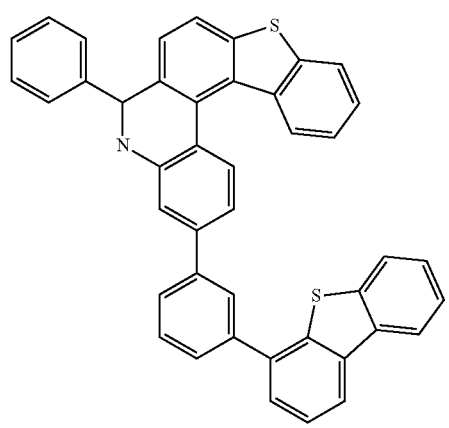

-continued
641
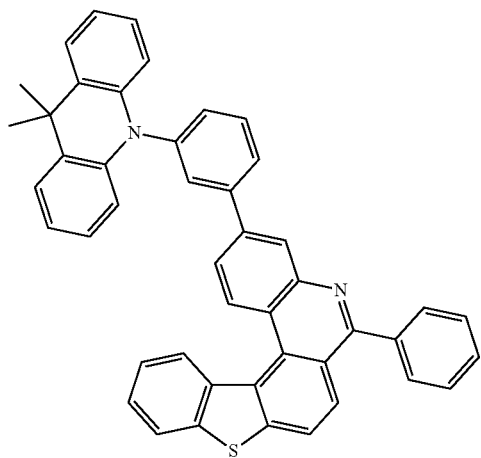
642
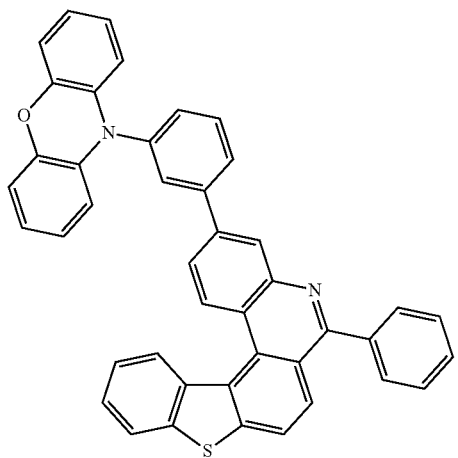 [SMILES: c1ccc(-c2nc3cc(-c4cccc(N5c6ccccc6Oc6ccccc65)c4)ccc3c3c2ccc2sc4ccccc4c23)cc1]
643
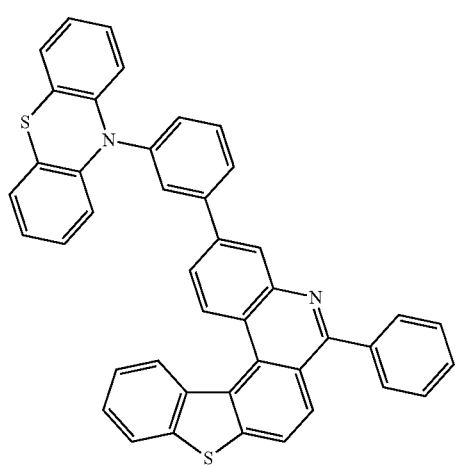
644
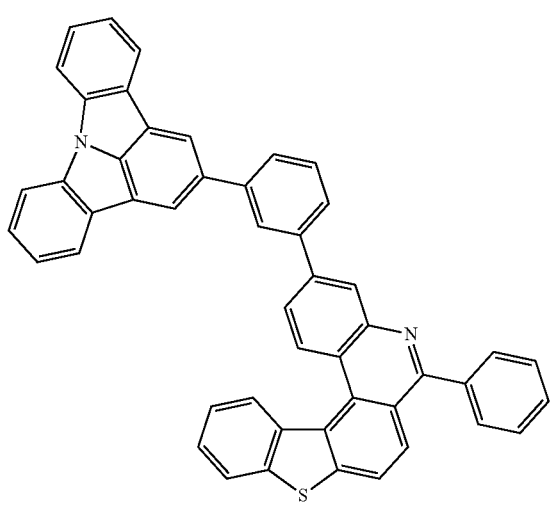
645
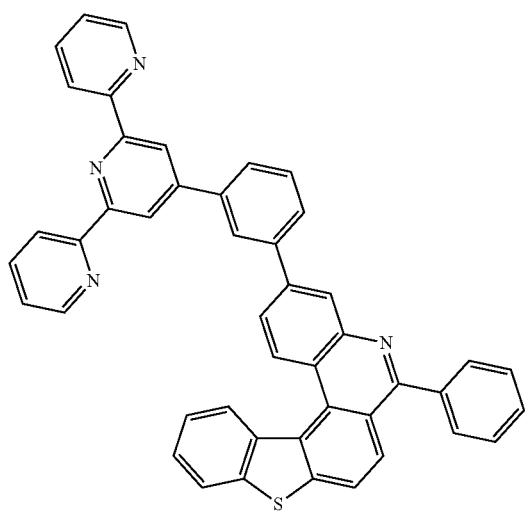
646
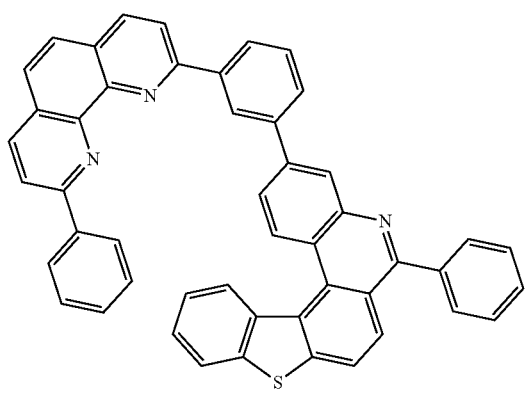 [SMILES: c1ccc(-c2ccc3ccc4ccc(-c5cccc(-c6ccc7c(c6)nc(-c6ccccc6)c6ccc8sc9ccccc9c8c67)c5)nc4c3n2)cc1]

-continued
647
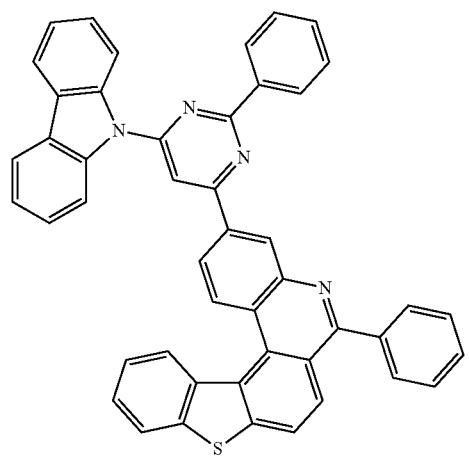
648
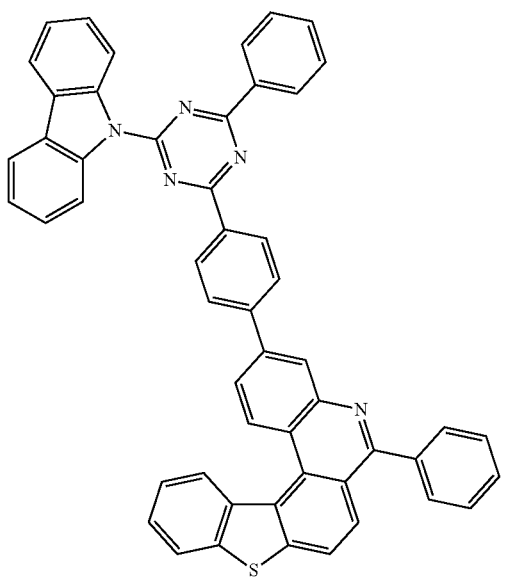
649
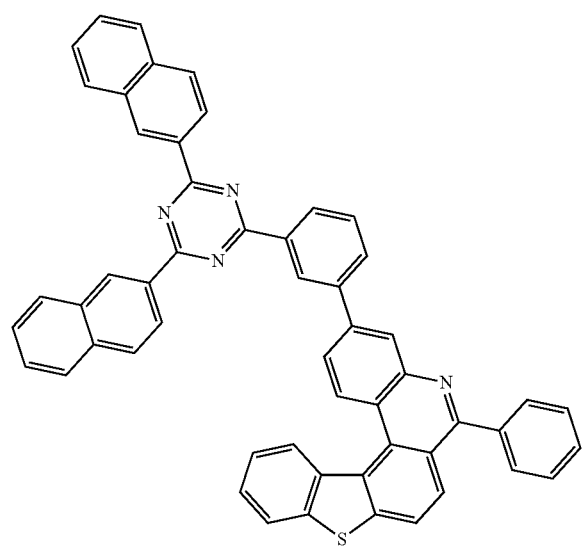
650
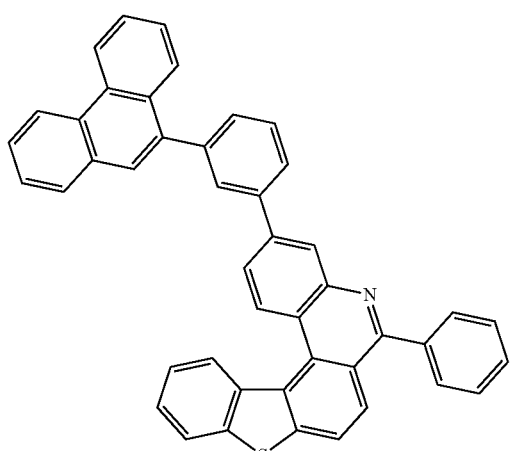
651
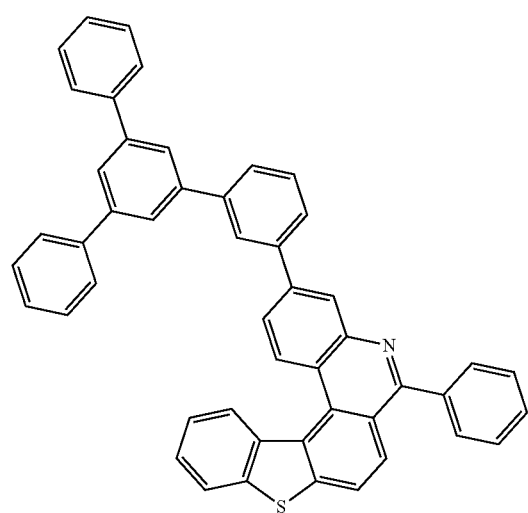
652
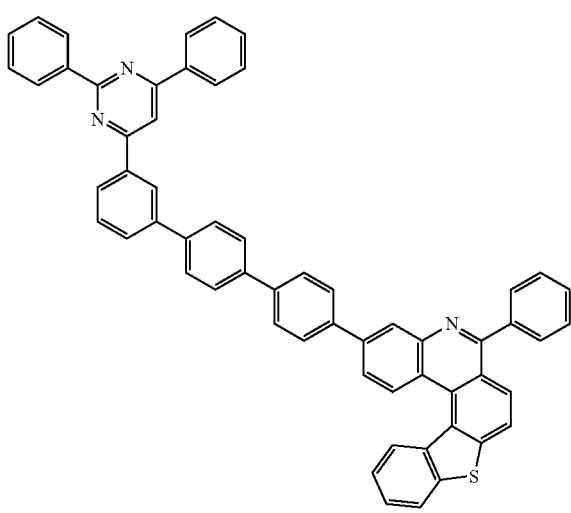

-continued
653
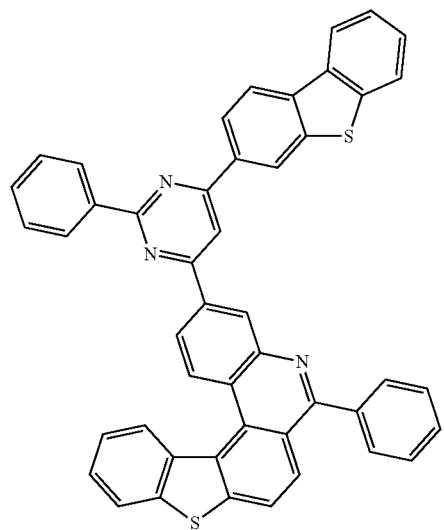
654
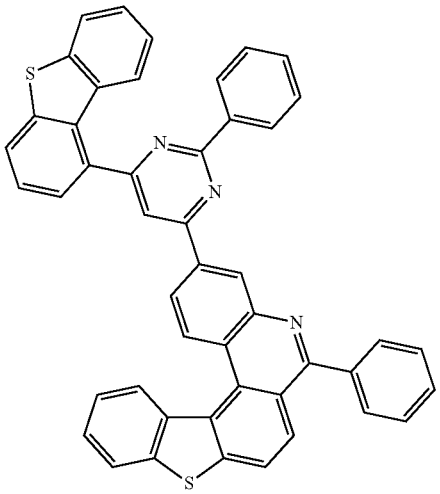 [SMILES: c1ccc(-c2nc(-c3ccc4c(c3)nc(-c3ccccc3)c3ccc5sc6ccccc6c5c34)cc(-c3cccc4sc5ccccc5c34)n2)cc1]
655
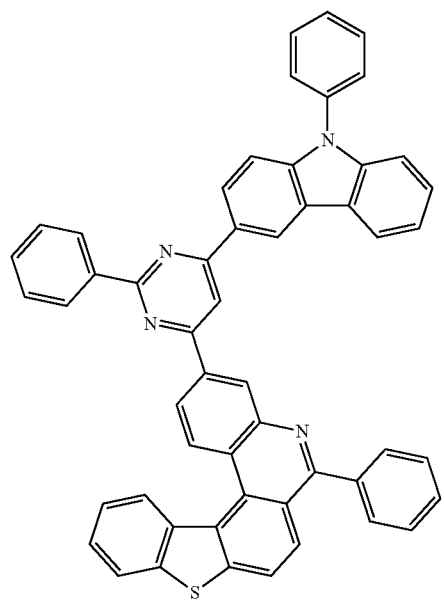
656
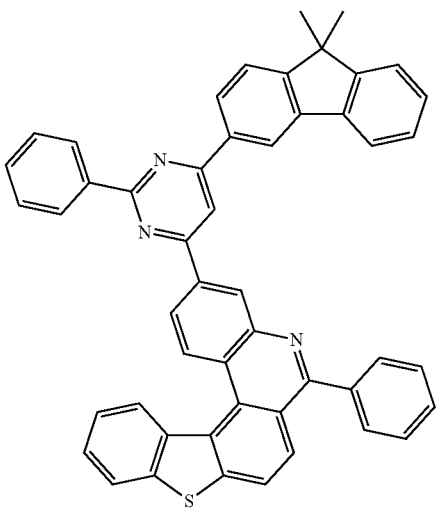

-continued
763 657
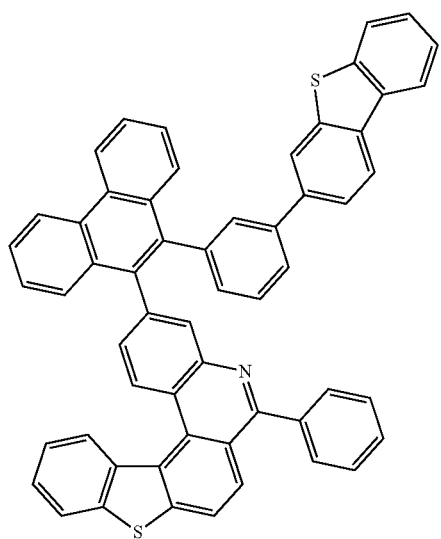
764 658
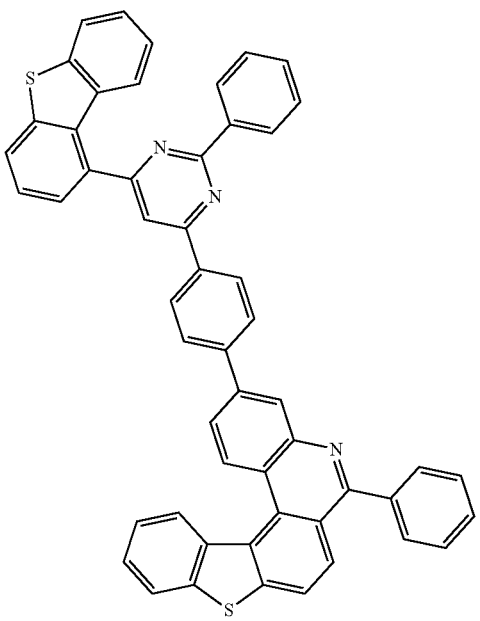
659
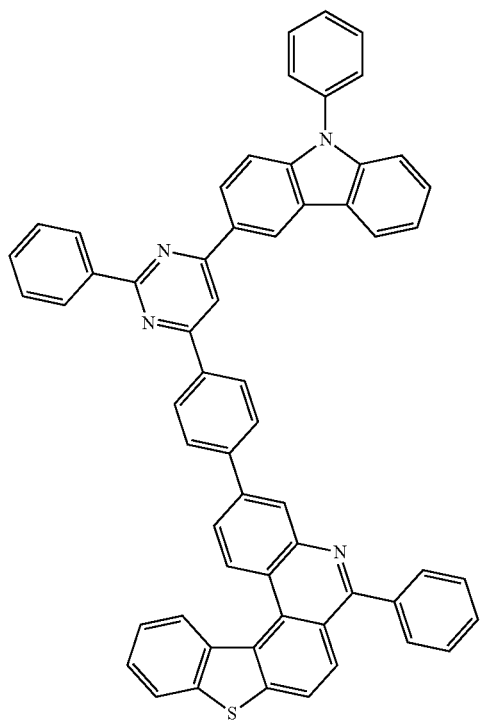
660
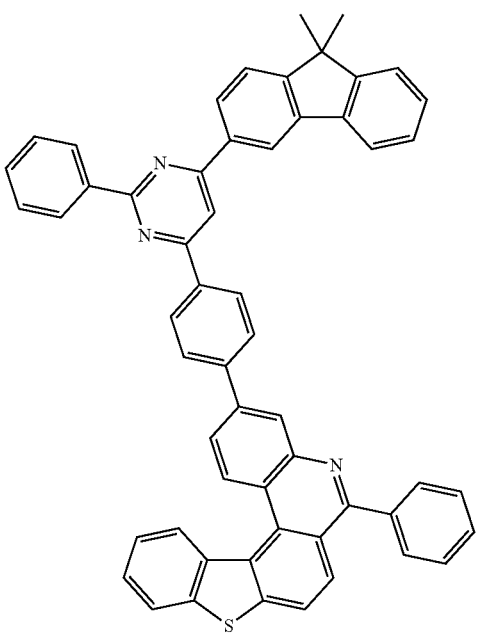

765 766
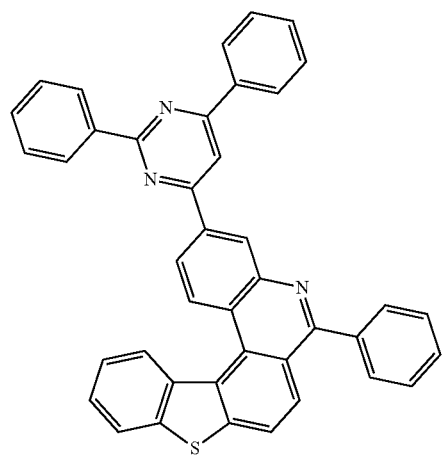
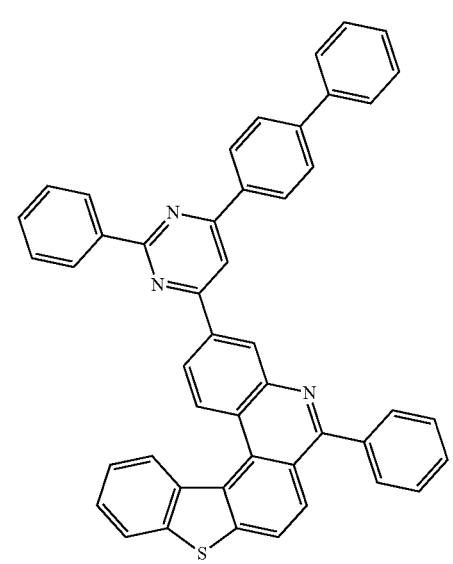 [SMILES: c1ccc(-c2ccc(-c3cc(-c4ccc5c(c4)nc(-c4ccccc4)c4ccc6sc7ccccc7c6c45)nc(-c4ccccc4)n3)cc2)cc1]
663 664
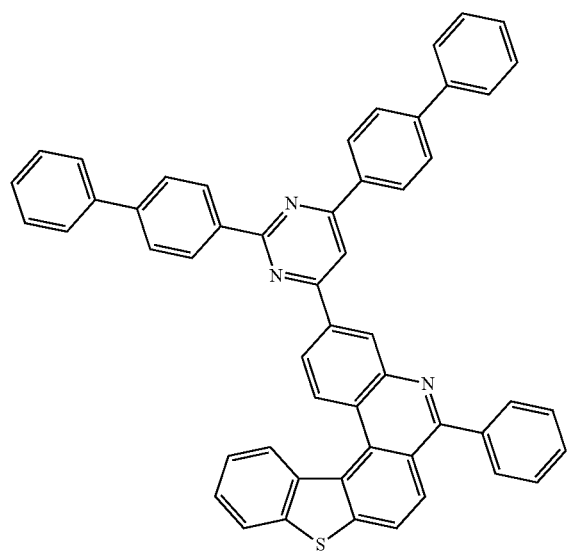
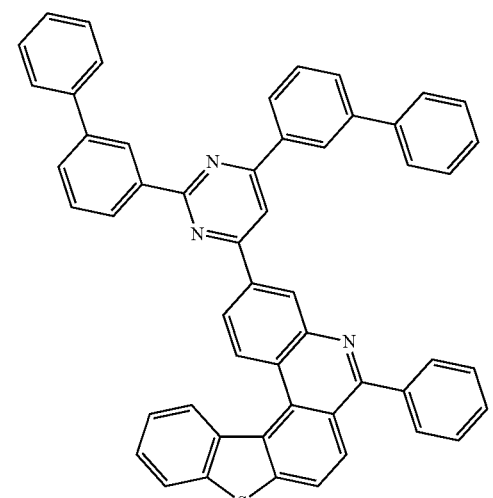

-continued
665
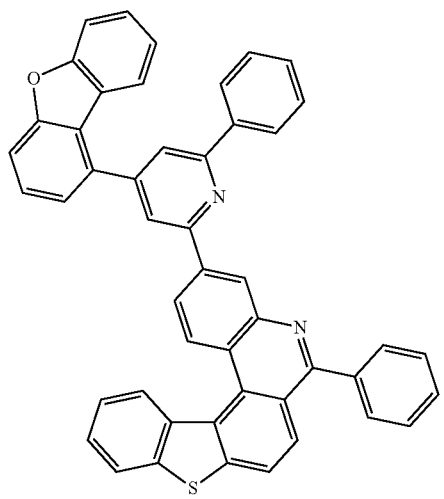
666
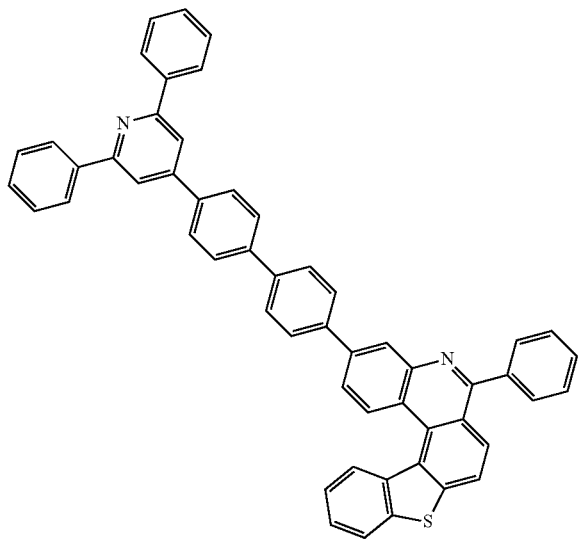
667
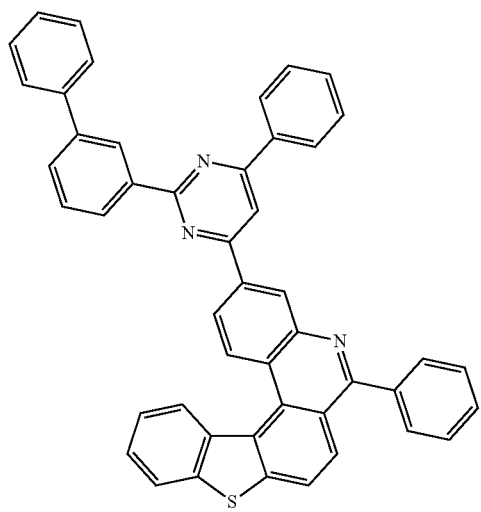
668
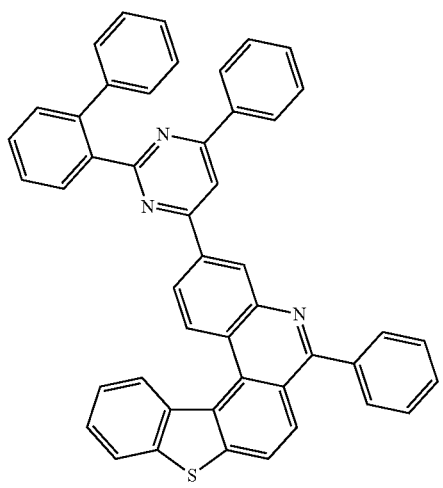
669
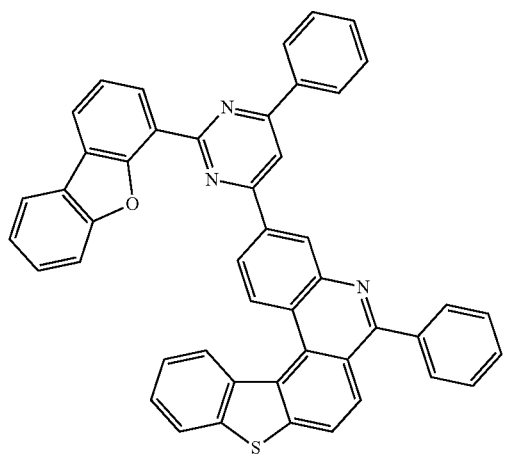
670
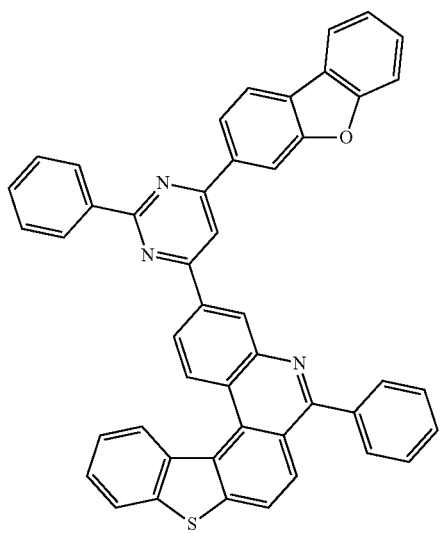 [SMILES: c1ccc(-c2nc(-c3ccc4c(c3)nc(-c3ccccc3)c3ccc5sc6ccccc6c5c34)cc(-c3ccc4c(c3)oc3ccccc34)n2)cc1]

-continued
769
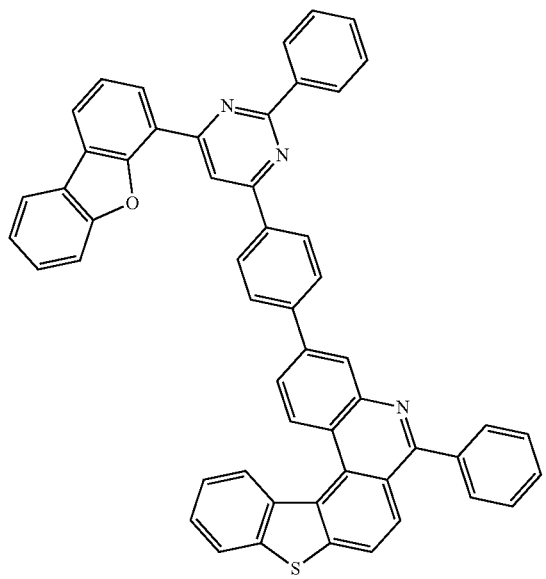
671
770
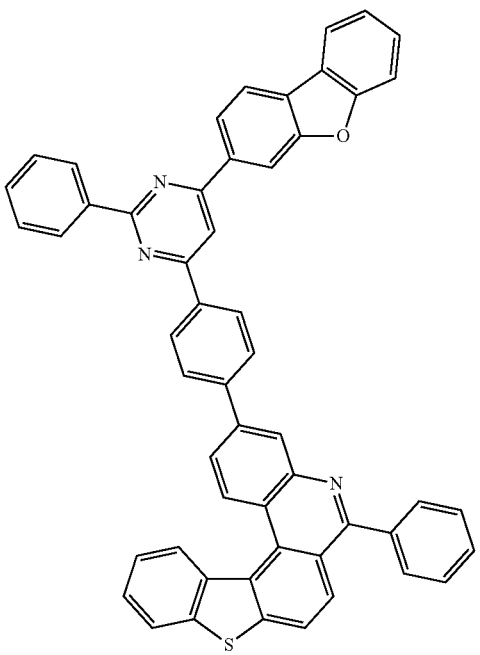
672
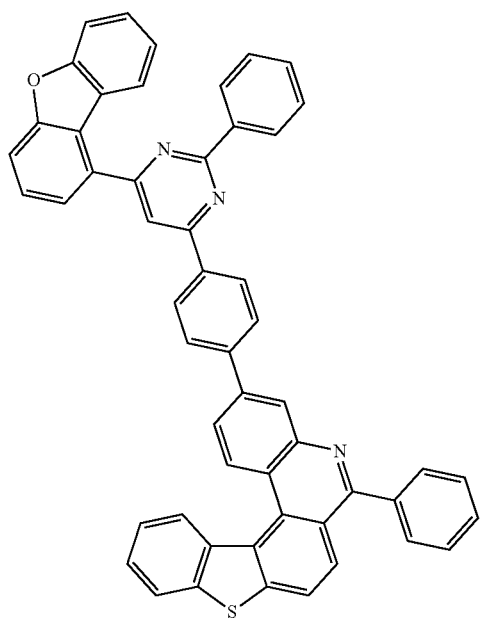
673
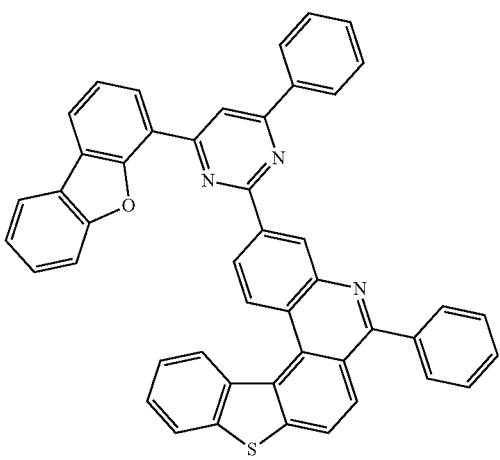
674

-continued
675
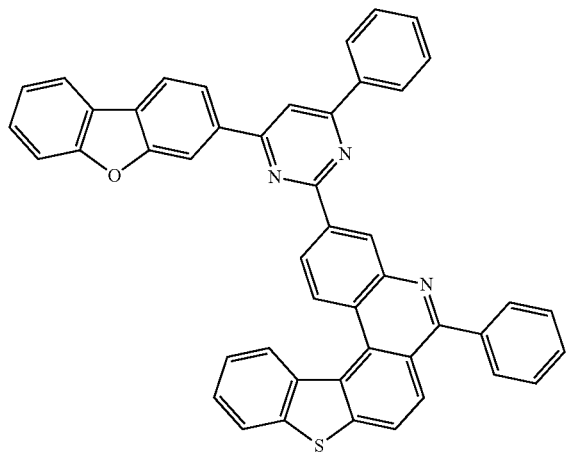
676
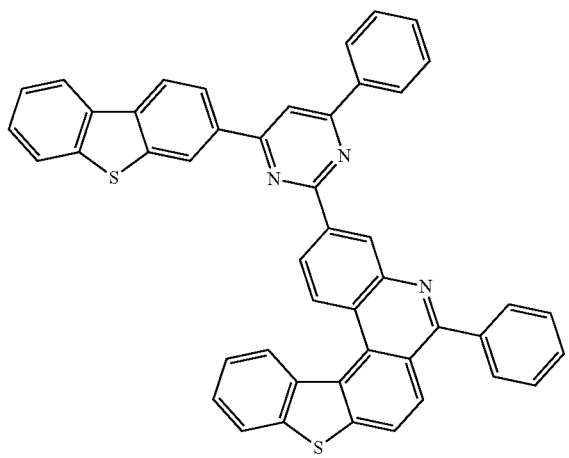
677
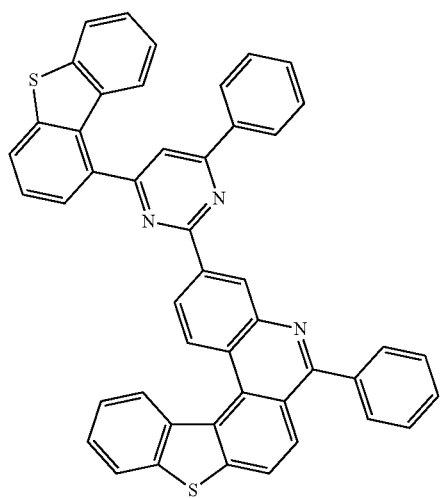
678
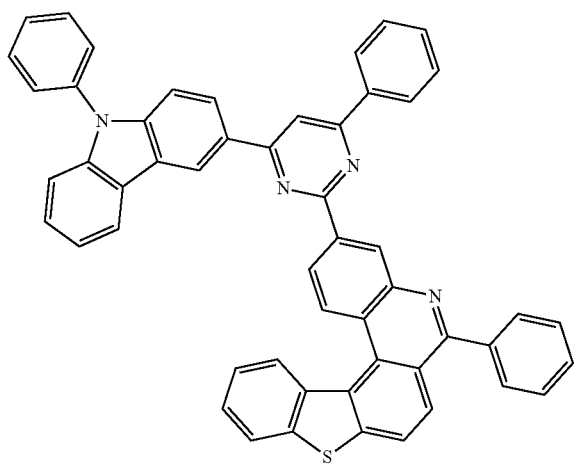 [SMILES: c1ccc(-c2cc(-c3ccc4c(c3)c3ccccc3n4-c3ccccc3)nc(-c3ccc4c(c3)nc(-c3ccccc3)c3ccc5sc6ccccc6c5c34)n2)cc1]
679
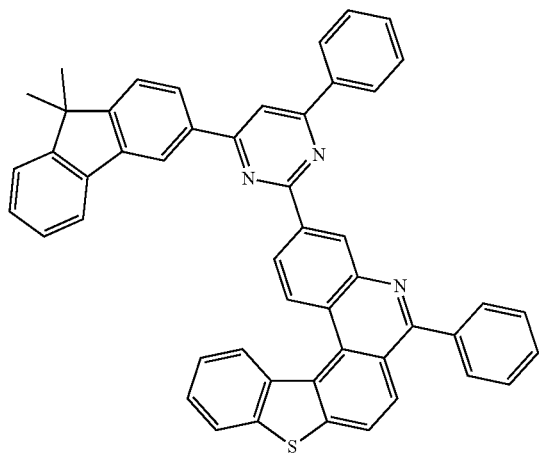
680
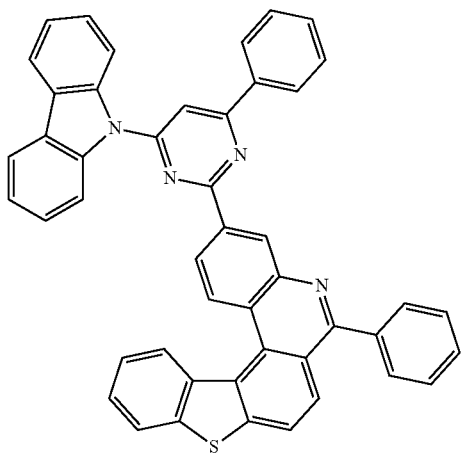

-continued
681
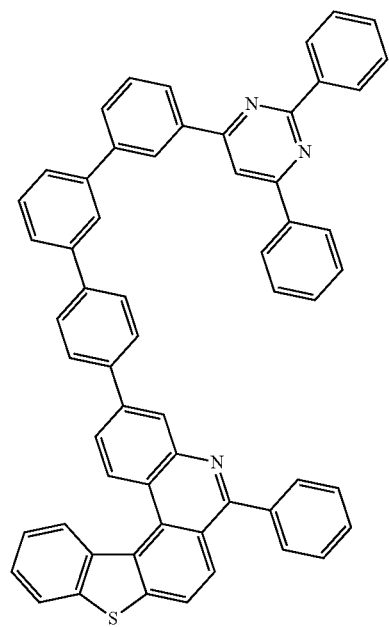
682
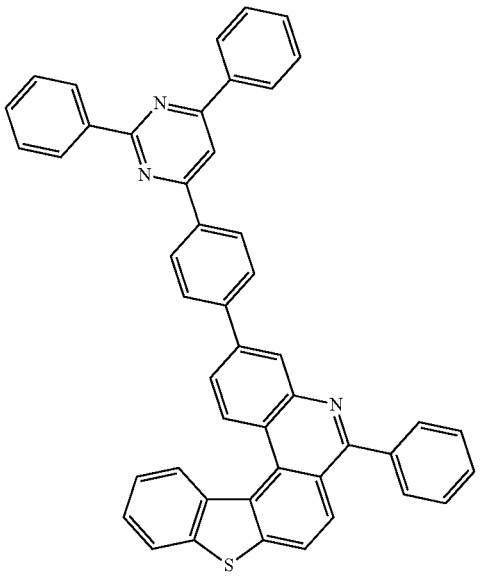 [SMILES: c1ccc(-c2cc(-c3ccc(-c4ccc5c(c4)nc(-c4ccccc4)c4ccc6sc7ccccc7c6c45)cc3)nc(-c3ccccc3)n2)cc1]
683
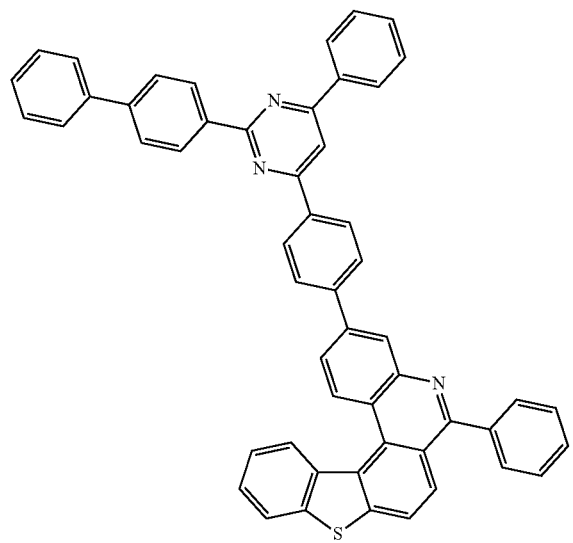
684
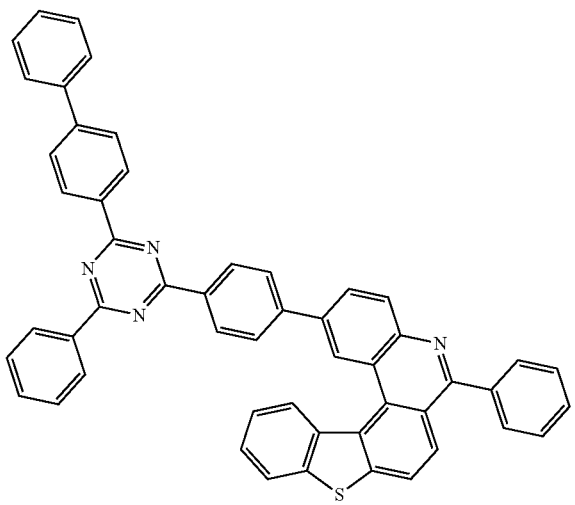

-continued
685
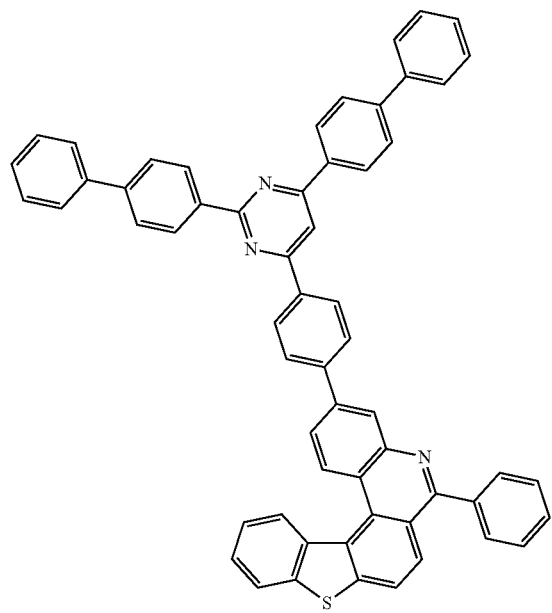
686
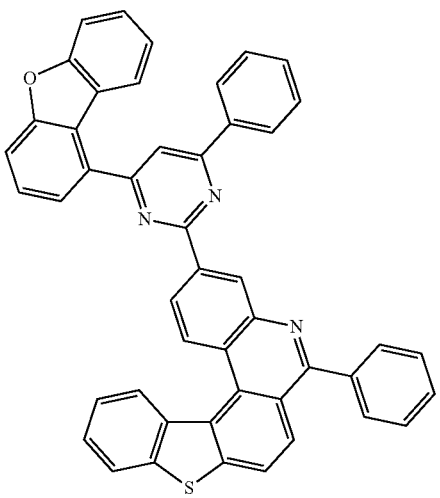 [SMILES: c1ccc(-c2cc(-c3cccc4oc5ccccc5c34)nc(-c3ccc4c(c3)nc(-c3ccccc3)c3ccc5sc6ccccc6c5c34)n2)cc1]
687
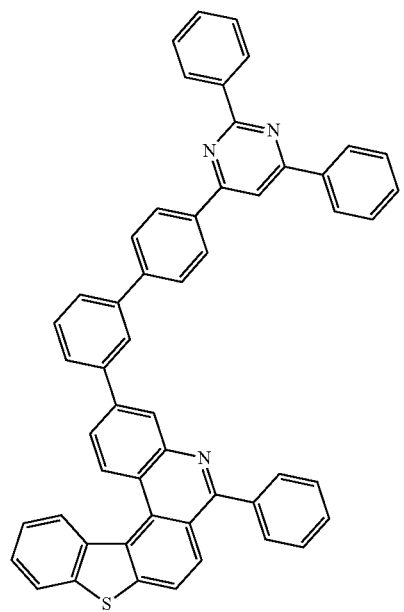
688
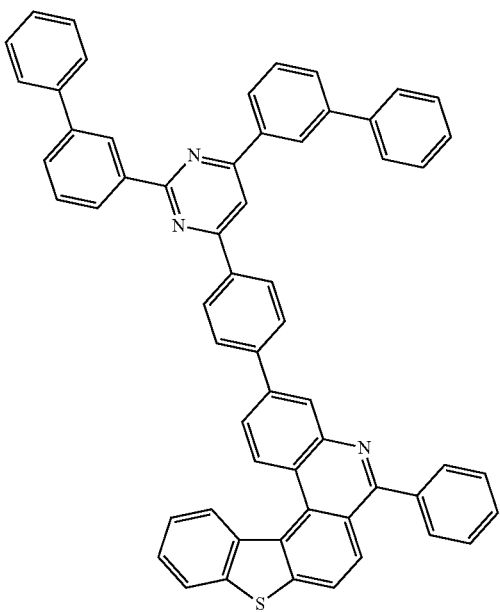

-continued
689
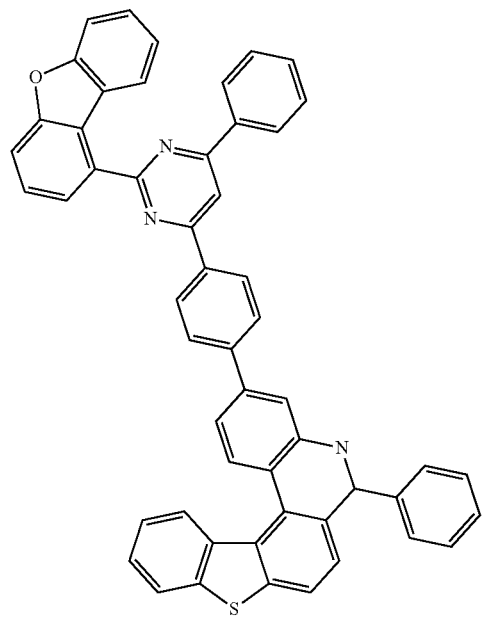
690
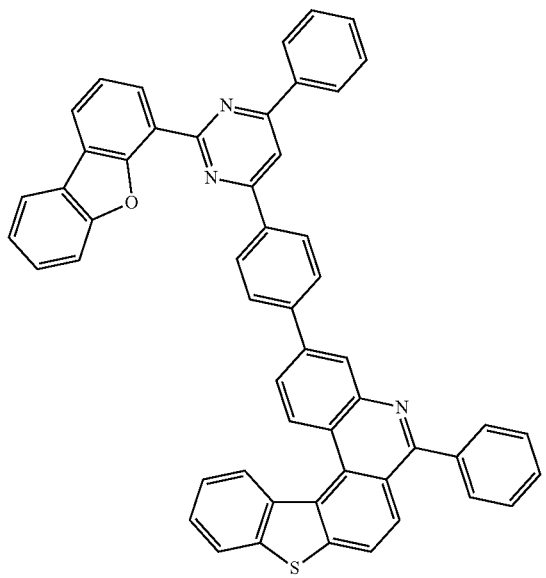 [SMILES: c1ccc(-c2cc(-c3ccc(-c4ccc5c(c4)nc(-c4ccccc4)c4ccc6sc7ccccc7c6c45)cc3)nc(-c3cccc4c3oc3ccccc34)n2)cc1]
691
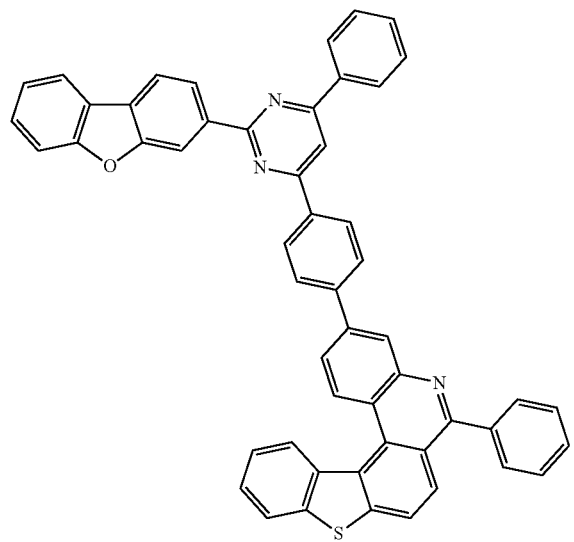
692
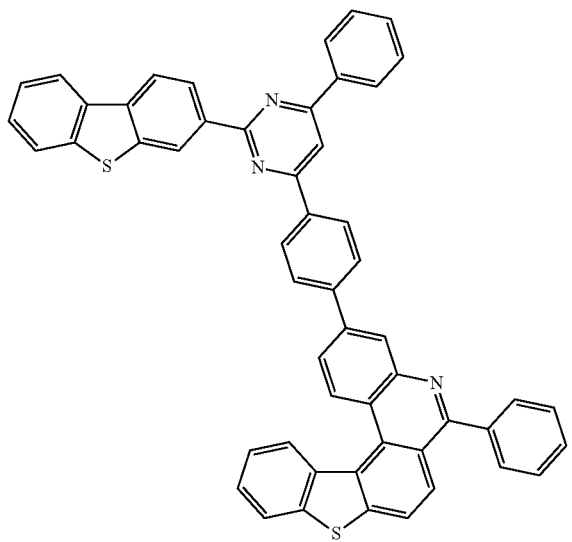

-continued
779
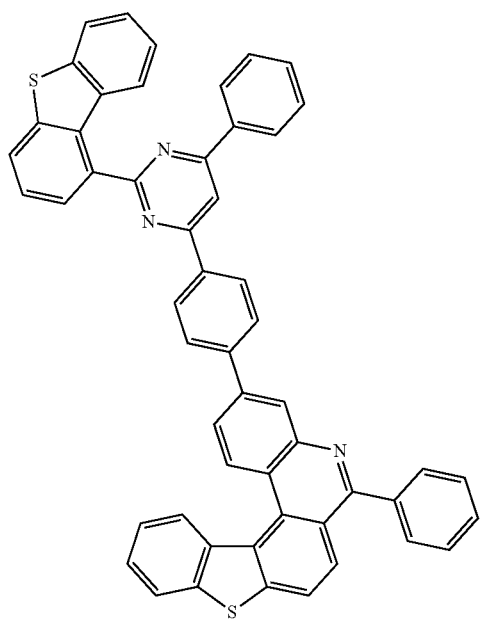
780
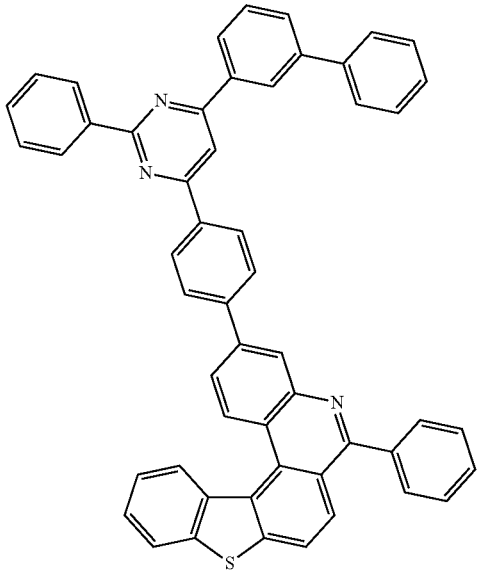 [SMILES: c1ccc(-c2cccc(-c3cc(-c4ccc(-c5ccc6c(c5)nc(-c5ccccc5)c5ccc7sc8ccccc8c7c56)cc4)nc(-c4ccccc4)n3)c2)cc1]
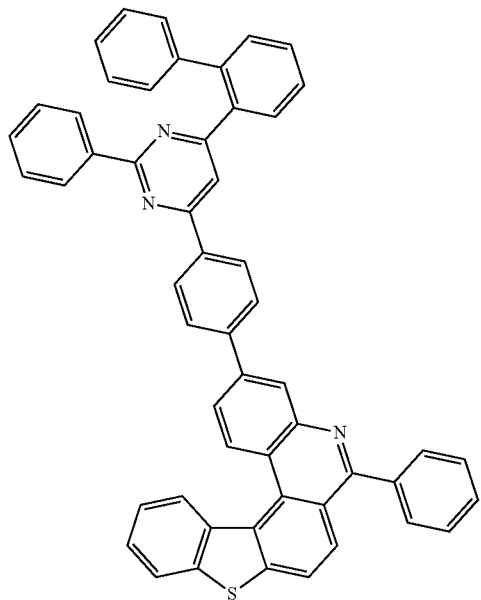
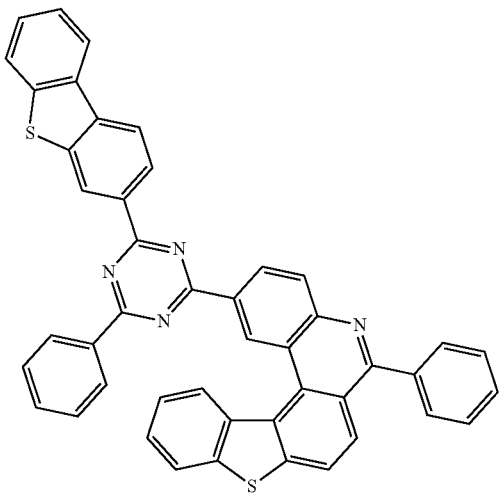

-continued
697
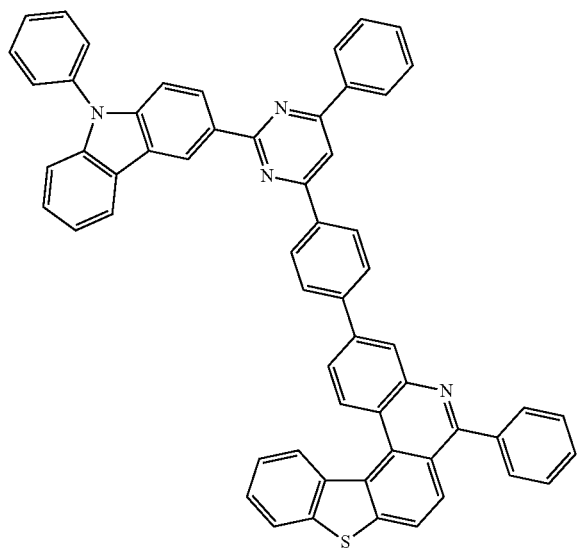
698
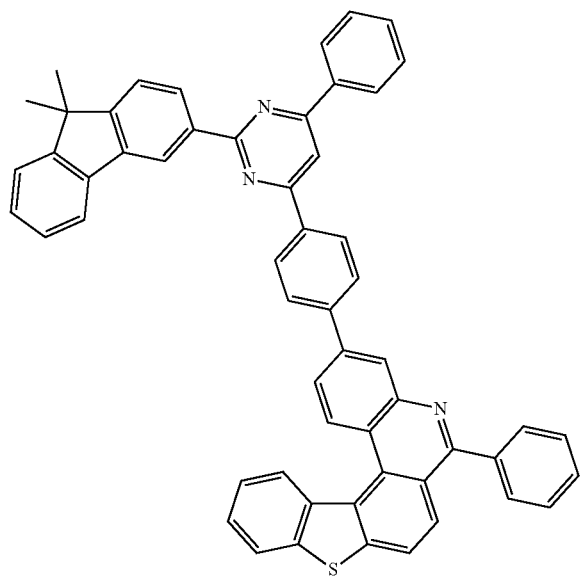 [SMILES: CC1(C)c2ccccc2-c2cc(-c3nc(-c4ccccc4)cc(-c4ccc(-c5ccc6c(c5)nc(-c5ccccc5)c5ccc7sc8ccccc8c7c56)cc4)n3)ccc21]
699
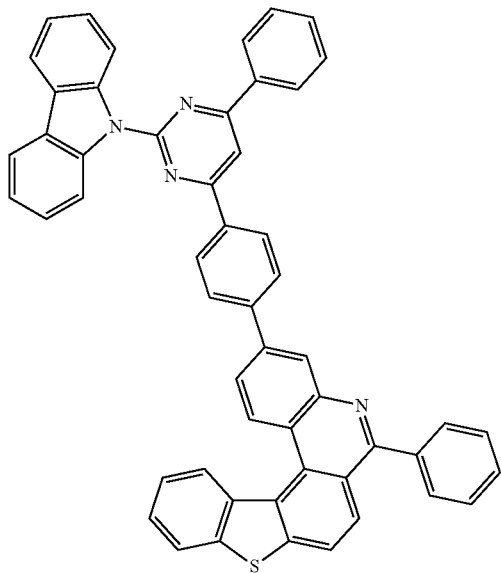
700
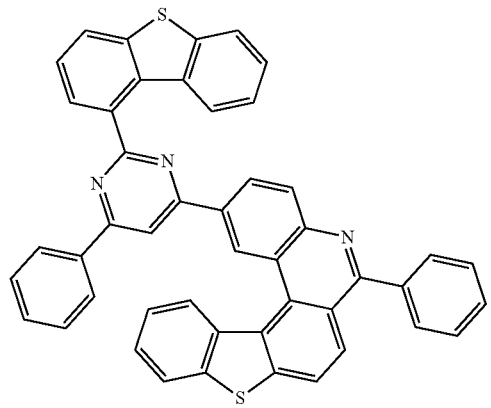
701
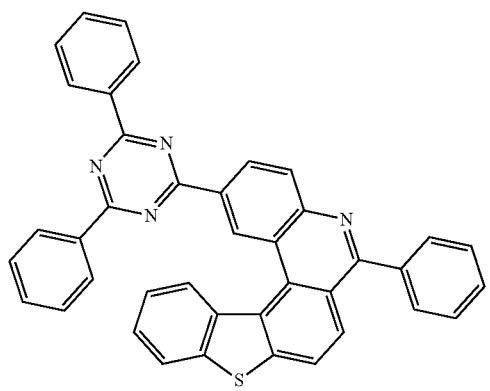
702
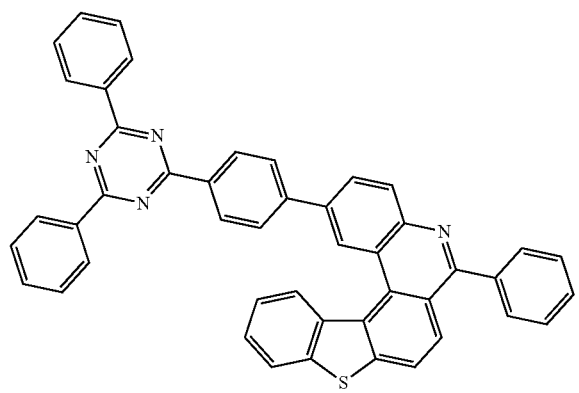 [SMILES: c1ccc(-c2nc(-c3ccccc3)nc(-c3ccc(-c4ccc5nc(-c6ccccc6)c6ccc7sc8ccccc8c7c6c5c4)cc3)n2)cc1]

-continued
703
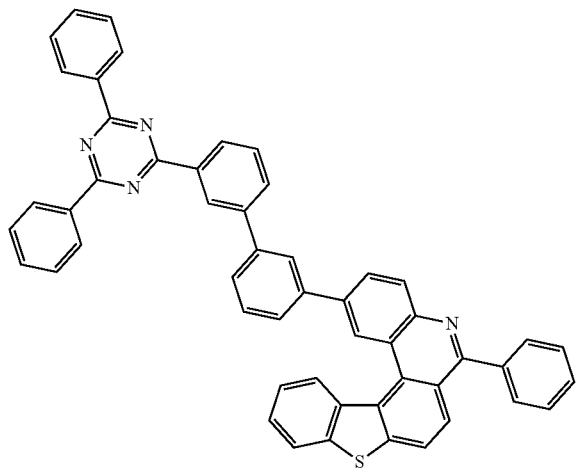
704
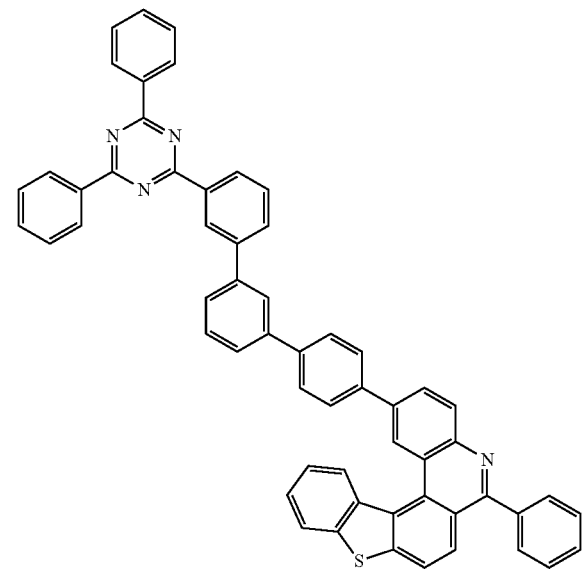
705
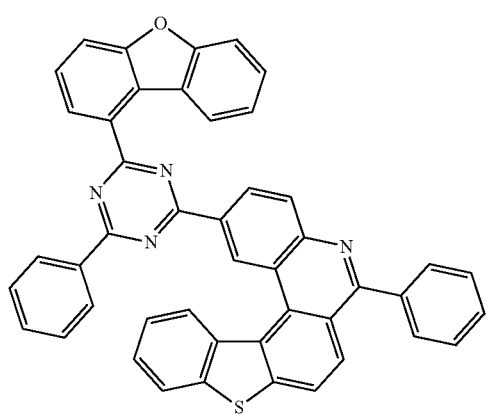
706
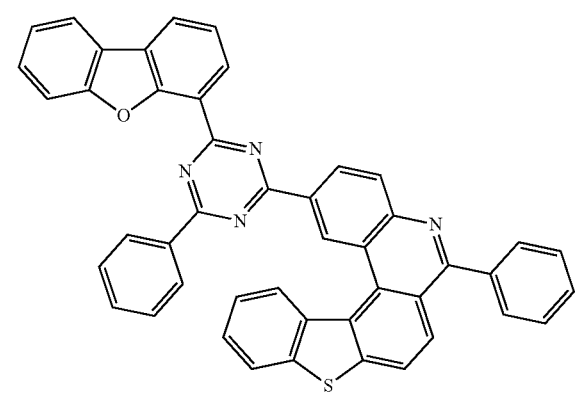 [SMILES: c1ccc(-c2nc(-c3ccc4nc(-c5ccccc5)c5ccc6sc7ccccc7c6c5c4c3)nc(-c3cccc4c3oc3ccccc34)n2)cc1]
707
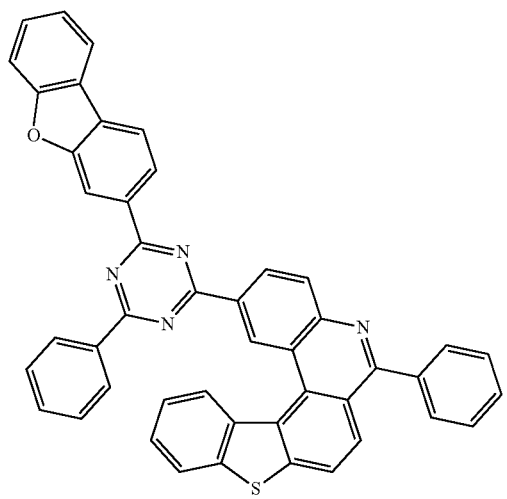
708
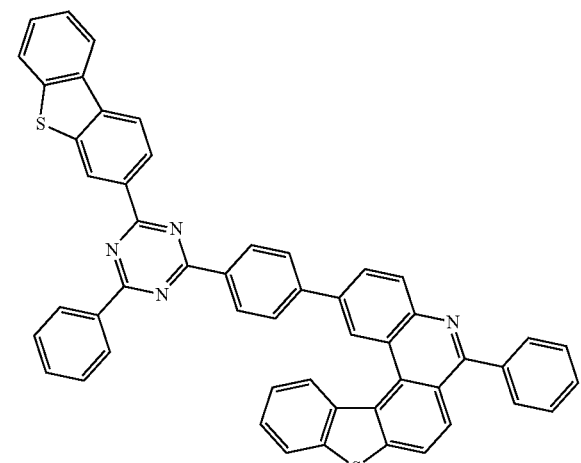

-continued
709
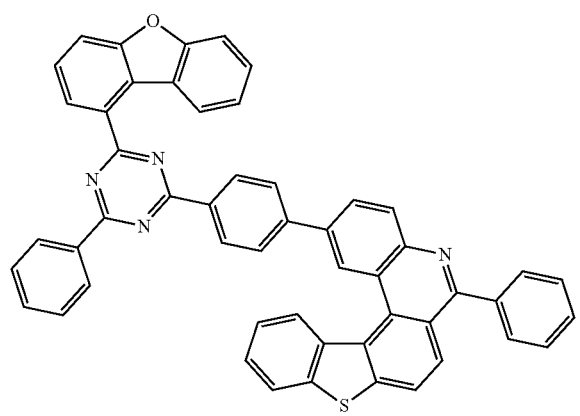
710
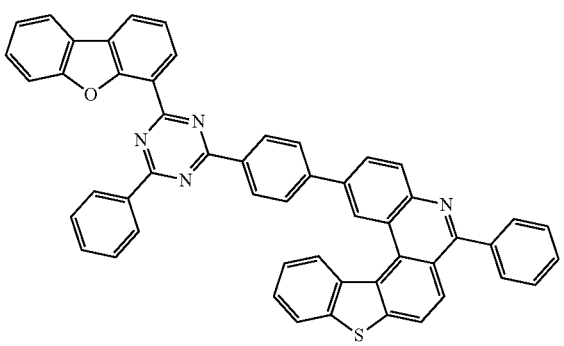 [SMILES: c1ccc(-c2nc(-c3ccc(-c4ccc5nc(-c6ccccc6)c6ccc7sc8ccccc8c7c6c5c4)cc3)nc(-c3cccc4c3oc3ccccc34)n2)cc1]
711
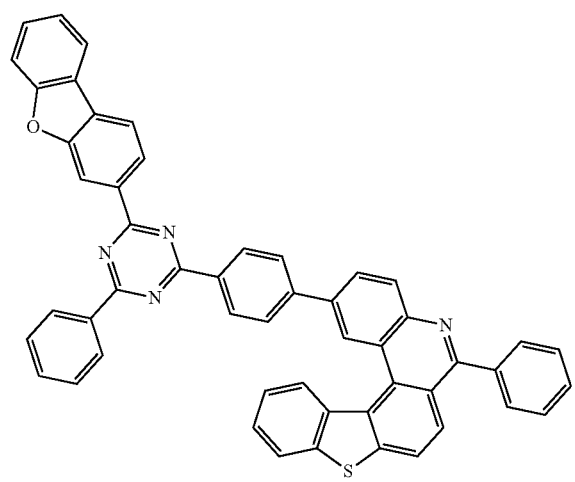
712
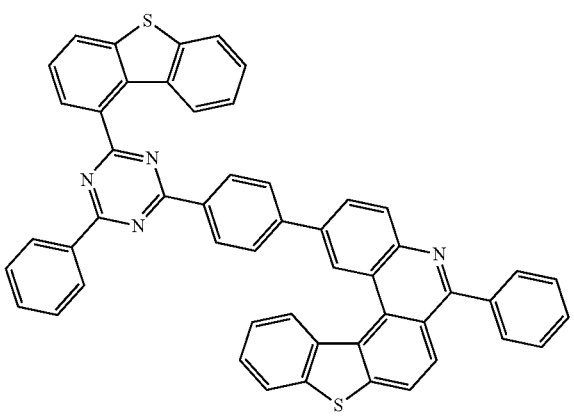
713
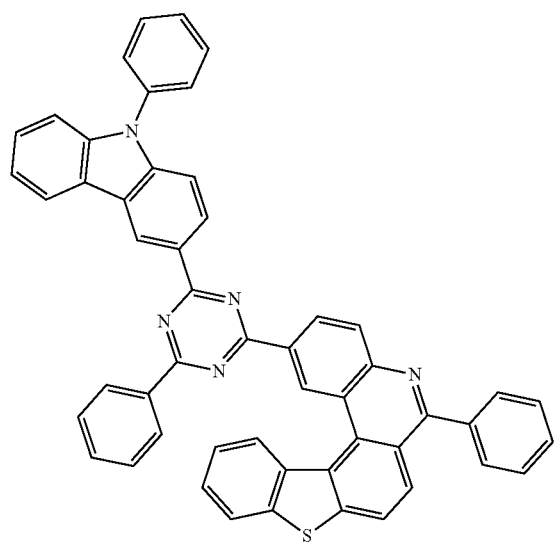
714
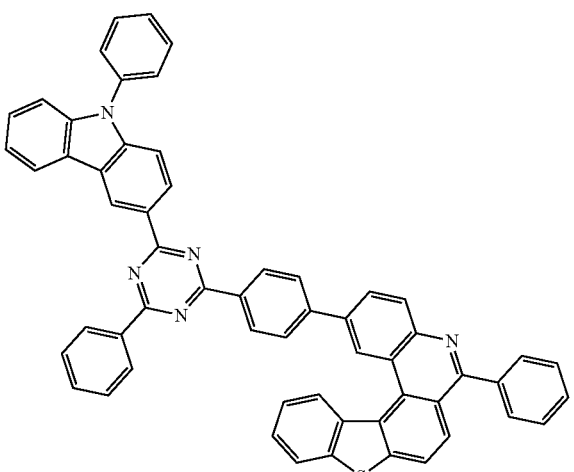

-continued
715
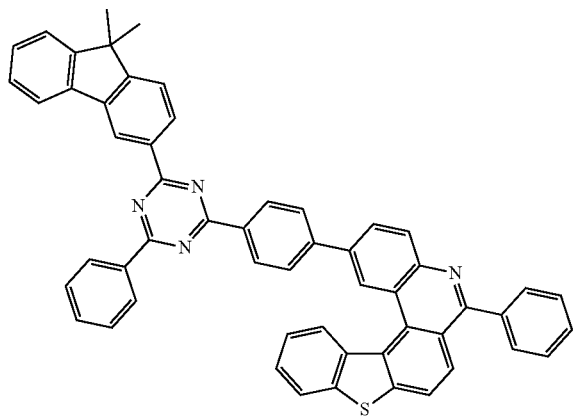
716
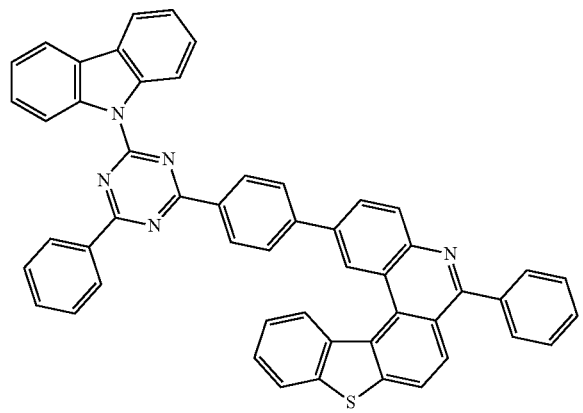
717
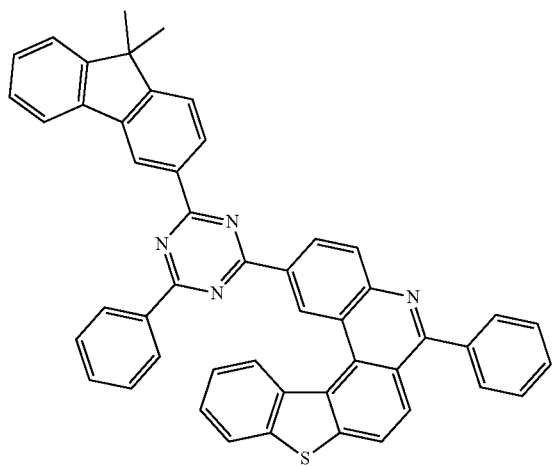
718
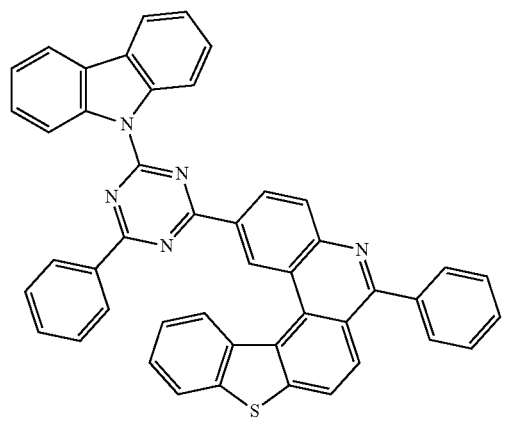
719
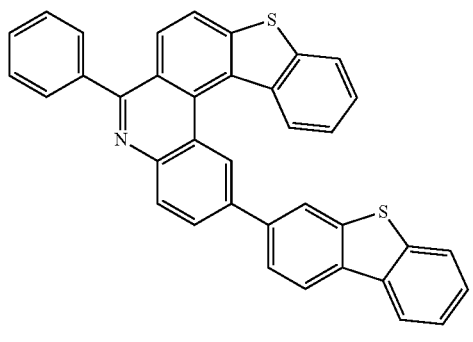
720
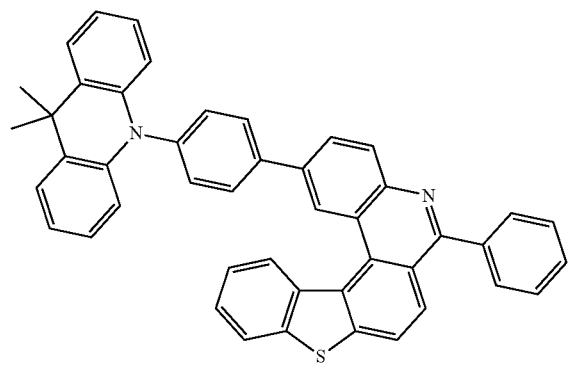

-continued
721
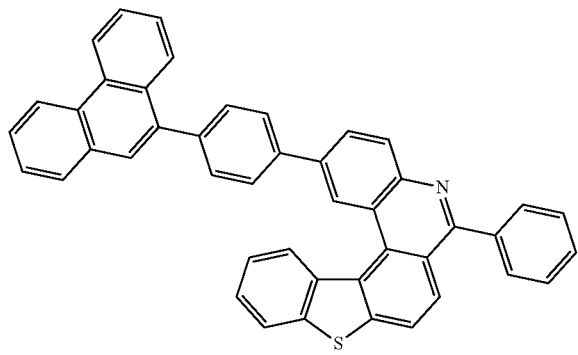
722
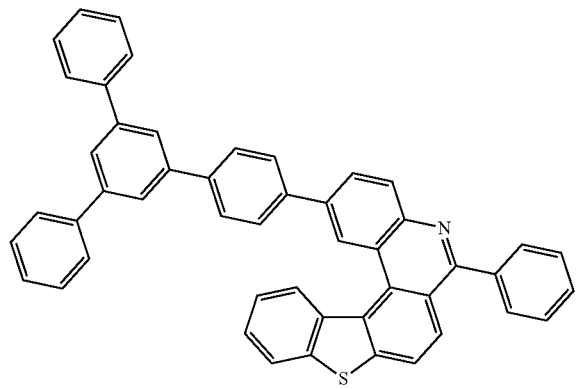
723
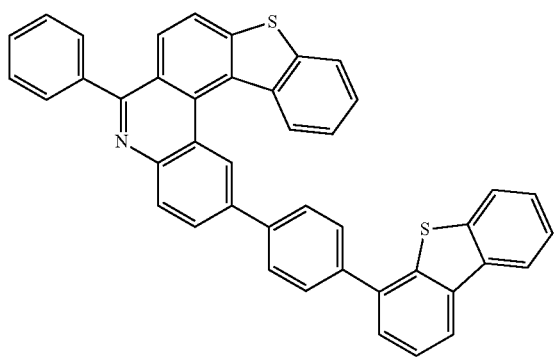
724
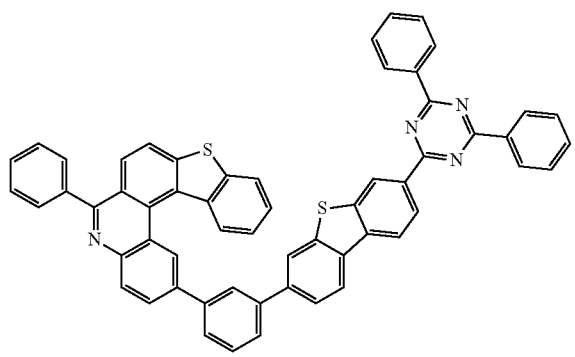
725
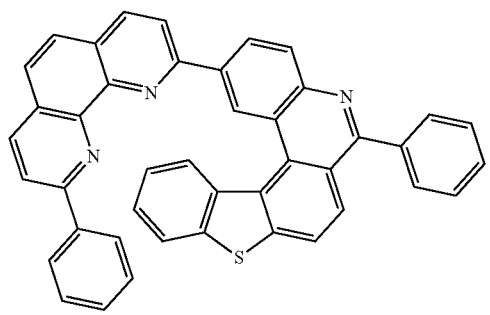
726
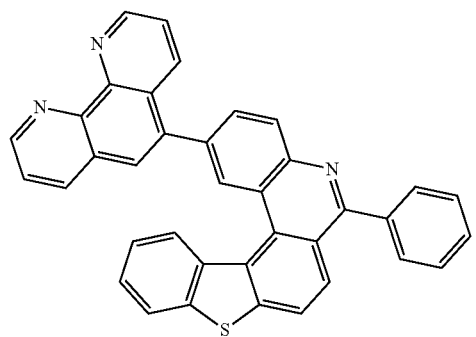 [SMILES: c1ccc(-c2nc3ccc(-c4cc5cccnc5c5ncccc45)cc3c3c2ccc2sc4ccccc4c23)cc1]
727
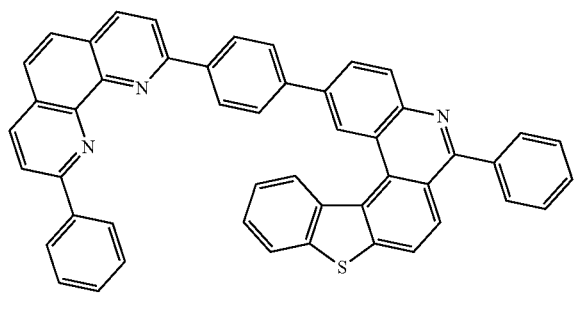
728
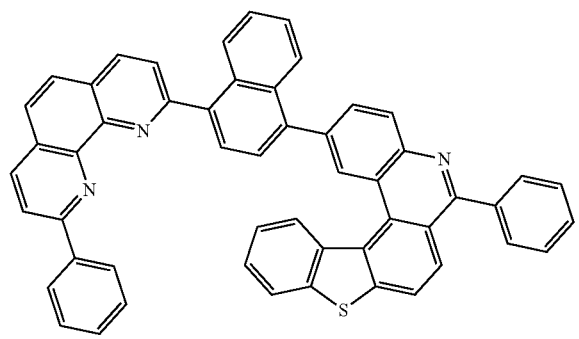

-continued
791 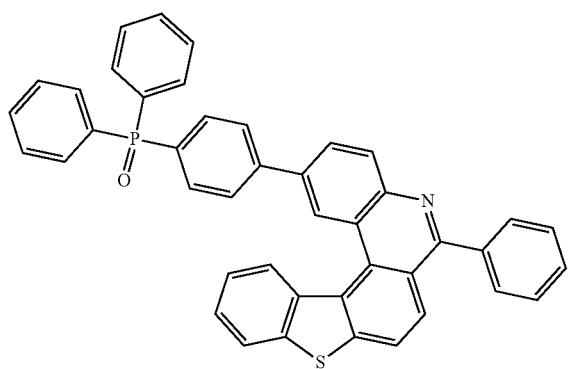
792 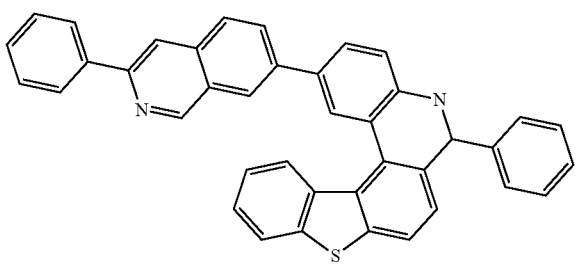
731 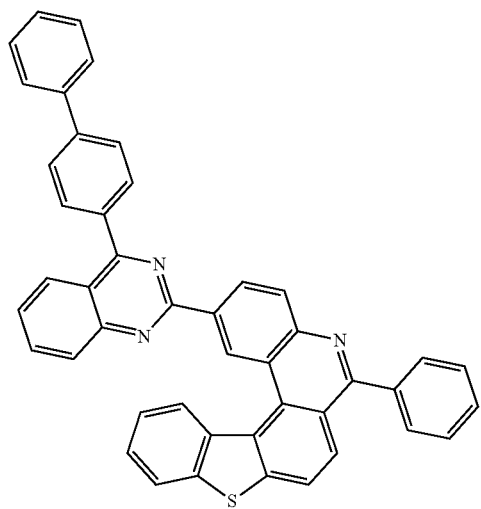
732 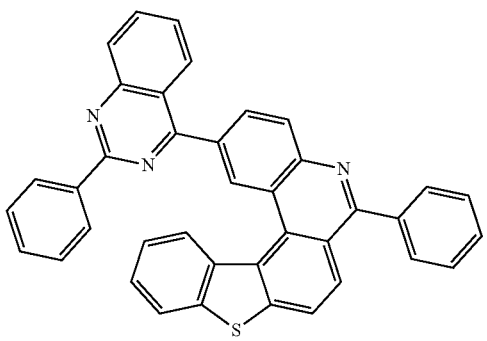
733 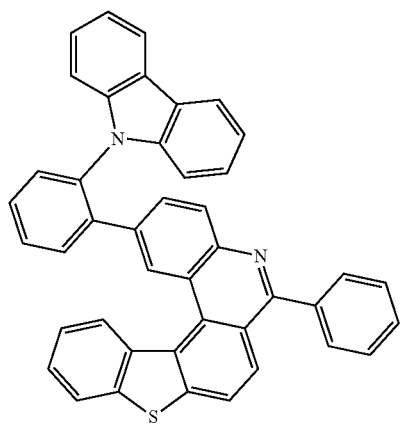
734 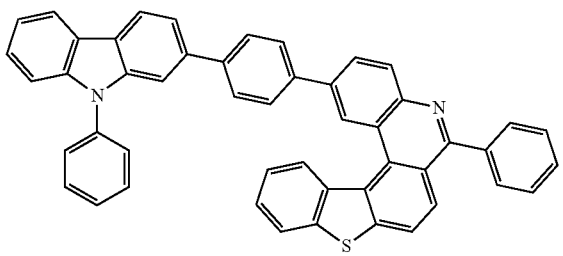

-continued
735
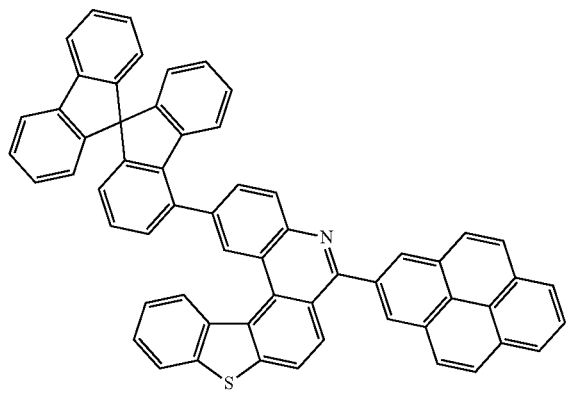
736
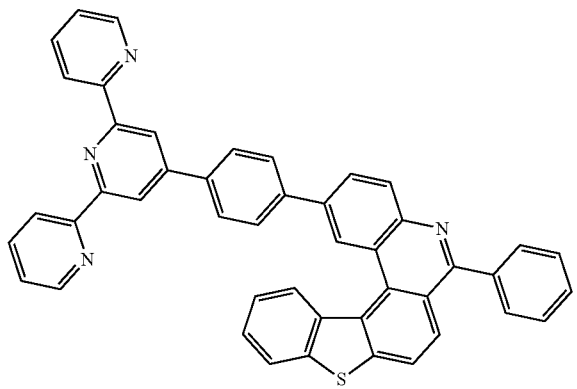
737
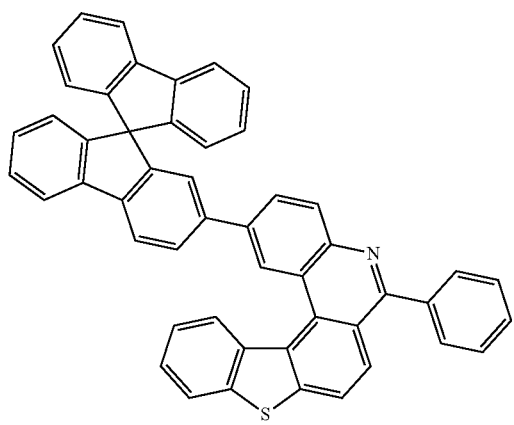
738
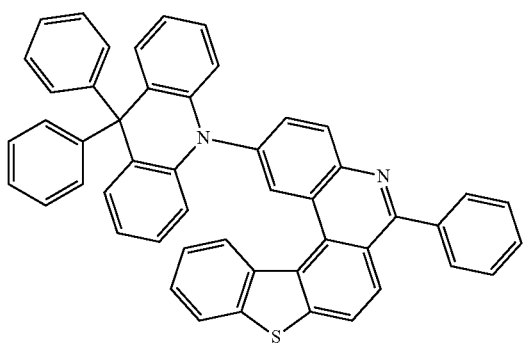
739
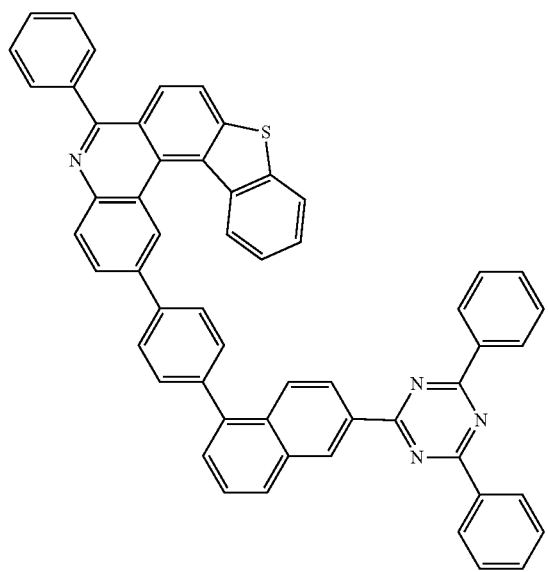
740
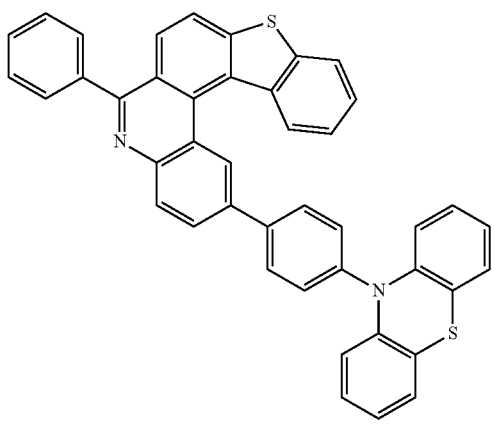

-continued
795
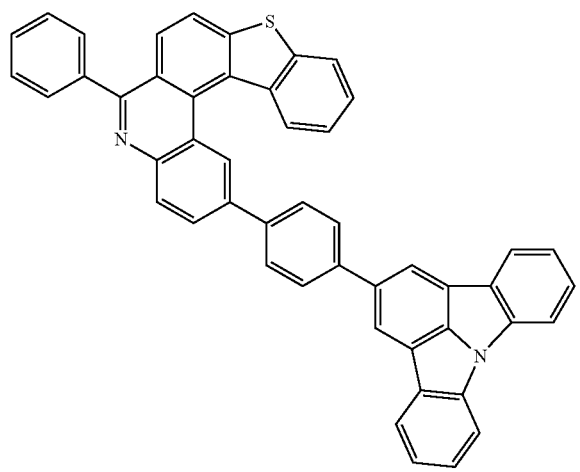
741
796
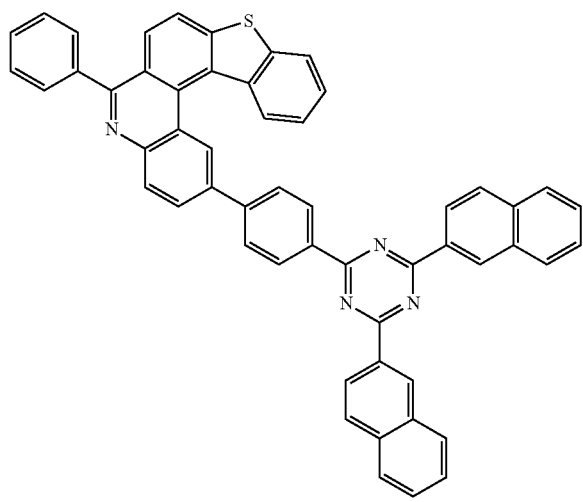 [SMILES: c1ccc(-c2nc3ccc(-c4ccc(-c5nc(-c6ccc7ccccc7c6)nc(-c6ccc7ccccc7c6)n5)cc4)cc3c3c2ccc2sc4ccccc4c23)cc1]
742
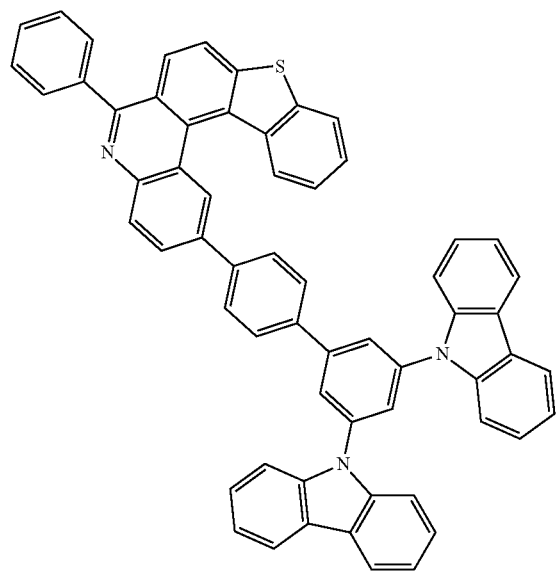
743
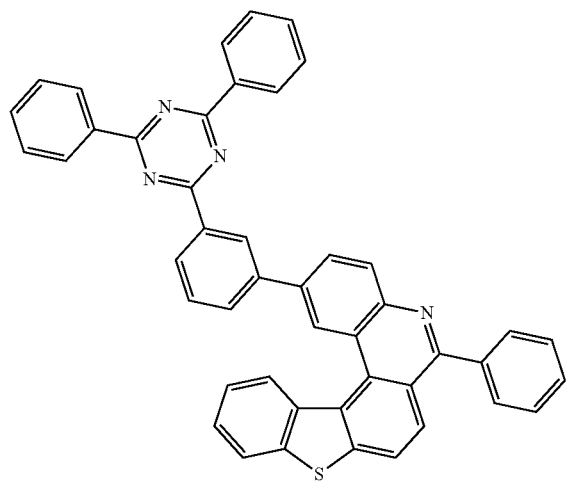
744

-continued
745
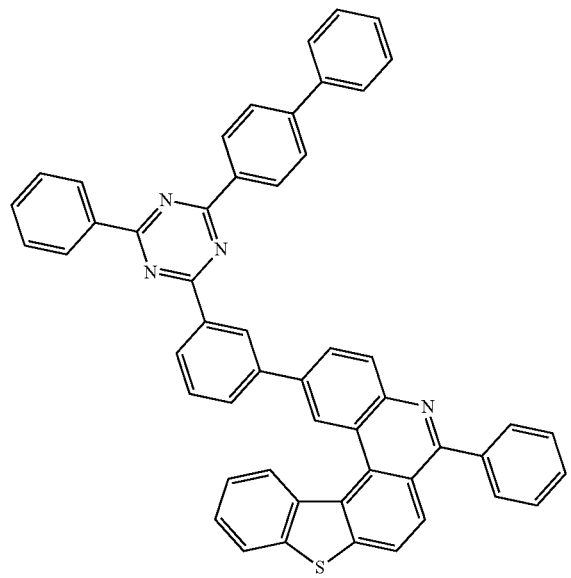
746
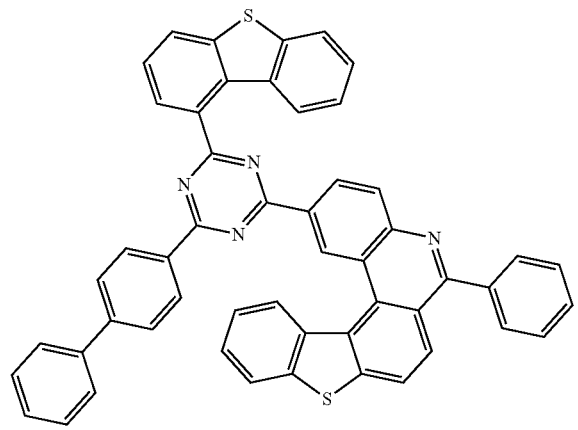
747
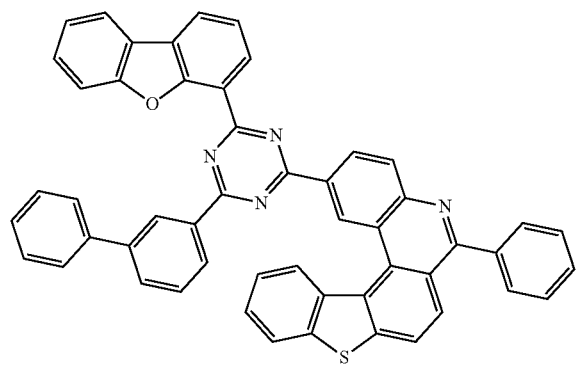
748
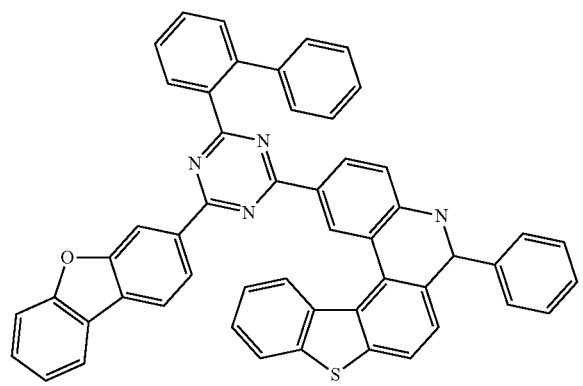
749
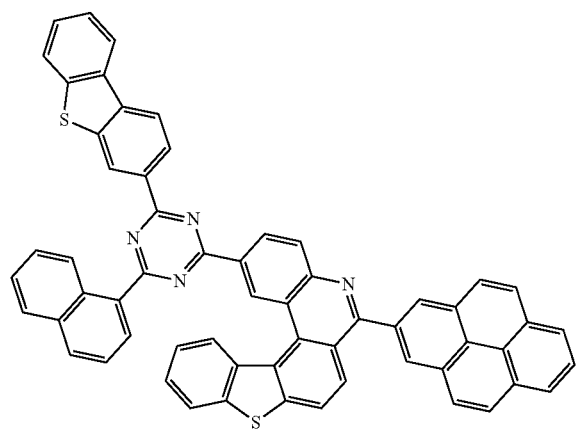
750
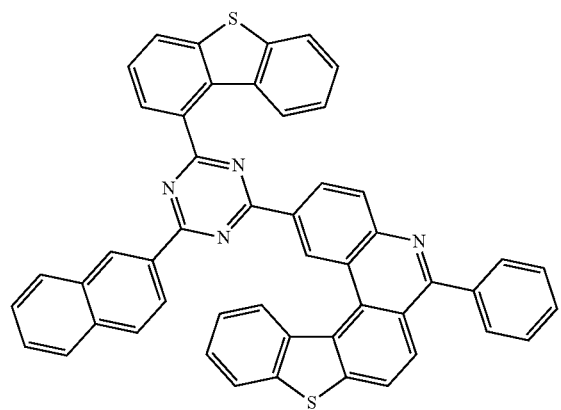 [SMILES: c1ccc(-c2nc3ccc(-c4nc(-c5ccc6ccccc6c5)nc(-c5cccc6sc7ccccc7c56)n4)cc3c3c2ccc2sc4ccccc4c23)cc1]

-continued
751
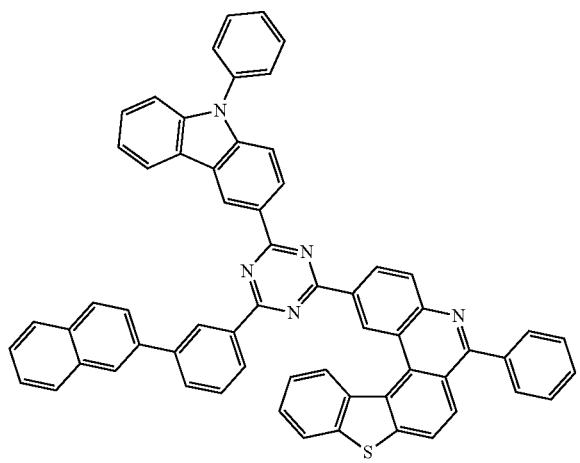
752
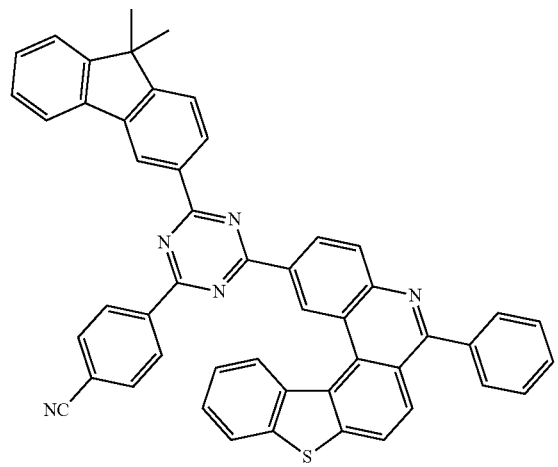
753
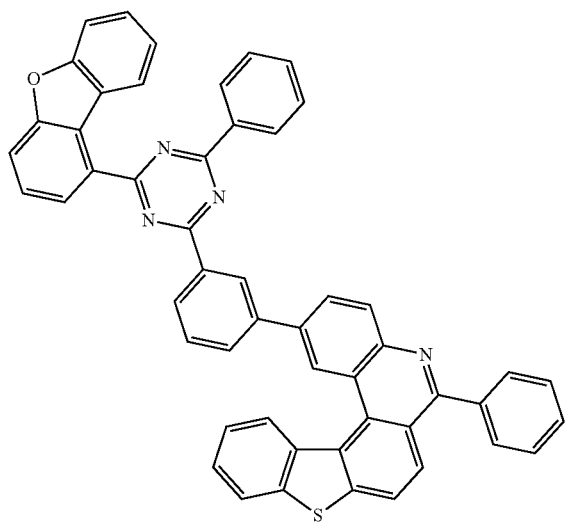
754
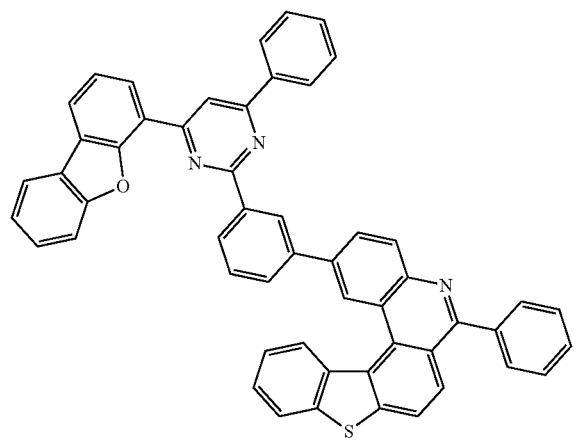
755
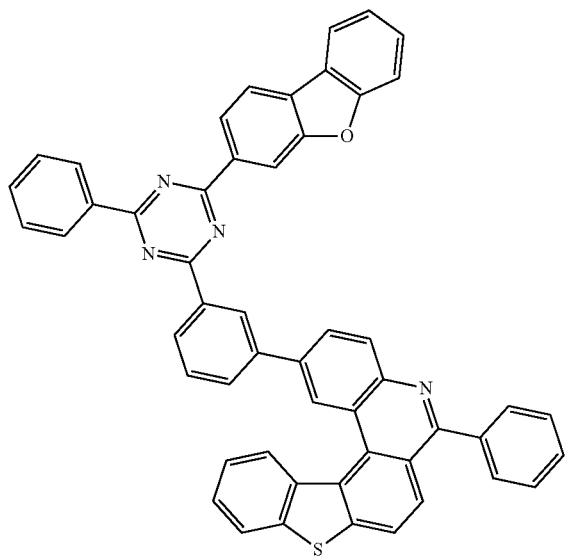
756
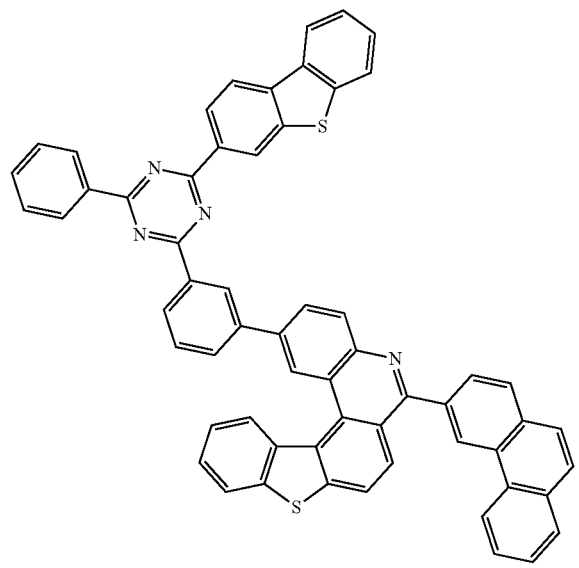

-continued
757
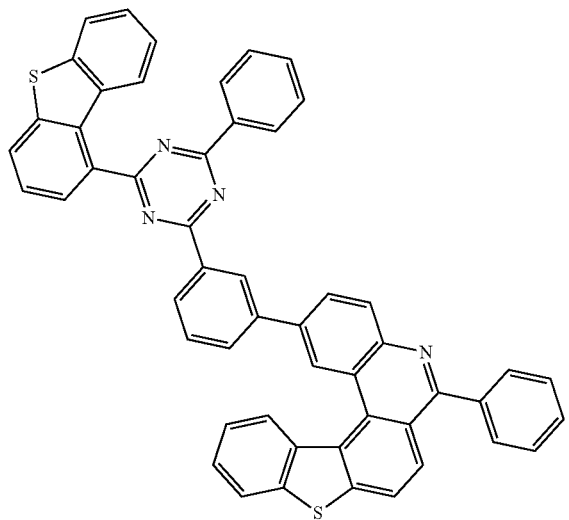
758
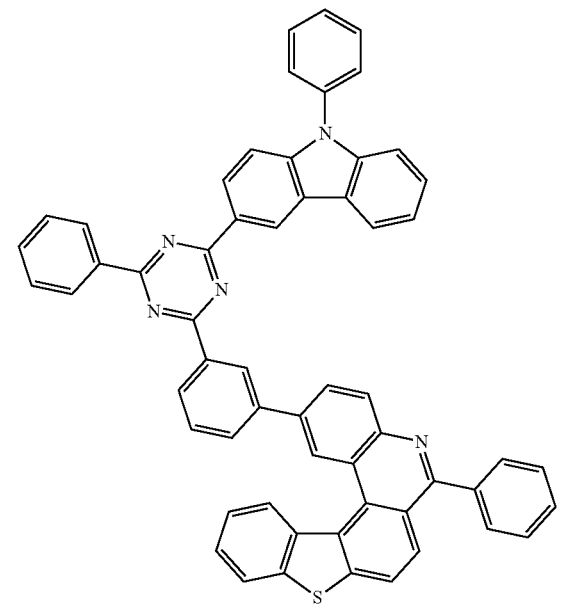 [SMILES: c1ccc(-c2nc(-c3cccc(-c4ccc5nc(-c6ccccc6)c6ccc7sc8ccccc8c7c6c5c4)c3)nc(-c3ccc4c(c3)c3ccccc3n4-c3ccccc3)n2)cc1]
759
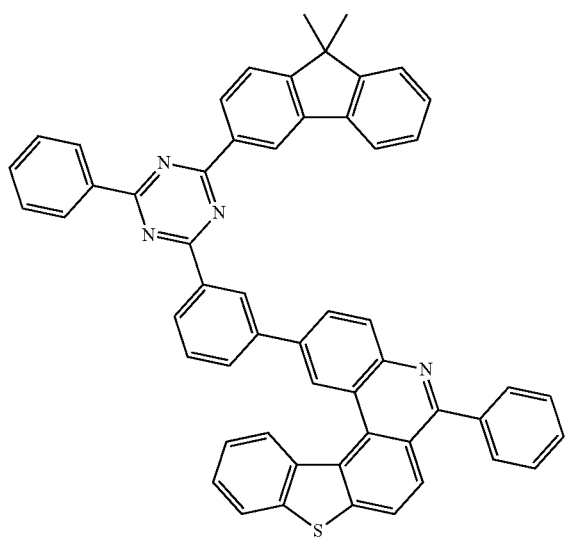
760
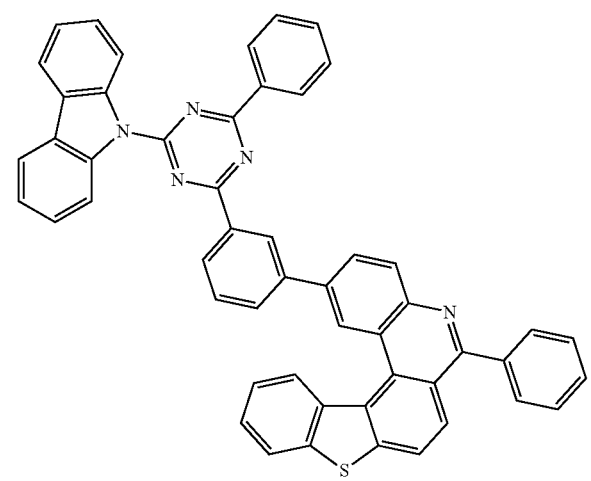
761
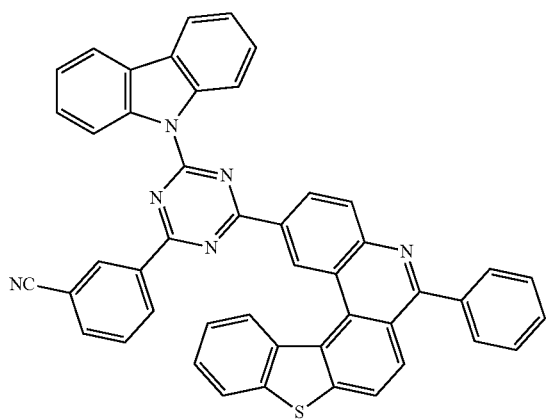
762
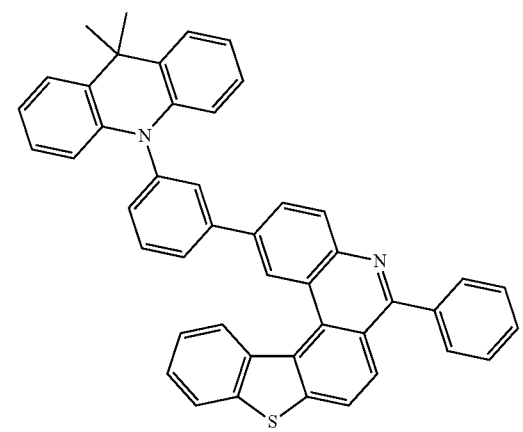 [SMILES: CC1(C)c2ccccc2N(c2cccc(-c3ccc4nc(-c5ccccc5)c5ccc6sc7ccccc7c6c5c4c3)c2)c2ccccc21]

-continued
763
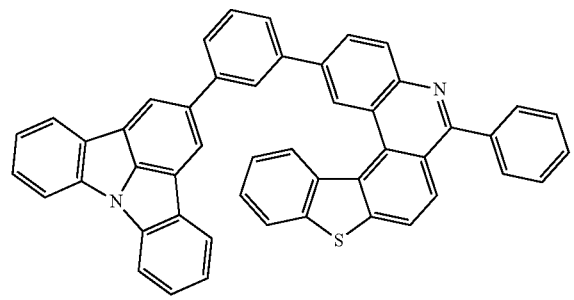
764
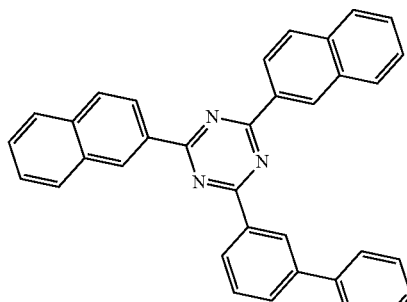
765
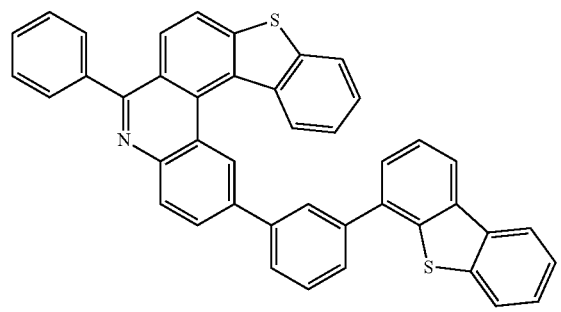
766
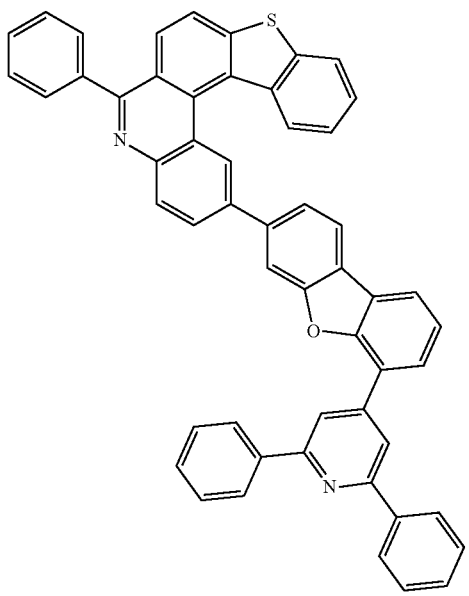 [SMILES: c1ccc(-c2cc(-c3cccc4c3oc3cc(-c5ccc6nc(-c7ccccc7)c7ccc8sc9ccccc9c8c7c6c5)ccc34)nc(-c3ccccc3)n2)cc1]
767
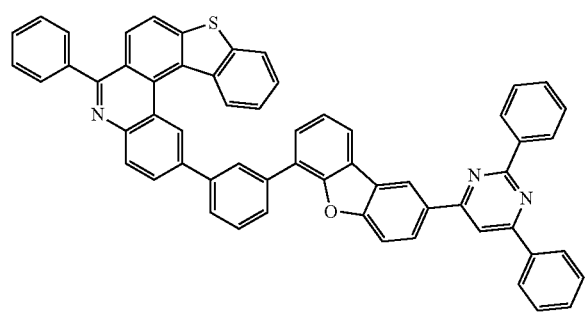
768
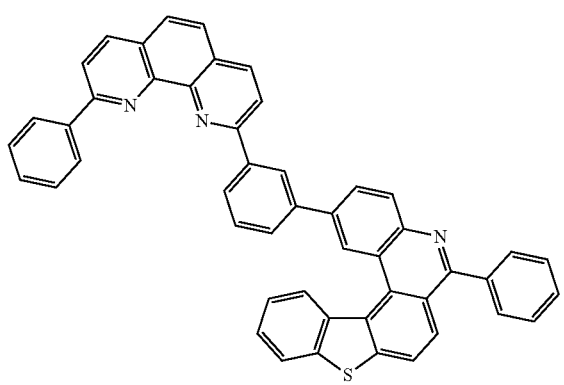

-continued
769
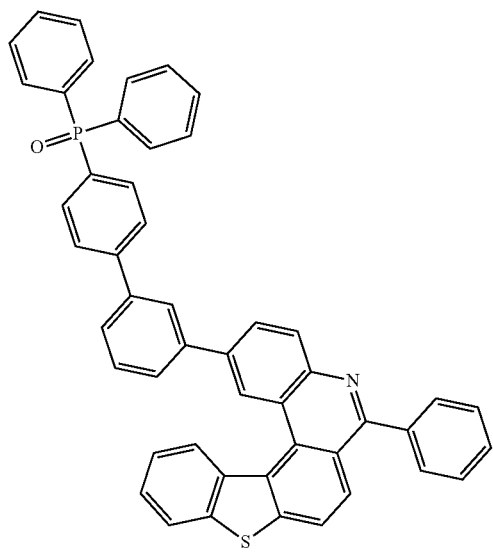
770
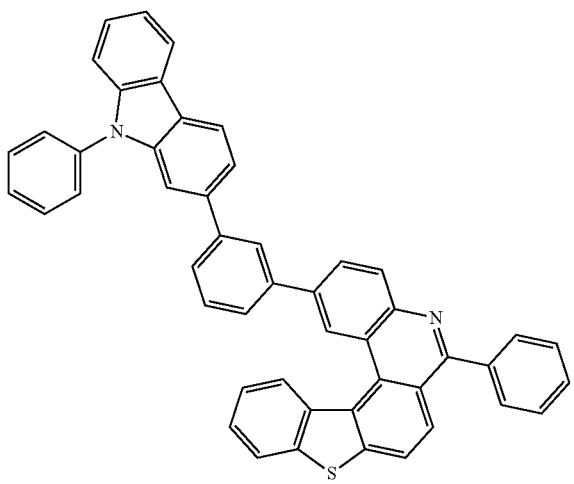
771
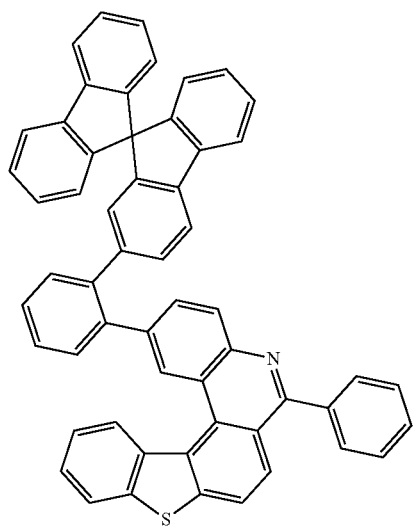
772
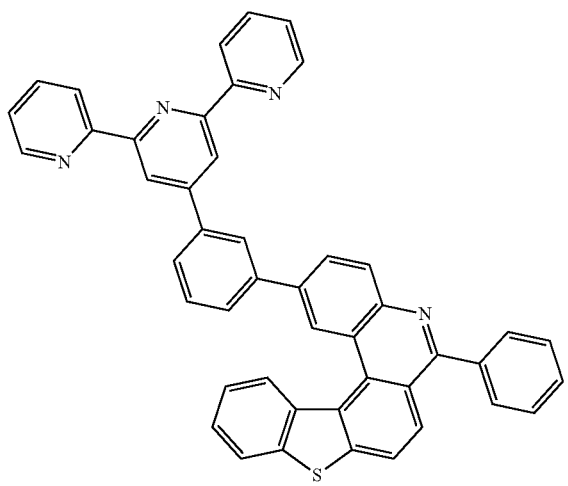
773
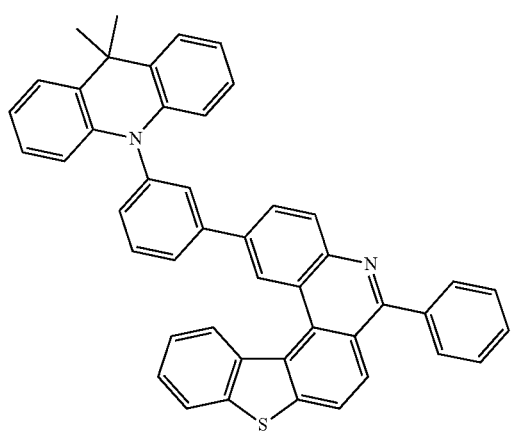
774
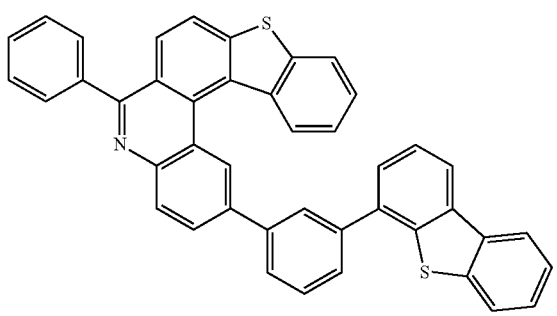

-continued
807
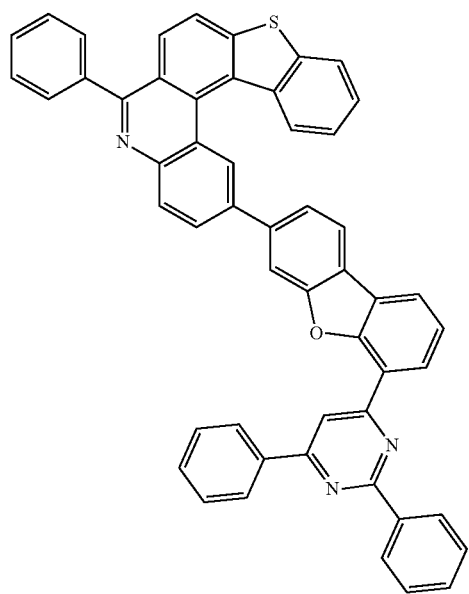
775
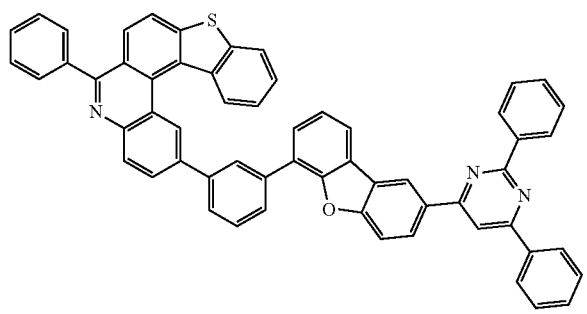
808
776
777
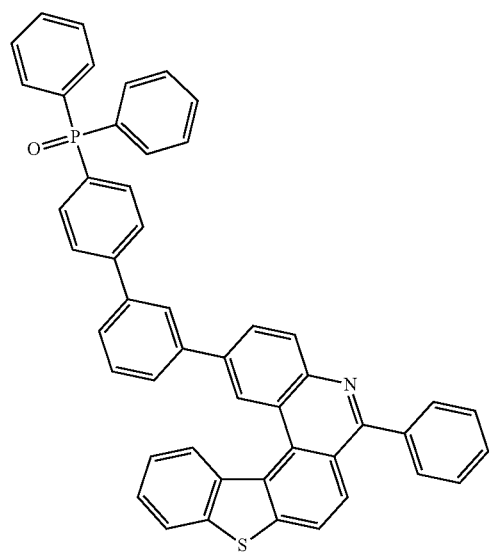
778
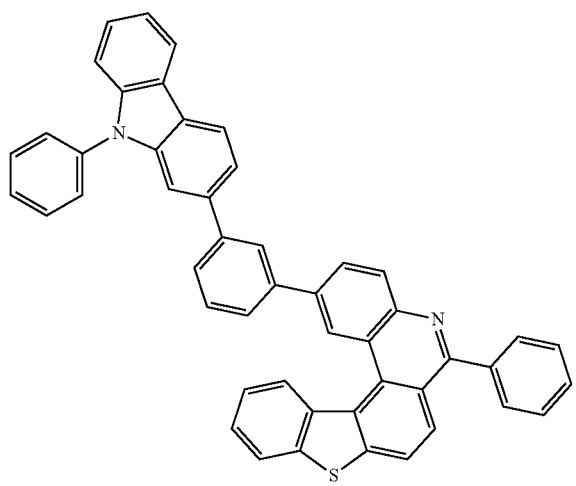 [SMILES: c1ccc(-c2nc3ccc(-c4cccc(-c5ccc6c7ccccc7n(-c7ccccc7)c6c5)c4)cc3c3c2ccc2sc4ccccc4c23)cc1]

-continued
779
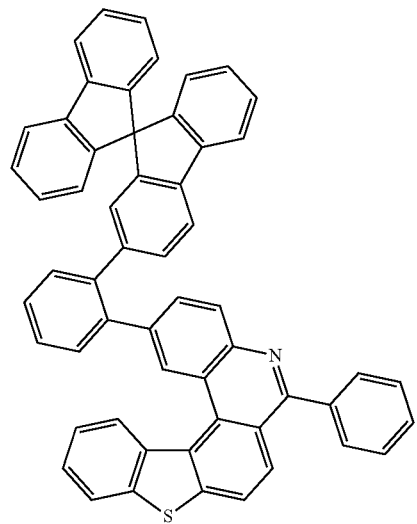
780
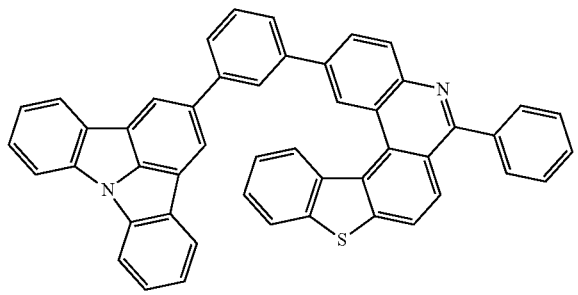
781
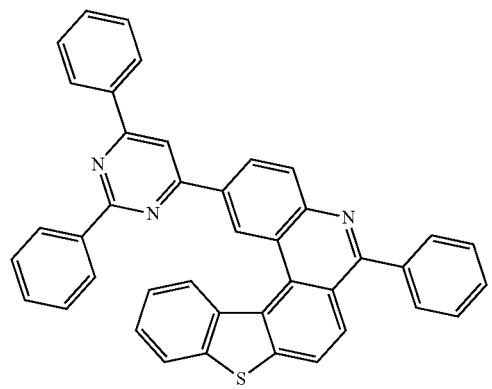
782
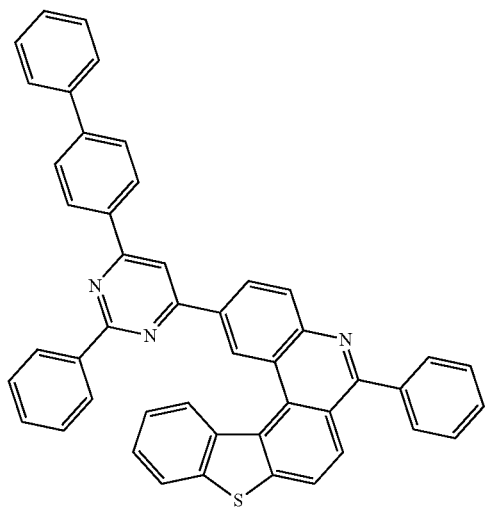 [SMILES: c1ccc(-c2ccc(-c3cc(-c4ccc5nc(-c6ccccc6)c6ccc7sc8ccccc8c7c6c5c4)nc(-c4ccccc4)n3)cc2)cc1]
783
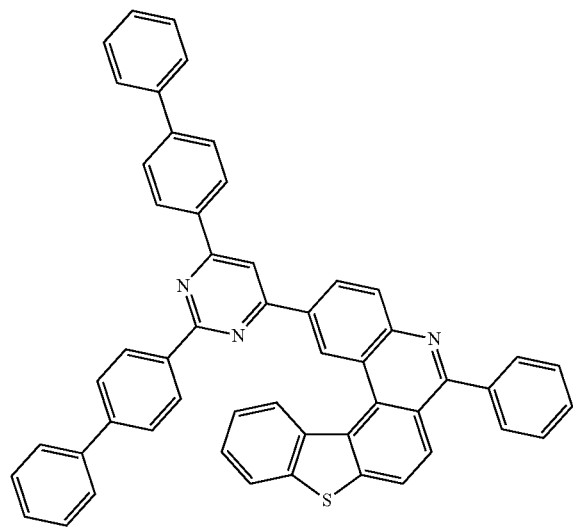
784
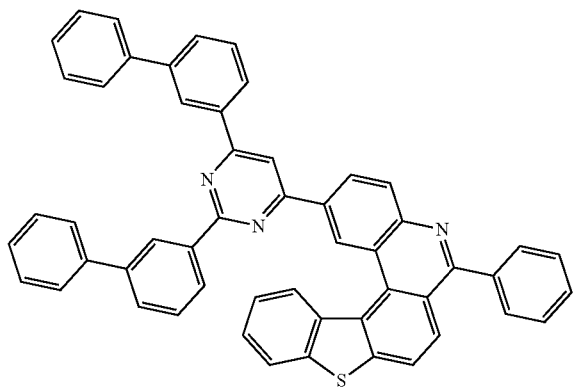

785
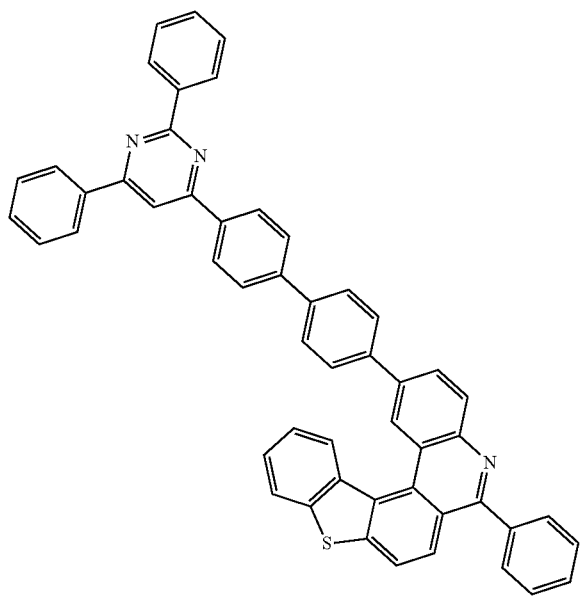
786
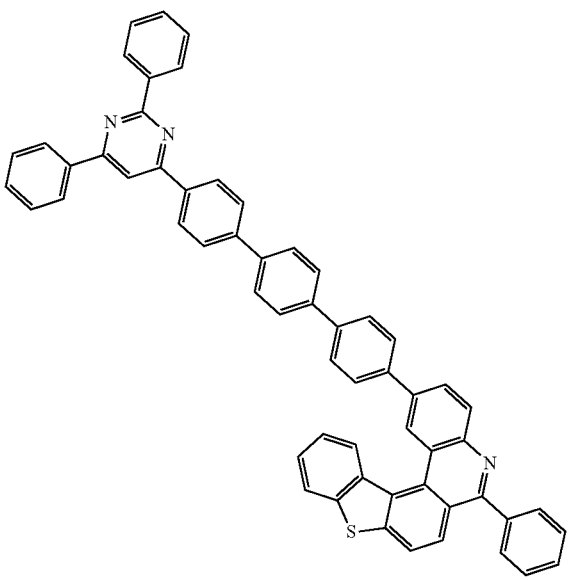
787
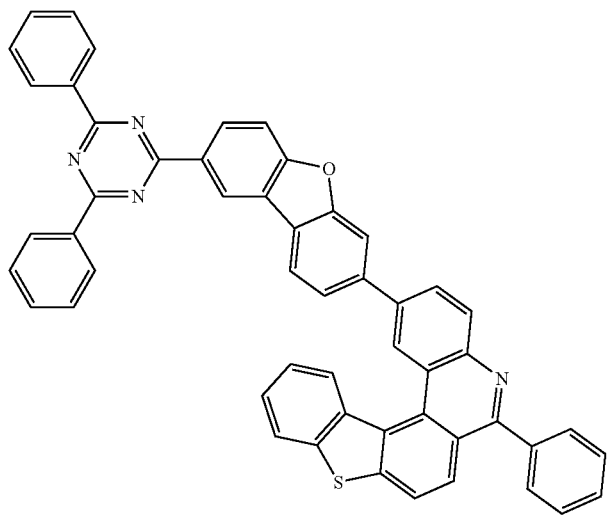
788
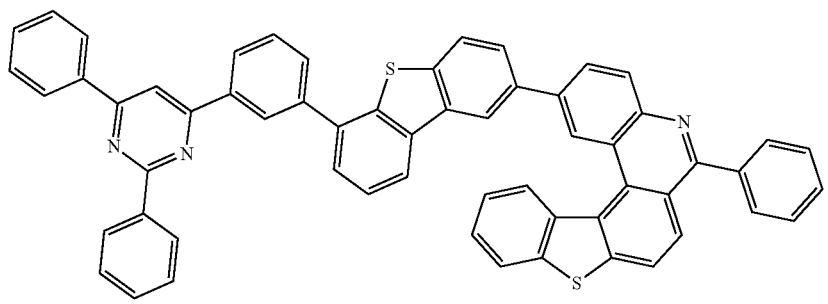

-continued
789
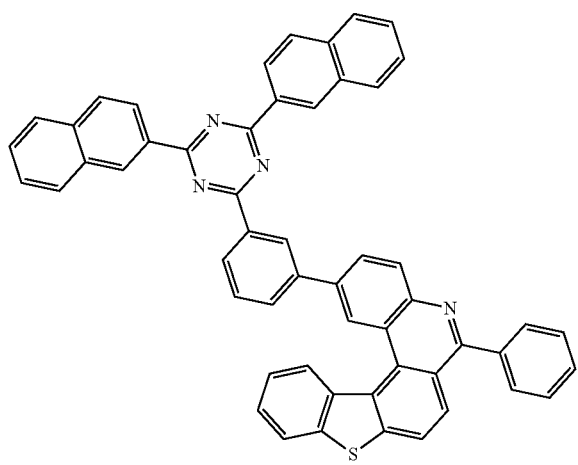
790
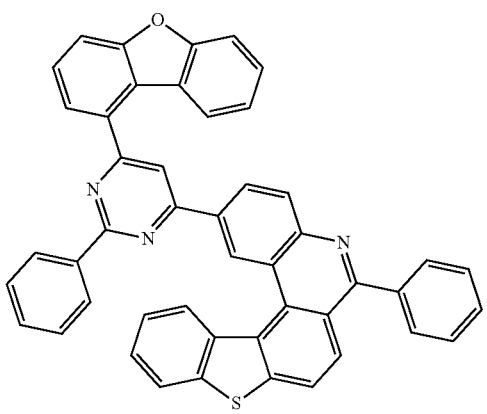 [SMILES: c1ccc(-c2nc(-c3ccc4nc(-c5ccccc5)c5ccc6sc7ccccc7c6c5c4c3)cc(-c3cccc4oc5ccccc5c34)n2)cc1]
791
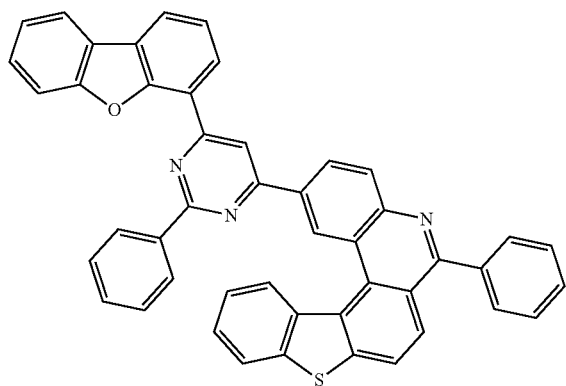
792
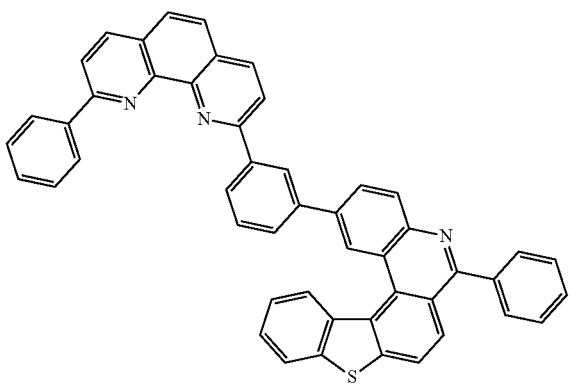
793
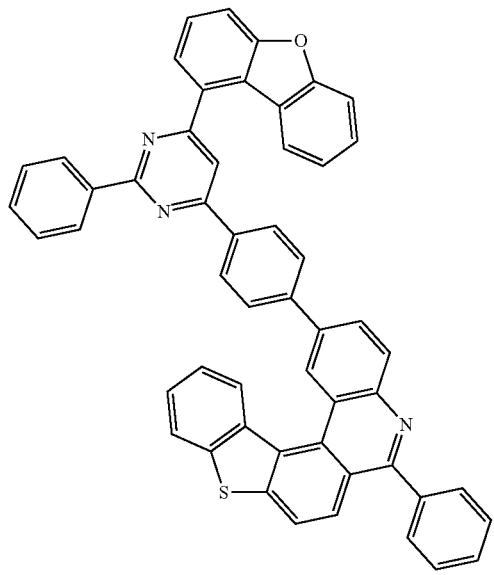
794
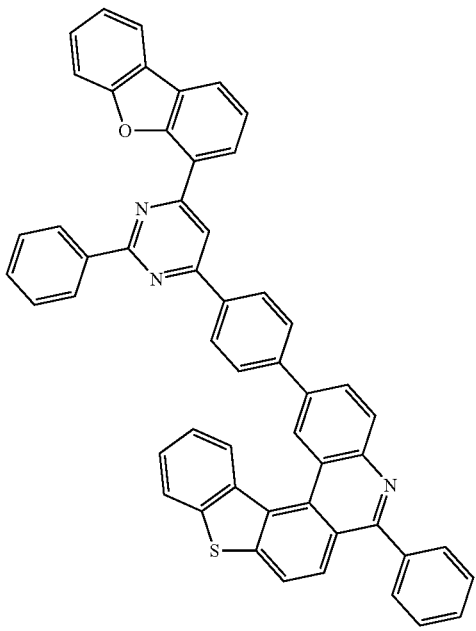

-continued
795
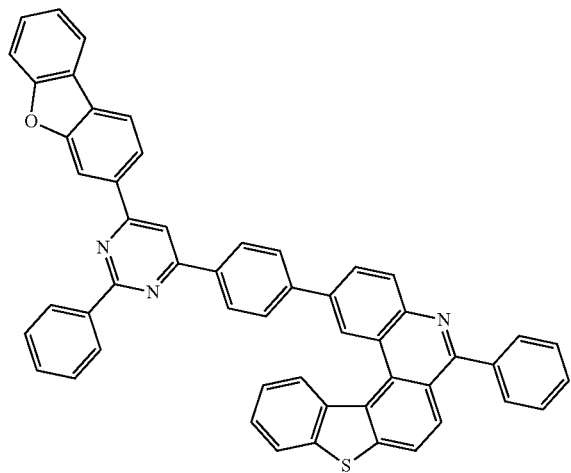
796
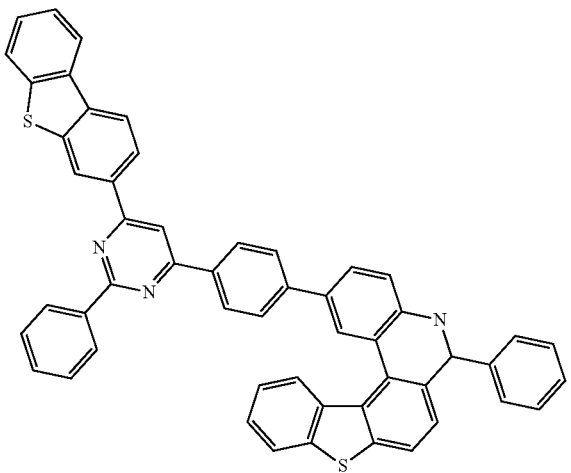
797
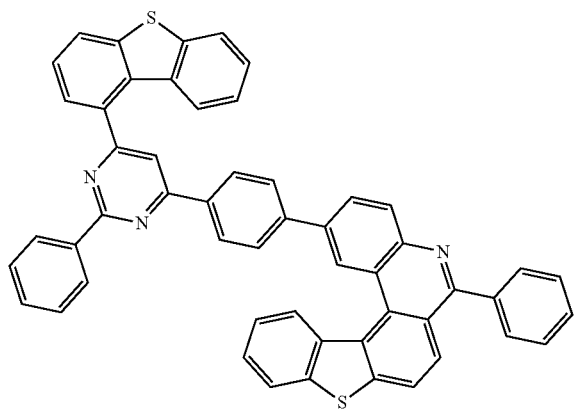
798
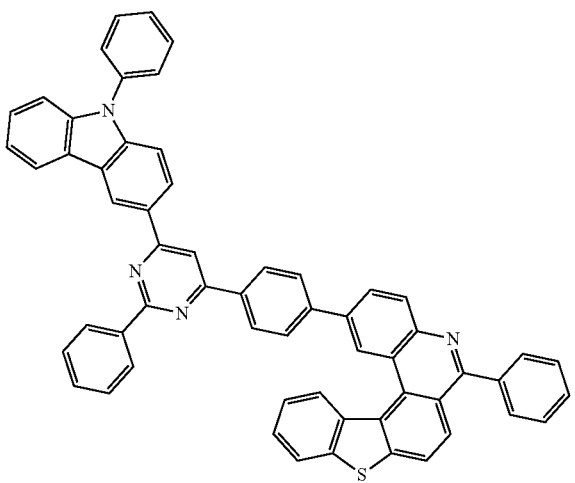
799
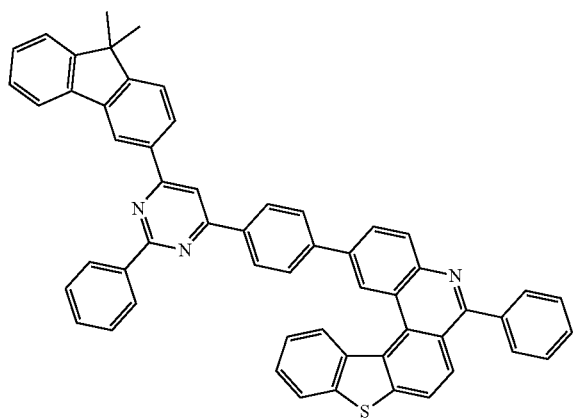
800
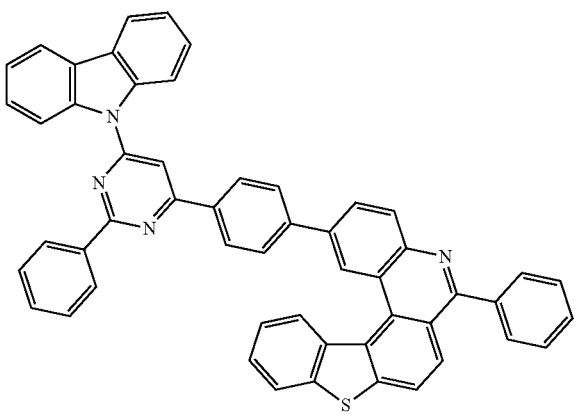

-continued
817
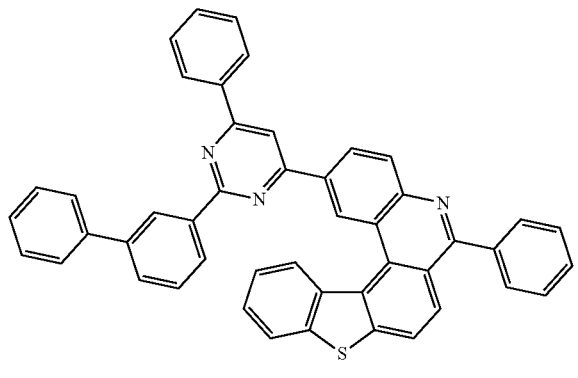
801
818
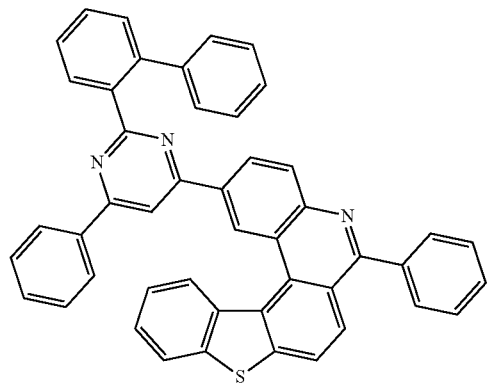 [SMILES: c1ccc(-c2cc(-c3ccc4nc(-c5ccccc5)c5ccc6sc7ccccc7c6c5c4c3)nc(-c3ccccc3-c3ccccc3)n2)cc1]
802
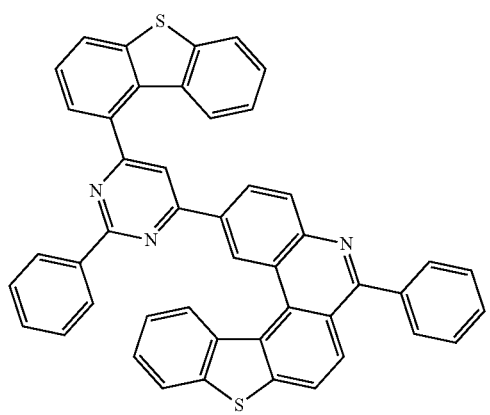
803
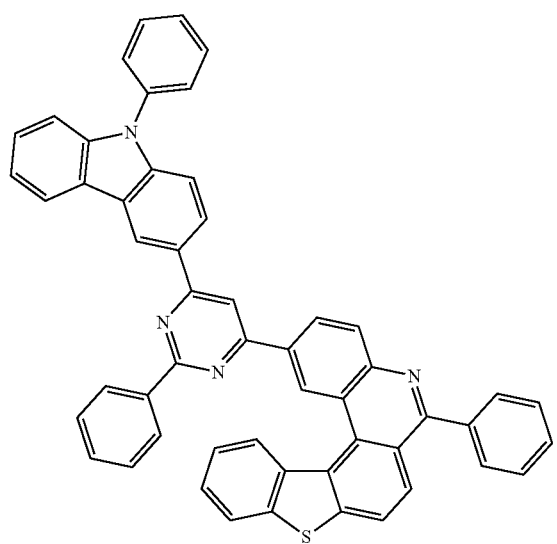
804
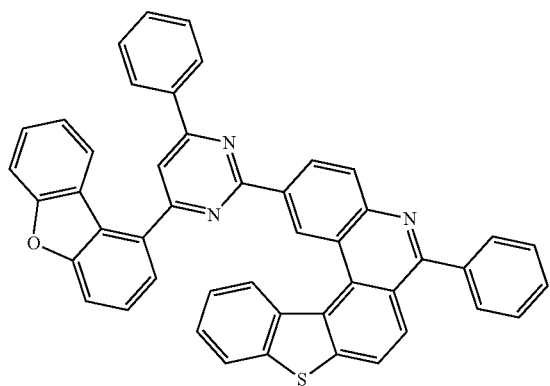
805
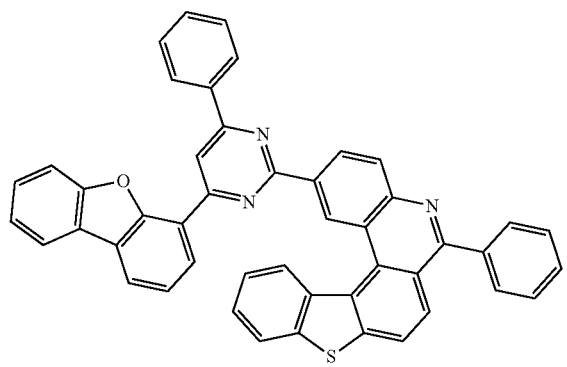
806

-continued
807
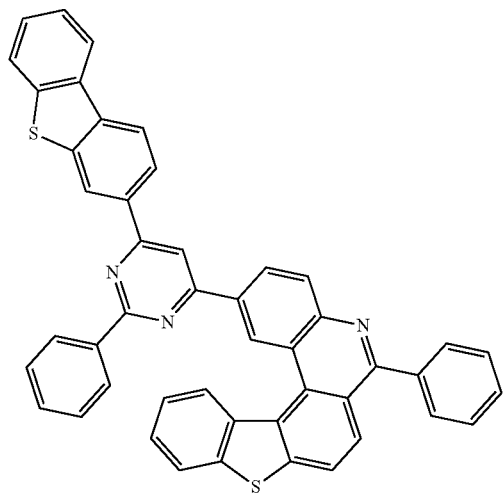
808
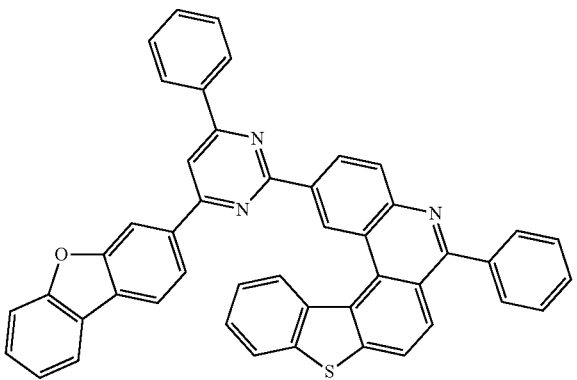
809
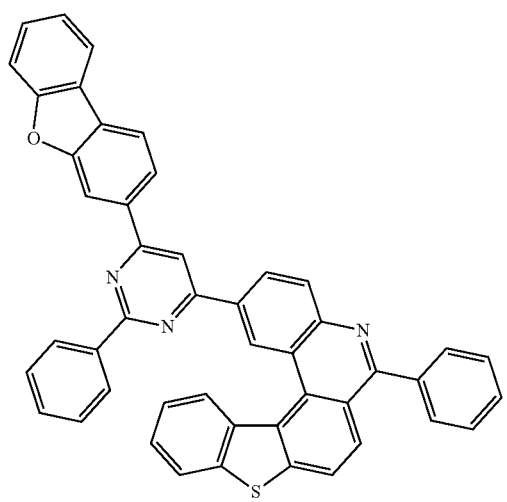
810
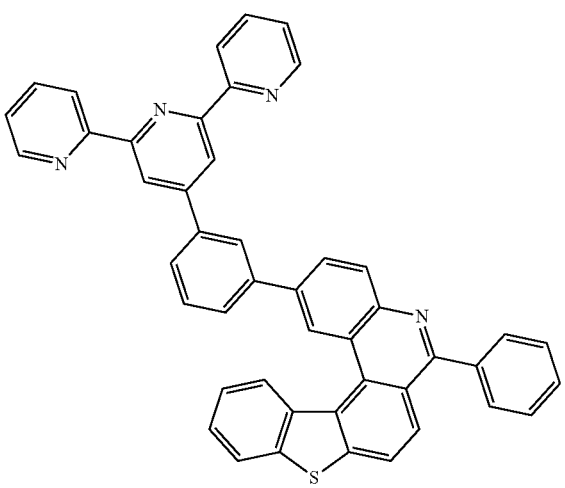 [SMILES: c1ccc(-c2nc3ccc(-c4cccc(-c5cc(-c6ccccn6)nc(-c6ccccn6)c5)c4)cc3c3c2ccc2sc4ccccc4c23)cc1]
811
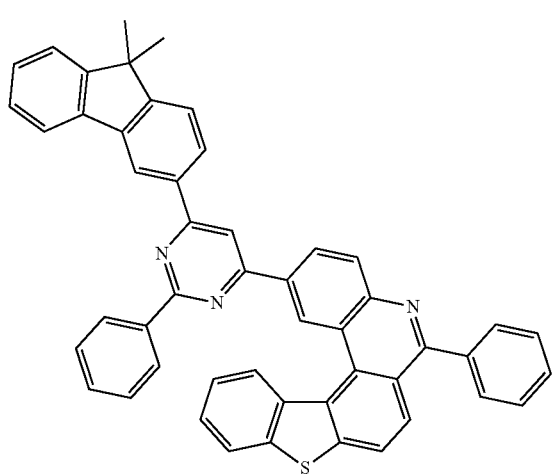
812
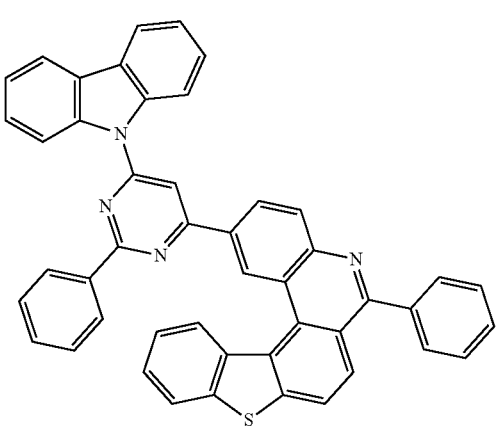

-continued
821
813
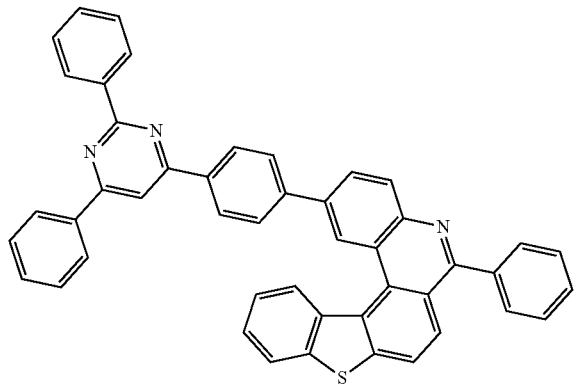
814
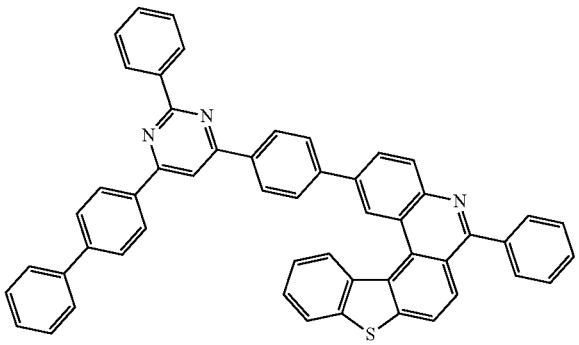 [SMILES: c1ccc(-c2ccc(-c3cc(-c4ccc(-c5ccc6nc(-c7ccccc7)c7ccc8sc9ccccc9c8c7c6c5)cc4)nc(-c4ccccc4)n3)cc2)cc1]
822
815
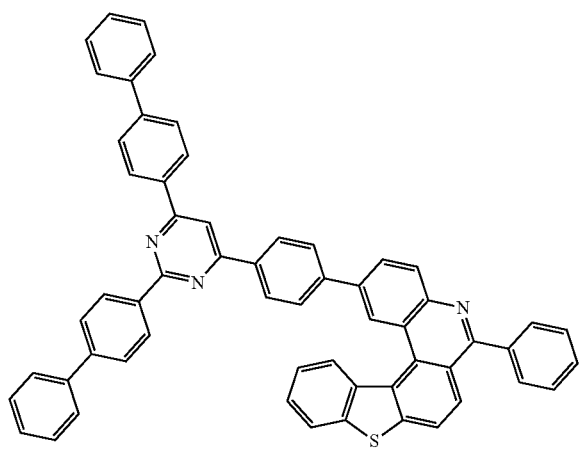
816
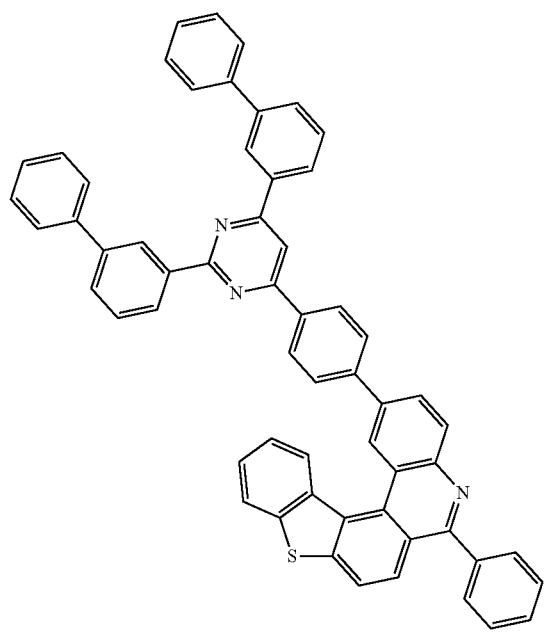
817
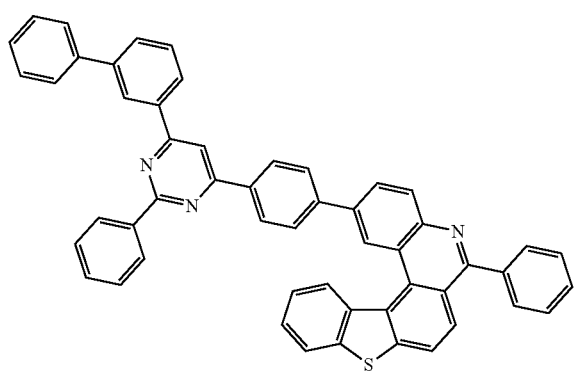
818

-continued
819
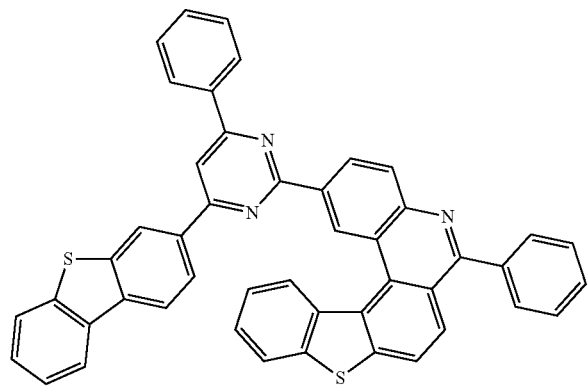
820
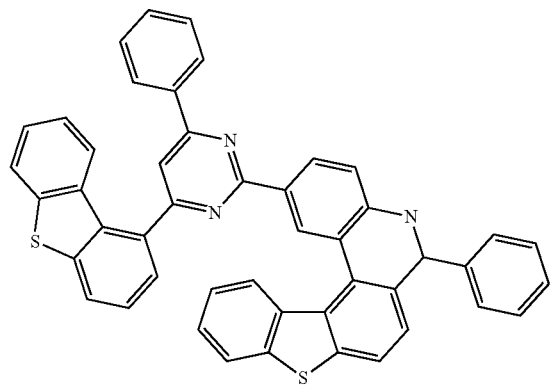
821
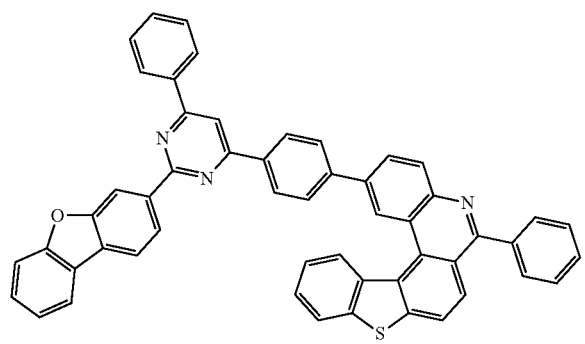
822
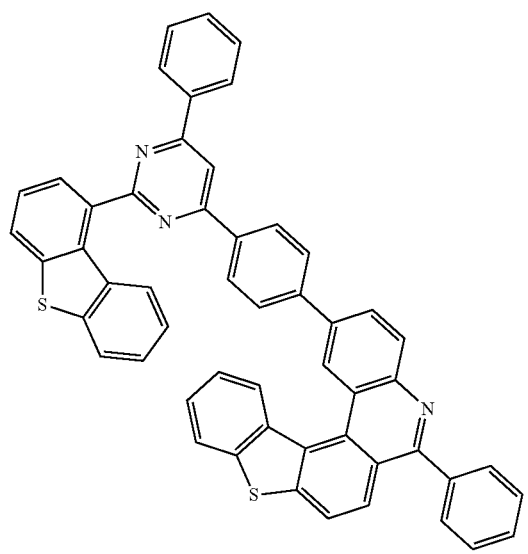
823
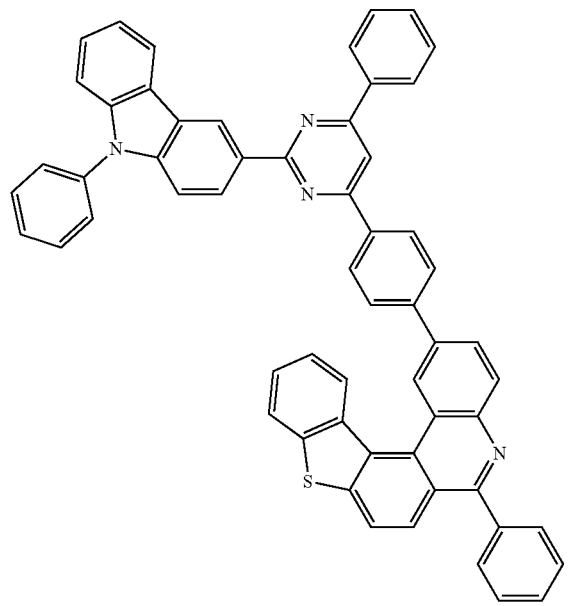
824
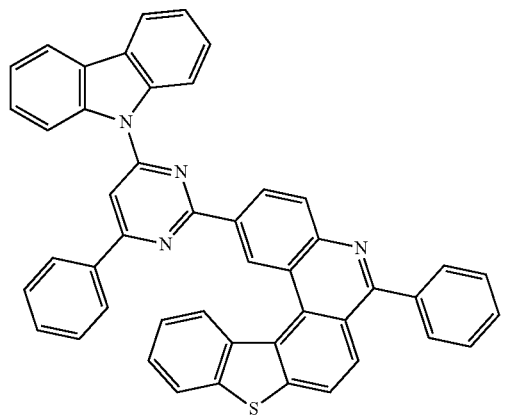

-continued
825
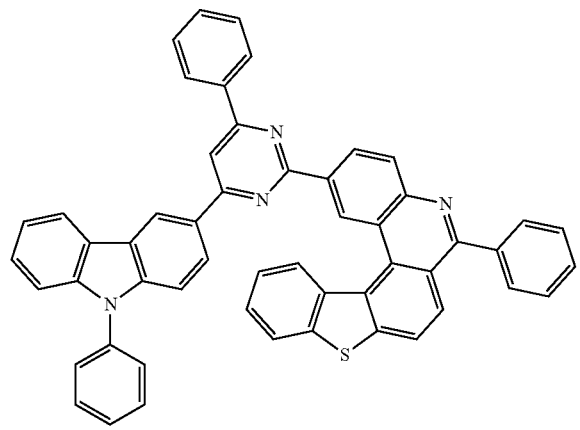
826
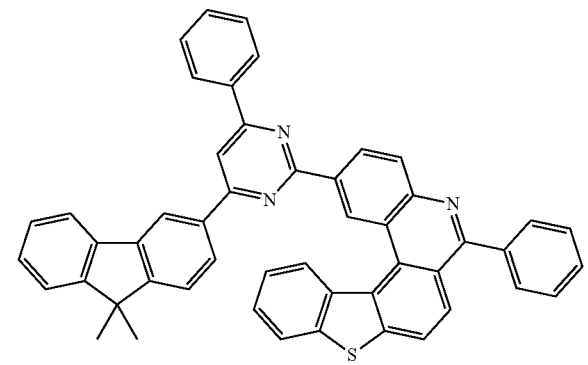 [SMILES: CC1(C)c2ccccc2-c2cc(-c3cc(-c4ccccc4)nc(-c4ccc5nc(-c6ccccc6)c6ccc7sc8ccccc8c7c6c5c4)n3)ccc21]
827
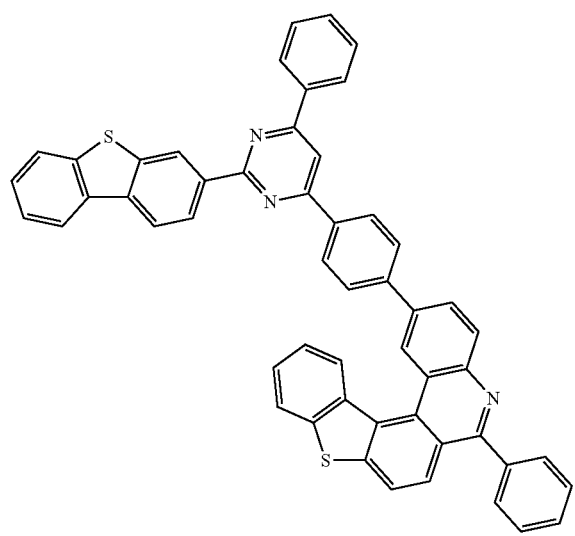
828
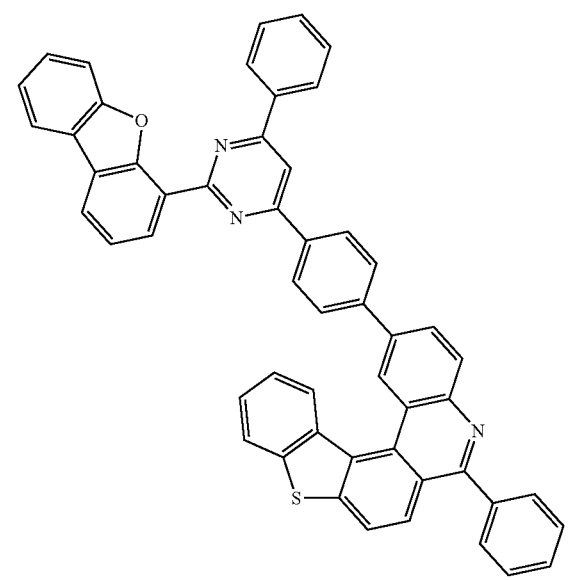
829
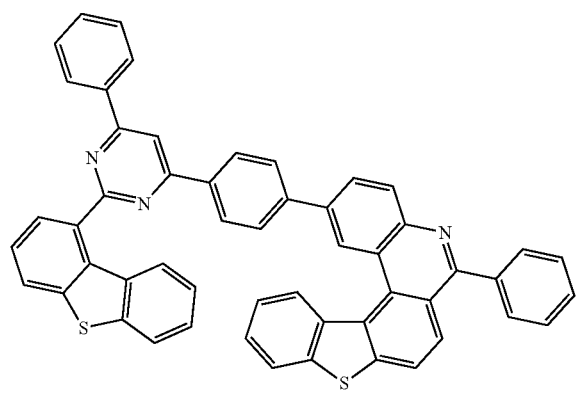
830
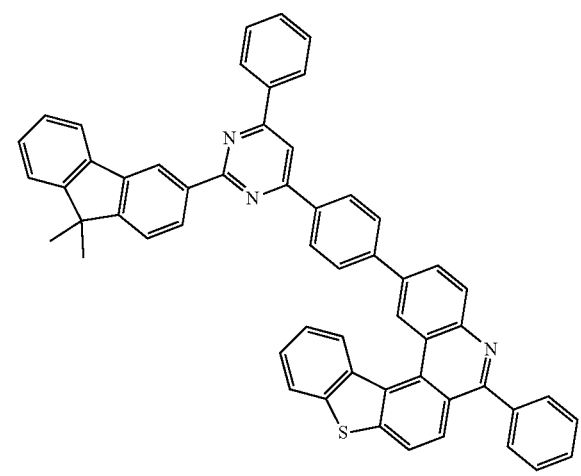

-continued
| 831 | 832 |
|---|---|
| 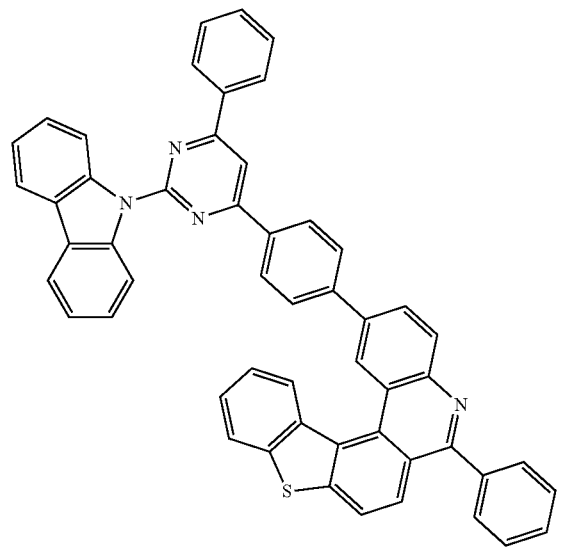 | 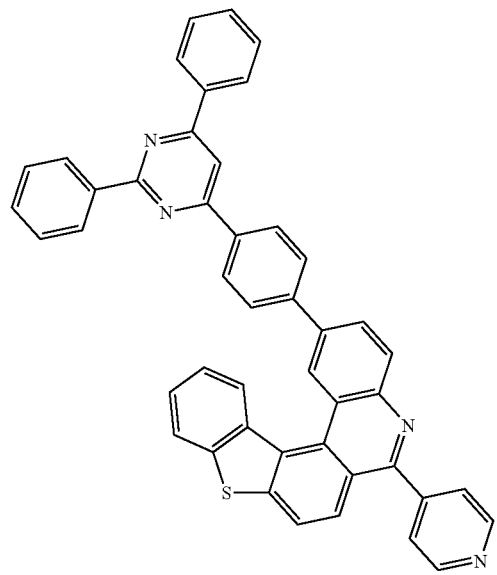 |
| 833 | 834 |
|---|---|
| 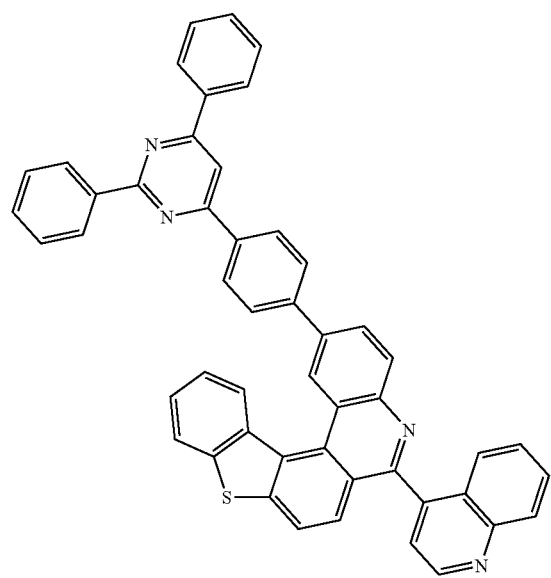 | 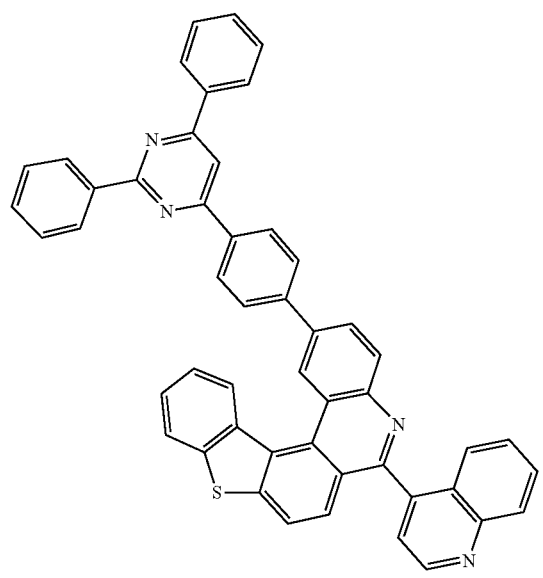 |

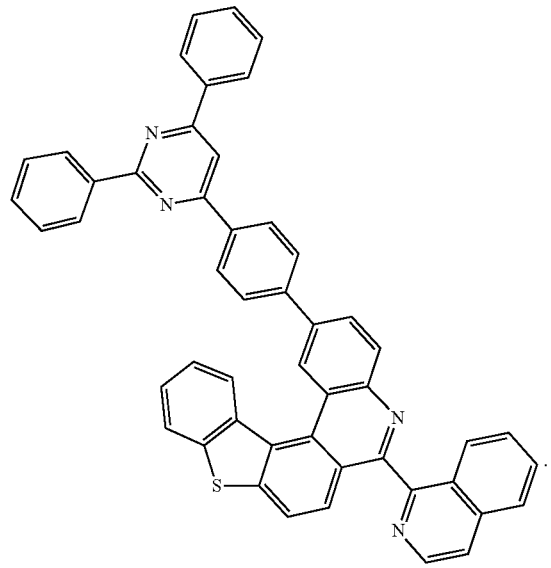

8. An organic light emitting device comprising:
a first electrode;
a second electrode; and
an organic material layer provided between the first electrode and the second electrode,
wherein the organic material layer includes the heterocyclic compound of claim 1.

9. The organic light emitting device of claim 8, wherein the organic material layer includes an electron transfer layer, and the electron transfer layer includes the heterocyclic compound.

10. The organic light emitting device of claim 8, wherein the organic material layer includes a charge generation layer, and the charge generation layer includes the heterocyclic compound.

11. The organic light emitting device of claim 8, further comprising one, two or more layers selected from the group consisting of a light emitting layer, a hole injection layer, a hole transfer layer, an electron injection layer, an electron transfer layer, an electron blocking layer and a hole blocking layer.

12. The organic light emitting device of claim 8 comprising:
the first electrode;
a first stack provided on the first electrode and including a first light emitting layer;
a charge generation layer provided on the first stack;
a second stack provided on the charge generation layer and including a second light emitting layer; and
the second electrode provided on the second stack.

13. The organic light emitting device of claim 12, wherein the charge generation layer includes the heterocyclic compound.

14. The organic light emitting device of claim 12, wherein the charge generation layer includes an N-type charge generation layer, and the N-type charge generation layer includes the heterocyclic compound.

* * * * *